US012649948B2

(12) United States Patent
Ounzain et al.

(10) Patent No.: US 12,649,948 B2
(45) **Date of Patent: *Jun. 9, 2026**

(54) DIAGNOSTIC, PROGNOSTIC AND THERAPEUTIC USES OF LONG NONCODING RNAS FOR HEART DISEASE AND REGENERATIVE MEDICINE

(71) Applicant: UNIVERSITÉ DE LAUSANNE, Lausanne (CH)

(72) Inventors: Samir Ounzain, Lausanne (CH); Thierry Pedrazzini, Le Mont-sur-Lausanne (CH)

(73) Assignee: UNIVERSITÉ DE LAUSANNE, Lausanne (CH)

( * ) Notice: Subject to any disclaimer, the term of this patent is extended or adjusted under 35 U.S.C. 154(b) by 1269 days.

This patent is subject to a terminal disclaimer.

(21) Appl. No.: 17/505,153

(22) Filed: Oct. 19, 2021

(65) Prior Publication Data

US 2022/0136054 A1     May 5, 2022

Related U.S. Application Data

(63) Continuation of application No. 15/105,319, filed as application No. PCT/EP2014/078868 on Dec. 19, 2014, now Pat. No. 11,193,171.

(60) Provisional application No. 61/964,591, filed on Dec. 20, 2013.

(51) Int. Cl.
*C12Q 1/6883*          (2018.01)

(52) U.S. Cl.
CPC ..... *C12Q 1/6883* (2013.01); *C12Q 2600/158* (2013.01); *C12Q 2600/178* (2013.01)

(58) Field of Classification Search
CPC ............... C12Q 1/68; C12Q 2600/158; C12Q 2600/178; C07H 21/00
See application file for complete search history.

(56) References Cited

U.S. PATENT DOCUMENTS

| | | | |
|---|---|---|---|
| 5,045,694 A | 9/1991 | Beavis et al. | |
| 5,118,937 A | 6/1992 | Hillenkamp et al. | |
| 5,510,270 A | 4/1996 | Fodor et al. | |
| 5,539,083 A | 7/1996 | Cook et al. | |
| 5,545,522 A | 8/1996 | Van Gelder et al. | |
| 5,556,752 A | 9/1996 | Lockhart et al. | |
| 5,578,832 A | 11/1996 | Trulson et al. | |
| 5,716,785 A | 2/1998 | Van Gelder et al. | |
| 5,719,060 A | 2/1998 | Hutchens et al. | |
| 5,891,636 A | 4/1999 | Van Gelder et al. | |
| 6,028,189 A | 2/2000 | Blanchard | |

| | | | |
|---|---|---|---|
| 6,225,047 B1 | 5/2001 | Hutchens et al. | |
| 11,193,171 B2 | 12/2021 | Ounzain et al. | |
| 2005/0048542 A1 | 3/2005 | Baker et al. | |

FOREIGN PATENT DOCUMENTS

| | | |
|---|---|---|
| WO | WO-0105935 A2 | 1/2001 |
| WO | WO-2011005793 A1 | 1/2011 |

OTHER PUBLICATIONS

Song et al., "Integrated Analysis of Dysregulated lncRNA Expression in Fetal Cardiac Tissues with Ventricular Septal Defect", PLOS ONE vol. 8 No. 10, Oct. 16, 2013, p. e77492.

Grote et al., "The Tissue-Specific lncRNA Fendrr is an Essential Regulator of Heart and Body Wall Development in the Mouse", Developmental Cell vol. 24 No. 2, Jan. 28, 2013, pp. 206-214.

Schonrock et al., "Long Noncoding RNAs in Cardiac Development and Pathophysiology", Circulation Research vol. 111 No. 10, Oct. 25, 2012, pp. 1349-1362.

Klattenhoff et al., "Braveheart, a Long Noncoding RNA Required for Cardiovascular Lineage Commitment", Cell vol. 152 No. 3, Jan. 1, 2013, pp. 570-583.

Li et al., "Transcriptome Analysis Reveals Distinct Patterns of Long Noncoding RNAs in Heart and Plasma of Mice with Heart Failure", Plos One vol. 8 No. 10, Oct. 29, 2013, p. e77938.

Ounzain et al., "Small and Long Non-coding RNAs in Cardiac Homeostasis and Regeneration", Biochimica Et Biophysica Acta (BBA)—Molecular Cell Research vol. 1833 No. 4, Apr. 1, 2013, pp. 923-933.

Ounzain et al., "Functional Importance of Cardiac Enhancer-Associated Noncoding RNAs in Heart Development and Disease", Journal of Molecular and Cellular Cardiology vol. 76, Aug. 19, 2014, pp. 55-70.

Ounzain et al., "Genome-Wide Profiling of the Cardiac Transcriptome after Myocardial Infarction Identifies Novel Heart-Specific Long Non-Coding RNAs", European Heart Journal vol. 36 No. 6, Apr. 30, 2014, pp. 353-368.

Database Geneseq [Online] May 26, 2011, "Human SCN10A (SCN10A Sodium Channel Subunit) DNA with SNP SEQ ID: 2379.", Retrieved from EBI Accession No. GSN:AZH12782.

Database EMBL [Online] Nov. 11, 2009, "Sequence 262 from Patent EP2113572.", retrieved from EBI Accession No. EM_PAT:HC054269.

International Search Report and Written Opinion Issued in PCT/EP2014/078868 Filed Dec. 19, 2014.

Communication pursuant to Article 94(3) EPC from European Application No. 14 828 456.5 dated Jan. 24, 2019.

(Continued)

*Primary Examiner* — Ethan C Whisenant

(74) *Attorney, Agent, or Firm* — Harness Dickey & Pierce P.L.C.

(57)          ABSTRACT

This invention generally relates to lncRNAs and methods for diagnosing cardiac pathologies in a subject. The invention also provides methods for treating a cardiac pathology in a subject comprising administering to said subject an effective amount of a modulator of one or more lncRNAs of the invention.

9 Claims, 27 Drawing Sheets

Specification includes a Sequence Listing.

(56)            References Cited

OTHER PUBLICATIONS

Anonymous: "Hit details for GS_NUC_ALERT:WO2011005786.
476445", Jan. 13, 2011, XP55537132, Retrieved from the Internet:
URL:http://ibis/exam/hitDetails.jsp?id=203291191.
Anonymous: "Hit details for GSN:ADO46714", Apr. 11, 2004,
XP55537221, Retrieved from the Internet: URL:http://ibis/exam/
hitDetails.jsp?id=203290939.
Office Action from corresponding U.S. Appl. No. 15/105,319 dated
Dec. 10, 2018.
Office Action from corresponding U.S. Appl. No. 15/105,319 dated
Jul. 18, 2019.
Office Action from corresponding U.S. Appl. No. 15/105,319 dated
Jan. 14, 2020.
Office Action from corresponding U.S. Appl. No. 15/105,319 dated
Jun. 24, 2020.
Office Action from corresponding U.S. Appl. No. 15/105,319 dated
Mar. 25, 2021.

Figure 1A *(cont'd)*
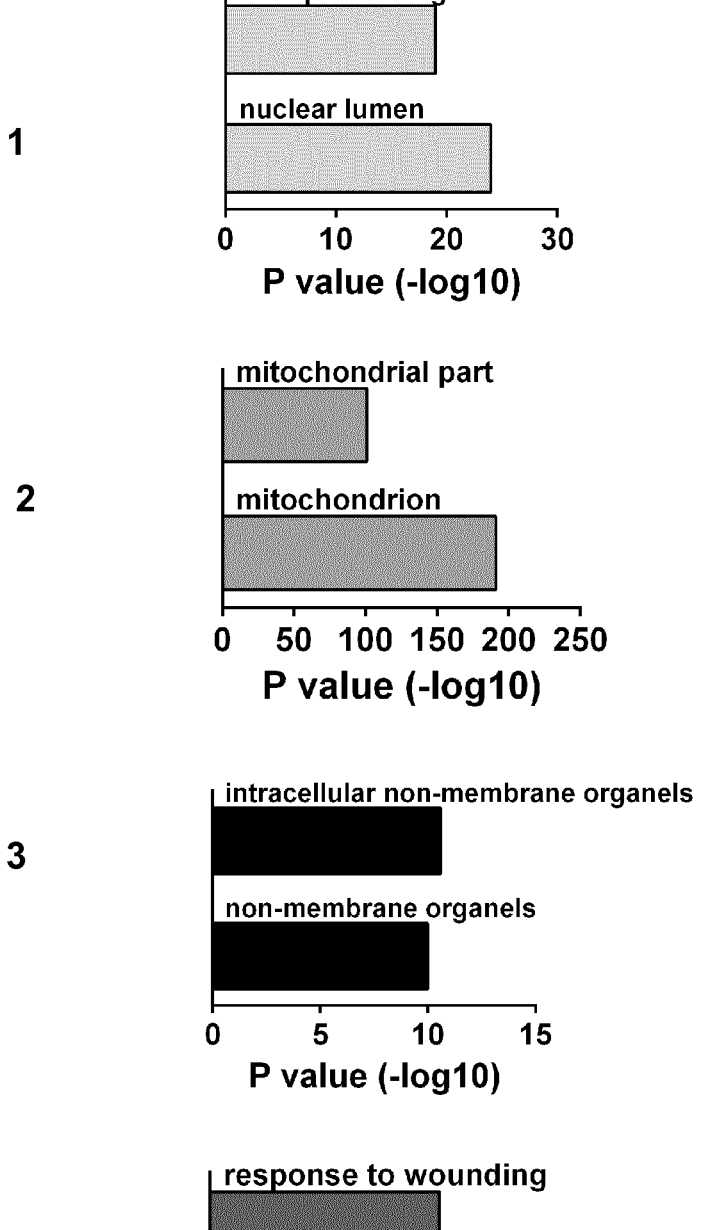

Figure 1B *(cont'd)*
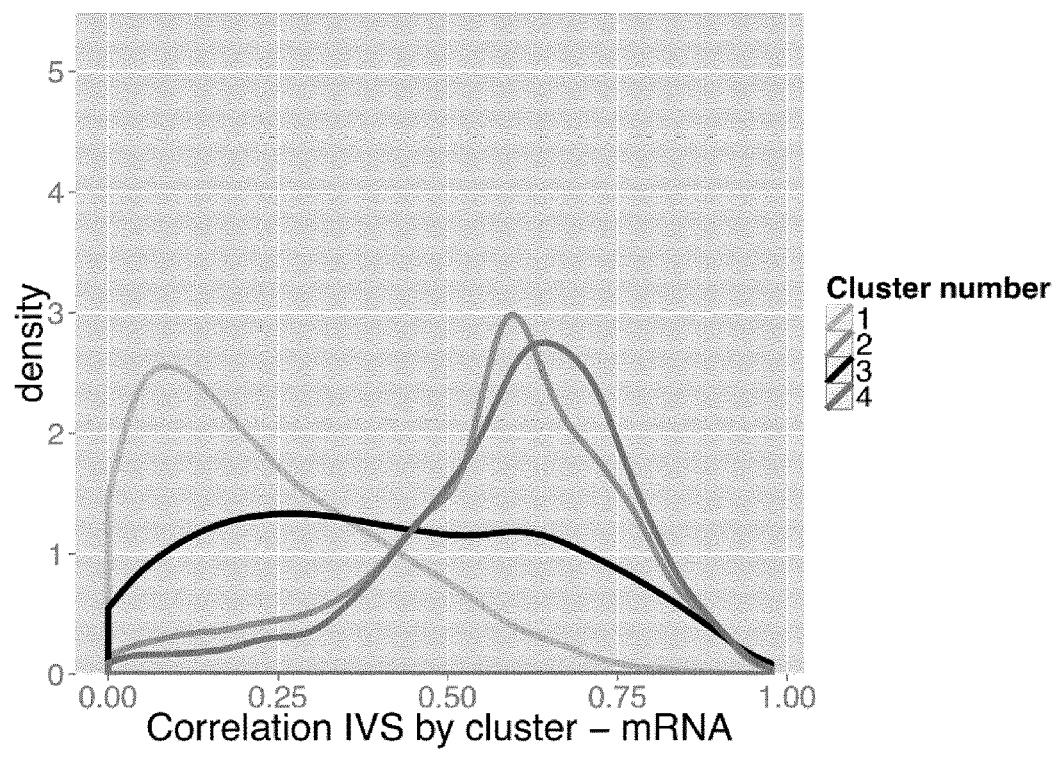
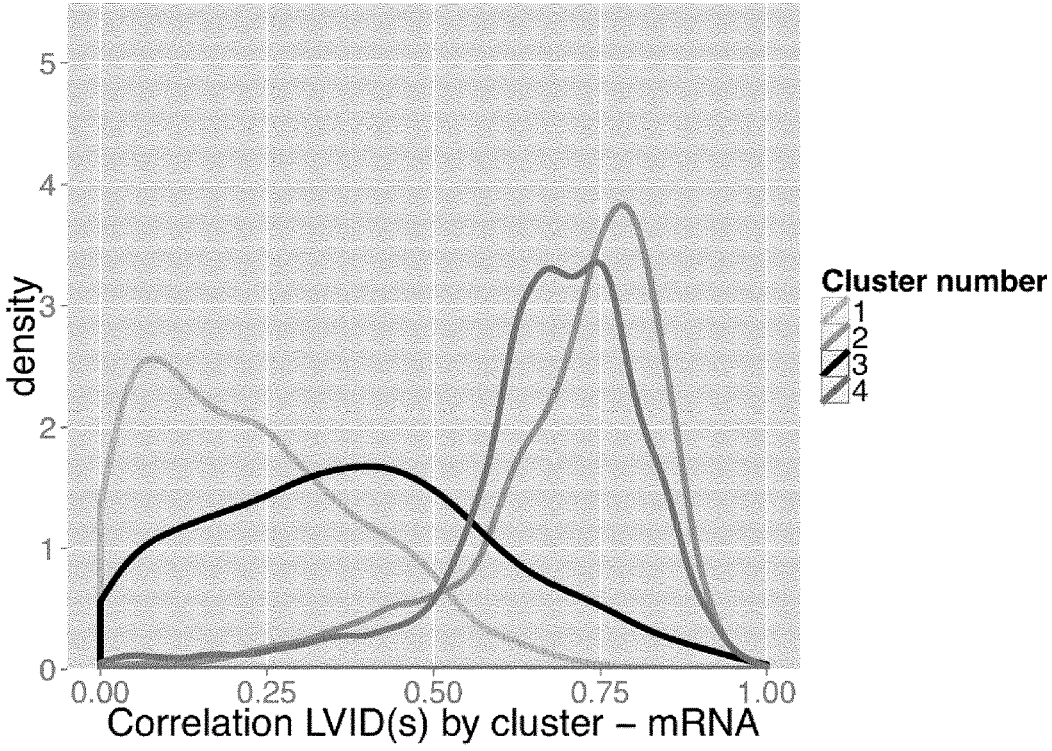

Figure 1C *(cont'd)*
1
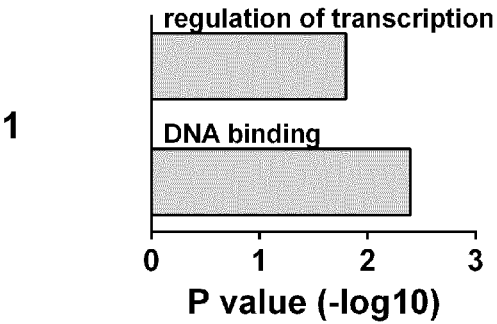
2
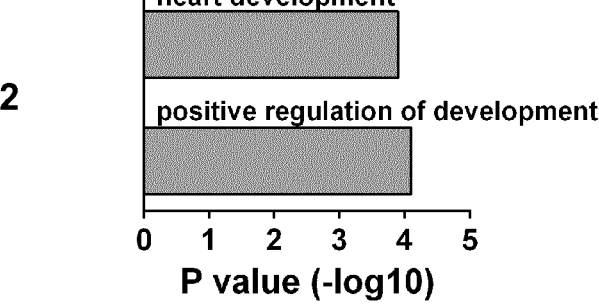
3
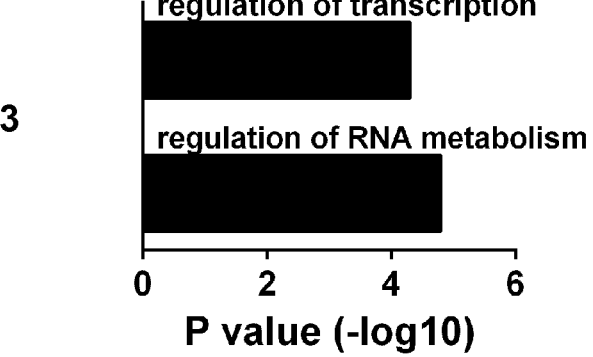
4
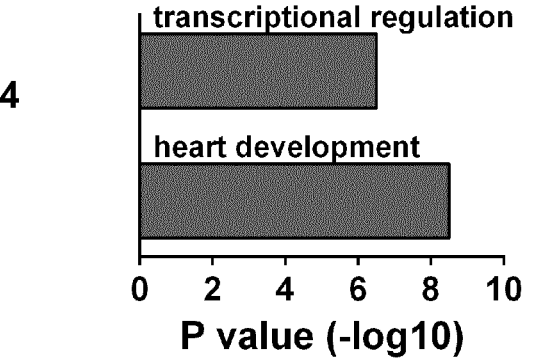

Correlation EF by cluster – novel lncRNA

Correlation LA MI trace by cluster – novel lncRNA

Figure 1D *(cont'd)*
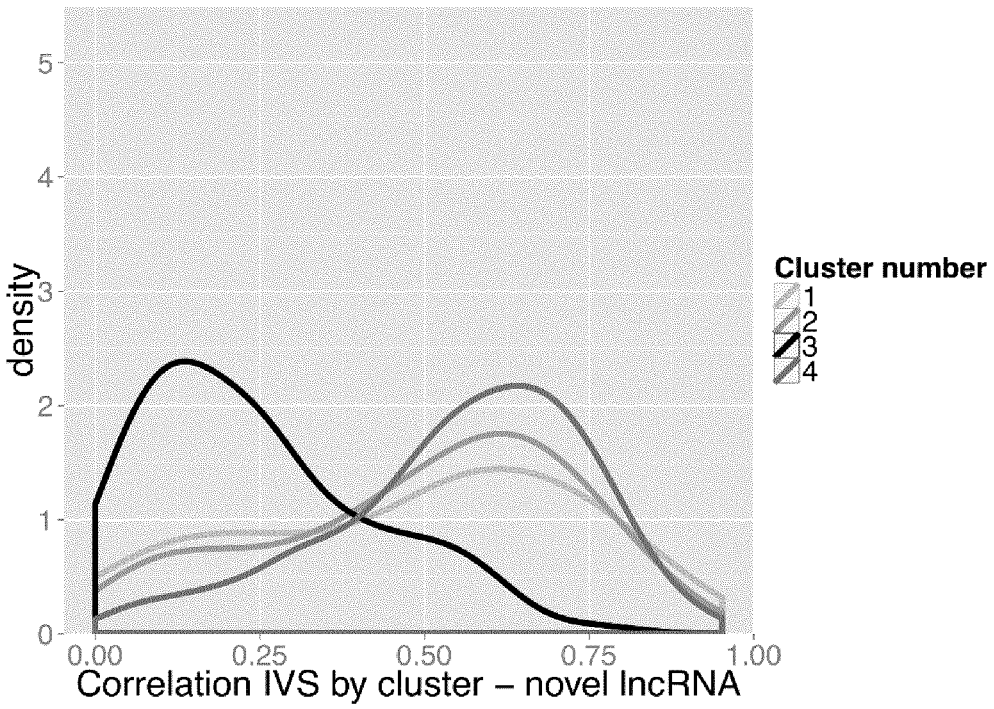
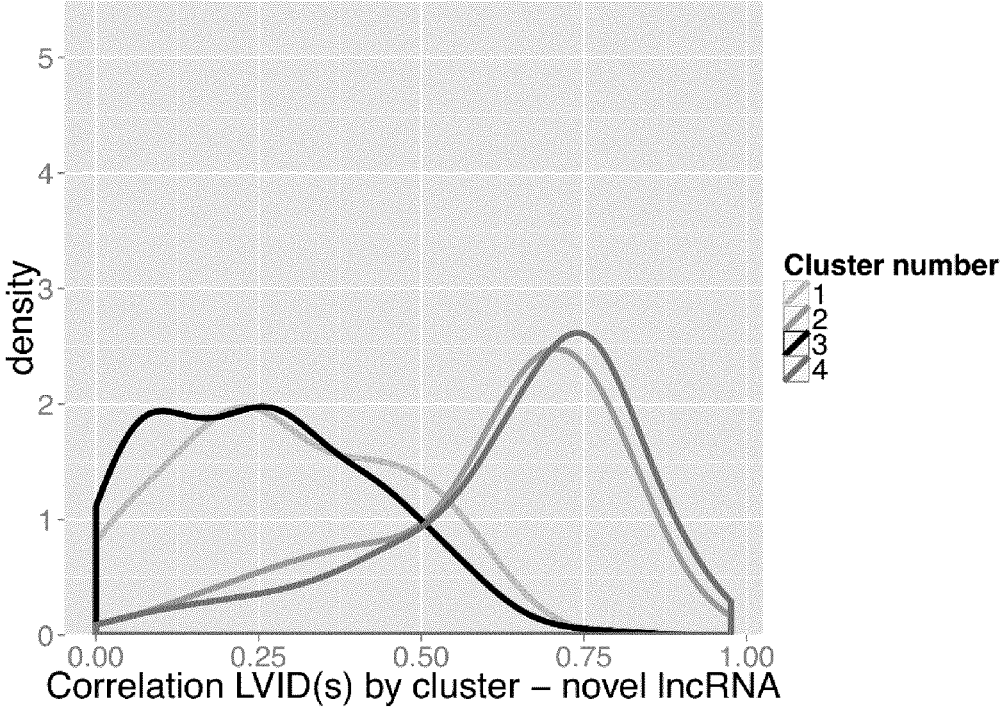

Figure 2B & C
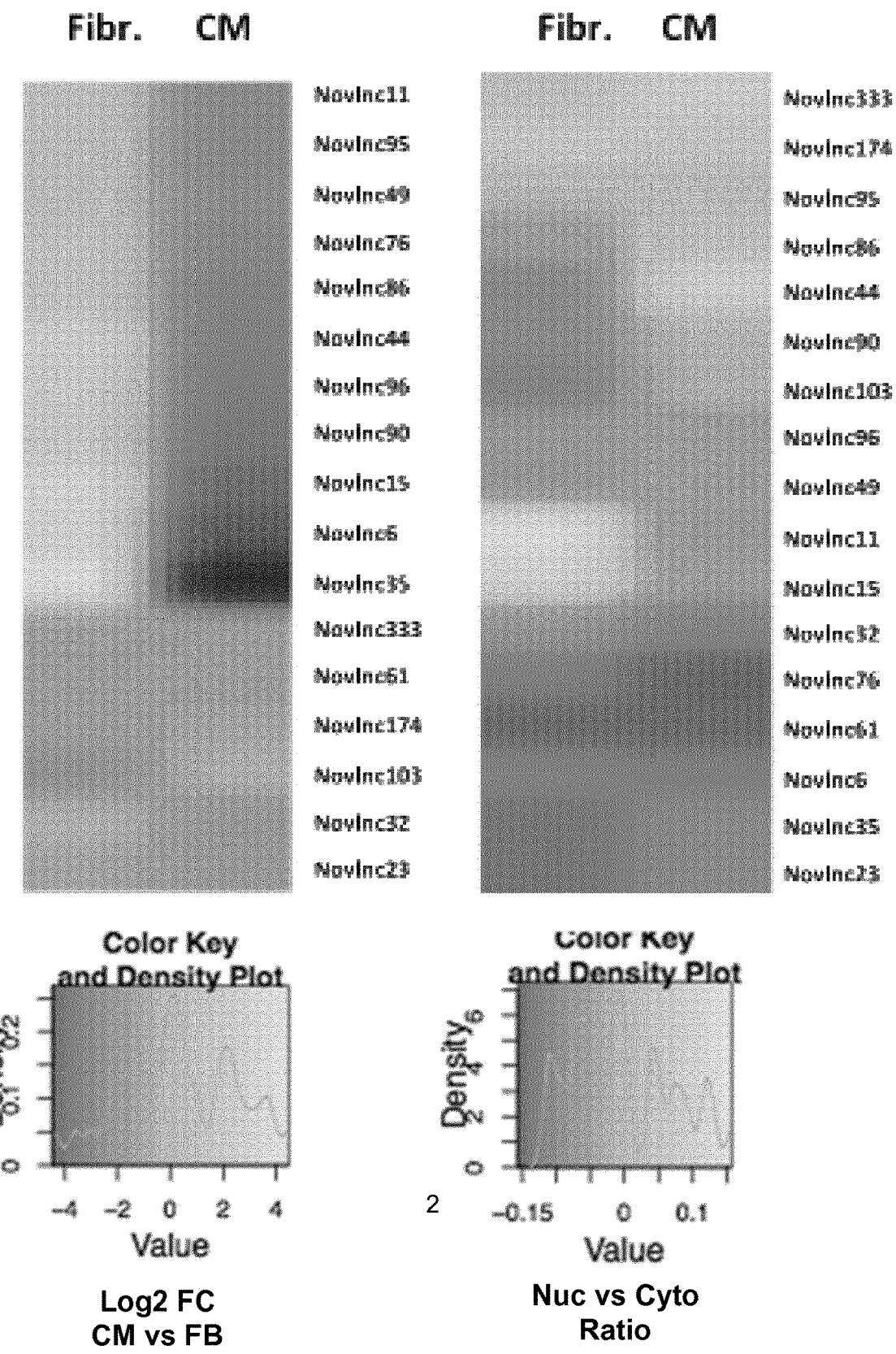

**033521 downregulation *in vitro***

Figure 5B *(cont'd)*
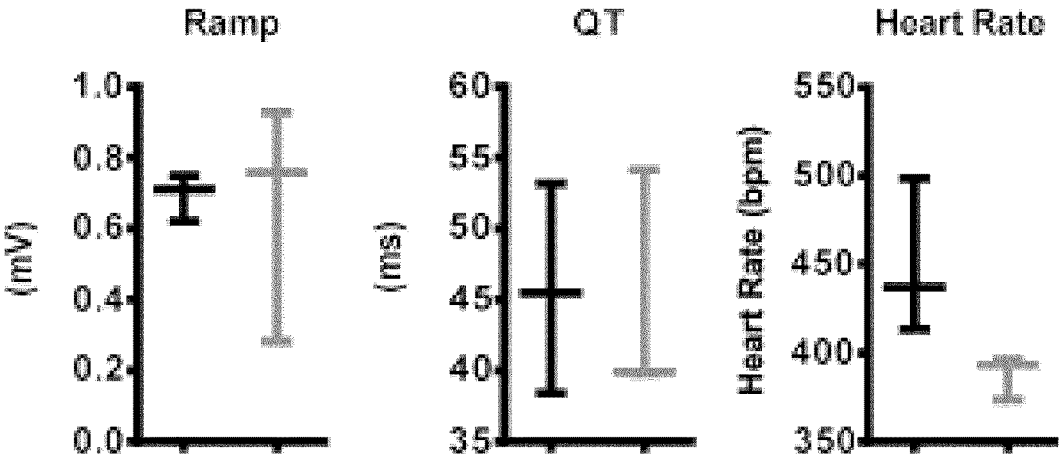
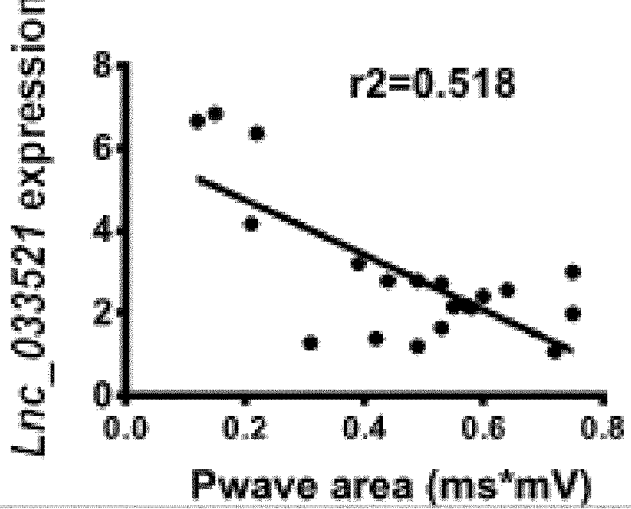
Scrambled GapmeR
Lnc_033521 GapmeR

DIAGNOSTIC, PROGNOSTIC AND THERAPEUTIC USES OF LONG NONCODING RNAS FOR HEART DISEASE AND REGENERATIVE MEDICINE

CROSS REFERENCE TO RELATED APPLICATIONS

This patent application is a continuation of U.S. patent application Ser. No. 15/105,319 filed on 16 Jun. 2016, now U.S. Pat. No. 11,193,171, which is a U.S. national stage filing under 35 U.S.C. § 371 of International Patent Application No. PCT/EP2014/078868 filed on 19 Dec. 2014, which claims the benefit of U.S. Provisional Patent Application No. 61/964,591 filed on 20 Dec. 2013. The entire disclosures of each of the above recited applications are incorporated herein by reference.

REFERENCE TO AN ELECTRONIC SEQUENCE LISTING

This application contains references to amino acid sequences and/or nucleic acid sequences which have been submitted concurrently herewith as the sequence listing text file "Sequence_Listing.txt," file size 528,492 Bytes (B), created on 19 Oct. 2021. The aforementioned sequence listing is hereby incorporated by reference in its entirety pursuant to 37 C.F.R. § 1.52(e)(5).

FIELD OF THE INVENTION

This invention generally relates to lncRNAs and methods for diagnosing cardiac pathologies in a subject. The invention also provides methods for treating a cardiac pathology in a subject comprising administering to said subject an effective amount of a modulator of one or more lncRNAs of the invention.

BACKGROUND OF THE INVENTION

The recent statistics on heart disease from the American Heart Association reports that one in nine death certificates in the United States mentioned heart failure as the cause of death in 2010. The burden of cardiovascular disease remains particularly high, with an overall rate of death attributable to cardiovascular disease of 235 per 100,000. Coronary artery disease is the most frequent cardiovascular disorder and typically leads to acute myocardial infarction and ultimately heart failure (HF). Despite continued advances, no approach currently exists to reverse the loss of functional myocardium, and HF is thus rapidly evolving into a major global epidemic requiring novel therapeutic approaches. In light of this, the elucidation of novel pathways and mechanisms involved in HF pathogenesis holds the promise of identifying new avenues and targets for this prevalent and deadly disease. In the adult heart, stress-dependant pathological hemodynamic and neurohormonal signals induce a maladaptive remodeling response, a process characterized by increased cardiomyocyte size (cellular hypertrophy), interstitial fibrosis and ultimately cellular dysfunction resulting in contractile and functional failure. At the molecular level, these signals activate a network of interacting cardiac signal transduction cascades that converge on a defined set of evolutionary conserved cardiac transcription factors (TFs). These core cardiac TFs (SRF, Nkx2.5, Mef2c, Gata4, TBox) interact in a combinatorial manner to elicit specific temporal and spatial gene expression programs. This integrated modulation of protein coding gene expression is ultimately responsible for cellular fate and is integral to the pathological remodeling process.

The notion of gene regulatory networks (GRNs) being primarily protein-based regulatory systems has been somewhat premature. A number of recent studies have demonstrated that GRN activity is under the control of a myriad of interleaved networks of non-coding RNAs (ncRNAs). Non-coding RNAs control every aspect of GRN activity including transcriptional control, post-transcriptional processing and epigenetic targeting (Ounzain et al., 2013). The best-characterized ncRNAs in the heart are the small microRNAs (miRNAs). Cardiovascular miRNAs adjust entire functional networks of mRNAs via post-transcriptional gene silencing, implicating miRNAs as important stress-dependant modulators. In addition to small ncRNAs, global transcriptional screens have identified other functional classes of transcripts, which are larger than 200 nucleotides, collectively known as long non-coding RNAs (lncRNAs). The functions of most lncRNAs remain unknown, however many have been shown to exert non-redundant roles in a diverse array of biological processes including X inactivation, imprinting, splicing and transcriptional regulation. In particular lncRNAs appear to be important for the global modulation of cell-specific epigenomic states via directing chromatin modification complexes to their sites of action. Furthermore, mammalian lncRNAs appear to be expressed in a highly cell-type and context-specific manner Considering the functionality of these transcripts, this raises the possibility that lncRNAs are an important class of regulatory mediators of cardiogenic lineage-specific developmental or specialized cellular functions. The majority of lncRNAs functionally characterized to date regulate developmental processes. However, their potential role controlling mature tissue homeostasis and adaptation to stress remains largely unexplored.

Identification of novel regulatory molecules and/or pathways that participate in the adaptation of the heart to stress is an important step towards the development of new therapeutic strategies aimed at preventing the progression to heart failure. Importantly, the hallmark of pathological remodeling in the adult heart is a global transcriptional reprogramming, resulting in the reactivation of a "fetal" cardiac gene program. The intrinsic-cis and -trans activating and epigenomic orchestrating properties of lncRNAs warrants the need to explore and generate catalogues of cardiac-specific lncRNAs in diseased adult tissues.

SUMMARY OF THE INVENTION

The Invention relates to a method for diagnosing a cardiac pathology in a subject, the method comprising: a) measuring the level of a plurality of biomarkers in a biological sample derived from the subject, wherein the plurality of biomarkers comprises one or more lncRNAs selected from the group comprising one or more lncRNAs selected from the group comprising SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ

3

ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99, SEQ ID No 100, SEQ ID No 101, SEQ ID No 102, SEQ ID No103, and SEQ ID No 104, fragments thereof, isoforms thereof and variants sharing at least 80% nucleotide sequence identity thereto; and b) analyzing the levels of the biomarkers, fragments thereof, isoforms thereof and variants sharing at least 80% nucleotide sequence identity thereto, in conjunction with respective reference value ranges for said plurality of biomarkers, wherein differential expression of one or more biomarkers in the biological sample compared to one or more biomarkers in a control sample from a normal subject indicates that the subject has a cardiac pathology.

A further object of the present invention is to provide a method for treating a cardiac pathology in a subject comprising administering to said subject an effective amount of a modulator of one or more lncRNAs of the invention, fragments thereof, isoforms thereof and variants sharing at least 80% nucleotide sequence identity thereto.

The invention also contemplates a composition comprising a modulator of one or more lncRNAs of the invention wherein wherein the modulator is selected from the group comprising a chemical agent, an antibody, an engineered protease, a CRISPR based technology and enzymatically active RNA.

A further object of the invention is to provide a method for modulating one or more lncRNAs of the invention wherein the modulator is selected from the group comprising a miRNA, a siRNA, a piRNA, a snRNA and an antisense oligonucleotide.

Another object of the invention is to provide a pharmaceutical composition comprising an effective amount of a modulator of one or more lncRNAs wherein the modulator is selected from the group comprising a chemical agent, an antibody, an engineered protease, and enzymatically active RNA, optionally in combination with pharmaceutically acceptable carriers, diluents and/or adjuvants.

Also comtemplated is a kit comprising the compositions of the invention.

Other objects of the invention concern a method for diagnosing a cardiac pathology in a subject, a method for monitoring the effects of a treatment on cardiac tissue in a subject, a method for monitoring the efficacy of surgical and/or pharmacological cardiac therapies in a subject, a method for measuring cardiac tissue regeneration in a subject, a method for monitoring in vitro cardiogenic cell differentiation, a method for monitoring in vivo cardiogenic cell differentiation, and a method for monitoring efficacy of agents and/or small molecules that can induce cardiac reprogramming.

The invention also concerns a microarray comprising a plurality of probes that hybridize to one or more lncRNAs of the invention, fragments thereof, isoforms thereof and variants sharing at least 80% nucleotide sequence identity thereto.

BRIEF DESCRIPTION OF THE FIGURES

FIG. 1A shows that mRNAs are highly clustered in their correlations with cardiac physiological traits and that such clusters are associated with genes implicated in expected processes. FIG. 1B shows that for specific traits, each cluster globally either correlates or does not correlate with each individual trait. FIG. 1C shows that novel lncRNAs are highly clustered in their correlations with physiological traits and that the closest coding genes to lncRNAs in each cluster are associated with specific biological processes. FIG. 1D shows that identified novel lncRNA clusters correlate specifically with individual physiological traits. FIG. 1E shows the heart specificity of mRNAs in clusters 1 to 4. FIG. 1F shows the heart specificity of novel lncRNAs in clusters 1 to 4.

FIGS. 2A-G show the validation and manipulation of selected novel lncRNAs in vivo and in vitro. FIG. 2B (left) shows the relative expression of candidate novel lncRNAs in isolated mouse cardiomyocytes and fibroblasts. FIG. 2C (right) shows the nuclear and cytoplasmic enrichment of candidate novel lncRNAs in cardiomyoctes and fibroblasts. FIG. 2D shows the correlation of candidate novel lncRNAs with physiological traits. FIG. 2E shows the expression of candidate lncRNAs in mouse embryonic stem cells undergoing cardiogenic differentiation. FIG. 2F shows the chromatin state patterns observed at novel lncRNA promoters during cardiogenic differentiation of mouse embryonic stem cells. FIG. 2G shows that modified antisense oligonucleotide mediated knock-down of specific novel lncRNA (Novlnc6) results in specific modulation of a key cardiac transcription factor, Nkx2-5 in isolated mouse cardiomyocytes.

FIG. 3A shows an example of a transmapped human lncRNA orthogous sequence (Novlnc6). FIG. 3B shows the expression of novel orthologous human lncRNAs in patients suffering with dilated cardiomyopathy (DCM) or aortic stenosis (AOS). FIG. 3C shows expression of validated cardiac biomarkers, ANF and Col1a2, in DCM and AOS patients. FIG. 3D shows ejection fraction percentage (EF %), wall thickness, left ventricular (LV) mass index, and end-diastolic dimension (EDD). FIG. 3E shows the relative expression of Hs Novlnc6, Hs Novlnc23, Hs Novlnc44, Nkx2.5, Nppa, and Col1a2.

FIG. 4A shows the relative expression of specific lncRNAs in isolated cardiomyocytes versus cardiac fibroblasts. FIG. 4B shows the relative expression of Lnc-019010 in fibroblasts derived form the heart, the lung and the tail. FIG. 4C shows the impact of Lnc-019010 loss-of-function using modified antisense oligonucleotides in cardiac fibroblasts on a panel of coding genes that control the fibrotic response. FIG. 4D shows the impact of Lnc-033521 loss-of-function on predicted target genes in isolated cardiomyocytes.

FIGS. 5A-B show in vivo LncRNAs downregulation in 12 weeks old BL6/C7 mice that received one intraperitoneal injection of GapmeR (20 mg/kg). FIG. 5A shows lnc-019010 loss-of-function impact on cardiac functional parameters as assessed by echocardiography in vivo. FIG. 5B shows lnc-033521 loss-of-function impact on cardiac conduction parameters as assessed by electrocardiogram in vivo.

DETAILED DESCRIPTION OF THE INVENTION

Figure 1A:
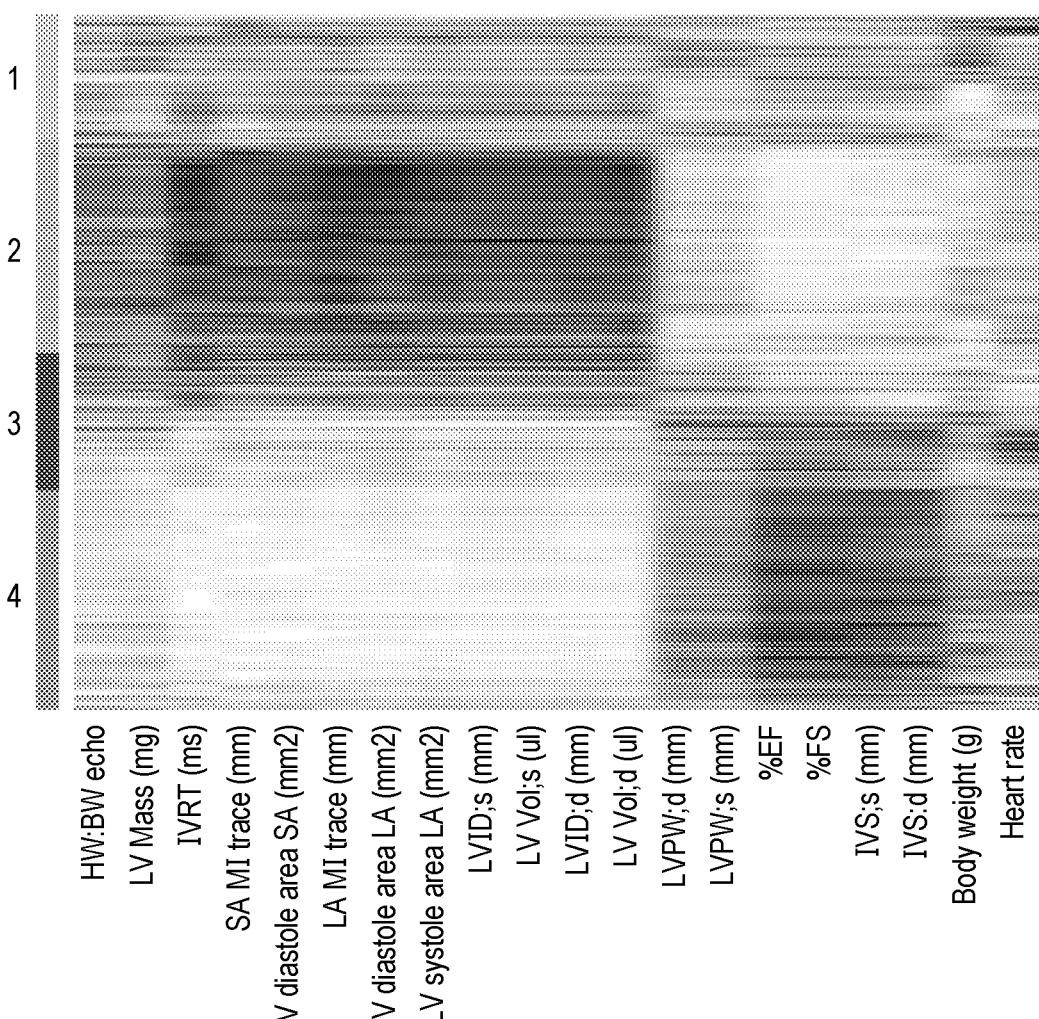
FIGS. 1A-F show that the cardiac coding and noncoding transcriptome is highly correlated with cardiac physiological traits.
Figure 1A:
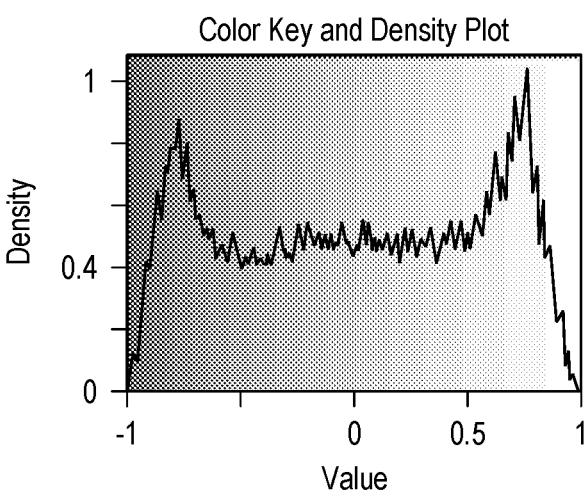

The Inventors set out to characterize the cardiac long non-coding transcriptome and in particular the dynamically modulated fraction post myocardial infarction. The Inventors coupled deep RNA-sequencing with ab initio transcript reconstruction, and integrated genome-wide data sets to systematically identify and annotate novel heart-specific lncRNAs.

Surprisingly, they showed that the lncRNAs of the invention are highly cardiac and context specific, correlating with cardiac physiology, suggesting a role as modulators of the pathological response and critical for physiological homeostasis. Using functional inference based on developmental chromatin state transitions, the Inventors functionally annotated these novel lncRNAs demonstrating that they are predominantly implicated with cardiac developmental, structural and functional gene programs. In particular, novel lncRNAs are predominantly associated with active enhancer states. The Inventors validated several novel lncRNAs in developmental and pathological models in vitro and in vivo and identified hundreds of predicted human orthologs and validated their expression in human samples. A number of these validated human orthologs were differentially expressed in human pathological cardiac states, supporting conserved roles in cardiac remodeling. Collectively, the Inventors have described a novel class of mammalian heart-specific lncRNAs with unique regulatory and functional characteristics, relevant to maladaptive pathological remodeling, cardiac function and potentially regeneration.

Accordingly, the present invention relates to a method for diagnosing a cardiac pathology in a subject, the method comprising:

a) measuring, directly or indirectly, the level of a plurality of biomarkers in a biological sample derived from the subject, wherein the plurality of biomarkers comprises one or more lncRNA having a cDNA sequence selected from the group comprising SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73. SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90. SEQ ID No 91, SEQ ID No 92, SEQ ID No 93, SEQ ID No 94, SEQ ID No 95, SEQ ID No 96, SEQ ID No 97, SEQ ID No 98, SEQ ID No 99, SEQ ID No 100, SEQ ID No 101, SEQ ID No 102, SEQ ID No103, and SEQ ID No 104, fragments thereof, isoforms thereof and variants sharing at least 80% nucleotide sequence identity thereto; and b) analyzing the levels of said biomarkers, fragments thereof, isoforms thereof and variants sharing at least 80% nucleotide sequence identity thereto, in conjunction with respective reference value ranges for said plurality of biomarkers, wherein differential expression of one or more biomarkers in the biological sample compared to one or more biomarkers in a control sample from a normal subject indicates that the subject has a cardiac pathology.

Preferably, the biological sample derived from the subject is selected from the group comprising whole blood, serum, plasma, semen, saliva, tears, urine, fecal material, sweat, buccal smears, skin, cardiac tissue, liver, brain tissue, amniotic fluid, nerve tissue and hair. More preferably, the biological sample is cardiac tissue.

Usually, the cardiac pathology is selected from the group comprising Interventricular Septal Thickness (IVS), heart failure, EF, LVID, MI, HFrEF, viral myocarditis, brachycardia, arrhythmia, congenital heart defects, diabetic cardiomyopathy, idiopathic and dilated cardiomyopathy, pathologies characterized by malformation such as congenital heart disease and inherited heart disease; by tissue remodeling such as hypertrophic cardiomyopathies, dilated cardiomyopathies, hypertensive cardiomyopathies, ischemic heart disease, coronary heart disease, myocardial infarction and cardiac fibrosis; by affected function such as systolic dysfunction, diastolic dysfunction, heart failure with reduced ejection fraction and heart failure with preserved ejection fraction; by disorders of the right heart such as right ventricular heart failure, pulmonary hypertension and pulmonary embolism; by arrhythmias such as cardiac arrhythmias, fibrillation, channelopathies, syncope and sudden death; by valvular dysfunction such as valvular heart disease, valvular stenosis and valvular regurgitation; by inflammation such as viral, bacterial, protozoal and metazoal infection of the heart, myocarditis, pericarditis, endocarditis, cardiac disease associated to HIV infection, Chagas' disease and restrictive infiltrative cardiomyopathies; by intoxication such as toxin-induced cardiac disease, drug-induced cardiac disease, alcohol-induced cardiac disease, pharmaceutical-induced cardiac disease, chemical-induced cardiac disease, cardiac disease following exposure to heavy metals and cardiac complications of anti-cancer therapies; by cancer such as neoplastic infiltrative cardiomyopathies, carcinoid heart disease and primary tumors of the heart; by neurologic disorders such as muscular dystrophies; by autonomic disorders; by emotional stress such as cardiac disease associated to acute and chronic psychological stress; by metabolic disease such as diabetic cardiomyopathy, heart disease associated to endocrine disorders and mitochondrial disorders; by trauma such as traumatic heart disease, consequences of cardiac surgery and angioplasty; by a change in hemodynamic such as renal disease, thrombosis and rheumatic disease. Most preferably, the heart failure is heart failure with preserved or reduced ejection fraction.

The present invention also relates to a method for treating a cardiac pathology in a subject comprising administering to said subject an effective amount of a modulator of one or more lncRNAs having a cDNA sequence selected from the group comprising SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17. SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99, SEQ ID No 100, SEQ ID No 101, SEQ ID No 102, SEQ ID No103, and SEQ ID No 104, fragments thereof, isoforms thereof and variants sharing at least 80% nucleotide sequence identity thereto.

Usually, the modulator of one or more lncRNAs is selected from the group comprising a chemical agent, a RNA mimic, an antibody, an engineered protease, a CRISPR based technology and enzymatically active RNA.

Most preferably, the enzymatically active RNA is selected from the group comprising a miRNA, a siRNA, a piRNA, a hnRNA, a snRNA, esiRNA, shRNA, decoys, RNA aptamers and an antisense oligonucleotide. One will appreciate that any compound with different formulations capable to inhibit one or more physiological actions effected by lncRNA is encompassed by the present invention.

The siRNA of the invention may, e.g., comprise a nucleotide sequence as set forth in SEQ ID No 105, fragments thereof, isoforms thereof and variants sharing at least 80% nucleotide sequence identity thereto.

Another aspect of the present invention relates to a composition comprising a modulator of one or more lncRNAs wherein the modulator is selected from the group comprising a chemical agent, an antibody, an engineered protease, and enzymatically active RNA.

A method for modulating one or more lncRNAs wherein the modulator is selected from the group comprising the modulator of one or more lncRNAs is selected from the group comprising a chemical agent, a RNA mimic, an antibody, an engineered protease, and enzymatically active RNA is also part of the invention.

Preferably, the modulator modulates cardiac fibrosis, myopathy, hypertrophy, apoptosis, inflammation, extracellular remodeling, cardiac regeneration, CM and CF cell cycle and activation of endogenous CPCs, direct reprogramming of CF, ECs, in vitro reprogramming and differention of cell types for generation of cardiac cells for cell therapy, Cardiac epigenomic targeting of ubiquitous chromatin remodeling complexes, cardiac physiology and heart rate.

A further aspect of the present invention relates to a pharmaceutical composition comprising an effective amount of a modulator of one or more lncRNAs wherein the modulator is selected from the group comprising the modulator of one or more lncRNAs is selected from the group comprising a chemical agent, a RNA mimic, an antibody, an engineered protease, and enzymatically active RNA, optionally in combination with pharmaceutically acceptable carriers, diluents and/or adjuvants.

Another aspect of the invention relates to a kit comprising i) a composition comprising a modulator of one or more lncRNAs wherein the modulator is selected from the group comprising a chemical agent, a RNA mimic, an antibody, an engineered protease, and enzymatically active RNA or ii) a pharmaceutical composition comprising an effective amount of a modulator of one or more lncRNAs wherein the modulator is selected from the group comprising the modulator of one or more lncRNAs is selected from the group comprising a chemical agent, a RNA mimic, an antibody, an engineered protease, and enzymatically active RNA, optionally in combination with pharmaceutically acceptable carriers, diluents and/or adjuvants.

Also encompassed in the present invention is a method for diagnosing a cardiac pathology in a subject, the method comprising:

a) measuring, directly or indirectly, the level of a plurality of biomarkers in a biological sample derived from the subject, wherein the plurality of biomarkers comprises one or more lncRNAs selected from the group comprising SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22. SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69. SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99, SEQ ID No 100, SEQ ID No 101, SEQ ID No 102, SEQ ID No103, and SEQ ID No 104, fragments thereof, isoforms thereof and variants sharing at least 80% nucleotide sequence identity thereto; and b) analyzing the levels of said biomarkers, fragments thereof, isoforms thereof and variants sharing at least 80% nucleotide sequence identity thereto, in conjunction with respective reference value ranges for said plurality of biomarkers, wherein differential expression of one or more biomarkers in the biological sample compared to one or more biomarkers in a control sample from a normal subject indicates that the subject has a cardiac pathology and/or a cardiac pathology thereby alleviating the need to execute echocardiography.

This invention also concerns a method for monitoring the effects of a treatment on cardiac tissue in a subject, the method comprising:

a) measuring, directly or indirectly, the level of a plurality of biomarkers in a biological sample derived from the subject, wherein the plurality of biomarkers comprises one or more lncRNAs selected from the group comprising SEQ ID No 1, SEQ ID No 2, SEQ ID No 3, SEQ ID No 4, SEQ ID No 5, SEQ ID No 6, SEQ ID No 7, SEQ ID No 8, SEQ ID No 9. SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99, SEQ ID No 100, SEQ ID No 101, SEQ ID No 102, SEQ ID No103, and SEQ ID No 104, fragments thereof, isoforms thereof and variants sharing at least 80% nucleotide sequence identity thereto; and b) analyzing the levels of said biomarkers, fragments thereof, isoforms thereof and variants sharing at least 80% nucleotide sequence identity thereto, in conjunction with respective reference value ranges for said plurality of biomarkers, wherein differential expression of one or more biomarkers in the biological sample compared to one or more biomarkers in a control sample from a normal subject gives an indication on the effects of a treatment on cardiac tissue.

Further encompassed is a method for monitoring the efficacy of surgical and/or pharmacological cardiac therapies in a subject, the method comprising:

a) measuring, directly or indirectly, the level of a plurality of biomarkers in a biological sample derived from the subject, wherein the plurality of biomarkers comprises one or more lncRNAs selected from the group comprising SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99, SEQ ID No 100, SEQ ID No 101, SEQ ID No 102, SEQ ID No103, and SEQ ID No 104, fragments thereof, isoforms thereof and variants sharing at least 80% nucleotide sequence identity thereto; and b) analyzing the levels of said biomarkers, fragments thereof, isoforms thereof and variants sharing at least 80% nucleotide sequence identity thereto, in conjunction with respective reference value ranges for said plurality of biomarkers, wherein differential expression of one or more biomarkers in the biological sample compared to one or more biomarkers in a control sample from a normal subject gives an indication on the efficacy of surgical and/or pharmacological cardiac therapies.

Also comprised in the present invention is a method for measuring cardiac tissue regeneration in a subject, the method comprising: a) measuring, directly or indirectly, the level of a plurality of biomarkers in a biological sample derived from the subject, wherein the plurality of biomarkers comprises one or more lncRNAs selected from the group comprising SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99, SEQ ID No 100, SEQ ID No 101, SEQ ID No 102, SEQ ID No103, and SEQ ID No 104, fragments thereof, isoforms thereof and variants sharing at least 80% nucleotide sequence identity thereto; and b) analyzing the levels of said biomarkers, fragments thereof, isoforms thereof and variants sharing at least 80% nucleotide sequence identity thereto, in conjunction with respective reference value ranges for said plurality of biomarkers, wherein differential expression of one or more biomarkers in the biological sample compared to one or more biomarkers in a control sample from a normal subject gives an indication on cardiac tissue regeneration.

The present invention also comprises a method for monitoring in vitro cardiogenic cell differentiation, the method comprising:

a) measuring, directly or indirectly, the level of a plurality of biomarkers in a biological sample derived from a cell in culture, wherein the plurality of biomarkers comprises one or more lncRNAs selected from the group comprising SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID) No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99, SEQ ID No 100, SEQ ID No 101, SEQ ID No 102, SEQ ID No103, and SEQ ID No 104, fragments thereof, isoforms thereof and variants sharing at least 80% nucleotide sequence identity thereto; and b) analyzing the levels of said biomarkers, fragments thereof, isoforms thereof and variants sharing at least 80% nucleotide sequence identity thereto, in conjunction with respective reference value ranges for said plurality of biomarkers, wherein differential expression of one or more biomarkers in the biological sample compared to one or more biomarkers in a control sample from a normal subject gives an indication on cardiogenic cell differentiation.

Another aspect of the invention concerns a method for monitoring in vitro cardiogenic cell differentiation, the method comprising:

a) measuring, directly or indirectly, the level of a plurality of biomarkers in a biological sample derived from a cell in culture, wherein the plurality of biomarkers comprises one or more lncRNAs selected from the group comprising SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99, SEQ ID No 100, SEQ ID No 101, SEQ ID No 102. SEQ ID No103, and SEQ ID No 104, fragments thereof, isoforms thereof and variants sharing at least 80% nucleotide sequence identity thereto; and b) analyzing the levels of said biomarkers, fragments thereof, isoforms thereof and variants sharing at least 80% nucleotide sequence identity thereto, in conjunction with respective reference value ranges for said plurality of biomarkers, wherein differential expression of one or more biomarkers in the biological sample compared to one or more biomarkers in a control sample from a normal subject gives an indication on cardiogenic cell differentiation.

Another aspect of the invention concerns a method for monitoring efficacy of agents and/or small molecules that can induce cell reprogramming, the method comprising:

a) measuring, directly or indirectly, the level of a plurality of biomarkers in a biological sample derived from a subject or a cell in culture, wherein the plurality of biomarkers comprises one or more lncRNAs selected from the group comprising SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96. SEQ ID No 97, SEQ ID No 98, SEQ ID No 99. SEQ ID No 100, SEQ ID No 101, SEQ ID No 102, SEQ ID No103, and SEQ ID No 104, fragments thereof, isoforms thereof and variants sharing at least 80% nucleotide sequence identity thereto; and b) analyzing the levels of said biomarkers, fragments thereof, isoforms thereof and variants sharing at least 80% nucleotide sequence identity thereto, in conjunction with respective reference value ranges for said plurality of biomarkers, wherein differential expression of one or more biomarkers in the biological sample compared to one or more biomarkers in a control sample from a normal subject gives an indication on efficacy of agents and/or small molecules that can induce cardiac reprogramming.

Another aspect of the invention concerns a microarray comprising a plurality of probes that hybridize to one or more lncRNAs selected from the group comprising SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99, SEQ ID No 100, SEQ ID No 101, SEQ ID No 102, SEQ ID No103, and SEQ ID No 104, fragments thereof, isoforms thereof and variants sharing at least 80% nucleotide sequence identity thereto.

In describing the present invention, the following terms will be employed, and are intended to be defined as indicated below.

It must be noted that, as used in this specification and the appended claims, the singular forms "a," "an" and "the" include plural referents unless the content clearly dictates otherwise. Thus, for example, reference to "a lncRNA" includes a mixture of two or more lncRNAs, and the like.

The term "about," particularly in reference to a given quantity, is meant to encompass deviations of plus or minus ten percent.

The terms "microRNA," "miRNA," and MiR" are interchangeable and refer to endogenous or artificial non-coding RNAs that are capable of regulating gene expression. It is believed that miRNAs function via RNA interference. The terms "siRNA" and "short interfering RNA" are interchangeable and refer to single-stranded or double-stranded RNA molecules that are capable of inducing RNA interference. SiRNA molecules typically have a duplex region that is between 18 and 30 base pairs in length.

The terms "piRNA" and "Piwi-interacting RNA" are interchangeable and refer to a class of small RNAs involved in gene silencing. PiRNA molecules typically are between 26 and 31 nucleotides in length.

The terms "snRNA" and "small nuclear RNA" are interchangeable and refer to a class of small RNAs involved in a variety of processes including RNA splicing and regulation of transcription factors. The subclass of small nucleolar RNAs (snoRNAs) is also included. The term is also intended to include artificial snRNAs, such as antisense derivatives of snRNAs comprising antisense sequences directed against one or more lncRNAs.

The terms "polynucleotide." "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms will be used interchangeably. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, microRNA, DNA:RNA hybrids, and hybrids between PNAs and DNA or RNA, and also include known types of modifications, for example, labels which are known in the art, methylation, "caps," substitution of one or more of the naturally occurring nucleotides with an analog (e.g., 2-ami-noadenosine, 2-thiothymidine, inosine, pyrrolo-pyrimidine, 3-methyl adenosine, C5-propynylcytidine, C5-propynyluri-dine, C5-bromouridine, C5-fluorouridine, C5-iodouridine, C5-methylcytidine, 7-deazaadenosine, 7-deazaguanosine, 8-oxoadenosine, 8-oxoguanosine, O (6)-methylguanine, and 2-thiocytidine), internucleotide modifications such as, for example, those with uncharged linkages (e.g., methyl phos-phonates, phosphotriesters, phosphoramidates, carbamates, etc.), with negatively charged linkages (e.g., phosphoroth-ioates, phosphorodithioates, etc.), and with positively charged linkages (e.g., aminoalklyphosphoramidates, ami-noalkylphosphotriesters), those containing pendant moi-eties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. The term also includes locked nucleic acids (e.g., comprising a ribonucleotide that has a methylene bridge between the 2'-oxygen atom and the 4'-carbon atom). See, for example, Kurreck et al. (2002) Nucleic Acids Res. 30:1911-1918.

The term "complementary" and "complementarity" are interchangeable and refer to the ability of polynucleotides to form base pairs with one another. Base pairs are typically formed by hydrogen bonds between nucleotide units in antiparallel polynucleotide strands or regions. Complemen-tary polynucleotide strands or regions can base pair in the Watson-Crick manner (e.g., A to T, A to U, C to G). 100% complementary refers to the situation in which each nucleo-tide unit of one polynucleotide strand or region can hydro-gen bond with each nucleotide unit of a second polynucle-otide strand or region. Less than perfect complementarity refers to the situation in which some, but not all, nucleotide units of two strands or two regions can hydrogen bond with each other and can be expressed as a percentage.

"Administering", as it applies in the present invention, refers to contact of an effective amount of a modulator of one or more lncRNAs of the invention, to the subject.

Administering a nucleic acid, such as a microRNA, siRNA, piRNA, snRNA, antisense nucleic acid, or lncRNA to a cell comprises transducing, transfecting, electroporat-ing, translocating, fusing, phagocytosing, shooting or bal-listic methods, etc., i.e., any means by which a nucleic acid can be transported across a cell membrane.

"Pharmaceutically acceptable excipient or carrier" refers to an excipient that may optionally be included in the compositions of the invention and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corre-sponding inorganic acid form of any of the preceding, e.g., hydrochloride, etc., or salts prepared with an organic acid, such as malate, maleate, fumarate, tartrate, succinate, eth-ylsuccinate, citrate, acetate, lactate, methanesulfonate, ben-zoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including sub-stituted ammonium).

An "effective amount" of modulator of one or more lncRNAs of the invention (e.g., microRNA, siRNA, piRNA, snRNA, antisense nucleic acid, ribozyme, or small molecule inhibitor, CRISPRs etc) is an amount sufficient to effect beneficial or desired results, such as an amount that inhibits the activity of a lncRNA, for example by interfering with transcription. An effective amount can be administered in one or more administrations, applications, or dosages.

By "therapeutically effective dose or amount" of a modu-lator of one or more lncRNAs of the invention is intended an amount that, when administered as described herein, brings about a positive therapeutic response. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information pro-vided herein.

"Homology" refers to the percent identity between two polynucleotide or two polypeptide moieties. Two nucleic acid, or two polypeptide sequences are "substantially homologous" to each other when the sequences exhibit at least about 50% sequence identity, preferably at least about 75% sequence identity, more preferably at least about 80%-85% sequence identity, more preferably at least about 90% sequence identity, and most preferably at least about 95%-98% sequence identity over a defined length of the mol-ecules. As used herein, substantially homologous also refers to sequences showing complete identity to the specified sequence.

In general, "identity" refers to an exact nucleotide to nucleotide or amino acid to amino acid correspondence of two polynucleotides or polypeptide sequences, respectively. Percent identity can be determined by a direct comparison of the sequence information between two molecules by align-ing the sequences, counting the exact number of matches between the two aligned sequences, dividing by the length of the shorter sequence, and multiplying the result by 100.

Alternatively, homology can be determined by readily available computer programs or by hybridization of poly-nucleotides under conditions which form stable duplexes between homologous regions, followed by digestion with single stranded specific nuclease(s), and size determination of the digested fragments. DNA sequences that are substan-tially homologous can be identified in a Southern hybrid-ization experiment under, for example, stringent conditions, as defined for that particular system. Defining appropriate hybridization conditions is within the skill of the art.

"Recombinant" as used herein to describe a nucleic acid molecule means a polynucleotide of genomic, cDNA, viral, semisynthetic, or synthetic origin which, by virtue of its origin or manipulation, is not associated with all or a portion of the polynucleotide with which it is associated in nature. The term "recombinant" as used with respect to a protein or polypeptide means a polypeptide produced by expression of a recombinant polynucleotide. In general, the gene of inter-est is cloned and then expressed in transformed organisms, as described further below. The host organism expresses the foreign gene to produce the protein under expression con-ditions.

The term "transformation" refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome.

"Recombinant host cells", "host cells," "cells", "cell lines," "cell cultures", and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

"Purified polynucleotide" refers to a polynucleotide of interest or fragment thereof which is essentially free, e.g., contains less than about 50%, preferably less than about 70%, and more preferably less than about at least 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences to target cells. Thus, the term includes cloning and expression vehicles, as well as viral vectors.

The terms "variant" refers to biologically active derivatives of a biomarker, i.e. one or more lncRNAs. In general, the term "variant" refers to molecules having a native sequence and structure with one or more additions, substitutions (generally conservative in nature) and/or deletions, relative to the native molecule, so long as the modifications do not destroy biological activity and which are "substantially homologous" to the reference molecule. In general, the sequences of such variants will have a high degree of sequence homology to the reference sequence, e.g., sequence homology of more than 50%, generally more than 60%-70%, even more particularly 80%-85% or more, such as at least 90%-95% or more, when the two sequences are aligned.

Alternatively, the term "variant" also refers to posttranscriptionaly modified lncRNAs of the invention, i.e methylation, phosphorylation, etc.

A "biomarker" in the context of the present invention refers to an lncRNA which is differentially expressed in a biological sample (e.g., a biopsy taken from a subject having a cardiac pathology or a cardiac tissue undergoing regeneration or a stem cell undergoing cardiac differentiation or a cardiac tissue undergoing surgical and/or pharmacological therapies) as compared to a control sample (e.g., a comparable sample taken from a person with a negative diagnosis, a normal or healthy subject, or normal, untreated tissue or cells). The biomarker can be an lncRNA that can be detected and/or quantified.

One will appreciate that the control sample can vary depending on the situation. For example, the control sample can include a cell or sample of cells that provide a reference expression level of the same gene. Alternatively, the control sample can be healthy cells from the same source tissue as the target cell(s).

As used herein, an "isoform" of an lncRNA results from alternative splicing of the gene encoding said lncRNA.

As used herein, a "fragment" one or more lncRNAs refers to a sequence containing less amino acids in length than the respective one or more lncRNA. Preferably, this sequence contains less than 90%, preferably less than 60%, in particular less than 30% amino acids in length than the respective one or more lncRNA.

Biomarkers are one or more lncRNAs selected from the group comprising the cDNA sequences: SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, and SEQ ID No 95, SEQ ID No 96, SEQ ID No 97, SEQ ID No 98, SEQ ID No 99, SEQ ID No 100, SEQ ID No 101, SEQ ID No 102, SEQ ID No103, and SEQ ID No 104, fragments thereof, isoforms thereof and variants sharing at least 80% nucleotide sequence identity thereto. Most preferably, the one or more lncRNAs is selected from the group comprising the cDNA sequences SEQ ID No 25, SEQ ID No 28, SEQ ID No 48, SEQ ID No 52, SEQ ID No 53, SEQ ID No 82, SEQ ID No 84, SEQ ID No 88, SEQ ID No 96, SEQ ID No 97, SEQ ID No 98, SEQ ID No 99, SEQ ID No 100, SEQ ID No 101, SEQ ID No 103, and SEQ ID No 104, fragments thereof, isoforms thereof and variants sharing at least 80% nucleotide sequence identity thereto.

TABLE 1

| XLOC_ID | SEQ ID No. | Physiology Cluster | Lnc |
|---|---|---|---|
| XLOC_007900 | 1 | 1 | Lnc7900 |
| XLOC_008052 | 2 | 1 | Lnc8052 |
| XLOC_006224 | 3 | 1 | Lnc6224 |
| XLOC_013471 | 4 | 1 | Lnc13471 |
| XLOC_002075 | 5 | 1 | Lnc2075 |
| XLOC_023749 | 6 | 1 | Lnc23749 |
| XLOC_008063 | 7 | 1 | Lnc8063 |
| XLOC_024203 | 8 | 1 | Lnc24203 |
| XLOC_019889 | 9 | 1 | Lnc19889 |
| XLOC_008229 | 10 | 1 | Lnc8229 |
| XLOC_014116 | 11 | 1 | Lnc14116/NovInc11 |
| XLOC_003166 | 12 | 1 | Lnc3166 |
| XLOC_010335 | 13 | 1 | Lnc10335 |
| XLOC_021863 | 14 | 1 | Lnc21863 |
| XLOC_012367 | 15 | 1 | Lnc12367 |
| XLOC_007833 | 16 | 1 | Lnc7833 |
| XLOC_023850 | 17 | 2 | Lnc23850 |
| XLOC_029624 | 18 | 2 | Lnc-TEAD1 |

TABLE 1-continued

| XLOC_ID | SEQ ID No. | Physiology Cluster | Lnc |
|---|---|---|---|
| XLOC_022865 | 19 | 2 | Lnc-SE-22865 |
| XLOC_018239 | 20 | 2 | Lnc18239 |
| XLOC_022715 | 21 | 2 | Lnc-COL16A1 |
| XLOC_013413 | 22 | 2 | Lnc13413 |
| XLOC_005390 | 23 | 2 | Lnc-MEOX1 |
| XLOC_010961 | 24 | 2 | Lnc-WISP1 |
| XLOC_000709 | 25 | 2 | Lnc-TGFB2/NovInc11 |
| XLOC_013407 | 26 | 2 | Lnc-SLC8A1 |
| XLOC_020214 | 27 | 2 | Lnc-CYR61 |
| XLOC_012723 | 28 | 2 | Lnc-SE-12723/NovInc174 |
| XLOC_022262 | 29 | 2 | Lnc22262 |
| XLOC_000719 | 30 | 2 | Lnc00719 |
| XLOC_004951 | 31 | 2 | Lnc4951 |
| XLOC_026589 | 32 | 2 | Lnc26589 |
| XLOC_019010 | 33 | 2 | Lnc19010 |
| XLOC_022236 | 34 | 2 | Lnc22236 |
| XLOC_011236 | 35 | 3 | Lnc-SLC38A2 |
| XLOC_012015 | 36 | 3 | Lnc-KCNJ6 |
| XLOC_012884 | 37 | 3 | Lnc-NKX2.5 |
| XLOC_004797 | 38 | 3 | Lnc4797 |
| XLOC_003851 | 39 | 3 | Lnc-SPNB2 |
| XLOC_011237 | 40 | 3 | Lnc-SLC38A2 |
| XLOC_014898 | 41 | 3 | Lnc-SE-14989 |
| XLOC_030839 | 42 | 3 | Lnc-CDH13 |
| XLOC_012194 | 43 | 3 | Lnc-ACAP2 |
| XLOC_031308 | 44 | 3 | Lnc-IRX3 |
| XLOC_026621 | 45 | 3 | Lnc-ATOH8 |
| XLOC_002721 | 46 | 3 | Lnc-TXLNB |
| XLOC_003170 | 47 | 3 | Lnc-KITLG |
| XLOC_002849 | 48 | 4 | Lnc-NovInc6 |
| XLOC_016279 | 49 | 4 | Lnc-NovInc25 |
| XLOC_024141 | 50 | 4 | Lnc-CARD11 |
| XLOC_021524 | 51 | 4 | Lnc-NFIB |
| XLOC_021715 | 52 | 4 | Lnc-FOXO6 |
| XLOC_020321 | 53 | 4 | Lnc-ANX5A |
| XLOC_006274 | 54 | 4 | Lnc-MAX |
| XLOC_021416 | 55 | 4 | Lnc21416 |
| XLOC_003767 | 56 | 4 | Lnc-LIF |
| XLOC_014118 | 57 | 4 | Lnc-LCLAT1 |
| XLOC_004833 | 58 | 4 | Lnc4833 |
| XLOC_009582 | 59 | 4 | Lnc-PPIF |
| XLOC_024449 | 60 | 4 | Lnc24449 |
| XLOC_006146 | 61 | 4 | Lnc6146 |
| XLOC_033521 | 62 | 4 | Lnc-Dedbt (Lnc033521) |
| XLOC_025643 | 63 | 4 | Lnc25643 |
| XLOC_004910 | 64 | 4 | Lnc-SPARC |
| XLOC_010967 | 65 | 4 | Lnc-miR30b |
| XLOC_002503 | 66 | 4 | Lnc-SOCS2 |
| XLOC_017764 | 67 | 4 | Lnc-ID1 |
| XLOC_020119 | 68 | 4 | Lnc20119 |
| XLOC_001065 | 69 | 4 | Lnc-GPC1 |
| XLOC_009131 | 70 | 4 | Lnc-OTX2 |
| XLOC_000264 | 71 | 4 | Lnc-FAM124B |
| XLOC_032325 | 72 | 4 | Lnc-TALIN1 |
| XLOC_002546 | 73 | 4 | Lnc-KRR1 |
| XLOC_006241 | 74 | 4 | Lnc-DACT1 |
| XLOC_029781 | 75 | 4 | Lnc29781 |
| XLOC_030722 | 76 | 4 | Lnc-SE-30722 |
| XLOC_032031 | 77 | 4 | Lnc-KCNJ |
| XLOC_020634 | 78 | 4 | Lnc-SE-20634 |
| XLOC_031524 | 79 | 4 | Lnc-IRF2BP2 |
| XLOC_020212 | 80 | 4 | Lnc-CYR61 |
| XLOC_000336 | 81 | 4 | Lnc-HDAC4 |
| XLOC_015960 | 82 | 4 | Lnc-ITPRIP |
| XLOC_004067 | 83 | 4 | Lnc-MYOCD |
| XLOC_015277 | 84 | 4 | Lnc-SMAD7/NovInc23 |
| XLOC_020313 | 85 | 4 | Lnc20313 |
| XLOC_008190 | 86 | 4 | Lnc8190 |
| XLOC_033125 | 87 | 4 | Lnc33125 |
| XLOC_032788 | 88 | 4 | Lnc32788/NovInc90 |
| XLOC_014917 | 89 | 4 | Lnc14917 |
| XLOC_014935 | 90 | 4 | Lnc14935 |
| XLOC_007419 | 91 | 4 | Lnc7419 |
| XLOC_006561 | 92 | 4 | Lnc6561 |
| XLOC_024370 | 93 | 4 | Lnc24370 |
| XLOC_006255 | 94 | 4 | Lnc6255 |

TABLE 1-continued

| XLOC_ID | SEQ ID No. | Physiology Cluster | Lnc |
|---|---|---|---|
| XLOC_029637 | 95 | 4 | Lnc29637 |
| XLOC_010855 | 96 | 2 | Lnc10855 |
| XLOC_007852 | 97 | 4 | Lnc7852/NovInc15 |
| XLOC_009335 | 98 | 4 | Lnc9335/NovInc32 |
| XLOC_019782 | 99 | 2 | Lnc19782/NovInc35 |
| XLOC_010735 | 100 | 4 | Lnc10735/NovInc44 |
| XLOC_007917 | 101 | 4 | Lnc7917/NovInc61 |
| XLOC_033357 | 102 | 4 | Lnc33357 |
| XLOC_023848 | 103 | 4 | Lnc23848/NovInc49 |
| XLOC_016979 | 104 | 4 | Lnc16979 |

Figure 1B:
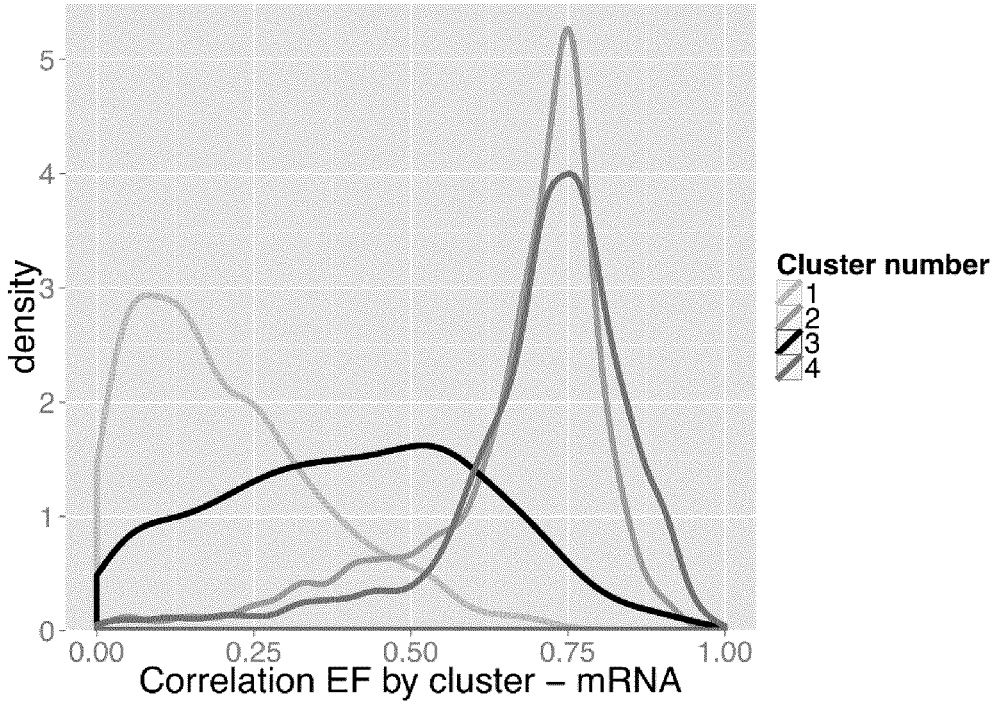
Figure 1B:
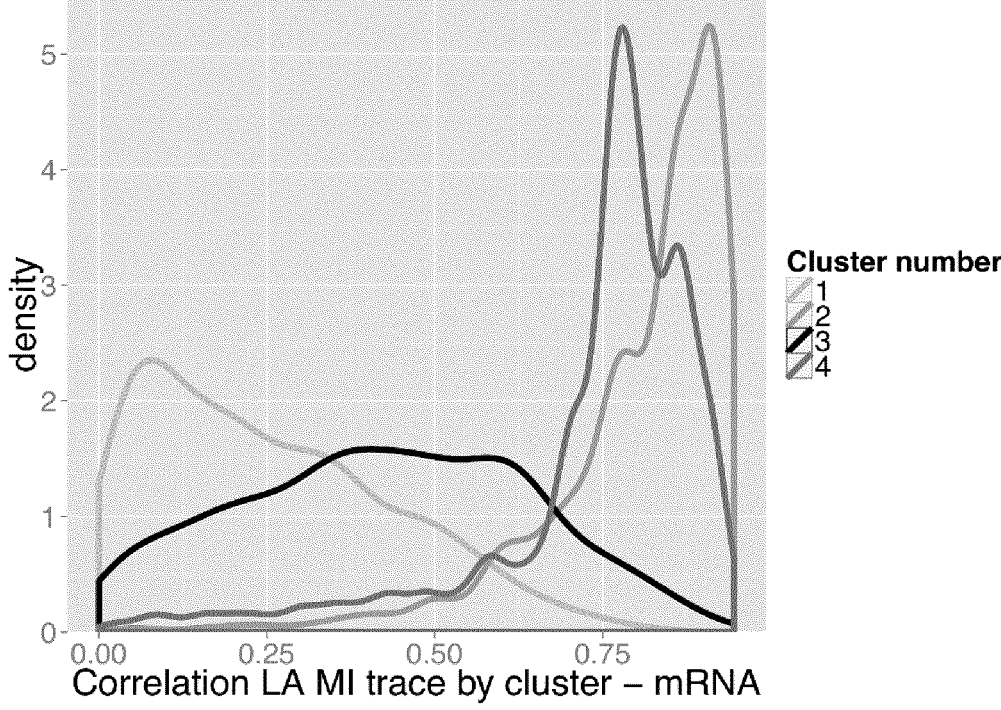
Figure 1C:
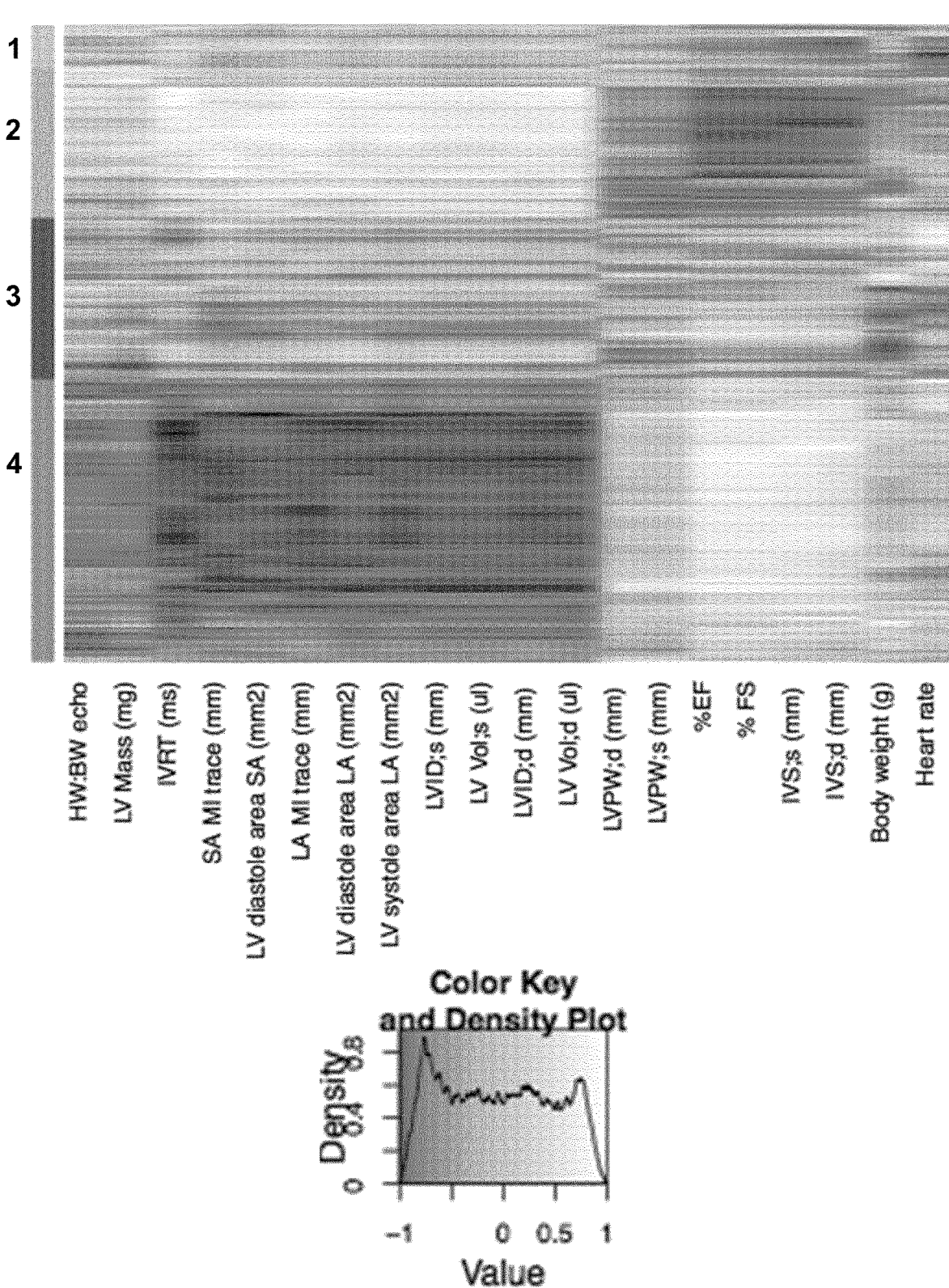

Within the identified transcripts, the Inventors identified four clusters for both coding (FIG. 1A) and novel lncRNA (FIG. 1B) transcripts. In each case, these consisted of one cluster that correlated positively with cardiac function and negatively with remodeling parameters, one cluster with the inverse of these correlations and two clusters with non-specific intermediate correlations. Gene ontology (GO) and heart specificity analysis was executed on individual clusters with GO analysis being executed on the most proximal coding genes with respect to novel lncRNAs. In the coding gene group, the most heart-specific cluster was Cluster 2 (FIG. 1E), which was positively correlated with cardiac functional traits and associated with genes involved in mitochondrial biology (FIG. 1A). The least heart-specific cluster (Cluster 4) was positively correlated with remodeling and associated with genes involved in wound healing and extracellular matrix (FIG. 1A). Within novel lncRNAs, and in particular within the 104 lncRNAs of Table 1, the most heart-specific cluster, i.e. Cluster 4 (FIG. 1F), was again positively correlated with cardiac function associated traits. Proximal coding genes to novel lncRNA in Cluster 4 were enriched with heart development associated processes (FIG. 1C). Since novel lncRNAs that cluster specifically with particular physiological traits were likely to be involved in biological processes associated with those traits, these findings indicated that novel lncRNAs within this cluster could represent a class of cardiac-specific regulators of developmental gene programs, which was reactivated in the damaged myocardium. Finally, the least heart specific clusters were one and two, which was positively correlated with remodeling traits.

Figure 1D:
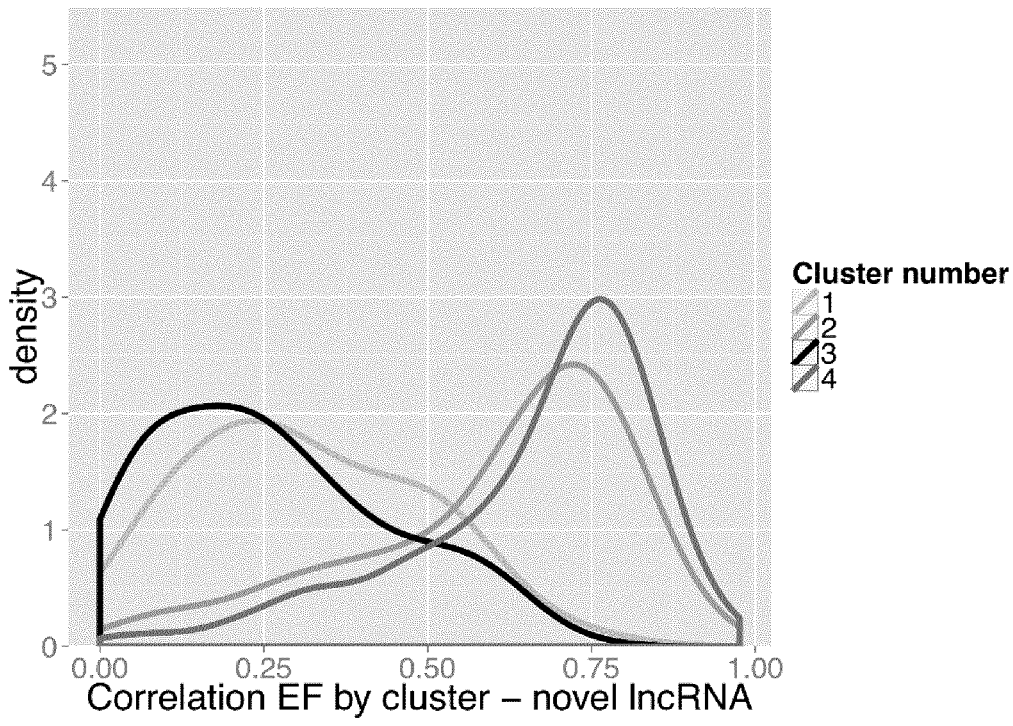
Figure 1D:
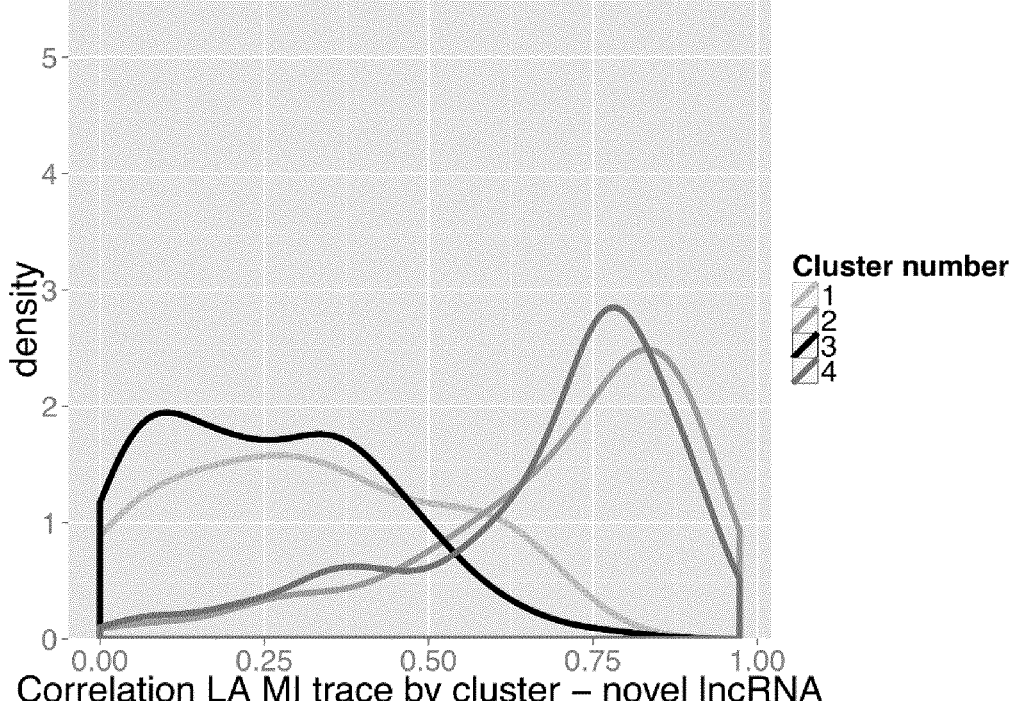
Figure 1E:
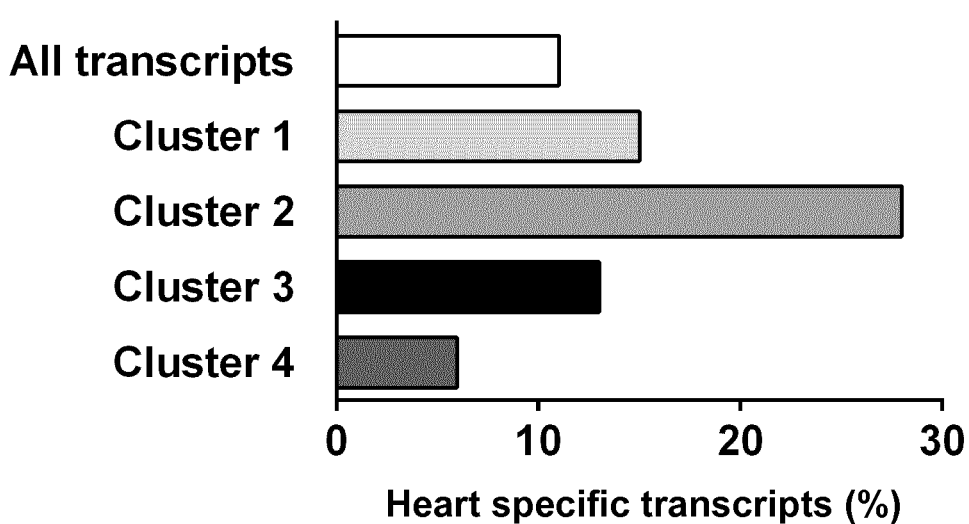
Figure 1F:
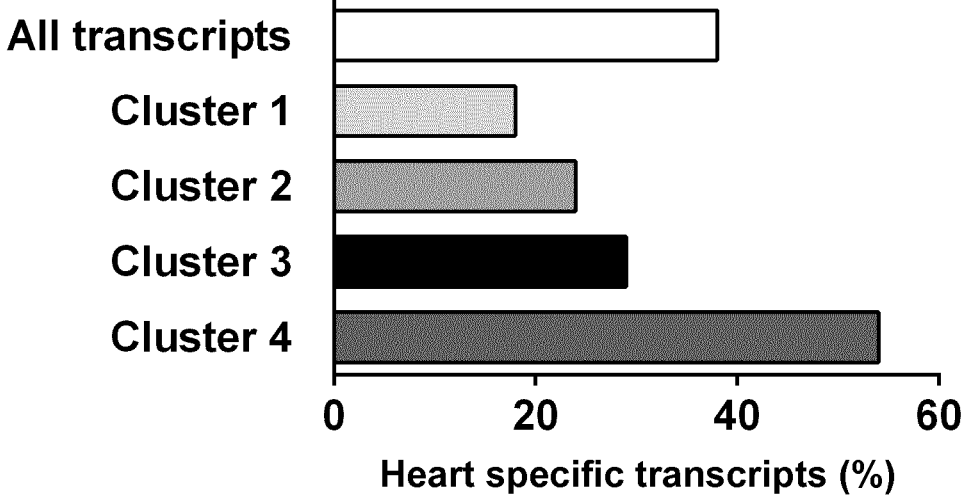

These data demonstrated that unsupervised clustering of transcripts was able to distinguish physiological traits. In addition, it indicated that lncRNAs could represent specific markers of particular physiological traits. To test this, The Inventors compared correlation distributions for each UCSC coding gene and novel lncRNA cluster, with each of the following traits: ejection fraction (EF), interventricular septal thickness at systole (IVS), myocardial infarction trace (MI trace) and left ventricular internal diameter at systole (LVID) (FIGS. 1B and D). UCSC coding gene Clusters 2 and 4 strongly correlated with all these traits when compared to non-specific clusters (Clusters 1 and 3) (FIG. 1B). A similar pattern of correlation was observed with novel lncRNA clusters 2 and 4 (FIG. 1D). However, novel lncRNA Cluster 1 was particularly interesting since it exhibited poor correlation with LVID, EF and MI trace but correlated well with IVS which is typically linked to EF. This unique characteristic is likely a consequence of the exquisite context and cell-type specific expression of lncRNAs, and has intriguing implications for the utilization of novel lncRNAs as biomarkers.

Preferably, in accordance with the method the method for diagnosing a cardiac pathology described herein, an up expression of one or more lncRNA having a cDNA sequence selected from the group comprising SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 96, SEQ ID No 99, fragments thereof, isoforms thereof and variants sharing at least 80% nucleotide sequence identity thereto, in the biological sample compared to the expression levels of one or more of these lnCRNAs in a control sample from a normal subject indicates that the subject suffered from myocardial infarction or is suffering from cardiac pathology associated with maladaptive remodeling of the myocardium.

Preferably also, in accordance with the method for diagnosing a cardiac pathology described herein a down expression of one or more lncRNA having a cDNA sequence selected from the group comprising SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 97, SEQ ID No 98, SEQ ID No 100, SEQ ID No 101, SEQ ID No 102, SEQ ID No103, and SEQ ID No 104, fragments thereof, isoforms thereof and variants sharing at least 80% nucleotide sequence identity thereto, in the biological sample compared to the expression levels of one or more of these lnCRNAs in a control sample from a normal subject indicates that the subject suffered from myocardial infarction.

Also in accordance with the method for diagnosing a cardiac pathology described herein wherein wherein a differential expression of one or more lncRNA having a cDNA sequence selected from the group comprising SEQ ID No 1. SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, fragments thereof, isoforms thereof and variants sharing at least 80% nucleotide sequence identity thereto, in the biological sample compared to the expression levels of one or more of these lnCRNAs in a control sample from a normal subject indicates that the subject suffered from heart failure with preserved ejection fraction.

The phrase "differentially expressed" refers to differences in the quantity and/or the frequency of a biomarker present in a sample taken from patients having, for example, a cardiac pathology or form a cardiac tissue undergoing regeneration or from a stem cell undergoing cardiac differentiation or from a cardiac tissue undergoing surgical and/or pharmacological therapies as compared to a control subject. For example, a biomarker can be a lncRNA which is present at an elevated level or at a decreased level in samples of patients with a cardiac pathology or a cardiac tissue undergoing regeneration or a stem cell undergoing cardiac differentiation or a cardiac tissue undergoing surgical and/or pharmacological therapies compared to samples of control subjects. Alternatively, a biomarker can be a lncRNA which is detected at a higher frequency or at a lower frequency in samples of patients with a cardiac pathology or a cardiac tissue undergoing regeneration or a stem cell undergoing cardiac differentiation or a cardiac tissue undergoing surgical and/or pharmacological therapies compared to samples of control subjects or control tissues. A biomarker can be differentially present in terms of quantity, frequency or both.

A lncRNA is differentially expressed between two samples if the amount of the lncRNA in one sample is statistically significantly different from the amount of the lncRNA in the other sample. For example, an lncRNA is differentially expressed in two samples if it is present at least about 120%, at least about 130%, at least about 150%, at least about 180%, at least about 200%, at least about 300%, at least about 500%, at least about 700%, at least about 900%, or at least about 1000% greater than it is present in the other sample, or if it is detectable in one sample and not detectable in the other.

Alternatively or additionally, a lncRNA is differentially expressed in two sets of samples if the frequency of detecting the lncRNA in samples is statistically significantly higher or lower than in the control samples. For example, an lncRNA is differentially expressed in two sets of samples if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of samples than the other set of samples.

The terms "subject," "individual," and "patient," are used interchangeably herein and refer to any mammalian subject for whom diagnosis, prognosis, treatment, or therapy is desired, particularly humans. Other subjects may include cattle, dogs, cats, guinea pigs, rabbits, rats, mice, horses, and so on. In some cases, the methods of the invention find use in experimental animals, in veterinary application, and in the development of animal models for disease, including, but not limited to, rodents including mice, rats, guinea pigs, and hamsters; rabbits, primates, and transgenic animals.

As used herein, a "biological sample" refers to a sample of tissue or fluid isolated from a subject, including but not limited to, for example, urine, blood, plasma, serum, fecal matter, bone marrow, bile, spinal fluid, lymph fluid, samples of the skin, external secretions of the skin, respiratory, intestinal, and genitourinary tracts, tears, saliva, milk, blood cells, organs, biopsies, and also samples containing cells or tissues derived from the subject and grown in culture, and in vitro cell culture constituents, including but not limited to, conditioned media resulting from the growth of cells and tissues in culture, recombinant cells, stem cells, and cell components.

The terms "quantity," "amount," and "level" are used interchangeably herein and may refer to an absolute quantification of a molecule or an analyte in a sample, or to a relative quantification of a molecule or analyte in a sample, i.e., relative to another value such as relative to a reference value as taught herein, or to a range of values for the biomarker. These values or ranges can be obtained from a single patient or from a group of patients.

"Diagnosis" as used herein generally includes determination as to whether a subject is likely affected by a given disease, disorder or dysfunction of the invention. The skilled artisan often makes a diagnosis on the basis of one or more diagnostic indicators, i.e., a biomarker, the presence, absence, or amount of which is indicative of the presence or absence of the disease, disorder or dysfunction.

"Prognosis" as used herein generally refers to a prediction of the probable course and outcome of a clinical condition or disease. A prognosis of a patient is usually made by evaluating factors or symptoms of a disease that are indicative of a favorable or unfavorable course or outcome of the disease. It is understood that the term "prognosis" does not necessarily refer to the ability to predict the course or outcome of a condition with 100% accuracy. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition.

When analyzing the levels of biomarkers in a biological sample, the reference value ranges used for comparison can represent the level of one or more biomarkers found in one or more samples of one or more subjects without cardiac disease (i.e., normal or control samples). Alternatively, the reference values can represent the level of one or more biomarkers found in one or more samples of one or more subjects with cardiac disease. More specifically, the reference value ranges can represent the level of one or more biomarkers at particular stages of disease to facilitate a determination of the stage of disease progression in an individual.

A "control" sample as used herein refers to a biological sample, such as tissue or cells that are not diseased. That is, a control sample is obtained from a normal subject (e.g. an individual known to not have cardiac disease or any condition or symptom associated with).

It is understood that the expression level of the biomarkers in a sample can be determined by any suitable method known in the art. Measurement of the level of a biomarker can be direct or indirect. For example, the abundance levels of lncRNAs can be directly quantitated. Alternatively, the amount of a biomarker can be determined indirectly by measuring abundance levels of cDNAs, amplified RNAs or DNAs, or by measuring quantities or activities of RNAs, or other molecules that are indicative of the expression level of the biomarker. Preferably, the amount of a biomarker is determined indirectly by measuring abundance levels of cDNAs.

LncRNAs can be detected and quantitated by a variety of methods including, but not limited to, microarray analysis, polymerase chain reaction (PCR), reverse transcriptase polymerase chain reaction (RT-PCR), Northern blot, serial analysis of gene expression (SAGE), immunoassay, and mass spectrometry, any sequencing-based methods known in the art.

In one embodiment, microarrays are used to measure the levels of biomarkers. An advantage of microarray analysis is that the expression of each of the biomarkers can be measured simultaneously, and microarrays can be specifically designed to provide a diagnostic expression profile for a particular disease or condition (e.g., a cardiac pathology).

Microarrays are prepared by selecting probes which comprise a polynucleotide sequence, and then immobilizing such probes to a solid support or surface. For example, the probes may comprise DNA sequences, RNA sequences, or copolymer sequences of DNA and RNA. The polynucleotide sequences of the probes may also comprise DNA and/or RNA analogues, or combinations thereof. For example, the polynucleotide sequences of the probes may be full or partial fragments of genomic DNA. The polynucleotide sequences of the probes may also be synthesized nucleotide sequences, such as synthetic oligonucleotide sequences. The probe sequences can be synthesized either enzymatically in vivo, enzymatically in vitro (e.g., by PCR), or non-enzymatically in vitro.

Probes used in the methods of the invention are preferably immobilized to a solid support which may be either porous or non-porous. For example, the probes may be polynucleotide sequences which are attached to a nitrocellulose or nylon membrane or filter covalently at either the 3' or the 5' end of the polynucleotide. Such hybridization probes are well known in the art (see, e.g., Sambrook, et al., Molecular Cloning: A Laboratory Manual (3rd Edition, 2001). Alternatively, the solid support or surface may be a glass or plastic surface. In one embodiment, hybridization levels are measured to microarrays of probes consisting of a solid phase on the surface of which are immobilized a population of polynucleotides, such as a population of DNA or DNA mimics, or, alternatively, a population of RNA or RNA mimics. The solid phase may be a nonporous or, optionally, a porous material such as a gel.

In one embodiment, the microarray comprises a support or surface with an ordered array of binding (e.g., hybridization) sites or "probes" each representing one of the biomarkers described herein. Preferably the microarrays are addressable arrays, and more preferably positionally addressable arrays. More specifically, each probe of the array is preferably located at a known, predetermined position on the solid support such that the identity (i.e., the sequence) of each probe can be determined from its position in the array (i.e., on the support or surface). Each probe is preferably covalently attached to the solid support at a single site.

Microarrays can be made in a number of ways, of which several are described below. However they are produced, microarrays share certain characteristics. The arrays are reproducible, allowing multiple copies of a given array to be produced and easily compared with each other. Preferably, microarrays are made from materials that are stable under binding (e.g., nucleic acid hybridization) conditions. Microarrays are generally small, e.g., between 1 cm2 and 25 cm2;

however, larger arrays may also be used, e.g., in screening arrays. Preferably, a given binding site or unique set of binding sites in the microarray will specifically bind (e.g., hybridize) to the product of a single gene in a cell (e.g., to a specific mRNA, lncRNA, or to a specific cDNA derived therefrom). However, in general, other related or similar sequences will cross hybridize to a given binding site.

As noted above, the "probe" to which a particular polynucleotide molecule specifically hybridizes contains a complementary polynucleotide sequence. The probes of the microarray typically consist of nucleotide sequences of no more than 1,000 nucleotides. In some embodiments, the probes of the array consist of nucleotide sequences of 10 to 1,000 nucleotides. In one embodiment, the nucleotide sequences of the probes are in the range of 10-200 nucleotides in length and are genomic sequences of one species of organism, such that a plurality of different probes is present, with sequences complementary and thus capable of hybridizing to the genome of such a species of organism, sequentially tiled across all or a portion of the genome. In other embodiments, the probes are in the range of 10-30 nucleotides in length, in the range of 10-40 nucleotides in length, in the range of 20-50 nucleotides in length, in the range of 40-80 nucleotides in length, in the range of 50-150 nucleotides in length, in the range of 80-120 nucleotides in length, or are 60 nucleotides in length. The probes may comprise DNA or DNA "mimics" (e.g., derivatives and analogues) corresponding to a portion of an organism's genome. In another embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone (e.g., phosphorothioates).

DNA can be obtained, e.g., by polymerase chain reaction (PCR) amplification of genomic DNA or cloned sequences. PCR primers are preferably chosen based on a known sequence of the genome that will result in amplification of specific fragments of genomic DNA. Computer programs that are well known in the art are useful in the design of primers with the required specificity and optimal amplification properties, such as Oligo version 5.0 (National Biosciences). Typically each probe on the microarray will be between 10 bases and 50,000 bases, usually between 300 bases and 1,000 bases in length. PCR methods are well known in the art, and are described, for example, in Innis et al., eds., PCR Protocols: A Guide To Methods And Applications, Academic Press Inc., San Diego, Calif. (1990); herein incorporated by reference in its entirety. It will be apparent to one skilled in the art that controlled robotic systems are useful for isolating and amplifying nucleic acids.

An alternative, preferred means for generating polynucleotide probes is by synthesis of synthetic polynucleotides or oligonucleotides, e.g., using N-phosphonate or phosphoramidite chemistries (Froehler et al., Nucleic Acid Res. 14:5399-5407 (1986); McBride et al., Tetrahedron Lett. 24:246-248 (1983)). Synthetic sequences are typically between about 10 and about 500 bases in length, more typically between about 20 and about 100 bases, and most preferably between about 40 and about 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., U.S. Pat. No. 5,539,083).

Probes are preferably selected using an algorithm that takes into account binding energies, base composition, sequence complexity, cross-hybridization binding energies, and secondary structure. See International Patent Publication WO 01/05935.

A skilled artisan will also appreciate that positive control probes, e.g., probes known to be complementary and hybridizable to sequences in the target polynucleotide molecules, and negative control probes, e.g., probes known to not be complementary and hybridizable to sequences in the target polynucleotide molecules, should be included on the array. In one embodiment, positive controls are synthesized along the perimeter of the array. In another embodiment, positive controls are synthesized in diagonal stripes across the array. In still another embodiment, the reverse complement for each probe is synthesized next to the position of the probe to serve as a negative control. In yet another embodiment, sequences from other species of organism are used as negative controls or as "spike-in" controls.

The probes are attached to a solid support or surface, which may be made, e.g., from glass, plastic (e.g., polypropylene, nylon), polyacrylamide, nitrocellulose, gel, or other porous or nonporous material. One method for attaching nucleic acids to a surface is by printing on glass plates, as known in the art. This method is especially useful for preparing microarrays of cDNA A second method for making microarrays produces high-density oligonucleotide arrays. Techniques are known for producing arrays containing thousands of oligonucleotides complementary to defined sequences, at defined locations on a surface using photolithographic techniques for synthesis in situ (see, U.S. Pat. Nos. 5,578,832; 5,556,752; and 5,510,270; herein incorporated by reference in their entireties) or other methods for rapid synthesis and deposition of defined oligonucleotides. When these methods are used, oligonucleotides (e.g., 60-mers) of known sequence are synthesized directly on a surface such as a derivatized glass slide. Usually, the array produced is redundant, with several oligonucleotide molecules per RNA. Other methods for making microarrays, e.g., by masking, may also be used. In principle, any type of array known in the art, for example, dot blots on a nylon hybridization membrane could be used. However, as will be recognized by those skilled in the art, very small arrays will frequently be preferred because hybridization volumes will be smaller.

Microarrays can also be manufactured by means of an ink jet printing device for oligonucleotide synthesis, e.g., using the methods and systems described by Blanchard in U.S. Pat. No. 6,028,189. Specifically, the oligonucleotide probes in such microarrays are synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes). Microarrays manufactured by this ink jet method are typically of high density, preferably having a density of at least about 2,500 different probes per 1 cm2. The polynucleotide probes are attached to the support covalently at either the 3' or the 5' end of the polynucleotide.

Biomarker polynucleotides which may be measured by microarray analysis can be expressed lncRNAs or a nucleic acid derived therefrom (e.g., cDNA or amplified RNA derived from cDNA that incorporates an RNA polymerase promoter), including naturally occurring nucleic acid molecules, as well as synthetic nucleic acid molecules. In one embodiment, the target polynucleotide molecules comprise RNA, including, but by no means limited to, total cellular RNA, lncRNA, poly(A)+ messenger RNA (mRNA) or a fraction thereof, cytoplasmic mRNA, or RNA transcribed from cDNA (i.e., cRNA; see, e.g., U.S. Pat. Nos. 5,545,522, 5,891,636, or 5,716,785). Methods for preparing total and poly(A)+ RNA are well known in the art, and are described generally, e.g., in Sambrook, et al., Molecular Cloning: A Laboratory Manual (3rd Edition, 2001). RNA can be extracted from a cell of interest using guanidinium thiocyanate lysis followed by CsCl centrifugation, a silica gel-based column (e.g., RNeasy (Qiagen, Valencia, Calif.) or StrataPrep (Stratagene, La Jolla, Calif.)), or using phenol and chloroform, as known in the art. Poly(A)+ RNA can be selected, e.g., by selection with oligo-dT cellulose or, alternatively, by oligo-dT primed reverse transcription of total cellular RNA. RNA can be fragmented by methods known in the art, e.g., by incubation with ZnCl2, to generate fragments of RNA.

In one embodiment, total RNA, lncRNAs, or nucleic acids derived therefrom (such as cDNA), are isolated from a sample taken from a patient having a cardiac pathology or a cardiac tissue undergoing regeneration or a stem cell undergoing cardiac differentiation or a cardiac tissue undergoing surgical and/or pharmacological therapies. Biomarker lncRNAs that are poorly expressed in particular cells may be enriched using normalization techniques known in the art. As described above, the biomarker polynucleotides can be detectably labeled at one or more nucleotides. Any method known in the art may be used to label the target polynucleotides. Preferably, this labeling incorporates the label uniformly along the length of the RNA, and more preferably, the labeling is carried out at a high degree of efficiency. For example, polynucleotides can be labeled by oligo-dT primed reverse transcription. Random primers (e.g., 9-mers) can be used in reverse transcription to uniformly incorporate labeled nucleotides over the full length of the polynucleotides. Alternatively, random primers may be used in conjunction with PCR methods or T7 promoter-based in vitro transcription methods in order to amplify polynucleotides.

The detectable label may be a luminescent label. For example, fluorescent labels, bioluminescent labels, chemiluminescent labels, and colorimetric labels may be used in the practice of the invention. Fluorescent labels that can be used include, but are not limited to, fluorescein, a phosphor, a rhodamine, or a polymethine dye derivative. Additionally, commercially available fluorescent labels including, but not limited to, fluorescent phosphoramidites such as FluorePrime (Amersham Pharmacia, Piscataway, N.J.), Fluoredite (Millipore, Bedford, Mass.), FAM (ABI, Foster City, Calif.), and Cy3 or Cy5 (Amersham Pharmacia, Piscataway, N.J.) can be used. Alternatively, the detectable label can be a radiolabeled nucleotide.

In one embodiment, biomarker polynucleotide molecules from a patient sample are labeled differentially from the corresponding polynucleotide molecules of a reference sample. The reference can comprise lncRNAs from a normal biological sample (i.e., control sample, e.g., biopsy from a subject not having a cardiac pathology or a cardiac tissue undergoing regeneration or a stem cell undergoing cardiac differentiation or a cardiac tissue undergoing surgical and/or pharmaccological therapies) or from a reference biological sample, (e.g., sample from a subject having a cardiac pathology or cell sample of a cardiac tissue undergoing regeneration or a stem cell undergoing cardiac differentiation or a cardiac tissue undergoing surgical and/or pharmacological therapies).

Nucleic acid hybridization and wash conditions are chosen so that the target polynucleotide molecules specifically bind or specifically hybridize to the complementary polynucleotide sequences of the array, preferably to a specific array site, wherein its complementary DNA is located. Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self-complementary sequences.

Optimal hybridization conditions will depend on the length (e.g., oligomer versus polynucleotide greater than 200 bases) and type (e.g., RNA, or DNA) of probe and target nucleic acids. One of skill in the art will appreciate that as the oligonucleotides become shorter, it may become necessary to adjust their length to achieve a relatively uniform melting temperature for satisfactory hybridization results. General parameters for specific (i.e., stringent) hybridization conditions for nucleic acids are described in Sambrook, et al., Molecular Cloning: A Laboratory Manual (3rd Edition, 2001). Typical hybridization conditions for the cDNA microarrays of Schena et al. are hybridization in 5×SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS). Particularly preferred hybridization conditions include hybridization at a temperature at or near the mean melting temperature of the probes (e.g., within 51° C., more preferably within 21° C.) in 1 M NaCl, 50 mM MES buffer (pH 6.5), 0.5% sodium sarcosine and 30% formamide.

When fluorescently labeled gene products are used, the fluorescence emissions at each site of a microarray may be, preferably, detected by scanning confocal laser microscopy. In one embodiment, a separate scan, using the appropriate excitation line, is carried out for each of the two fluorophores used. Alternatively, a laser may be used that allows simultaneous specimen illumination at wavelengths specific to the two fluorophores and emissions from the two fluorophores can be analyzed simultaneously. Arrays can be scanned with a laser fluorescent scanner with a computer controlled X-Y stage and a microscope objective. Sequential excitation of the two fluorophores is achieved with a multiline, mixed gas laser and the emitted light is split by wavelength and detected with two photomultiplier tubes. Fluorescence laser scanning devices are known in the art. Alternatively, a fiber-optic bundle, may be used to monitor mRNA abundance levels at a large number of sites simultaneously.

In one embodiment, the invention includes a microarray comprising a plurality of probes that hybridize to one or more lncRNAs selected from the group comprising SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25. SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79. SEQ ID No 80, SEQ ID No 81, SEQ ID No 82. SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, and SEQ ID No 95, SEQ ID No 96, SEQ ID No 97, SEQ ID No 98, SEQ ID No 99, SEQ ID No 100, SEQ ID No 101, SEQ ID No 102, SEQ ID No103, and SEQ ID No 104, fragments thereof, isoforms thereof and variants sharing at least 80% nucleotide sequence identity thereto, most preferably from the group comprising SEQ ID No 25, SEQ ID No 28, SEQ ID No 48, SEQ ID No 52, SEQ ID No 53, SEQ ID No 82, SEQ ID No 84, SEQ ID No 88, SEQ ID No 96, SEQ ID No 97, SEQ ID No 98, SEQ ID No 99, SEQ ID No 100, SEQ ID No 101, SEQ ID No 103, and SEQ ID No 104.

Serial Analysis Gene Expression (SAGE), can also be used to determine RNA (e.g., lncRNA) abundances in a cell sample. SAGE analysis does not require a special device for detection, and is one of the preferable analytical methods for simultaneously detecting the expression of a large number of transcription products. First, RNA is extracted from cells. Next, the RNA is converted into cDNA using a biotinylated oligo (dT) primer, and treated with a four-base recognizing restriction enzyme (Anchoring Enzyme: AE) resulting in AE-treated fragments containing a biotin group at their 3' terminus. Next, the AE-treated fragments are incubated with streptoavidin for binding. The bound cDNA is divided into two fractions, and each fraction is then linked to a different double-stranded oligonucleotide adapter (linker) A or B. These linkers are composed of: (1) a protruding single strand portion having a sequence complementary to the sequence of the protruding portion formed by the action of the anchoring enzyme, (2) a 5' nucleotide recognizing sequence of the IIS-type restriction enzyme (cleaves at a predetermined location no more than 20 by away from the recognition site) serving as a tagging enzyme (TE), and (3) an additional sequence of sufficient length for constructing a PCR-specific primer. The linker-linked cDNA is cleaved using the tagging enzyme, and only the linker-linked cDNA sequence portion remains, which is present in the form of a short-strand sequence tag. Next, pools of short-strand sequence tags from the two different types of linkers are linked to each other, followed by PCR amplification using primers specific to linkers A and B. As a result, the amplification product is obtained as a mixture comprising myriad sequences of two adjacent sequence tags (ditags) bound to linkers A and B. The amplification product is treated with the anchoring enzyme, and the free ditag portions are linked into strands in a standard linkage reaction. The amplification product is then cloned. Determination of the clone's nucleotide sequence can be used to obtain a read-out of consecutive ditags of constant length. The presence of mRNA corresponding to each tag can then be identified from the nucleotide sequence of the clone and information on the sequence tags.

Quantitative reverse transcriptase PCR (qRT-PCR) can also be used to determine the expression profiles of biomarkers (see, e.g., U.S. Patent Application Publication No. 2005/0048542A1; herein incorporated by reference in its entirety). The first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TAQMAN PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TAQMAN RT-PCR can be performed using commercially available equipment, such as, for example, ABI PRISM 7700 sequence detection system. (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700 sequence detection system. The system consists of a thermocycler, laser, charge-coupled device (CCD), camera and computer. The system includes software for running the instrument and for analyzing the data. 5'-Nuclease assay data are initially expressed as Ct, or the threshold cycle. Fluorescence values are recorded during every cycle and represent the amount of product amplified to that point in the amplification reaction. The point when the fluorescent signal is first recorded as statistically significant is the threshold cycle (Ct).

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and beta-actin.

A more recent variation of the RT-PCR technique is the real time quantitative PCR, which measures PCR product accumulation through a dual-labeled fluorigenic probe (i.e., TAQMAN probe). Real time PCR is compatible both with quantitative competitive PCR, where internal competitor for each target sequence is used for normalization, and with quantitative comparative PCR using a normalization gene contained within the sample, or a housekeeping gene for RT-PCR.

Mass spectrometry, and particularly SELDI mass spectrometry, is a particularly useful method for detection of the biomarkers of this invention. Laser desorption time-of-flight mass spectrometer can be used in embodiments of the invention. In laser desorption mass spectrometry, a substrate or a probe comprising biomarkers is introduced into an inlet system. The biomarkers are desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of markers of specific mass to charge ratio.

Matrix-assisted laser desorption/ionization mass spectrometry (MALDI-MS) can also be used for detecting the biomarkers of this invention. MALDI-MS is a method of mass spectrometry that involves the use of an energy absorbing molecule, frequently called a matrix, for desorbing proteins intact from a probe surface. MALDI is described, for example, in U.S. Pat. No. 5,118,937 and U.S. Pat. No. 5,045,694. In MALDI-MS, the sample is typically mixed with a matrix material and placed on the surface of an inert probe. Exemplary energy absorbing molecules include cinnamic acid derivatives, sinapinic acid ("SPA"), cyano hydroxy cinnamic acid ("CHCA") and dihydroxybenzoic acid. Other suitable energy absorbing molecules are known to those skilled in this art. The matrix dries, forming crystals that encapsulate the analyte molecules. Then the analyte molecules are detected by laser desorption/ionization mass spectrometry.

Surface-enhanced laser desorption/ionization mass spectrometry, or SELDI-MS represents an improvement over MALDI for the fractionation and detection of biomolecules, such as lncRNAs, in complex mixtures. SELDI is a method of mass spectrometry in which biomolecules, such as lncRNAs, are captured on the surface of a biochip using capture reagents that are bound there. Typically, non-bound molecules are washed from the probe surface before interrogation. SELDI is described, for example, in: U.S. Pat. No. 5,719,060 and in U.S. Pat. No. 6,225,047.

Biomarkers on the substrate surface can be desorbed and ionized using gas phase ion spectrometry. Any suitable gas phase ion spectrometer can be used as long as it allows biomarkers on the substrate to be resolved. Preferably, gas phase ion spectrometers allow quantitation of biomarkers. In one embodiment, a gas phase ion spectrometer is a mass spectrometer. In a typical mass spectrometer, a substrate or a probe comprising biomarkers on its surface is introduced into an inlet system of the mass spectrometer. The biomarkers are then desorbed by a desorption source such as a laser, fast atom bombardment, high energy plasma, electrospray ionization, thermospray ionization, liquid secondary ion MS, field desorption, etc. The generated desorbed, volatilized species consist of preformed ions or neutrals which are ionized as a direct consequence of the desorption event. Generated ions are collected by an ion optic assembly, and then a mass analyzer disperses and analyzes the passing ions. The ions exiting the mass analyzer are detected by a detector. The detector then translates information of the detected ions into mass-to-charge ratios. Detection of the presence of biomarkers or other substances will typically involve detection of signal intensity. This, in turn, can reflect the quantity and character of biomarkers bound to the substrate. Any of the components of a mass spectrometer (e.g., a desorption source, a mass analyzer, a detector, etc.) can be combined with other suitable components described herein or others known in the art in embodiments of the invention.

Biomarkers can also be detected with assays based on the use of antibodies that specifically recognize the lncRNA biomarkers or polynucleotide or oligonucleotide fragments of the biomarkers. Such assays include, but are not limited to, immunohistochemistry (IHC), enzyme-linked immunosorbent assay (ELISA), radioimmunoassays (RIA), "sandwich" immunoassays, fluorescent immunoassays, immunoprecipitation assays, the procedures of which are well known in the art.

Biomarkers can also be detected with any sequencing based technologies know in the art.

In yet another aspect, the invention provides kits for use in diagnosing a cardiac pathology or a cardiac tissue undergoing regeneration or a stem cell undergoing cardiac differentiation or a cardiac tissue undergoing surgical and/or pharmacological therapies, wherein the kits can be used to detect the lncRNA biomarkers of the present invention. For example, the kits can be used to detect any one or more of the biomarkers described herein, which are differentially expressed in samples of a patient with a cardiac pathology or a cardiac tissue undergoing regeneration or a stem cell undergoing cardiac differentiation or a cardiac tissue undergoing surgical and/or pharmacological therapies. The kit may include one or more agents for detection of lncRNA biomarkers, a container for holding a biological sample isolated from a human subject; and printed instructions for reacting agents with the biological sample or a portion of the biological sample to detect the presence or amount of at least one lncRNA biomarker in the biological sample. The agents may be packaged in separate containers. The kit may further comprise one or more control reference samples and reagents for performing an immunoassay, a Northern blot, PCR, microarray analysis, or SAGE, DNA/RNA-sequencing, In certain embodiments, the kit contains at least one probe that selectively hybridizes to a biomarker, or at least one antibody that selectively binds to a biomarker, or at least one set of PCR primers for amplifying a biomarker. In one embodiment, the kit comprises at least one agent for measuring the level of a biomarker.

The kit can comprise one or more containers for compositions contained in the kit. Compositions can be in liquid form or can be lyophilized. Suitable containers for the compositions include, for example, bottles, vials, syringes, and test tubes. Containers can be formed from a variety of materials, including glass or plastic. The kit can also comprise a package insert containing written instructions for methods of diagnosing a cardiac pathology or monitoring stem cell therapy or regenerative medical treatments.

The kits of the invention have number of applications. For example, the kits can be used for diagnosing a cardiac pathology or monitoring and/or evaluating the efficacy of a treatment for a cardiac pathology, stem cell therapy, or regenerative cardiac medicine. In a further example, the kits can be used to identify compounds that modulate expression of one or more of the biomarkers in in vitro or in vivo animal models to determine the effects of treatment.

By "therapeutically effective dose or amount" of each of the modulator of the invention is intended an amount that when administered in combination brings about a positive therapeutic response with respect to treatment of an individual for a cardiac pathology.

Thus, for example, a "positive therapeutic response" would be an improvement in the disease in association with the combination therapy, and/or an improvement in one or more symptoms of the disease in association with the combination therapy.

The actual dose to be administered will vary depending upon the age, weight, and general condition of the subject as well as the severity of the condition being treated, the judgment of the health care professional, and conjugate being administered. Therapeutically effective amounts can be determined by those skilled in the art, and will be adjusted to the particular requirements of each particular case. Generally, a therapeutically effective amount will range from about 0.50 mg to 5 grams daily, more preferably from about 5 mg to 2 grams daily, even more preferably from about 7 mg to 1.5 grams daily.

In certain embodiments, multiple therapeutically effective doses of each of at least one lncRNA and at least one additional therapeutical agent will be administered according to a daily dosing regimen, or intermittently. For example, a therapeutically effective dose can be administered, one day a week, two days a week, three days a week, four days a week, or five days a week, and so forth. By "intermittent" administration is intended the therapeutically effective dose can be administered, for example, every other day, every two days, every three days, and so forth. By "twice-weekly" or "two times per week" is intended that two therapeutically effective doses of the agent in question is administered to the subject within a 7 day period, beginning on day 1 of the first week of administration, with a minimum of 72 hours, between doses and a maximum of 96 hours between doses. By "thrice weekly" or "three times per week" is intended that three therapeutically effective doses are administered to the subject within a 7 day period, allowing for a minimum of 48 hours between doses and a maximum of 72 hours between doses. For purposes of the present invention, this type of dosing is referred to as "intermittent" therapy. In accordance with the methods of the present invention, a subject can receive intermittent therapy (i.e., twice-weekly or thrice-weekly administration of a therapeutically effective dose) for one or more weekly cycles until the desired therapeutic response is achieved. The agents can be administered by any acceptable route of administration as noted herein below.

A lncRNA modulator of the invention can be administered prior to, concurrent with, or subsequent to at least one additional therapeutic agent. If provided at the same time as the additional therapeutic agent, the lncRNA modulator can be provided in the same or in a different composition. Thus, the agents can be presented to the individual by way of concurrent therapy. By "concurrent therapy" is intended administration to a human subject such that the therapeutic effect of the combination of the substances is caused in the subject undergoing therapy. For example, concurrent therapy may be achieved by administering at least one therapeutically effective dose of a pharmaceutical composition comprising a lncRNA modulator and at least one therapeutically effective dose of a pharmaceutical composition comprising at least one additional therapeutic agent according to a particular dosing regimen. Administration of the separate pharmaceutical compositions can be at the same time (i.e., simultaneously) or at different times (i.e., sequentially, in either order, on the same day, or on different days), so long as the therapeutic effect of the combination of these substances is caused in the subject undergoing therapy.

In other embodiments of the invention, the pharmaceutical composition of the invention is a sustained-release formulation, or a formulation that is administered using a sustained-release device. Such devices are well known in the art, and include, for example, transdermal patches, and miniature implantable pumps that can provide for drug delivery over time in a continuous, steady-state fashion at a variety of doses to achieve a sustained-release effect with a non-sustained-release pharmaceutical composition. The pharmaceutical compositions of the invention may be administered using the same or different routes of administration in accordance with any medically acceptable method known in the art. Suitable routes of administration include parenteral administration, such as subcutaneous (SC), intraperitoneal (IP), intramuscular (IM), intravenous (IV), or infusion, oral and pulmonary, nasal, topical, transdermal, and suppositories. Where the composition is administered via pulmonary delivery, the therapeutically effective dose is adjusted such that the soluble level of the agent, such as the lncRNA modulator in the bloodstream, is equivalent to that obtained with a therapeutically effective dose that is administered parenterally, for example SC, IP, IM, or IV. In some embodiments of the invention, the pharmaceutical composition comprising the lncRNA modulator is administered by IM or SC injection, particularly by IM or SC injection locally to the region where the therapeutic agent or agents used in the cardiac therapy protocol are administered.

Factors influencing the respective amount of the various compositions to be administered include, but are not limited to, the mode of administration, the frequency of administration (i.e., daily, or intermittent administration, such as twice- or thrice-weekly), the particular disease undergoing therapy, the severity of the disease, the history of the disease, whether the individual is undergoing concurrent therapy with another therapeutic agent, and the age, height, weight, health, and physical condition of the individual undergoing therapy. Generally, a higher dosage of this agent is preferred with increasing weight of the subject undergoing therapy. Below are examples of specific embodiments for carrying out the present invention. The examples are offered for illustrative purposes only, and are not intended to limit the scope of the present invention in any way.

The present invention also concerns a method for increasing and/or improving cardiac function comprising administrating a pharmaceutical composition comprising an effective amount of a modulator of lnc_019010 wherein the modulator is selected from the group comprising a chemical agent, an antibody, an engineered protease, and enzymatically active RNA, optionally in combination with pharmaceutically acceptable carriers, diluents and/or adjuvants. Preferably, the modulator of lnc_019010 is an enzymatically active RNA consisting in one or more antisense oligonucleotide targeting said lnc_019010. Most preferably, said one or more antisense oligonucleotide targeting said lnc_019010 is a modified antisense oligonucleotide (GapmeR) having a sequence as set forth in SEQ ID No 148.

Also envisioned in the present invention is a method for increasing and/or improving the conduction system in the heart comprising administrating a pharmaceutical composition comprising an effective amount of a modulator of lnc_033521 wherein the modulator is selected from the group comprising a chemical agent, an antibody, an engineered protease, and enzymatically active RNA, optionally in combination with pharmaceutically acceptable carriers, diluents and/or adjuvants.

The present invention further relates to a method of regulating the heart rate comprising administrating a pharmaceutical composition comprising an effective amount of a modulator of lnc_033521 wherein the modulator is selected from the group comprising a chemical agent, an antibody, an engineered protease, and enzymatically active RNA, optionally in combination with pharmaceutically acceptable carriers, diluents and/or adjuvants.

Preferably, the modulator of lnc_033521 is an enzymatically active RNA consisting in one or more antisense oligonucleotide targeting said lnc_033521. Most preferably, said one or more antisense oligonucleotide targeting said lnc_033521 is a modified antisense oligonucleotide (GapmeR) having a sequence as set forth in SEQ ID No 147.

The present invention further relates to a method for diagnosing dilated cardiomyopathy (DCM) in a subject, the method comprising:

a) measuring, directly or indirectly, the level of novlnc6 having a cDNA sequence as set forth in SEQ ID No. 48, fragments thereof, isoforms thereof and variants sharing at least 80% nucleotide sequence identity thereto; and b) analyzing the levels of said novlnc6, fragments thereof, isoforms thereof and variants sharing at least 80% nucleotide sequence identity thereto, in conjunction with respective reference value ranges for said novlnc6, wherein a decreased expression level of said novlnc6 in the biological sample compared to a control sample from a normal subject indicates that the subject has a dilated cardiomyopathy.

The present invention further relates to a method for diagnosing aortic stenosis (AOS) in a subject, the method comprising:

a) measuring, directly or indirectly, the level of Novlnc44 having a cDNA sequence as set forth in SEQ ID No. 100, fragments thereof, isoforms thereof and variants sharing at least 80% nucleotide sequence identity thereto; and b) analyzing the levels of said Novlnc44, fragments thereof, isoforms thereof and variants sharing at least 80% nucleotide sequence identity thereto, in conjunction with respective reference value ranges for said Novlnc44, wherein a decreased expression level of Novlnc44 in the biological sample compared to the control sample from a normal subject indicates that the subject has aortic stenosis.

The present invention further relates to a method for diagnosing dilated cardiomyopathy (DCM) in a subject, the method comprising:

a) measuring, directly or indirectly, the level of Novlnc44 having a cDNA sequence as set forth in SEQ ID No. 100, fragments thereof, isoforms thereof and variants sharing at least 80% nucleotide sequence identity thereto; and b) analyzing the levels of said Novlnc44, fragments thereof, isoforms thereof and variants sharing at least 80% nucleotide sequence identity thereto, in conjunction with respective reference value ranges for said Novlnc44, wherein a decreased expression level of Novlnc44 in the biological sample compared to the control sample from a normal subject indicates that the subject has a dilated cardiomyopathy.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

The foregoing description will be more fully understood with reference to the following Examples. Such Examples, are, however, exemplary of methods of practicing the present invention and are not intended to limit the scope of the invention.

EXAMPLES

Example 1

Extended Experimental Procedures
Transgenic Mouse Enhancer Assay

Mouse transgenic enhancer assays were previously executed and described in Ounzain S, et al., 2014. Images can be found at http://enhancer.lbl.gov/.

Mice

Animal experiments were approved by the Government Veterinary Office (Lausanne, Switzerland) and performed according to the University of Lausanne Medical School institutional guidelines. Animal experiments were approved by the Government Veterinary Office (Lausanne, Switzerland) and performed according to the University of Lausanne Medical School institutional guidelines.

Cardiac Injury Models—Ligation of the Left Anterior Descending Artery

Myocardial infarction in mice was induced as previously described (Ounzain S, et al., 2014). Mouse was anesthetized by IP injection of a mixture of ketamin/xylazine/acepromazin (65/15/2 mg/kg). Mouse was placed on warming pad for maintenance of body temperature. In the supine position, endotracheal intubation was performed and the mouse was placed on artificial ventilation with a mini-rodent ventilator (tidal volume=0.2 ml, rate=120 breaths/min. The thorax of the animal was shaved and disinfected with Betadine solution. A left thoracotomy was performed. The pectoralis muscle groups were separated transversely, exposing the rib cage. The fourth intercostal space was entered using scissors and blunt dissection. The pericardium was gently opened and a pressure was applied to the right thorax to displace the heart leftward. A 7.0 silk ligature near the insertion of the left auricular appendage was placed and tied around the left descending coronary artery. Occlusion of the artery was verified by the rapid blanching of the left ventricle. For animals undergoing a sham operation, the ligature was placed in an identical location but not tied. The lungs were re-expanded using positive pressure at end expiration and the chest and skin incision were closed respectively with 6-0 and 5-0 silk sutures. The mouse was gradually weaned from the respirator. Once spontaneous respiration resumed, the endotracheal tube was removed, and the animal was replaced in his cage.

Echocardiography

Transthoracic echocardiographies were performed using a 30-MHz probe and the Vevo 770 Ultrasound machine (VisualSonics, Toronto, ON, Canada). Mice were lightly anesthetized with 1% isoflurane, maintaining heart rate at 400-500 beats per minute, and placed in dorsal recumbency on a heated 37'C platform. Hair was removed with a topical depilatory agent. The heart was imaged in the 2D mode in the parasternal long-axis view. From this view, an M-mode curser was positioned perpendicular to the interventricular septum and the posterior wall of the left ventricle (IV) at the level of the papillary muscles. LV free wall thickness in diastole (LVWTD) and in systole (LVWTS) as well as LV diameter in diastole (LVDD) and in systole (LVDS) were measured. All measurements were done from leading edge to leading edge according to the American Society of Echocardiography guidelines. The measurements were taken in 3 separate M mode images and averaged. Ejection fraction (EF) was calculated using the formula % EF= [(LVVD−LVVS)/LVVD]×100, where LVVD and LVVS are LV volume in diastole and systole respectively.

Mouse Tissue Collection and Preparation

Hearts and testes were dissected from sham and MI mice one and seven days post artery ligation. Tissues were rinsed in diethyl pyrocardbonate (DEPC)-treated PBS, snap frozen in liquid nitrogen and stored at −80'° C. until use. Note, specific care was taken to gently squeeze the hearts with forceps in DEPC-treated PBS to minimize residual blood contamination.

Embryonic Stem Cell Culture and Differentiation

Nkx2.5-EmGFP BAC reporter ES cell line (129/OlaHsd strain, subline E14Tg2A.4) were kindly provided by Edward C Hsiao (Gladstone Institute of Cardiovascular Research, San Francisco) and maintained and cultured as previously described (Ounzain S, et al., 2014). Cells were cultured on mouse embryonic fibroblasts feeders or on gelatinized plates in standard ES cell medium supplemented with 1000 U/ml of LIF. Cardiac differentiation of ES cells was induced by aggregating aliquots containing 1000 cells in hanging drops to form embryoid bodies (Ounzain S, et al., 2014).

Primary Cell Cultures and Transfections

Neonatal C57B6 mice were sacrificed within the first 24 h after birth. Beating hearts were removed, atria and great vessels were carefully dissected away and placed on ice in ADS buffer (H2O, NaCl 116 mM, HEPES 20 mM, NaH2PO4 1 mM, KCl 5.4 mM, MgSO4 0.8 mM, glucose 5.5 mM). The hearts were minced using a sterile and sharp razorblade, and placed in a 1.5 ml tubes (5-6 hearts per tube) containing 1 ml of PIB digestion buffer (ADS buffer+0.05 mg/ml Collagenase type II (Worthington)+1 mg/ml Pancreatin (Sigma). Place the tubes at 37° C. with shaking at 1000 rpm per 15 minutes, collect the supernatants on a tubes containing a volume of complete medium (DMEM 75%, M199 25% ml, Pennicilin/streptavidin 1×, L-Glutamine 1×, Horse serum 10%, Fetal Cow Serum 5%) equal to the sum of all supernatants from digestion tubes. Add 1 ml of PIB buffer to undigested tissue fragments still in the tubes and repeat the digestions process other 2 times. After the 3 steps of digestion spin down the cells by centrifugation at 800 rpm for 10 minutes at room temperature. Discard the supernatant and resuspend the pellet in adequate volume of complete medium (2 ml each 5-6 hearts). Plate cells in 10 cm dish for 45 minutes in an incubator 37° C., 10% $CO_2$ (pre-plating 1); after this step the non-myocytes will adhere and the cardiomyocytes will remain in suspension. Transfer the supernatant on a new 10 cm dish to repeat this step another time (pre-plating 2) Add fresh complete medium to the pre-plating dish to culture the non-myocytes cells. After the second pre-plating collect the supernatant in a new tube, count the cells and seed 300.000 cardiomyocytes on gelatin coated 3.5 cm plates. One day after isolation, a final concentration of 100 nM of LNATM longRNA GapmeRs (Exiqon) was transfected on cardiomyocytes using FuGene 6 (Promega). After 72 hr, RNA was extracted using miRNeasy kit (Qiagen) and the knock down confirmed by qPCR. Gapmer Sequences, Scrambled; TCATACTATATGACAG (SEQ ID No 106), Anti-Novlnc6 TACAACCTGCTTACT (SEQ ID No 105).

Nuclear and Cytoplasmic RNA Fraction Isolations

Nuclear and cytoplasmic RNA fractions were isolated using the Cytoplasmic and Nuclear RNA purification kit (Norgen Biotek Corp, CA, Cat No; 37400) according to the manufacturers instructions.

RNA Isolation, Reverse Transcription, End-Point PCR and Quantitative PCR.

Primer sequences for qRT-PCR are provided below. For TaqMan probe based qRT-PCR expression was analyzed using fluorescent-labeled TaqMan Probes (ABI). Analysis was carried out using an ABI Prism 7500 cycler and relative expression quantified using the ΔΔCt method. For end-point PCR aliquots of PCR mixtures were taken during different cycles for agarose gel analysis to determine linear range of amplification. All reactions were run on a 1.5% agarose gel stained with Ethidium Bromide. Primer sequences were as follows (Fw, Rv).

```
Novlnc6;
                              (SEQ ID No 107, 108)
GTGGGGAGGTCAGCTACAAA; CGGAAATGGTTTGAAATGCT, Novlnc11;
                              (SEQ ID No 109, 110)
ACAGACCTGCAGCAGTGAGA; GCTAGGGAACGCAGAACAAG, Novlnc15;
                              (SEQ ID No 111, 112)
AAGGCTTCCCAGAGAAGGAG; ACTGGGTGAGTCTCGCTGTT, Novlnc23;
                              (SEQ ID No 113, 114)
TGGGACAGCAGAGCTAAGGT; AGATTCCAGCACGCACTTCT, Novlnc32;
                              (SEQ ID No 115, 116)
AAAGGGAAGAGGGAAAACGA; CGTCTAGAACCAGCCCAGAG, Novlnc35;
                              (SEQ ID No 117, 118)
CAGCCCTGCTTTAGTTCCTG; TTCGTTGGGGATTTTACTGC, Novlnc44;
                              (SEQ ID No 119, 120)
TTTGGAGATGGAACCTGGAG; TCTGGTATGGGGGAGACTTG, Novlnc49;
                              (SEQ ID No 121, 122)
AGCTCTGGGTTGGACTGAGA; TGCATACATTCTGGCAGAGC, Novlnc61;
                              (SEQ ID No 123, 124)
GGTTGGGTGCCTATTAAACG; GGTTCATGAGCCTTTGGAAG, Novlnc76;
                              (SEQ ID No 125, 126)
TGTTAATTCAGGGGCACACA; GGTGGAGAGCCACTGAAGAG, Novlnc86;
                              (SEQ ID No 127, 128)
TCTCTGTCCCTTGTGTGTGC; CTTGGAGGTGTGGGCATAGT, Novlnc90;
                              (SEQ ID No 129, 130)
GAGCCAAGTGCACACAGAAA; TGGTCTGTTCCTGGCCTTAG, Novlnc95;
                              (SEQ ID No 131, 132)
GTGGACGACAAGGGAGGTTA; CGGAATGGCTCCTACAACAT, Novlnc96;
                              (SEQ ID No 133, 134)
GAGGCTCCTGGATCTCTGTG; TTGGGAGGCAAAGGTAGATG, Novlnc103;
                              (SEQ ID No 135, 136)
GAAATGAGTGGTGGCAGTGA; CTTAGGTCTGCGCCTAATGG, Novlnc174;
                              (SEQ ID No 137, 138)
GCACAGATGCATAGCCTCAA; GCAGCCTGGACTTTTCTCAC, Novlnc333;
                              (SEQ ID No 139, 140)
TCACCTCCAAGTGGGTCTTC; AGCTCGGTCTGTCGTGAGTT, MmMyocardin;
                              (SEQ ID No 141, 142)
CAAGGCTTAATACCGCCACTG; AATGTGCATAGTAACCAGGCTG, MmBMP10;
```

-continued

```
                              (SEQ ID No 143, 144)
ATGGGGTCTCTGGTTCTGC; CAATACCATCTTGCTCCGTGAA,

MmTbx20;
                              (SEQ ID No 145, 146)
AAGAGATACCGCTATGCCTACC; GCTGCTCGCCAGTAAAGGG,

Col1a1;
Mm_00801666_g1,

CTGF;
Mm_01192931_g1,

NPPA;
Mm_01255747_g1,

TGFb2;
Mm_00436955_m1,

Nkx2-5;
Mm_00657783_m1,

GATA4;
Mm_00484689_m1,

Tbx5;
Mm_00803521_m1,

Myh6;
Mm_00440354_m1,

Myh7;
Mm_00600555_m1,

NPPB;
Mm_00435304_g1.
```

RNA Sequencing and Analysis

Total RNA was isolated from adult mouse hearts using the RNeasy isolation kit (Qiagen). Sequencing libraries were prepared according to Illumina RNA Seq library kit instructions with Poly(A) selection. Libraries were sequenced with the Illumina HiSeq2000 (2×100 bp).

Sequence Analysis of Long RNA Reads

100nt paired-end reads from 8 samples (4 Sham, 4 LAD) were mapped to mm9 reference genome using Tophat software version 2.0.5 (Trapnell et al., 2012) with option "Gene model"-G, using mm9 UCSC reference genes GTF (Karolchik et al., 2003). An ab initio transcript reconstruction was performed using Cufflinks, version 2.0.2 (Trapnell et al., 2012). The option "masking" (-G) was used, using mm9 UCSC reference genes GTF. The other parameters were default. The resulting GTFs were merged using Cuffmerge, version 2.0.2, using option -g with mm9 UCSC GTF as reference, allowing distinguishing known and novel transcripts.

Classification of lncRNA

Using the output of Cuffmerge, the transcripts were classified into 3 categories: known mRNAs, known lncRNAs (UCSC as reference) and novel lncRNAs. Novel transcripts were filtered for minimal length of 200 bp and at least 2 exons. Read counts were then calculated per gene from the alignment bam files using HTSeq (v0.5.4p2) with options -m union --stranded no. Genes were then filtered for minimal expression (mean counts>=5 across all conditions). lncRNA genes were classified into several categories by comparing the lncRNA exon and gene coordinates with coordinates of known protein coding genes. The categories were as follows: 'Intergenic Same Strand' was where all exons of the lncRNA gene were between two protein coding genes; 'Intergenic Convergent' was where a protein coding and lncRNA gene are transcribed on opposite strands but pointing towards each other; 'Intergenic Divergent' was where a protein coding and lncRNA gene are transcribed on opposite strands but pointing away from each other; 'Exonic Sense' was where at least one exon of an lncRNA overlapped with an exon of a protein coding gene in the same direction; 'Exonic Antisense' was the same as for 'Exonic Sense' but with lncRNA and protein coding genes on opposite strands; 'Intronic Sense' and 'Intronic Antisense' were where a lncRNA was completely contained within the intron of a protein coding gene on the same, or opposite strand respectively; 'Overlapping Sense' and 'Overlapping Antisense' was where a lncRNA gene's coordinates overlapped with those of a protein coding gene on the same or opposite strand respectively.

Differential Expression Analysis of lncRNAs

Count data was fitted to a statistical model based on the negative binomial distribution using the R package DESeq, which is useful for detecting significant RNA-Seq variation with a low number of biological replicates. To perform the normalization and differential expression analysis, raw read counts per gene were normalized to the relative size of each library. Empirical dispersion (the squared coefficient of variation for each gene) was estimated using the pooled method. Here, samples from all conditions with replicates are used to estimate a single pooled dispersion value, which is applied to all samples. The dispersion-mean relationship was then fitted using the local method and the fitted value only was used in subsequent calculations. The difference between the means of treated vs non-treated samples was then calculated using a negative binomial test and p-values were adjusted for multiple comparisons using the Benjamini-Hochberg method. Genes with an adjusted p-value of ≤0.01 were considered to be differentially expressed.

LncRNA Analysis

Coding potential—The protein-coding potential of transcripts was evaluated using the program GeneID, version v1.4.4, applied to transcript sequences in FASTA format, with parameters adapted for vertebrates as provided by the authors in file GeneID.human.070123.param, and with options -s and -G.

PhastCons score—PhastCons scores (calculated on a multiple alignments of 30 vertebrate genomes to the mm9 mouse genome) by chromosome were downloaded from the UCSC website. For each gene, scores per base for exons, introns and promoters (defined as 1000 bp upstream from TSS) were summed and divided by the fragment length. This result was used as the score per fragment. 50000 random intergenic regions were generated (size=3400 bp±20%) and the same score was calculated. Log 10 of the scores was plotted by category using R package lattice. The scores of the intergenic regions were added to the 3 plots (exon, intron, promoter) as a comparison.

Chromatin Marker Levels

For the analysis of chromatin marker levels at promoters, we used data published by Wamstad et al. (Wamstad et al., 2012), observed in cell lines representative of successive stages along cardiac differentiation (ESC, MES, CP, CM) (downloaded from data repository of the Cardiovascular Development Consortium (CvDC), part of the NHLBI Bench to Bassinet Program). Levels of five markers (H3K4me1, H3K4me3, H3K27ac, H3K27me3 and RNAP Ser5P) were evaluated within 2 kb regions centered on the TSS of each transcript, using the map command of the BEDTools program, version 2.17.0, with default parameters. These levels were normalized by computing the ratio of ChIP to input WCE DNA within the same region. Based on the resulting profiles, transcripts were distributed among the 31 ChIP clusters identified by Wamstad et al. (Wamstad et al., 2012). Each transcript t was ascribed to the nearest cluster, as measured by a distance d(t,C) based on the Spearman correlation S(t,c) of profiles between the transcript t and the n members c of cluster C:

$$d(t, C) = 1 - \left(\frac{1}{n}\sum_{1}^{n}|S(t, c_n)|\right)$$

Chromatin States

To analyze the presence of chromatin marker peaks at promoters, we used data published by Wamstad et al. (Wamstad et al., 2012), observed on cardiac differentiation cell lines, and data observed in adult tissue (heart, kidney, liver, spleen, testis) published as part of the ENCODE project (The ENCODE Project Consortium, 2011), generated and analyzed in Bing Ren's laboratory at the Ludwig Institute for Cancer Research, UCSC. Four markers were considered: H3K4me1, H3K4me3, H3K27ac and H3K27me3. Depending on presence of these markers, each transcript was ascribed to one of eight distinct chromatin states: H3K4me1, H3K4me3, or H3K27me3 alone, combination of H3K4me3 and H3K27me3, H3K4mc3 and H3K27ac, H3K27me3 and H3K4me1, H3K27ac and H3K4me1, or none of these previous combinations. A marker was considered present if a non-empty intersection could be detected between the TSS region and a marker peak, in any of the replicates. The intersections were detected using the window command of the BEDTools program (Quinlan and Hall, 2010), version 2.17.0, with option -w 1000.

Mosaic Plots

Mosaic plots were used to visualize joint frequency distributions (e.g. across ChIP clusters, gene categories or differential expression status). These plots were generated using the cdv R package.

In some of these plots, a residual-based shading was applied to visualize the pattern of deviation from independence. Most data processing, statistical analysis and generation of graphics was performed using the R language (R core team, 2013).

Gene Expression Across Tissues-Expression Heatmaps

Expression of the genes (RefSeq+novel lncRNAs) in 18 mouse tissues (Adrenal, Bladder, Colon, Duodenum, Heart, Kidney, Large Intestine, Liver, Lung, Mammary gland, Ovary, Placenta, Subcutaneous Adipose tissue, Small Intestine, Spleen, Stomach, Testis, Thymus) was measured on ENCODE public data (CSHL Long RNA-seq, PI Gingeras, Lab CSHL-m) (The ENCODE Project Consortium, 2011). Counts on plus and minus strands were summed and mean counts were taken for the two replicates per tissue. Expression for the same genes was also measured on the 8 LAD/Sham samples. Between sample normalisation was performed using DESeq (estimateSizeFactors function. Only genes with minimal expression were kept (mean counts>=5 across all conditions). Heart Specificity (HS) score (per gene) was defined as:

$$HS \text{ score} = \frac{\mu_{cardiac}}{\mu_{non-cardiac} + 2*\sigma_{non-cardiac}}$$

Where μcardiac is the average expression per gene in our 8 samples, μnon-cardiac is the average expression per gene in non-cardiac ENCODE samples, and σ non-cardiac is the standard deviation per gene in non-cardiac ENCODE samples. (adapted from (Anders and Huber, 2010b)). A gene was considered heart specific with HS score>1. Heatmaps were generated using heatmap.2 from the package gplots in R, version 2.11.0. The clustering was performed using hclust, version 1.3.1, using Spearman correlation and euclidean distance, average linkage clustering. A scaling by row was applied. The same sample order was used for all heatmaps to enable comparison. The HS bars were generated using the HS score defined above. The filter for differentially expressed genes is adjusted p-value for differential expression<0.01. P-values for significance of difference between percentages of HS between groups were calculated using Pearson Chi-squared test.

Correlation of Expression Between Novel lncRNAs and Closest Coding Genes

The coordinates of the novel lncRNAs were compared to RefSeq coding genes reference. If the coordinates of the lncRNA overlapped with a known gene (at least 1 bp), this gene was considered as the closest overlapping gene. If there was no overlap with a known gene, the closest gene was selected and classified as upstream or downstream depending on its position. For gene expression, the same data as in Expression heatmap was used. The correlation of expression was calculated between the lncRNA and closest coding gene using Pearson correlation. This was done for novel and UCSC lncRNAs. As a comparison, the same method was applied on 2000 non-redundant random pairs of closest coding genes. To generate a set of correlations between random mRNA pairs, a pairwise Pearson correlation matrix was calculated between all genes, and 100 k random pairs were selected from it (excluding redundant ones)

Correlation Gene Expression—Physiological Traits

All heatmaps were generated using the R heatmap.2 function, from package gplots. No scaling was applied. All clustering was performed using the R function hclust. Physiological traits were correlated using the Spearman method, and clustering was using euclidean distance and complete linkage clustering. Correlation between physiological traits and gene expression was calculated using the Spearman method, comparing 2 vectors containing 8 values of gene expression and 8 values of trait measure, respectively. Horizontal and vertical clustering were performed on the expression and traits values, using the Spearman method for the correlation, and average linkage clustering. The density plots of the Heart Specificity by category used the same HS scores as described above and were performed using R package gplots, function ggplot.

TransMap

The GTF file containing the novel lncRNAs to transmap from mouse to human was converted into a psl file using utilities gtfToGenePred and genePredToPsl. pslMap utility was then used with the new psl file and ENCODE chain alignment hg19.mm9.all.chain downloaded from the UCSC website. The orthologs discovered by pslMap were then filtered using pslCDnaFilter with option -globalNearBest=0.005 and -minCover=0.2. The 4 standalone programs used above were downloaded from UCSC utilities.

Visualisation on UCSC

Bigwig files were generated using Bedtools suite, version 2.17.0 from the bam files generated by Tophat. The tool used was genomeCoverageBed, with options -bg, -ibam and -scale. The size factors used to scale were calculated using DESeq (as described above). The bigwig files were then uploaded on an ftp server and the link was uploaded on the UCSC genome browser.

GO Analysis—Enrichment for Biological Themes

The genes lists were submitted online to the DAVID Functional annotation clustering tool using default parameters and databases.

Human Methods

All human material was obtained during routine sampling used for clinical purposes, stored in a coded way and available for research purposes in accordance with the Declaration of Helsinki and the ethical committee at Maastricht University Medical Center. Right ventricular septal biopsies were obtained during routine clinical sampling from patients with idiopathic dilated cardiomyopathy (DCM) and decreased ejection fraction without cardiac inflammation. Controls (n=6) consisted of patients with unexplained ventricular tachy-arrhythmias but with a normal ejection fraction and the absence of systemic or cardiac inflammation at the time of biopsy. Left ventricular biopsies were obtained from patients with aortic stenosis (AOS) and from control patients undergoing coronary artery bypass grafting (CABG) (Suppl. Table Y). Cardiac biopsies were immediately snap-frozen for total RNA was isolation with the miR Vana miRNA isolation kit (Ambion, Austin, TX). Total RNA was reverse transcribed using iSCript (Bio-Rad, Hercules, CA) and SYBR Green quantitative PCR was performed on a Bio-Rad iCycler.

Statistical Analysis

Data throughout the paper are expressed as mean±SEM. One way ANOVA was used to test significance of data comparisons between experimental groups, with p values <0.05 were considered significant.

Results

Global Identification of lncRNAs Expressed in the Heart and Regulated During Myocardial Infarction The Inventors first set out to characterize global transcriptional regulation during myocardial adaptation to stress for both the coding and non-coding transcriptome alike. The Inventors utilized a well-characterized pathophysiological model of cardiac stress in the mouse, namely myocardial infarction obtained by left anterior descending artery ligation. The Inventors identified lncRNAs expressed in the infarcted adult mouse heart by employing a RNA-Sequencing (PolyA+RNA-Seq) and ab initio transcriptome reconstruction approach. Illumina-based massively parallel sequencing was used to obtain paired-end reads (2×100 bp) of experimental libraries, and Cufflinks ( ) was utilized to perform ab initio transcript assembly on mapped paired-end reads.

This analysis reconstructed 17584 multi-exonic transcripts, of which 15075 (2204 up-regulated and 1338 down-regulated) correspond to University of California Santa Cruz (UCSC) annotated protein coding genes (See Ounzain S, et al., 2014). Our lncRNA annotation pipeline identified 2509 multi-exonic lncRNAs (>200 bp). There were 988 (67up-regulated and 66 down-regulated) UCSC annotated lncR-NAs and 1521 (86 up-regulated and 225 down-regulated) novel previously un-annotated lncRNAs, encompassing all known lncRNA locus-types (data now show). To verify the non-coding nature of our novel lncRNA candidates, The Inventors used GeneID coding potential score algorithm and found that these novel transcripts encode minimal protein coding potential comparable to UCSC annotated lncRNAs (see Ounzain S, et al., 2014). Furthermore, novel lncRNAs and UCSC lncRNAs were expressed at significantly lower levels than coding genes (FIG. 1B). UCSC lncRNA exons were less conserved than coding exons although promoters were equally conserved (FIG. 1B).

Novel lncRNAs are Heart Specific and Proximal to Cardiac Developmental Genes

The majority of lncRNAs identified in our analysis represent novel lncRNAs that have previously escaped annotation. The Inventors aligned 17 mouse non-cardiac ENCODE RNA-Seq data sets (Mouse et al., 2012), and found that 16% of UCSC mRNAs and 23% of UCSC lncRNAs were classified as heart specific (see Ounzain S, et al., 2014). By contrast, 38% of the novel lncRNAs were heart-specific, a significant enrichment versus UCSC mRNAs and lncRNAs. Furthermore, differentially expressed novel lncRNAs were significantly more heart-specific than all transcript classes, with 60% of these novel lncRNAs being classified as heart specific (see Ounzain S, et al., 2014). LncRNAs have been shown to regulate coding gene expression both in cis and in trans. If cis-regulation was common, one would expect proximal coding genes to also be more heart-specific. In support of this, The Inventors found that overlapping, proximal upstream or downstream coding genes were significantly more heart-specific than the entire coding gene collection. Furthermore, gene ontology analysis of these proximal coding genes revealed significant enrichment of biological processes associated with heart development, cardiac function and transcriptional regulation. Interestingly differentially expressed novel lncRNAs were more associated with transcriptional control suggesting that modulated expressed novel lncRNAs may be implicated in transcriptional reprogramming observed in the remodeling heart.

The Cardiac Transcriptome is Highly Correlated with Cardiac Physiological Traits The Inventors correlated the cardiac transcriptome with echocardiography derived physiological traits. Both the coding and non-coding transcriptome correlated tightly with cardiac physiology (FIG. 1). Globally, novel lncRNAs were better correlated than UCSC lncRNAs with all physiological traits assessed. To gain a deeper molecular insight and potentially identify molecular pathways associated with physiological traits, The Inventors executed unsupervised clustering and further downstream analysis of UCSC coding genes and novel lncRNAs. The Inventors identified four clusters for both coding (FIG. 1A.-B) and novel lncRNA (FIG. 1C, -D) transcripts. In each case, these consisted of one cluster that correlated positively with cardiac function and negatively with remodeling parameters, one cluster with the inverse of these correlations and two clusters with non-specific intermediate correlations. Gene ontology (GO) and heart specificity analysis was executed on individual clusters with GO analysis being executed on the most proximal coding genes with respect to novel lncRNAs. In the coding gene group, the most heart-specific cluster was Cluster 2 (FIG. 1E), which was positively correlated with cardiac functional traits and associated with genes involved in mitochondrial biology (FIG. 1A). The least heart-specific cluster (Cluster 4) was positively correlated with remodeling and associated with genes involved in wound healing and extracellular matrix (FIG. 1A). Within novel lncRNAs, the most heart-specific cluster, i.e. Cluster 4 (FIG. 1F), was again positively correlated with cardiac function associated traits. Proximal coding genes to novel lncRNA in Cluster 4 were enriched with heart development associated processes (FIG. 1C). Since novel lncRNAs that cluster specifically with particular physiological traits were likely to be involved in biological processes associated with those traits, these findings indicated that novel lncRNAs within this cluster could represent a class of cardiac-specific regulators of developmental gene programs, which was reactivated in the damaged myocardium. Finally, the least heart specific clusters were one and two, which was positively correlated with remodeling traits.

These data demonstrated that unsupervised clustering of transcripts was able to distinguish physiological traits. In addition, it indicated that lncRNAs could represent specific markers of particular physiological traits. To test this, The Inventors compared correlation distributions for each UCSC coding gene and novel lncRNA cluster, with each of the following traits; ejection fraction (EF), interventricular septal thickness at systole (IVS), myocardial infarction trace (MI trace) and left ventricular internal diameter at systole (LVID) (FIGS. 1B and D). UCSC coding gene Clusters 2 and 4 strongly correlated with all these traits when compared to non-specific clusters (Clusters 1 and 3) (FIG. 1B). A similar pattern of correlation was observed with novel lncRNA clusters 2 and 4 (FIG. 1D). However, novel lncRNA Cluster 1 was particularly interesting since it exhibited poor correlation with LVID, EF and MI trace but correlated well with IVS which is typically linked to EF3. This unique characteristic is likely a consequence of the exquisite context and cell-type specific expression of lncRNAs, and has intriguing implications for the utilization of novel lncRNAs as biomarkers.

Inferring Functions for Novel lncRNAs Based on Developmental Chromatin State Patterns Pathological cardiac remodeling is associated with the global reactivation of the fetal gene program. The Inventors reasoned that many novel lncRNAs likely represent 'fetal' genes with important roles during cardiogenesis. To investigate this, The Inventors utilized ChIP-Seq data generated in a directed differentiation system that recapitulated the step-wise differentiation of mouse embryonic stem cells (ESCs) to differentiated cardiomyocytes (CMs) (Wamstad et al., 2012).

A previous study demonstrated that co-expressed genes during cardiac differentiation could be functionally grouped based on different chromatin state patterns (Wamstad et al., 2012). Each sub-group of genes appeared to be involved in distinct biological processes, including signaling, metabolism and cardiac muscle contraction. The Inventors reasoned that novel lncRNAs that shared specific chromatin patterns as those described for coding genes were likely to be involved in comparable biological processes, thus providing an unbiased chromatin based proxy to functionally annotate novel lncRNAs. The Inventors mapped the predetermined chromatin patterns (ChIP clusters 1 to 34) to the novel lncRNA promoters (and UCSC annotated genes) during ES cell differentiation. The Inventors classified the novel lncRNAs based on which chromatin pattern they were associated with, and inferred a biological function based on the coding genes and biological processes previously linked to each cluster (see Ounzain S, et al., 2014). For clarity, The Inventors present nine ChIP clusters and inferred biological processes associated with each of our transcript classes. ChIP clusters 1 and 3 are associated with ubiquitous housekeeping and non-cardiac developmental processes (see Ounzain S, et al., 2014). UCSC coding genes and lncRNAs were enriched within these clusters while novel lncRNAs were depleted. On the other hand, novel lnRNAs were enriched in ChIP-clusters 23, 24, 25 and 26 which are associated with cardiac developmental and functional processes including contractile fiber, z-disk and heart development terms (see Ounzain S, et al., 2014).

The Inventors also identified ChIP-clusters that were enriched or depleted in up and downregulated novel lncRNAs post myocardial infarction, providing a functional insight into the roles of novel lncRNAs in this response (see Ounzain S, et al., 2014). Novel lncRNAs in ChIP-clusters 23 and 24 were enriched in down-regulated lncRNAs post infarction. These clusters are associated with cardiomyocyte maturation and sarcomeric genes (eg. Myoz2, Myl2). The enrichment of ChIP-cluster 23 and 24 novel lncRNAs in down-regulated lncRNAs could be indicative of the re-activation of the fetal gene program in the border zone post infarction and/or a loss of mature cardiomyocytes. Furthermore, ChIP-clusters enriched in up-regulated novel lncRNAs included cluster 18, which is associated with immune and inflammatory responses (eg. IL17b), and cluster 28, which is associated with calcium homeostasis and G-protein coupled receptor signaling (cg. Gnb3), processes that are typically activated in the border zone of the infarcted heart. Finally giving further support to the notion that our novel lncRNAs may be cardiac developmental associated transcripts, The Inventors mapped them to a list of bona fide in vivo validated enhancers active specifically within the E11.5 mouse heart. The Inventors found that seven of our novel lncRNAs map to validated cardiac enhancers including novlnc6 (see below) which maps to mm77, a cardiac enhancer specifically active within the embryonic left ventricle (see Ounzain S, et al., 2014).

Validation of Novel lncRNAs

Figure 2A:
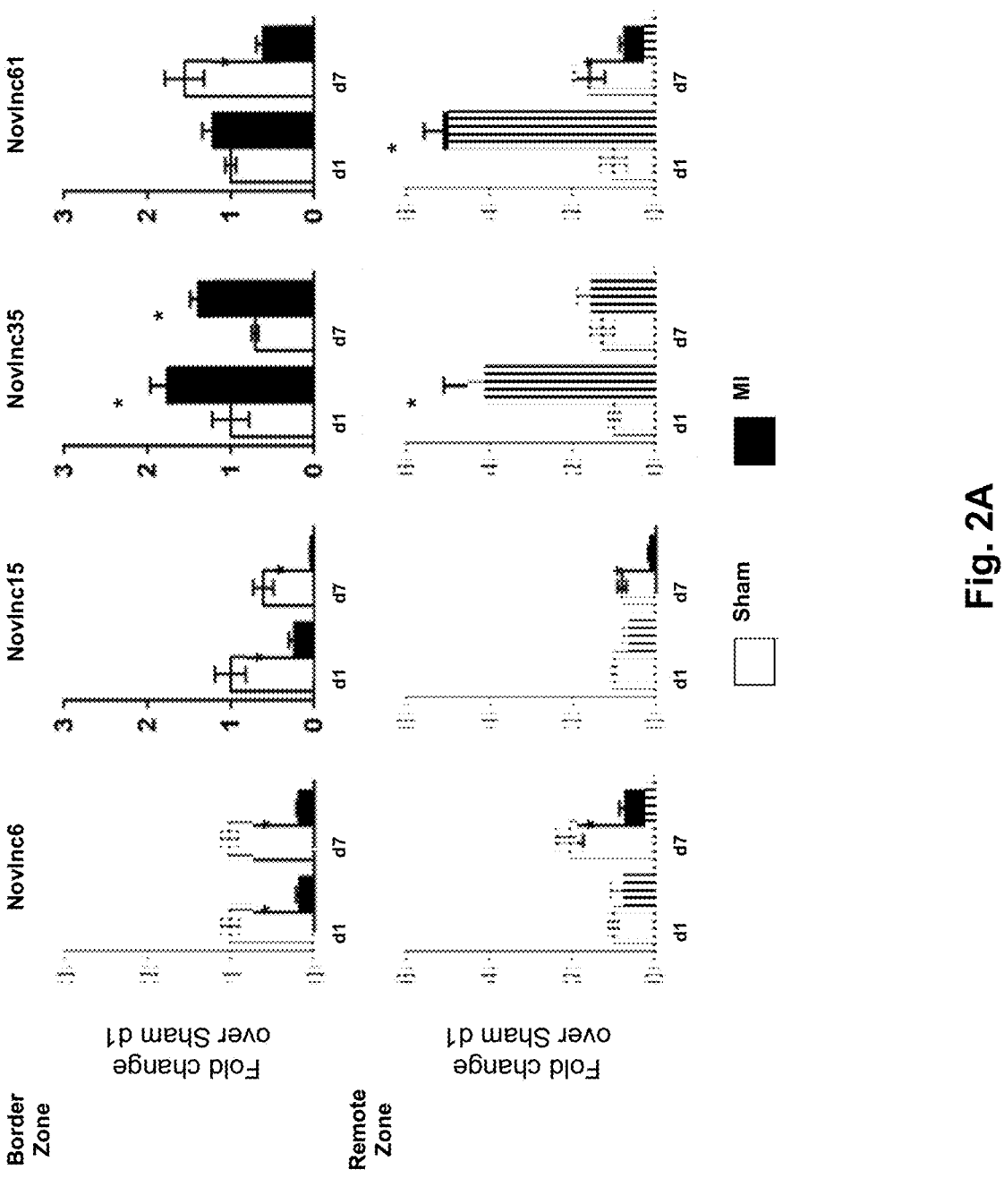

To gain confidence in our transcript nominations, The Inventors validated multiple unannotated novel transcripts by quantitative real-time PCR (qPCR). Seventeen high priority novel candidates were selected, and their expression was quantified in the border (BZ) and remote zones (R7.), one and seven days after infarction. The novel lncRNAs exhibited various kinetics of expression in both the BZ and RZ during the acute and chronic phases (FIG. 2A). Many lncRNAs were downregulated; e.g. Novlnc6 (SEQ ID No. 48) and 15 (SEQ ID No 97) some were transiently induced at day 1 in both RZ and BZ (Novlnc35) while others were gradually increased in BZ and RZ (Novlnc74). These distinct kinetic and spatial patterns of expression demonstrate that novel lncRNAs are dynamically regulated in response to myocardial infarction, and suggest that they likely play important roles in the adaptive process.

Figure 2D:
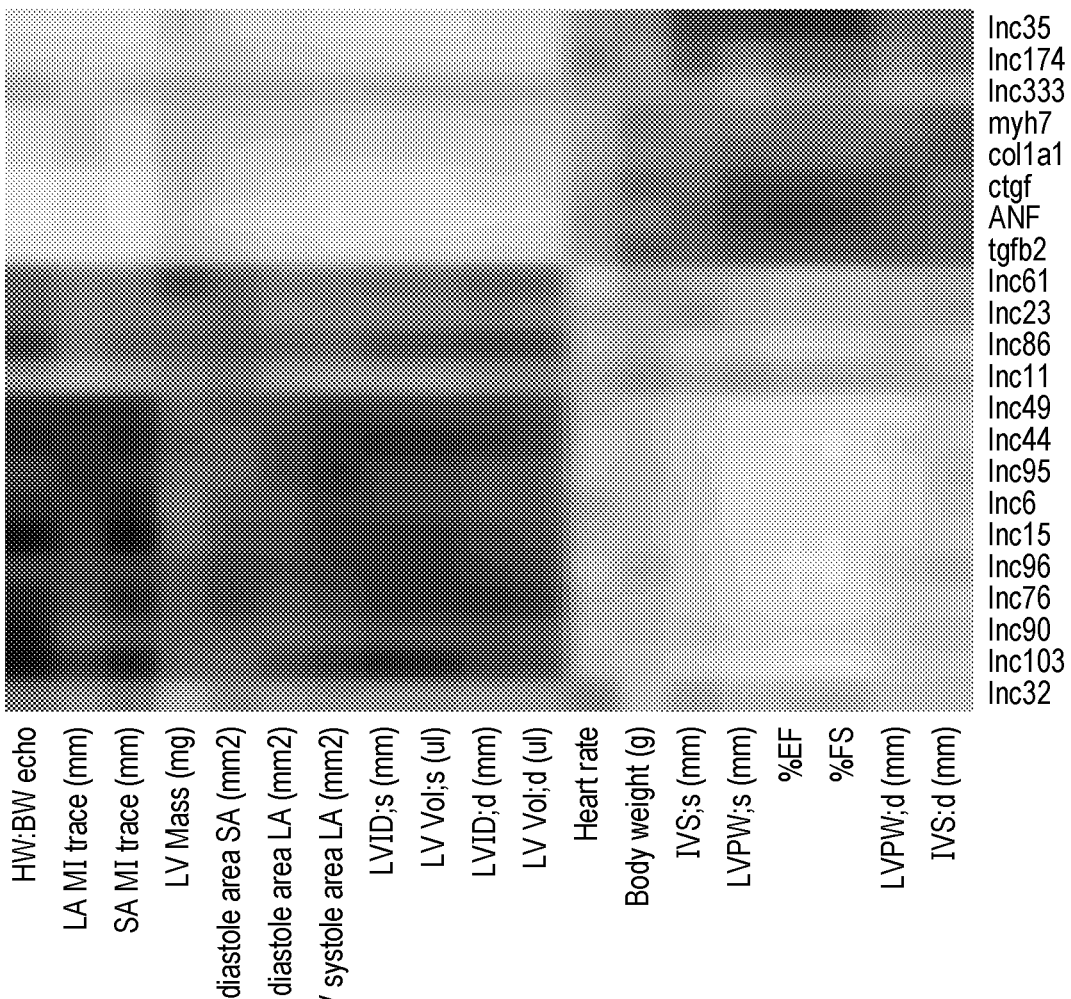
Figure 2D:
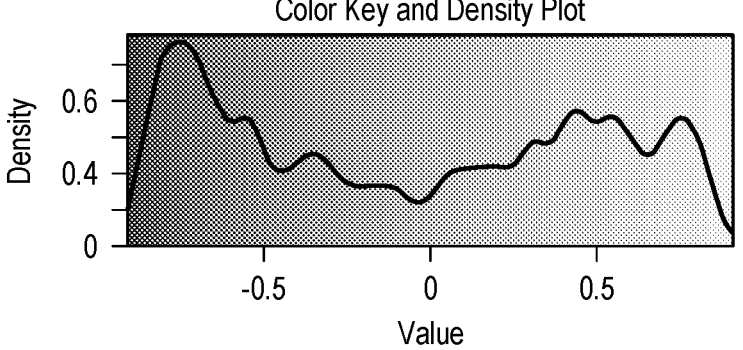

The two major cell types within the adult heart are cardiomyocytes (CMs) and cardiac fibroblasts (FBs) with both being important in maladaptive remodeling. To better characterize the novel lncRNAs, The Inventors quantified their expression in CMs and FBs isolated from the neonatal mouse heart. The selected lncRNAs were either highly CM-specific (Novlnc35; SEQ ID No 99), equally expressed in both cell types (Novlnc61, SEQ ID No 101) or primarily expressed in FBs (FIG. 2B). LncRNA function is also dependant on subcellular localization. Cis-acting lncRNAs (i.e. enhancer-associated RNAs) tend to be more enriched in the nucleus whereas lncRNAs involved in post-transcriptional and translational processes tend to be more cytoplasmic. Therefore, nuclear and cytoplasmic RNA fractions were isolated from neonatal CMs and FBs (FIG. 2C). Validated lncRNAs were either enriched in nuclear (Novlnc174; SEQ ID No 28) or cytoplasmic (Novlnc61; SEQ ID No 101) fractions, in addition to being equally present in both (Novlnc15). Some lncRNAs interestingly displayed differential nuclear versus cytoplasmic enrichment in CMs and FBs (Novlnc90, -49, -11; SEQ ID No 88, SEQ ID No 103, SEQ ID No 25). This may be of functional relevance to roles in these different cell types. The Inventors also correlated the expression of these validated lncRNA with physiological traits in day 1 and day 7 control and MI tissue samples (FIG. 2D). The majority of the lncRNAs correlated well with physiological traits both in border and remote zones. Interestingly, some of our novel lncRNAs were better correlated than stress genes with cardiac function and remodeling.

Figure 2E:
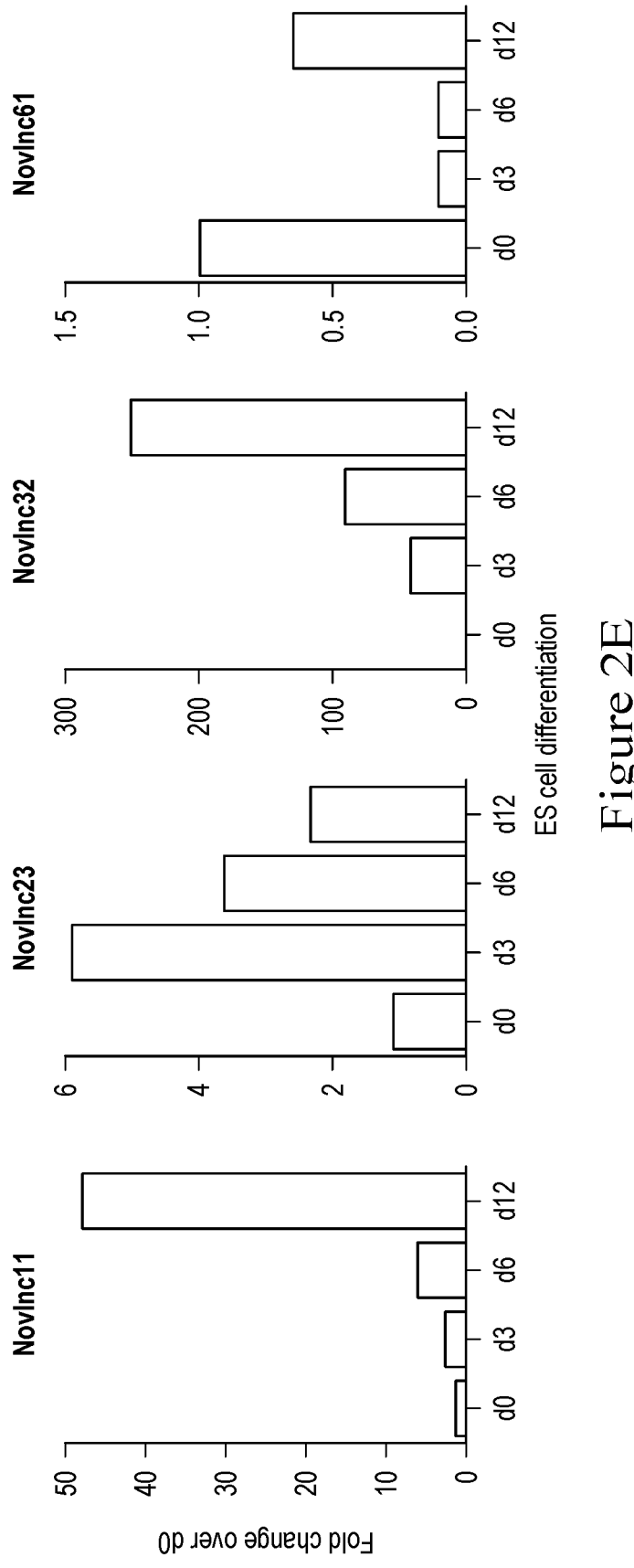
Figure 2F:
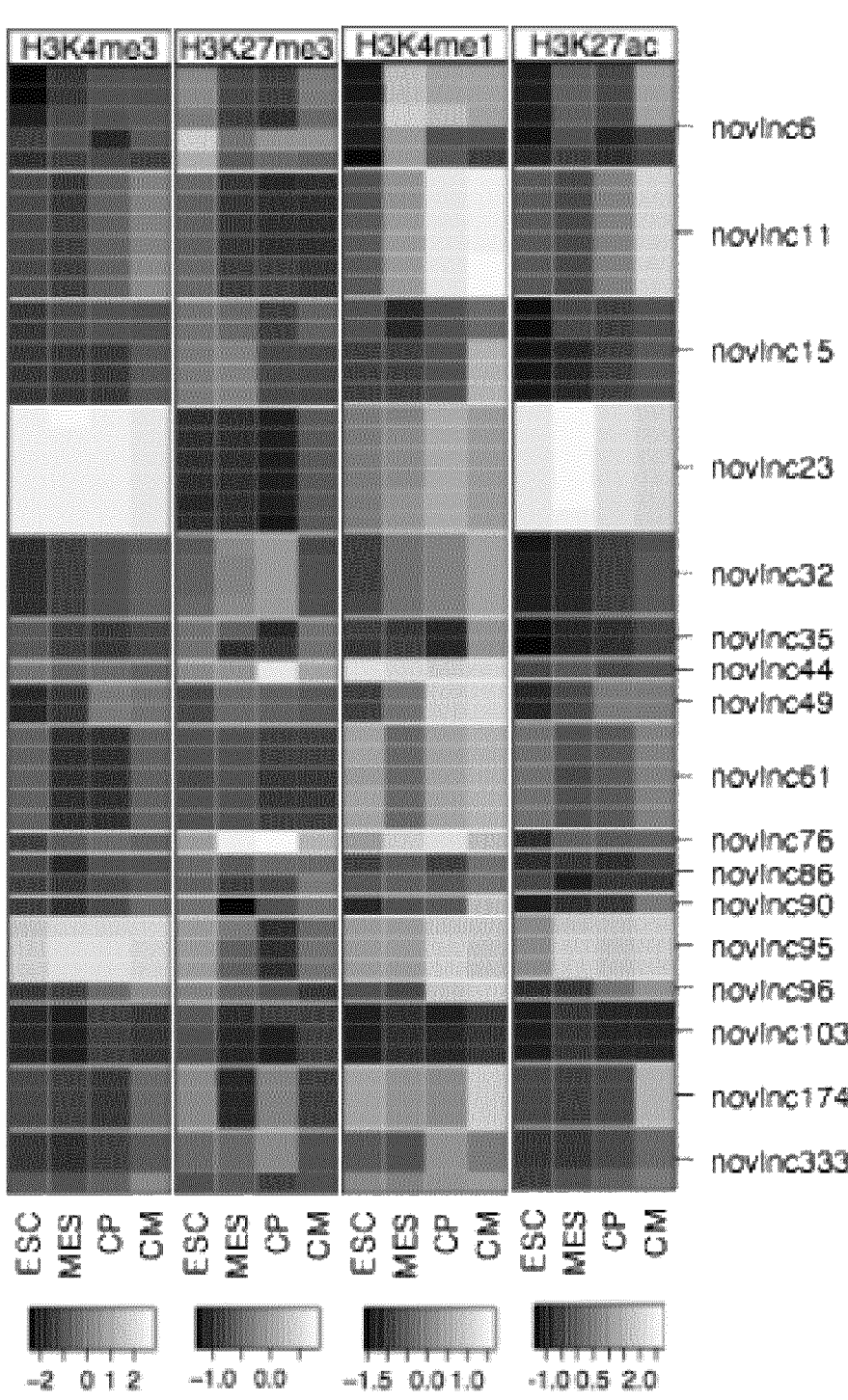

Many of the validated novel lncRNAs were associated with dynamic changes in chromatin states during cardiogenesis in ES cells, suggesting they may have roles as 'fetal' developmental genes (FIG. 2F). To confirm this, mouse ES cells were differentiated through embryoid body (EB) formation using the hanging droplet model recapitulating embryonic cardiac development in vitro. Novel lncRNAs were dynamically expressed during cardiac differentiation with expression correlating with the dynamic changes in chromatin states observed at their promoters (FIGS. 2E and F). Some lncRNAs were induced late during differentiation at the CM stage (Novlnc44, -11, -32; SEQ ID No 100, SEQ ID No 25, SEQ ID No 98, FIGS. 2E and F), and are therefore likely involved in terminal CM differentiation and maturation. Novel lncRNAs exhibiting this profile were mapped to ChIP-clusters 24 and 25, which are predicted to be associated with heart development, z-disk and sarcomere function, cardiac maturation associated processes. Other lncRNAs were maximally expressed at MES and CPC stages (Novlnc49, SEQ ID No 103) and are likely to be involved in more specific developmental process.

Figure 2G:
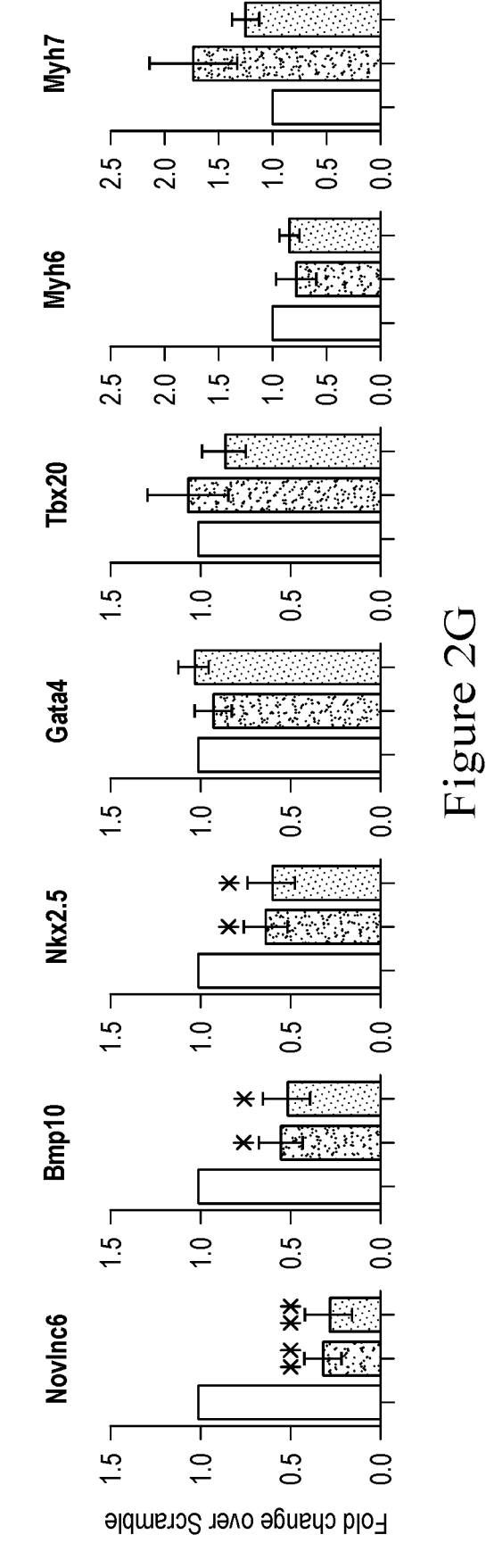
Figure 3A:
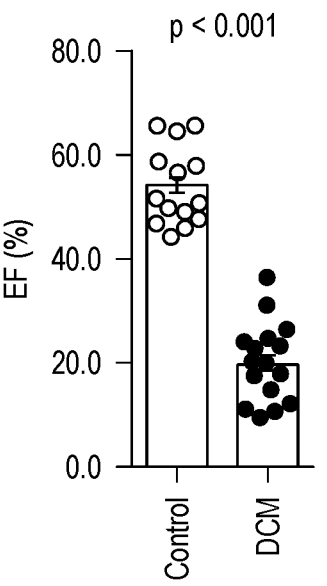
FIGS. 3A-E show the characterisation and validation of human orthologs in cardiac pathology.
Figure 3A:
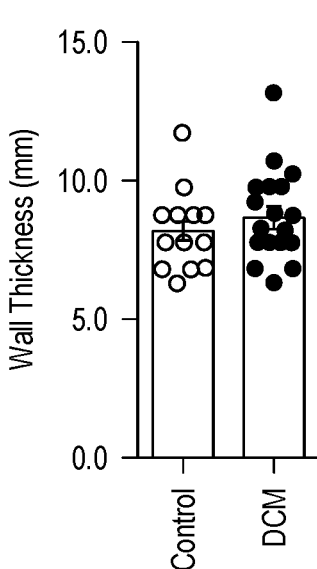
Figure 3B:
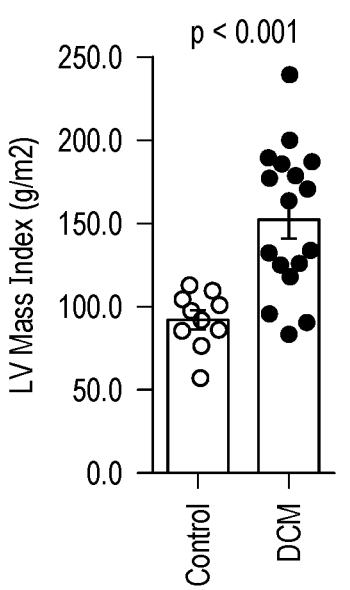
Figure 3B:
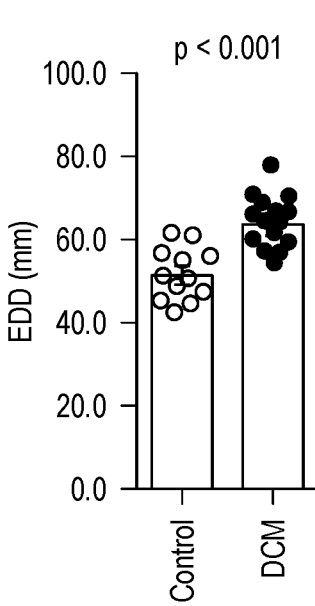
Figure 3C:
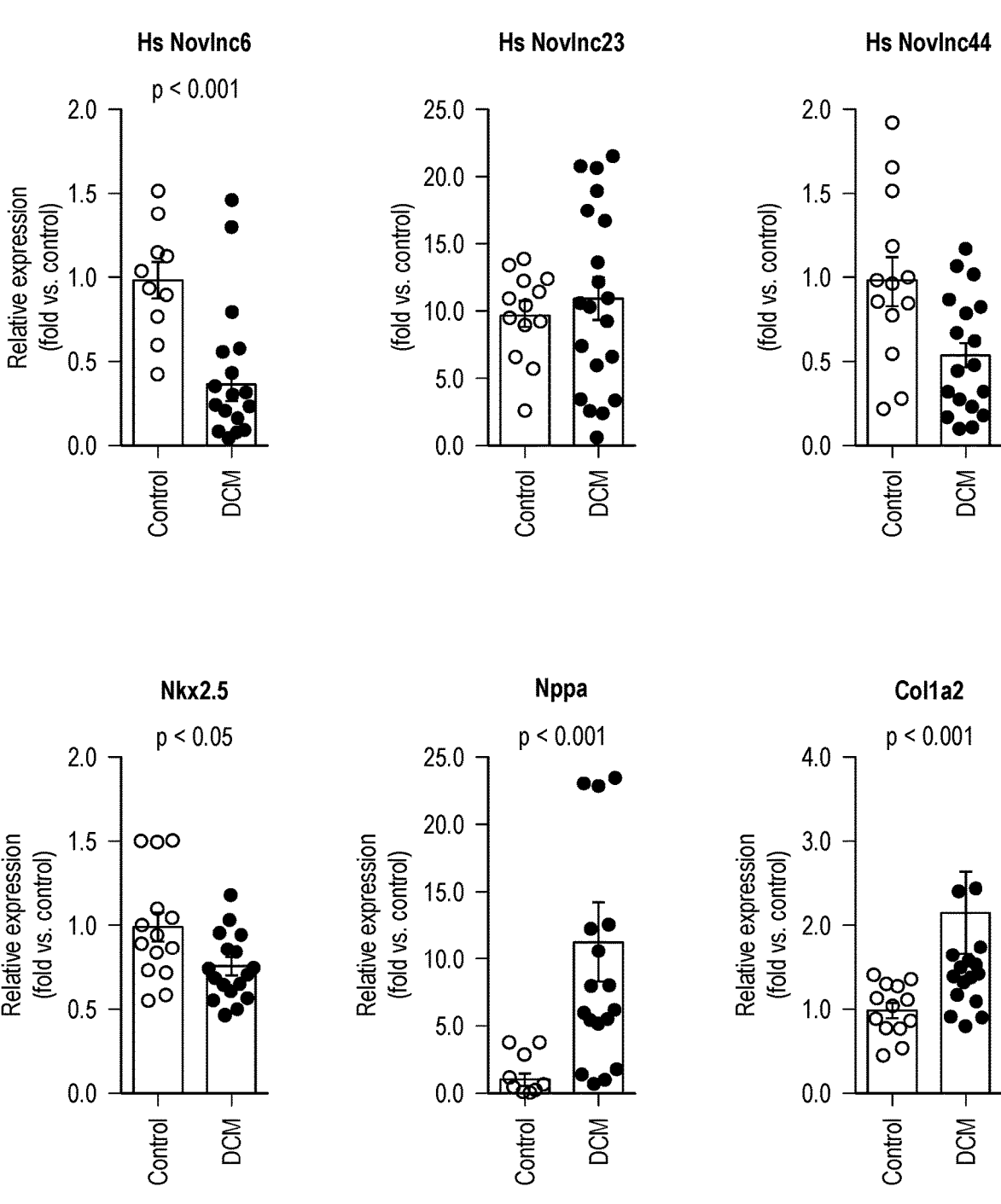
Figure 3D:
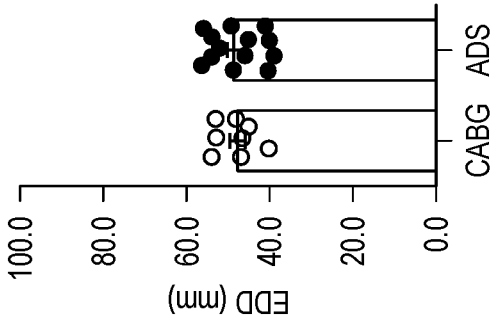
Figure 3D:
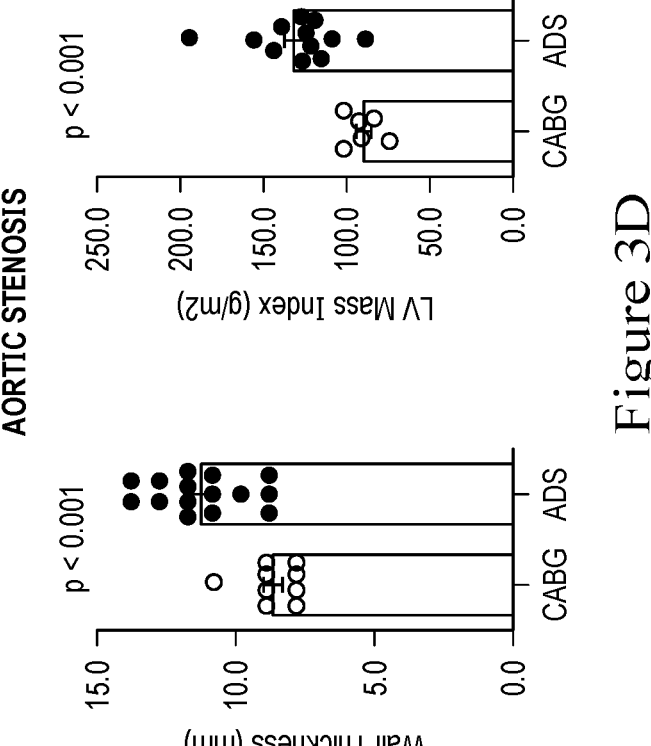
Figure 3D:
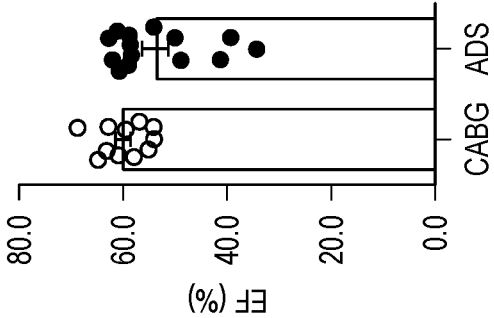
Figure 3E:
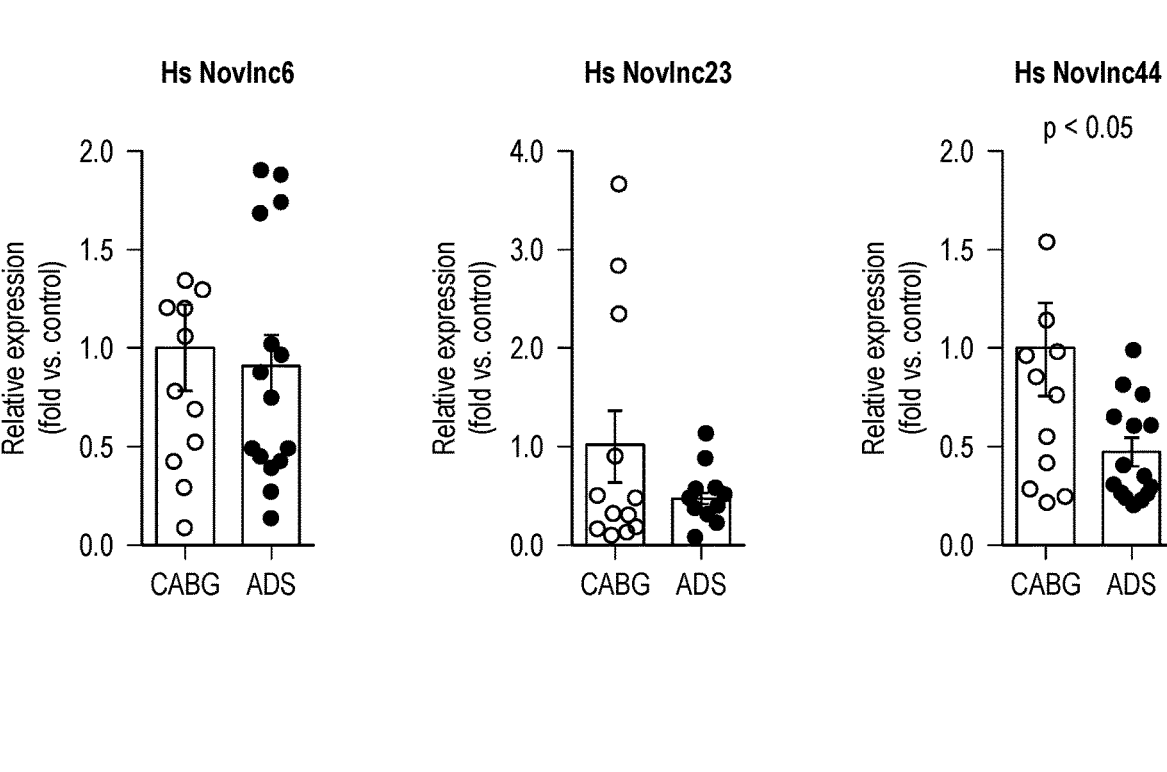
Figure 3E:
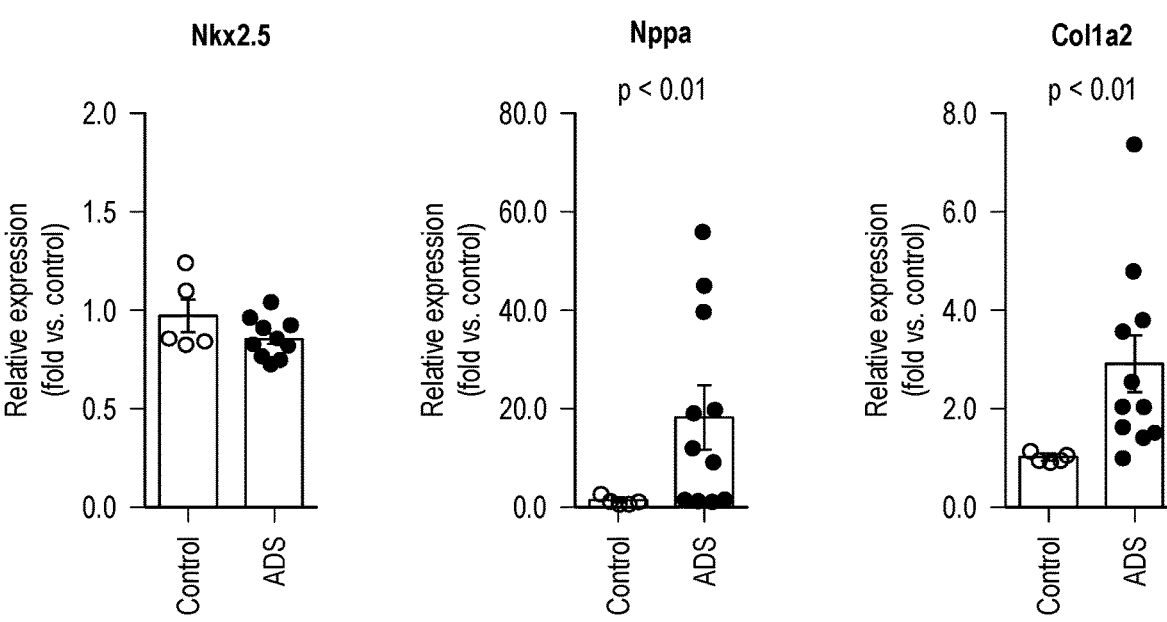

To evaluate whether novel lncRNAs could be associated to specific function involving regulation of cardiac protein coding genes, the Inventors focused on Novlnc6, which fulfills several criteria and unique features prototypical of lncRNAs identified in this study. Furthermore Novlnc6 (SEQ ID No 48) shares a chromatin pattern in differentiated ES cells with the key cardiac signaling ligand BMP10, suggesting Novlnc6 could be involved in similar regulatory pathways. As an experimental model, The Inventors used primary isolated neonatal mouse CMs expressing high levels of Novlnc6. Cells were transfected with modified anti-sense oligonucleotides (Gapmers) targeting Novlnc6 (FIG. 2G). Key cardiac TFs and downstream cardiac target genes involved in stress signaling, contractile apparatus and BMP10 signaling were examined. This screen identified Nkx2.5 mRNA as a potential target of Novlnc6-mediated regulation. Nkx2.5 encodes a core cardiac TF, high in the regulatory hierarchy of the cardiac GRN and critical for the regulation of other cardiac TFs and downstream cardiac differentiation, structural and maturation genes (Bruneau, 2002). Furthermore, Nkx2-5 has been shown to be downstream of BMP10 signaling during cardiac development (Huang et al., 2012). Novlnc6 positively regulated Nkx2,5, supporting the notion that our collection of novel lncRNAs contains functionally important regulatory transcripts. Dysregulation of Human Orthologs in Cardiac Pathology Considering the unique characteristics associated with the novel lncRNAs, The Inventors searched for human orthologs. The Inventors therefore mapped our novel lncRNA catalogue to the human genome using TransMap, a cross species mRNA alignment tool. TransMap maps our novel mouse lncRNAs sequences across the human genome using syntenic BLASTZ alignments that consider conserved gene order and synteny. Of the 311 modulated novel lncRNAs, approximately 72% were confidently mapped to the human genome. To validate and characterize predicted orthologs, The Inventors designed primers encompassed within the putative exons of three human orthologs, corresponding to mouse Novlnc6, -23 and -44 (SEQ ID No 48, 84, 100;

FIG. 3A). Quantitative RT-PCR was executed on RNA isolated from the left ventricle of a healthy male. All three putative human orthologs were readily amplified and expressed at relatively high levels (FIG. 3A). To determine the potential roles of these orthologs in cardiac pathology, The Inventors examined their cardiac expression in two independent human heart pathologies. Patients with dilated cardiomyopathy (DCM), and with aortic stenosis (AOS) were assessed. These two cohorts presented with perturbed cardiac functions and associated maladaptive remodeling as expected for such pathologies. Furthermore, cardiac stress marker genes were also differentially expressed (FIG. 3C). In patients with DCM, all three human orthologs were significantly modulated with novlnc6 and -44 downregulated and -23 upregulated (FIG. 3B). Interestingly, the predicted target gene of Novlnc6, i.e the key cardiac TF Nkx2-5, was also significantly downregulated in patients with DCM. In contrast to DCM. patients with AOS were not associated with differential expression of Novlnc6 or -23, or the predicted target gene of Novlnc6, Nkx2-5. Novlnc44, however, was significantly downregulated (FIG. 3B), comparable to its modulation in DCM.

Example 2

Figure 4A:
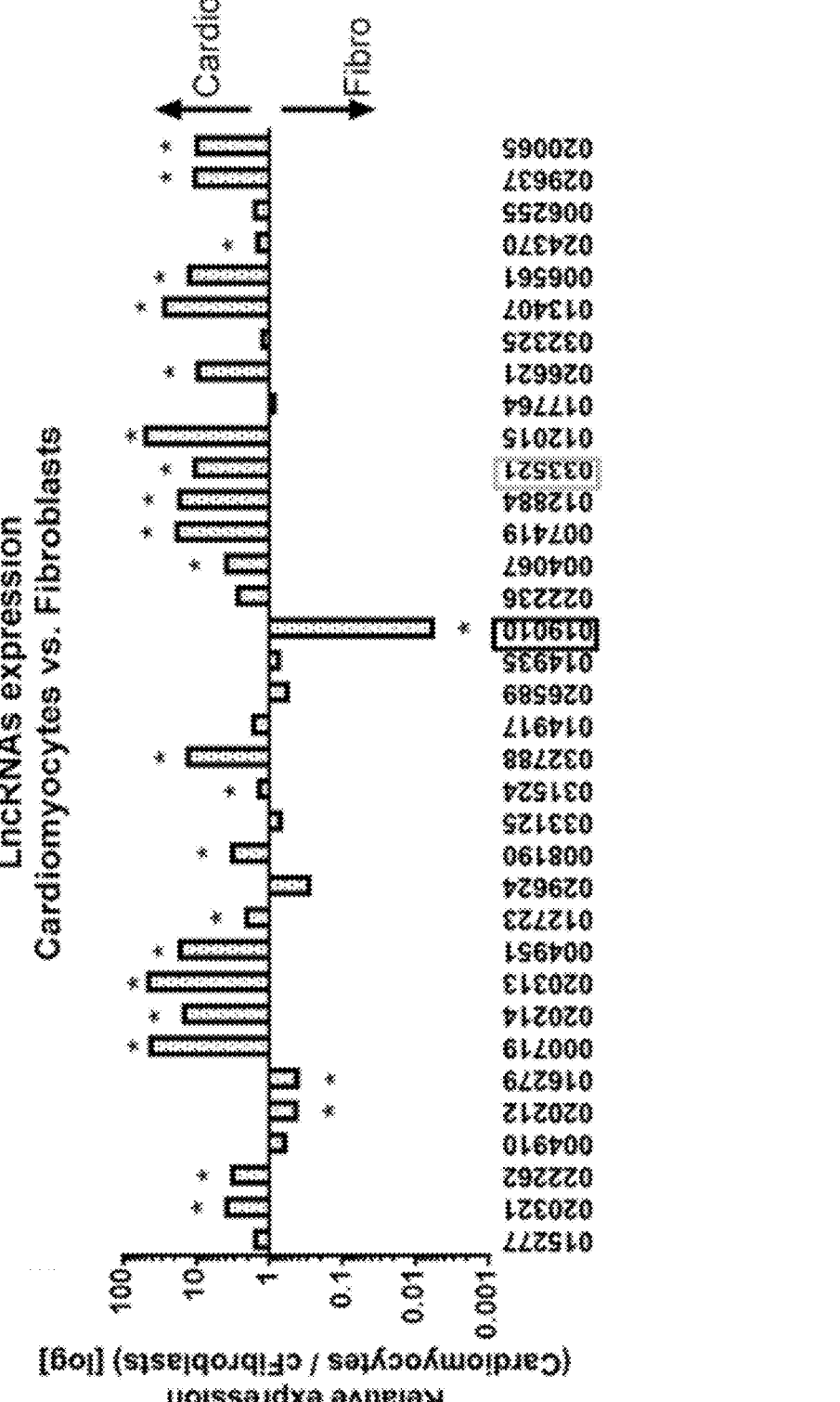
FIGS. 4A-D show in vitro cell-specific lncRNA expression, and effects of lncRNA downregulation in cardiac fibroblasts and cardiomyocytes.
Figure 4B:
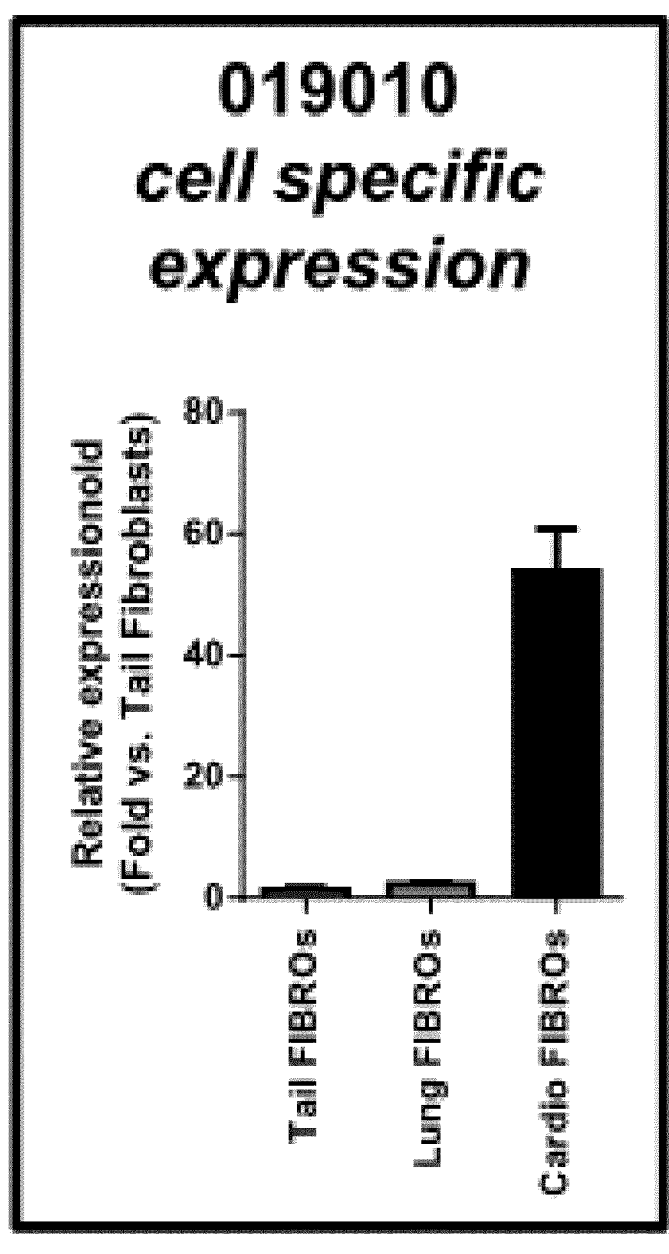
Figure 4C:
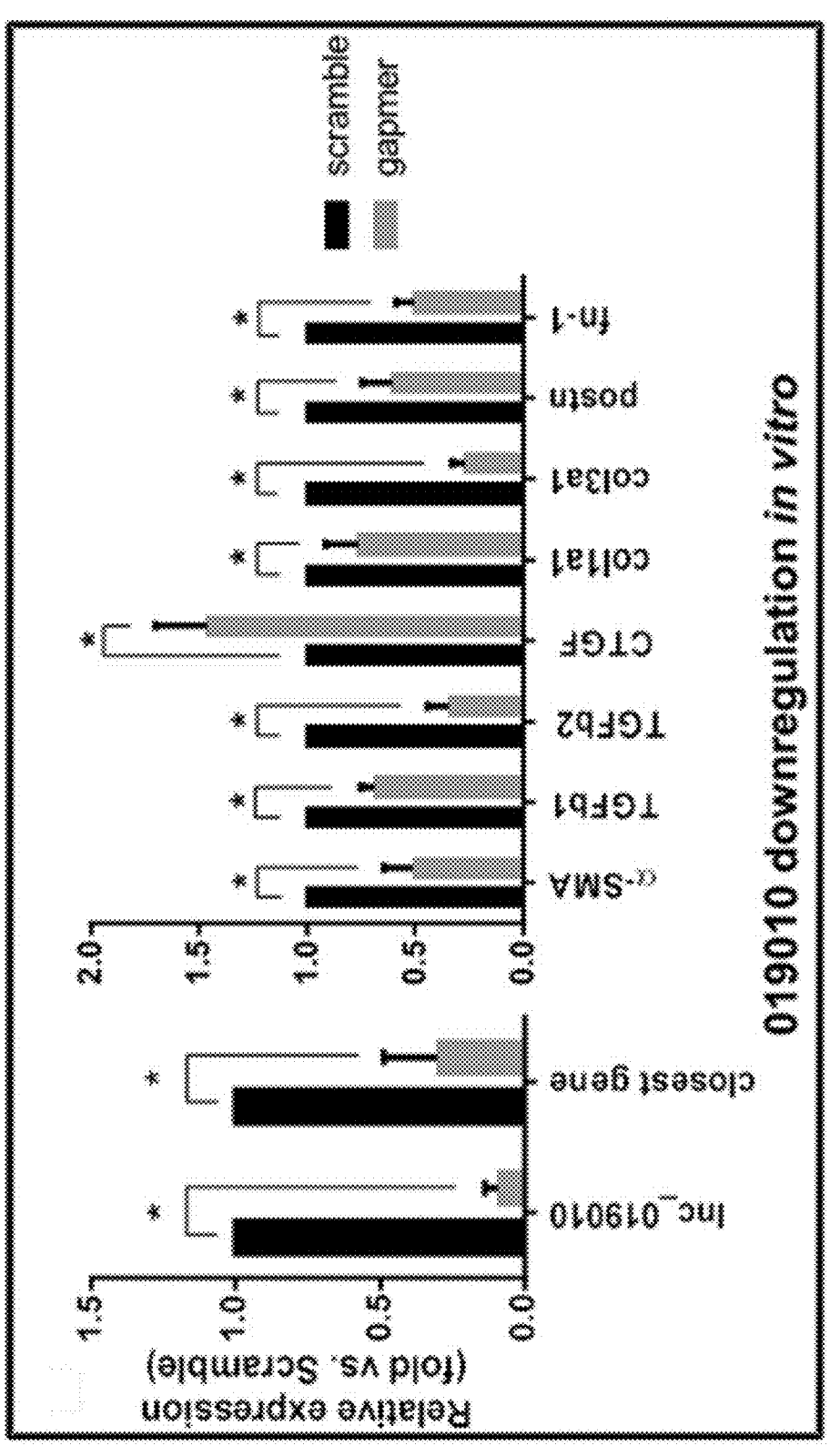
Figure 4D:
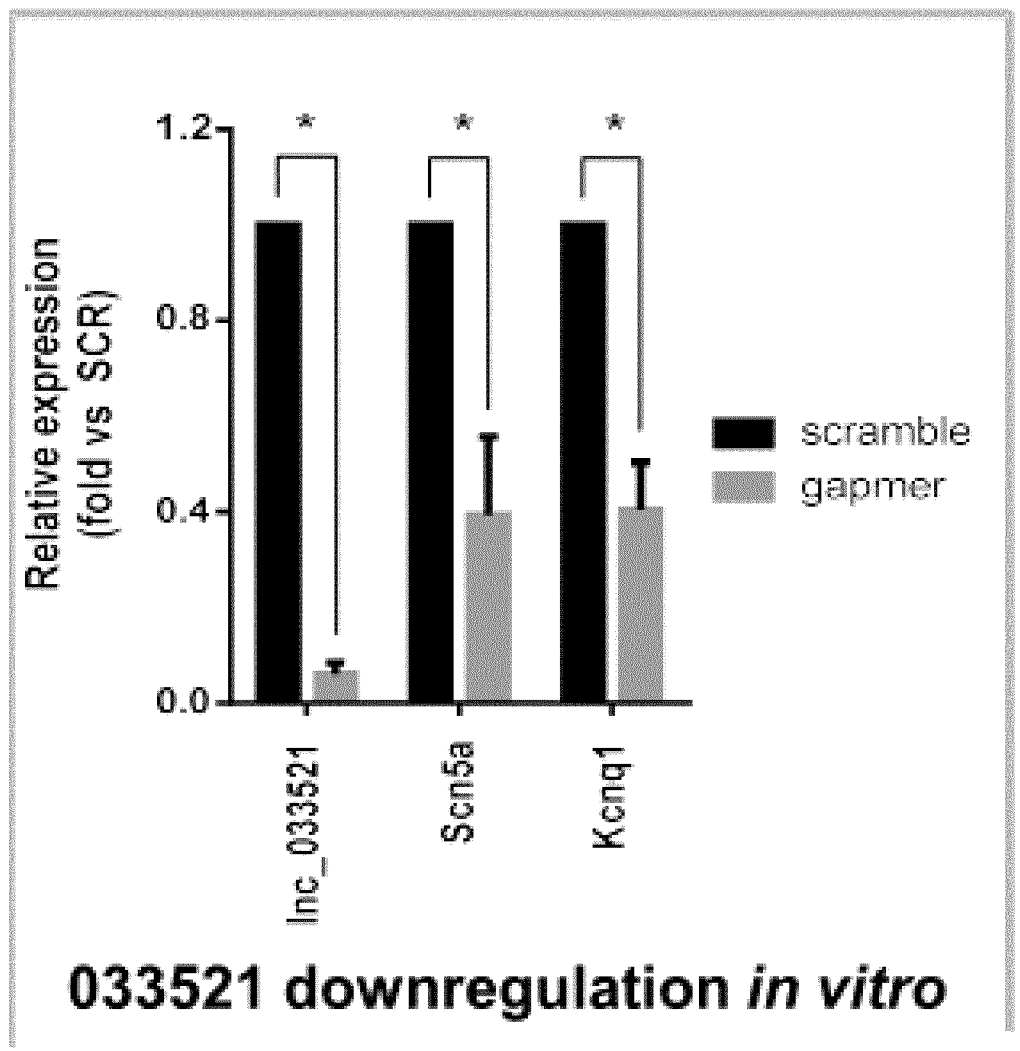

Cell-Specific lncRNA Expression, and Effects of lncRNA Downregulation in Cardiac Fibroblasts and Cardiomyocytes In Vitro RNA was obtained from cardiomyocytes and cardiac fibroblasts isolated from neonatal mouse hearts. The expression of novel lncRNAs were quantified by RT-PCR in the two cell populations. Ratios in logarithmic scale of cardiomyocyte versus cardiac fibroblast expression of lncRNAs are presented (values below 1 correspond to fibroblast enrichment; values above 1 correspond to cardiomyocyte enrichment). Bars represent mean±SEM (n=3) *p<0.05. The two highlighted lncRNAs: lnc_019010 (fibroblast enriched) and on lnc_033521 (also named Lnc-Dedbt) (cardiomyocyte enriched) have been more extensively studied (FIG. 4A).

The expression of novel lncRNAs in fibroblasts isolated from the tail, the lung and the heart of neonatal mice has been quantified by RT-PCR. The expression of lnc_019010 in cardiac fibroblasts is approximately 60 fold enriched compare to the other sources of fibroblasts. This data show the high cell-specificity of this lncRNA (FIG. 4 B).

Cardiac fibroblasts isolated from neonatal mice were transfected with modified antisense oligonucleotides (GapmeR, 5'-AGGTGTGCGATAGAG-3') targeting lnc_019010 for degradation. GapmeRs were transfected at a concentration of 50 nM and RNA was harvested 24h after transfection. Compared to control (scrambled) GapmeR transfected cells (black bars), lnc_019010-specific GapmeR cells (grey bars) show a strong reduction of the target lncRNA expression and also of the closest coding gene. Interestingly, the downregulation of this cardiac fibroblast-specific lncRNA impact the expression of important fibroblast coding genes such as a-smooth muscle actin (α-SMA), collagen I and III (Col1a1, Col3a1), fibronectin (Fn1) and periostin (Pstn) and transforming growth factor β1 and β2 (Tgfβ1, Tgfβ2) and connective tissue growth factor (Ctgf). These data, shown in FIG. 4C, suggest that lnc_019010 is involved in cardiac fibroblast differentiation and represents a therapeutic target for limiting fibrosis. Bars represent mean±SEM (n=4) *p<0.05.

Cardiomyocytes isolated from neonatal mice were transfected with modified antisense oligonucleotides (GapmeR) (SEQ ID No. 147: 5'-TGCTTGCTAGTGTGGT-3') targeting lnc_033521 for degradation. GapmeRs were transfected at a concentration of 50 nM and RNA was harvested 24 h after transfection. Compared to control (scrambled) GapmeR (black bars), lnc_033521-specific GapmeR cells (grey bars) show a strong reduction of the target lncRNA expression. Moreover, the downregulation of this lncRNA has an impact on expression of important gene encoding fundamental cardiac channel such as Scn5a (sodium channel, voltage-gated, type V, alpha subunit) and Kcnq1 (potassium voltage-gated channel). These data shows that lnc_033521 has important function in the conduction system in the heart. FIG. 4 D; Bars represent mean±SEM (n=4) *$p<0.05$.

Figure 5A:
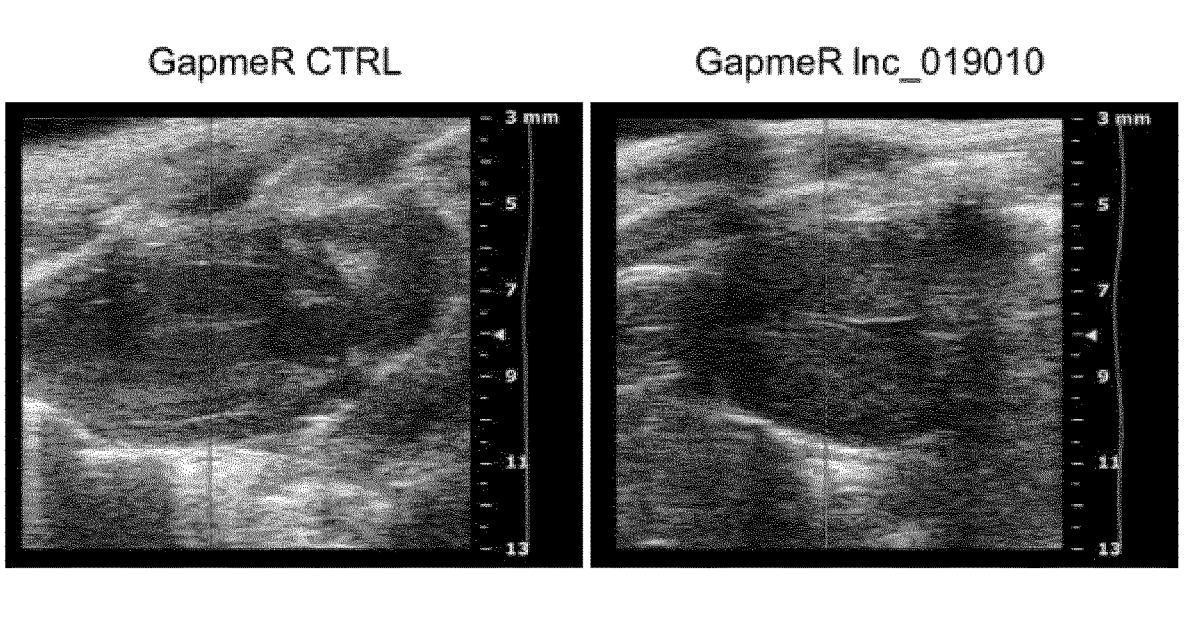
FIG. 5A shows the validation of expression via quantitative RT-PCR of novel lncRNAs in the border and remote zones of infracted hearts one and seven days post myocardial infarction.
Figure 5A:
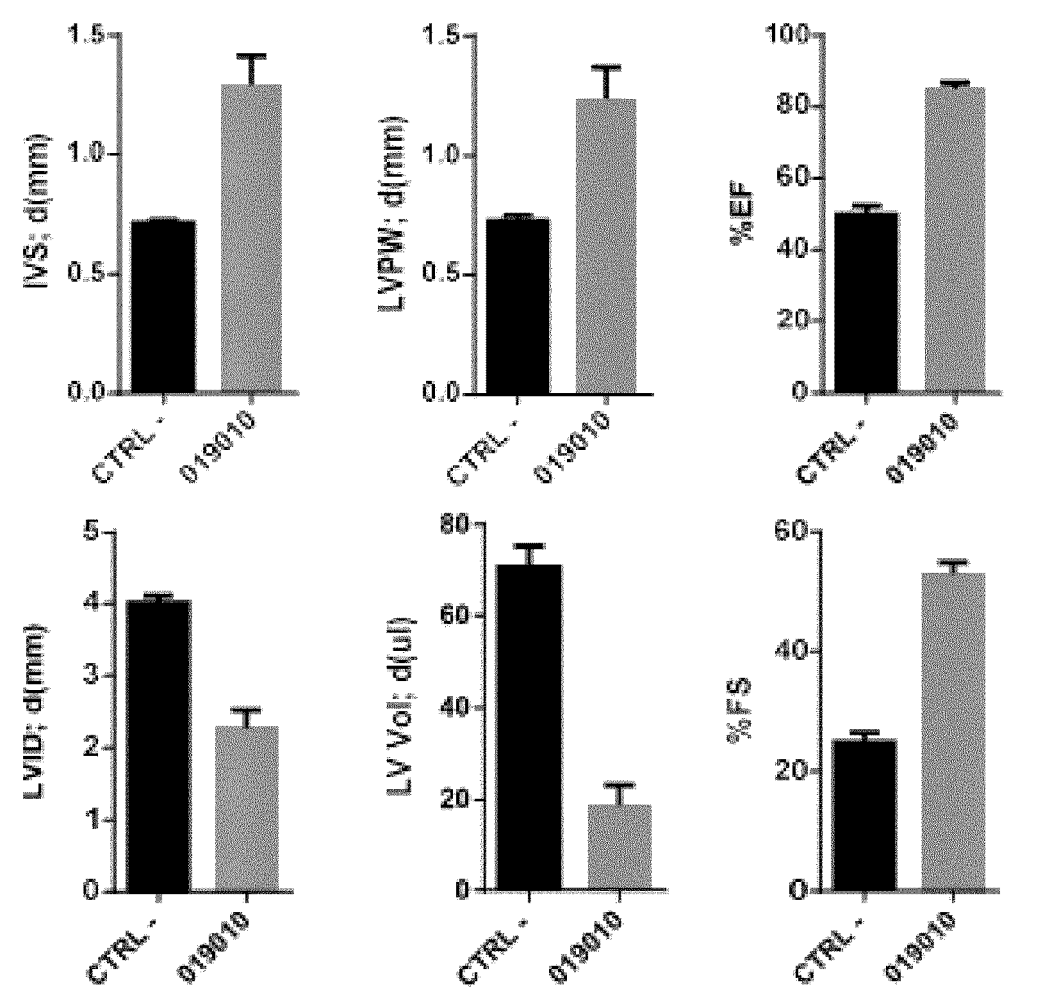
Figure 5B:
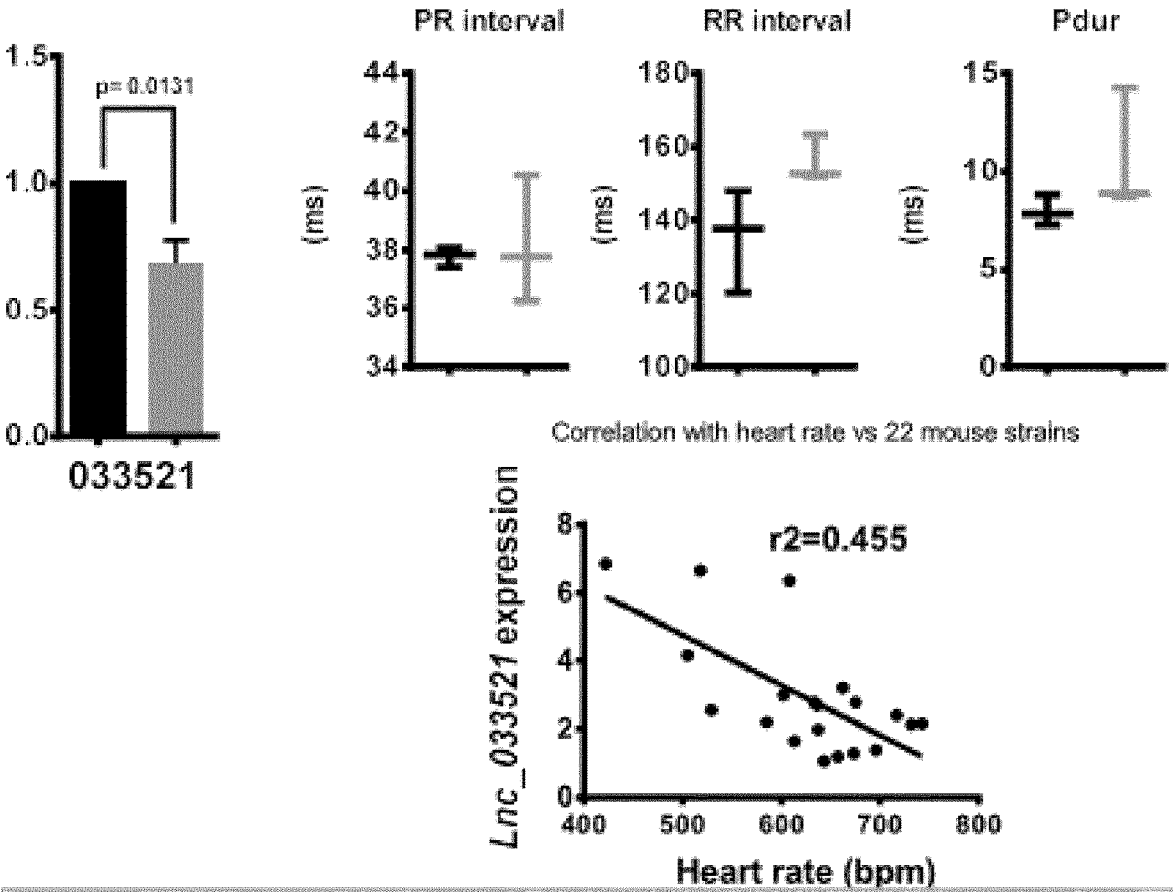

LncRNAs Downregulation In Vivo 12 weeks old BL6/C7 mice received one intraperitoneal injection of GapmeR (20 mg/kg). Echocardiographic images (long view axis) of mouse hearts 4 days after GapmeR injection are shown in FIG. 5A. Left panel, heart of a mouse injected with control (scrambled) GapmeR.

Right panel, heart of a mouse injected with GapmeR directed against lnc_019010. Bar graph shows a significant increase in IVS (intra ventricular septum) and LVPW (left ventricular posterior wall) thickness, and a significant decrease of LVID (left ventricle internal diameter) and LV vol (left ventricle volume) in mice injected with GapmeR targeting lnc_019010 (SEQ ID No. 148: 5'-AGGTGTGC-GATAGAG-3') (grey bars) compared to control (scrambled) GapmeR (black bars). These data show that lnc_019010 depletion in the heart in vivo induced a significant increase of heart mass. Ejection fraction (EF) and fraction of shortening (FS) are increased in mice receiving GapmeR directed against lnc_019010, indicating that cardiac function is increased in this case.

RNA was obtained from the heart of mice injected with GapmeR directed against lnc_033521 or control (scrambled) GapmeR. The graph depicted in FIG. 8 B, on the left, shows the downregulation of lnc_033521 expression in mice injected with GapmeR targeting lnc_033521 (grey bar) compare to mice injected with control (scrambled) GapmeR (black bar). Upper panels, electrocardiogrameters showing the effect of lnc_033521 downregulation on cardiac electrophysiology. Heart rate is reduced following downregulation of lnc_033521. Lower panels. correlation between lnc_033521 expression and electrocardiographic measurements of heart rate (left) and P wave area (right) as measured in 22 different mouse strains. These data show that lnc_33521 plays a role in the regulation of important cardiac electrophysiological parameters.

REFERENCES

Trapnell, C., Roberts, A., Goff, L., Pertca, G., Kim, D., Kelley, D. R., Pimentel, H., Salzberg, S. L., Rinn, J. L., and Pachter, L. (2012). Differential gene and transcript expression analysis of RNA-seq experiments with TopHat and Cufflinks. Nature protocols 7, 562-578.

Ounzain S, Crippa S, Pedrazzini T. (2013) Small and long non-coding RNAs in cardiac homeostasis and regeneration. Biochim Biophys Acta.1833 (4): 923-33

Mouse, E. C., Stamatoyannopoulos, J. A., Snyder, M., Hardison, R., Ren, B., Gingeras, T., Gilbert, D. M., Groudine, M., Bender, M., Kaul, R., et al. (2012). An encyclopedia of mouse DNA elements (Mouse ENCODE). Genome biology 13, 418.

Wamstad, J. A., Alexander, J. M., Truty, R. M., Shrikumar, A., Li, F., Eilertson, K. E., Ding, H., Wylie, J. N., Pico, A. R., Capra, J. A., et al. (2012). Dynamic and coordinated epigenetic regulation of developmental transitions in the cardiac lineage. Cell 151, 206-220.

Bruneau, B. G. (2002). Transcriptional regulation of vertebrate cardiac morphogenesis. Circulation research 90, 509-519.

Huang, J., Elicker, J., Bowens, N., Liu, X., Cheng, L., Cappola, T. P., Zhu, X., and Parmacek, M. S. (2012). Myocardin regulates BMP10 expression and is required for heart development. The Journal of clinical investigation 122, 3678-3691.

Kurreck J, Wyszko E, Gillen C, Erdmann V A. (2002) Design of antisense oligonucleotides stabilized by locked nucleic acids. Nucleic Acids Res.; 30 (9): 1911-8.

Sambrook, et al., Molecular Cloning: A Laboratory Manual (3rd Edition, 2001) Innis et al., eds., PCR Protocols: A Guide To Methods And Applications, Academic Press Inc., San Diego, Calif. (1990).

Froehler et al., (1986) Nucleic Acid Res. 14:5399-5407

McBride et al., (1983) Tetrahedron Lett. 24:246-248

Ounzain S, Pezzuto I, Micheletti R, Burdet F, Sheta R, Nemir M, Gonzales C, Sarre A, Alexanian M, Blow M J, May D, Johnson R, Dauvillier J, Pennacchio L A, Pedrazzini T. (2014) Functional importance of cardiac enhancer-associated noncoding RNAs in heart development and disease. J Mol Cell Cardiol. November; 76:55-70.

---

The invention claimed is:

1. A composition comprising a modulator of one or more cardiac-specific lncRNAs selected from the group consisting of SEQ ID No 18, SEQ ID No 26, SEQ ID No 27, SEQ ID No 28, SEQ ID No 29, SEQ ID No 30, SEQ ID No 33, SEQ ID No 48, SEQ ID No 62 and SEQ ID No 64, wherein the modulator is selected from the group consisting of a miRNA, a siRNA, a piRNA, a hnRNA, a snRNA, esiRNA, shRNA, an RNA aptamer, and an antisense oligonucleotide which selectively targets said one or more cardiac-specific lncRNAs.

2. A method for modulating one or more cardiac-specific lncRNAs selected from the group consisting of SEQ ID No 18, SEQ ID No 26, SEQ ID No 27, SEQ ID No 28, SEQ ID No 29, SEQ ID No 30, SEQ ID No 33, SEQ ID No 48, SEQ ID No 62 and SEQ ID No 64, comprising administering an effective amount of a modulator to a subject in need thereof, wherein the modulator is selected from the group consisting of a miRNA, a siRNA, a piRNA, a hnRNA, a snRNA, esiRNA, shRNA, an RNA aptamer, and an antisense oligonucleotide which selectively targets said one or more cardiac-specific lncRNAs.

3. The method of claim 2, wherein the modulator modulates cardiac fibrosis, myopathy, hypertrophy, apoptosis, inflammation, extracellular remodeling, cardiac regeneration, CM and CF cell cycle and activation of endogenous CPCs, direct reprogramming of CF, ECs, in vitro reprogramming and differentiation of cell types for generation of cardiac cells for cell therapy, cardiac epigenomic targeting of ubiquitous chromatin remodeling complexes, cardiac physiology, electrophysiology and/or heart rate.

4. A pharmaceutical composition comprising an effective amount of a modulator of one or more cardiac-specific lncRNAs selected from the group consisting of SEQ ID No 18, SEQ ID No 26, SEQ ID No 27, SEQ ID No 28, SEQ ID No 29, SEQ ID No 30, SEQ ID No 33, SEQ ID No 48, SEQ ID No 62 and SEQ ID No 64, wherein the modulator is selected from the group consisting of a miRNA, a siRNA, a piRNA, a hnRNA, a snRNA, esiRNA, shRNA, an RNA aptamer, and an antisense oligonucleotide which selectively targets said one or more cardiac-specific lncRNAs, optionally in combination with a pharmaceutically acceptable carrier, diluent and/or adjuvant.

5. A kit comprising the composition of claim 1.

6. The composition of claim 1, wherein the modulator is a siRNA comprising a sequence as set forth in SEQ ID No 105, a fragment thereof, an isoform thereof, or a variant thereof wherein the variant shares at least 80% nucleotide sequence identity thereto; and the siRNA modulates a lncRNA having a sequence as set forth in SEQ ID No 48.

7. The method of claim 2, wherein the modulator is a siRNA comprising a sequence as set forth in SEQ ID No 105, a fragment thereof, an isoform thereof, or a variant thereof wherein the variant shares at least 80% nucleotide sequence identity thereto; and the siRNA modulates a lncRNA having a sequence as set forth in SEQ ID No 48.

8. The pharmaceutical composition of claim 4, wherein the modulator is a siRNA comprising a sequence as set forth in SEQ ID No 105, a fragment thereof, an isoform thereof, or a variant thereof wherein the variant shares at least 80% nucleotide sequence identity thereto; and the siRNA modulates a lncRNA having a sequence as set forth in SEQ ID No 48.

9. The kit of claim 5, wherein the modulator is a siRNA comprising a sequence as set forth in SEQ ID No 105, a fragment thereof, an isoform thereof, or a variant thereof wherein the variant shares at least 80% nucleotide sequence identity thereto; and the siRNA modulates a lncRNA having a sequence as set forth in SEQ ID No 48.

\* \* \* \* \*

SEQUENCE LISTING

<160> NUMBER OF SEQ ID NOS: 148

<210> SEQ ID NO 1
<211> LENGTH: 540
<212> TYPE: DNA
<213> ORGANISM: Homo sapiens

<400> SEQUENCE: 1
aataaagcaa accttgaata tattcagcta ggaaataaac cttgaaatta tatggttacc      60
aataacagta aatagagttt caacaaataa ctctgctaaa cattttgttt ttgttaatca     120
cccatgcgtg gcaacatata ttattctttc ttttaggtaa cgcagttgaa ggaccagaac     180
gcattcctaa acaacacctc ccttcggtgt aagttgcagc atctgtgact tagagaacct     240
acagttagaa ttctgttttc cagatattat agttttagtg gaatgcctgt aatcattatt     300

-continued

```
attttttttta gacaaagtag ggaaattgcc ctagtagaaa atgtaattca atataggcaa      360
aatagaatta caaccatttg atcatgtcta tgataaatcc agcattgcaa taaacatttc      420
taggattttc tatttctatc tgcttgcttc ttgtttagac atcttaaaat gcttgttagt      480
gttaagtgat tgcagtgcca ataccgtaag agaaatttat gagaaaaaaa attgagaaaa      540
```

```
<210> SEQ ID NO 2
<211> LENGTH: 614
<212> TYPE: DNA
<213> ORGANISM: Homo sapiens

<400> SEQUENCE: 2
cttttctata attactgttc tgttttttct gacaggctat caaatattgg ctgccttaag       60
ctctctgtga actgagttat tctcaataat actctgtatt atgaaggcat tatttgagtg      120
gctgtccact gtgatctggt tatttggagc tttacataaa acaggctctt gctatatggt      180
tatgccaaaa ggctttgcaa tagttgtatt tgtttggctc tgtgagatga cccaggcacc      240
ccgattccaa gggccactta cttttgagtgg acatgaggct gatgcccaga accaaagagg      300
aagcagcctc tgatccatga tcctatagtc acagtgctgc tcaatcgtgc cgtttctgct      360
gacccaaatg cctggagttg accctgtttg tctctccaaa cctctttctt gacttagatg      420
atgctttgaa cttgatctgt tgtactatga ctgtaattcc aagagcacag gctttcccgt      480
catgtagagc aatatcaatc ctgcctcaat cgtttgttac cttttgattc tgtgggtttc      540
agtttcttca tctgtcaaag gagaatacac tggcagagct cctttagaaa gcctggttct      600
gtatcatgga cact                                                       614
```

```
<210> SEQ ID NO 3
<211> LENGTH: 2884
<212> TYPE: DNA
<213> ORGANISM: Homo sapiens

<400> SEQUENCE: 3
gaaatgctat agttgtaaaa tttaaaatca aatcagagtc cagattttca aaaactgaaa       60
taataagtta aaatgaaaag gtaatggtga tgactataaa ccttgtactt gggaatttta      120
aaatatatca ggatgggagg gtctagtttc acagcctggg ggtttgagtt gtctgcaaag      180
gctcagaatg agctcacaga gagctgttgt gccaagagtg tggctcgccc tccaactgaa      240
gtgttcatct aggatccaga gcacagggca gattccctca agctctgtat ggtcagagct      300
ctgggagcaa gcatcagttt atcccaggac tggttaatgg agcccatcca gaggaagacc      360
gagatgccat ccagggatct gggagtttaa gctggacaag agaagacttg gaggggcctg      420
ataataactg taatacgcgt tgatcattat gtacaaacta tgcctaaacc tggtttcttc      480
caacaataac cgtttgttca cagttctgca gttgggccag ggagctttcc tctgtatggt      540
gtgggctcct atagatctgg ggccagctgg acatctatgg cccatccctt ctcatgttct      600
ttcattcttc tccacaggcc tctcatactc agggaggcag cctagacatg acttctcaag      660
gcagcaagac agtgaaagtg gctgctacag ggctctaaaa gcccgggctc agaatttctg      720
ttgctttcca ctggactgag aaactcacaa gagcagccaa agaagaatgt agaaactgcc      780
aacaaccaca tgactgagct tgcaagcaga tccttcccca gtagccttca gatgacacca      840
gccccagcca gcaggttatg caactgagac catgaggcag aactgccaac taagccccag      900
attcttaacc cacagaactg tgagatcata tttgttgttt taagttgctt agtttaagaa      960
```

-continued

```
taatttgtag tgattcgtta catagcaaca gaaaaaaaca ctgggttttt ttcttggctt      1020
tttttttttt tctaggcaaa caagaaatcc ctgcatccac atagctagcc aacaaggcct      1080
tgtcctaagg ggtgaaactg gtgaatcaga ataaagaaag cttcccagga ggcctggggc      1140
aagtggcaca agacttagtg atctttccag gcctaaggga gagaattccg tgggctgcta      1200
gaatacacca gcttccttta tagaagttgt ggccagtgca aatgttaacc aaacgtaatg      1260
tatgagcctt ataacaccaa atggaggttc ctctggctgt tctgtaactt aaggggagta      1320
agttgacttc ccatgactct ggcttccag ttgggatggt tccatatgat gttttcagaa       1380
gtaatggtgg aaccttcact cactatgtcc tccccatctg ctcacccta tattggtcca        1440 gccctgtctg ccccacacac acctccaaat tttgaaaaaa agcatcctac aaatgcataa      1500
gaacatggtc acacgtgctc tttctgacac acttagtcat tggtgggtcc agagctgcag      1560
ggtccttaat gctcatctat gtgccctaag ttgagctctc ttgctgcaga aaacctgtgg      1620
ctagaagcaa aagcttccta aaatcagcta aactaggtaa cgcttttttc ttgaccttga      1680
agtggagact cagagccttt gggaaccttc tgttttaaat atccaacagg aatactgctt      1740
taccatcctt tcagcggggg gacgggacca gacacaccag agaggtagca cccattggac      1800
ctcttaggcc aggtggagac agtgagagct gctaggcatt cctcagcgat gccagtatgc      1860
ttactataca aaacagtgct gagttaattt cacacagctg gggaggactg gaggtgcttt      1920
tggggcctat tgtgtgtgag ccagcaaact catctctcca gctgttcctt ggtagaagta      1980
gaagtagaag aaaacgaaga agttggagcc agaagtcagt ttctgccaac gggaacaatg      2040
ggtgcaattg tgcatctcac atagcagcaa ggagtattaa acagaagtac acactgttac      2100
tacatgagaa ccttgccatg ggaacttccg gatgtacttt tttggaatcc aggggatcta      2160
ggaagaccag tcagggagtg gccagttctt ggatgacctc tccaagcaag agaaaacata      2220
aatgtgtact ttaggagttt caaaagcaat gaagatcttt cttagtgcaa agccctgttt      2280
tccccttaat attaaagata gtcttggtct tatttctggg aagtttccaa ggacagaggc      2340
taaactgtga ccaaactcac aggaaagaga ccctcagagc tgggaaatga tcacttcaaa      2400
tggtttcttg cctgccttga actgcgttca agtgagggac ttctccaaag gaagacgcag      2460
gtggaatccc aaaggcaatg tggtgtgcct cagtctcttg agctgttcac ctcagaagag      2520
tgtttcatct tctcggcaat ggagatgaca cctacctcat ggatttgcag tgaaatttta      2580
acaagagtat gaataaggtt taaacactga aaaaacatct ctgagttgca tttagttgtg      2640
ccggacccac cacattaaca acctaagaga gctctgcccc gtgccccatg ccacacgagc      2700
cctcatcctg ggcctacctg gctggctgga tatggggaca tctcaggtgg cagagcaatt      2760
tgcccagggt ctgcccccag cagtagagtg atgcggagat tttattccct cctcttcctt      2820
ccctctctcc tcaagtgtgg tgcgtgctcc atttctcacg tggccatgtg caagccagga      2880
agaa                                                                    2884
```

<210> SEQ ID NO 4
<211> LENGTH: 1851
<212> TYPE: DNA
<213> ORGANISM: Homo sapiens
<400> SEQUENCE: 4

```
cagagggatt agttgtaatt gctaagttct tttgagtaca tttaaccaag tagcagagca        60
cattcttcca tgaattcaga agcctgttaa aacagctgtc taatggggta aaatacactt        120
tctgttgttt ggttgaaaga caagacttca aataaatact aaaatcaggg ttggtcaatt        180
```

```
ttcaccagga gcccaggcac ctagggaatc ttgttctttt tcttctgcct ggagttactt         240
cactggaatt gtgagaaaaa ctgatatgat gcaaacacta gtgatctgaa gacttgggtt         300
caaaccattc tttttcgtct tgcaaagtat aagcgtgtgt gtatgccgta atatagggaa         360
aaggtggctc atgtataaaa tcataacaag aatttctatc caaaagtttc ttgggagtat         420
taaaataatt atctgtgaaa tccttagccc attggatatc acatattcag ccctcaataa         480
aggtagttga tgtcaagtca actttcaggt tactttctgc ttattatact gtcactgaag         540
ctagaaaggg acaggatcat gcactcttgt tgactggaac atggctatgg agagcctctc         600
attgttcttt gttccatggc aaatagagca atgcctttct attttcccag tgaacattat         660
atataaatat attttaaaaa tcaatctagg ttctctctat tgcaccttct tgtcactgaa         720
gtgttgaata actgttggag tcttggctaa gcaggagcaa tatttgatgg aatctgacat         780
tgctttaata ttctgggttc atacacatat gcagcagaag tacctggatt gcccatttca         840
aggtactctg tggattttta aactttcgtg acagtgtaat aagagaaatt taatctaaat         900
tgacttgaca ttcaaaacca gacatttctg tgctctaaaa taattctatt tgtttctggg         960
cactgttttc aatctctaaa ttataaaagc cctttagctc actggctcat tcttaacctg        1020
attgctgtga cttcgatctg tctcctacat cgtgtccact ttcttcacct cttttttctgt        1080 gggtctcact ctcctgcctc cttactctgt tcatgacgtg ctttaacatg tgtgaatgag        1140
tgacataagc atatgactac accatttatg ttgagttcac agccatttat atcattaagt        1200
agatgataca gagaaaaaga aacacattta attttaatca ggccactata catgatgaat        1260
caagtgcttc agcagtcata agaaactgct cactaaaact ttgattatga tttaatgatt        1320
aaatagagat ttgctatggg ggacagattg ttcatttggt cttttctttaa agactgattt        1380 atactcatct aagtaaataa actattcctg ctctgtgctc tcagacagtc ttttatagcc        1440
aagatgcctg cattccccac agcttagaca ggtttcttcc tgactttagg cttctggtct        1500 ccctttttgtt agagcatttg ctttagaaaa cttgtcactg taaattcctc tatccctttg        1560
agatgtaaat ctcccaacct cttgtctgaa tttctggctc caggactact gcctctgtct        1620
cccagtcgct gtgggagaat aggaggagcc taactttgat aagcaaatgc agctggtcta        1680
agcctattgg ccagcctccc cgcaagcctt cctccaagga cgaaagtgtc ttcctttcct        1740
gtttaactct gtcgtgcagt tttttatatgc ggtcttagtg atgaaggttg ttcctgactg        1800
tgagtctatc tgtctcactt cactgtgagt cctgaggtct gggaataggg a               1851
```

```
<210> SEQ ID NO 5
<211> LENGTH: 2627
<212> TYPE: DNA
<213> ORGANISM: Homo sapiens

<400> SEQUENCE: 5
gtttgggaag agacaggcta tgagcatgac atgcaggctg tgggggctgc cattcctgtc          60
tcagctcctc cttcttgagt tttgagcagg caaaattgcc tctgtctaat aacacccccc         120 actactttc tctttctttc tttcattctc ctcctgcccc ctgtatgaca aaataggcaa         180
aatgagtaat cagagggtga gatggagaaa aagaactata gttggagatt ttggacggtc         240
tcttttaggt gggagaaggt aggatagtgg aaacatgatt gcaaagaaga agccatataa         300 tttttttccct ttgactttaa gtcctaagat gggcaggctg gaggcctggg tgaggagagg         360
ctgggagggg acaacgcaag tggtagagct gtctggagag gttttctttg tgaaaaaggc         420
```

```
agctgaagtc tcgaaagtga tctggactga gaatcgggag aagtggattc agttcatact    480
cagccacttt ttatgtgacc ttgggactag actattgatg cccagtttct ttatttgtaa    540
agaaaacact gtactttttc ttctgcttta aaatgactgt tagaagttat gaaaattgaa    600
aacagttcac aaaagcccag taacttgctt tcttcatcat tctaagagag aaaagttaag    660
cgaactctcc agttcattgt taaaaaacaa aagaaaagaa aagaaaaagg catcttttct    720
ctttgagaaa caccaaaatt actctgcccc taatagtcgc ctgggcagaa ttttccatct    780
tagcacaaag cagctcgacc ttgtttcaac taatcccttc tctgtattta acaagaggaa    840
ctggaagagt cagacagtgt gtgggaagac tgaagaaaat aaggaaggta tagaaactac    900
tagagatgga gataagttaa acattctggc aaattgtcat ggtgtattgc tcatgctgaa    960
ggttaggcag ttgggaaggt agttaagaga atggctttaa atgcttcatc taattgcaag   1020
cagctgttga ttagtggagc ttgaccaact gttttttaatt cagtggtgat gaagagaatg   1080
agacttttaa gggaaactgg cacggttgtg tatacgcatg gagttgctta cactttttct   1140
ggaggtcata gagtgcagta actactaaga gatgttctct gaaaccattg caggctttca   1200
tgataatgac tttcctaaat tttaccagca tttgttgggt ttggcaggag gcaaacttct   1260
ccgttatcca aattctggaa tgattttagg gactgattca tcaatcgcga ggtcttgtgc   1320
caattcagaa gcaactgttc agtggaagca gtaaatctag aatgagagct gataatgcca   1380
ttttagagtc ttcttggaac atttaatttt ttgaaacata ccacttacct gaaacaactg   1440
tcaggttggg tagagaacgt aagtgtctta tgagagttct aggtagagtg ctctgggact   1500
tcaaagaaaa aaagatgcct acctttaaga caaaagtagt aaaattcaaa tgctaaataa   1560
aatgctcagc tccactaatg gaatttttgc gcatgaaaaa aagcaagcta taaaggttaa   1620
gataaccaga ctggctgtat ttctgtccct gctgctgtgg gtggcagaga aagacaaatc   1680
ctaaaaaggt tttttcttcca gttagtgttg ggccaggata agacctgttt atgtcaatga   1740
aataactttt taagcagaag atttcagagc caagagaaga acttgcagtc aagacaatct   1800
gccacagtgt gaacgatcca tctgaggaca attgggctga ttgtgcaagc tgatgaagga   1860
acatggcatc ctctggaaac agggaacaac tgtcaatgtt gaaaatgtgt ggaacataag   1920
gaaagcatgc caacttttgg tttcaagata ttgctcaatc agaaatccgg aatttcaaca   1980
catctgaaag taaggcggag ggactctagc agtctgatct ttacgaacta aagactcagc   2040
aaaattccca ctcaatggaa gtgcaaaagt ctctgcagac ttttaaaaaa tgccaatccc   2100
atcagatggg caaacacaaa acaacaaaaa ccctaacacc taacaatacc agagatgata   2160
cggagcaatt ataactcaaa tacattctgg cgggaggcta aatatgtaca acaccttgga   2220
actgtttggc accatctccc caagatgagt ctgtggccca gcaattccac tcctacttta   2280
tacccaagag aaacaaatgc atatgtgcat caaagacata caaaaatgtt cccagcagta   2340
ctattcacac tagcccccaaa ctggaaacaa ctcaaatggc catcaacaga ggaatgaata   2400
aaaattgcag tgtattttac agtgaacaaa ctatgacaaa ctacaacatg gatgaatctg   2460
aatcccacaa acagaatgtt gagtgaaata agccagacac cgaataatac atagattaat   2520
gtgccatttc tataaaactt aaaaacaggc aaaactaata catgatttta gaagctgggg   2580
taatgtttcc tttgcagcga ggtagtgagt gggaagggcc atgagag                 2627
```

<210> SEQ ID NO 6
<211> LENGTH: 915
<212> TYPE: DNA
<213> ORGANISM: Homo sapiens -continued

```
<400> SEQUENCE: 6
ctcttcctcc tcctcctcct ccccggcaga gctgtaggcc tcacagtggt gacgcggggt        60
catccggggg cccgttacca cctcattctc ataggcgcgc ggaggcggtg cgcgcgggac       120
gactcggcca actgaggagg gagaaagggg aagcggatcg gcgggcgctg cgcctcgagc       180
gggacgcacg gctgcggccg ctgggtcggt cagcgaatta gttccatgat gaccccggc       240 ctgaggccgc cgccgctcga gcccgggttg ggagggggct ccctctcgcc atagggcggc       300
gggggccggg gagaggcggg gggtgagacc ggctctgccc ctgcccgggg aaagcgcctc       360
cgaggggaaa tggtgaaagg gggggagggg agaaaagaaa agaaaagaaa ggggaaaggg       420
gggaaaaata agaaaaagcg agacagaggc gctgccgcgt ccgctcgcgg ggaaggctgg       480
ggagggaggg gaggaggaag aagtgccggc ttcctggctc cgccctcgcg gaccgatttc       540
gcccactcct tgtaaactac gcggacgtct ttcacccttc ctgttcctcc ccgccgcctt       600
cccggtccaa cgaaagtaca gagaagtgcg gccgaaagga gacgggctgg ggaagtcgtt       660
ggcactagga tggaaggagg gaggacgttt tctgtggcta agaaaagccg aagtcttgag       720
actgtagcat ttctgcataa tctattgtaa cataaccatt gttagaccat gaaattgctt       780
ctgattttca ctccaataag aaaattgaag tgtcttctga cacttgagg ataaggtaag       840 gtaaagacaa aaacataatg gtggagaaat atggtgagag gaaccaatct ttatggggca       900
gaaacttccc tcctc                                                        915

<210> SEQ ID NO 7
<211> LENGTH: 1001
<212> TYPE: DNA
<213> ORGANISM: Homo sapiens

<400> SEQUENCE: 7
gcaggagtct gtagtgccct gaagaatcca agccgtcaca ccagtgattc gaacatttca        60
gagaaacaca acggagggaa ggagcagtgg cttccccggt gggctagggc gtgtcacagg       120
tgtgaaaaat aaattcaaac tcaaattaac tggctatgta tctttgttac aagggctcag       180
tcaggaagaa caaaggttcc tgttggctaa agtgtgtcct gaaaattatc ttcaatcctg       240
catgtactcc tcgtgttcaa agatgagctc acaggaggca actacctgca gggggcagga       300
catccaggga cctccagtgt gggtactggg ctctcatatc tctggcagtg tgtgcctctc       360
ctcaatttct cctttccttc tggaccacct acagacacag cccactgcca gagacgccca       420
gatataaaca caggtgcaaa acacatctgc attactggat ggcagcacgg ccatatggtt       480
ggagtaacag taataccata tccctgctgt agaaccagct ttatttacaa ttttcttatt       540
aaaatatgca aatagcaagt aaatagaaaa ccacagagct ctgttttgct gtaaaattga       600
ttggagacgt ttgactattt taaggacttt tgatatacag atctgaagcc aacataaaag       660
aagatggtta agtccactta aaggcatttg ctaggagcac accatagtac gattaaggtt       720
aaaacaaaag gatgtaaggg gcttccttaa ctaataggtc caatccagga attgctaaaa       780
cagagttgaa acttgcagtc ctgcagaatt tcaaattgtc ctgtaatcct aacagcaaag       840
catggcaatg ctggtggtat ttggtgaaac atctcaatcg tccatttatt gtcaagatgt       900
atcaaatttt gctgattttg tgtctttaag tggccactca gcatattttg aactagacaa       960
ctggacacag gcatctcctc caactctgat gtacattctt a                          1001

<210> SEQ ID NO 8
```

```
<211> LENGTH: 1203
<212> TYPE: DNA
<213> ORGANISM: Homo sapiens

<400> SEQUENCE: 8
ctgctgcaaa atggctgtgg tctgcaaggc tgggaacagt tttgtggggtt tgcagtgata      60 tttgaagttt gatgaatgaa tacaaaatgc atcactggta taatctaaat gatgtgacat     120
aatttatgct ccaactgtta aactccaata aatcccagcc aatgacagga aaatcccaga     180
tgttggccat tctggaaact atcaagccta taacttgata ttaatgcctg atgaatagca     240
taaagcagca gcattttcca tatgtgtact tagagtaaag ttaatgtaat aaacataatt     300
gcactcatat agcttagtat aagcaattat cactaattac tggtagagtt tctctctctt     360
ttctaatgaa gagtacagtg gaaggatagt ttatctctag atactaattt aatttaaacg     420
ttaataggaa tagttgtttc tgcctaaaag atttgatgaa ttttcattgc atctaactca     480
attccagcaa tgtctttatc cagcctttct tagtctgtca cttggaggat gttctatcct     540
gtcctactgt ccataagacc aagcagctcg gaggactccc ataatcagtg aaaagcacct     600
tgcaccattc tgggaagcag tgggactcag cttctgtgga ttttaaatca gtcagtattt     660
cggagcatcg gtgatcagag gtgtctccta tgtttgtatt cctataagca tccaacacaa     720
tggccagtag gtagttaatg ctgattaaat gtttactgag agaagagaca atgcaggtat     780
ttatgtatat ttgggtttgg gtcattgttt tcttctcttt ttttcctttc tacacatagg     840
ataaagagtc tgtaatacac gactagaata atttgatact taaaaaatgg ttgaaaacaa     900
tgacacatta aactatctac tgtgcaaacc ttcaccacca aagccacctc tggccacagt     960
gcaggactgt tagaagttga ggggaccttt aatttctgcc agaagcccca agtggttgac    1020
aattatatca tttctctatc tcttaatctt aactgatttc ctgtttgtgg acaaaagaaa    1080
gccatgttac agtttgttca gaaaccaaga tggaagcctt ttaattctgt cttcattggt    1140
gaagctattt attgctgtgt tttgtgcttt gaaaaagttg aataaagata caaatacaga    1200
gca                                                                   1203

<210> SEQ ID NO 9
<211> LENGTH: 1029
<212> TYPE: DNA
<213> ORGANISM: Homo sapiens

<400> SEQUENCE: 9
cacaacaatc ccatgaggta attgctacta tcttcacttt atagatggga aaacaggttc      60
agagatgtgc ggagggctca caggtaatac acagtgcact gcacctacag gatcctgctt     120
gaatagccag tcagaaaggg agaagcaagg aaacggctgg ctgtgtagac agaggaggga     180
tgggcaaaga agaaaagcca gggagaaaat caagacttca gagggaaagg aggcatgtgt     240
tgggtcagag gtcaaaagac tcagcatcac tctccagtgt gggaaggtgg ggcacagaaa     300
cacaggaggc caagtagatc acgcctctgc tcaggtctga gtgtcagagc tggagccaat     360
ccatacccct gagtagtctg tgaaggctgc cagagacatg tacagttacc cgcctggaag     420
ggcatgcaag tgcctcgata tgggccaggt tctgggactg aacacaggga gcagcctgac     480
ctctaacccc cagactcctg ggggagctgg aagagggcct agtacaggat gttggcgtta     540
gaagtgactg agaggaggtg tatgcaggga tcccttctga gccatccacc aagtcatgtc     600
agtgagttag caacactatg gagttcctgg gccccagacc aggtgctgga gagtggagga     660
acccagtgat actacatgca gacagtagcc ccttggagat gagggccgag tgggggggaag     720
```

-continued

```
gggagaggag agatggagct ggatggccag aaattggtgg gtgagagggt gttcaaggaa      780
ggatggatga gcacaatttc cgaacagcaa acatttcact gctgggtgct gagaatacag      840
gagtagacat ccaatcctca aagagcttcc cgtgtactgg ggaaacagaa gcagttacaa      900
tagagcatga tgaattgtaa gggatatcca gaagtgacag gggagatttc taggaaatga      960
catgtagtat aaattgagtc ctgcaagatg aacaaacatt agccaggtga agggtcaggg     1020
aatagcaga                                                            1029

<210> SEQ ID NO 10
<211> LENGTH: 1948
<212> TYPE: DNA
<213> ORGANISM: Homo sapiens

<400> SEQUENCE: 10
ggaaattatt tcagcgcatg tttttcttca actcaaggct tttatgaaga aaacatttct       60
taaagctgtt attaaggtat tcaagctgga actcagacga ttctaaaaca ctcctctata      120
ttcttcctca tctaatgtct ttggaagaat tgttagggtc ctggaaaaag aaaaccaaca      180
gatcaggtgg ttgaatatgg cttcctggtg gggcaggagg catctggcag tgcacaaaag      240
ggcaaagctt ccagagagta gcaagtcact gaagaaattc tgttatagag aaaaactgtg      300
tgtgtgtcac atacatacac atatatcttc aaattaggtc atttatgaaa aaatggagaa      360
aaatgcttct ataagatatt cacactgtta actagttttc aaaagttcat caagcttact      420 ctcctttttct ttgaatactt ttggaagaga cacaattttc caagccaaaa cacagttcag      480
gcaatagaat agatgaaatt tttacaaaca ggatgaaagc ctggcacata agacactcaa      540
tatgtattga aatatctttg gcgaaataaa actataatgc tctttgcgat atggttttct      600
ctcttaacaa tatattttgg gcctcaccta ttagttacta gaaatcggta gcatcattgt      660
taatcgctgc tttgtattac cttgtagggg tgcactttag gtgcatccaa tttattttct      720
gtcacgacca aagccacaaa gaacatcatt ttgtgttact tttgacatga gtgtaagtcc      780
tgtaggataa acaactacga gggaaaagac tgggtcaaag ggaatttcag gataatccac      840
ttcttcaaaa actttaagtg ggaagtgaga ataagatcag gaactcttct gccttgtcct      900
tttattccaa ctctctactc aacagggctt caccaactgt gttagtttga gcaaatctaa      960
gagcagaccc aggcacaagt gccagtagcg gcaggagatc tgcaggccta caagtagggg     1020
tgtgcagatg agacaggtaa gaaagggtgt tatcatgcca cttctcactg tggacagctg     1080
ggactaatct tgctgggaaa caatgtagta cacacccaga gttaccccag ctgtgggaca     1140
cggaagctat ggtattcatt cacatggcca tatcgaattg ttggatgaga actgaatcag     1200
gggcatcagg tatctgctct tccgcttgtc ccggggagag gtcaagtgct tctgcagctg     1260
gcagagagct gcagtgttgg aaaatcacct ctgctggtag gggtgagtgc agagaggatg     1320
gcagggctac ttagtgatag aaatcagaag tctactctag ataacacatg ccaattttta     1380
gctgcccaga atatccccct tctttggggg agacttcttt attctgcatg tctttgagag     1440
agagagcccc cttgccaaag cttatactct gcctgctgca tgaggccagg cagtggcaca     1500
aagattcagg tacagtcagt gactatttat ggtggcagta gccaagttca aagtccagca     1560
gcagcacggt gagtgttggg aacagcagaa caggcaacat gtcataataa aatggaattt     1620
gtgttctgga aaatcaaata aaggaaatct ctcaccccaca cattacaaaa ggcaaaaaat     1680
atccacaaca accaaaagca aatactaaat ataatgagta caagataaga taataagtag     1740
```

-continued

```
gtctgggagg tctgataaat aaataacagg agatccttaa ggcaaaagat aactttaaat    1800
gtagaaaaat ttacatttta agaactaaat ggctgcaaat caaattccaa actgcacaaa    1860
aagccccaaa ctcgtcatct cctggtgaaa tttcttaaat ctgagattaa agagaaagtt    1920
caacactttt ccagggagaa agtttact                                       1948

<210> SEQ ID NO 11
<211> LENGTH: 1075
<212> TYPE: DNA
<213> ORGANISM: Homo sapiens

<400> SEQUENCE: 11
tttattaata actgttttct cacttatatg cttatatgta caacctgagt taaaataggt      60
gcttcctatg aaaacacagc ttcatgaccc ctccaaccag agaaattccc ccacctccca     120
agctaaacgc attctcttcc tctgggggtg ttgcctgatg gaggggctaa agggagatgc     180 tgcaggggg gttattgttg atgtcctgca cagagggtgg ggaagcttct cagtgtcact      240
agccaggtgt ggcacattgt catctaggca gccaaggaga cgccaatgct ggagagcta      300 gtttccaggc tgagacttcc aggcactcag aggaaaatgt ctgggctaga ccccgggtgg      360
gcaggatgaa gccttctgcc acttcttccc aggcaatctc tggtgaggct gggatcaaag      420
actgttgcgc cactttttaca cataacagac acactttatg tgtttgtgat tattgccttt     480
caaactccct ccccatttc ccaaatatct aaagtcaaaa tggcctttg gagaagaggg       540 tggggagtaa ggcctccacc agctgttatc tggcctctgg aaaaatcctc tacattggag      600
tgcattgagg gaatacctgg tttctgtccc tactgccttt gaataaatga agaaacagaa      660
acacaagcga atgaagttac ttagagcccc agaaccttag agctgaacga gaccttccaa      720
ataccttgtc ccagtctcct cgttttacag gtgagaagac acctaagaga ttaaatggca      780
tgtccaaggt caccaggcta ttagtggtat agatggaacc taactcttca gactgctggt      840
cagatgttct ttccacttta acactgcagt gcaaaggtca aacacaacct ggactctgta      900
aaccaccaca gtccatcacc aacatttatt gaacatctac tagtcagtga actaaagcct     960
ctgcactccc tccttctccc gtctttgtct ttgggactaa agagttgaat tgcaattctg    1020
cttcaataga atccaggtgt aatcagaatt gccttgcttt ctgacattac ataca         1075

<210> SEQ ID NO 12
<211> LENGTH: 1113
<212> TYPE: DNA
<213> ORGANISM: Homo sapiens

<400> SEQUENCE: 12
taaagttacc tacagtgaca atgaagttga tcagcactct caatgaccca ctgagatttt      60
ggtggataaa gttgcttctt ctcagtatgc ttagctggag gaaaattatt agtgaccgct     120
attatctgat tggcctttga tttttctttgc cctcaggatg aattcttttc ctgtagactt     180
tcacctttca aataaataat agcctagaat tcctgtccta caagttcttc aagtatgtcc      240
agacataaat atttgccaaa tatattaaga aatatctagc aaacttggga ggactactta      300
tattcagcac agaacaatta actgactctg taataccaat aaatgaatac agtggggaac      360 atattttga agattaagag atgcacaatt gttagtacca aaaattacag agccctataa       420
aatgaaagga aaccttggaa agggcaggtg ggtttgaggc tgggccacag accatttgga     480
accaggaact caaattatgc catcatgaat gcattgctgc tgctatttct ctgtgtgtta     540
aaaacgtgtt tgccaacagc acttgaattt tgtgtatgac cactttagcc atccggactc     600
```

-continued

```
tctcagttct atttctaaaa atccccagaa aggactctta ttatccagct tgtgaagcct       660
tagatctgtt acgggttgaa ttacgtcccc ctaaaagatg ctaatgttct aaccgcacct       720
gtgaatgtga tctttctttt tgtagattat caagttgatg gttcattaga gtggttccta       780
atccaataaa actatgagtt tgtaaaaaag gacaatttgg atacagatat agacaggtat       840
acagggagag caccatgtga acgtgaaggt ggagattgga tgaaacttct acaaggcaaa       900
gagtgccgaa gtttcagcaa accactaaaa actaggagag catgaaagat tctccctcaa       960
agcactcaga gggaactacc ttgctgacac cttcctttag ccgctagaaa ctgtgagacc      1020 cttctatttta aaccattcag cttttgagac tttgttgcaa taccctagca aatgaataca      1080
gaaatagtgg cttgggggtg ggattatcag tac                                    1113
```

<210> SEQ ID NO 13
<211> LENGTH: 614
<212> TYPE: DNA
<213> ORGANISM: Homo sapiens

<400> SEQUENCE: 13

```
gttcaaatca cctgttcttg tgaatatgct aatttacatg ataaaagaga ctttgcagat        60
atggtcaagt gggatcttca gacaaaaaat ggaaagtgga cttagtgaat aataataaat       120
gtttatgtaa agcttatgcc aagcactgca accacataaa tgtatcaaat catgcaaaac       180
gcaccaactc aatgactcct ctctgtgacg cagatgctgt cattgtgcct attttacaga       240
tggagggact gaggcatttt ccaggctggc acacagtcca acacagctag gaagtggtgg       300
gctggcttca gattctgtgc ccctcatgct atgctgcctc tctgaaggaa gtaggggctc       360
tttgggatac ttttgacatt aagaaaggat taaatagtac aatataatga aaacgtttga       420
atactcgttt taaaagtaca aaaagagaga gccacacaca cttttatgtg ggtcaggagt       480
gactgttgtt gcactctttg gcatctgcca agcatgattt ctcaggatgt ggtggttggc       540
cgactgccct tgtggccact ggattccatt ctctctctgg tttttctccc tttcccctg       600 ccctctgaaa cctt                                                          614
```

<210> SEQ ID NO 14
<211> LENGTH: 233
<212> TYPE: DNA
<213> ORGANISM: Homo sapiens

<400> SEQUENCE: 14

```
gtttacccac acttttttcca cctactgcaa gctcccaggg gcaagctgat ccctagaaca        60
ctttggctga atgagagaag cctcaagact gcaaatccac cccatctccc caagggcctg       120
ccaagactaa agaagaagaa gatctacatt aaagaggctc tcctaaggtc ttcaggcttg       180
ggatttgtgt gagaaaattc taatttaaga cttttcttgtg attcataggc aaa             233
```

<210> SEQ ID NO 15
<211> LENGTH: 1618
<212> TYPE: DNA
<213> ORGANISM: Homo sapiens

<400> SEQUENCE: 15

```
attctggaga gtccagaggt ctctctgctt ggcttgcaga tggccattct tgctgtgtcc        60
tcacatagcc ttttctctgt gcatgctcag gtgtttcttc tttgtgtaac agcagtccta       120
ttcccaccct tatgacctca tttatttatt accttttttaa agacctgtgt ccaaatatag       180
```

```
tcagcttcaa catatgactt ttaggaggac cttagagcaa tgaccttcat ccatcaagaa        240
actggaggga tctcactgac catgagatgc tccattggtt gtactctaga ggagaccgac        300
gaggatctgc ctcttcctct tgttccctat ccaggtaggc tgaacatgag gagaagggtc        360 ttttttttc ttagtgggca agttattgga atctttaaaa aaatgatcat ttatgattaa        420
aacttggaaa aggaattatg cccatttttt tcagtttact ctcatggctg tactacaaag        480
cactagtcag taacctcccc ttgaaaagtc tttggataag tgcatcatta ttctagctac        540
cagcacttgg tgaatcccca tgttaaactc aacgtgtttt gaaattaaac ctcagagatg        600
ttcccaacct tcttttatgt ccctagagat aagtttacca aatgttaaca aagaaataat        660
tgttctcaga acttatggca gaaagtgatg agatgtaggg ttgctttgac cgaggcacaa        720
atggtgctct gtggcaaacg taaagaaact gttcaataat tactgttttc agcaaagtaa        780
aactctaaac caggggccag caaacttcct gtacagatcc agatagtaaa tattgtcagc        840
tttatgggct acacggtctc tgtccaagct actcagccat tttaccctga aagcagccat        900
agacaataca tatacaaaca ggcatggctg tgttccaaca atactttatt tacaaaaaca        960
ggtggcagat ttgatagttt gccgtcacct cctcaaaccc aggcttgctt tccctctttc       1020
tgtagtaggt ttgaatgcct aatacacaca ttttctctct cctgcctttt aaaacttcat       1080
gcttatgctt tccatatgtt tcaagcatga tcttgtgtca tcttttttgg aggtaaaatg       1140
ttgggttgag tgggttagga aactgacttg tgagtgtgac attggagatg ggtctaatca       1200
tgatgttggc ctggacatat ctcatttctt cccatgggac ccatctgatt tgatttgact       1260
ttaggaataa gagttcagat ttgggattgt gcttggtttg gagctggctt ggtgagcaga       1320
aaatgctctt caggacgtaa gctctgtgtt tcggagttca gggagtgggg cagtcataaa       1380
gagcccccag ggagaaggcc cagggtcctg gcttctccgt gggactgttt cccgggtcac       1440
agaaagggag acccaagtgt cagaggcaga ttgaactgtc cctgccgtta tggggagcct       1500 ctttttaaatc tccccatttt atatatggaa gggaggtggg aactattcag tcttggaaaa       1560
ataaagttta aacccctgtg aatctcaaaa tatcaataaa tgaaaggaca cgtaactg         1618
```

```
<210> SEQ ID NO 16
<211> LENGTH: 1611
<212> TYPE: DNA
<213> ORGANISM: Homo sapiens

<400> SEQUENCE: 16
```

```
tcctcctcct gtccagcggc tggctgtagg ccctacgaga gagctggctt ggggcgcagc         60
ccgtacctct gggagaggcc acaaaggggt cggagagcgc ggtcctgtgc acagttaggg        120
ttaagtcagt ctgccctgtg tgccctccga agggtgccca gctttgctca gtgggttgga        180
gaattgcaga attctcggcc cgaatgaaaa gctgtcaaaa atagtgaagt tagtttggcc        240
ttccaaggtt aggtggtgtg gtagattgcg ggaccgaggt tcagaatttc tggggggctgt       300 atccccgagc cccactcctc agaatgcaac tctgtacgac gaaggaactg ggtaatcaga        360
tgactaacca cctaaacggt ccacacaatt atcattgact cctaggtacc gaattggcat        420
ggatttgaca attagcgatt cacggttaag cagactttat ctttaatcca tcaaaggaga        480
atttctgcct gcgtgtttgg agagaaacgc gtggatgtga gttaaacttt gttaaaccca        540
acaagcttta agataaaacg actgatattt aaaatggcaa tttaaataaa aatgttctct        600
gatcagcctt tttgtggtct taaccatgaa atgtctttgc atattcaaaa gtgagtccga        660
aatcttagaa tgcaatgtgt caagaaaact tgttcaagtg cagactccag ttaagatcaa        720
```

```
tgtttaaact ttttgaatac ttttacata taagtttgtt gcaactgatg tctcaagaac      780
ataactggtg aggacagctg tattgccttt tagaaaattg ttacagttat atttacaaaa      840
aacaatgttg cttcagttaa aatgagtgaa tttagtacag gtaagggtgt ttgtagttag      900
gcttatgtgg taccttccta atgacaaagg ccaaacaaca ttatgctgtg ctctggagat      960
attacaaaat atatagaaaa ctcccccttt tggaagaaat gtgtatcttt ggaacagttt     1020
tttctccatg ttatattgga ggcatttgaa acttcctagt catgatgttt tctgagcttt     1080
tatacaagat tgtatgtatg taactgccac cttttttttc ttttacacct gttttcagga     1140
aatatgactt attttctttt ctcctgttct ttcatgaatt taaaagtttg ctgcgtgttg     1200
aaaattactt aatagtaaaa aagaaaattt tgattttgac tccagctgct tcggaaattc     1260
tgattcttct aataattata tactagactt ttcaaaaata tgggattttt ttgtttcaaa     1320
aaaagttatt acttgcaatc ttagctcaag gatgccattt ccagtatgct cccaatgtct     1380
atggcaaatg tgggtaattg gctcccacgc tttcctgctg gcttcaagga gcctaagaat     1440
catttactca gcactgtcaa tagagaaggc aagaaaggtg aaccctgttt gccctccttg     1500
gtttctagtt tatgcctaat caaagtccat gattgttttc atctctcagc tggatttgag     1560
tcagcttcag caaaagccaa atatccactt tatataatgc ttatttcttt c            1611
```

<210> SEQ ID NO 17
<211> LENGTH: 8709
<212> TYPE: DNA
<213> ORGANISM: Homo sapiens

<400> SEQUENCE: 17

```
gtttttttgaa atggttacca cattacaagt tctttgtaca tgctatttcc caattctttc       60
aatcttcttt ttttcagatt ttagatctga ggaaaagaca ttgaattctc acagcaacct      120
tctgagtgcc taccattatc accccccattg tccagatgag aagaggcttt gagaggcaca      180
gattctttca aggtcataca gaggtgggat ttgagtctgt taaccccaga ctgtatgctt      240
ctccatgcct cctttctgct gtcggcagaa gccggcactt gggcatgaaa ggccagcatg      300
cattatccat cttagacaga cttttttgttt ctaagactgg aaaatgctag aaagaagttg      360
gcagcccaaa gccattcctt ttgtttttgag tgtttgccct gcatgtctgc atgaagctgg      420 ggttttttcta tcagtgagca tctctggagg ctggggaagc aattgtgttt tcgacattcc      480
tcttcattcg cccaacacct ctctctcatc aagagcctcg tggaatcttg agcgggcaga      540
cgctattcat cagaaagagt tgccagccaa cccgctattt cttgtttcca acagttaagg      600
ggaaaaattt cctagatatt tttacttcgc aattctattt ttgtctcaac ttatctgatc      660
cttaattctg actttatttc cttgtgatgt taaagcccct gaagaccta ttcagggcta      720 agccagatac ccatcagccc ttgtggagtc actcaagtca ctcacttgct tacaaatcct      780
ccgaggattt taaggagttg ggtgacagat agcaactgaa gagaaccatg ctccagggga      840
acaagctttg cagactgagt cccagcttgg gggttcactg ccaatcacta tctgacctca      900
gaaatatcat tggccccacc atggaccagt gacatttgtc attcacccgg ctatgacttt      960
ttctgacaca tagacgaatt ctcagtccca tcttctggtt acccacccat gctcaagcct     1020
tgactatctg ggtaaattac atcatccccc accccatatc tggcattttg agggtatgga     1080
ggagggattg taaagctatt tgctaaactt tctctggacg ttccctccct cctgaccacc     1140
ccaccccact tcctggcaag ccttctggct gtgatttcat ctgaattact ggaatcacac     1200
```

-continued

```
tgtctcctgt cagcctcccc cggccctcct gctgatgagg ggtcccggca ccacccagcg    1260
catgcactca cgcacgccac tggctcacct cctccatccc atgcctcccc tgtctccagg    1320
tctctgtctc ttactttatt tttctctcca cctccttgtg tctgcctgcc taaagatttc    1380
tgatgcttaa tcctcctctg tctcccttgc tgtctttctc tgtgtcttct gtttctctct    1440
ctttctcctt ttcccttcag aagcatttta ccccaatgtc tctgtatgtt ccttggcatt    1500
ccctctgcag cactgtgagg ctggcctgct tgaatgcaca cctgagctcc ggattcacag    1560
gtaggtgtgt gacctttctt aacttctctg ggcctcagca tactcctttt tacagtggga    1620
ataacaatag cacctctcac acgaagttct ggaggtgtgc cactacattt tgggaaattt    1680
attatgcagc catagattac acactcacta tttctttttt ctgatgccat actatatttt    1740
tgtttgctga tttttgtctc tcccactagg cattaattcc ataagggctg actgtgtctg    1800
tccccacagc ctggcatatg gatcactaat aactcaggct gggtaaatgg agatcactca    1860
ttttaggctc agcctaataa atctccctag agagcagtaa aatttgccca ttcttttttct    1920 gtctttctgt attgatttct cactttctgt ggctttctgc tgttttattc ctggctgcct    1980
gacagagggt ggtgcagata aagaggcacc tgtgggagga agggctctgt gtgctttctc    2040
ctttaataag ctgtgtctaa aaaaaaaaaa aaaaaaaaa tagctcccct ttgcaaaagg    2100
gacgaaaata gccaggattt tccagtttta atggctggga ggctgaagac tgaggcagcc    2160
ctcttctctc tgagcagccc ccaaccccgg ctgatcactt cacacacccc acttgaatta    2220
ttattcattt atccatcttt ccaccaagtc attaattaat tccctttatt tgcttatcta    2280
tttatacatt cattatctat cttttttactt atgaattaat ccatttatcc atactcagct    2340
attcatccat ccatccactc tccatctatc cacccatcta tacatttatc catccattca    2400
cccaccatcc acccatcttt ccattcatcc acccattctt tcatgcatcc atctatccat    2460
ccaccaaccc atccatctac ccatctatcc acatatccat catccatcca ttcacccatt    2520
catccaccat ccatttgtca tccatctatc tatccatcca tccatgcatc catccatcca    2580
tccactcatc catttatcca ctcatctatc cacttatcca tcatccattc attcacccat    2640
ttatccacct atccttccat ccacccatct atccacttat ccatcatcca ttcacccatc    2700
ctgcattcat ccattatcca ttgatatact tttcatttaa tcgcctttat gttaattaat    2760
gaatttattc acttaaccat gtgtctattt atgaataata caaacctgcc ttttaatttt    2820
cactgagctc tgctttgtga tcccagggag attgttactt ctctgagcct ccatttcctc    2880
actataagtg cagcttagaa atacttccaa gcacatgggc agcgtgggtg cctagtaagt    2940
gttggctgtt gtcattcaag aaggatggtg tgagcctgca catgagtcag caggggagag    3000
aaggcaagat tctgcccaga actcaaggaa aatcagatgc agttttcaat tattgagtca    3060
cagtctctcg tggcttggaa ggagatagag gatcctcctc ccaaccaata cctttacgat    3120
gttctttcca cacagctctg tggtttacaa ggcaggctta atcttcaacc tgcacgtatg    3180
agtggggtcc ctccacccct ttttcctcag agcattagaa caagcattct tagagctggt    3240
ccagtccaga gatcttggac tgggcctgca ggctggcgac tctcatctgg tcccaaccag    3300
atcaggaaag caaaactcag tgaagccaca tggctagtgt tgggtcctcg ggtggagccc    3360
aagaagcttg gtgggcactc ttccttcctc acctcaaatc atcttgaact ctgtgcaagt    3420
cccagaatga ccctggctgt cttggccttt gtaaaagttg tcttattcct aaaattccct    3480
tcggtagagg aacaggaggg aagtcaggag cagcaagcag gaaatggaag ctaggctggg    3540
gctgggaaga gcagcccgag tttcatttcc aggtggccca gttcccatcc ttgaccttgg    3600
```

```
tgttcacctc aagagttttc agccagtcca ggatttgcgt agaaaagtct ccccatctcg    3660
ttttcccagc caggtctcag atcggttcac atgaggcgaa atatacatca gcgtggattt    3720
ttttcctttt ccatttgcat ttgtttgttt cctgcaggct gacactagcc agccttgaat    3780
ttggtcctgt tctctgcaca gctggactca gggagcccaa cccagatgtg ctagaacagg    3840
tggcctgcct gggggccttg ggtacataca gcgggtgctg catccctggg atctgtaaga    3900
aaatgggagc aggtccccca aaacaccagc agactgcact cccatcatga cctaatgaga    3960
tttgaccaaa atagcccaat cctactagca acagccaaca cgggaaattg aatgaaccca    4020
gggcgcagac caagagacct ggctagctgg ctctttagcc ttgggagcct ttggtttctt    4080
catgtttcat gagttgttgt aaaggttgcc agatttagca aatagaaaca caggatgctc    4140
agttagatgt caatgccaga taaacagtgt aagtatagct tgtgcaatat ttgggacaca    4200
gttatcccag aaatttttct ttgttcctct gaattcaaat ttaatggggc atcctatatt    4260
tgatctggca accctcgatg ttgtaacaat aaagtgaaat ggtgtgtaca catccttcac    4320
ggcgtgcttc accccaggtg atcagagccc agtcaccatt tctgttagac caggaatact    4380
agatatctaa tactaatttt atcaattact atattattaa tgataattaa tattaatcag    4440
cacaaatatt aaaactcatt tactgagtag ctactatgct ccaggcatgt ccttcacatg    4500
actttgtcat cacatcactc aatgatagag gaacactgtt ctgagtgcct tgcaagggct    4560
gcctccttaa atgtcatcaa ctctgtgagt agatactatt gctaaactat tactagatct    4620
ctgttttgca aatggggaaa ctgaagacta agcacgggct catcaatggc tatgaggctt    4680
caaacccagg cagtaggctg cctggctcca tccctcctct aggctgcttt atcagccaca    4740
tgaatagata gaacgagggc aactgtggat gtccctagag ggagagcaca gggctaccag    4800
gctgtggcac attaccagct gtgtcccatt tagccctctc cccctgtaaa caaagacatc    4860
actattccta tttctgatgg tattgaggct tccctgtat gcagtgaggg tgtcaggaca     4920 aatgtttcc agagctgagc actggagcaa ctcggaaggt caagataggg ttcccaacag     4980
agaagctctg acacttcctg gctgtgtgac cctgggcaag gtctccacct ctctgatctc    5040
gcatctcctg cctgtaaaaa gggactgatg tcaatccatg agagtagtta cggtcatttt    5100
tagggcagag cttgagataa gacttcaggg caggtggttc ctttgggagg tgaactcagg    5160
atgccccagt agaggagtgg gagacaggaa aagaagaacc aatacatgtg tgaatgagca    5220
ggtgactgct gccggcactt ggagcacagt cctgctggga actctggtag gctgcacaga    5280
gcacacctgg gagttgtctc tcccaggggt gagggatggg atatttatcc tccaactccc    5340
ctacatctct ggcctaatcc cttgcacatg cccagtgtac tcagtgggcc agagaaagcc    5400
ctgggcaaag gcagtagaag tgagtgggca tgggaaggca agcaggcatg gtcagggcac    5460
ccactacatc ttgacaaatc tctggaagat ttcagttaaa aagcaacctt ctgctaaaat    5520
aataacaatg acaacaacaa tggcgttgac aacgataata ataattcagg ttgaaaacca    5580
agggatctgt ccccacccac agacccccag accagtgttc tcctggggta accagctgtc    5640
caaagaagca acccagattt ccttcggctc caggaagggc aggctctctg agttctagga    5700
gaggcctggc atcctgcaga ggccgtgccc ataaagcatt ttcagagctc ctgtcaggga    5760
ccagcactca gctttgattt agcgtcagag tagataaaag aaaaaggagg aggaggaagc    5820
cattggtgag cgaaaatact tgctaagtgg ttgggccatg agtgtatctg tcaacctgga    5880
acaagaagag aactactatt tagataacta tttgctgcac ctcccaaatg tctggggctt    5940
```

-continued

```
tacctggctt gcctcttgtg tccccaaccc agccacttaa gaatattttt atttccattt      6000
cagagatgaa ggagtgaagg ctcagagggg gaaggtgact tgcccagggc tacacagtga      6060
ggaatggtca gagctgggat gaggaagtaa taaagaatga aatcaagtga ctttccctgg      6120
ataccaggcc acgttagctc atggcccggt ttctgggtca gggacagggg tgtgtgatac      6180
tcttatgcaa ggcatttggc ggcagagaaa ctctagttcc taaagattat tattttaact      6240
aacccagtgt tgacgtgtcc aaaggcagcg ggaggctctg aagggttttc caagaaagcg      6300
tgtgtttctt ggggttattt tttcagtcaa gttcagggag ggggctgttt tgctcaactc      6360
atgtttctgg aaaaacaggc acttggaaag agtcaggatg tggatggaga gctgtgggcc      6420
tgcggggagg ggacggagga ggcagccagg gccggcaccc tttgctcagt ctcttcttga      6480
gctggggagc ctggaaggaa gaggctgaag atgaaagctg aagtctctgt gcctcactct      6540
tgagaaatat gatcacttgg cctctggagc aggatgacga caggaggtgg ggttgagggt      6600
tgcttctcat ggagtgctgt ctagatatcg ctgactcatt gtgtgcctcg gtttcccctc      6660
tgggctcaag agctttgaat gctttgtgta acccagtccc tgcttgtccc tgcaggttca      6720
ttccacgtca ctctcttctt cacgggcccc cacagaagcc cacggtcctg cagccttgag      6780
gccttccctt ctgcctggaa cccttctgct cctaacctac ctctgtcgtc ttcctggcac      6840
cttgaatatc accttccctg atctcccaaa tgagccaggg cctcccttgt gcattctttt      6900
ccttggagca catttctcta taattccttt tccagtgtct acctctctca ctgactctga      6960 ggccccttc tcatttactg tggtgcctga cagagcgaat ggaaacacct cccaagcagg      7020
gctacagccg tgggtgtccc aaccaaaggc agagcccagg acaccaggca ggcagacagg      7080
tgatggacag atggcttcta caccttctta agattatgca gaaagccaca ctctaggcca      7140
cccaccttca ttatatggtg atcaccagtc aaaagaggga aattccatcc caacctcttc      7200
cctggccctt tcagaatcct ggggacagag acttcgacag actccccaca gggtctcatg      7260
aggagactct gttctcactt ctcccctgct cctggaggac ccacaactct ttcaagctca      7320
gaggtgagtc atccatgcat cacgtgtctt ggtgaatgtc aagtgtctcc tgctttagag      7380
ccttgagccc tggactttgt tttatggggt ttggctgtct ggggccgccg acgatttcat      7440
ccatcaactc aggatcgctc caacactaat gctgaattta tagaagtggt taaacaaagt      7500
gttgacaata gggaccgcgt gtttctgatt aacacgcaat tccaagggaa gctgccaagt      7560
gtggggaagt cagtaaaaca cagcagcgat ttcccaggct caggggggatt tgacatcacg      7620 ggattaacag atgttgcgca aggaacttgc aaagcggagg ctgctgcaca ggcttatata      7680
caaaccggag ttgttccttc ctgtctttct tttttttttc ctgagagatt aaatctgaat      7740
cctctttcag ccttaagagt ttccatcagg aattgctgtc agcttcagca atgctcccag      7800
aatcctgtcc ttactccttt ctgagagtga acagtaacac tggctaacat ttatcaactt      7860
actgggtacc agatacttct acaaatcatc tcctgtcatc ggggaagcag gtgtgatgat      7920 ctacactta aaaatgtttt agtctgaaac ggtcgaagac tcacaagaag ttgcaaaatc      7980
agacaaaggg ttctcaggtt cccttccccc agcatcctcc atgataatat cctatatgac      8040
catagtacat tgtcaaagcc aggaaatcag ctttcacaca tcttatgcag ctttatccag      8100
tgtgtactgc atttagaaaa atagcctatg attttttagca catgtttagg ttagcaacca      8160
ccaccgcatg agacgataaa attcccttgg gttaccctag aagtcattga gctgttcccc      8220
atcactataa gttcatttct tcttgctgct ggtcagtatt cctttgtata gatgtaccgt      8280
gctttatcta tccacctgtc gaaggacatc tggtggtttt cagtttgtga ctattgtgga      8340
```

```
taaagtgcta cgaacatgca tgtaaaggtt tctgtgatga tctgcaccca gcagatgagg      8400
agatggaggc aagagagggg atgcccaagc tctcatagcc acacttgtaa tgagatttga      8460
acccaggtag tcactccaga ggcttcatgc ttaaccacct ccaagactga aaatcttgta      8520
ggtaagaata acccaccctc tgctctgtct ttcttacaga ggggctatga acaggcatgg      8580
agttaattca tatgcaaaca tactttctcc ctgggctctg gcctccttca ctcgcctggg      8640
acaaccagac ccaagatccc agagtcagcc agtgccattg cagctgcttc tttgtctgca      8700
ggatgcgag                                                             8709

<210> SEQ ID NO 18
<211> LENGTH: 5221
<212> TYPE: DNA
<213> ORGANISM: Homo sapiens

<400> SEQUENCE: 18
gtttggctcc agttaattac tttctcctga gggcagacct tgttaagaag aataaaatgc        60
actgggtact tcaaaatggt tcctctcctc tctctgctag cagcacgagg agattttccc       120
ccaaaatcac tgtgagaccc tgtggattct agcagttaaa acccactaaa gtgtagggtc       180
cctgatgact gggaccccat ggagttttta tctccagcaa tttatcagct cagttcagat       240
ttctgtaccc cagcattggt tctgaggaag tttccgcatg tggtttctgc tgtgatttga       300
tcttttgtaa tttattctag tatatagtgt gaagaaagaa cagggcagtg ccgagtcctg       360
ctctatcatt gatttgagca agggcagggt ctttgccggt gttctgggcc aaagaggctc       420
catgcatttt ttcgggactt tggattgttt gcagtttgcc ccataactcc cacacatttg       480
cttcttcatg tcccaaagct ctggctgctg cagcattccc ataggaatgt ggatgcctgc       540
caagcgacct catgtgcatt ccattcatct ccttggctgg gaggcagcag ggaagcaaat       600
tggctggttg cttaactgtt tgggtcccaa ccctgtgttg gacttttcca ataattgaag       660
aaaaaacaga agagagatat ttatttattc atatgaccat ctggaaaaca gctattttca       720
agtgtagctt aatgaaaatc acatcctttg gtttgtttga aatcatcttc caccagaaag       780
gcattttgaa gcaatgaggc tttgtgaggt gtgattaaaa caatgtgagt agtttttttt       840
aagcaatcac accaaactgt agctactcaa attcaggttg ttgccttcca ataatctcag       900
tgggctgtga cccattccaa gatgctccaa cctgtgtaaa attcctaagg aaattactac       960
actctttgtt ttgctttttg tttatcattc agtcagcaca tatgggccat tcttgtgctt      1020
agctttgact acttctagtc aaagaatggc aaactaaaga aatacaacgg cttcttaagg      1080
cagccctggc aatgtcactg gaatggtgac tgcttgaagc agaaaatgct gatctgattg      1140
gataattctg aatgttttct caaaacatct cattattcta ttcctggaat attgaaccac      1200
cctcaaatgc tacttatttg aaaaatggtg acattttagt ccagacagaa ctgccatgaa      1260
acccctccag gacgtataat acatagacaa atctttcttt cgctggcaga aagagtcaag      1320
gatgcagaga tttcagacag ccactctaga agcagctgtt aagattccca ctctaatttg      1380
ctgccacagc ttgaaacagt gaaatgtatt aaaatgtgcc acatcagtta acatgggttc      1440
agttagatgg aggttgccag tttggaagga gggcaaatgt tccttggtgg ccatctttgt      1500
gatgcccagg ctgtgtgtgg agctcaatca gagagaactt atacatgagg ttctggcaca      1560
atccaggtac aaataagacc cagggattag ctttcctgga tgaataatta tttctgaatc      1620
atgggaaagg cacacgtgga aaggaagatg gaagtctttc taagaagtct ccgctgtcag      1680
```

-continued

```
aggcaccagt cctcaaatga gctccatgca aatgaaaacc ggtcccaaca gcatcttgag    1740
ccaaagaaaa ttcttggttg gggttgaaaa aaatgccaga taaatagttt cttcttgctt    1800
ctcagcaggg cccagctatc actgcaatcc agatctggcc tctaagcagt tctggcaggt    1860
ttagcttgga ccagctgctg tgatgaaatt gcaataattc caggtttccc tcaaatctgg    1920
actgagccaa aggcagtcta ggcttctagc aaccgctgac ttcattgcct tctttcctgt    1980
ccctcttcaa ctttcaagct tctggttttt attttaactt agatagggtg atagaggaaa    2040
cctgttcagt gcaacccaga agtctggaaa atgtttattt caggtcaatt aagaaaccta    2100
tattgagtac ttagtgagtc tatttaggtg agctgcgtgg tataactact gcatcagtga    2160
tacgccaggc tttgttgctt cctacacaga agatctcatt taatcaacca acagcctatg    2220
aggtaggaat gattatccct gtatacaaaa agtctcttac cttaaaacaa acagctggca    2280
aatggaagta tctggatctg aacccagtgt agcctgaatc tcaggcctct acttgtgctc    2340
gctatgacac tggccataag caaatgagtc cttaattaga ggtgagtaaa agagctcgga    2400
caagaaaaac taaagtgaac aaaggcagaa aaccgtggga gaaagtagaa gtaggcagat    2460
aaagagtgtg gaaaaaacag tagaggctag attcatgctc attctgagcc caacctctga    2520
agaccttgtg ggtcctggag cctagtgggg aggtttcccc agattataaa gaacttccag    2580
ccattaacac aaagactgaa tataagttgt ccaaaactct ttgctcccaa gagaaacgtt    2640
caacatggaa gttttaatgt actctaagag gttcaagatt tcagataagt cccagggcac    2700
tgagacttgc agtgtgacgc atttaaaaca ggctttctag accagatggg tggctcactg    2760
cccctactcc tttatgggca cccaggagaa tgaagtagat ctgtttctag agaataaagc    2820
atctttaacc cagaaaggga aaagaactct gggcagagta cacctcagca acccagcagt    2880
cttggaggat ccagaaccac ctggccaaca atgtcttcca tttttgcctg tggcatctga    2940
gactcttcgg ctcatcccga ggcagaggcc cagagatacc agaggctggt ggtaacaaag    3000
gtgatattca aaatggtgga aatgattcca ggaatgattc accaatggtt ctgacctgag    3060
gaagacttat caaaaagtaa agagagaagc agcatcccac cctcttccct gactgcaaca    3120
ttttaatctg tgaattattt attgggaatt aatcgtgaag ccaagaacca gcagaaaatg    3180
agcagctgcc caactttgca tctcaggtag gggaggggga gcccccactg aatagagtaa    3240
aaagtacaaa gagacagaca aatattgtct tttcacagta acttttgaga cctacatatc    3300
cacatactgg cttcatgata tgttttttat tatactctgg aacatttagt aggataaggg    3360
acatgtagaa tgtgattcac aggaaagtgg tgggccctga gcaaggacct gagtgtgttt    3420
ttggtctgaa actgagtgat ttggggcaag taacctcagt ttcttgtctg ccaaatggaa    3480
taattatcct gaatcttgat agaatgttat atatttccaa aatcccaagc acattatgtg    3540
tgctaattaa atgctaggta ataaggagaa aaatgtagac caaaacatat aaaaaaaccc    3600
acataactaa acaaggagca gaaaaggaga gatgaaatgg atggatgttt ttggaaaacc    3660 atttgggaa agtggtgatc ttctctagaa aggatttcat gccctctccc taccagcttt    3720
gcaaataaca caaccctttc ccagtggttc taaagggctg tagagcagag gtgaaagcca    3780
tggagtccct cggacgatga cctacagctc tcgtctatta atagctttta agtccttaga    3840
tgcagcccaa gcccctccca cctcagggac atgagagggt cacaaggctg cctgatacag    3900
ctgcagaaaa ctgtggtccc cagaattctc ccagttagga atcctgttca aggtcacaca    3960
aaggaccttt ggttttaggt ctcaatccgc ctgtctcgtg ctgtaacatt tgtgttccat    4020
cttgaactct gggagacttc tgggccttca acaagaccat taaatccctc aatcatgttg    4080
```

-continued

```
gaaagaaaag gagactgtgg ggggagcaaa gacacagctg gcctcacact tggactcggg     4140
gtcagaaggc atcgatgtgt gcattgatac aactctggtg gcagggtgtt gctgagcatg     4200
tcagtgtggg ctctgggcgc aggcagggcc cttggcccct tactgcatgg tcacatctga     4260
ttgtatcacc tccaagcctt agagaccttc tgtgatttcc tctgtgcagg acaaagtcag     4320
gtcccatagc tcgatgtcga cccaactcct gtctttcaaa actcattata ttcatagctc     4380
cctcattgta gtcatcctga gaggttcctc ctgcctcctc agtgagccac atcttggatc     4440
acaacattgc tgagtcttgt gtacagagtg tgaatgtgac acatttctac cacctttggg     4500
gacatccctg gggaggcagg atatttggtt taaatcctgg ccctaaagct gcggcatccc     4560
tgggctggaa tgtagagtaa cagggctgcc ctgaggaatg agcgggaact tgatctgcca     4620
aaggaggggc tcgctgaggg tgtgtgcctc ctccacagag ggcctccctg ggaactacgg     4680
ccctggagta gcagggcata ggacccacgc aggtctggga agcctcataa caatccaaag     4740
accccctctt tcccaaaaag ccagaggaaa tgtgccatcg aagaatgtgg gcgtgggaca     4800
ggggttggat cccacctctg ccacgtgcaa gcagtgcaac cttgagcaac tcacttacaa     4860
cttcttggag ggttttatca tctgtaaaaa cacacctacc tcagagggtg ctgtgatgat     4920
tagagaaaat gcttacatac aaataacatt caaacatgtc agcagtttta atatcagccc     4980
caaaatggag ggaaggggg tcagaggtcc ctggagccag ctttgccatc aagggcaaac     5040
tctctcccct ctgcagtggt ggggctagat gcgattattt ctaagacgct gagcgtccca     5100
cctccaggat tcttctttct cttttctttt agcagtctgg tctcagggag gcaggttctg     5160
agatggagat atgagcaggg gcttactggg gagtgagccc aggaacaaca ccagtgaggg     5220
a                                                                     5221
```

<210> SEQ ID NO 19
<211> LENGTH: 3815
<212> TYPE: DNA
<213> ORGANISM: Homo sapiens

<400> SEQUENCE: 19

```
ttgaatgact ctgagaggag ccactggtgg taaacccaac tcccctgtca ggaattgtca      60
cgctgccacc ataagtacca cagcctgcag cttaggggta gaccccttt tacacatgaa     120 gctcagagac gtaaatgtgc ccagtgtcct gcagagcagg gacgccaacc cagagctgcc     180
tggctccgaa gtctatgcgg ctgctcccaa ggccctgagc tgtgggctgg aatttcccac     240
agggtcgtaa gtgacagccc ccagtgctcg cagaggcaaa gggccagagc ctgatttgca     300
acgtgcgcct cgacagccat ggtgctccag gggggcagcc tttcccatgc cttcctgggg     360
ccacagagtg cagttgagct cagcagcttg gaggaggtgc aggggccgg cctcagcccc     420 tgggtctcca ggtgtgggga cctacatcag gaacagacag tctttgcagt cccagctgct     480
ctgtcccctg gaaccttgtc tggaagctca gtcctcccag gaggggaaga aaccagcctc     540
cgcttgcaga tttcacctcc ctgtgaactc ccaaagggcg ggaggccaag ccgcagctga     600
ggtcagagaa agtagcaggg tgaccgtggg gctccacgtg gccctccctc actctctcac     660
gggccctcca aaacaggctt ctgccctca gcaacagttt cccaccacc agacaaaaga     720 tgagctgagc tgcccagggt ggatcagggc tctgaggctc tgctgtgaac tccgcttggg     780
cagggacatt gtatcatttt tacgattaga aaacatggct agtctgcgca gcggagcccc     840
actcacgagc acaactcaag ggattgtgtt cttgacatga ttggccccaa actgggtcca     900
```

-continued

```
tgggaaagat ggctctgggt ccagcagagg cagcctatgg gtccccatcc cagaatatag    960
acctcggggg tctatatctg ggatggtcca atcctccctt cctacagaga cctcaggcct   1020
gtcagcacca aacgcctccc cagggagaga agaaagttac agatggcagg gacaaagcat   1080
tcgggttttc atttcctcca ggggtgttgg ccacattgga acgtctgtga ctgcgagaac   1140
ggggccaaat gctcccacgt gcttgccaag ctgcgagtac aatcctcctc ctccatctct   1200 ccagggatg ctcgcttccc aagcagctgc attttttttt tctcctcctc ctggagaagg    1260
ttgatactga gttcccattt tacagaaacc caaactgagt gcagggcctg aagccaggat   1320
gggaatgaca gagccagaag gactggctcc cacctcccag aggtgggtcc tccatgtggt   1380
ggacaggatc agaggcctcg ttagggagat ggggtttcaa caacaggagg acaatctacc   1440
aagaagccca agggcgaatc tcagctcatg accttggcgt ggccctgct atttcctggc     1500 ccgtaacact gcctgccag ctctcgactc agctcacacc actctcctta cacagtcctg     1560
tcattcggac ctcagccaaa ggccacctcc tctgactgtg ctgaccccac caaagctgcc   1620
ctcaaggatt ccatccacct ggcatttgcc ctgtgggtgg ctgtgccac atctgtctgc     1680 cccctcctgc cccctctctg ttctcccctc tgtggacgcg caccagccca gtgctcagca   1740
tgccacagcc tggagtgaag ggacatcagg ccacttcttg tgcccgcctg ggtcaccctt   1800 cacccccggcc gagcccacgt ggatttgggc cctgcatctt cttggggaac catcgaggat   1860
ctgggctggg caggcagcag cgaggagatt ggcagagaag gcggcaggag gccggggcct   1920
gtgaccaggg tctcgtcctg ctctcctgct gacccaccta gaggtttctg tccatgatgt   1980
ctggtccagt gggctccagt gagtgaggc aaacctttgg ggcaggagcc tggggcatgg    2040
ccattgcact tttccagagg gaggggctct tcccttctcc tgaaggtgga gctgtcccgt   2100
aaggggtggc tcaggttgaa gagaagaagg gttgggggtc acgcctgcag ggccacagat   2160
ggaatgaggc ccccgacaag ggtcccctgt ccctgtcaag ggcagtcgcc agggttgtgt   2220
gaccggccaa gggcattgga gagggaggga aagccctgag cttctgaagt acgagagctc   2280
ctctgtcccg agccctccat cctcagcctc acctgggctg gcagtggggg aagaggcagg   2340 tgacaaccccc cccgagaggt gacagccctg gggcgggagc cgccgccacc tgagagtggg   2400
tgaggagcag gttagctggg tgaaaagttc acagtgaggg gagctgtctg ttccctcgct   2460
taatttatcc actatttggc taaccttgct ctgaacccag gcccgagacc cctctccctt   2520
ctcccccgcc tcccactggg cttctgagcc gccaccagac ctcccgccca agcccaggca   2580
gggacgtgct ggccttgaag aggcctgggg cccgggcgcc gggagaggat ggctacatgg   2640
ctgtcagtta tttatgaccg cagtcttccc atcttcagta accaaaataa agtccggttg   2700
ccgcgaggtg caggcccccg aacgccagac atccgccaag cctcggaagg cgccccgccc   2760
gccgccttcg ccaaacacac aactgctcgg gagacagtga cctttccttg ggggccatct   2820
gtcatcctgg tttgggcggg agccagacac atggacccgg cctcggaagg gaggccggcc   2880
tccttccctg gccctggggt ggcctccggg ccttcggtct gcctctgatg gctcagggtc   2940
tgctctgaag accccttcctc acctcggtct ccctttccct tttttcattc tttcattgaa   3000 atcttttttgg caactataaa agccatgtgt tggcagcagc cagtggaaca aagatagaca   3060
aagagtgaat catcccagcc cccccatatc tcagtctcca cggtctgcac tcacaaatgc   3120
acacaagcgt gtggacacct gggcgtgtgt gagcagggaa tcgcttgtaa taataggatc   3180
cccaccacac attcctccgc agctgtttac taacctgctt gcttttgtaa tggggtaggc   3240
cccacacaca ttctgaagtg tacagctcag tcagtgtcac gtgtgtggcc acccctcaga   3300
```

-continued

```
tcatgacacc caacattctg cccccagagg ttttcccccc aaccatagca gccctaaagg      3360
tggccactcg ggttacctcg atctctcttt gaacctcatc atacagaaga cagtcttttg      3420
tatctggctt cctttgctca atgttttgtt tgtgtcaccc gtgttactgc atgtggccgg      3480
gaggtgttca ttttcattgc tgtgtagtgt tccattgtat gagtcctaac tgatgcaaat      3540
ttgcatcgtt ttcttgtttc tttttcaaca caaatgatgc tgccatagca ttggtcctca      3600
ttcccctttg tgtgctagca cttttataca tagagactcc atcttcccat gtgttaatga      3660
gaatgaaatt ttttctttaa tacttgtcca gaaagataat gtttcttcca ctctggaaaa      3720
tcacccacaa aacttatgga ccctcattgg ctggaccagg tcagaaagag cctatcctgt      3780
gggcaatggg gagccattga aggttctaca cagaa                                 3815
```

<210> SEQ ID NO 20
<211> LENGTH: 4291
<212> TYPE: DNA
<213> ORGANISM: Homo sapiens

<400> SEQUENCE: 20

```
cagctttgca gacacaaagt ctgaaaaagc acttttggtt tttgccatca tcacaacaca        60
agatattatt cacatcctgt aagaaatggc cctgaaaaag tgatgactgt tctcttatct       120
ggagcacaga attcccagtc ccaaacattc cgtttctcag gtacttcaag gccaggggct       180
tttgaacaaa tggcgtctga ggatgaatac attttagatc aatgattctg aactcaagtg       240
aggtgagaaa ggggacaaag gaatgggaat acgggctagg cgtccattga ttcagagaaa       300
ataacaagtg gaatttattg ctctgatttt gaactgaatc ttgtggctgt ttttattgta       360
attcaaggca ctgtttaatc agaagccatt ggagtgaaaa tgttcatgtt gcagatttac       420
tttgtgacaa tgatgtatgg gaagattatt ctgcaagaac cagaaaatat gatacttgtt       480
ggaagaaatt gaaataaaga acatccaatc ccatgtgcta acaaagtggg gattcctttc       540
caaagctttg tactatgcaa aggatacttt tctggtgtgc cgagaagtta tctctgggac       600
tgtcacactt ggaattccag cagattaccc tatcatcaag tcatcagtat gctgctattt       660
gaataaacac agctgttgtt ttccaagaaa tatggctagg agcagcaagg aaaaaagggc       720
aattagtgtt attgaaatga aggggtactc aggatggcat atatatattt atgagcattt       780
tcgtttccga atagctattt accatgctgt gacttaacag tggtgtagga tgcatctttg       840
taaatcataa acatacgtag tgtttttgga gatggcattc actcccccat attgatctac       900
cctacgctga ctctaatcct gtcaatctgc atgtctggca taggagcccc atctcctttt       960
cagactgatt ttataattta tactgtagca acttactctc cctatacca ccagaaacct       1020 cctttcctgt tggctttgta ttataactac tacatctttg gcattccac aagccctcag       1080 gaacaacctt cagtctgctg taggtcacat acatcagtac ctgggagact ctgtctacaa       1140
atatatcttg aggttcccct tgtgaatgtg aggatcttgg agaactatga gattgtgtgt       1200
gaaaattatc atcaccatca tcatcatcat catcataacc tcaaccattt aattatctat       1260
taaaggagaa tgaggttgtc aaagcaggac cagctgggat tcgttggctg actcccagat       1320
gcgactgtga agaagcggat attgggtgct ctcccacctc gtcaggagca gcgttctcct       1380
gcctgctctt ggcaccccct agcatcctgt gccctgctaa ggtgttaact gacaactgac       1440
agattttact aagagcctac tcttcccagt agtattttca cttcaaaagt tgacttaaaa       1500
acttaaaaaa aaaaacctct gagagtcaag gcataaagtt tttccactac agctcataaa       1560
```

-continued

```
tagatcacag ctctaccatc ttcaaggcaa ataaacaaat gctccctcga ccctggagat    1620
tccattagct accatcccat gtttatcaat tttcaagcaa aattttcaaa ggaaatttca    1680
ttgtctcttc tactaactgt ccaatcatta caaatgaaat caagcttcat cttctcccct    1740
caattgcgct ctttaagatc accattgtta agatctaatt gccaatctga gggacttttc    1800
ttcaatgtaa ttcagtactc tttgggagag ttgtgttgtt aaatttgtct gtctgtctct    1860
ctccctatct tggaggtgta gttctttatg tctgagtctc tgcctcaacc gtcttcataa    1920
tactgttgtc ttacataatg cttagcccct tacaataatc tgatatctgt tgaaaactaa    1980
atgatttggg agccagtgct ggtcacatag ttgaattgaa taaagaaatg ttagactgag    2040
ggagcaggtt aattcatcta tcagcccttc aatacccacc cactcttaag attggctctg    2100
attgcacaaa ttaggaaaag ctgggcagga actcattgag gtttgattga aagaaaagag    2160
tggcatctac agtataacac tgagtaaagc atggaggtca gagaggagga gagagttatt    2220
ctgacgcaga gcaagaaagt gattctagtt ttaatcagac attataaaag acacagaaat    2280
atgcatagca gtggaagtga agatggcctt taatcacttt taacggcatc tctaagcaag    2340
tgagatagtg ctgaagagat aggtacagga tttcaacttt acacatcagt tttcaaaaca    2400
ctgtagtaaa aaatcctgct tctgaacatt cccccacctc tcaatagttc aaatcctgtt    2460 ttggggggtgc tgggaaggga tagtgcatag gggagaaggg ggcacaccac ccaagggata    2520
aatttgctaa gctgaactac aagtaacttt ccttccattg aacacctcca aaattagaca    2580
gcataatttt acatagagcc tgccctgagt gtaacagaaa tagagtcatt gtaatagaag    2640
tcatcacttc taaacaaaca tcttggctgt gcctctgtgt ttgttttggc ttcagaagct    2700
gagtccttta tcaaacagta ggagactatt atctggtgat aatgtatttt gattctattg    2760
ttatcttaaa actggtttct tctgggccca tccttttgtt taatgacatg tttaaaaatc    2820
tttgtaagag ctgtattaaa atgacagata ttttgtgttg ccaacataaa ccacaatctc    2880
caaggctggt gataaactcc actcctggcc tcagctactg taggctttga agctcttagc    2940
tgcttttcaa atgttggcat cgttgtcaat cattctgtat caaccttata gtttgtgtga    3000
gaagccattt gttaaattgc agcctcctag actcaaagaa catttaccaa atgctttcag    3060
ataaaatgcc atcttattaa tactgggaag ctcgcaaagg aagaaatact tgagggaaat    3120
caaattgcaa cgcattactc tattctccat tgcacttttg taagaactga gaacagcact    3180
tattcccctc tcttctgtgt gtgtttgtgt tattcatttg taaagctctt tggggcaggg    3240
tacacatacc atactggtgg tctaaattat aaaggggcca ccccaccatg gtaactcact    3300
cctgagccaa aggagcatct cttggatttt cctcatattc tataatcctt tcctctgctt    3360
ttgagtgacc ctactcttct ctgaaggtct tctaaattat gggaaaatgt atggcagaga    3420
tggtgaaagg tcagtgaata ttcctttttt tcccaacact atcaccagtc tcctgctcca    3480
aggttgccta gtagctggtc ccatagtcta ttttcataaa tccttttgt atttaccccct   3540 ctcatcctgt tattttagtc aaatatgcaa aagatgcaga ctctgaagtg ccaactcaaa    3600
tgtctaccat tgtcttttaa cttacaggat ctaagctagt ggttctcaac ctacatctgt    3660
acagaaatgg aaattgcaaa tcatcttgca gcagagttct ctcattatag gaagatttaa    3720
gtaattcttc ttaggcaaga aagtgccatt gtgctggggg aatcgcctct tggttttcag    3780
agttagtgtt tggggagaag gatgaagaat taagattctc tcttatctct gagattagga    3840
gtaagggaaa cctacctggg tggacaaagc tagttggtgc taaaggatgc caaagtccta    3900
gagaggctct gactataagt taaatggctg gcaacctcat ctcagtatag attctggtgc    3960
```

-continued

```
ttttatagga gattagagct agtgtggcat gtgtctgagc caagatgtac ctgcaggtcc    4020
tgccaccctt tggactgaag gtactaggag tcttgtttga ggaactatgg aggtgctgac    4080
aggaaacaat gacaaaggcg tcactgcaca ctacacatgt tccttgtgcc acagggtatt    4140
attgttcagt agcaatacgc caatatggca gtggtcatga accggtggga tttagttctt    4200
tctccacttg gtgtttagaa ggacatggta tattttttcc aagtaagccc aaatattatc    4260
taataggatt catggaaatt ttgtaataga a                                   4291
```

```
<210> SEQ ID NO 21
<211> LENGTH: 7731
<212> TYPE: DNA
<213> ORGANISM: Homo sapiens

<400> SEQUENCE: 21
```

```
ctctccgtga cggtcacggg tccccagctt cctggcgctc gagctctccc ggctgtctgc      60
tgcccggcgc acgcctgccg gggactgccg gccactccgg gtgggggaag agggcggttc     120 caggggctg ggggcctgcc aggacactaa tggaacacag ctggaccggc ccgccaggga      180
ggaggaggag gagggcctag agggtccagc ggcaccagag gcgctagact gcggggtgca     240
cagccccgcc ccgggtctgg ccgagctccc aggcccgccc ctcctgcctc accgccaggg     300
gaatgggcca taaacctggg gtcatcctcg ggtggagcac ctacagaaca ggccctagga     360
aggagagagc tgccaggttc ggggatcccg accccacccc gccgacagcc acgcctccag     420
cccactctgg ccacgccact ggtctgcctt tggaccacac tcatggccgg gtgccttccc     480
tgactccgcc ctagccctgc ctcctatctg gctccgccca gccctggcca accttagaac     540
ctgtcccaag gtccagaggg cctagatgag gggtagcctg cctctgagag gcatggagcc     600
ctcctcccgc gtggggtcag ggaagaaggg cgtcgagggt ggcgggtgag ggaacggcga     660
acgggaagcc tccaggctgc aggacgtagc tgcgggagtc tgcgaggctg gagtggccga     720
ggccgccccg agcatagaaa cagccctgta tacgtgggcc ccagggaggc gcctgggcag     780
aagtgtctag gacgatgcct gccacggagc cctggagtgg gggcagctga tggctcaaga     840
cacatgagct ctggtgggac cggggtttgg ggaggcccaa gtcaaggtcc atccttctgg     900
gatgaggggc ggaggatggg aggcggagcc cggtctccag gctccaccta gcgggaagct     960
tgggaatcgc ggagtgcaga ggtggggtgc ggaaagcgcc tgggctcctt tttctccttg    1020
tcccactggc gcctacccac caccatcctg cccagtatct cggggattcg ccccagatag    1080
aaaggggagt cattctaaca tctatcttcc atctccaggt cctatccttc ccttcttcct    1140
tgcagttatc cctgagctgc ctctgccggt tccagtccct ggaacacctg acaactgctc    1200
ttcctgccta ccctctcccc catccatttt tcatagccat gcggtgtttc taaacaggaa    1260
tctggttgtg tcactttctt gattagaatc attcaatagc atcttatggt ccaaatagac    1320
tccaaacttg ggacttgagc tcttcaccat cagctccacc tccctcagcc ccagtccctc    1380
ttggggcttt ctgtgtctcc tcatcccttt tacgccctcc ctggcctcat ccttgctgtt    1440
gggaggtagt tagctcccac caccccagt atgtgcctgc ctctctcaga gcagtcactg     1500
cctgggtctc taatgactta ttcggcagga caattgattg agatattaat tgctttgttc    1560
tcctgttttc ccctcccact tgcaagccaa gccctttgat ttttctagcc tcagggaact    1620
gtgcagggcc aaacgcaaaa gctgcttgaa gtctgatggc ttgtcctgag tttggaaaga    1680
gtaaacttct ggaagcaggc gtgccatgtg ttcccaaggg atggggagaa gaggacagag    1740
```

-continued

```
aattgagagg cagaagctag ctgcaggggt gcagaagctg ggggtcctgg tggtagggac    1800
tgtccttgac aggtgacagg tggggatgtg ggtaacgcac ctggggtggc tggagtgcaa    1860
acacttggga accagcagtg ctccaaagta gcaggggaac agcttagtca ctgagcctca    1920
aggaggacaa tggacatctc tgtgtgacca atgtagacta agacaggagg cacctcttct    1980
gtggtgcagg gagggccagc agctccttgc atgggaaagg tgggagggag cccagtgatg    2040
gttgagatta aatttttgc caactcatag gaaagcgttt agagtgagtc agactggagt      2100
tggtttaaag tgaatacaga aacagggtat ttcttgtgcc aagcttcctc cctactacac    2160
ctgtctgtgt gtctcttagc tgcagagctg agagtatgtg cctcattcag aattgtatcc    2220
tcagcaccca gcgtggtacc tggcatatat tgactgctca aaatgtatcg gttgaattcg    2280
cttttcctcc gtagagtcta aaacccaagt ctgcttccgt ggttcccctc tggccctcag    2340
aataaaatcc aaaccccgat gatatcccac aaagccactg tgatctcacc gccccgtatc    2400
cgcagcccat cctctccagc gaactgcact atttgcaatt ccccaaactt gccaagttgt      2460
ttcatgcctc gtgcctttgc ttatgaggca cctctgcctg gagtgccctt tcccctttct    2520
ctgcctgctg agctttcaat tagtctgagc tcagtgcaag tgtttccttg tcttccctga    2580
caccctcttc tgaaggcaga ggaaacttct cctgctctgc agcctaatgc tcaggcccat    2640
gtctgtctcc tcccaagcct ggtttccggg cttctctagt agagtgagtt ccccatgccc    2700
aacatggtga ataaatgggg ctttagcctt gatcctccaa ggactcatgg tgtgacctca    2760
gcaacctctc cagcctcaga tttcctttct gcacaaggga ggagtggaac tgaatgttct     2820
ctagggccct ttcttccctc attgagcctg gaaatgagag catgtaaaac acaactcacc    2880
tgtgtgcacg caggccagct aagggcagaa catgctcaga cacagagctg cccatagcac    2940
catgcatggc caccgggagc aagcccttgc ccagcagctg cacgtgactc acacaaaagt    3000
gcatgtggcc ctctggacgt ggatgtgctg tcctcccaac ccccatcccc catcaaccac    3060
tggccctgac agtgaaaaat tcagcagcag tcagggatgc cagtctggca gtgagttaat    3120
attcaaggaa ggagccttct gcaatatgca tgccctgagg ctggtgtcct atggggctct    3180 cccttccca ggcctgcaca ggcaaagccc tccccacccc accacaggca cagacacagt      3240
ctgcctgcgg cagggcactg agaactagac cttcagctct aattgcttcc tggacagccc    3300
cctcccaatg tctcctcatt cattcattca gcaatatcta tgcagttcct atcctgtccc    3360
agcaacagta tgaatgtatg accctgttct gccctcaggg gctcatagtc cagtggggga    3420
gacagactaa atatataaac tcagatcagg agaaatgata ctgtggaaag gattaggtga    3480
tgtgattttt aaaaaatgac tgaagagact ttcaaattga gggcacagca aacacaaagg    3540
ccctgggaag ggagaatcca tgaaatgtgt ttgaggagca gagaggaggc catagctgct    3600
cagacagtga cagcaagtgg caggacattg gacagagcgg caaccagagc atgccgagcc    3660
tcctgtgcca cagtgagagc ctttgtttta gtcaaagagc aatgggaagc ccctggaaac    3720
agtatccatc ccttcccca gctcctccat cttgggagcc ttagagacta tgccttcctc      3780
atctttacgt tgtcagtgcc catcccaagg cccagcatac tgataaataa atgaccaatc    3840
aagttctcct ggctcaaggc ttgattcaat ggctcagagt aggtcaacag ggccagatta    3900
agacatttac atgccatcca gaagagtctg gcactccat acatattcac aatagaaata     3960
atactaatcc atgacatact tctttatgca catctggaat gaaaaccact tccttttgga    4020
ttttcaattg caaaattctg gattagttca tggaagcaga actttgtgtg cactgttgtt    4080
actgtcttgc tggcatccta aactgaactc agtccgccca ttgatcaccc agtgctagat    4140
```

-continued

```
ggcagggctt gcccaaccat cccctcaatg acatggtctt ggcttttgga cccagccaag    4200
cctttaaatg gggtctgccc ttaccccagc ccctctttcg ctacccagct gagccctaaa    4260
cctctaagct caatgctccc tcagcctcct ctctgggtcc tagagaggac cacatctcag    4320
gtcccccatg tgacttccac agcatcttgt gctctatgta tggcccccgaa gggaattaga    4380 ctcaatgtgg ggctgggaga aaagttgacc tccctcccc acttcactga cctccttagg    4440
aaactcagac aaagctgatt ctcagggggat tggaagctgg gtggttgagg ggagcacctc    4500
cacacaggcc agtttcccag gccaagtcca ggctgagctc tgcctctact aggctgcacc    4560
ccaccccacc cccagtgagt gggaagtgac aaatgagcct gaggaaggag gagggagctg    4620
gcgatcgatg gcattaacat ggtgcccaaa ttaaatattg actttcttgg ttgactctag    4680
ggacacttgg attgatggct gaggctttgc catgccacca caggggatag gcacataaca    4740
gcctggagca ggtccatagg gaagctgagg cctggagagg aggggctcac ctttgcttcc    4800
acctgctcag gaggagtaga agtgagggct tcagggagcc cggatgcctg cttctccacc    4860
ttccccatgg agtccagagt ccccgtcccg aaggtcttgg agtcaggcct tgttgagtgt    4920
ccccccaacc ccattcccac ctccaggaac tgtggctaac ctgaagtgca acaaatgagc    4980
agaatcaatc tctgtgatga taaccattac tggtctcagg acccggcctc aaggcgagtc    5040
tagggctgca ggggtaaggg taagggtgag ggtaagggtg accccttccc ccaggtctcc    5100
tcaggacctt cccctacttc cccacacctc ctccctaccc accagtatcc ccaggatatg    5160
tggagcccag gaaggctttg gacctccctt gtgcgggcac tgtgctggca actttccctc    5220
catggcccca tgaggcaggc tgtgcggaag tacctccttt tcagagggca ctgagtgctc    5280
aaggtcactg cctttgttct gcctaagctg tgctgtgaca tggtagcctc acgggagtac    5340
tgagcagtgt gagactgact tgagatgtgt agcacaatat attgaatgag atatattatt    5400
aaaatgaatt tcaccttttc aaactaagac tgtaggagtt gtcattatcc caattttgca    5460
gatgaggaaa tcaatgttca gggaggccaa cacagatgac agcagttctg tgtgatcatg    5520
cagtagtgac agtgcaccaa ggctgtgggg gcccagcgag tgctgactgc tgggccaggg    5580
gttcagggac agcatcacac aggggggctac ttaggctgaa ggagagtttc ccctctgtga    5640
ggaggaggga ttcaggcaga aggagaggca tggaggtgag agatgggcca gaggagggag    5700
gcagccacat caccaagggc cttgaactct aggctaattc caggatccac agaaggcatc    5760
tgagcagtgg cctggcagat ctgcattttg gaaagatcac ttgggccatg tggatgaagg    5820
gctggagact ggaggcagag aaaatgaggg caatgatgag aaatttgagt ccaggaaaga    5880
aatgcaggtt gttagatatt agctcaaatg gaagggagat cgagccaact cattttacag    5940
atagggaaac ccatgtcaga cagggtccag tggcctgtcc aaggtcacgc agcaagtcag    6000
tgcctggggg agcagggact gagggcaagg gagggacaaa gccccacccc aggaaagcta    6060
agtggctggt ctcaaagcca gcagaggcct ctgcaggtag ctgtggtttg tgtttgagca    6120
gaatcaacaa ggtaaataca acttccatgc aaagcaagaa tggacagggc agggacgtgc    6180
acatcacacc tcagccccag agggcccag ataagaccag gaaggaggga gagcacagga    6240
caaggcatta agagggcctt taggtgatgg tcagaggaag gaatgtggag taggatctgc    6300
tggtacatgg tcgggctttg tttgtgcaaa cccccttta ggaacaggcc ccctttctc    6360 agagacctgc tccctccccc atggttcctg atgggactgc caatcacagt gcctggggcc    6420
agccagagct cttccttcct tggggggtttt ctaattggaa ttcaagagag aaagtttctt    6480
```

```
ccctctagg ggcaatgctg agtgatggag gaggaagcct ggcaggccca gggggaagag    6540
gccttaaaga atgaagcatg ccaggagagg atgaaacacg gtggcactcg tcccatcacg    6600
aaggccagcc gcacttgccc actgctgtcc ttgcggcagc gcgctcctgg gtgaacaaag    6660
ctcccaggtg cctgctggct ggtatcggat tctgccactc ccagccacaa gtcccagtca    6720
caagctgagc tgtgggagct tgggaaagtc atgtcccctc tccaagcctc gatttactca    6780
tctccaaaat ggggcagtca aatacctacc tagaatcaaa tgaggtagtg cttgagtgaa    6840
ctctgtgtac ttaagtgcta gggaggcgga ggagtgcgca ggctagaagc acagtcctga    6900
gtggactctg ccctcctctg accaggtctc acagcaggca ggattggaat gagaccagaa    6960
agcctgtgcc aaggcctgca aaatgaagag gcctccgccc ctcctccagc acccctgggc    7020
aggccattat ctgtgatacc ccaccccagc agccagtcac ttctgtcact cccatgctgc    7080
agcacctctc tccagggacc tgtctgtgtc tccgagtccc tgggggccca gaggtgccca    7140
tgttgctaaa tgaccaggca agaaggacct gtgaccctgc tactgctcca gctgctgcct    7200
gactccagaa tatgtttcca gatgtaatcc tgtgccccct ctttctgggg gcctgaaact    7260
caggcatgta atgaatgcaa ctcagtacaa gcctccagcc ccccagcctg gctcccacac    7320
ccctggcccg gtccaacacc tgcatctcca ccacaaccca gcatctgcgg ctcccctgca    7380
gccatggtca agttccagga agctgagctg aagccccacc tccatcaagc gtgggtttga    7440
agtcccagct ctgcctctga ctgtggcctt gagccgggca ctgcccatct ctgtatccac    7500
aaaatgggca accttccaac agggttgttg tgaggggcca ggggagtgtg tgaagctcct    7560
agcgctaacc cgagatcctg tccctgata acaaccctgt gtaagcggct ctagcccatg    7620
ccccagtgaa tggcagccac gaccatcaca gccacccagc cataagaggt cccctcccac    7680
actcccaact gcttcccaca gcccagatcg gggaaaggat gaatacccag a           7731
```

<210> SEQ ID NO 22
<211> LENGTH: 5273
<212> TYPE: DNA
<213> ORGANISM: Homo sapiens

<400> SEQUENCE: 22

```
ctttctgcca ccgctgtcag ttgtgctggc agctttggat tttgatagga gagccataac      60
ttctgagatg aatatgccca catgtgttac tgaaacatgc tcatgcaaag accaggtgtg     120
agataaaact ggaggctgca gacgcctctc ttagtctgtg taagggctgg gtagggagga     180
tccaggaaag ctgatcttgt agttagaggg ctgggaattg gtttaggaga gggagaagag     240
tggctggctg gcaaacacat cctggttggg tacagggaga aacccactga ggcagaaccc     300
aggattcatt ccattcaatt aattagatac aatttttttga gtacttgcta catgccgagc    360
actcttctag gggctgggga cacggtgaag aaaacaacaa aagttactgt cctcatgggg     420
gcgctatgtt gtggctccat ttgtttgact atgaaacctc atttaggttt caagatccta     480
gcctcatcat tgtgcttggt tgcaaatggc tcaggtagga ttcccttcac tcccttctgt     540
tttcctttac acaaccctgg agttattatc atgtttctca gtggtcagat ccaagactct     600
tcttaagaaa gatcccaagt tctggtatag tgccatctcc agggcttctt gataaaggag     660
agacctttgg atctgaggtc atagacgata cctacctccc atctcccata ttttttctca     720
ctgcttccag ggagactgac tacatgctga aaagcaaaca cgaaggttga atcttaaaag     780
gcagagagaa agacacaaca gactgacaac tgactctcaa gtgaaactat ggactccaga     840
agacagttaa atgaatcttc aaagttagaa taactgccaa ctagaattct gtggaaagaa     900
```

-continued

```
aaataaaagg aaaatacaga cacttctaga aaaaaaatgt gataaatctc acaccaactg      960
acctgtagca aaggaaatct tcggcagaag gaaaatgaac tcaaatgtaa tctgaaagac     1020
acagaaagaa atgaagagcc tgtcctggtt gcctggttag gggtagatca ggggacagcc     1080
accaggtgcc agctccctcc tcctcccggc gccgctttgt gcagtggctg ctgggccgcc     1140
tctctaggac ctagggctct ccctgtgagc ggagggaggg aactttggcc gcaggaagga     1200
ctggaagcca gctcgaaaaa gcacattcct tggcaggata aaaaacttt ttttttttt      1260 aagtgtaagg acttaacctt tgctaggaaa tggttgcagt attttccttt aaatgaaaag     1320
accattgtga ttgaaacttc ggaaaacaca caacatcctg agttccgtgt aggggacaga     1380
ggacctggtc cctgctcagg agaaggcctg agacagaaag ggcttgttgt tgcttacagt     1440
gacctccact caggtcctgc tccataattt gtggggccca gtcaaaatga aaatgtgagc     1500
ccatggttca aaaattaaga gtttcaagac agggcatcaa aagtgcagga tccttctgag     1560
ctgactgccc aggtcgcatg ccaggaagct ggcccagcct ccagtggacc actcttattc     1620
tgctggccag gcctgagttt ctgcagcttc tctctcatgg gtagacacag accccagaga     1680
ttcagggcag gactcaggac ttcccccatc cttggctccc atataccaca actggcaaca     1740
atttcccaac ctggttcttc acttgatttc tcctcatggt ttagagacag tgcttcccgg     1800
ttgtgaaaac attctggttt catctgcgct tgcttgtaac ccggggggtct ggggaacaca     1860 gaacagctgc attgagtgct ggtctacttg gcgctcttca agctctttac aagcctcctc     1920
gtaggcctac tgtaaatagg aaagtacaaa cacatgccga ttttgccgca gattaaaacc     1980
atctcctgcg ctccctggat cgtaacacat aacagtttgt gtttatgcag catttattag     2040
cttgcatgct acttagggac tttcatagtt ctctgctagg cgaggcctta gtatttgggc     2100
tctccagcgt ctgggaggca ccatatggag agttgtaaag cctcatttcg ggtcagcctg     2160
accgcacaag gccagaccag agctgtgctg tgcaacagtg tggccacttg ccacttatgt     2220
ctcttgagca cttgaaatgt gctagtccga atgtagagta catactgaac tttgaaggct     2280
tagtacaaaa aatgtaaagg atcttgtttc tttttccttt tttaaatgca gctactagaa     2340
aattatatgc tggcatctta tttctgttgg atagcgctta aagcctctct ttgttgtata     2400
catacacaca cacacacaca caccatacaa actcctgagg atcttggaaa gaaaaccagg     2460
ccagtgagat catgtgactt aaccccaatc tctaggaaca ttcctcagaa gatcccgtgg     2520
ccacctaata ctagaggctt ttatttgcca atggtaatct gtctgccttg cctttaaaa     2580 ttaaaaaatt tattgaacac ctatatttgc aagggagtat gacttagtga tttcagagtg     2640
caggctccag acttggattc cttggtcttc tcatctgcaa cgtgggatta tgacatcaag     2700
gacagaatca ggatggtgac ccagtttcta cttcatgggc ttattgtgag tgaatgagat     2760
gaggcacaga acacccttgg cctggagtca ttctgctgta cagccaggcc tgatctggcc     2820
cctggacttt cacagggctc agcagactct gaggaaggga gggaaccatg atcccagaga     2880
gctccaagac agattggaaa gaccctagaa atgtaatgtc aaaagttagg atggaaaggt     2940
tccagtcaca atgtcaagca ggcccagggt ggagggtctg ggtggggcta ggattgattc     3000
gggaagccag aaaatgagtg agaaatagat gctcttagta cctgaactca gagcatcccc     3060
tcactggggc cacaatggcc aaggctgagg aagtgggccc aatcacattc caagtcctac     3120
attgggccta agtaggcaga tctggagtgt tggaccccatt tccttgcagt cttgtccctg     3180
taaggcaact gcattagggt aatgcgggtt gatgaaacaa atgaatccca aaatttcagt     3240
```

```
ggctgaacca ctatgggtgc tcctggtcgg taggagggct tccacgtggt gagtcaggga    3300
tccaagctct taatgactct accctccctt aggcctgagt cctctgcatc tagagagcag    3360
acaggaaaga gtgggggaga agacacaacc tcttctaacc accttggcct gaatgtaaca    3420
tgtatcatta actttatgtt caatctgtga caactagtct catgcccacc tagatccagg    3480
ctgggaattg ccggctctac acatagaata gagcttccct aaggcatttg ccagtcacca    3540
tgcccaggcc aggctttgaa aggaaaaatc atgaacactt ctaagggaat aatgacacaa    3600
caagcacact caaagagaca gcacacacac catagtctca gcacttcagg catcctgagt    3660
ggttccaaag gcctctctca gagccctcaa accatccca ggcactggcc tttgagctca     3720
gtgagccggg accagcaatt gcactggcaa aatcccaagt ccttactggc caggactgga    3780
tcaaagggag aggtgtgtgt ggggtcgagg caggtctcac ttattatcca acacaggcgc    3840
ggtgctttta accagtgctt cttccacacc tgctggcagg gggagggggcg caaagaaaaa    3900 ccagaccact gaacctcagg ttgctcatga ttttgtgaca agatggccag acatctgatg    3960
cagagaatgt catgcctctc aaagagggga agtggtgaat gccagagggg cactcataag    4020
tgaggtctgc agagccacgg agcccagcac cagtggagct agaaagaggc tagcctgctc    4080
cttgtgactc ccatcctgtt ggtggggaat aaattttctc caattccgca gccccatctc    4140
tccctacaaa gaggaatcct cccatgttca ggcctgttgg agacctggtt ctgtgtttag    4200
gaattgctgt tggtgtgtgt gtgtgtgtggt gtgtgtgtg tatgtatgtg tgtgtgtgtg    4260
tctgtgtatg ttgggaggcg atgacaacta actctgaaga ctgggctatg gactttgaag    4320
tccttcctag tgagggctcc aggcacaagc tgcccaagtt tattaggtac aggtttatct    4380
ggggctaatt taccttgtta acataattgt gccagaggat gcagccctga ggccctgcct    4440
cagtaattac ccttctcttg atctgtttca tctctaaggg ctgtgccttc atgcagagct    4500
tgctggcccc cacttctcct tccaaggccc cgggaggggc cctggcaatg ctttcacatt    4560
tttgtaaaat ttgcaaaagt attgtatcaa ccacaatcat tcaaggctgc tgtttctttt    4620
caccctgact tcccctctgt cacatttccc ttctgtcaag ggatatcgga actgtggcat    4680
tttggggatc cagcttaggg aagcttgatt gagggatgca tttaatgtga caaatgggat    4740
gtatttatgt gggatgcaat atatgtatat aatatttcat gagtgtgctc agtcacttcc    4800
atgttcatga caattattgg ggaggattgg tttccaggaa tactcctacc acccatggtg    4860
ttgtggggtg atgcagcatg agaagcatgt aggaagtgga aatgaaacaa gattgaaagc    4920
acacagccag aagctggtct gtggaaagtc cctgtagtct tacagctcat gttagagttt    4980
actcctaatt gacaactgtg tgattaattc tgtgtgtcag cccagatatt ttgggatgtg    5040
tcgtgagagt gtttccagaa gagatttata tttgaattag tagattaaga agactgccct    5100
catgtgggtg gggattcaat ctgttgaggg cccaaataaa acaaaaggc agaggaacct     5160 agtgctccgg gctttggact tggactgaat tacaccacca gctttcctgg ttctctagct    5220
tgcagatggc agattgaggg agctctgagc ctctgtaatc acataagcca act           5273
```

<210> SEQ ID NO 23
<211> LENGTH: 2775
<212> TYPE: DNA
<213> ORGANISM: Homo sapiens

<400> SEQUENCE: 23

```
gaggtgggaa agtaggtatc tttggggaca gatgaaccag gatgccagga actcttgggt      60
taggtccaag gctcttcagg ccttggagct gctgagcatc tcccttccca cctctctgga     120
```

-continued

```
agacttagaa acttgttatt tattatctga gaacagagaa tcctagagcc ttggacatga    180
gcatggccaa aaacctgcgg gggaaaaatc caagcacaat gaaaaatgag tgctggacaa    240
ggagattagg ggagacacag tgacgcccac ctggacagcc ccaggcagct caaagttgtc    300
ctgtcccatg tccccacgct gggtgagact gcacacccag gccggaagca agtacagaga    360
gccacaggga gagggagcac tggagtctgg gccaagaata aagaacaggt gcccaagcct    420
agccaaagag gtagcgagca ttctggggaa gaaaaatggg ctaatcccag ctacccctga    480
ggtcaggaaa cctttccctc tctgggcctc aatatcctta actgtaaaat ggctgcaagg    540
ctattaagcg ttcttttccg agttgtttgt gggcaggaga agccttgaaa ttgcaatgaa    600
cagaggcacc tggctcccca gggacaattt ccgagtccat ctccccacct tgtttatttg    660
taaaatggga acacagacac aactggtgta tgttttcatt aaaccaagta ggagcttgtg    720
gcatttctgt ctgcacttga gacatgttta tactgctgag tccattatga atctgtttaa    780
tatccttcga attctccgag tccttccatc cctgcagcca ggaagtgggt aatgtgcaca    840
cagggaagaa atttccaggc actcagacct ttaggtaaat gaggactctt ttttttttctt    900 taaagagggg aaagcctgtt gcaaaaaaat taaattcttc ctgttccagt gatcctttcc    960
ttgtaggaaa ttggttggtc ctagagagat ggtgaaggag caccagctag gggagcctgg   1020
gagtgagaat agcatccctt tgccctggga tggaggcatg gaggtgagtg actatccatc   1080
aggggatctg tagccaggag ctcaaggtca cctgagggct gccttggctg gctcctggga   1140
agccagggaa caggcttccc actggagagc tccctgcttg ctggcagaac agagagatat   1200
tattttaagg agaaaaatga gattcctgtt attgctttat tcctcctgca gaaacgttgg   1260
tgcgtcccag ccagggccaa gatgagaggc aggtggtgcc aaggaaggat gagctcatcg   1320
catgtgggga cgtaggtgat tccagcaagc acagtgtgga aaaaaagctc cattcttggg   1380
atcccaaatc cctgtcaaag cagaaccctg cttccctccc ccacctcctc cccatccatc   1440
taagcccact cccatttaat ctctctctct tcttgcatct tcaaccaaac actcaccact   1500
taccatatga tcttgcagct agatgagaaa gaaaatagga aaatatctag cacatactag   1560
atgttccctt aatatttcct tcctcccttc cttcctgtgg aagcaaaggc tatagtataa   1620
ttaagaaatt gtagcaattg tgagactttg aatctacaaa tgtcaaattc ctgcaggact   1680
ctggaaaata tgggtcacag gttatttctt ggactcatca tcagattcct ggcaatggtc   1740
tagggatgac acaagtcact gtgaatggaa cctggcatga tgaagaaggg ttccagagag   1800
tgggggaact ttcctggtct tggccaagaa agaaatgtca tggccaggag ccaggtcaga   1860
gagggcagga gagtgggttg gagggaagta gcctgaagtt tgcggatcaa gaagctccaa   1920
aaagtggcca tgaaatcgga atagttggaa attctgaaag gtgagagtga tccatggggt   1980
gagtcacctt tggtaggaca cagagcactg gcattcggct gcctcaggca agggtctgaa   2040
acaccaaacc aactttggtt ttccatctag gaatcatagg aggtgttatt aaccacaggc   2100
cttctggaag cttcctatgg aagggccaaa tccctttgtt tctgtgtcat gcaggggtgc   2160
atgtgctgtc aaaatgttaa aaatgtcaca acagtttcac tttcatcact ttccgcaatt   2220
attgttttaa attccatatc ctctaaattt ccagccccct gggcaaagcc caatcacact   2280
gccctgggta atggccatga tggggcgagg tatctctgtg atggaaactt gattgctttc   2340
tgcttcattt cttgggttcc gttgactact cttttgtagtt tacgattttt aaaaatccat   2400
cctgtctcca ttttgctaag gaaaatcaag aaaagggatt tgggtccaca cgttggtgaa   2460
```

```
tggggataaa aggtaggcaa ggggtgttag gtgccagagc aggggcgcaa agggatgaca      2520
agtgagggac tgagttgaga taaggctaag atgctggaag aaacaaaaat ataacacaga      2580
agagaatttt attttttctct cactttgacc agggttgggc aggcaaccag gcaaacacca      2640
ggagcttgtg tgaccagatt ccttctgctg tgttactcct catcctggag tgttgtcctt      2700
gtcttcatgg ctgaagctac ctcaccatgt gagcccacat tcagcccaag gcaaggacag      2760
aggaagggag acatg                                                       2775

<210> SEQ ID NO 24
<211> LENGTH: 2679
<212> TYPE: DNA
<213> ORGANISM: Homo sapiens

<400> SEQUENCE: 24
ggggggtttt attaaagcaa gatctgacgt cagggtgaag gacaaaccct gcattttcct        60
ctgaaaaaac ttttcctgcc tctctctctt tttttttttt tcttccctct gtccccacct       120
ccagcctagc ttggccagcc tccccgctct gacagttctt aaagggaaag ttacagactt       180
cacacagagc aatccttgaa ctagcgtcat gtatagatca tcttctggat acaactgtcc       240
aaagcctgcc ctctctgttt ctcagatccc tgtggcaagg cactgctggc tgcttctagc       300
caccaagcct gggtttttgat tctttaatgc aagctgagct caaggttcca aagtgttcct       360
aggaggagga gagtgtgggt tggaggtttg gcagacttgg tggaagatct gggtgcacgt       420
ggggcttgga ggctgactgg tttgggttgg cagcgagcag gaagtctccc ttttgcacgt       480
gtctgtgttc taatctcttt aatgacacca attataccac ccactgacct tgctttattg       540
catctggtgt cagcagaccc aacagtccat gctggtacag aagggatgca aacatgaaca       600
aagcgacaag ccactgcagg gatcacagga gaaaacctag aaaggtcata gaagggctaa       660
aaggcatata aaggatgaat aggagtccgg tatctgggta aggggatatg aggggactca       720
aattttaggt ggaggaaaaa atgtgcacat tcacaataca atgtagcatt taccaagctg       780
tttgtatgta ccaggtgtta tttaaagcac ctcacacgta gtcattcact aatcttcacc       840
atgaaacaaa acgctttcct tctttcagct ccatttgtat gtagagaaca gagatgcaga       900
gaaatcaaat cacctgcccc aagttccatg gctggaaaat ggcagagtcc actcctcaac       960
tctattctgg tctagctttc tataatgctg atggtgaatc tcccattgtt cactgaacac      1020
ctcctatgtg ccagacactg gaaggagctg ggattacagt gctcaaataa ttacagtctt      1080
ggcccccaag gacattaata cataagcaaa tagtcaagtt caatcctatg ccataggttt      1140
gcagttgagg caagcccaag aattatgaga atacagggag acccttcact cagccagagc      1200
catggggtat gaagccagag gtgggtgaga gttgaagcat agaattaagt taggtggaga      1260
aagcaattgt ggctttccag gcagaaggaa gagtagtggt ccaggcgag aaaaattgcc       1320 acttgattgg gggccaaagg agttcagcct ggctgggcac tctgagataa gagagccccc      1380 aaaacccta tgaaaaattg tggcatccct ctgggatggc actgaaaggt gtcaacagga       1440
ggctaatgtc agatcttcta gaatattccc tagggctacc ttaggaagg ggcatggtgc       1500 ggagagggtt ggcatctggg agtccaggtg gtttggaagt ggggtgcagc aagggctgg       1560 ggctcaggga catgagagaa ttagtgaaat agaggctcca ctttgaaaga gacagtgtca      1620
ggacagaggt gacttcatcc tctgggtggt ggagagcgat ggatgaatga agtcatatgc      1680
aggattggat gaatggatgt gtggactagt cgtgttggaa agaaagaaca gaagtgggga      1740
gacagcctct ccgtatccat atttcccagg ataacagcct ggagaggtga cagccctcta      1800
```

```
agctgagttg attgacttaa taatctgaat tctgcccatg tgggcaacgc tgcatctgtg      1860
agaaaagttg agtggagagt gagaggaaag atggctctaa ctgtccaaca gtgtgcttgg      1920
tgctgcagca atggcccatg tcctcatgga atgcacgcct ggaggaatga tgggagcaga      1980
gattccgtat tgaaacccaa ggcagagttg gggatagctg ctgctttgaa tgcttttagg      2040
tcttctcatg tccagtgtgt ctcctccata taggtttaag cctctagcca gaggtttctc      2100
tccttttgat tctttggttt tctctgtaca gttcaaatga cagttacaca taataaaata      2160
tacatgtgtc tcatgtatta taatatttgg atgtactgtc aattctatgc gatctgagga      2220
ctcattcacc tgtgtccctg tgctgtatgt ctgacctgtg ttcagttaag tgtttacagg      2280
aaggaagagg ggaatggaaa gaggaagaga gtgggcagag aggaaaggag aaaaggaaca      2340
gagagcagca aaaataagta taaaaaaaag aataaaattgg gaaaataaat atatggataa      2400
atgaatgaat ggatgatgga tggatggtgg atggatgggt ggatgggtgg atggatgggt      2460
gggtggatat aaggatagat gaatagtgat tacatagatg agtaaatgaa ggaacacata      2520
tctgggaaac tgaaaaagat caaattctga ggtttgtaaa ccaggggatg gcagggcctg      2580
ccctacgtct atgctctggg ggtctcagag aacttggcgc tagtttgagg acccaggctt      2640
agagctcctg actgaattta tgaatatttt tatgagttt                            2679
```

<210> SEQ ID NO 25
<211> LENGTH: 10820
<212> TYPE: DNA
<213> ORGANISM: Homo sapiens

<400> SEQUENCE: 25

```
atccagaaat tctgacaaaa tgtcagtatt ccaaagctcc gcaaagactg cctatataat        60
tattatccct attgtttcat aggcatttgg cttgatagaa agctaatgat gggcacttaa       120
aagtcaaatg acatgagtaa ttaagaatag ccatgaagga tgatgtaaag gcatctccat       180
ttcagactgg ggaaagcaca gaaatgttct acctagtgga tcatagataa aaatagctgc       240
catctgctgg tgccaggtac ttttcatgat ctctcattga atactcacag ccaatttatg       300
agatggtgct atattattcc tatgtaagac atgaggaatc caaggcaagg agaggttttg       360
ccacttgtca aaggttacag tcactggggc tggaactcag tcccacattg atctgatttc       420
aaagcctcat ctcttaacca cttaaccagt gctgagatga gactgtctca gagtgtggat       480
tacccactca aatttatcat cagtaaaata ataacgaaga ggatgactta aataaggaca       540
ggcatttgct tcaaagtggc ggtatggaac ccgatttcac agtggctgag gtcagcctca       600
catggatgac tcacacacat ggctgatcta cataaatagc atgtgctaag attaccatct       660
ggtataacaa tctacatcac aagactccac atttcctgtt acccaggcta aataggtaaa       720
tcttatctct ggcagaaaga gctatatatt agtcagtaac ctggaggata ttacttttgt       780
cttccaagtt atttacatcc agttggcacg gtatccgagt cttcaaaagg ccatcccact       840
gttctaccat gccgactgct ttatagtgat tgggaacata gaaagaccac taaatccatg       900
agtatgagcc ccacgttgca cttaatttgc tgtaaactga attgctttgt aatgtgtagt       960
gatagcagca ttctgtgagt tcatagatgg tagtattggc actacaggaa gttaaggcaa      1020
atctaaatct agagtaaatg tctgttctag taacaacaaa gtgctggtgc tgtctgtaac      1080
ctgatggaat tgatccaaaa tcagcctcca accaggtgcc ttcttaaacc caccaggtag      1140
tggtgcccaa gtgttgttct tgctgttggt aggacagacc cttagagtgg ctaagccaag      1200
```

-continued

```
tcagccttgc ccatgcataa cttctaccct ttcttttatg cctactttct tcatagagcc      1260
ccttgggcaa ggatgggggt agctggagag agaaactgac tgatgtccat aagacaggtt      1320
atctcataca cctgatcatt agatcctcct ctgcttagac tgctctttgg tgcaaattca      1380
aagaggtcca tcgacaaatc ttttccccag acctcttttt cactaatttt ctaatagggc      1440
tttccctaac cttccagata tactcataga tacagtcaat gagtcactgt acatccatac      1500 tttttcccttt tctcctttca agcaaaatga gcaactaggt gcacttgttg aagttctgcc      1560
tgctggtagg tttttttcctt agagtggggc tatagggata tagctatcta cttttgggca      1620
ttgaccacac atcatcaaga gcgatctata aaccaggctg aaatcgtttc ttctttagtc      1680
aacatctgtg cctttgcatg tgcaatttac ctttgccttc aatacctgct tcaagctgat      1740
ctcatttata ccattttcct ttaataatgg agcacttcta tcgcacacac tttatgagaa      1800
aaatatgtgt gtcttaaccc ataatcttaa ctattgtgct cacttctgtc ataacaaaca      1860
ggaactagca tatttaacat agaagaaaag gtcaggtgac catcattctt acatcactgt      1920
agcatttatc gtgttagcac ttctaattac gagtataaag cggaattaaa ggaagagcta      1980
tgacttaagc agcttctgag aaaataacaa tagaggaagt ctgatttaca ctcttggaga      2040
taatgacctg tgactggaga aaagatctcc cagattatat ataatttaaa ttctaagtat      2100
cttaagtaaa taagtgtttc acaatttttt ttctgttaat gacacattcc catagtaaaa      2160
gaataaagga tttggtctct tcttgacctt ttatttcttc aggctttcta aaataaaact      2220
ttatacagat gatggtattg ctcaaaaata acatttattc atcaccaacc tcaaaacatt      2280
ctgcatcata ttatgacact tataaacata agcttggttc aggcaggttt gaccccctgaa      2340 cttataaata aaaggagaga gaagaaattc cttaacaaaa caaaacaaaa caaaacatgt      2400
tgcaggaaac agagtgcaaa gacctggaaa aagcacagct gtaatgtcca tgttgctact      2460
tcacccatca tggaccaaag gaaggctccc tataagcagc tatcccttga attttccttc      2520
tagtcttctg ggtgactttt acactctggg ttcatgatgg tggctgtgac ctgcaaatct      2580
tggctctatt ccctaagctt ctagtatctt gggatttctc tagtgacata aatgagaaat      2640
gaagataaaa atgcagtcac tgtcaagggt ataaaaaaaa ggaagtgata acaagcataa      2700
tccaagaatt gcagttactg tcaaatgcaa gagaatctaa gaattgcagt taagcgaggg      2760
catgcttagc tttggaatgg atcatcaaat ttagatagcc ttctaatata aataagtctg      2820
agccctgggg atacccacca ttatagttct gagaggccag cctgcatttc acatttttct      2880
tcagttgagt tacaaagtgg acaatccaca taaacaattg tatatgttga gtgttatgcc      2940
agtggggaaa agggaagaag agatgaagca aggaggcaca tttcacatgt agccaggcgt      3000
acagggcctc caatcagatc cgtcattcta tctcccacac tttagatgat gcttacaata      3060
gtcacgggtc acaacacgaa atcctttatt cccatggcaa atagcatttg aaaatgaagc      3120
tccgtgcaat taaggtttgt tgggaatttt ttccctttttc acatatggca atatttatct      3180
tcaaagtctt ctcttgggct cacagtctcc tttataaagc agctggtctt gtgtggccta      3240
attgtgagat gatttgtgtg attcagtagc ttatttgtac agcggttcgg tggaatttat      3300
aaactgcata atattgttct agactgtttt cctttttagta agaagccaca ttttctccag      3360
cattcatgac tgggattata attagtggag cactcaagat attttcatcc caacttcctc      3420
tgttaattaa tgacattaaa caagaaactc ttgcaattaa atgaaaagat gtgagcagaa      3480
catggaaaga gaactagagt gatgaatcaa gttgaactca atctttgttt tgcatatgag      3540
agcttgtaac aaaatgctcac atgtaactaa tacaagctgt aagttatttc taattagtcc      3600
```

-continued

```
tagctgttct caggaaaacc gaatcaaata tggagtgttt tagaaaagat ctcttttgct   3660
atttctgtcc ccgagaaacc ctcagcaaat ggtcccagtt acttgtcaca cgttcttcaa   3720
tgatgaaatg tctccagtgc tgccaggcct ataaaaagtt ctaaaagcaa tttgaccttt   3780
cgtttccttt attaaaaaga agctgcatgt gggcattttg gtttttttcc aacagaatgg   3840
gggttaagta atagcagaga acgaaaaagg agaaaattct acctgctagg ctaggctaag   3900
gaaatgcctg tggtaactat aaaatttagc tctgaggcag ccaagataat ctatgcattt   3960
tattcttata atctcattta agaaagtttc ctgtgacatc aggaaagaat tttattaaca   4020
gttgactata agagaaatta ttatgtggta ttttatgtgt ggaaccataa ggaacatata   4080
gagatcatat tttaaatttt acccaaaaca gagatgtttc tctggcaacc atttctcatc   4140
ttctctcaat gctgtccaag tgcataatga tttgctttta aaattgaata tatttgtaaa   4200
aacaaactta agtcacccccc acatacgttt tgcaagttca gctcaggtgg tccatgttca   4260
tgttgtacca cgaagatcaa ccacatttag ccacactgca cagcatccaa cacaccacca   4320
cacctagact tgtggatagg cagaagacat agtaagacag tagagaagtt gaggaatttg   4380
aaggcttcat cacaactcca attggttccc ttggtaaagt tttcctttgt tgttttcttt   4440
cagggcttga ccaataactc atggaatgtg tcagctctaa ttgccggtct ggattggcac   4500
aagtcatgcc tcaaaattgg aatgttgtca catataacat agtcctgcag ggggataaat   4560
gtggaaaatg ttttatccaa acattcctta aaaacaactg tgttctgcca tgcaagagac   4620
agacaacctt taagaaccag ctgagtgaac tcccaggatg ccaaagtttc aacaggtgtc   4680
aggacaccac tcttccttcc tccaaggaca tcagacaatg gcaattcccc tctggggtgc   4740
tcttagccag ggcagctttc caaaagaagg taattggtga gttgtgagta tagaagaggg   4800
atctatgaac ctgggctggc tttgtgagtg cctcctaatt gatgagcaac ttacacaagt   4860
gttgcctgat ggccaggtaa tagctgtcaa gcaagcatca ttggaagggg ttgaagaaag   4920
catagaagct atctgtaggg ggagatttgc cactaagaaa gatgtcatga ggtaagcata   4980
taagaagaag aatggacacg gacatctgtg gagcacctat tgtgtgctag gcactatgaa   5040
ttttatctca agtacttaca ttctcattca acgtctgttt tcttcagaaa taaactgtgg   5100
caatctggtc ctggcaacca attagtagta aatactgggc tacgcagaca aatcagttct   5160
ttgcttattc attctccttt cctctgcacc aggcagacag gtgctgggga ggaaaacaga   5220
tgcttgaacc aaacactaca acatagtagg gaaaacatca tttcaaatgt agtaagctca   5280
gataatgttc ctcttacctc agaaacattc ctcattaaag gtgcatatgc agataccaaa   5340
acgttgttga acatgtaaaa ataataatta ttattttggc tacctaaaac taatcaactc   5400
attaatttaa tttttggagc agaattgaat tgctcttgag actgagttgg ctgtagcaaa   5460
gccaaaacca ttagttgggg aagtaaaatc aaaagctgcc accagggaag ggctctctac   5520
aagagaaaca ttcaaaaaag ttcccataga aagctcaagc ccacaggaaa tgtctagttg   5580
agatgatgga tcacagactg ccccaatcgc cagacttcca tggcaacctt ttgcaggcac   5640
catcatgtga aggaatcctt tttgtcctag gatacgtctt ttttgggaaa tgacaaaccg   5700
tgatcttcta aacatttcat gtttgatatt tgacattttc ccaaggcctc caaccctgac   5760
cttgccatgc aatagaatgg ggagaaagat gcttctttag agatgggcaa cattgctttt   5820
agagatctgg gcagatatac aaccatctct taacagatgg agttgatatg attgagattc   5880
ctggagaagt gagtatgagt ctgttaccag accacatcat agatcctcat cttctgatag   5940
```

-continued

```
tagttcaaat atttgcagtt acatgaaaat atctttcatt gaaatggcct cattttttgcg    6000 acacttggtt acaaatgcta gcattgtact gcatcagatt tacctggaat atatttctcc    6060
tttactataa aattcccttt ctattccccc aaatggtctc agtaggtttg ggatagactg    6120
aaaatctgta attttagaag ctgtcaaggt gactgttgtg tgccctggtt tgggatcagt    6180
gagtacaggg ggaagtgccc atccaagaaa tgtgcgaggt ttgctctaag tctacaactc    6240
tagacttttt cagaagaccg ggttacagag tgatctaatt gactcaaatt tttccccatt    6300
actggcagaa atatctggcc tttagcaggt tggtaaagcc cattttttcat tcagtttatt    6360 attccttgaa tttccccaga ataactatt cactctcttc tgcagttcag agttaaattg    6420
ttataggtaa attgtgtcct ctggagtcct gacccctagt acctcagaat atgaccttat    6480
ttggaaatag ggtcagaagc acagactggg aacactcact gatttcctgg gaatggggtc    6540
tgacaatccc aaaaacccag cacaacaggg tggatacaga acaaggagca tttctacaag    6600
cacttctttt aaagactcct gttgaaaaca atggcacagt gagactcctc actgaatctt    6660
ttgcttgaag ttctcagttg accaatttgt tttgttttc tctctacact tgctgtaatg    6720
gtatatacag gacatcaaac tcgactaaat gtgtggcaca catagtcagt gctcagggtc    6780
ccaactccct ttctggctca actccatttg tccctcctgc ctttctactt ctatcttgcc    6840
ctgaggtatt tcacttttcc aggtcctgga tagagattaa ataaatcaaa atccattcta    6900
gcattcggtt gaaattgttt cctgtgctgc cccattgatg attttaaaac tatatatata    6960
tatatatata tatatatata tatataat atgaatgtat gtatatgctt gtggaaaaaa    7020
tcctacaaga ataattcctc atggataact ctcagagctg taacaaaggg gtaaattaag    7080
ggggttgctg gacttccttg gggctccttg gtgcctctcc caccagtttc tgcctaaatt    7140
tccctttcag aaatttgaat ggagtcagtg atttcttgga gggccaggtt atgggcaagg    7200
ggaagatgtg cacacgtggt gatgtgaaat ttgatacaca actgccactt gatttaacat    7260
tctcccagtt ttcggtagag tttaatttg gttcaaatga agaaattagt gttacgccca    7320
tgcttgagga caagccaaac tgcatgactt cacatcgctt ttagagcagt attgaattac    7380
ataacttctt agcttgtttg ctcccaacag cctgagcggg attttcagaa ttgagatttg    7440
ggcctgagga gagggtttcc aactccaggg ctggccagac ctcggtgatg tcacctgagg    7500
aacacatgtg tgttctttca gttgggttgg catctatagg agagaaaatc ccatgttgga    7560
gggaaagcct aagagattat attgggcctc ttaccactaa tttttttttc tgtttaatta    7620
tgtctgttct cttaggctga atgattttcc tagttctgat cacacagcag tctctctcag    7680
tacattctgt tccctttaca aggtctctgc ccaattacag gaacacactc atctcttctc    7740
caaatgacca ttacgtgctg aaataaagaa actagctaca aagtatttca gggaaataaa    7800
gactcaatca gggaaaaacc tgaagcaact ctttcaaaaa aaggcaatta aaaagcatta    7860
cctttatata ttgatacaat tacctcatat ttacattaat tatttctcga atctcatcag    7920
atctagtcag gaagacaaag catgtccaac catagaaggc ttattagcaa aaggagcaca    7980
gctcagctta ttccctagaa aagtaatgcc atctcaaggc tagtgactca aggaacagtg    8040 agttttggc ttttttattc tcccctaaaa atggtagaaa atgttgtcac aggtacatta    8100
atgaagattt taagggcaga aatcatttca tacaatagcc caacttgctt aggggaggtt    8160
gtgctgttcc acttctttgc ttgtacgtaa ccatcagttt cacaagggct ttgccagtgg    8220
ggctgtattt tcattaccac attttttcagt cagcatcacc ttttatgttg aactctacag    8280
aatgtgaata ttcaacaaat tctgacctac aaaaactgca ctttcataag atatgaccta    8340
```

```
atattgttca atcatatgta aattacaaaa acaaaggctg gtaatatagc ttatgggaat   8400
accatggttt gtaaacagag ctgctttcaa attatttgcc agattttctg gtaactgtat   8460
taaataagtg aaaaaaaaca ggtaaaatta ataatatact ttatttaatc ccatatattc   8520
aaaatagtat atgtaatcaa tataaaaatc attaataaga cattttacat tttacatttt   8580
tttgtactaa gtcttcaaaa tctggtgtat attttacaca tctggcatat ctcaattcac   8640
attagccatg tttttgattgc tcaatggcca cattggacaa tgaagtcctg gacccttcac   8700
ttacaagctg agtggcaagt aattagcatt ctgagtctgc tcacttccct ttaaaatgga   8760
gttatattct tttaaaaacc tacatcctag gatatgagat taaataaatc aaaagagaat   8820
actgtagtta gcattatcat gttagggagg tcattcaact agccaatttt cattgcgtaa   8880
ccaaaaggtt aacatataga gttatagaat attctcagga attactgatg tgagataagg   8940
gtctggaggt tttatacatt tagtatcaag atggagaaat atgagcccag gttatagtct   9000
ggagagttgc tgacaaattt gccaaagttg gaaggctgtt aggggctctt ttcatctctc   9060
tgattctata ataccttcta ttcttactca tcaattaaat ataatgtggg ttgggtgata   9120
gctctgggac tagccaggct gcacagaagc atgaactaat gttagagtga caaacttcct   9180
ctctctaaga tcaaacaaga tgagactgca gaaaagggaa ccattttctc ttctatctca   9240
atactcgaat tgatggtttg tttctatggt gtttagacaa cacaacaggc acacactagt   9300
tctttcacta gacaaagcaa gacaaccaga ttgagtcaca attactttt ttaatcctat   9360 ttattaagag attggcaact cgtttgagga gtctggtctt gtaggtagca gccaaaaaaa   9420
ttggaggaaa tagggtgggt tttttttgtt gtggtgcagt ggtaccagtg aaactgacag   9480
gagtagctga tcccaaacaa caaccccaga aagcacgtgg ctcttgttat atctggctgg   9540
ctcagcaact atccaagtta tggggctaca ggggatactg tctagaccag ttcttttggc   9600
cctggcgttg gcagaacata gaaccagaaa gccaaagcat ggtgcaaaca tctctctgca   9660 tttttttctgg tcggcagtca agctggatgg aaactaaatc tcaaacaatt accaaatagc   9720
aataaataag ggaataaaaa gacggcacag ggtttcttct atccttgatg gatatggcct   9780
gactcttgtg ctttaaagca tgacttctga agtgactgtc cttagggaga aagcacagag   9840
ggcaatcgga agtatgactt ttccagcttg agatagtctt attgcatcac aggtgttcta   9900
gactcgatga tggtactgat aggaaaaaga catccacata tcatcgaaat aatttattta   9960
ccactagagc accacaaaaa cagacataca tcgtgttaaa atacagcgta attggtcatc   10020
aaaatacaaa acagctaatc ttatattcca ttttttaacc atgccaacga tcaaattgta   10080
ctgctgatta acacaaaaaa attgctgccc acttgcatac tagcacttca ccccttcctt   10140
gccacctcca ctcccatggc aatatttact tatgggaaaa aagacctaca gaaccccaa   10200 attaaaaaaa aaaaagattc aagagatctt aaaatagaga tcagtgcatt catgaggaaa   10260
gacaaataat acaaaacaaa atgtcatcct atctgagagg aaaatgtctg cagaaataaa   10320
agtgatttac acataataga aaagtggaag acaaaaaaat aatcaacaca cactcaaatc   10380
tgggattggg ttacatccaa cacaagggct gtttactagc atcccatctc ttgctgtttt   10440
caaacttgca aatccaattc tttaattcag gaaattccaa aaaagaagta gaccatatca   10500
aacaacttca ctttggattc ccgcctcctt atgctgctct ttaggtgaaa ctgcaaatat   10560
tccattgctt tgcctattaa ttttttatttt aaagctccag catgaggata cctcttctgc   10620
aatgatggca aattatttaa agcaaggtaa actttagcct cagatataga taactctcac   10680
```

-continued

```
tcagaggaaa gaaagaattt tttgacatag gaaaaattgg cttgtgcctt ttccccttca    10740
aagaacattt ataaaaacct tataacttca gtgaaataca caaaatgact tatgctgacc    10800
tggattaaga aactgaaggg                                                10820

<210> SEQ ID NO 26
<211> LENGTH: 1764
<212> TYPE: DNA
<213> ORGANISM: Homo sapiens

<400> SEQUENCE: 26
aaagccaacc taatgcagct cagtgctaga catggtagat gggtgcttac ccaggagcca      60
ttcaataccc tctcttccct tactttttct actttagaag ttcaaaagca aaaccttttt     120
tcctattgtc cctcacacct ggagatgaca aggcaacata atattgtcca aacagatgtc     180
aataggcctg ggtgggactt caggaaagct catatttgtt aaaaaaaggc tcagcttttg     240
cccctctctt ccaccttttt ccttagagag taaacttgaa gcctgaaatt gcagcagagt     300
gggcaaacag aaggacaaag gctacaaggt aaggtaaatg gagcagatgg aaagaactgc     360
agttcttgcc agtattattg agtcactaca gcgagaaaaa taaaacgata attaatacaa     420
aaagtagatt ctacattatg aacccagaaa aaagctctgc tctggatctg actctgttac     480
ttactacctg agtgacattg atcatgtcat agagttctat tccctcctct gtcaagagaa     540
cacttgactt ctttagccta gattatccta tgaaataatg cagttatata tcttcataca     600
ttggaagatg ttgcttattt aacatgccag gtggttgata cataggacac gcagtgactc     660
cacagttaaa tataacagtg cccaggagtc tgctttccgt tcaaagaatt tgcagacact     720
tactttgact ggcttaattt cagacttctt gggaattctg ttctgaagtt aggaacttcc     780
aagcttttaa aagattacaa atattcaatc cttggcaatt taatatttgt cttcctttgt     840
ctatacgagg ggaatcttta aagacttgtt gaggcatatg gcaagttttg aaagaatttg     900
aaggtgaata agtaatgaaa tatattccct cttttaacat taaaaacaat tgtatttaac     960
caataaggaa aaattcaggt aaaaaaattc catgcatatt tttctttttt aatttaattt    1020
ctactaatat tatgactcag aggctgaatc caggataaag gtactatcat cagggctctc    1080
tttcagggca gaaagagaac atataaagac tagaaatgaa aaaaagagat taaacaaggc    1140
ttccacttca tctctggatt ctatccttag catagtgttt tcaaagttca ttcatttgta    1200
tcatgcatca gtacttcatt cctctttgtg gtggaaatgt tgagttatat ggaaactcta    1260
tgtttaatca tttgagaaac tgtcagatta ttttccaaag cagctgcacc attttatact    1320
ccatcagcag tgtaggaggg ttcaatttct ccacatactc accaacactt tgttatcttt    1380
ttgatacttg ctatcctagt gcctttgaag tggcatctat tgtggttttg atttgcattt    1440
ctttaatgac taataatgtt aagtagcttt ttatggctca ttggcctgta cgtctttctt    1500
aggaagtggc tattaagatc cttagctgat ttttaagtta tttgtctttt atgattgagt    1560
catgtcttta tatagtcttg atacaagacc cttatcagat atgtgattta caaatacttt    1620
tttccactct gtggtttttc actttcctga tgctggtctt tgaagaacaa aagtttttca    1680
attttggtga aatccaattt attatttatt tcttttgctc atgcttatat aattatatcc    1740
aacagattat ttgccaaagc taag                                          1764

<210> SEQ ID NO 27
<211> LENGTH: 12761
<212> TYPE: DNA
<213> ORGANISM: Homo sapiens
```

-continued

<400> SEQUENCE: 27

```
gtcccggcgg agaaggcgcg gagggcgcgg gcgctgctcg ggggcgctct cgctcgcggt      60
ctgcccaggc gcccggagcc cgccttttat agggccggcg gaggcgccgc gtgttgcagt     120
gacgtggctc tgtctgcgcg ttccagaatt ctcaaacatc tcaggaatgc tggttggcgc     180
gggctgctgc caagcgcctc ccctggctcc attgcacctt ttgtgtctgt ctcccagacc     240
cgtcaagaaa agaaaacagt tcgttttttc caccttaaat tacgacttat gttgggaagg     300
gttctttggg gcgtgatggt ggtgatggta gttggagggt cgtgaggggc gagggggggcc     360 agttcagaac tttgcctgga cgtgggagga cctgagaggg aggaacaaaa gtcgttttgt     420
ttggtgatgc tcacccggga aggcagtgag ctgtttgctt ttttacagcg aaggtgagag     480
gcaagttatc tgttgagagt agaacgggga agaggagtgt gtctctgagt caggaatatt     540
tgtggacttc aaagaggcgt gttcggaaca agtcccaaag ctttggcatg atgtttatta     600
gcaaagttca gtgaattgca aattaatacc cacagtggca tttatgaatg gggggggggg     660
gggaaacttg cccatcgtct ggcaaattcc caggcagagg tctcccccac tcccccttcc     720
ctcttttggg tatgttgtac ttgtttgttt ttggaggttc ccactttagt tccagcccac     780
tgcctgggtt ggaagtccga gaggaaacga acgcggagtt ctccgggagg ctgacttata     840
cttcctcacg gatgcaggag acggggtaag cccttcccgc ctccctccgc gggcaggagg     900
ctatgctaac caagcagcca gccagaagtg caggagacca ccgtggagtg gcctgaaatc     960
atcacctgca aagaccgcaa ggccaaacca gattccagga ccattgtgcc ctatgaatct    1020
ctgggaaaag cagactcctt caagctggac attttgtggg gttttttaact cctttcctag    1080 ggaccactgg aagcctccca tttttaaatga attgcaatgc ctctctccaa gtacagaaaa    1140
gagatttagg atgtaatatt gtaaaaatgt cagcagattt taagatcccg ttctacttgc    1200
aacagtagaa gaccccacca caagacaatt tacttgaaac cattagtgtg attgataaac    1260
taggataact acttatcctt tttaatgttt aaggctattc agacttcata atttagcagt    1320
cttgcttgaa aaggcccctta gtgctaatgc tgactttcct gataaggaga atctgtcagg    1380
cacactccag tgaagagaat tcttgcagga aggagttcag ttcattcatt ccaaagtgcc    1440
ctttcataaa tggaagcagc atttgctaga gggagtggga tctctaaagc tctttagggg    1500
tggggacttt tcaagacaat ggattgtcag gtgttatgca aatacagtga ggaaagtgtg    1560
ggcccaacac gtacacaggt taatttatta aaacactgtt tttcctgcct tcatttcatt    1620
gtttccttct taatgaagtg acggggggcg ggaggggggga ggagggggtgc agggacaggg    1680 ttgaactaga gagagaatgg agaggagggt tcctggcttc tgttgtggcg tcttttctat    1740
ttgacttcat ggttgtaagt atttccagat ggtgaatcag acaccagacg taacaatatt    1800
tccatatttg ggtatagcag tagcctgcgt ttttaacatt tttctgcctc tgttatccaa    1860
ccacaaagca ttcttgacag cttcaaatgt tgttaaatat agatttaact tctcttccca    1920
gagcaggaaa ttctttggaa ttccttgttt ttcacgcaat ctgtccatca tgatttaaaa    1980
taaaagcaca gtggatcatc caactggccg tatatacctt aattggaggt tggggggggg    2040
acggcagaga tccagtctgc cgcactgcgt tcaaacacac gccattccag agattccttt    2100
aaaatcacat taaagttttt taacaagggt gtgtgggttt gtttctggac ttcaactggg    2160
gaatcttgag gatgagtttg ccccagaaga gaaatttaga gaaccttacc gtcagctgcc    2220
catttaaagc aggggtgtg ttgtgggagg gggtgggaag ctggagcaac agggccagga    2280
```

-continued

```
ggtgtgggag cgggagacac tagagtaacc tatgtgcaca gcctctccat atagcctgct   2340
agtaatcaag agaaacagcg gctcctcaag tcctgcccaa agaccgtcca gaaaccccag   2400
cctcccgtcg ccttctcgcc gcctccgctg ggagccgcag atcagtcgtt gacggacagg   2460
aggcgaaatg tgcaaatgtt atgggtaagt gttgcttcgg gtgctaattg tatggctctt   2520
ctccttcacc ctccccatac ccaggaggct tgtttccttt ggattgcaat ccacggagaa   2580
ggggctactt gtcttctgca gctcctggct tgggctgaga gatggggtct caaccgctgc   2640
tgccagggaa ttttaggtta cctaatgaag ggctcactgt ctggcggcaa ccgagaataa   2700
taacggtaaa tctggcgact ccagtttcct agcccgaagg ctctcagact agcgtgcatc   2760
cgagtcgcct ggagggctag ttaatgaatg gttctctggg tcccacccca gagtttctga   2820
ttagttacat tttaacaagt ccccaggtga tgttgatgct gctggtccgg agatcacaca   2880
ctgccctgga cgaccggagt gctaaggtgg cgcccccgta ccatcccatt tctctcctct   2940
ccatttcccc gcccccatgg cttgacagcc aggagagccc caggaagcca ggatcctggt   3000
ggctgcggca ggaactgggt ggccgacgcg cgggtcggga gggagcggag gcaccgggtg   3060
cgggacgcga ggcccggacc tgctaccgcc gcccctgcc ggcccccgc ccgcgcgcca   3120 cagtcccgcg gttgccaaga atcgaggttt ccggcggcgc gcggcgcagg acgtttccag   3180
ccccggccca tatttggtga aagtctttca agactccgtc atctagcttc gggggggcgg   3240
cggcctgcga cccggcctgg caggcttgcg gccgccgcgt tcctgaaaag tgcgccgcgg   3300
cggcccgcgc ccaggcctcc ctccgcgcgg gaccccggag ccggcggggt cccgagtttg   3360
gccccagtcc tcacccctct gagggccgaa gtccgccctg cgctgcgtgg gaggctggcg   3420
cggagggcgc cgcggcagtt gtgtcacttt tcccgtccgc ccccctgttg actagtcctc   3480
ccagcggggc agcgagttgc cgtgctgtgc cagacgtaga gggtgcgtcc ggcgcaaggg   3540
tgtggggctg tgtgtgggag gatggcgttt gcgtggacac caagcgcacc cgagagcggg   3600
acgtgtagcc agctctgggg aaaagccccg aaggcctgg attccattat ccccagaagg   3660
gacacatggg gctctcggtt tctcctggta acaccatttt ctatctaaat gaagaaatgg   3720
aggcatggaa ggtaatgact ggtcactcac ctagcctgga tttgggccca gatcggtctc   3780
acacttaact actgtctata ctgcctactc tctatctctt acctcagaca ttcaggccca   3840
tcctcttccg taatgtactg gctcttttgt atttaggtct taatgcagat acattagagt   3900
ggtctttaag caccttggca ggctggtggg gaagatgttt aggacctgac acctcataag   3960
ccacattgtt caggcaatcc ctacttctgg aataaggctt ggcctggtag gagttgaatt   4020
tgtcattgag ataaaggttt cagcatcact tacttgaacc catatatttg aggactgtat   4080 ttaccctcc ctgaatccca gatttattca gagcttgtga tgtcatggca tagtgctagg   4140
tactggtgac atgagaaaga ggattttaat attgaacgtc ccccgcagga ctgtaaggca   4200
tattgcagaa gtgggtacat gagttagggg gaacgactaa tctggggctg aaaggatgaa   4260
caggagtttg atagcagggc aggacatttg agaggaaggg aacaaggcct tgactgggca   4320
taacaatcag tctgactgga ccataggatt ccttctgaaa actggcaaga gatcagttgg   4380
gacatggcct tgctgtcatg gcattggaac tttgcagagt ggccatgtga gcttttttgcc   4440 taggtttcct tgtctataag ataacaggat tctcctagct cagaggacac acactcaagt   4500
gcctgcagga ttcagccagg taacaccatg ccatgactca ggattagtgc tggctgatat   4560 ttggcccttgg ccttgggaac catggggaca tggaaatgag agtgaatggt tactaggtga   4620
aaatgtaggt tcactgtttg catattttct cattttaaaa agagatacta gagatctgat   4680
```

```
ttttatgtga agtcttcaaa attttaaaag ttggcaatta attacaatgt taccatctag   4740
actaatcctt ggaaaaccca agaagacaat ctgtgggtgc catttgtgat ctctggactg   4800
aatatctcta agaatctgtc ttgagcattc tataactccc agccacctgt gaaattgtag   4860
ggaacagcac cggctccatt taattgtcaa gttgactaga cttttatttaa gagtcagggc   4920 tgctacttac ctcttggttg taggaattta taacctatta agaaaattgg aaacaaattt   4980
tctacttcat ccactctcca gccactactc tgtctccctc cttcccctg aattgatgat   5040 gtaagcagct ggcattgcct tggcaatatg ataggaaaca cttttttagg gcatccatat   5100
cccgtgggaa ccttatctgt ttattttctc cacttggcat ctatccacag gaagccagca   5160
ttcctaactc ccttacctta cagaacttct tgtttgtga taacacagaa acattttatt   5220
ggaaaggact ggaaggcacc tctcccacca caccctgcaa tccatcttct agagatgatt   5280
gagcaatatg aaatataata attgtaagtc attatcaaat ggcttggcac ctctgccttt   5340
cgtgttttat ttctggagat acctgtctct taaccaacca ctaacatcac acgtagcaca   5400
tccagaattt agaaaggatt tgctctgggc acagtagatg agcacacaga ttctacagag   5460
agattgaagt gatttatttg tgacaaattt ttgcaagtct tggggattga gtgtaaggga   5520
gtattcaagc attggactta ctatgtgaaa gaagacataa gacatattta ctgctcagcc   5580
tgatgcctgg cacatagtaa gtgcttaatt acaattattc ctactgccaa gcaccatcat   5640
tatctttact ttcactgcaa taacatagaa tgagctagtc ttattctaga gaatactttc   5700
tattctttag aactctagtt ataaaatcac tttggtatat ggtatataga tgatatgatt   5760
aaaaggatcc atccagccag gtattctggc tgcactggac accagtgact atctaaaaaa   5820
ccactcaaat gggcttacct ctcatggcac tccgcagtgg tgagccatgt gagttttgct   5880
ttggtttcct catctatgag atgataggat tgcaccagct ggagtcactc aagtgcccca   5940
ggaatcagag aggtaaaaaa tgccatgcct gagcgttagt gccggctgac acttggcctt   6000
agcaatagga atagttggaa gcatctatgg ggcctgggct ttgcctccca ttggctaaat   6060
ggttagtata cacaatctca tcagacttta taaacaactc tgtaggatat tttattaaaa   6120
gatgagaaaa tgaagctttg gatgtcagta attggtgcaa gggggcaggg ttgttggtag   6180
agcagaattt tcaaagacca ttcctttcgg ggagagcatg gtatttgtcc ttcatgaaat   6240
ctgccttaaa gttcaggaag ttgcctgcaa cttcttgact ccccttaaca actgaatctg   6300
tcacttaaat attgttctaa atgtgtcttt agcttgtgtt ttcagtaact gtggcccaca   6360
gtttcttaat gagagtctga taataaacaa gttaaaaaag ggttctctcc ttagggccct   6420
tgcctgagct tgtttctatt tcctctggga ggaaaaaga aagagatgtg tcagaacaga   6480
ggtggaactt ctcagagatt gagagatccg tctactgtaa cttagtcatc accatcaatt   6540
ttgttacctg aggcaggcag agctgctacc tcccacagcc tgtggttatc ctcacaacag   6600
ttactaagca cggagccctc caggcccctg ccaagcgcac cctgcatgtg ccttaggtgt   6660
ccctgagcat tgaatgggtg ggggtgccca aggttatagc aataaagaaa aaacatagtg   6720
ccaggtgctt ctccatttac cccttctttt gtagttaggt tttggctttc aaaagacaaa   6780
aaaaaaaaaa aaaaaaaaaa aagaaaagga caaaggattg tatgcttaaa atttccaagg   6840
ctctggaaaa ttgggagaat tagaaagtgt agacatatgc taaagcattg cagacccagt   6900
tcagttcatt ctaataaaca taacatgtat ggcatgctgc atgctaggca gcaatgcaaa   6960
gaggaataat attggacttt gcttcatggc tctagctgcc taggggagat gcagatgctt   7020
```

-continued

```
aaacagataa tacaatactg tggattaaag ctctagaagc cgtgcagctt tgggagtaca      7080
gacaagggat gtccaactct gagtctaccc tttaaagatg tgaggtcttg ttagtgtgta      7140 cattttttatg gatgagaggg attgggcaca gttattccta acatacacat tcccttttgaa    7200 gctgggaact gcaaggaatg tgcacattcc tgagagatta gaaaacatct aaaagtgaaa      7260
ctttcaggtg agcctcttaa aatgcattga ttacagagga ccgacccttt ggattgaaaa      7320
ttcttatcat tatggatcct tcttcagaag gggaaagaga agtgacattt actgggccaa      7380
acgccttaca ggttcatgtt caggagagcc ctctgagatg agctttttga catctttcta      7440
agcttaggga atgaaggctc atgatgctat cttaaaatag cttcttacct aagaataaaa      7500
atggtagtca attctggctt cattatttgg agggattaga agcaactctg tcaaacaggg      7560
tgacccttga tgccatttgc aaattcttct tagaaagaaa ctgcaaaagg aatcattcac      7620
ctactaatcc aacatccaat aaagtttagt tccgtgagct agtatcatca atggcagcaa      7680
aattagaaca gtagccatag aagtctaagt tgaccttcct ttgggtgaca agagtttagt      7740
aatgcccatg gattcattgt ggcaggcagt tctctggtct ccatcattac acctaacatt      7800
ttaattgtgt ctttaatttt aattttaaac gtgactttaa ttttaaatgt gactttctca      7860
gtaagaaccg tgagagagta cttaacacaa tataatacac tagattctta atatatgtaa      7920
gagatcacag taggatatga gggagaagag aacacatgag aaatgaggcc cagagacatt      7980
tagcatcatg tctgtcagct agttagtgat agggtagaac taaagtagac ctaatagttc      8040
tcaagtagtt ttttttacaac atctgtattt tttatctctt tggatctagt cctctagcca      8100
tagtatagta attttttataa attatagtta acactcttat agtacttgct attttcctgg      8160 tagttttttaa atgctttcaa tatattaatt catttgatcc tgaggtaggc actattttcc     8220
ctacattaca ggaaactaca ggtatgaagt aacatgctca agtcatgtaa agctaaggtt      8280
ggaacccaga tagtcgtcta tatgtaaacc actaggatac actccctgaa atggaatgac      8340
attatctttt tgttaaagtc gtatgaggaa aagtaaacaa atatttaatg attagaataa      8400
cataatatag attttattac acaaagaaca tattttttaaa aatttcagtt aattttgtgt     8460
taaagatgct cattaatttg tttacaaaaa atgtagaatc aataggaaaa aaaaccaatg      8520
tttatacatt aatattaatt agagacacat taaagattct cattagataa catacacttt      8580
ttcaaaatca gtttcttata agcaataatc agtcagtcag aattgatact tagtttctcc      8640
aaaggattta agccttattc ttttttttatt ttctatatac ttccaatgtt aaaatcattc     8700
taatgctact tatttttttta attgattgct ctggggtttg taaacttact agtctctctt     8760
caaatagtat tagactactt catatataat gtaagaacct tacaataacc ccactttgtg      8820
ctattgcatc atatatcgta cttctatata tgttacaaac gccatacttc attgtaaata      8880
tttttgcttc aattatcttt taaagaatat ttcatattta ctcacatgtt tatcatacat      8940
tcattattcc tttgtataga tccaaatttc catatgattt ttcttttact agaggaactt      9000
ctttgaacat ttcttatagt tcaggtctgc caacagtgtt ctgtttgctt ttattttttat     9060 tttgccttca tttaggcaga atatttttttc tgggttcgga attgtagatt gacaccttcc     9120
cctgagcatg gatgttgttc cattgttttt tgcttacata tttctgacaa aagctgttta      9180
tttcatctct tgtaggtaat tatttctctc tggctgcttt tggtattttc tccttggttt      9240
tcaatgattt gtcttggtgt cattcatttt ttatcctgct gggatttaat tagattcttg      9300
gatctgtggg tttattcttt ttatcaaatt gggaaatttt tcaccataat ttatactcgt      9360
tcgacaagtt tgcatgtgct gcttgcttat tccacaagac aaaaagctct gttcatttca      9420
```

```
gtcttttttct gtgtgcttca tttttgggtat ctaatttgct atgccctcat gttcactggt   9480
cttttttctg cagagtcata tctgcttcta cactcatcca gtgaaatctt tattttagat   9540
gttatactct tcatccctag aagttctatt tgattcttta aaaaaagatt ttcacttctc   9600
atcacattat gttttacttt aaatactagt acatagctat aatagttgtt ttagtattac   9660
cttctaattt cattatctcc atcatttcta agtttgcttc tattgatcga ttttttttcct   9720 cttttggatc acattttctt gcttcttggt atgtccagta tttttaactg aaagctgagt   9780
attatggcta ttatgttgtt gagttgggga tttgttgtca ttctttaaat agtattgagc   9840
tttgtcttgg ggagtaaatt acatgtagat cagtttgacc cattcgaggc ctattttaat   9900
atatttctag ggcaggtcta gaataacttt cactcaagag atagttcagt cctactacta   9960
agatgtgact ctggatgaca ctgaggtctc tactagtcaa agaaaagtca tgcaatttca  10020
aaagaatggt cagagatact tcactgtgaa aatggtcttg cacattaata ctttcttata  10080
cctttcatta ctgagtcagg ggtatgaatt cttttaataa tgatatataa tgtcaaactg  10140
ctttccagtt tatacttcca ctaccagttt agaaaagtgc ctgcttcata ataaccttgt  10200
tagtattgaa tttaataaat tatagtatat cctttgggag gaattatgca gcattaagag  10260 catgatttt gagacttgag aaaaggctct caaaccaatt aattaaacaa aagcagagca  10320
aaaaattcta tgtacatcaa gatcccattt tgacataatg tattctttgg taatagcatt  10380
tatattatga atgattttca tattcttatt ttattttatt ttagtataac ttcaaaagtg  10440
tctgttgttg aattttggct cctgtccaac tttgaacaag atatctggcc tttctacact  10500
tcagtattct catcgaggat ggcacaagca catatcttat aacattgttg taagcattca  10560
attatttaat tgatgcagaa ctcacagaat agtgcatgtc acatagccat acactaagtg  10620
ctcaataaag attagctgtt actgttatat caaattatct catctgtgta gctatttaac  10680
actgtactta acacggagat atagtggtaa atgcaaaaga cagttcctgt cttcactgaa  10740
gagagatttt cccctgaatc tagatgttgg tcttatttct ggtacttta ttctacttta  10800 aaaaattctg tatagaaata cttttctaag ggatactgaa cagtcaaagc atgtttgatc  10860
tctctgactt tccctcattg aaagcattga ttcttgttat acgtggttgg tagatttagg  10920
gagatgtaaa ctctgaaaga aacttgaaat aataaatcct atatctcctt tatgattact  10980 ccttttttttc taccccttaa acaacacaca cacacacacc tttagctgtg cggacacatt  11040
atctaattcc acgtgcgcaa attctgcatc tagataatgt tgtcttgtgg tatctacctc  11100
attaagcagt ccttctagaa tgctttgatg actaaaaata cagatgacgt gtccttcgta  11160
caccgctttc tcacccgcat gtaggaacat gtgctttggg tacattttca agcaaggact  11220
tgtggtgatc tacctcatac attaatccta gctgtagtaa tactttggga aaggaatatg  11280
atcccaaaat aaccaccagg agaagagtgt catgaaaggt catggcaatg gggcagagga  11340
tgttggacag gagtgttcta aaaatagaga gtaagagatc aaagaaccag cagtaatgag  11400
gaactttttt ggctttggtt cccagggaag gaggaggagg aggcggcggc ggtggcactc  11460
cccagcctgt tcgtccgcca ctcatatctg tgttgcagaa gtagggaggg gttagcacat  11520
tttcctgtcc tgggtgctga ctgcctttaa attatttatt tatataatgc ttaaaaacat  11580
gtcaaaataa gaagcatgga gattttacct tactgccata ttgctactat tgcaaggaag  11640
cctaaacatt ttggatcaag aatcctcaat ttcagctttc tggaccagac cttttttttac  11700 cagttcaaat tgactttttg tcatcttcct aaactatacc tgatgattaa gagtgtttgc  11760
```

-continued

```
agagccaagc actgagtttt gtgcattcat gagaagttgg gtcgatcagc cactctgagg    11820
tgtgggcata tctggccgag tgaagaaata tatcttagat atgctgttca atccctcccc    11880
tgaaatatag cttttgacaat aatgaggcga gtagatgagg acatgttaaa atcacaggcc   11940
tcttgaagga attttttggca gatgattgtg tgtatgtgtt tgtgttcatg tatgcacaca   12000
atatagtaat tccatacagt agggaattaa aaaatctggg atgaatcccg taaccttcct    12060
aaggacaatt tactcaatag tgaactaaac ttattgacac ttggctgaca gacgataaat    12120
gtatggaagt gcttccaact atacaatgct gtacaaatgt tccttaaatc ctgtggttgt     12180
cagagaacca gtctatatgt tcaagtcgaa tccactatct cctattcaag gaggtttctt     12240
tctttttgtt cattccaaaa cttttactgt gccactccag tgtgcaaggc actatgccag     12300
gcaccaagaa gcatttaaag atgaatcata cccagatcct gcctcaaaga acttaggata     12360
taaggaggca gataaactac tgaaaaatgc tctgcttggt ctctaattta gcttcaaatg     12420
atgtcataac tgagcataat atgacattta aaaagggact gcacttctta aatatttaaa    12480
taacaatgta catgttaatt agtatgcatt tgcctgttaa tagacttatt aacatgtatg    12540
ctagtagtca agagtactga gaaatgcctg tgcaggcaaa ggtgttcagg acaggcaatg    12600
tgaggtactg tagtgattag caatgactga cagtgcacta atcacagccc ttgttgagca    12660
atcagtcttc attaggctcc ccaaaccaaa actgacccaa aaacaattga ttcttctggc    12720
tttaaagcca atttctccat ttgttttgat ttgaggcttt t                        12761
```

<210> SEQ ID NO 28
<211> LENGTH: 10907
<212> TYPE: DNA
<213> ORGANISM: Homo sapiens

<400> SEQUENCE: 28

```
gaccaaaggg caggtgcatt ttgagtgcgc caagctgctg gtttgacggc agcgtacagg    60
caggaagaga gagggagccc ttgaaatgga ggaagggcca tggggcaggg tgagaagggg    120 cagagggggac taacccatct ctgtttttat agctgtctag agtttgttag tgcctatgtc    180
tacacagaaa tatatgttat ttttataata cagtgagatc atatatatta ccgcgtactt    240
ttctcctgac tgcgtcatta ggattttcca tagggataaa tttaaaagta gtaaacttag    300 aaatttttcac attgataact ttaaaatta atgcatgcta ataaaaatat ggatataaat    360
taattttgac tgttttttgat tttatgaaat tattcagtca ttttttattat ggaacatgca   420 ttcttttgct gggcttctct caccaaattt taggattttg agatttctat gttattgcat    480
gtgcctataa tatatgttta ttgcaatata gattctattg acagataaat cttttcacat    540
atcaatgatt atttgctcag cacaaatttg aagaagtaga attgataggc caaatagaga    600
aacattgata gatatatgta gttactctcc caaaaggata cacttactct tccactaatg    660
tgcaggagtg tgtctaatac tcacccacgg cctgcagtga gtatgaactt tatttttgca    720
cctgtgccaa tctgagagac aataaaacat attgttttat aactcctctt agaacatttt    780
gttagtaatt tgcacaaatg cataaaacat ttataaatct tttactatta acattttttct    840 ttgtctctaa atccacaact gtgtcaccat tttaaattaa tgcatcataa tctataatat    900
ggatatgcca aaatttactt tctgagaggt cactgtataa aagacattgc ttttttttag     960
tgaactcact gtcataattt cccttaatcc tcaagaaaat cccatgaact gtggtctctg    1020
aatatatgca ttttaacaac aaggaaattg aggcacagaa agattggaga ataactcgcc    1080
taagattaaa cagctagtga gatttggaaa caaaatttga acctagtcag gtctggtttt    1140
```

-continued

```
aacagcgata attttaatac cctcaaaaac tctcttcact aattatcata ctttttctctc     1200 cttcaaaaca aaaggtggtt tattcccact gcattttcat agcctcttgt agattgtaat     1260
tgcccgataa atgcagcttc ctttatactt cattttttta tgtcttaagt tttatactat     1320
gaatttttat tggtccaaag aacaattcta atatacttct agattttagt ttctacatag     1380
gacaaacttc ttaaactcag cccggtaaag tggaagagtt tatgcattgt ccagataaca     1440
gaataattct tgacagtttc tccagaatta gcagataact ggcttactcc tcattacatt     1500
tgtagctctg gaaattgaca taggataaaa ggtaatagaa ggattattgt attagggtta     1560
ttaaaaattc cagatacacg aaaaagtgta cgtaaaaacc acccacacaa ttcaactgtt     1620
aactgtgggt taaaaacagt gtgttcagcc aacctctttc aacagtagtc acctaaattg     1680
ctgtttttaa aagctagtgc cttccctgcg aagcccaata gccgtcacat gattaatgtg     1740
ctagtgtctt attaactgct ctgttccaga agctgaccaa ttcacagcca ccctttctgc     1800
agagaccttt ttgtaaaaac ctagttgaaa tcatggtgtt ctgactgcag gctactgcat     1860
cccccaccaa aacatcataa agagcaaaga attactgttt ccagtaatcc aggccataaa     1920
tcaacctgct gtgagcacag gaaaaaaaaa aaaatcacga gcacttcctg cattcatatt     1980
ccaaagccta gcggtaccag caggttctgg aacacgccag ccccgtgtgt gtggtgtttg     2040
tatgtgtgtg cttgtaagca gacgtggggg agggcaaaag aaatcccagt aacataattc     2100
caaatgcttt gatcttatca cgaccttcct tgctgtaaca atattttaag attgttaaaa     2160
attgccacct tatctgtctg ggggtatcac ccactgctta acttatctgg gcccagttgt     2220
ttgagagaaa tgcagtatgg catgaccttg gtttcttagc acctgacttt aatatctaat     2280
cagttgtgtg tctcggtgaa gccatccaga catgtcacac aggcgcctct ggcacccagc     2340
aattctaatg atgtttactt cattcacccc ttttagagag cttccagcag cagactcaac     2400
caccccaccc ttccaatctg ggctccaggt ccttccaggc ctagagcgta tttttaaatc     2460
ttggatgccc tttccattga aaataatttg gatgccttga ggtcagtcgc aaaaattttc     2520
tgagatcata tagagacttc tgaagagaag cctcaatttg gatcaagaaa aacattaaac     2580
ctcatggctg ttgtagtttt caaaacacaa acccttcccc tccagcaacg tcaagtctta     2640
aggtcataca atacaatgtg gagaacacac atgcacagct tcgttaattt taaaaaggtt     2700
tcttagaaag gtcccaaata ttttggcccc agatcgaagt aaagtcttaa aatctagaaa     2760
tgagagaaaa gatgtcagtt attagagtac catataataa aagtgacata aaaggagttg     2820
attttctctc tctcagtgac ttaggaatca aatttccttc gttgagaaag caatagagtt     2880
cctgccagcc tggcgggctc aacctggaac ctagctgttt tctttctggt tctgacgctg     2940
tcaccaggaa taaatgttct accatcgcga tgctgctggg gcaggagggc accctggtta     3000
ctctcttttc tttattatag cattcattga catgacctgc tacactgtag tgaactcttt     3060
tggactaatt ctggagaatg attttctgca aaataagcag tgatattctt ctacacttaa     3120
gagaccaacc aagaccctgt gttttcttgc ctcctcccta ataaagctgg acactggggc     3180
cccagatgct ctcccggttg agggggctgt gaggacatcc ctgaaactta ttttaattga     3240
cctgcttgtc cctccccaga tcacacagcc tgtccagatg tccgaggtag ggtatccatg     3300
agacgaggca ggtctgtgct gggggcacct gcagtgcttc attggggaag gcgtgggctt     3360
cctgggagag agtctcctaa cccctgccct ggtgagctcg aggtcagact gtggcaccca     3420
ggggatcagt gcccggcgcc caaggtggct tagtccatcc ctgtctgtgc tccatctgct     3480
```

-continued

```
gtgcaggcag ctctgaaacc cttcagcaac ttctcattgg ctcccagctg ggtgcccctg    3540
cgtggttcac aaccaggctc caccgaactg gccttcaaag cacactaaac ctgcacagct    3600
ttttattatt ttaattgaca aaaataatta cgtattcaca gggttcaatg tgatgttttg    3660
gtctagtata caatgtcgag tgattaaatc aaacttatta acatatccac cactcttatt    3720
gtccatggtg ggacacgtga aatgtactcc cttagcaatt tagaaacatg caacgcatta    3780
ttaacgatgg tcaggaggtc agccacggat ctcaagagct ctgagcctga gaatccgcct    3840
ctgggggagg ggggcctgac gagagaggct tacactgaag agcacttggc tttgcggccc    3900 ttgcctacc cttgcacttg gaatccaggt ttgtgtctct ctccaacaag aggcctgtga    3960
cgctcgccct gcttgttctg ttgaatgtta ctttgcgagc gcgtttacac aactgtcact    4020
tgaggtttgt ttttagcgga attgtccttc tcctgaattc ctctcacctc ccccacttat    4080
ctcccggtaa actaaagcca ccgagctggg tgggaagacg gttcacatgc tgacattttt    4140
ttgtgtttag aggctggtct tcaaaaatcc tcacatgtac aacaaggccc cagatttgag    4200
gaggaaaata actctgcagc ccagtcagcc gttccagcca cctgtcccac tcgcttctgg    4260
taggtgtgtg gctgtgaggg cccggttgga gctccaggct aaataaagct gcaggaacag    4320
agataaacaa gtgctcccaa ctcaaatgcc tgcacacaat atcctttatc tgggcaagga    4380
gagtggccgc cccccataga cggacccaca ggcgccccc gaattaattg ggacatattg    4440
ttaaagggaa ggcccctcag aatagatgcc aaactccaag gacacaatgt caaattccag    4500
aaggacagcg gcatgggcca atgggaaaaa ccccagccgt tccgcgctga atcggatccc    4560
atagagcccg cctgcttcac atgctaacgt gatgatgaac gtatccaagt atcagcatca    4620
aatccttgag gactatattt gcaatgtcat gtaaaccgtt tcagggagca aactgtcctg    4680
ctgtgacttt atattaatct ctggcttctg gctggtcaca gggtgtcaca tgtactataa    4740
ttagattttg gaagtgtgta cagggaggag gtggtgtaat taaggtaacc tatcagatgc    4800
ccaactgcat ccttcagaaa ggagctgaaa cgcccgccct cccagctttc acactgccct    4860
tcaagggcag aggcaccaga acctattctc cacaccagaa tcaatccggt gaggttgtta    4920
gctcgtggtg catatccggg gaaagccgga gggcacttag actttgactt tgcatttgta    4980
caaagtccca gatggggac tataagggag ttggatgcgg ggcacttaaa tagttccaac    5040
aagtgcacgg gggctctaga agctgatttg gccaaggtga gctacagcga gcaacaccct    5100
gcacctttct gcatcttcca ctcaaggatt ggcgcttcac accaggcagc tagctcctaa    5160
cacccacctc taagagcaag aagagaagga actgacagaa agtctaaccc agctgtccaa    5220
gtccaacccc cgggtattga gctctgccca cctaggactt agtgatcagg cctcagtggt    5280
caaaggaagc atgtgggttc gaatcccagt tcctcctcac ctgggctggg ttacttcagt    5340
caagttactc aacctcccag gccacccgcg cctcttcttc acctccctga ctacctcccc    5400
ttcccactgc ctctggtgtt ggctagagga tcactttggc cactgggatg atgaggagtg    5460
acatggctga gatctgggag tacctgctca ccgccatgtg ctcccctggt aaccctctca    5520
ccatatttgg aggagccaag gccaccaggc tggaggaagc aggaaaaggc cagtggccct    5580
gtcatccacc gagctctaca cccccgcagg agccattctg gccgaccctg aagcctgaat    5640
cagcccagcc tcaccccggc aaaatcaaca gtggttgttt gaagccactg aattttggga    5700
aggtggttaa cagcaattga agactgacat agttcctaag cctccatttc ctcatttcca    5760
gaatgaggac aatgaaagtc attccctgaa gggcagtcgc caggacaagg gaggggcacc    5820
ccagccctga gcctgggcaa acccagaagc ttttccaaat ttctaagttt taaaaacaac    5880
```

```
agttgggcat gtaagaaata caagctctac cttttttttt tttttgtcag agcaaataaa    5940
agaatggcag tgagcttgca tcatttctcc caccttttca tccccagtga ctgaaatgat    6000
agagcagcac tcacggcaca gggcaggttt tgtagccccc aaagctgaaa acggagggtg    6060
agagagggct ggtgccaggt gccccagaag cttatgtatc ctcctcaaca gcagctccca    6120
gccctgcaca cgttggagac accaaaagtt tttctccctc ctggtcttca gacaaagcgt    6180
gggaaaggca gggctaatta atggggcacc agaaggcatt tgccatagtc tccaaaaatc    6240
aaggaaaagg agaaagttgc tttctgaaaa aagccctcta ctttattctg tcaataagag    6300
ctaaattaca cacaagtgtg taaggagtgg aacgtagaag agagggagga gaggggcccg    6360
ccgtgcaccc ccccaggtgc agcccaggag cggagaggag ccgggttgga gccttcctga    6420
ctccagcgtc aggattcttc ctgctcctcc atgccagcca gcagagtgcc tgattcaggg    6480
ctgggagaaa cgcagcgcac ccaggatgaa gctggggctg cagggattac ctctgtggaa    6540
ttaagggaag ctgataagat tcattattac aagagcgatt ggtaaggtct gttatttggg    6600
cgtgtgactg gagcttctgt tggaatgaca tttttattca ttcaggaagc atttattaaa    6660
cactgaaaga atagctcgcg gaaacaggag agcgagcttc ccgatgttgg gtagatgaca    6720
cgcgagggag ggggcatgag tgcccacatg ttcgtgaagg aggcaggcct ggagctcgct    6780
ggaacagccc actcagggtc aggagatagg aaggagctta gcggaaccgt cgctgggatt    6840
taaaggggac acattggggc ccctgaaggc tgctgtggac tttcccagag aaagtcccag    6900
gtatctgtga aggtgatgtt ggtcaatctc agtgttaaag taaaaagaat caggtttctt    6960
gacgataaaa ataattgcca atcctgcgca ttttgtcagg tccaagtgaa ttagaattag    7020
ggtggccaaa tttagtaaat aacaacagag tgcccagtta aattgaatac tttagcagca    7080
tgtcccaaac atggccaggg tgtcgtattt tgtctggaaa ctctacttgc aagcaggagg    7140
caggaaagaa ttctggtggg acttgcattg cattgaacaa gagagcagca tgaccacagt    7200 gccggggggcc taacaggaat tccccattct ttgtcatatt caaagtcttt gaaggaattg    7260
aatacgtttt tggagtagag agtatttctg taatggactc ggggaaagaa agcggtttga    7320
acagtaagac tgcaaagtcc tgaaagaatc ctgaaagcac ctatctggaa gctttgctga    7380
gaggccccgt tcctctccgg ctctgtggga aactgaaggg tgtgttttga cccagaatcc    7440
gcagggagag ttgaatttta caaatcactt caggatgcag cgttgagacg gggattggag    7500
aattaatttt ttcctcctga gtaaagcagc tcttcctaaa gctgagaatc ttagcagaat    7560
gaataaacaa tggcagcagt ccggtaagca ctgtatgacc ctaatcattc tgaccattac    7620
cacgttttac aggattaaat aggagagaat ccacgtgaca tggtgctcct gagaacaaag    7680
ctaaagtatg ccaatcaaac catgtgccct ggaggaaaaa cttgggcact ctcttctagc    7740
agctaataaa aaataggaca acacttgaat tctacacgga gaactgtttc ttacatttag    7800
ttgatacagt aagaagtaac cagctacaga gaaatcacaa gactggatta gaccagaaca    7860
tttgtttatt aaaatgtaat ttaagtaatc agaaccttgt gaatgtttca aacggaaacc    7920
ctagaaaatc taagtttcta catgagatat tttctagtaa acacttccat tgccgtcaca    7980
cctataaagt gagtatgcac ctgtgtatga tcccataaga gcacttttaa agtaaaaaac    8040
cactataata tgaatatgat aatttccttt tgattttatg agaagcgctt gatcccaaaa    8100
ctgtatgaca gctcactctt ctacatagaa tcaatacttt attgcctata aatctaagat    8160
gcatataatt cttaagtctt cttttcaaac actgctaact gttaaagtat gtccattaaa    8220
```

-continued

```
actaaggaaa aatcattttt ataaaatatg gatgaaccta tgtctaaacg aagatattca   8280
taaagatagc acaaaaaaaa tgaataaaaa agaatattaa gaaatagctt tgaaacagaa   8340
gccttagaaa aaataaatgc ccatggtcaa acaagtttag gaaaaactct ttgtacaaaa   8400
tgttttcata ttaaaggcac tgagaagttc tgcaacaaag aatcatgttt aattgtattt   8460
aatccaccat ttccaaaatt tgaaatgaga aaacccact gctcatacct tttattaacc   8520
aaaagaatca tttcttagga aattctaatt tgagaaacaa tagatcgttt aaagagatct   8580
gtatttgcct ttcttaccaa actttcaaaa ggaaaggaag tgtattgaaa aaataatttg   8640
aggttttatt gactcatgct gtcagtcgaa gctttctgtc cattttttac gaattgggta   8700
tattccagcc tcctggtctc cagccttggg gagtgacctt cgtttccagg ggaaatacag   8760
gtgcccagaa cttccagcag ggggctctgt ccgctagcac tgactgtgaa ggactcaaag   8820
ctggttcaag gttaagatgg ctcaacaagt gacgagccag aaatgtcatc tggccactag   8880
gacgccgcat tatgaaagtg tgatcatggt tcaagaacgt tgccatgagg aaaatctgtg   8940
acggaattct attattaggt tttatcgtgt gtgcatttc aaacatagta agacagccca   9000
aaagggaaaa agtagaacaa gccaaaaagt attttaaaaa aataattatc caattatagg   9060
gctcctgttg aaaatattaa aagacttaaa agtttcccta catggttgac aactcaagta   9120
tgcccacttt ctatcaaaaa taatgcagaa aatacaaaat gcgagagaaa agttgaaaat   9180
aaatggaaat aaactacttc cattgaaacg acaaatataa ctcttcagaa ataatgtctg   9240
caaatgagag aagcacattg ttttgaggaa gctgtatttt gatacccta taatctggat    9300 tatttttct taaactcttt cttccatatc cccaacatcc accttctcca gccaaagcaa    9360
aaacgtgcta tttacaaatt aaattgtaaa gaatggaaaa tacttgattt aaggtgaaag    9420
ccgcaccact ttagccagaa gagttggaaa gaaataaagt ggccaagcaa gatcaaaggt    9480
gcaaaataga caatggacac acacagcttt ctgcccttcc tttattgcca gggatggtgg    9540
cttattgaag gcattagtat tcccactggg agagaaattg cagcatgaca ggtgcaagtg    9600
gctagtaaat tacggcattt gcaggagaga ggaacacttt attccctccc aagccttagg    9660
agagtgtata cataacacac ccctcatggg taagacaatc aaacgtggcc attctcttgt    9720
tgaaatgcca caactatctc tataaataaa gcaaatagac cacacactga ttttcatgta    9780
ctcatgtgtt gcttctgaga acatgatttg ttttgatctt actaaggatc aatgttatat    9840
aaaggtgtta tttccacata gccagtactt ttatgtactt ttcattttcc cggaatgggt    9900
acatgatgta cactgtaaag ttttggcagg aggcagaatt gcaggggata caatgtaatg    9960
tacgtaaatg ataataccaa gcatttgcgc ttagattggg tctcgtcttt tcattggaaa   10020
tgtgacttca gggaagagaa gctgaagaat gtccattcct ctgggcatac ctcatgcaag   10080
caaggccatg tggtgactat ttctagcagc taatgatgag gatctggaat aacagctctg   10140
actaaagggg agaggcagcc ccaagacgca ttcacagagc cacttgccac tcacccatcc   10200
ctagctgacc aagccccgcc tggagggctt tgagacaaaa tgtaattctc tggagtttat   10260
gtcactgtag tggaaactaa gagctaaaag caaacaattg ctccatagaa tcagaccagc   10320
atggaatttt cagagtatcc taaatatcag cccaacagaa gtgttggcaa actttgagaa   10380
cctctacagt aaaggacagg gaggcactgc tgaggactag atggggtggg ggagggcaga   10440
agaacagcag gagcctccag agctgtcctt aacccctggc ctgtgttctc aaaaccgatg   10500
cttggaagcc acctccatct ggggcttcta tcctcttgtc tcttagtgcc atgtaaaaat   10560
gaaatttctt cttatgccca taagttataa agctctatgt ggccatatga acttcaaagc   10620
```

-continued

```
atttaaattt cttatggatc ttatgtgatt aaatgtgtgg catcctgaat aatgaatatg   10680
agggtaacaa aagtggtact gttgagaaag acatttataa tggtctaaga tacagtatca   10740
aacacttagt ctggacaata agatcttgat aatatgtttc ttttttttaag ttttaaccaa   10800 gggtcaccaa tgacagaaaa atttataata aaccacttcc aaacaatgaa tatcttagat   10860
gaacaaagct gaaaaatttc agattccaat tcatcttttt acgattc                 10907
```

<210> SEQ ID NO 29
<211> LENGTH: 3962
<212> TYPE: DNA
<213> ORGANISM: Homo sapiens

<400> SEQUENCE: 29

```
atctcagaag caaggaaggc tctttggagc accagagcat agtctgggaa caaatgagtg     60
acaggctgaa aggtgttcca aagaatattt tatttcaagg ctgctttgca caaatgagga    120
agatgagacc tcacattccc aacgctaggc cactgcagaa cttcattcca acctaacact    180
cctgaccctc atcctccgcc tgcacatgag gtcatagaca aaaagaactt aggtaacctg    240
ccttgagtca caaacaagc aggtgaggaa tttaaacctg attctactca gacccatatt     300
cttgagccac ctgctcatta tatgcagaag aatgttcaga agttaacggt tggggggtat    360
atatgcactc agaaaattct agaaggaatg ccatccttga agcagccttt tctgactata    420
ctaaaagagc cctcccacct tgttgttatc tctttaacct gcttggttgt ctcatgacac    480
ttatgtaaca tatactggat ctatttattc tctagcttcc ctctagaatg aggaggagga    540
caatgcctag acattgttga tttgaaaaga acttaaaatg gtctttaaag tgcaaaaagg    600
taatctcccc cttcctggac agagcttctc tagagcagaa agttcttttg attgcaaaag    660
agaagaccat tggaaatctg cttagataaa cttgctttga gtcaaaagtg aatcattaat    720
gtttcaactg ctaatccact tagcgtccta ttcacccaga tggctttttga gcactcacat    780 catgcttttt gaaagataaa atttccagtc accagaattc aattgagaag acaattgatg    840
gtagatgaag agattgaagt ttctgagatg agtgaacaca cttatctggt caatgtgaaa    900
tgaatgaaac atttgaaatg aactgatatg agttggttgg gttttatccc tataataaac    960
tctttccctc caaaaaggat taggtcttct gcgaatagag ttataaccaa ctcatctctg   1020
tcctcaagcc atatggcctt gacctttctt agtgacgcct agtcactta aacctgttgg    1080 agatttttct tgtttgcgtc cttctgaagg gtgactttcc cagcttcagg agccatctaa   1140
aagccaggag caatgcatcc ctgcattccc tgaggctgct ctggctggct tcctccctct   1200
tccccgaaca gaaccaagct cctatagaaa attcataaat tcttggcagg aaagaaatcc   1260
tcccattgga aggaacagat gttgtacgag taactttgcc attatgctat tcctaatatc   1320
atagttttaa agtgtggggg gatgttaact tttttacaaa tgtcaacatg ttctgggcag   1380
tttttccatc tccatctgtg gcatgcacat accaatcctt ctgctgattt tccagggagt   1440
agttggaaat tggaaatata ttaaaaagtg aaggcggaaa ttcaacaata tgctaatgta   1500
tagtaatatg ctaaatgtca gaaatattct ttctcgtcgc ctagaacttg gatggtgtac   1560
agacttctaa caaagtaatt aactgtggga aaatcagtgg agctagctgg ggtcccctcc   1620
ctggggacag cgatgcccgc tgccagagcg cccgctggct gtggccgggc ccagaacacg   1680
cctgatcgct tttgggttca aagtcagaat cggggggtctg ggtgggatgg ggtgagtgg    1740 gaatcgctgc gcagaagcag aggaaggtga ccggggcgcgg ggcgaggaag cagcggagcc   1800
```

-continued

```
agatttaagt gcgccgccgg atcgtcccgc agtttccgct caggccaggt ttccctccgc      1860
caggtcgtac aaaccagtcc ccagatccgt gtggggcccg gaagcacccc agaacgttct      1920
tgtccgtgct caagtggagg tgaaatggga gcgcgtgggg cgcggctcgg gggagagccg      1980
atcacccagt cccagtgggc ccctgtgcgg cccccgcatc cgggaggccc gagggccgga      2040
gctagaggcg ggcgcagcgc ggtctgcagt gcccccacc ggacggcccg gcacaggacg       2100
gctgctggag ggagtcactg cctggcttcc agctcccggg gactgacttc taggcttccc      2160
tttggctaac gaatagacgg aggtcatgta accattttct acctttccgt agaaaaggaa      2220
cctgagcacc cagctggggt ccagtcatct atggctgtgg cctcagctgt ctcctttttg      2280
aacctaatat tctcattgca aaatgggagt aatcatatcc acccacagag tgagaaatga      2340 aggacccttq ttcggggcat cagctggcgg gtcccagacc acctgtactg tagcacgtag      2400
caggtgcagt gcataacttg accctactca caggcggcgg gtcctttttt gaaacacata      2460
gtaggtactc aatgtgtggg aggttttaac tgttgggatt cttcttcctt ctctcccctt      2520
gacacccctt ccacaaatgc ctgggatcct ttctgaattg gtgatgttag aaactttaag      2580
tgagaaaaaa aaaatacaga aaaccagtgt tcaatattta catggcctca ccagtcacag      2640
tgcacttctg tgtacattat atccatttaa ccattttcca gatgaacctc aaagaggtag      2700
agcgactttg gacacagtgc tcatctctac aacacagagt cttctctcaa ttcagcctta      2760
tctctatgct gttagacaaa gatgctgctt tcctaggtat caaagtggga cttttcaccg      2820
gccatctgag caagcgttct ttgagactct ttggaaatga taggacacaa actttattaa      2880
tacagaacat tgaacaaatt agagagtgtt tacatattat gacaaggcat gcagcagctg      2940
ttactttacc aaaactattc attatgggcc gtttgtttaa aggttgccct ggtggcttgg      3000
agacagtgcc ttttgctctc tgactcaagg aagcaaaaat aagttactat caggtgatga      3060
gcatacttag aagccaaact aaaaatgaga gggtttatca tcctctggcg taaagcagtc      3120
ggctccactt tcaaactggt aaatgccagg cagttgaaaa ccatgttatt gaatgtggct      3180
ttaattcata cttctgtgta gtattccact gtgtgaatag aaatcttatt tatttgttgg      3240
tcattatgct tatttgtagt tttttttttt tgaccattat ttacaattct gctatgaaca      3300
ttcttatatc tccagggctt tatctaggta gatctcaaga agtttattgc tggatggtaa      3360
gataatgaga tgtatcttgg cctggcattc agaggtatcc gtgacctggc ctaggatacc      3420
ccccacctgg ctcccacatc cctagccaag cactcccctg tgtgccattt ccggattcac      3480
cctgcacttc catgtctcta ggactttaac catgctctag tctcctgcct gtgcccctct      3540
tccctctcct cctcttttaa agtctggctc aaagcccctc ctccctgcct gatagtctct      3600
tctgtgcctt tgcactttgt gtttggggag gaaagatcca gttaagcccc ggctttatta      3660
tctcctggca ttgtgactct agagtgttta atctctctga cctcaggtcc acatgccaca      3720
tgtagaaggg aaatgctgca acttattgta ctgaggctgg gcttactttt tttttagcat      3780
ccctcaatta ataaaatgag gtgtcacact gtggttaaga tcatatgctt tgggattaga      3840
tcatcctggg cttgaggatt aaatgagaca acgtatataa atgatttagc actgcctgcc      3900
cacagaaaat ttccagtaat ttctggctgt tattatactc ataccttct acaggagtca       3960 ct                                                                     3962
```

<210> SEQ ID NO 30
<211> LENGTH: 1533
<212> TYPE: DNA
<213> ORGANISM: Homo sapiens -continued

```
<400> SEQUENCE: 30
tgaaggttaa gtgtaaaaat tattgaattg tgaaaattac gctgcatccc tctgggagaa      60
gcatttgcag cctaggaagg gggtggtgct cataataaaa actcgagaag ccaaaatcct     120
aggcctgatt ttcctttggt ttgaaatgca tactgttgca agggcaagta ttgacgaaat     180
cttgaacatt tctttcacag tctgttgctg catgcctgac cgagcaaatc ctgcttaatt     240
cctctgctcc ctagaggaac tcaggaccac ctggaaaaag tgaatgatcg attaatgatg     300
aattggccaa cttgccaata acgataaatt gctttgttca tccccaagga tgccacctgt     360
gcctagagac aaaggatggg aactcttcaa ttaacataga tgagctttca gacctatact     420
gcacaatgac aacatctcgt ttttgaccaa cttaaaatgt ttcacaagcc ttatgatcag     480
atatttatat ttgcagaaga aatacaatgg agcagtcaaa attgttacag caggcttctt     540
tttttatttg ggtggatgtg agtgtcgtgg atgaacatgc aattttaatg tgtataaaac     600
tctctgaaga aaaccactag aagatccact aggaatctgc agccccttga gaaaataaaa     660
tctgcacatg aaacaacaaa ataaatacaa acgacagtca acaaggacaa attaccaaac     720
agtcactttt tatttagtat ttttgaaatc atggaatgaa tttatgtttc aagatataca     780
agaactttaa aatgctcctt aaatataaaa tcatttctaa gccattagta acaagtagta     840
agttagccag attatagaat ttgaagtatc ctgggagttg acagattgag actctgagtt     900
catagtagtc ccctttagtc agtgactcat ataaactgat atttatccag taactacact     960
ggctgcagac aagctgaggc tatcaggttt agcatgttat gaaaaactct taattataca    1020
aacttctcag tggaaagtga tctctagatt tagttttgtt tttgtatttt gtttgaatgg    1080
attagagcaa tcttagcttt ctctgtgcct tgggtgcatt ttgtttaata cttcccagtt    1140
tacctactag gatttttgta tgttaatata tatggaaaca ctttgaaata aaacaaaaga    1200
tattattagc taaggacttt tattatacaa cctcataaaa taatttggaa aatgaattaa    1260
gattccatgc agagtcaagt agctgactgg cgtttggaag tatgtgggaa atattttttg    1320
tagatatacg tttgtataaa tgaaaaactg agcatcttta aagagataca tcactaaaaa    1380
catattatta aaaagaagac agttattctg tatacagcct aatgttgtct ttttatgatc    1440
gtatttgaat ttgcattcag gcatctgatg ctgcttgggg caagaactat gattagttat    1500
aacccatctt tggtgcctgg gacagcgtct gac                                 1533

<210> SEQ ID NO 31
<211> LENGTH: 77
<212> TYPE: DNA
<213> ORGANISM: Homo sapiens

<400> SEQUENCE: 31
gtggctgctg tgtcacattt gtgttattag gtggcagaga gaagagaggc tatgtctatg      60
ctcagtgttc tgcccca                                                     77

<210> SEQ ID NO 32
<211> LENGTH: 298
<212> TYPE: DNA
<213> ORGANISM: Homo sapiens

<400> SEQUENCE: 32
aaagaagaga taagacaagc aagtacatag tttatttgga ggtgatattc aaaaactgga      60
gtagggaaaa gtaacacaaa aaaggaggaa atgccaggac gcggtgtgtt tcctaagcag     120
```

-continued

```
cagggcctca gctcctggga acatgacaga atgcccccgt ctgaagaact aaggctgggt      180
catttgcccc tggccccaat ccctactggt tgaggggtgc tcctgggatg ttaggctaca      240
cctgcacaaa ggtgagcttc tttcagcttt ggagaaagcc caggagcaga aagtgaag       298

<210> SEQ ID NO 33
<211> LENGTH: 598
<212> TYPE: DNA
<213> ORGANISM: Homo sapiens

<400> SEQUENCE: 33
agagactttg gtccattgaa tgtggtggaa gtgaccttgt gctagttctg agtgagccca       60
aaaagaatgc agtccttgca gtctctctct ctctctctct cccaccctct gctccccacc      120
ttcccccacc cccctggacc cacccccgcc cctcctcccc atgatcactt taagtcacaa      180
acatggtctc aactcaaatt taaaatgtcc agtcaagcta ttaatccaaa ctcccaattg      240
gatctatgtc ctgtccttct ctggacctcc tcccctcccc cacaagtggg ggctgtggag      300
atagtaaggg gaggggaagg gtctcacttg agctgccgcc atcctgctgg cttccagctg      360
acagtgtcac agatgtccca cagatggcca tctgcagggc tccctcactc ttgaccctgg      420
gggggatgca cttctccttc tggaggtccc ttgcaagtcc ttccttcagg aatctccaac      480
tccagcttct ttccaccctc caggaggccc tagggaacaa gacacccctg cccccacccc      540
agcccacaac gaatccccaa acccttccat gtccctgccc tggcatctgg aggggcag       598

<210> SEQ ID NO 34
<211> LENGTH: 5448
<212> TYPE: DNA
<213> ORGANISM: Homo sapiens

<400> SEQUENCE: 34
cgtggagacc gagagcagca tcagcagaca ccagcactgc ccgttcctcc tgcaagatgt       60
ggagggagaa aagacagccg ctgagctcca gccccagga aggctggaat cagtgatttc      120
cttatatgat ggacaaggag actgaggctc agagaggtgg agcgatgtcc caaagtccca      180
agctgcactg agctcctaga tgctgtgacc caccctgcac gcctgacacg gaccgacttg      240
aatgcccagg agtggacctg cggggccata agggatacat acaacgtaac tgatgatacc      300
caattcactg gaatctaaaa atgaagtttc ccaaagcaca cttctcatct aatgactgga      360
aatagactcg tgttaaggtt gttgatttgc acctatttct cctgggaaat tcaagaaggg      420
ctctcagttt gcagcttgtc cctgaactca ggcagatgaa gaacagggag ggtctcaggc      480
ctgggagctg aagtgggggc caaatggtcc cctgtgggtg tgggagggat ggggcaggaa      540
gccaagcaag acattttacc tcctgccaga cagtgttttt agggcttaag tgatttcctt      600
ccattcaatg ttaagttgta gaaatagcca agaggaagct tcgtgtcata cccaagctga      660
tctaaattgt ttaccaccgt tcagtgtaat ctgtgagatt gggatgtgtg aagactgggg      720
atcttatgtc ccaactctta cagaactgga ctaaattaat aggctgtcca ttttcccata      780
atctacccaa tgtccctgat aactcaatat ccaaaagcat tctccatact gtctcaagca      840
gctggaaggg cacaaaaatc tgtggaaatc atctaaaact tggtttctga agaagttacc      900
aagaattagt gcatgtcatt ctagacctca gtttattcac tacatgggta caatgcctcc      960
cttgtgtcta caggaggtag ttagagcttg catatcatct gattaatgtg cagaaaaagt     1020
agatttaact agctaactag aatagaattt actagaataa ctaaagagat agctgccttt     1080
gggataacca agagaaaata atgactgttt agcccacaac taccttccaa ggaggacttt     1140
```

```
tgttctgctg agcatcttga tgtgtttatg caaagaaggc tgagacaaca ttggttcaac      1200
ataagagaaa atgatggatt tgaaaatctg acaatccaag aggaaaagaa aaaggaggga      1260
gaatgtatca gacaccttgt gccctgcaac atctgtccag atcccctcca tcttgtcatt      1320
tatgtgcagg gtggctgtct tccactgcca gcacctgcat cccttcacct gagcgctttc      1380
tctggccctg gagcctgctc tgcccacaag cacagtagat gtatttttct cccttcctct      1440
tccagatgca ctgtgcgtaa tttataaggc atctcagaag atggtcacac aatgcttgca      1500
gctattgcct cttatgggct cttcctccta ccctcccttt ccttttcact tctgctctct      1560
aagatcacac tccctacata gaggcacaca agacttgcct cagatgctac tatctgaata      1620
acccaggatg agacagggga gcttatctct cagcttctga cctattcatg catctaacag      1680
agtatctaag gcaattgtcc cttcctgctc actatcttca gtcagcatga tgtcaccagt      1740
ataagggacc agcaggatag tggcatgttc ttatggacta tattataaca aagagctgtt      1800
atgatactcc tggggcaaaa cagtgaaata tactactgta tctgccatgt aaaagtgaac      1860 tggtttttctt ccttgtgatt ccacttgcca ggtcactctg catcccacca ccaaaggcta     1920
tgttggtata ttccagtaaa gataccgtat ttgcatggca gctgcaatgg atgctaccat      1980
ctggccaagt ttatggaaat ccactatcat ctgccactat caatttggct ttcgcagggg      2040
ccttaccata ccctcatcat ttaagtcatg ataggggttc taacccctgc aatactttct      2100
gagaggtgat ttgcttctga tctactgcct tgaagtggag gaaaagtttc aaggacttcc      2160
acttgacttt tcctacacaa gtcaagttgc taatgtaagg gttctgccag aagctaagac      2220
tatctatgta tttgagatca ggccgggtgg tttcctacaa ccagtaatca gttaaggaaa      2280
gaacccagtt gcttcacaca tgagcctgtg tgatatgtca gtgctaatga gctgttgctg      2340
cattgcagcc ttctcaaggg tggccgcaaa ggactcctcc cagggggtag aactatgagt      2400
ggggcactgg tcaaactctt tgaaagagag agaagtagta ttatgtagat gcctgagcag      2460
tgggccttcg atgttggcca gaggcctgaa agacaagatt ggatgatctg ggacaggaga      2520
tctagggaag cataatgtag attgacctac agaaatgagc agtctttgta tctcaatgct      2580
cacgagaaac catccaccac agaggagatt caacagccag gatcctgtgg atgtcagcca      2640
gtctctctcc ttgcccagaa gcatgggccc catccctcta aagcagatat agctgctgac      2700
attgatgaat gcccagcctg ccagctgaaa agactgacac ggagccctct atggcacccc      2760
tccgagaggc cagccaaccc tttggtgata agttgattga gtatgttttc ctcttcagca      2820
tcagtacaat ggaaatgggt ttgccctccc tgaccaaata cttgggtctg gaaaccaagg      2880
agtagtggtg gaattcagtc cttttcctct cccagtgatc cactgaaact aagctctggt      2940
ggggtagggt gctagtgttc agcagaactc ctccaaaaga acaataaggc cactaacttg      3000
aagttgtgac cactaggtca ccttgagctc ctcatgccag tgggcaagca ggcaaaaaaa      3060
gagtgactgc ataagtgggg ctattgagcc ctgatggcca ccgggagcca cagtagcagc      3120
tactttatgg ggcagagaag atatatttac aaagggaatg tcctggtgta tttctggtac      3180
atgcatatcc tgtaatgata gcaaatgggc acatgagcaa tcaaggcagc tgagaggtca      3240 gaccccttaaa ggataaaggt ctaggtcacc tcactaggct agcaagccag atcatccaaa     3300
gtatggactg agaataaagg aaatcagact gggtggggga ggaggatat ggcactagct       3360 acagctgagg gtttggcttg tttcactctc ctgcttctca gagatctaag ttggttatga      3420
tcttgaaagg gattctgact actggactcg taccctctt cttagaaaat aaggagaaca       3480
```

```
tcatattctt tcaaaattga aggtcctata tgatagcata cacatctcta accatttcaa    3540
attctctgaa tttcctgcct ccaagtggtc attcattcca gccacagcca ttgctgcaga    3600
gatcaactca ccatccaatc aattacgggt aaaactggca gtgccttcat ttttgataac    3660
tctcacctca tacttaggga cttcattaat cctgagacat gagatgctgt agggttcatt    3720
tagtgcccac acataagcaa cttggaaatg cgaaggaaat aatatgtggc cagctttgaa    3780
caatgagaga tggaaaccag tggatgacta tttctccctc cctatcacac atcagccctg    3840
agcagcagct tctcaaaaaa acacaaggag gacagacctg ttatttgctc ttacttcttc    3900
cctgcttctt ttcccctcc aagtttgccc gacacacgaa tgctataaaa atggactttt     3960
gtggtatcaa ctgagacatt aatacaacgt cttggtcaat agaacagaac aagcacacat    4020
tgatgagtta taaccagaac ttagaaacaa gagctcagca tcagaggtga acataagaag    4080
ataagcttct gggaatgtgc ttaaatattg aaaatggctg tgggcttcca aaaaccacag    4140 aatagggga gatagaggcc attcccaagg gacaaagaag tccccatcca acatctgaca     4200
aatgagcaat ataaagtatc caaaatcaga caacaggggt ttaaatccag agactgttct    4260
ttaccagctg gaatatccag agatcttcaa gcctagctcc actcatgccc agagagaaga    4320
aggggattgc ccagggccac tgtcaatcca atgtcctgac tcctatccaa tgctcttttc    4380
tctgctcagt ttccccacat tcggggtcaa gaccactaca aataagaact ggaaatgcat    4440
atccatgttt atcatgtgtc tcaagtctct gcatgctctg ctaagcactg ccctagaggg    4500
tgtcactcca ccaaacaaca ttggtcagcc acggttgact ggttttttta cctgtggccc    4560
gcctgcatca gaatcatttt gtggaaagca tgttaaaagt acagatttct agtctctaca    4620
caatcaaatc agaatgtcta tagcgggctc gagaattgca attaagaagc tccctggtct    4680
tcttatgcac ggccattgac ctaaagtcac acttcggcac ctgttcctga attctatctt    4740
ggaatttctt gcatgggggt agccccaggt atttaatact gtctccacga tgatgcattt    4800
gaacttttta gctcagacaa actgccaaga cctctcttag atggattttc ccatttgccc    4860
acccttggaa aagcaagaaa aaaatgtatt ctgttgagtt aaggccttta ggatccaaga    4920
aagcagccaa gagctagaag ggaccttgta cctgatccca agcccaatag aggctctgct    4980
gtacaaattt atttaataaa gaaataagac aactaaggaa tcttctaggt accatttgac    5040
cacagcctgt caaagagttt gtgggcaaaa cgccacacgt ttgggctgct tgccttccat    5100
tctacccagc tccctcatca gtgcacagac aatgactgcc gcttccacag tactgtaaag    5160
aagatggggc aaatgtaaaa acactacatt taactgctat ttttgtctca aggatgaggg    5220
ttgataaatg tgtccttgag ataagccaga gacggggaca aaaatctgtc caaagagata    5280
gatgttccca aatggcaggg ccacacctta ctcttgagag tggccagtga cagactttct    5340
ctgttcccct ttatctgcct cactgcctcc tgcccataac tgttagaaac agctctgctg    5400
gacatgactg tgaagtggtc actcggagct gccacaggtt gtggcttc              5448
```

<210> SEQ ID NO 35
<211> LENGTH: 6087
<212> TYPE: DNA
<213> ORGANISM: Homo sapiens

<400> SEQUENCE: 35

```
cctctctagt tacctcaaca ttcctcataa ataatatttg acagaaaaaa aataactcat      60
agtacagcta taaaaaaaat cttcaaatat gcacatctaa tgtttgctac atgatttcat     120
catccaataa agggagaaaa atgccttaac atatcaatta ccagtatctg ccttgatcaa     180
```

-continued

```
aatagccaga tagttaccaa aatcttaatc tcacatagag ttacgtggat aagtaaagta      240
atgacagtat ttaacaccac cacaaatgaa atttccatat tatcaacaaa catcaattga      300
ggaatcactc tattagacta gaatattgtg ctatagtgac acaggtacca accacaaaag      360
cctagccagc cactttttta ctccactctg gaaagtctaa agactgaaga gtagaatcgt      420
cctttagaat gaaggagact gagaattaaa gtcagcagag caggatttga attgtggtac      480
aagccgtctg gtcagacagg ccttgaaatc atttaatatc ctgagccctt aattttctca      540
cttaaaacag aaacaaaata tctcttcttt atttcaagag gttgggatgc ttgaatggaa      600
ccataggaaa gaattttatg aaatattatg tgaatatgaa gctgaaacga actgaagtcc      660
tgtgtcacat tcaaacgttc ttcactctga ctctatttaa tggtatgatt caataaattg      720
taggttcatc ttaatctcct caaaatactc ttggcctttg caaagtgggg gaaggaatta      780
gtaactaaaa tagcaagaga agcttgctgt cagttagtct cctggaaaag tactatactg      840
aagattcaat aagcaatact gtaacttact aagatatatg tgcagataaa atgattgctt      900
agctggagaa ctcaagagaa tcagctgaaa aactattaca aatagtgaaa gaatccagca      960
tggggcccag gtaagaaatt atggaaaaat caatactatt cttacatttc cacaaccaga     1020
agacataata gaaggaatca ttctattcac aaagagggca aaaagataaa aaattccaag     1080
agacaaactt aacagtaatt tttttaaaga ctgaagcaaa ttgaattatg tttttcattt     1140
taaagacttg gcatcttaag atgttgattc tttcagagct attttataaa tactctattg     1200
tgaatcacat ccccaaaatt attagtagga ttttcaaatt aaacaagttc ctacgtaaat     1260
ctaaaaaagc aataagagcc aggaaaaagc atctaggaa aaataagatg aatgaggaag      1320
gactgataat accaattaaa aattggagag gagaaggaac aaagagaggg agggaaggag     1380
ggaaaggaga aaaaagaaa ccctaccttt tatataaatg agcaattata aatggaataa       1440
atgaacaact aacaagtagc ttttaatctt aaattaagca caattttaat aaaataggaa     1500
atataaaatc tactaaaatc cttaatataa tccctggcac atagaggcat atttgttgaa     1560
taaatagtaa gtagtagaga tatttggtaa attgtctttt ggagtcctaa tgccatgaga     1620
tttagacatt atgctaatat gtgttttta aaggttaatt agtattattt ttaactcaat      1680
tttgaaaagc tgaaattata ggaatcagga ccaaaagttt caattcaaaa gtaacgaaaa     1740
aaggaaataa attttatatt tttaagtaaa tatagcaaaa atttctaatt gttctcctgt     1800
gcttggtcat acaaaatccc caatcattgt agcattataa ttatagcagc aaaactaaat     1860
atccatcaat ggaggacaga ttcgaacaaa tcctggtaca tttatgcaat ggaataccat     1920
ttagttattt taaaaaataa agtagatcct agcacttgat ttgtttcttc caaaatatta     1980
tgaagcataa acaatgtctc aacttggact gtctctttt ttgtgtctct cttggttaag     2040
ctacgagctt agagaggtca ggaactacac taaccccagt gtcagaacac aataagaaga     2100
gtcaataaac tgaggtgaac tgaaactttg gaccagttca ctgaacttta gtacctattg     2160
tgctattctt tagcaaattg ggtaacagat aatatggaag gatttaaaat gctgaaacta     2220
aaccactaaa ataaaatact agattacttc tcttgagtat ggagaaaatg agccttgctt     2280
ttaagaagct taccacatta gcaaaagtct ggaaatacaa agcacactca aaattaataa     2340
agttaagatt ttcacgctgc catttgtgca ggctttatct gacttctacc tgttattttt     2400
ttattctcta attctatatt gatttctgtg atgatggagg tgaagagcct gtcactggca     2460
acatagcacc atcctcgttt agagtaaata aaactattta aagcaaattg gaaactgaat     2520
```

-continued

```
gacagaaagt gccacagatg gaccacactg ggaacaggag tggaatgccg cgttgttcat    2580
catccccacc atccaagaat gaagaaatgt ttccccttaa cttgagtcat tattgctcat    2640
ttcctctttc ttttcatgtc ttcttttctc tttggagatg tctctagaat ggaaatacat    2700
ggaactcatc caattgacac ttaactgtaa cctctatgat acaaagttac ttcgtttacc    2760
ataaagctta agcgccccaa tgcagctctt tattaaagtc atgataattc agaaacttaa    2820
ataaaagtat tgctaaaagc atcatgaatg gcaaaagtct gaggacttct ttcagggtga    2880
aaggaccaaa ggttaacact ttgctgccta ccttagaaaa ttgcttattc ttttaaagac    2940
caagtattcc tttgtcctgt tcaatccagg aagacatcag aggagaatga aagaagaaag    3000
gtttatgaga accgagcagt gctcagacaa gaactctacc cactgaagtc aactgggtaa    3060
tttacattac ctatgcagta gtaggtctac ccagccttgc tctaaatgtg tacaatctcc    3120
caaactgatg tatgacctat aattgatctt acctcctgct ttccctataa ccactattca    3180
ttgctccgag cctggaagat cagatattca aatttaccag ctcaggctcc atgttcctac    3240
cggaactctt gacctggtta caggaaggaa aaatagtgac acactttca ctgcctaaat    3300 gtttcagtct ttctgatttg agagcccact gaaatccatt atcttggtta agcttaaaaa    3360
aaaaaaaaaa aaaaaaaaag aagaagatac ctgtggctgg gaatagcggg gtatactggc    3420
tcaagatggg agaaataatt ggtaaaatat atatcttcag tttctttctg tattttctg    3480 ctcttttacc cttttttttcc ctttccaccc ctcacaccct atgcttctgt caatgactgc    3540
aaagatacca caattggtaa agttatttct gttcccttct cctttcatt cgtcaggtag    3600 tggcaaaggt ttaatccaag ttagtgtaga ctaaccaact tatctaagtg ctctgatatt    3660
tactgagtag tgctctgtac tagatgcagt gaaagcgaag aggaggacct tcatccttgc    3720
ctgcaagaag tctacactcc aaaggggggga aacaagcatg ccaactaaaa caagagatag    3780
gaaacagagg gaaaagcaac taaatgccaa tgaggagata gtttcactaa tccctaccag    3840
gaaattatac tacagaaaga acacttagga agaccaaagt gcaaattaag tttcactgga    3900
tgtcatgcaa ggaatcctca agctcaaaga gcatctctcc tctcaagttt ttgcacaggg    3960
tggggaattg cacagtacaa atgcttacaa ttccaatcac gtctactctg tgttatgttt    4020
ccacctgtgg tgactctatt ttgagaacag aacttatttt gccaaaaatg gtacaaacga    4080
agctgcaaat tgactagggt tgcacaaaca agctaagcat ccaggtctat aaacattaaa    4140
ggagtagata tctgactggt aagttacccc tctttccttt tttttgttat ccagggaatt    4200
aagcaagttc agagaaggta attacccaat taaacattct ccctgatgca tggaaaggac    4260
aacacgcagg aatgcagaag gagacaagtg ccaagaggcc cttgctataa ataattgctt    4320
ttcccacgtc cttgtcacct cttcctaaaa ttagaattag cttcctggcc tgaaggctaa    4380
acctcactcc cacaccctcc tttctcacaa agcaatattc cctaatgcaa taaggtggtg    4440
ggatttcaac aacagcaaga gtttaggagt caggtaactc tttgctcaac cctgcttttc    4500
atttcaagct ttattaatct gtgcaccaag cttatctgaa aaatgggatg aggatgatga    4560
tggtaacagc tagtaatcgt aaaacaagca ctgtgcaagt gctttacatg cattatttat    4620
gtaatgggca gtattcatga ttattactag caattgagtc ctcctttaca gatgaagaaa    4680
ctgaaattct agaggagtta tgccaactct tgaccctttc tactactata ataataactg    4740
ctaaacaagg attgaaaggg ttaacattaa catatatgga cacaccaatt aatgctattg    4800
tcatcgcttt tgatgttgct gagcatgata ctgtttttgt tgcttttctc tctccccaga    4860
tactagcagt tctaagatca aataagcaca gaccatccac ccatatactg gcaagtgtaa    4920
```

-continued

```
accaatgtct gggaacattt ttgagcacca aataacaaag ctgatattag atctttcatt      4980
attaaaatat ttctgatgaa tgagagagga agagaaaaag aaatgggatt cagtactaac      5040
taaaatgatc ccccatgcct aagtttttaa aaattcagaa taacaaatga aaggtacact      5100
gttcttacat gtgtcactta gatttcttaa aataaaatta tgtatcatat gctaattttt      5160
gactattcaa actgcacttt gcttcattct tatcttttaa ttcactttc attgtaatga      5220 aataactgta atacatgttt aaacctctaa cacgctaaaa tgccaatcag ttaaacacaa      5280
tagcaagcat ttggcataca cctggagact ttcctaaata aaataaaatt attattacat      5340
ttcatcactt cctttcttat tgccaactaa tgtccccgtg tctgaaaggg tcattttcaa      5400
ctacacatct atttataata gtgtgttcat tgtcttcctt cctctggtgc attatctatg      5460
accttgacca tttcaggatg gataaaatgg tgccataaac atatgtttat gaagctccag      5520
acatcttgta agagatttcg tggttattaa aagcagcaaa gagtgacaag gacagttcta      5580
tactataata tgcctgtcaa gagaaaaatg tcacccttac cataaagtac ccagaggcat      5640
aattaagaag tggcaaagga atgatttcct gggcacagta ataacagggc tgagatgaaa      5700
tccagcagca atggaagctg cctctccaat gtgcctgagt ggagcccgtc cacaccaagg      5760
gtccagggca tagtcatgct cccacgtcca aaatgtaaca tcaaggaatg cccaggacag      5820
ccacactcag aagaggtggc aacaagaatt tctgggagga tgtttctgac tttcctaatt      5880
gcatcattat gaacctcctg ggcaccaact aagaacatta aagaaattga aacttcacag      5940
ttcctaatgc tccatacccca taaacacaga tccatacagt ccccacagaa ctataaataa      6000
atcctgcctg aaggtctcct tcctgttcac gtttctccat aaaacttggt agtatctctt      6060
tccttttatc taacttttat ccttgtg                                          6087
```

```
<210> SEQ ID NO 36
<211> LENGTH: 2007
<212> TYPE: DNA
<213> ORGANISM: Homo sapiens

<400> SEQUENCE: 36
```

```
ggaaggattt gcggacgcac gctcttgaac gtgcgtgttc tcagaactct gatatgtgtg        60
tctcggcagc tgacaccacg tgccacatct atctttgcag actgccccat ccagcttagt       120
gaacagctga gccagaactt ttgcaaacat ctgccgtggt tgagttgggg atggaaaact       180
gcggagcctg atggttctgt ggagatggac caacaatggc accacaggta agaagggtta       240
tcttcttcct ggcagaaggt ggcaggctga tgctgtcgtc gttcctgtgt gtctgacaaa       300
tcacaaatat gtcagatcgt cacagctgag tcaaggattt ccatgagccc tgctggggtc       360
agcttgcagc gccaggcacc agtgtgactc gcctgtggaa gccggggctg ctcagtgggg       420
ctgagaggag ggggagagag aggcccatca acaaacagtg caaacgccgc agctgccacc       480
accgagttcc agtccctatg agacgtttta tctttcactc aagaggactg aggctcagga       540
ggtttgaatc caggtcattc tgacccagga gttcagactt tttcccagcc cagcctttcc       600
actcgaccaa ttagcacagt caggtgccaa agactttgct tgcgggatcc atttgaaatg       660
gttttttagg caaaggagac tagatgaacg tggaggagag ggaaagtata ggcgcgaact       720
acagaacagg cttattccag tgcactccaa acccaggcgt ggtgttcttc cttctcgctt       780
actggtatca cctgttgtcc tctgggcacc tgaagctcag catttcccag gttgcttttc       840
cctgcatagc cctggcaagg ctactctgtc ctcactttac cccagccaca tttcccatgt       900
```

-continued

```
ctttgggatt tccttgagac tgatctgccc aagcctcctt gggggatggg atgatttcag      960
gattttgaga gaaaataaac atggagctgt gatttaggaa aactgtaatc aagcagctgt     1020
tgggaagacc caaagtgggg aagaaagatc atattatatt attcgtgctg gctaaggaca     1080
gctgccataa aatatacaca tatattttat gtgggagaca cgtgctgcat gctttcgtct     1140
tgtccgtgca cagacatact tggattgagt aaagggagtt acaaaaggac caaaaattgc     1200
tgaatcattt caaagtgctt gacagttgtg taaagacctt ttggtttttgt ccagtgaaaa     1260 ttatttttta attcaatcta aagacttcag agcctttaag atgcaatgat gggtttatca     1320
aaatactgtt catgctattc gtttcttagc ttagaagtct ctataaatta gcaccagttt     1380
tccaaatgca ttttttatcaa atcctatgat cctaggctgg tctaggtacc atcccccaat     1440
cttaccttgt gtgtttctgt tttaagaccc tctcccatgc tggcatgcct ttgcttttgg     1500
ctctctcttt ttaaagcctg cccaaaccta agcaatgtca gggcatgtcc ctttcttcct     1560
catgaggcca tttcttactg cttacgcaga aactgatcta ctttctttac attccagcaa     1620
atttgttgtg cctgtccctc ttcgtttagg tatttctaaa actagactca gttacttcac     1680
gtgtgaagtg ggaagcagta ttttctcaca gggtttttgtg tggtcactta gtaagggctg     1740
gcagccacag gcttgttgag gacagtgggg gatgttactt tttctcagag tcttcatagt     1800
aacttgtcaa ggacatcact cactgtactg caagtgttca tcatggccag cactcaggaa     1860
ctttcagaat attttgagtg gagttttgtc ctgttttagt tgcctgttgg gatccctgag     1920
tataaaaata agtgtgtgcc tgctcccagc attgacgagc ttcatgaacc ttgaaaatgg     1980
aaactttatt tctctgtagg atgtgag                                         2007
```

<210> SEQ ID NO 37
<211> LENGTH: 16213
<212> TYPE: DNA
<213> ORGANISM: Homo sapiens

<400> SEQUENCE: 37

```
ctctggatgt gtccgggcag caggtagcgc tgagcacaag gggcaggaga ggcgggacca       60
ggccagagga gggggactca gcctgccatt gggccagggg cctcgatgac aggagcgatg      120
agcagtttcg tgtcacctaa tatagtcata cggaaaaaaa aaaaaagccc tgcccagctt      180
ttttaaaggg gccacgacgc atttggaagg gtctcctgct cctgcagtgc gtttgctccc      240
tgtgagcctg aaaagcctac cagaggcatg cagagtcagg cctctgggca gggctggatg      300
ggtgtgggtt tgaagaaata ttcctcgcac ccaaaccagc atgggagaga gaaggatggg      360
gtgggaagcg ggggaggaga gtgatttgag gaaggcttta ttactgaagt gggatgaggg      420
agagtctgaa taggaagaga agcctggagg acagggctgc tttggggata gcagcagggc      480
gagattctgg acaattcggg ggtttggttt ggcttggcct acagggtcag tcatgccgca      540
ggctctgggt gcttctgggc cgaaagtaag ggcaaggtga gtgatggtgg ggtaggagtt      600
gctgcctcct acagacaact ccaggggggcc cagtaccctc ccaggaaaa ggaatcccag      660 ctggtaagct cagcttccca ggagacacct gtcttgtgga gtgcccacct tgtttcccct      720
ggatcccacc tccctccttc ccgtgccctc ccaggccctc atcagggtcc tagcccaggt      780
ttagctcgct cctccaggat ttctctgggc ctctacttcg tggggcagcg gctcggtcag      840
gcgcgtgggg gaacattttt agcccagggt cagtagagta ggaaatctgc cagagtttca      900
ggagcccaga tcctgcccgg gtgcatttct ctggtctga tgaaagcttg gggtctccca      960
gacactgcag agaggagttt tattttgctt acaattcagg aggggcaggc agagcgggcc     1020
```

-continued

```
caggttaagc cttctagagc tggggatgac aggatttgtc agtggaaaag cgttggcttc      1080
tcacgcggag tgcgggttgg caagaggcgc ttggagtaga ataaaggcgg cgcagggcca      1140
aaaactacct aaagacacag ctcccgaggc gcgcccaagg tgcggaggaa acgctccatg      1200 tatgggagaca aaatagtgtc tgtccagaac gtacatcttg ggtgctcaaa cccgacagcc      1260
gtctgagacg cagtgaagtc agcattggcc tgatttggga cttttcctgt ccctcatcaa      1320
agccacactc ccaggacctg gggcctccat gctgggggag aggtgagccc cgccccagga      1380
ggcgcgcaac gcccgcttct aggcgccagc cgtcagtaac aggcctgggc gccacgccga      1440
aatcacgccc cagggactac tgggggtctg gaattgttag tctgccttgc ggcccttcct      1500
cgcctggact tttggccacg ttaccgttat ggctgtaaat taacctagct tgggggcccg      1560
ccttgcttga agattgtttt gtgtcgttgg agaggatgcc tatcgccgag gcggtgacgt      1620
ctggcaaacg agccacatcc gattcaatta aatgtctcgc tgaaaagagc tcggaacgag      1680
ggtcctggga gcgctgttaa gtgaatctgc tggccaggcg gctcgcgatg acagtttgaa      1740
agattagtgt gagcggacgc ctgaaatatt accgtttaat gggggacatc gaggctacat      1800
ccgggatccc tgttttttagt tttttttttga gagctctgga gaaagaacat tgcccttgca      1860
aatcaaggtg gcaaggattt atttcctttt tcgggtaagg gggcttccag aactgtcagt      1920
cctgtgggtc aggtgttaca aaaagggaag aaaactctcc ctatttgaac aagatcagtg      1980
actgttacac ctctatgctc tttgtgaatc ggctcttggc ttcctcttgg gagaggagat      2040
ggggcaaaaa cggacaaata tgcaaaatag aattggggcg acccatgctg gtctccttag      2100
aggaaagtcc agagccattt gcagcttttc ttcagtcctc actgtttccg agtgagttaa      2160
aaaaaaaata gaaattgcaa tagttggggg tgggtgggag gaaacttgat tctctgcccc      2220
aacagggaca catcttttttt cccaagggcc gctgacccaa cctggccgcc tctctgaaac      2280
aaacagcctt cagccgaaag gcagagagag acaaaaggag agagaagaga tcgaaaattc      2340
tgtgtatttc cttgactttt aaagagttgg tgctttaaga taatccaaat tccagggtgg      2400
ctcgagcgca ttctccgtga ataaattatt attaattgaa aagcgatcgg cgcagccgga      2460
gcggcccccc tttcgtgcaa tcagccgcaa aaggtatata tgattaattg aaagataagc      2520
tggaactatc accgggaatg tcattaatgc gctggggaga cgtccattgg agacaggcgg      2580
cgttatccgc ggctttatct tcaacaacgc ctcgctctcg gcccgcgcgg gggaaacaga      2640
tgggagtttc tgtctgggac gctcgcccca tgtttatatt ttgggaagaa tcgcaactcg      2700
tgggagtccc cggctggccc cctgataaat gaacattagc acttttttcgg actactgtat      2760 caacaaaggg gctgcggcgc tgcaataatt ggcgagaaag caaacagagg gccgagagcg      2820
cgactctgct cttcgtccgg ctgatggatg agcagcgcgc cggactcccg gcctggcccc      2880
tgcttccttc ctgcgggggg cgaagggccg ccgagctccg gaacaggcgg cctccgcggc      2940
ttcaggtgct cagctgttca gtgcccacgg cgctctcacg gatctcgtca cggatcctct      3000
tatccgactg caggcctagg agaatgaggt tcagagagga gtaagttgct cagggtcact      3060
ggaggaaagc aagacccccca ccatcacccc ccacccgca gccagggggag aggaccaggc      3120 tgttggattt gagaatagac aagggcataa agtgagaaag agaggggagg agaggaattt      3180
aacatgcgtt cacctcgctc tcccactttt cctttctttt gataacactt tatcgagata      3240
taattcgcat accatactcc acagacaatt ttagaacatt ttcaccccaa aaacctttag      3300
ccatcaactc caatcccccc ttcccagccc taggcactgc taatctattt tctgcccta      3360
```

-continued

```
tagatttgcc tgttctggac atttcataca aatggaatca tacaatatgt ggctgtttgt   3420
gtctcgcagc gttcacttaa cataatgttt gttcgtccat gctgtagcac tatcagcatg   3480
gctgaacaat attccattgt atgtctatgc caccttcgtc cattcatcac ttggtaaaca   3540
tttgggtatt tccacatttt gctattatga atactctacc ttacagtctg agaaagcttc   3600
cccctcctcc cctattggca tctgagtctc acagggtggt ttaatgttcc gctgttctgt   3660
cttaaaactc ttcataagtt tttaagcaga gtctccacat ttctattttg cgctgagccc   3720
acaaactatg tagtcaatcc tgctttctgg gctgtctggc agagcactgg aatactaact   3780
ctctattgcc tagctgggtt ttggctcccc tccccagtgc tagagctagg acagacagaa   3840
agtctccaag ctgctttaag agcgaaactt gctcagccat aggaagggct agagcccaca   3900
gaaggaaaga gcagatccac atggctaggt gtgtgtgtgt gtgtgtgtgg ctggagaggc   3960
cgtagctttc acccagctgc caaggactcc acagcttggt cactgttgga ttcttggcct   4020
gattttctcc atcccttcac ctacattgag tggatccact ttattgaggt ctaatgtacc   4080
tagaacaaaa gtgtacagtt cgatgagtct tgacacttgg atgtgcaccc ccataactaa   4140
tcaagataca aaaacattta acctcaaaaa tgcttccttc tccccttctc agcccaagct   4200
gccactggtt ttaaaaatat atcctcttag agtttttttt gcaaatttaa aacatattat   4260
aggatgtata tatattttc tttacgtttc acaaactcct ttgcattttg tccttgtcag   4320
ttttgttttg ttgtcagttt tcttaggctc tggggagtat gtttcccaac ccgaatttgt   4380
cctggattag tggatatgat cgattccgag gatccgaggg agtcgctttc agacttccgg   4440
tgtcctttcg cttaatttcg tcctcttttc ttctctgggc tgggtggtgg ctgccacatc   4500
ccaccccttc tgccccgacg gctgcaaacc gcttcagcca aaacgggcgg agaggcggag   4560
agatcgagac gctgtcagtt cctcggagtc ccgtcgctgg aggtcacagc tgggaaaatc   4620
aggtgacatt cgagttggac aacgactcag ggttgtcctg gggctctgcc cggcgggttg   4680
aagcccgggg aagcgacttt ggaagaacct tcggcttggc ggttcaggtt tgggaaaaga   4740
gagctggcgg ccgcctgttt ttgtgcccgc ggaccagccg ggccgacggc agcgctgcgg   4800
ggggtcgtca gaggtgaaga gtcgcaccta ccaccgggtg gccgaaaccc ggccgcagct   4860
ccgggagccc ccagccctgt gctgctgcgg ccggctcagt gctgaattga tgctggaaac   4920
ggctggccag cgggcctagg gtcgccgcct ttccctcctc gcctcttcct tcttccgggg   4980
tcgtgccctc caacctgctg tgcgttaccg cagccaagtt tccaccgccc ggcggagcgc   5040
attgtgaaca gcagctgaca aattgtcaca ccaaaaaaac ccaagtctcg tataattcgg   5100
aagcggtgtc tgtggagagc ctcccgggt ggcacggggg acccggaggc caacccgcct   5160
ttcgcggagg gcgttctgcg cgcaaattgg cgaaatgcgg gacgagcgcg ctagagggtc   5220
gtgttgacac atcccatact ttaagtgtac acatgacagt tgcagacatt caagccctta   5280
aaaggagcag tgggtgcccc tcgccgcgtc cctgccgcac tctagctgct ctgggaacac   5340
acacgtttgt gcactctaag cggccgaatt gtgcgtcgcc tgtgcagacc ctccgttgtg   5400
tggccttgtg tctttaggca gggaacatct tttgtctctc cgcaagaagc tttcctccag   5460
gaaagataaa gtaatcgata gggtctttta aatagctccg cgtttcctgt cgggagagga   5520
gtatcagcgc gcgcaccaaa tctgctctgg tatgtcacct tatctctcgt ccccgctgtt   5580
gtccccaaac gccgcctgtc aaaggagacg ccacccgcat taggacctag actggggccc   5640
ttccgctcgg ggtcaggcgc agcgccctcg gctccgccgc ccttaggggt ccgggagggt   5700
ggagagaagg ggcgggagcc aggatgaggg tcctagaacc cgaggctggt aggagagcaa   5760
```

-continued

```
actctcactg aaaccgggcg catgtgggct tccttttaac cacgaaaata gggaacaggc    5820
tagtagcgaa tcctcctttg tccgcgtgga ggaaaatcag gtttattctt cagagagggc    5880
attggacttt aggaagtgcc tgccgggtcc aagtttacct tccggactgc gacgaggtga    5940
ggtttcgcca ccgtcctgcc tctgtcctct ccccaacctg cgtcagctct gactccggcg    6000
gggccggagt gcagggcaga ggggaaagaa ggtgccgcca aggctggtcc ttcagtccgc    6060
taggccctgg gccccttcag acgtccaagc gctgttatgc aaatctcctc attttttttc    6120
tgtattcagt cggctgtatc cagtttttta aaaataaaaa taaaccctct cagctgcctt    6180
ccatgcacaa accctcaatg acctctataa acatagtcag cctctttcca gcctcacaat    6240
tacccacggg gtcttgagaa gctgtaggga aatacctctt ggcttcaaca cagacttgct    6300
cccttccgat tgcccgggat cactctggat tactccaact gctgacggag gaccacccac    6360
caaaacacag cctggccttg ggaaagcgtg ggttctcatt tatcagggtt tatttatcca    6420
aaataaaaat tactgtagaa aagtaaagga gggaaaaaca tcttcctccc ttaggaggct    6480
tttttgactc tttaggcctt cctattccct gtggtccttt gacattatct cagccttaag    6540
tgaatttgat tattatcagt aaccaaaggt tgctggtgga actagctgtg ttttcttatg    6600
atggttcatt tgcaccgtgt gctatgctgg aaccagaaga acatgaactg gacagcccaa    6660
tgcttgaatg cccttgtctc tggcctcttt ggttactctg gtgactagtt actcagtcct    6720
gggtagccct ggagatggct gcctctccca ctcaggcggg gccctcaagc agggctttgt    6780
tagaaggagc cctgggagag tttcttttct tctaacaaga ggtgggagat gaggaagtga    6840
caggcatcgc cctctcccta gatgtgacag tcatcgccta gggacccagg ctctttttcct    6900 aacagaagct gtactgcccg ttcattagaa gtgggagagg ggaggtggga ccaggtggca    6960
ctgctctggt ctagtgacat acttctgacc ttgaggttgt agcactgcta gtctacatct    7020
agggtatctg tggctgggat attttcttgt ctggactacc aggcctgcca acatggtaaa    7080
atcttgaaga cagaatccag ggctggttct gcttgttttt ctcatagtta ctaaagcttt    7140
gtctatttta atgacccatt aaatgggacc ctttgctgaa ttcattatca tgcatccctt    7200
tttaatgggt cagatcttac agagcaatgc aaccgagtgt aaattctttg agtttggaaa    7260
catgcacagt gtaaagaagg agagctgagg ccttgattgc tgctgttcag gaagagaaca    7320
tgagtgaaat gtgggtataa ttttgaacaa tccttctgca atttgggaat tttcaaaaaa    7380
tctttacaaa atacaaggtg aaaatagcat aaaattagtt ttagttattt taatcagtgt    7440
tttaaacccg tttgtatttt tcttttata tcttaacaat tggggtatta tctgtttca    7500 tctttgatct ttgagatctt aggaacccctt tgtcatttta ttttgtgctg caaatatttt    7560
tgccattctc ccgtttgtct tttcaaaacg ttcattttag ttgaagacac ttgataatgt    7620
acgaaggggc cactcaaaca cggtggggtt ttgattccca gttgggactg gtcaagagca    7680
atgtcagggc cagctggccc ggtgggatt ccagaggaca gaggcctatc ccactctacc    7740
ttgggcttca gagactgggg aaacctggtt ccttgaagct tccatcctgg gccccaggct    7800
ggagggagtg ccactggcta ctcccaggga agaaggaaat tgagagcaaa tccaacagaa    7860
agaagtgagg aagacttgag tttgggctgg tgggtggagg ggacttgggg aggatccaga    7920
agaaaggaga acatcagcca gggaaatctg atgggcagac tcaggctctg gagtagggct    7980
gcaacctact gcatggaatt gtttaatctc cctgaacctc agtgttctta tctgtcaaat    8040
gggataatac ttgtactttg tcaaaagatt gtgagaacta aagaagataa cattgtaaat    8100
```

-continued

```
tcacaagatg aggatctgaa gtcagtccaa gactgtctca aacaaatgct ggaatccagc      8160
ctccagcttc acccttttcct tctgtccgac tggtgggcat tggggtagcc ccctgaggct      8220
gggggaaggg cagtgaatga ggagtctcat ttgtgggagg ccctacccca taggagctct      8280
ttgtgtcagc agagggtttg cagaggttga tttcattctt gaccactcgt ggctaactca      8340
gggacaatcg aactgctgtg acctgagggg aaagacccca gatactgtta ccggctcctt      8400
cgggaaacct ccactctctt cccccctcct ttctgtgact aatttctgaa atctctgtaa      8460
ctgagaaggc attggatgag gtttcccact ctgggagggc cctgggtgcc agactggggc      8520 aaggggggggc tgaggctcct gtgcagtcac atgccatctc tcaagagcag gagcgcaggc      8580
ctccagattg ggtggcagca gctgtggggt attgggataa cctcactgat gactgggtag      8640
atagggctct cttgtgttag cagagtccag aaaacagtgt gctccctgat gaaaaggcca      8700
cggtcactgt cttctgggct ctgcctggct ctgacagttc tcagctgctc cataaatctt      8760
ccatcagttc catctggcca aaaagatgtc atcaccgttt tctcctagcg acgaaaagta      8820
aaaggtcatt aactcctctc tgcctgttca aaccaaagaa gatgatcttc agtttttcag      8880
tggaaggggt tgggttgttt atgtaagtaa tagtttatat ttatatgttg acatgaggat      8940
aaggaggatg attgtttttgg gtattattaa cactctgggc acccacatac ttaaaacaca      9000
gaacattaca atctggaagt taaaaggaac attagtgctt atccagttgt tttcgagttt      9060
ttttttaaag caatggaaca ctcatagcaa atgatatgtt tatgcaaaat cccaatacat      9120
caaacagaag gactgagcgt agcagaggcc ccggctcccc ctgacctctg gtggctcctg      9180
tttaacttct ctgtttttag tacctgtgct ggagacggtg gatatttcca actgctgagc      9240
cactttgctt ggactgtgtg gtctgccggg gatctggttc atcttgtttg caccgtgtgg      9300
atgctgtcag gggctgtcac ccctcctccc tcgaaggctg ggagcctgtt cttaccctct      9360
ggtctgatgc ttttccggca cacagggata gccttgggtt ttcatgttct tttctcattt      9420
cttttccccc ataattgcat ttcaggaagc gtcgggttag ttcttttttct ttagtttttg      9480 tgtctagagc agaccccagt gtgcagcagg aggatccctg gacttggtta aaagaaaacc      9540
tccaaacctt gacctccctg cagctggggc cccttcacac ttgttttggc ctttgtgaac      9600
tgcgcagaac cagggctgac cctgccgaac tgtggatgtg tggccaagac aggtcccagt      9660
gtcctgcccg ggctgtgcat gtgagggagg cggtgatgca acgtgatggc attgtgacag      9720
ggtgagggaa agattgctgg ctggggcttc aaggggtgat tagattacgg cggagttgcc      9780
tgtttggcgg agatggaaga cttggttctg ttcatttcat aggcagcgga tcccgcagtt      9840
tcagactggc cagagaaatc catttagtag taggcagaaa tgtggagctg agaggctcat      9900
tccacaatgc tcctgagctt ttgcttttta cttcttcact ttttttccctt ctctttgctt      9960 tttattgttt ttctgtatat atattttaca tagttgagat catatatgca attttgttct      10020
gattttctac ctaatttaaa attatacgca tttcctcata tcagcaaata ttctcttcaa      10080
atttgatttt gggagctgag gttcctgtgg tggcccaggg tggcatacaa cttcatggac      10140
cctctttgga caaggtctct attgctggtg agctgatggg actctgaggt gggcaagctg      10200
tccacccatt tgcagcttac aacttggggc tcagagattt gtgcggctta tgttttgctt      10260
tcactggatc tttatgatct tattagaagt tgagagcaca gtgactttca tctgtggttg      10320
actaggaaac atgtttaata aagtgacgtg aaactccaaa caaaaataac attattcata      10380
ataagcgttc tctaatcaga atcagagaac agcctctcag aaaccagtca agagtcctgt      10440 tcatcccccac tcctagattg catgtaggtg acacatgttt ctgtttcccc ttccttctgg      10500
```

-continued

```
tttgttctgg gcggttcctc tctccttttc ccacgtatag taacgccggt tctgtaagga    10560
atcacatatc ttgggtgctc acaggagaat tccttctgag gcccagctcc caccccttcct   10620 ctgggcacct tgcggctctg tcttagggtc ctcacgtcgt agctcagccc aagcggctcc    10680
agtgccggcc actctgtcgg ctctctgcgt ctgagagagg gtgcctcaga agggatctga    10740
gtgcccacag ccttcagaag tgcaactagg aagccaggtc actggtggct ggggatggct    10800
tgtccatcac tagcagccag acaatcgaat agcgccctag gacaggagga gcgcctgagc    10860
cttcacgcca tcccgccagc cctcatttct tgttggagca taatgactga ggacagcaaa    10920
gcccagtggc ttctcccaga tggctgcgag ctgccttctg gatcccaggg gtaactactc    10980
tgagtggcta gtgcctcaga actgaagtca gaaacctggg gttatggcca cagatcgacc    11040
accctggtgc tcagggccag agtaagacct gaccctccca aactagagga caataatata    11100
ctcatgatga taatacccag aggttaaaaa aacaaccaaa ccccgaactt agatgatccc    11160
atgtatatca tcacgtgtct caacaaagag cagggagacc aggttcttgc tggaagctca    11220
gaattttcat ggtgcctcta gaaaaatcat cccatcccag gccaagctgt gattagaggt    11280
gcttttcatc aggtctcttt cttccagttg ctctccgctc tccagctttg ttctggctta    11340
gactctcagc ccaggccacc caggggcagt ggccgctgaa gggggcagcc ccgcagctgc    11400
ttcctccaaa tgctctggga ttcaaggccg ggtgctgggt gattacaccg ctgttatctg    11460
ggattagcta ttttcactcc ctgtatttat atcatggaag ctgcagcgtg atgctgccag    11520
atgccaatgt gggcaaactt cttccttttg gacccacctg ctgttctgct gacacccggc    11580
aaggtggcag ttggtgggga ccagacctgc caaccccctcc tcccacttcc cacatgtcca    11640
gagcagtgaa ctgcgtcatt gtgagagact caggtcagca gcaacaggcg aaggctggaa    11700
cagacttggg ggcgggaggg gtggagggct ggcagcagtc cctgcagaag atgcctgtca    11760
cctccctaat cccctgaagt cttcaagtct aggaaccctc tcgcctgccc cactcctgct    11820 ccacccgac ccacgtgtat ctccctgttg cagtgaggcc agaaaaggcc aagtgcctga    11880
gagtcccaaa tgtaagtatt aaaaggcccct gctgcattta cttgctccat cttcgtttcc    11940
atctcgcctt ccatccctgc ttgtcagctt gtctttcagg aaatggacag gttttttttga  12000 aggtatgttc tatctcactg gggctgcata acttacctca gcaaacttct tagagagcag    12060
agactgtagg tgggatttgc ccccagcccc ggtgcattga gggaggcttc tcccacttgc    12120
ctaggaaggt tgcctgcagg ctcactccct ttccggcaaa aataggcaat gccaggtgtt    12180
atcacatcag gaggaggctt cagatgagcc ccagggattc tgcccagaaa aaaacaatat    12240
gtttggtgtg gccactggct tctcataccc ctgtggagct ctgtccgtct gggcttctct    12300
gccctcatct ctcagggcag aaatctcaag ggtgacaagt tagccctccc aggtatgttt    12360
aaaaatcacc cagccccgtc tatatgggag tgaaagtcac ctggggcaag ctgagcagag    12420
aggccagcca gtgaagtggc tacccgtggc ggtgagagta cttaactcag acttggaata    12480
aggcttcact ttccagaaac ttccacacat tcagatcact aagttcagat gagaaagcaa    12540 cccctttatct ctcataatct ttgacatgga gcccgctccc tgcagcccct gggagacaga    12600
tactcaatct gtgggaagtt ggcctggagc ctggctctgg ctgctgcgta gacaccattc    12660
cgtgatgaag gctggcacag gaggccctg ggcagggttc aggcttccag acaggcccac     12720
gtgggagtgt tttgaatcca acttgtttgc cgggttattc tcagtgcctg aatgtgctag    12780
aagcgaacag aagccaggat gaggcccaga agagcttgag ttaataaacc tggggaaaaa    12840
```

-continued

```
aatcaggaag tgttgtgaat acatgacatc agagagtgct ctgaatgcaa cttttcaatat   12900 atacttttat atctttttctc cttttcccac gttctgttaa cgtaagatga tagggaatca   12960
accaggttag ggaggcggca gggcccagct aaatgcctgc gtcctctctg ggctctagag   13020
aggtgctgag tggtgagggg gcctgggtgg acgctgggct tctcctcagc agggaaggag   13080
gcccagggca gaaatagacc tgggggagga tgcatgctgt atgagccaga tttggccaca   13140
tatattagga agacatttct aatcacaaat gtcttaatga aagaacaaaa tgcctcatgg   13200
agcaaggatg ccctttgcag tttaagtgga gattggaagt tctaggggtg ttggtatttt   13260
cagccagtgt cactttgagg gttagtaaat ttcctacctt tgctgtcagc tgtgtgaagt   13320
ggcatgcctt tgctttatct ctagaattgt tctttaagtg tcgcgagtag tttggttctg   13380
ttagtctagg ctgggagaag agaggagagg ggagccccct gggtaggttg aaatccaaag   13440
ctcaatgttg ccttcaagtg agaacatgta ggaactgcag ggtcgggaga tgggtctctg   13500
ccttggatgg ggcatgagtt tgggtgtagg attgagatct ttactggttc agagatggac   13560
ctggggcaat tagatgacga tcaccagata gttgactttc tcgattcatt ttcgattcag   13620 ttttttattcc attcagttta tttccttacg aagaagagga agaagaggga gagggagtaa   13680
aaactgctat tcgccagtct tttgctaggt ggtttacata catccatgct aaattttatg   13740
ataatactct tataactact gttttacaaa tgagaaaact gagactcgcg aggtcaagtt   13800
atttgcccaa agtcacccag ctgtcagatg caggaggtcc aaataaagtc tgttgggttc   13860
taatcctgac cattttgcta tagcaggctg atctccgatg aaactgtcag gacgatgcag   13920
atcccagccc aggttgattg gcaaatcttc ggtgactcca tggccctgct attctcaccg   13980
gagctctgcc tctcggcccc actggaagcc ctctatgtca gcgccagggc gctttacaag   14040
cacgcagtac ctcatgcatc ctggttcctc aaggcagccc tggacagtta aatggcgccc   14100
cctgtcctga ggctcagtca agtctcctgc cccagcacta aactgtctcc cttttaaaaa   14160
cattaggtta aaaaaccaag aacgtgaaga aaggaaaagc aaacaaaaaa tcttcccaat   14220
cccaatttcc agatagagag aatacattcc cacggcaaaa cagtcattca aacagcacag   14280
aaagcagaaa aaaaaagtaa actgctgggt ttccttcaag aattttctta agtaatgcat   14340
ctagttacac acatttagaa tccacaaagg ggtggcactc caggcgcgtc cagcacgttg   14400
cttttctccc gggatctttg caaaacccca ttctcgcaga gttgtctggt ttgaaggtgc   14460
cccattggtt gctccagttt cctagagcac tctcagccac gcccccgcca ccccagcggc   14520
gctgcaggaa ccagctgctt acccggcggc ctggctgtgc gcggatgctg cagactgctg   14580 ccccgtgtg gcctggtgcg ggggctcctc gcgcgtcccg gtaaaccaga acctcagccc   14640
atcaactcac tcgtggggtc tgaggaggag aatctttggt tctcaccgtc atggctcacc   14700
cagtggctga atcctgccgc atccaggcag ctgtggaaac tggttgaaac caggatggtc   14760
agctgctacc ctgtgtttgg gggactatgt gacagtgcct gctgtgtccc tattctggtg   14820
ctaaaaagca ggagctctct tatgctcaca tggaactgtt ggagtcagat aaacttggct   14880
ccaccactta tatgctgagt ctgttcatcc atcatccacc atccatctat tcgttcaccc   14940
tcccatccat ccattcatcc gtccgtccac tcatccaacc acctgtccat ctattcatcc   15000
accacccttc accttgagtg ctgagctcta tgactttgga taagtttgag cctcagtttc   15060
cacatctgca aattgaacat aatgacacct aaattagttg ttggaagact taacaaaata   15120
atgtaggtga aatacatggt acataggatg ctctgtaaat ggcatttata atcttgtaga   15180
agcttatgta ttagttaggg aggcctgacg taggtacatg caattggagt ataaaatatt   15240
```

```
gcaagactgt tgtgcacatg tgtgtgcttg cattgtgtgt agcctgtggg ctgaagcagt   15300
gcaaagtgag gggctagagt agtctttaag aaccaggagt gctagagaga agagggtgta   15360
ttcggacagg gactgctcaa gcaaaaatgc ctatcagcca tggaaccaaa caaaacaggt   15420
gggccctgtc cctgtctgag attaaaaaac aacgagagac tttagccaca gattgctaaa   15480
ttcacttagc tcaggagtcc actgtgaacc tagacagaat ttgctagatt gcttgcaggg   15540
gcgggttcaa agattctgta cttgctactt gccaatgatt attaagtgct ggattcctca   15600
catacctata aggtggaatt attacactca ttctcgagga agagactgag ggtcagagag   15660
gataaatgac ctgcccaggg ccacacagac ttttctccta tacctcctct acctttagct   15720
tcaggtaaga actacctgaa gctaattggg tcttccatgt tggcccgagc atctgctctt   15780
cccagggagg acataagtgg ccctcttcat ccagaatgct tgtcaggact ctctctcttt   15840
aaacggtaac cctgaccaca agcactgact tttcagtctc agagtttatt aagaaaggtg   15900
cacctgactc cagtttcata aaaacatact gcaaattcct ctttgtgcat ggaaataatt   15960
acttagttga ttgtgcatca aattatttat gggtacatag gggttgatat ttctctgatt   16020
ttaaaagttt gtgtcatgta ccgtaagtgg ctggcctgcg atgtctactg gtcaaagcgg   16080
gcagtctccc tctggaggaa caccagggat gcggggtgca cccaggctgt ggggtgcaaa   16140
ggcgggaggg gggaagtagc tgtgaggtag accctggctg cgtggggtgg gggccacttc   16200
ctttctacct ctc                                                       16213

<210> SEQ ID NO 38
<211> LENGTH: 2693
<212> TYPE: DNA
<213> ORGANISM: Homo sapiens

<400> SEQUENCE: 38
ctctttctca tcaggtctca cctcaaatgt cactcctccg agaagccctc tgatctctca      60
catcactcag tctcattttc atcacatccc ttatcattac ccaatatctt tctgttcatt     120
catgtacttc cccttgtgag aaggctcaga gcagcagcat ggtctggggt cccataatcc     180
tccaagtccg gatccatctc cagcggcttc cagtccagt ttctaggcac agcaccagcc      240
agcttcttga acgagtgttg gcatttcttt ctcagtggct ttgaaatcag acgtcagccc     300
ccaacctcgt gactcagccg gcagcgtgag aaggctggct tggggacaca aagtccttcg     360
atctttagag agatagcagc cctcctggga acggggccac agatgaaggc tgagcatgaa     420
gcctgggcac tggcctgcca ctggaagctg accctctgct ggaccatgcc aactttgaca     480
tttcccaaac taggcaatgg cccagctttt gaaagccagt atcgcctagc tatggaatcg     540
ccatgcagat agtgctggaa tgaaattaaa tttccctttt cagaacaaag acaaacacac     600
tcctctcacc catcctacga gagctgggcc gggagccctg cctccgtgcc aggattcaaa     660
gcccacgggc tctcctgctt gcttcagcag ttcctggcaa gtgcaacgga gttctcccgc     720
tttaaaatct aattgcctgc cacgcccgtg aatcccatct ccaaaggcaa gaaaaaaaaa     780
aattttaaaa aaaagttggt gggggtggga gggggggttc tcacacattc agcccagatg     840
agcccattta agcttttgac attatgcctt ttggggaggc cgattcaaaa taaaccagcc     900
cgagaagctc ctgttttaaa cagaaagatc cataaatgca gctctgtcag taatgagaaa     960
atggaaatca caagcaaaac cagaaaactc attcccccag aatcttaatg atctccagaa    1020
taattgtgct ggtctctcaa atcaaggagt ggacggtgac agccctgtga gggtcagatg    1080
```

-continued

```
ggttcatgtt tttctcattt ctaagcaatg tgcttgtctt aatcccttcc ctgtgcccag      1140
caaaaatgct ttctttgtct ccctcaaaca aatgcagctt ctcaacaggg aaatgagctt      1200
ccctgtcttg caaacagatt tcttatcata gactgatcca ctgtgggtga acttgcattt      1260
ctcttgcata agaaagcaat ttcctgaaga gagaaagggg ggaaaatcaa accgcttacc      1320
tctccttttt tccatattag catccttagc tgaagctcct gaagatatgg gaaagtttat      1380
ttcagaggat gaatatcaat ctttcagata gcagtgggtg tttaggctct aagaggcagc      1440
caggttttcc tgcatttgtt tacaagaagg aacaaattct ttgacaattt caaagtttct      1500
ccagacaaac tgctaccttc tgataaaatc taaagttcaa caatgacaaa caaattagaa      1560
aattctgcca ttatagcgga atataaattg gcaggttcat ttaggaggct aaaacaaag      1620 aatgagatct aaaataata aaaaataata atgagctttg ggattaagaa gcaccagtga      1680
tttggcagac agtaaccata gcacacagtc tggggggggcc tcagacctgt cttggccatt      1740
tcacttctct tgtaggttct ggctttcagc ttcgttgcac cagagagggt ggtgagccca      1800
gcacaccagc atgaggatca gcccttgggc tgggggtggg gtcagaaaaa gaggaaagaa      1860
ggagggagga gaagggaagg aagaaactac tgttttaccg ttggttattc aatttgaatg      1920
cttgttgtac cccactatgt gccagctgag gccagaggcc aggagaaaat ggtgagcaaa      1980
gcaggaaccc agctcagccc ttttggagct cctgggatga ctttaaccac gcctgcaaga      2040
agactttgtg agtgtgtgga tggatgtgac gcccttggag gtatgggggga gatgggggcct      2100 gggaagggga agagacagat tcctggggtc tccatggcat gggaagaaag gggggacatg      2160
agggatagca ttggcagtct ccctgggact ggtatggttt aaactcactg caaggccccc      2220
tctctccagc aggtttgagt tgctggtgaa ataagtgggt caagggaagt tacgatgttt      2280
gggagatgct ggcatctgct accaagagcc taccacctac agccaggcag tacctctgtg      2340
ctgcccatgt gctggctgcc caaggatgct caaggctcag cgagccctgg acactggcaa      2400
ggaggccagc actttcctgg gtcttggaag gcccagggag acagctaggg aagatgcctc      2460
agagggtggc atccaggcgt aggatagaac aacacccaca gcatttctgc agccaccaca      2520
gaagtgcaat attggtttct ttctggcttc tcttgaaaaa ctagaagatt ccatggccct      2580
tccctcttac catggcagtg cctttaagaa cttctgtccc caaggcccac ggcagtggcc      2640
tctgagggca accgtgactt aatttaaatc tggagtttta aacaacgtta agt            2693
```

```
<210> SEQ ID NO 39
<211> LENGTH: 1861
<212> TYPE: DNA
<213> ORGANISM: Homo sapiens

<400> SEQUENCE: 39
ttttatttgt agctggcctt atacttggtt gagatagggga gaaaattcta agtaacatct        60
caatgccagg tttctgaggt catctaaact ttaattgtcc atagacatat tgagaagcaa       120
agacttagga aagttgccag gattgctcct cgactagagt cagtcactta agtcagctga       180
cagtgttagg acaatgtttc caaacaatga gagaaataag tcaatatagg gagtttccta       240
aagcacagtt tattcaattt aaaaacgaag tttatatctt ttacttttg gaagttaaat       300 gtcctttatt ttatgacatg atgtgacagt gatgataaaa ttcttccttg gcaaaataaa       360
aataaaatga ttcctcctca tcttttctg gacatttagg gattattgtt tgcattcctc       420
tctttgttta caacaccctt cccctgacat ctcttgctct ctttggcatc ccaatggcat       480
ttactattct ccaaacaatt taaaattcaa ggtcatgctg gaattagtac ccagttacca       540
```

-continued

```
tgcatgcttt ctgtgataat taccctcagg ttttgtagga aaacagaccc ccagatgcat        600
tcacatatgc aaatatgcac tcagtaagca atgactaaga cagatgagtc ggcagggatt        660
atggagaaat ttccagttta tgtgcataat taccagaata actggtggtg gccgtgggaa        720
aggaatgggc cacttcagat gggggccggg acagctaagg aggaagtgat gtttgaactg        780
agatctgaat gaccaagggg agctgtccat gagactggtg gaagagtgtt ccaggcccag        840
agactgtgca aaggccctaa ggtaggcctt tgcaggata agagtgtgga gggagggaac        900
aaaatcacaa gtgtttactg gccttccgtc tgttgcactc tggggagggc tagtgtccct        960
atgcggggag ggcattagag aggccctgct tactcaggct agggattagg gcagagaagg       1020
ggaattctct agagacaaga ggtaggttgt agttgtcaag ggctggaagg aatggggaat       1080
gactggtaat ggatttcttt ttgggttgat gaaaatattc tggaattagc acaacttcat       1140
gaatatatta aaaccactga cttgtgtgtt tcaatgtgtg aattttatgg tgtgttaatt       1200
acatttaaat aaaagaaatg tgaacaaaga aggaatggtg aattttggag caatgctaag       1260
tgctgtcagg accagctgct ctccccaggt atcctgcctg cattcataaa cattttgtgt       1320
catatatttt cataattttc attttgtagt ggattatggt ccactgtgta ccacaattca       1380
caaagagata tctccaagtt ggtcatttag gaatgtttct tttttttgtta taggtgtcaa       1440 caagggcaat agagctcttt cactctgccg caaatcttgg ttttttcacaa accttctctg      1500 gaatttatat tcccacacta ctgtgaatat atagttaaat tgtttgctat ttattcttgg       1560 tgccttttc cttttacatg gtctccttca taatcttttc tcaactctgc cagctctctg        1620
cttacctacc tcacccacct catcatgaaa atcaagctct tctgacctca tctgtttcca       1680
ctgctggact tacagcactg tttttgtaatg tatttacccca cctggctcct ttgccagact     1740 gtgagcccc tgaggtcaca cacagtgtct tattaatttc tgactccctg ttgcctttgc        1800
ttgcagaagg aaggtgtaaa atatatgtta attggattta attgaattgc tgaggctgaa       1860
g                                                                        1861
```

<210> SEQ ID NO 40
<211> LENGTH: 2864
<212> TYPE: DNA
<213> ORGANISM: Homo sapiens

<400> SEQUENCE: 40

```
attagacaga tacaggcata aatacaaaca gatgaagaag agagtctatc ctaagcctta         60
caggatcagt acaaatcaaa agcgtcaaga atctggagtg ggaagagaat agtgaataac        120
gaagccctta tgaaaaaaaa aaaaacacag acaagaagtg caatttggaa gagaagggta        180
taacacgaca ggagtgtgag agggcaaagg cacagagaca aaacggtatg tcctcactgc        240
agggactttg cacttgctgt tcccttgact gagatgcttc cccctagata tgcatatagc        300
tcacccctca ctttctccag gtctttactc aacaccaccc tctcagtggc taccttatcc        360
agtcaatcct aaatttcata ttacctcttc cactttagat tttctcttca gtatttgtca        420
ctacctaatc tactttatat tttaattatt tatctttgtt attttttctt tcttccacta        480
gaatgtaaac tccctaaagc aggaaatttt gtttgtgttt ttactggatt cccaaaacct        540
agaacggtgc ctggcacaga gtaagtaccc agtaaatatt tgtgaaataa ataaatcaag        600
aggacaaagg gattgaagaa gagctattat taaaatatca gttgacagaa atagaaattt        660
tacatgggag aacagattca caaatttgga cagtatggag acaatttgga gagaagctag        720
```

-continued

```
aatgtcctgc cactcataaa taaaaggctc ctaggagaat ctggggtcac tttgtctacc      780
tctctcattt ctaggcaatt ccacacctaa gccatctcag acaaaacaag atattcagct      840
ttccattgca tgtttcttag agttgaggca aacatcacaa agctcaaatt tctagccttg      900
ccactccatt ttcaaaattt acatctttgt ggagctactg aactccctca gtgtttcagg      960
tgattgggcc aggatactat tggaaagcaa gggtggttta gtgttgctct gaactcaggg     1020
agaaacagct ccctgaaacc tacaagaggc cctggtgcat tggcattcac cctatggttg     1080
tgctcacaag cagaggaaat tctaagcagt tggagcctta aatgacaagt ctacctgttc     1140
gtgtgcccta tcctaaactc tacctgcatt catttctgca tctctcacct gtctatatag     1200
atgggaagga gaggtatata tatttcaaat attctatatg aaaaggaatc agattctagc     1260
cagctgtcac tccataccga aagccacaga gcattcacag gtgcagtatc cattgcaatg     1320
taagtgcact cctaccagca ggaagcatgc gatttagaaa agaaaatgtg taaaaggaaa     1380
tgagaaaaag aagtcagatg gggcagaaac gggagacatc aagtcaatca caaactgcac     1440
aaaatattca cttccttaat tacttgttga aagctgaatt tgttaagaaa catttactcc     1500
tacttagttt aagtgtgcta gaaccaacaa taagctgttg caccaactag caaaaacaag     1560
cttctgactg catgctctga ttgatgagtg aaaaacattc ctaattagca tttaaattca     1620
tgagtaaaat agtcaacaga ctgcaataaa aacaaaataa tttaaacaaa gcaaattacc     1680
ctcttttctt gactctctct ttaaataagg caggaagata actttctgtt tttaaattat     1740
ttttattgca ttttcacatt acatataata cttgcttttc cagaacatca cacagttcat     1800
atttacttta tagcaggaaa ggcatagata ataaggagcc aaagttcagc cacaagctag     1860
tacggaaact ccattaaaca acaacagctc tccaaatctc agtttctccc tgcagtgttt     1920
gcattgcaat tatggaagga aaactgcagg tcctctgata atagctcagg agagaacgct     1980
gcacacttcc tcctccccac cctcagaaga gcgtaggaga gtacagccaa ttcctgatta     2040
tgtgtggtaa ggaggaagga gaaggaagga caacatggac agcccccaaa ccacatttta     2100
tggctacaag cattgtctcc tttaccacag aacttttgcc agaactgaac attagaaacc     2160 aaactgggc ctgcctttcc cccctggctg ccagtccttt ttggtagagg aggttataag     2220
caagtaaagg gcccaaaagc ccaagggaga tggcagggag aatatagcag gaataatcca     2280
cagaaaccag aaaggcagct actcatttct gagggaatca agaattagct acattcttgc     2340
tctctaagca acaactgtca tgtgatcttg ttaaatactg aggtttgatc aatttctaaa     2400
aattattttg atttcccaaa acacatatgt ataatctgct ccatctcaat ggttaaaaat     2460
gtgtactcac caccctttagt catctgattc taatttagaa cacatttcct ggctttcaca     2520
accaaaacta ttcattgcac tgatcataac aattctccta aaacaggcaa taaaaggagc     2580
agaacttcct cctgtggcca gaaactttcc caaagcttag gccttccagc aattacagcc     2640
ttttcactgc agtaccttaa cctattgcta ataaagcctc tttggccagt cagagttgcc     2700
atctttagag acagagggca aaaacaacaa aaaaagtctc agagcggtca tttattcaaa     2760
ctgcccatcc gagaagcctc tattcttggt aaggaggaga ctacataaaa gtacacatca     2820
agagaattct gagaatttta tatcctgaat gattaagaat ggtg                      2864
```

<210> SEQ ID NO 41
<211> LENGTH: 4579
<212> TYPE: DNA
<213> ORGANISM: Homo sapiens
<400> SEQUENCE: 41

-continued

```
ctgcctttga gtcacccatc ccggtgaatg tttcagtggg gctgacccat catagggcac        60
ttttggtaga ggatgcctgt gtgaagttgg gaactggcaa ggcgcagagg atccgctggg       120
agatgacaag tccctgttca cactctccac agaaatttgg ttacttgttt aaactcttaa       180
gtaactgaac taaatggatt ctattacaca atcataattg cttcaaatta aacaataaac       240
gttttactgt ttttctacac cctaggtatt ataaagaaag tgtaaagcat gccagtttaa       300
gcgcctggag ctaaggttcc ttttggggag ttgtcaaata tgcagatgcg agtggtggtt       360 gttttttccct attgtggaag tgtgacaacc caggactgtg gccacaaaga gatggaggag      420
aacgaggagc gttaagaatt ggcccaaagt ctggtcttta ttttgccttc ataatttttt       480
ccaaaatgaa caaatgccct gctatagaaa tgccaagcat tttccaaatg acatttcagg       540
tggagtccat tctgcatttc tgaaaaagta cttccgaact tcagagcaga tgtcagcatt       600
ttggaccctc ctgacatgat taaaggtgca ggtggcagct ggcgctgggg agggacaggg       660
cgggagctgg cacaggcagg aggcaacacg gttcatcatt ctcccgttaa ggaagttggg       720
gaaagaagca taaacttgaa aacacacatt tttacttaaa attaggtgtg agcattataa       780
cacaaatgat cccaggctgc cactgctgat gaccctgagc ccatgcccaa atctggatta       840
tgtccaggga tctcagatca ttctctctgg attctgggtc tcagacagag tgtgcagtag       900
cagtctgtca gggttgggaa gaccaagggg cccagcccct ggtgtctctg ctcacatttt       960
caccctggct gcctccatgg gctgtcctat ccctgacag tgctaccggc agggtcctgc      1020
ctggaacaag ggggtagatc ccatttcagg agaaacgtgg cctctcccct aattgtaggg      1080
gggaagcaga aaggcaacca caggcctttt gttggccaac agaaaggctg aagtttggtt      1140
ctccctggtt gcatttcaaa gaagtctaaa aaaaaaggtg gccccagtct catctcaggc      1200
ctgggctcaa agtgagttga ctcactcacc ctcccctgtc tactcagcca tgccatcgga      1260
gcctcccctc ttgaccttga ctcgagctgt catttagaac ttatcatcag cacatagcta      1320
gacttttgat tcctccagtc acatattata tatatttttt atttgaaaag tgcttttca      1380 ggtatgactt ggaagagaaa tttattgcag gaaagttagg aaaccttcca actttaaaca      1440
cacgtgcaca cacacacaca cacatcatga acttttttcaa taatagatga ttaaagaagt      1500
ctgtggagag ttcttaatga gctccttcta tgttgtctag gagcaatgat cgttaaaatg      1560
atcgggggga ttgaattata aatttccagg gtgtcccaca cggggctggg gctgatggcc      1620
ttcatccggc ttgttaaaac cagtagttgt gtaagactct gactagttaa tttgaaagct      1680
cccctttggg atcgatatat ttaatttcaa gaccttaatt catgagaatt tattcgaaac      1740
aggcacgggg catgagcaga gcaaaaagtg tccaccaggc ccgctgcacc aacgctgctc      1800
ttggctgggc gcgtcatggc tacgagaaag cgcatgacca cttccctgtt tggtttggtt      1860
tgtgttgtgt gtcagggcgc aggggtttct gctttcactc aagttaattt atttcctttt      1920
ccttggtaat tgtgaaaaaa caaaataaaa cctcctgtga gcctttgaac ttctggaaaa      1980 gcccttttgct gtgaaccgct gactctgaga aagctttgag cgggctggaa accatttttc      2040 tgcaacctttt tctttcctgg ggtatgtctg ggtgcacacg gctccccaca aggcaaaggc      2100
tgtccctgga tggttggcaa aatgcgccac accagagtgg gtttgtgttg gcaggaggca      2160
tgagaaaacc tgctgatggc aggggaggac ggcgacacct gggaacaaat cctccttacc      2220
tctaattaca aagaggaaaa agtcactgaa aaaaaaagta aatgtcttaa tatgtcatat      2280
ataatccaaa gctaccaccc cacttcaggg ggatttaaag tggtgatttg gttccaggta      2340
```

-continued

```
tgcgtcctgc caacctgggt gggtgttccc ttacaaaaaa acaaatgatg gagagttttt          2400
actaggattg gtctgatcag ggtagacaca ctgccagtgt tcttggctct gactccatca          2460
gtggccccca tggatacccca gtctccttct ggggctcaaa tcctaatgcc tgtcacgttg          2520
gatgctgccc tagtgggatg ggcagactca ttctctcctc tctgggtctg cttgggccat          2580
ggaaggcatg caaagtcctg tgatgtgagg ccgattatgg ctcagaatct tccagacact          2640
aactctgcat ggctccccga gtgcagaata ccatatcttt agaatcctgt cttttgtttt          2700
tctacattag tacagttgca cagccctcag gagaaggtgg gaggtgagaa agctcttcca          2760
tggaagctgt gtgtactaca ggaggacctt gaggttaata aatgtcactc cacatcagca          2820
tggacctcta ggtaggagag atctaagtgg tcccttggcc ctctcatttc aatatctacg          2880
acatcacctt gaccaccccca gaactctcat cttctgaagt ctgccttgtc tgttgccata          2940
gctagctgtt gccataggct ggggctacac acacacacac acaatttatt tctcgtgatt          3000
ctggagcctg ggaagtccca atgaggcccc agcagattct gtgtctttgc tctctagtga          3060
cagccaccac cttcttgttg ggtccttaca tggtgtaaag gatgaggctc atgactcaat          3120
cccctcccaa aggctcccct tcctaatacc atcccttgg gggttgaatg tcagcatttg          3180
aagtttgggg agcattcaga ccatggtgcc ccatctgttt tctcatggga ctggcactgt          3240 ctgggactg tcatatcttt ctatggacca tgtcctgccc atttttttgt tgttccctca          3300
ccttctcctc tcaacctcat aagacctggt ccagtcttct gcatacccac ttctagaaag          3360
catttaaggt gattccaaga taaagaaaat agagtgagat gagagaaata attttcagat          3420
taaataaatt ctagttcttt cagatctgag aacctaaaag ttgatgccta caagatgcct          3480
tccacataga aatacacaca tgagaaggtc cagggtctgg cactgcacac ttggttatat          3540
ggagatgctt gtttttctcc agtttcatac atgcatcttt tttcactcgc tggattattt          3600
gcacttagag gaggtgtccc gagctacatt tgcatccatc ataaggcata ccaaaacggg          3660
cctacaggag gtgtgcaatc caacctttgg cctgatggaa gccctgcctt gaaactgaaa          3720
gttgcccaga aaggttagga aatgctataa tgttttcatt actcattccc ttgctgcatg          3780
cccttaagtc ttttagaatg tttgtattat tttatggaat atccaatttc tgcaccagtt          3840
agggatcaga ttacaagcta actctggtga gtttataaag aaagaattta atgggaagat          3900
gtgaggtgcc tgacagcatc tgtgggaggt gttgagagcc acactctgga aataagcagt          3960
aggggagcaa gttcactctg cagggacggt cccgttgtgg gtgtttattt ccataatcgg          4020
gtccttgtcg tagccatcag cactctctca accgtggtgg ggctcacccc ttcaagagtt          4080
aaacctgggg tttcagtcaa tgccttaaga agcaaactta gttttcctc tcacataaac          4140 tgtccaattc tattataggc agccacctca tcctagaatc cctgaatcct gcttctgtgg          4200
cagactcagc ccagtccccc acctgccctc aataagcact tcaatcctca ggtcataatt          4260
tagctagggc tttagattcc tcctcagcca gataacagtc cagctttccc ctggagttgg          4320
ttatgggcag cccactcaca gttagcaatg tctcttcgct agattgtaaa ctgtggagga          4380
gcttcgtctt attcattagt gtggggccat tggctagaat attgtgagca tgcaataggt          4440
atttgatcaa tgtgtgaata aatgatttga atagcattct gcacagaact atacttagga          4500
ttatttactg gaattctaac cccaggaact ggctgatggt gagaatatta aatgaaacca          4560
aacttcagca aggtggaag                                                       4579
```

```
<210> SEQ ID NO 42
<211> LENGTH: 2397
```

<212> TYPE: DNA
<213> ORGANISM: Homo sapiens

<400> SEQUENCE: 42

```
ctgggatgta ggtctgagct tttggtgctt ccatctctct gtcaccctca gacatattct      60
ccttccagtt cacagctcca tttttctcgcc tgcatttcta gctaagctct gagtcatcga     120
tctcaacctt taattcaagt ttgtgcctgg atctgaacca aaccatagat agatactcat     180
aaggttgtgc agatgagaat gtgtggttgt tctgcttttg atcagcagca ggctgagatt     240
gcttccagga taacgggagc caagtctatt ttcttaggtt acaatgaagg actcaagtcc     300
tgcctggagc tggctgagtg atgaactaaa ttggagaaat gtgccatgtg gctcgccgtg     360
ttgattgagt tcacttgagt cccctttttg cagccaagtg cattcgtaac ttccatagca     420
tggtactata aatctgctga ctatttctgt ggtggttact attccagttt gaagagaggg     480
gtgtggagaa acagtagtga aagcaggaaa aatttagttg tatgtgcaac acacataatt     540
gcaagatgtt tattattcca ttaggcagtg ctggtctaca gttaggagtg gtagaagagg     600
agaaaaggtc atgacaagga gaaccctact atttgccaga cgctaggccc tgccctgtga     660
gcctcttggc agcccaagtt gggaactact tatttatttt actgtttag gtgaagcttc      720 tggagaagaa actgtttgct cagagcccaa cattgaatgt gtcaaatttg gtgtttggac     780
tcagcagttc aatgtcttaa ctattaatta ttgcctttgc caagatgctc aataatgtat     840
gccttgccaa gtgattttga ggattaaatg caatgttgta ggtgaacact tagcttaata     900
agagcctcgt aagtaaggat ggctgctatt aatgtaaaaa taataataat gaggaggaga     960
aagtggagga gatggagaag aagaagaagt agggaggaaa agaaggggag gagtagaagt    1020
ggggaggagg agaaagagga gacaagttat tgccatcacc acaatacgtg ccagggctat    1080
cttgggcact ttacgtacat tatgtaattt aatgctcaca gcaagcctag ccaatactca    1140
cccgcccttt ctgcctctaa ttttttctgg tatgacgtag caaagtccgc ctgacacttg    1200
aatatttact tccacttcac gactcttcat cgtggtctgg gtgcgtagga agcttcagat    1260
ggcaagggag gtgctggcag ggactggcag caaatgagca aacgagatga gagggtggga    1320
cagagcctgc gtttttggct gccctaattt tagcttctga ttcacccaag gaaattttga    1380
gcagtgtccc catccagaaa ctgcgaatac taaggaaggt ctgaccagcg gctgaagata    1440
tcagtgaggg tgggaaagaa aaaagaagaa cgacaatgat acctttaata aggatctaat    1500
tttaaactaa ttaaagccaa ttggaatgga aggtattttt ctttaaggaa ttctagaaac    1560
tgatttcatg caattggcct tgccgcatac gttaattaga ctaaagaatg aagcgggtac    1620
tttaaatcaa aaagccttga gagatgtgag gaaggtggtg tgtgtctacc agggtcctgg    1680
aaacttccaa taatagaatt tatatccgat cctggtcaga cacacaaggg cacaaagtta    1740
gtaagtaaac catccctact actctatgct ttattaaccc aaagcacaga gcttctcact    1800
caaagaccaa gacagatccc catcctccaa aggtggtgga tagcaaggga caacgttttc    1860
cgacttcttg ccaggcccag gtctagctgg atttgaatct tcatgctaac cctctgaagt    1920 atttttacc ctcaatgtat aggtgagatt gaattattct gccaggtcat ttaattacaa     1980
gttggcagag tgcgaatcct aaattacgtt gatctgactc ccacatcctt gctgatctac    2040
cacgtcatgt ggccttctct ttcaattcca catcatgact agagctttct ccacctacac    2100
cggtctggct gctgggacct cccagggtac agagctgatt cacttcaacc ggcatccagg    2160
ggcgtgcctt ggaaagccat ggaggggtag taggaaattg ctcttttgtt aaatgcaact    2220
```

-continued

```
tgggtttatt tggaaagaaa aagaaaaaaa gaaaaaaaaa cgttctgaaa aagaatcaag   2280
ttgctccatg taatctgtaa attgaaatta gatggttgtc aataattctt actatatata   2340
taaaattcca tatatatgca tatatgtatt tgcttatata gatatatagt ttgggtt      2397

<210> SEQ ID NO 43
<211> LENGTH: 5727
<212> TYPE: DNA
<213> ORGANISM: Homo sapiens

<400> SEQUENCE: 43
ctcattctga ttttggggtc tgggtgggct tgagcatggg tgtctctggc tctggactct     60
ccaatagctg gcttgggctc agcttgtcac cacctctccc tgtggctccc gttctgggca    120
cagtgaaagg caggggtttg cagactggca agcacacgat caactgtcaa cctaggagct    180
gcaggcagtg ggaggaggga catcgggctc tagctttggc accgcgtgac cttgggcaag    240
tcacttcccc tctctgggtt tcaggctcct cttccgtcga aagggcaat gtctgcctcg     300 gtccttgaag atggcgtgaa cgtggccttt gaaaccagtg cagagccgct ggtaggaagc    360
ttcctgagga aggacagcaa aggggtttgg aatgagagct caaagtatca gcctgcgtac    420
aagatgccct cggggggagc cttgtgggcg gtcacactgg gccaggcccc tgctgaggcc    480
cagcactgca caggcacccg gagccctgcc cttctccctc aggcacccca gggcagtacc    540
gccctctggc ccagctgagg gccaggctcc cctggcttcc caagtggagg aggaggaaat    600
ggtgccagca ggccaccacc ctcgaggagg tggggtcttc tttggggctg tgggctagga    660
gtggacggaa gggctcagag gccaagctca gatgttccct atggctgagg tccctgacaa    720
ggatcctcaa acagggagaa tgctggtacc cttccagttt gggcctgggt gtcacttacc    780
tgggacactt gtcacatccc ctttaaatct ctgtccttgc ctggctctgg gattctgaag    840
agcagtaggg tttccagggt tctctcctga agctcgcagt ggcttcaggg taaaacagct    900
ggtaaaaagc catgggtctc tcccttaaac ccaacccagc agatgtctac tctggaggcc    960
cgaaaacacc ttaaactcat cgcacagaaa accgccaggc aataattcaa tgttccagcg   1020
atgtcctttg tgacccattc atttcagttg atttggttct attgcgatcc cttttttttca  1080 tttgttcatt cattcattca ttcattcatt cattcattcc agacacatta cagccacaga   1140
ggtgaggagg attcaggtcc tgcccgcaga gacagttgca catacagcca gccacacaag   1200
gggcaagaag tagtctgtgc tgggccacag gggcagctct caggaggctc tcgcccacgc   1260
tgtgctacat tcatcacaaa tctgacagta tgcaacaaaa agcaggccac aaaataatgg   1320
atggtattaa cagcagagtc aagatgtggg aaaatggaat aaaatgagct ctccaggtac   1380
catctatttt tagaaaatgg agaagcttga tggataaatg aagtaggcca gacagggaga   1440
atacaaatag cagcagctcc tgtgggaagc ctgcccacat catccgaagt tggtacgatt   1500 cccatttttac agaagaaacc atgacaggaa tgatgtggct ggcttacagt cacagagctg   1560
aactcagtct gtctcactcc agtttctgct tggaaaagat tcctcatttc caccagcttc   1620
cttttaatca aggcagatta gacattcatg cattggctaa tctaggcttt gagtgtagat   1680
gtagtgccta caaagcaaga ttagccatta cacgttttgt cgttctggaa actgactctt   1740
ggcaattccc agcggcttta tctcaacata cttcctgaaa tctcaccatg tgtattttcc   1800
tacagagtgg ctctgaaaat aaagtaggct ggaagtcagg tgactgatgt catcctggac   1860
tcgtaggcga ttaacagtat gaccttggag aagtcacctt cctcgcaaga attaggacta   1920
gaagagctgg gcattcagaa gcatgcccaa gtgctcatgg cagtgccgcc tgtgagcatg   1980
```

```
agaaacggga ggccacctgt gagaatggag aataacccgg tgaccatatg tgtctccaag    2040
tcaatccctg tgatctccac ctcctggcat cccccagtt cctcttccac actgaaccag     2100
ggaagatctg cttgaccaac agcatatggc aggaatggca tggcactccc gggcttagta    2160
aaacctaagc cgcttccatc ttgttttctc tctccctctt gaatcccttg ccctggggaa    2220
gctgcctgtg agcagccctg tagagaggcc cacgtggaag gaattgagtc cttgccaaca    2280
gccatgggcg ttagccatct tatctgtgga tcctttaacc ccaatcaagc tttcagatga    2340
ccacagccct gccagctcag ctgcaacccc acgacaggcc ctgaccagaa ccaccatgag    2400
gggctgtttc agggctcctg atctcagaat ctgtgtgaaa taataaattg tttttgtttt    2460
aaagctgcta aatttggggg gtaatttgtt atccagcaat ggataacaaa tacaccccat    2520
actatagatt atggagcaaa gagtggaaca ggtctatgtg tactgataca gaaagatttc    2580
tgagatatgt gttaagacac ccttagaatg tgttgttaga aaataataat tacaaaatat    2640
cttttatgta aaaaccacaa ctcactatat ttatgcattt acatatgcaa gtagatatgt    2700
agcaaattac ccatcatgta gcaatgatga acatcaattt accctcagta agagaaggaa    2760
ggtgcaaagt ggaattttca ttttctattc aatagattat atatataata tatatataat    2820
tttaccatga taatgttgta ttacttatac tcaatttaaa aattctttaa acgaaggcat    2880
ttgagtactt gatcactgag gtctctttca actctggtgt tttatagttc tattaaaatg    2940
tcattggaat gtaaattaaa agaatgggat aacatttatc acgggagggc agggctggcc    3000
tttgaatcca gttatattga ctccaatcta gggcccttcc tgttatttta cctttgtgcc    3060
tatagtttac atgcaggtgt ctgtgttaga ggagcttgtc tctggcctct gttttgctga    3120
ggacaatttc tcatttccca ttacttataa gagacaggct ctgtgagagc ctccaatttg    3180
ccagctgctt ccacttcacc acctctgagc tccgggtcca gcccaactaa cttgactgcc    3240
gagggctttg ctccgtcttg ggatggctgg ggcctccctc acctgacggg tgttcagctg    3300
tgatgattga gcttcgctgt catgaaactt ccccagagtt ggtgccacgc ctccccctcc    3360
ctccagcttg ccacaccact cgggctgaag gatctgcctg cccaaccctg ggttggtctg    3420
cataaagacg gccgggaaag atagcattta tacacagtaa aatgcctctg cattatctcg    3480
cttggagaaa gaaataactg atactggcct gggagctaag aagaggggtt ctctggcttt    3540
gcggagaaac ctgtgctccc ctctccattc tgacggaatg gtctgggggc ttgggcatgg    3600
gtattgtctg aaagtgcctc agatggcttt aataaacagc cagggttgag aacatctgta    3660
ttggagggaa tgtgaaaagg acattgaggt aaatggatgg gattaattat gtttgctaaa    3720
tcaggaaact ctctagagag ggaagtgaca cgcccaccgt tttgcctact gttggaaaat    3780
taaagtttca tcttaacaag ggcggaagag ctttgggggtg gtcccaagag gaagaccatg    3840
gggtagtgaa gcggaggagt ctgtcgcaag ggctcactat gggttttttga aaagctgtga    3900 tcttccgtag gaatctccac ctctttgtgg ggggacagtc tcattatact ctcttgggca    3960
gaagcaagct cccatccctg cagctattga agcagagcat gtataacata ctgacaggga    4020
cgtggtgaag gagatccctg aattggatag acaaaacgcc ctttaacggc ccttccaacc    4080
ttgaggtttt atgattctat aattctatgt attgtaaaga acttaacaaa aaaattactt    4140
ccatcctatt caaattatag tgacctgcct tttagcttgc ccaagggaat ggacttaaaa    4200
ctgctgtgca ctcagaatag atgatgtgat tcccacactc tcattccagg tcagttctcc    4260
taagtatggg agtaattatg atggaggaga tgcaccgcgt gctgactgga gagttagctg    4320
```

-continued

```
cattcgtctc tctagagcag gcatgatgga ccagctaaaa acagagtgtc agtttgacac    4380
atactctttt tgtttgctga tgactttttg aatttttttgt tactaagctc acattttcct    4440
tgttgactct gggttttgtt ctctttagag aattttattt agttcttatg tcttagaagt    4500
agctcactaa aggacatagc aagaggaaga agagatgtct tatatgattc tggctccaaa    4560
cgtaccacag atctctgact gatggcagga cacccaattg aatcgtggtt actccatgtg    4620
tcctggaata aaacacagga aataatttct tgacctcatg tggcatctga acatactgag    4680
attaaaatga gaaactattg ataccatcct tggctgtttc taaatagatg ttaaactctg    4740
atacaggatc cataatctat aggattcttt agccagaata gaatgagaac cttcagcaag    4800
atggaaagaa tcctagcctg agtacaggta ctacaacagc aactgacatt tagccctagt    4860
ttagacctcc acttagactc accatgaagt taaaatatca tgattcttat aagaaatagt    4920
tacttgtgtt taccaaacag gtgggtagat gcagggtaag ttgatctact gtaaagtccc    4980
gggagaaagt agcctctagg aaatgtgcca caaacacctg gataaaatgt aaaaaagtaa    5040
acaatagcca agtgcaagca agaaaagaaa attaccagac accagaaaca aacaggggat    5100
aaacagctac agtggagagt gaatgagttg gcctactctt ggggtaattg tggggagaga    5160
ttgatggtgg cgatggggtg gtggtcatga tggcatcagt ttcagcaacc agggcttggg    5220
ccttcatgct cacataaggt caggaaatga gacctggaga aggaacggag acagaaggag    5280
actctgcaca ccctcaggga aagtagagat tcggggaaaa cccgtccact ggcacagcaa    5340
gatacaaaaa gcatgtctgt ttctgcttgg gcacagagtg aatcagggct ttcatataga    5400
ttacatgtga atttatacta tccagaagtc cggaaactac caaaccaaag cccttaaata    5460
caaggggtcc taggctgctg atactttttga tttgcctaga gaaatacagc aacactttag    5520
agaaactatt ctataatcta ggatgaaagg gtttcactga atacacaagc tacactaaag    5580
atgagaaaaa tatccactaa gtacaagagt ctgatgatat aattaacagg actaaagttc    5640
caggaaattg ggatatagcc agataaagaa aaagaacttg cacataaaca acctatgtac    5700
aagatttctg cagtattgca tgttaaa                                          5727
```

<210> SEQ ID NO 44
<211> LENGTH: 7301
<212> TYPE: DNA
<213> ORGANISM: Homo sapiens

<400> SEQUENCE: 44

```
ttgattcaaa ctctgctttt aagctaaatt gaacactaaa agatggctgg gaaccaattt      60
ggacagccac agcagctttg ggagataaga acctttcttt gcgatttgga taaagcaaac     120
atgatctctc tgcctccttt gtttttagaa attaatagag cttttcaaca gaccgcccct     180
tgccactaat agtgaacagt caaatcatgg cttttattcc cagctcacta cgtcaagtaa     240
atagaagctt acaggataga ccagggaacg ataagcaatt ctcactgcag cgaattctta     300
atatataaat tcatccagca gcagtttagt atctactggc aaaaccagaa acaatgggga     360
acaggcaggc ctggctctga cgaggtcaac catcaaggtt atctatattc aattactggt     420
atctacaaac ttgcatagct gtcagctggt cagggcccaa atgaaaactc accatgcact     480
cagaaagcaa atatagtttc cgaggagagc ctcaaattag ctctgtgaat gacttgactt     540
caaacgcaca ccaagccatc agcctttggg gacgtttctg ccagcagtgc ctcaatgtct     600
aaatttgggc atcatcttat aaatctctgt tcctgaagta ggaaaggact ggaattgctc     660
cttaaccctt ggcgatgata aattatatca cttaacaata gataaactta agacactttt     720
```

```
cctgtactgc ggacctattg tgaggtaact gctaatctct ggcatctctt ctctgtggtc      780
ggtaccacta aagacctgtc ggtggtgaag agacacaata atttgttttc taactcctcc      840
tccggaacca tatatcatgt gtggaaacaa agcttcccaa caacagatat gtatctgttt      900
cctttagagt tgcccttccc atcagactca gagaggacat gttttcagtg tgacacttcc      960
ctgccccaga aagggggaca tttccttccc aggccccact ggaagtgggg taaaggttaa     1020 tcacacccc attcttcctg gcaggtgcct ttcaaccagg accttttggg ggcccaatgg     1080
agatttactc tgcataagtc agggttaatc aatgccaagg taatttctag attagcttgg     1140
ggaggccata aattgtggac ctgttaagag ctagatgtct ttgattttct ccttgggtca     1200
gctgaattgt tactctctcc tcatccattc cctgtcacct tcttgataat ccctttccag     1260 gaccccctt ccaattctgc ttgaggctag tatgccagcc atgggctcac tctatttgag     1320
ccacgaaatg aaagactgta cattcatcaa tgcaatctgt ttagattgct tcaggacaga     1380
ggtaaaacca agagtatctt cacaagaaac cgtttgacat gagttcatat gcggagggaa     1440
aggcacatgg agcaaggtca gtcctgactt tcaaccaggc cagtctgggc ccctgggtcc     1500
acccagacag agccgtcata tgtccagctg tgcaggttgt gcactgcaca aggccatatt     1560
taaggggtgc cattcacatc atagcttttg tagatttcta tatttattat gacaactttc     1620
tggacaatga caatatcttg agactgggaa cattttctaa tcaacacaaa gccaccatgg     1680
aggctagggc agtcccgcaa aggaacccac ttcttatccc taaagtcaac tggtcacttt     1740
ctagatcccc tcctacatgt cggggagggt tattgtaatg agatgatcta ttcgtgagtc     1800
tgtctcctcc tttgggatct ccttgtcctt gtttgtatcc cagcatagag cctggctcgt     1860
gaaagtgcct gatccatggt tggctggtcg tttccatcct gcaggcatg tcacaggtct      1920 ccaggagggg tgcttgccaa gggcataagc agccgttaaa gaaaggcagc tgttccctct     1980
tttcattttc cgtttttgtc cgccctcgtc caaaacacca ccctctattc tgttttttctt     2040 catgaatccc acgtggacaa gagaatagat tactgaaggc acacaacaat ccttcctttc     2100
ttctgtctta aagcaaaatt tcaaaaacat gtcttggttt gtttagaagc agcaagatga     2160
ctgctacttt atttttgatg ctgcacacac cgaggcagaa aaacaaaaca gtggactcat     2220
cagccagagc cggtatttat gtgtaagtga tatgagtaac tcaataggtt tcagggctgc     2280
tgccattaag aaaataacac taatacaaga cacatgtggg tgctggccag gacatgtccc     2340
cagagctcat gggcagccca agctggggat caaggctgag agctcaccct agctcacaac     2400
ctttgctgtg atcccaggtc agaacctggt aatgtaattt ggggaatcca tgtgttccca     2460
gtgacccatc aggaggtttt gttttgatct attagacgtg gaatccttga tctttaaagt     2520
ttgagatctt taggttttgc ctgccctttt tcagaggagt agcccagaga agttaagtga     2580
tttacacagt gagcagcgtc aaaaccagca ctttgatatt aatagctatg ttgcagtcag     2640
tgttgccaaa gaaataaggt gaaccacaca ccacttctac ttagcaccat gcttggtttg     2700
ggtaccattc tgagaaattg ttatgagaat gtattccaat gatattattt gggattcctc     2760
aactttgatg gctgcttcct ttgtgagcca tttctctttt attttgctca tgttttgagt     2820
ctcagcttga aggtcaccag tcaggagacc cagtccaaag ttaccttctc cccaccacat     2880
cctagcctgt cacctttctt gtttccttcc cagtaatgat ggtggttatt catctgttta     2940
cttatttatt gtcttttttgt tgaattccca gccagtcata cagtaggcac tcagtgttga     3000
atatttgcat gtatgaatga attccactgt ggattcaatt tcttccctaa aacctccatg     3060
```

-continued

```
ctttgtcttt tacacactta tggcactagc attctgcctg cccctttctac cagattaaag    3120 gcctttgaag gcatctgtgt ttgcacctgc agcagtgctt agaatcacat cctgcccacg    3180
ttggttctaa aattgataca tagatcaaga tttcggagct tttccataaa aaaaccctgg    3240
gctaaaggaa ggcacattta aacgcagagt tcccatcaca actaattaat gttttggtct    3300
ctccctttct cctggacttg aagctgggca cagccaaaat atggtgttaa acaaagatat    3360
cttggaccaa attcttgttt gtgtctcctc aacagctact tccagctggc tttgtttaag    3420
tgatcatggg ataaaatttc atcacaatca ccagtgaaca tgacgaaaga ctgcttcatc    3480
tatcaactcc agggctggtg ttcacaatcc cttagcccaa aatgggacat aagacaggga    3540
gggagccatc acccaccctc aggcagccag gttacaacgt gggcaagact gccatgtaga    3600
ggagtgagca gtgtcgttgg aaccagatag atctgcgttc taatcacagg tcttttaacg    3660
ggctggttgg atatcagttt tctcatttgg aaaatgggta taatacatat cttacatatt    3720
tgcacaaaag catggtatag tttagacaaa ggaagctttc caagcagctg agagaactta    3780
agagtgtaac caaaagagag cgtatgttct gggctaatct attgaaagga caggaccttt    3840
tcccactctg gatgttgtta gcatgtttca aaagtcaagt ggtgaaactt cccagccacg    3900
ccctcccacg ccgtccatgg caaccggaac tgagcaaagc caagcaaaca catccttaac    3960
ctcctcccaa cccaaaacca tgagatctgc aattgcaagg gcctcgcctt ggctagaaac    4020
cagcccggca tcatgatcca ggcctcggag gctaaacccc tggggggaaa aaatcctgcc    4080
ctttacaagt tcgttctctc aattttatta accagaaggc tgagagctga ctgtgggttt    4140
gcaataccac ttaccagctg gtggaatcag agagcaaagc cctttctcct ggaaccagcc    4200
tgaaggccac gccaagccac cagatgggca gtaaaatctt ttaaacagct gctgtctatg    4260
gcatgccact acttgtgtgt aagttgattt tatagggatt gtagacaaac agagcccttc    4320
agactaaaaa tttacaaaag ctggttcatc ttcctagcat cttaggattg tagctgctcc    4380
ctggatttag cttggggaac cctaggctct tatactctgg ggccagaatg aggaagtgtt    4440
ggtagtaaga tatgacaacc gtgtaagtag gcaatatttg atccattcaa tagatgggta    4500
tttaggctta gaggtgttaa ggatcagaat tacacacctg gaaattggta gagaaatttg    4560
aatcaaggtt acctttgggt atatttccct acttgagtaa ctccaataaa gaaaagggtc    4620
tatggctcag tgctcagtaa cacatggcta cacagcttct tctgactcca cattccatgt    4680
gctgcctcaa tttccccagc tataaaatga ggatgctaag attatccctt cattgggttg    4740
tgttgagaag tgataagata ataaatgcaa aatgcttagc gtgaagcttg acctatagtt    4800
aagaatccaa taaacgtggc tcttcttatt gtttgtctta ttaccattat ctataaaacg    4860
atatagggca tccctttgtt ctgttccctt aagaccattt cagtcatgtc tgtactggga    4920
agaaaacctc gctttgtttt tagaagccaa actagtcccc tctttctttc accatattgg    4980
tagaaagttc ataacattca aaccagatcc tgtttaacct ttgcccaaca tagctttacc    5040
tacttcaaac ccctttggct ctctgaggcc tggcttcctt caggctcagg ctgtaaatgt    5100
ttgactttga tttgagatac atgacaataa attaggggac atttatcaaa gctgcttttt    5160
gcataaatta ctgcattata caaatacact tagcaggatc ctgcttcttt gatgttggga    5220
ccaaagattt atgtgcaatg gagttttat ttatctgccc tgttcacctc tacaagagct     5280
ggacatattc ctcaattagt tccatacttc tcgaaatgac atgtatctct tgcaacttga    5340
gtagagggaa caaagacact taaatgcctt ccgagtggct gttaggagag gagaagcttt    5400
atctgacgag agtgtctctg agagcggatt gaaaggcatt caaacctgtt gctctggaat    5460
```

```
cctcccccac caaaaagaaa aggaggaagg atttattctt taacattatt tatatcatta        5520
ccacattatt aagagagcca cagaaacata agtgtctatt ttcaacagca agtaggttag        5580
caatacagag atctccttgt catggcttct ggtttctgaa tttcatggag taaggtttgt        5640
gtgacctggg gaatgggcaa gatttttagg ttcattggcc attaaattta ccttttccag        5700
aatgtcatat agaagatata tgtagctttt tcagattggc ttctttcatt ttgccttgtc        5760
tttttgaagc ttgctaattc atttattttt atactgaaaa caataaaact gtggttgaac        5820
gtaccacaat tcacctattg aaggacattg gttgctttca gttttcggta attatgaata        5880
aagctactta aacattcgca tgcaggtttt tgtgtatgtg tcttcaagtc agttgggaaa        5940
atccctaggg gttgaattgc tggatcatat agtcagacta ggtttaacct accaaaatgt        6000
cttccaaagg gattgcacct ttgcattccc accagcaatg aataagagtt cctgttgctg        6060
cataaccagc cgttggtatc atcagttttt ggatttactc ctcctcatag atgtgtagtg        6120
gtgtctcatt gttattttaa tttgcaattc cataatgaca catgatgcca agtattcttt        6180 cttacccta tttgccatct gcatctcttt ttttagtata tttgttcaaa ccttttgctc         6240
atttttaaat tgagtcatta tgctttctac ggttcaattt taagagtgct ttgtgtattt        6300
ttaataaatt attttttctg ggccagctcc actcatgttg tccctacctc cctgcatctg        6360
aagagtttag attcatgttc ccactcagag aattaaaaag gggagctccc cagctgtgac        6420
cacaacttag ctgcctaaga gtcctggatg agccgaaaaa gctcagtcag gagcccaccc        6480
ttttggacat ccccaggacc ccagtaaact tcagaaattg cccatgtacc catcccagag        6540
ctgccccagc aacaatttca aagcaatggc tatatgtttt aagctgcaag gtccttgaag        6600
agctttgttc attttacaaa tgaagttcag ctcatagatg ttactaggtg ttgcaccaga        6660
aaaaggcaaa cagattttga tatatttagg attaatacag ttaaactctt caactccttg        6720
ctattcaaaa tgcaaaatca gcatcacatt ggagcataca aactcttagc ccccagttca        6780
tacctgttga atcagaacct gcatttgaat aagtcccccc tccacagttt atttgaatgt        6840
tcataggaac tttgtaagtc aatggtttct caaatcatta tcgagcatct actacatggc        6900
agacattgtg ccgaggattc atcacaagac atcatacctg atctcatgga gttagtcttg        6960
agtggacacc aacatccaca aattacttct caagtaactg gttccttagc tacatttgtg        7020
atttatacca taatgaaaga gtatttgaga atcagagacc tggagggtac tattaccaag        7080
agttaaataa aggaaggtat gccttcatgc tgaagacttc atctagcaat gtgacaataa        7140
cacgtgtcac tgtcagccca ggccctgctg gcaacacctt gaaaactatg cagaggttta        7200
gaaaataaac agcagtctct ctgattccag tgataaaata ccagtgtaag gagagcctcc        7260
tgagatccat aatctggaat tgtcagggga taagaattgt c                          7301
```

<210> SEQ ID NO 45
<211> LENGTH: 2299
<212> TYPE: DNA
<213> ORGANISM: Homo sapiens

<400> SEQUENCE: 45

```
ctggctttca gtttgtcctt tgaaaaaagc cgcctttgaa tttgttcttc caaagcctgc          60
cctatgctcg gcctccagaa ggatggacac ttgatcccat ccatggctgg ccaagggcgt         120
ggccttcgga gcagctgcaa ggatagtgtt gactccagat ggaaagtgtc tggagaattc         180
tgacctgaca tcacaccatc acgaactgca caggcagtca gtgatctggg ggtgccctga         240
```

```
agctgttccc agcctggctt cttgtcaaaa gctggctttg agttggagtc cagaacaaaa      300
gcgtggccca gggagaggcc agcttctctg agagcagcct ggaggcaaac gggcgtcctt      360
catatattcc ctgtgatgtg agcccagccc tgcactcacg gtactggctg caagcggggc      420
ccggtatggc ctctcttgac tctcctgccc accctggggc cttgccatct ctcccctccc      480
cgctgggcct ccactcccaa aggttctaag tccccacatg tggcctcatg cagctcagcc      540
cctgccctgc tgagccctac ttagccaggt ccagaataaa aatctcaatg caaaaggaga      600
caatagaatt ggggcgaaga gaagctcttg gaaaggaagg gaagtggggt agccttgcca      660
gacctgaccc ccagcatgcc tggcccccac tcctgggtga ctgggtctga ggggtctatc      720
ataaacaagt tccttgaggg ccagaccctt cccttttcccc agagatcaat gaacctgcca      780
ctgggtgcca gacctgggct ctggattcct ttgtgaaggt ctctggaaaa agatctgcat      840
ctaacaaaag gaaagaagac aaagtgcagg gaaattgctt tcaaaggaag tattctcacc      900
actgtcattt aatctggaag gaaaacctt tccagaacct ctccaccaga attcccctat      960
cttggccaaa ctgtgtcaca actggtaaga gcaaatgaga ttaccccttc ccatgggagg     1020
gattgtttag gacaatcctg attcatgatg ggggagccac cttctctgag cacactgcag     1080
ctggatcatg aacaaagaca aattctgtta tcaaaatcat aggaagcaat gattgttggt     1140
ttggccaaga gcagacatta acaatcaatc ttaactctct cacagtcatt acaaatcaaa     1200
aagttggcac atgagataaa gcatatgtat tatctcagtc ttagataatg ggaagtaagg     1260
aagccgtaat tcaaggcatc tttagtgacc cagttatcgt gtcattgtct catggagtgc     1320 tttttaagtcc acaaattctt tgtcctccct acaaaaggtg agctaattcc cctggctcta     1380
gtgattcatt tctaaggaat agaaagtagc agaatgatac tgtatgagtt ttgagagtcc     1440
taaaaggcag gatagctttc accctgctct ttcttggacc acttgctgtg agggagccag     1500
ccaccatgcc atgaggaagc tccagcagtc ctatggagga ggaactgagc agttcgccat     1560
tttggaagtg gatttccagc cccaggcaag ccttctgatg actgtagcac tggctgacat     1620
cttgactgca ccccatgaga cacccgcgc cagaaccccc agctaaacca cttgcaaatt     1680
cccttcccac agaaactccc agatgataaa tgtttgttgt ttgagccacc aaattttggg     1740
taatttgtgc agccagagct cacctagggg aggcaaatgg cacaacataa ggagatgctc     1800 ccttcaggggc tatgacagtt cagggtcaca catgaccctg agacggaatg tcttcttaaa     1860
ttctgttccc tgctcctcgc ttgcctcagc cccgcccctg tgtctagcag cagatatacc     1920
tcttctgaac attctccagc ttatgttggg aatctgaaga aattggcttc ccaaggggag     1980
catgtgacta cgccagtctc cattaccctt tggtcagagt gattggatca gtgtggcatg     2040
tggcccagtc ctgtccaatc agagtaggtg gtgaggcttt agcaaggaca aatatgaacc     2100 cactttctg atggaaactg acttctggca gcctttttgg gacctccaag gggagccagt     2160
tcagggataa aactgatatc aggaaacagg gaaactgggt ccttggtgac attgttcagc     2220
tgttagatta acctgaagcc agcctcatct ctggactttt cacccagcaa ggtaaaaatt     2280
tcccttttaa aatttaaac                                                    2299
```

<210> SEQ ID NO 46
<211> LENGTH: 2685
<212> TYPE: DNA
<213> ORGANISM: Homo sapiens

<400> SEQUENCE: 46

```
ctggctgtgt tcttacaagg agagagaaac ccaatacaca cacacacaca tacacacgca       60
```

-continued

```
cacacacaca cacacacaca cgcccacagg aggtgggggt agggaaagga acatctatga    120
cacagcaagg ggaaaataca cccaagcttc cctagctgtt gccaggggaa ataccttaga    180
gagagaagca gctggaagat cattagactc tccatgtttt gtcctttcgg aaatttaaac    240
tctgatatat tacccccgaa tgcagtcttt caccattgtt gtccttttgg tagagatcag    300
tttttcttac ttcttgggtt atctccgtgt ggtggaagat tcagcactag cttaattagt    360
gtcaggtttc ttacaggaat cataaaagaa aaacaatggc ataagaacag ggaggtggtg    420
gaaccattaa ttctgatgtc attgtttggt ttgtttgcaa agtttgaaat aaacatgtag    480
atggtttttg gagctgaact gagtataatc tttgcacgtg tggtgtgacc ggagctccca    540
tctcatctgc ttttcttcc ttgcctgtct attaatttac atccatttgc cttttacttt    600
ctggagcttg tgttcccata cttccaaagc agattcaggc taggcatagc atcccttaga    660
ataatgccac ccaaaagatc tccaacctgt gaatatgttt ctttacatgc aaaagagact    720
tgcagatgtg aggaaggatc ctgaggtagg gagttatctt gaactactgg gtgggttcaa    780
taatcatagg gtctttataa atgagggagg aaggcagagg attggaggag atttgatgac    840
ctcagcatag gtcaggaagc tttagaagct gggaaggcaa ggaaacatta tactctagag    900
cctccagagg gatgcaatcc tgcgacattg atcttagatc aaagaaattc gttttggatt    960
tcgacctcca gaaatataaa atatccaacc ttgtgatgct ttctagaggt aataacataa   1020
aattgtagat attttttggg ggatttactt tatcattttt aaataaaata cttgcaaaga   1080
gccccacctc ttaagtagcc ttattactct tacatttta tattaacaat ttcatcatga   1140
acttcttata aataatgcag acagattcta ggataggctc ctttatacca attctctgtt   1200
gaattcaaat taatatgaca ttgctgcatg cattctacag gggacatttg gctcatgtca   1260
atatttgctt gaagatcaga ataaggtgtg ttattttgca ggaatattgg acctccccat   1320
ctttgaagag ctcttcctta tcccattgct ggatgtagta gagattcaga agcatagaac   1380
tgcatgttga cttgttcatg cagagtgtcc cctgagggtt tggattttag tggctactat   1440
gggctgcagc aatgacattc cctgttgcaa cccctgcatg caagaggatg tgaaggtcaa   1500
gtgattggtc ctgattaaag tatgtatcat tggcttgttc cggctggccc ctggctgctc   1560
ctggggggag ggattgcctt gttgctgcac atggtaagaa agcccagctg gggtcctgtc   1620
tagagccacc tgatctgtcc taggtagatg acatttgatg aaaaaaaaat ggctctttta   1680
aataagacag tacacttgcc aatagttaag tctccaaaga tgatagatcc atgatgtttt   1740
accatacaag cactgtgact cctttcagag gatacaaata gccttttga ggttttctaa   1800 ctaactaaaa ggtttctctg tctagtatga cagttctttt gattcccctc cctaagggtc   1860
agaagttctt ctctccctta cgtgagtgtc atgaagcccc tcctccccgc tgatcacaaa   1920
gcaatctcag gaagggtctg ttgaacttgt gttgaaagga aagcctgtca ttttgatgtg   1980
ttagaaaact ccttcttgca atgcacttat caaagagcat ggactaattt ttaaattcta   2040
tgtgtggttt tttctctgta acaattttgt ggctttgata ggatgtagaa caacgcaacc   2100
tgggaaagag atggtcaaca ggattgggac tgagtgagca aatgcttaga ccctgctacc   2160
ttgcctcttt attatgtctc tttttttccct cccttcatg gtgaggggat gcctaggcta   2220
attgtccatt gataggctta aagggagccc attacctgaa cctgtctgcc tttcggcttt   2280
cagagccttt ctgctcctaa tgtatcttat atgactcctt tgtccttaga agagaataac   2340
ttcccttgtg tgttccttat tcaagctcaa ggactacaaa ggacacatct cttctattct   2400
```

-continued

```
tctttaaact gtttcagggc ccccattctg tataaatttg gaattgtgcc agttaggagc      2460
ccaaactgta gatggatcct ggctgagatg cttgttacct aactccaggg gtcactgttc      2520
aaacaaaata gatgtgggac cccctgagtt tgtggaacat agagttccta gactcaactt      2580
gggaccttga taccagaaac tatggctagg cgaaatcaca aactcctagt tgctttctca      2640
tatataccca agagaggttg caaaattaaa aaatatgaag gaaaa                      2685

<210> SEQ ID NO 47
<211> LENGTH: 4757
<212> TYPE: DNA
<213> ORGANISM: Homo sapiens

<400> SEQUENCE: 47
gcatcgtctt atagctatag tcaagtacaa tttaaactta atagtacaat tataatattc        60
aacaactcta gaatttttaa tttgaaattc aaagatacaa taatatgctt gtggcaatta       120
attttgtttt taaaaatatt tataagccag taattcagta ctgtatatat accaactgca       180
atgtgtacat gtgttcacat acctgtgcaa aagtattcat aacagcacca agttccaaac       240
aacccataaa taaattataa gttatacaat ggaatgctat acagcacaag actaaacaaa       300
atctcacaaa cacagtgtta agagtaggaa gccagacaca agtgagtatg cattgtgtga       360
tttatttatg cgttcagaaa gagacaaaat tcatctatgg cattagaagt catgatagtg       420
gctatccgct ggttgggagt ggagggactt aagggccaca ggataatctg agattctgct       480
aattttctac tgggagctgg ttaaatgata tgttcagttt gtggaacttt tacatggtgt       540
atcattagat ctatgcattt ttcaatatat accttgtact ttggtaaaat ttcaagatat       600
atatacataa ttattttaca tatgtaaata ttcctcttag gaaaactggc attactcacc       660
atatggagac caggctatta atagaccaat agcgggaaca gaaattttaa aagattggaa       720
acactgatag caatagtcaa tgaattcttg aagggagccc tttcaaaata aaataataca       780
aaactaaaaa tacaaaatta ggcacacaat gaatatttag aacaagaaaa ttacaaaata       840
taacaatttt attaattacc tgtaacagct ataaaactta ttttctacat gttataatta       900
taaattcttt gtttcttcac atgatatgct taatatttgg tagagagatt ttgtttccct       960
gtatagtatg gtcgatgcaa ttttttagag attttataaa cagacatatt gtttgtattg      1020
ttagtacatg cttgggcttt aaaatcacag gaattctgat aaagtctact tcttgcaatt      1080
ctcgtaaaat gtatgatgct ttttttttatt ccttacattt ttaaatataa tccccaaacc      1140
acagaacttc cattttgatt ggaaatttta aagaagcgaa tcccatttaa aattatgcat      1200
atctaacaaa caggaagaat tttcaagaga actagtctcc tttccctcca ctacctacat      1260
tcttccaatc tctgtggaag gaacatgttt ataatggaac acctttatgt taagactctg      1320
ggtaagtcta cccaacagca agtaggagta ttcctggttt tcctgaacca ggacagatag      1380
gagaacttaa ttatagacag aagtgacaaa tatatctcgc taaagccaat aaatgtatct      1440
gtaactcagc ttccccactt ggatctcaga aatgcccatg actactctca cactctccac      1500
acaaggcgaa atggaaggct aaggaaagag actgtgatcc caaccaattg ctgttaaaat      1560
attataattt tgaaaatgtt acaaaaacaa atgaccatat gaacccagtg ctagcccctt      1620
gctggtgcct tgaaagatgc cagcgcaagc ttcatttgct tctctataaa ttcactctgc      1680 tgttttttctt gcctcactgg ttgcatacag cttctcctgg aagtgagctc ttcatctcta      1740
attactgtca aaacactaca cgcacctatg gttggctctt atgttgtgat ctctccccaca      1800 gtcaacacta ttgaagtttc tccttcagtg acttttttata atttcatctg actgcttcat      1860
```

-continued

```
agacagccct ttttagctta gtggacagta gctggtgagg tatctgggtt ttgttatcga    1920
ccattgttag gagatgacca gctgagcaca gtggggcggc cattaagctt tgttgcagca    1980
gcactggctg tgcttcaagt tcttaatgtt tttctcttgc catctgatgt agatttgata    2040
ccagcacata gggtggagcc tctatggata cacacaacag cagtattatc agtgttcact    2100
ttgattacac ggttcttgat tcaattcatc acttgcccag acaggaactg catttactta    2160
cttgtgctga cacctgactc tgttttacac cttgaaaaag tactcagagc tttttatttcc   2220 tttcacccgt aatgtagatt tgctcagcaa tatgatatac atttgatttt gcaagcactt    2280
agatcagaag aatacttcta taaggaaaat gtttacctaa caaaggaatt tttgcagtct    2340
aatgttattc tgtgttgagc atcttctctt tcacctaaaa aagtagttca ttattctaag    2400
ttaatctaaa gcttttgtat gcagcacaga aatttattta aactggcaaa ttggattaaa    2460
taacatgaat ttatactagc actcagacaa taaccattga aagaagcttt taaatttata    2520
attaaattaa ttatttcttc tttagttgca ctaacagtat ttcacaggta ttatttcatt    2580
taattctcaa agcaaaactg taaggaaagc aatgttagcc ttgtttttgag gaaactaaga   2640 tctaatagag caggaagata ggagcctggg tccctcacaa tgtgaagctt ctatccttcc    2700
ctgaaaagcc taccactgga tttgtttttac atgaatgaga aataaaccac tatttttcag   2760 attttttattt tctactatcc catatatcca cagcaatctg accataatta tttacaaacc    2820 aggactttttt cactgtatca attgatggtg acatccttca taaatctggg cattttttctt   2880 cacttgccaa caaaaaggta gttgtgggta ctacggctcc aatgaagatg agataaataca    2940 ggcatcatac attacatgcc ttccggaagt gagatgtgac tctcatacat gtaagccagt    3000
cttctaaaat gatattctgc atttttctgga tcactctgcc tgctcatcta ctatcagtgc    3060
agcatcggtc agcaccctac caggatggat ttctggcctc actcagaaac agctggacaa    3120
agagttttac gaactcatca aagatccgta agcaatttat ataggaactt caaattagct    3180
gataagcact tttatttttg gtcctcgttt atttattgcc acttcacact gatcaacttc    3240
aactaaaatg ttgctgtttt gtggcaatct tctaatcatc attgtattct gaagttggag    3300
agttcaatac ttgaatttta catttgagga atgtaaatgg ctaatcaaga gccatccgct    3360
aaattcaagt tagaactgag agccccggct ctcagttcat cgcttttctc tcagctaggc    3420
ttccctagaa ggccattcag attcctttcc tctacttgaa atttaatctt aactcgtagc    3480
atatactcac tcagcattta gactgcagat agtgctcaga atgggttagg tacttactgt    3540
gttcacaaga actctatgtg gtaggcactt ttttaccttta acagagaaca gagagaaata    3600
gcttttgcat ttacacagct agtgagtagg agagtgagga cttgaactta tgcattctga    3660
ctctagagtc tatactctaa tcctcttatc acccggtctc acaagtagag tgggtgttcc    3720
aaagaaagca tactcttcct acaaggacca tttccctaca tcttcctttc cagcttccat    3780
ggtaagtgac taaattttttt tattattctg ataatcttta cagaagggac ttaaagaact    3840
gaaaaataaa ccctacaaag gtatcatgca aaataaatga tataacattt tagcataaaa    3900 ttttttatcag ataaacatta ttggtccttg actcttaagg aaattggaca tgagacagac    3960
agtaagtcaa gttttgaaat ttggacaaat taaaaagttt gaatctgcta ccatcaaagt    4020
actctatact tacttctgtc ttgccttgcc taattttgaa tatattcatt ttattttaga    4080
ttatatttct ttctttagct caagctgcat atcttaagaa gtattattaa taagcatata    4140
gacatatttc tctcacctga agaaataatc tccaatttta tagtataagt ctagtgggaa    4200
```

-continued

```
agctgtgtct aatatagaat tttgctttag caattatttt atttacatct tgtttcaaga      4260
cacagccatt gagcttgaca gccaacctct aattttatt tattgcctgc caactttgtg       4320
ctttttaagc ttctaataaa gaacagttta agcaattttt agtcatccct catgtatggg      4380
cctcatgtaa catgttttgt aatgacatac atcattttat aataaaattt catcttatga      4440
gtctttcaag tattttgatt tctcgcagga taaagttcta catgtatatt atacatgaat      4500
catctgtttt ctttagcaat tcactgatct cataaagcat gcatctgggt aaagaactac      4560
tgaaatttaa acctctttat ttggaaatga aaaattgtta agctaacagt agcaaattcc      4620
atgtttcatc aagctttct ctaatccatt ggattttaaa acaattcata gttacttaag      4680
agtttactta aatagcctca gacagcagaa ctttctctgg aagcctccct caggaaatag      4740
tcttgtgtgt tctcttc                                                     4757
```

<210> SEQ ID NO 48
<211> LENGTH: 5297
<212> TYPE: DNA
<213> ORGANISM: Homo sapiens

<400> SEQUENCE: 48

```
ttttattttg aaagaagtta attaagacat tattagtttg atcattatac ttttccctag        60
aaagtaaaaa tggcatgtct ttgtaaacat gggcagaaca gaagagctcg gtgagatttg       120
tattttggtg tcatctacag gcactgtaca tagtttcttc aactgatttt tttttttctg       180
ttggtgcggt tcatttatct actttatgga actattacaa aatacctacc tttgctggtg       240
taatttaata gtcacattgg tactgctgtt ttatcacttt atactcaatt tttaaagtaa       300
ttcaaaagta tgtaatttgg aaggaggctg tgttttaaga cttggctggc attcacattc       360
tgcccagcta ggcattaaat gttgaaaaat agacttgagc ttgcaacaga gaccatacga       420
cccaaaagcc taaaatattt cctgtctggc cctttgcata tgcttctcca tgctatttct       480
aaagcaggtt attgtaaaac agtgctagcc catgaattct caagagaaaa atgtcatgag       540
aaagatacct aggaaatgta tctatttcct tattatattc ctatttcttc accgcttttg       600
cctgtttatc caatacctat attttgcctg gaaacttcgc ttaatattgg ggatcctggc       660
aataagatag gcaagatagt gttttctctc ataaatattg gggcttaaga gcagtttctg       720
gcctcaaatc tgattttgct acttccacga tgtaaacccg gatacattat tgtgctttag       780
tttccttaac tgacttttgt ttttaaatct gtcaggtgtt tgatgagatg attcctatgc       840
ttttaagccc agacctctaa tgaatactct aaattttcag atatgaattt acaacctgtc       900
attcattcaa ctgtttagca ggaggagttg gagatttggc aatgaatctc aaatagatgc       960
ctccttcctc agagagatta atctgtgatg aagacagata gtaaagaaaa gatagtaaaa      1020
catatagcat atcagatggt atgaattatc tgaagaaaac tgaaagcaag aagttggaag      1080 ggatctttc gattttcatt gtggttcact atgaagatga gatttgaaaa tttacctagc       1140
tgagatgagg gaggaggcca agcactatct aaaggaagag cgtgtcaggc agacagccat      1200
gacctccagg aggccaacga gagtgaagta aggggaaag ttggagaaga ccaagctgga        1260
aagggaagga ggtagaggtc tagacggtgg ggccttctag gccatgaaag gaaggaattt      1320
agggttttat gtagaggagt gtcacgttct cacttgtttt ctaaaggatc actctggtta      1380
tgttaagaat aggctgtcaa gcctcaaaat ggaagcaggg aaaagcgcaa caattcaggc      1440
tgacagggtt gtgctgtgtc agttaattcc agcaggcctg gaattggcct gagctgtttt      1500
gtcgtaggag atgtatctgg atgacactga tccctagtca aggcatgaaa tatacaggat      1560
```

```
aatagtgtta ctttgtaacc atgaggccaa ggcaagtttc agggtggtta ttaccaggtt    1620
ttcagcatta ttttgtttac tggtaacagt gagattgatg atttgtacct ggtttcagtg    1680
agacttccca gggctctgat gctgaggata aataataaga gggtctagaa tgactcccaa    1740
tttctttatc ctgggcaatt ggcatgatac agttaggaaa atgactgaga tgaagcctaa    1800
ttagcattca cttagttaac aaaagaaaag aaagatgagt ttagacaact ctcttgggga    1860
gatctgattt aaacagaagc agagaaagga aaatttgttg gagaatcaca gaactatgaa    1920
gatttaaaga gctggtaatc taggcataaa agggaattat ttcaacttga aaactcattt    1980
gaataaatta tttccttttt ccacactggc tattaaattt tagctaacac aacaaataga    2040
atgcagtaaa catcagtgcc atatttaatt atattatggg ttgtcctata tactatatca    2100
ttctatctct caggtatttt cattccaaag tgatattcca tttaacaaca aaataaaagg    2160
tgattgcaat ctatagcaca ataaaatcag aagctggagc ctagggaaat gtaaaaattg    2220
actcagtttc tatgtggaat attatattta agcaaaatat tattccttgt gattctggac    2280
ccaagattaa tcctagaatt atgtggatat tatatgagcc caagaaaaga atcccattaa    2340
aatgaattaa acctgccatt aatgttgcta tggcctttaa tatttatttt attctgtatt    2400
tacatttcat ctggaagtct tttgtaggaa atctgggatg attttttactt gtttgaaggt    2460 aaaaactttg aaaaccttaa ctgctgtgtt gtgcatgcag aataaatttt gctaaatgga    2520
tgaatgcata cattaatgaa tatatgaaaa agtgagagtt gcatgaatgg ttgacaaatg    2580
aatatatgaa tttagtgtgg catatataat gcaaaaacat tgcacataaa cagagaggaa    2640
gtcatgaatc ctttatgaat ccctttatgc gtgaatagga aaaatattga gagatattag    2700
cagaattcag gcagaaaaga gcattatcat ttatcatctt agaataaacc aggtggatgg    2760
aatatgggca gaatgagggg aaagcgcaag tctaatgcag attacctaca gtagcacaat    2820
ttgatagaaa ttaatcaaag aaatcagctc ttctagccaa gctgccacac tgcccactaa    2880
aaccacaaat ggggattcca ttcaaatagt tgcaaatat tctttgatac ttcagactct    2940
attaatggta ggattgtttc ttcagcgaaa cagaacaatc ctgccctctg taatgaaaag    3000
aaaattaaat taaatgttaa aagaaggcag tttgttgttt gtctttagac aatagacacc    3060
agacaccagg aggtaatgaa ataaatgcaa agagaaaaga tgtagaattt ccaaagtttt    3120
tcccacggaa taatagtcca gatgctccga gaaaagcgtg ctccatgctg aaaagagttct    3180 gcagcgctcc atatgctgcc ctctctaggg gacgcatagt gctcattaaa atagtaaagt    3240
ccccaaaatc ctgaactaaa aagcccattg agtggtgtt ccaaaattta tgagtccaca    3300
cagcttttaa aatataacac acatcaagat cctgcagagt tagtgatatg gaatatgcct    3360
ggggctttcc tatacagaca atgcaaacac atccaaatgt acacagagct aggccctagg    3420
gaaatggaat cacttcgtgg taatcaaagc ctttggtaga aaaacatacc tcttgatggt    3480
cagagcatgg aaaaaaaatt attcaggttg ggaacaatgt actataccac ttagggatat    3540
atggaattag aaaaaatttg aaagaagcca agaaactgga aacaaagctt aataattaaa    3600
tccactagac tgtattttaa attaatcttt ctggtggtac tggacacaac ttttctagga    3660
taaaggatat taatattatg atattgttca ctacaccagt gccttctaac tctgagatac    3720
atttatcttt ggaaaacccc acttcccagg ggttccaatg gggagaataa aaagactcac    3780
aaggcatctt ggacatcaaa ttcctcttat aaaacaataa tttgttgaat taagtgctaa    3840
tgaaacagat ggattacatt tccatcacaa tgtgcacaaa tttaaacatt aaagagtaaa    3900
```

-continued

```
agcacgtggt aaaaccagct ttgtgttttg ctgattctga aacagttagg aaaatggttt      3960
cagatgccac caggcctgtc tggctccaga caccagcctc attgactgaa atattctatt      4020
aagcaaacag atgggggagt ggtttgttac tgatttctcc ataaaagtga aacatgaaat      4080
gtaatattcc cggaagaata aaaaccttgt gcttcatact ttacaaagct gcattgagat      4140
tcatctctag ggcactctgg aaaaatagaa gctgggaatt tattttttac agagattaat      4200
tgtatcagta tgagataatt gagaaaagga gaaataagta cctaaagaaa acaaagtaaa      4260
aaaatgtggt agcatattgg tagcataaat tgtgaatagc ctgaatttct gcagctatga      4320
atacaattat tgaaatactt cttagaataa catttataga taaaaataag attttgtgtg      4380
tgctttataa aaattaataa actttatttt aagagcagtt ttaggttcac agcaaaactg      4440
agtggaaaat agagtcccta cccacccca cacaggttgt cctatcaaca tcgctcatca      4500
gagttgtgca tacattactt cagctaaagt ccatacttta cattaggatt cactctatgt      4560
gtgtttttaa caaggcagta acttggttat ggattattta tcttgtcaat aattgacaat      4620
gctatgtaaa gcatattatt cgtggatatt tgaggataaa gaagactgga attaatgctt      4680
tcaaaagaaa taatttaatt acatggttta tttgatttca aaacgaaata aattacagga      4740 aaaatgtaagt tttacacact taactttgat gttcatcaag cagataagcc taataaatta      4800
tgaaatacca ttgctaatgt aaaatgtaga aatattattt ccctgatgtg acccattctt      4860
tctttggata gctatctttg gaaagggcac atacaggaaa ttagctttat agcaatgctt      4920
tacatagatt atcgtaagaa caaaacaaag cccatattca tttctcttgc aaatgcttcc      4980
atttcaatat catgctgaga tcttcagtgc atcaattatg tatctcctct ttacagggac      5040
actaagatat attcatggaa tgattttgat gctgagactc taaaggttga actttggttt      5100
tctgagctct ggatcttaat ctattccctg acattaaaat tcctgagaaa gattagaaac      5160
tccacaatca atttagagtg tgaatattcc tgaggccttt tccacacatt tctggcatta      5220
actctcctca gatatattcc tgaagaggat gactgaagca tgcctttggc aacccaaaga      5280
atcctttttg ctcagca                                                    5297
```

```
<210> SEQ ID NO 49
<211> LENGTH: 17936
<212> TYPE: DNA
<213> ORGANISM: Homo sapiens

<400> SEQUENCE: 49
atgaatgagt gttgggtcat cctcagaaag aaaagtgtat ttacctttag gattctcctc       60
ctcaactttc tgatcaaaac caaaaatggt tcttttgttc tcagtgcata ggcattccac      120
aacaacagcc ttttccttcc tcttcctctt ctctacattt aaggaaattt caaatataaa      180
tccagctgac tttggttctg gacaaaacta caaatatgga aacctaaaag gggtcctata      240
aacagaaggg cttagggatt tctctgtgta aacaaaaat aagaaaaaca tgttactatt      300
ttccattaac actggaagac agggcaccag ttagcacatc agcattgtgc agctggaacc      360
ttcaggggag gggtgagaag gcctgccact caagatgtaa gcagctagat ccaaatctgt      420
cttgaagaag agtgacatgt atacagctcc acatgaaagg gagatagaat aaattattca      480
tgcccactaa aaagtaatat taggacatga ggcacatatt tgtgatacat ccaacagacc      540
gctgattgga agagagatgc tggaacacag ctggaagaca gctctcccat gagtcctccg      600
gaagcccacc tgtcagcact ttttgccctt ctgcattcac gtggaatttt gttcctgctt      660
atgtccattt aagagcttat gggcttaagg cttcaagttg aaataaatac tgagaattta      720
```

-continued

```
tggcaccttg ggcaagacta tggaggagga atatggacat tagttgcccc cagtgaaagc      780
agtggacaaa attttctcca ggttcctcct atgtgtaaca aattagaaac tagtctgaga      840
atccagacca ctggtccctg tctcatgtgt gcctccaacc agatgtgggc aagtctattc      900
tctctgggtc ctggtttgac tggtggtagt aggatctcta gagtcttttt ggctacagct      960
catctgcaat tctaaggaag gcctaaagac ccccatcctc ttgtgatgta tacccaggag     1020
ttcactgttc ccaaggagct ttagatgaag gacactgagg tccccaagct acccctattt     1080
gattttgtca agctcagtac tgtggtgaga gaaagataac ctggtagaca ttagaggcac     1140
ccagatatag agccatagtc atttgaaaga ggttgcctcc tgccttgcct tccctgtcct     1200
cctcactgag acacaaatgc cttcactctg cagctcagcc ttagatagtc cctaattata     1260
agttaacatt ttaacaaatt attatttcat caacagcatt atcatcccat tattgagagc     1320
cagttttgtg catgtctctg tgtcagattt acttggtcct ttacaataat tctgcaagga     1380
aattatagcc ctgtgttatt tgggactctg tggtagcttt ttattgtgta catttagaga     1440
agcaaaatta catctttata tgatttggga ttaggtttgg ccacaagaga aatttggatg     1500
agatttggaa gacagaagtg aagcagccat ttccacacca ggcttggtgg cagcttgcac     1560
acatgtcact gatctgctgg ctcccttgtg ggcacgggca gcatccaggc tcccagctcc     1620
tccatctccc actggatttt ctccttcagt ttctctgaag cccgagccag gcatgtgtgc     1680
agcaccatgg ctaagggcat tggcttctcc cacaggtcac tcatgctgcc aaggttggag     1740
gtgttttgtc ctgtattcca gtttgtcctc atgagttcct gcatgggttc tagtttgtct     1800
tactctttcc tgtgcagctt tccttcctgc cagcctggct gatctatagt ggcttaggtc     1860
caacgtcaga agcagaggca acagcctttt gtgtaagatc taaatcctat aataaatccc     1920
ttatcctaca gcatcatagt agttctctga tcatatcctg actgatattt ttgttgcaag     1980
taataaacca ccttcacata gcctaagcct agaaagggta attattttaa ggatgtggga     2040
gtatctcatg gaatccaagt gtggaaaggc aattggtcac agggaggggga agttcccata    2100 ttaaaacaac aacacaaaaa cacttccttt atcctctagt ctctacccca tttatgagct     2160 cccccttcaaa tgcaaaaatg gtcacaccct tctgcattcc ctcaactcct gaaaaccgag    2220
ttctaatgcc accaaactag attgtcaaga gcaacgtatg tcttcacact ctcaattacc     2280
tgctcagcac tgctgatgac ttgctgtctg gctggacctg tgactcacca cccagatccc     2340
ccttaggtga ggggctgttg cctcagcgac tgaggataag gagggctgtg cacctgttta     2400
gggatgaccc catccaattt cctccctgac aactgcactt tgctaactta taagcatctc     2460
aaaattgatg tttctaaaac tagacaatgt tctttcttct gaatttgttt ctccccctag     2520
aattgtccaa ttcagtcaac tgtatccacc atggttcagt cagacacctg gctccatcta     2580
tggtcctccc tgtctttcat cccctacgta tcattcagca tgtactgtca ctcatgtcta     2640
gccacagcca tgcagctggt acaaagggtc tgggatttct ttaggtttcc ttcttcctga     2700
ctccactata agaacagtag aagatctgtc tggaggcagg cagatgttga acaattagtc     2760
atgcatacat cttaggtcaa ctcccaaagt gccctttgtg ggctgcttag tttcacaaag     2820
gcacagagag atgcaacagg tctgaggatc ctgaattcat tcttatcatt ttgataaagc     2880
tatattcttt attctagggc attgtccagg aattgttgcc attaatcact tttattaact     2940
gaatatatcc ctatatgtgt gcactttgta ttgatataaa tagcgtacat tcctgttgat     3000
gggggcaggt gttgctttgc tttgtccaca gttcttagtc catggcaatc aagaataggt     3060
```

-continued

```
aagtattaca gatttgcaac aagaaagcaa gaaaacaaag tagagtgcaa atttctataa    3120
agaacatagt caatcaaata tttactgaat atccacttca taccaggtac cctgctaagt    3180
gctgtgaaag ggctcactga taaataaggc atggatcctg tgattccaca aagccaatat    3240
gtgaacagtt tataataagg aggaatttag tattatgact gtttatacaa agtaatacag    3300
agaaattgta tattggaatt gtttctaaac aatgctttgc aaacaattat aagagtaagg    3360
actgagaagt attaaaagat ccttcaattg ttttgggtcc agtggagtat gtatctaggc    3420
gcacctcagc acctcagcta ttcatttcca cagtaactga aaagtctaag ggagtaatac    3480
cattaatact tatcagggga attagaataa taatagcata tgctgaggct aactatgttt    3540
cgggcacagg caatgcactt tgctcatatt atatcattta aatctcacaa caaccctata    3600
aaggagcaac tattgaggct cagagagcat agacagtctc acatcctgta agtggtaaga    3660
gctacttgaa cccaggtctc gcttctaacc agtaagtgag atgtcaggat aggaactttc    3720
ctcatccctg tagctccttc tgagaagaaa gaatgaagaa agacagtgga attatatgga    3780
ggaacaggtt ggctggagac agggaagcag cataaattct ctcaggtaca ttcctccaac    3840
aaacttaagg ggagaaagaa gatttgtagg tgggtgttta cacacagatt gctagaaagt    3900
caacttctca tttgaaaaca ctcctggata tagggctgga gtgtgtccta gaatgtggat    3960
aaagaaagaa acatggaggt tgttattgaa ccttgtaggg agaatgtgta taagggtggt    4020 ctaatttta aagatgagct cacaaattcg agaaataatc cagaaaactg aactttagaa    4080
aaatgagcaa actcttccat aggactccat tattcgtcta gcagaaagtc ttaggaatcc    4140
ctggaaactg gggacttgca ccagcatgga gacctaactg ttaaattatc tggaacttcc    4200
caaacagact gacatcttgg tggttggaaa tcaacacgtt gggaatattt acactatgaa    4260
aatcagtaaa tgtgtaaatc ccccagagac attgttaagt atttaccagc acaccattgc    4320
ctagaagcaa caggggttct ttagtagaac taatgtggtg aaaactgggg gaagagtagg    4380
tgtagagaag gaagatgggg aatacagaaa tggagttaga gcaagtaata aatacagatt    4440
atgattccca catctgtgtt attcttgttt tttagaacct actgtttgaa tgcaagaaaa    4500
tgttgtacca cagatgttga ggacacaaat taaacccaaa gcaaatcaaa ctcccaacca    4560
ttaaaaacct ttgagaccat gtggctgact gtatatatta aacatatata atactggaat    4620
ttcctcaaat taattccatg ttaaatataa tgtttaataa gtgataatga tatgcattaa    4680
aatgcatacg ttacttaaac tcaaagaatg tagactaaga aaagattttg aggggagagg    4740
tatttcatca ctgatatcat ttagtactgc tagcacatag tggtaataaa aagagactga    4800
ttggttctat gattgttctt taaattctca gagaatgcac ccacttgcct gcacctgttg    4860
tactgctctt ggcatgccat gcctggatcc catctcaacc aaaatattaa gaatcttctc    4920
gggggtgagg cccggagtct attttcatga aaagctcttg catgtgattc taatgatcag    4980
ccagttttgg gagctgctga tatgggaaca aaagggacac aaatagctat gattcaaagt    5040
caagggatat ccaaggagct gctcaactct tcaaacccat tctttcactg gtctgggtag    5100
atggacgatc attgaaaaca accctgttaa aggaacctcc agggcaacta taggaagttc    5160
tcctattgtg tcagaaaaat acttagcata gatatttacg tgttaaaaca agaaaacact    5220
tatctgtaat taaaaaaaac atatcaatga gtcttcatcc ttattgattc ctctgctcca    5280
tcttcagacc atttcagaaa agtctatcct caaaaaaggc agaatttttg caaaacttag    5340
atgctattcc tttgcctggg ctttccgcct cactcagact aaagaccaac tctggctata    5400
catcctgcca ccaccactct ctctgtgact ctcagtgtct tccagccact tggcctcttg    5460
```

```
ctgttccgaa ctcattgagc actcccacct cagggccttt gcactgtctt gcctctgcct    5520
ggaactcttc cctcaggaat tcacaattca agtctgtgtc caaactcttg cctgatataa    5580
aagagcatta tttttcttca ttgcacgtaa caccatctaa catatcaata ttttacttgt    5640
tttttatttc ctctagatta ttgagggcag gattttagat gtttatctag tgttgtattt    5700
ctagaaccta tcttctgcct tgcccatagt tgacacttaa caaatatttg ttgaacaaat    5760
aaatgaatca aaatgcagat gaccaaacat caaataataa agaaataata ataataataa    5820
taatgactta caaaaaatct cttttttcccc aaaccttcta agtcatactt ctggtaacca    5880
cttcttctgc tagttgtcct gagatctcta aatgacatac ttctacttac atttcttgat    5940
ttatcccctg ctatgccaat gtaatcacta tgactatttt tatactttgt tatttgtacc    6000
ttagttatat tctctgtgtt tattttcatg tctttgagac agtgtctact gtctcctcag    6060
ttagataagg accctctttc tttccttcca ccctcccagt gtgactagga tttcaagtct    6120
catcactgaa gtcttcaaaa agatctctag gagtctgtgg ctgttcctaa caacatttca    6180
ctttcccccg atctccattt taaatttgga aaagaagtag tgtagagcaa gatttggaat    6240
gttgtctgga gcatctggag ggcaaaaaat tcttggaagc ttgcctgtaa atgagcaccc    6300
ctatattcct ttgggcattt cttctctgcc cccttggagg ctctagatga atcatatccc    6360
cagcccaaga agcaccctgg agtgagggtt ggttctatgc taattgttca cgagcatctg    6420 acttttttccc ttttattaat agaaagtgaa ggagaaataa ggagcttagt gggcaaagat    6480
ggagggagaa agctgcgaac ctcattaaca attttatctc atcgcatgta aattgaagtg    6540
tgtacattaa actttgtaga gttcatctat ggaatggctt cagttcccaa atagtcttac    6600
tgtcactgtt cttataaaaa attatactaa aggcttccct ttaggtatta aggggatagc    6660
ttaagcaagt gagtgcaaaa attttttttc ttattttcct agtgccccga ccatatagag    6720
taaataatga gggcttataa aattgcttcc cttccagggt gtagggataa cattttacat    6780
caataaattg aaggaaaaga cattgcccca tataaggcac atagtagggc tcaaggggag    6840
gaagaatcta gatcagcctt ggctgcatgg tggagcacca ggggtacttg aaaaaataat    6900
tccctctaga aattctgatg taattggtta ggtgtggtct gagtgttgac atttttaaaa    6960
gccagaaaaa aaaagaaaca caccctggtt tagagggaaa ctctgggttc ttctctacat    7020
tttccttctg atctttacag ggatgcatat catctttaac tcagccatgg gcttggaggg    7080
tcaagagctg attgtataga aattttatat tattctagat gtggtctact acatgttaca    7140
aagttgagtg tgtgtgccat atgcagcact ttcttgtgag ccctttgaag ctccatgtcc    7200
ttagcagggt tccctacact tagaaatttg gaagccttcc tttaagtttt ctgtccaaat    7260
ccaataatta gtagcataaa tcaacaagca gaatgtagca accagtacag agaggctggc    7320
ctgacagtcc tcaacgatac ttttattttt atatatccct atgctcaaga ttagtttatt    7380
aattctgtag caggttaagg gagtggaggc agctggtaat cgttgattca tttatatttt    7440
cattcaatag ccatctgctg aatgtcttgt tagggttggg gactcaatat tgaatagact    7500
gcacagcccc tgttctcagc ctagtgggag aaaaataagt aaatgagcaa ttgcactctg    7560
tgtgaatgtg cagtaatgcg gggacacagg atgctgagag agacaagttg ggacatccaa    7620
cccagacatg gttggtaggt tagggggtgg ttatgggaaa gtctcttggg aaaaaaataa    7680
accacttgga tttcccttca agaaagaacg tgctgtgctt ctagaaatgc agttatctga    7740
tagcatccag ctgttaggct ctcaggatta gccttagctt tcaagctgac cccacattct    7800
```

-continued

```
tataggcagg gggaacaagc agagtggaat ggatagtaga aggaaaggga ggagagagag    7860
gtaagcaggg agtttgtagc ccagatcatg ggggaccttg taggccattg taagaacact    7920
ggcttctact caaagtgata tgaggtgaga ggaggggtgg gcactgataa gctaattcat    7980
gtttgatgtt ctcagccttt gactttgctc cagcttccta gtcagtgatc caggggccct    8040
ccagggtact tgcacctagc aaagcaatac accagtgact cctagtctga cagattagag    8100
cagcttctgt gcagtgggag ttctaaagaa gctgaagatt tcatttctaa gttcaagagt    8160
gttatgtcct tatagatgag tatgtgaatt tttgtgccca aaagttgtag aggtcaaggc    8220
taggacatgc cagatgacat cccagaaact ttttagggtg acaggtaaaa taaaagaacc    8280
aacatctcta attgtcctcc acgttagact tgccttccct gacttgtgaa acctggttat    8340
cagtgagcct ggcaggggcc gtgaaaaggt cctggttggt gtacaagccc aaatttggag    8400
catgagtgtt tattttctat tctctgtcct ctgaagattt ccatgtagag agttgacctg    8460
ggccttaagg taacaatcca aaaaaaggaa taatttagaa gaaaattaat tcctcccttg    8520
aggaacaatt tctgtttata attttaaaat ttgtgtttta tttcactatt tcctaggatt    8580
tcattcctct agctgaactt aaagctgtct tcagaagacc catacttctc agcttctcat    8640
ccagctgcag aatacacacc aggactgggt gtgcttggaa gtccactttc caatagattt    8700
tgtggcacaa aaacaacttt ttcaaaacca cctggtgcca gggaatgcca gtttcggggga    8760 gagcaaatct gttcctgtct gcatcttttc ttcatctggg tctctgagct acctggcctt    8820
gataattcct ggtcccaagt ccacaatgaa gacagtgaca ccaccatcat tataaaaata    8880
aataaaagag atctgatgat tcacacatgt taatggtgaa taaacacaga aaagtattta    8940
gcatcgcttc aaagaggaag agaagcaatg tagaggcaaa agcaataaag ttaacaacca    9000
aaatggcccc caacaggcaa ttggttaaat ctggatacta tggaatatct ctgttaataa    9060
aagtattggc atcataaaat atcaagaaat caggtcacaa atatgcaaat atgttcttag    9120
ctttcaaaat aaaagcattt aaaaagaata ctctccaaat atcaacaata tttatttttg    9180
gaagtataac tatgaataat tttaattctt ccaaatattt ttctgtaatt tccaattttc    9240
tagaataaac atgaaacagg aaagccaaat caaaataaat tataagaaaa ataaaagaga    9300
tattaaaatc aaattttccc tatagtataa ttttcacaga aaaaatgttt gagaaaatat    9360
tttcaggaag tcatctaata ttgctgttgg cttttcctca caagaatatg atgtgatggc    9420
aataaaaagt tgttcataaa gttatgattt aaatggttag actggtctca gtgaaattca    9480
gggtcagctc tacagtttaa tcatattgtt tttactggct accaaggcta aagaagtata    9540
agtctgctaa attccttagg ggaagtggca catttaaagg gcgcaaatcc attctcttgc    9600
agccctcttt tcactgcaaa gaatcattta gttaatatga tagaaaagaa ggaagagggg    9660
gcacctttgg aatgcgacac ttgcaagatc ctatgaatga tgatgtaaat cttccctgt    9720 gttttgtaac ctgaaatttc caagatattc cactgtattc agatatcagc tgcctattgt    9780
gggccatttt ggttgtttac aattgcctgc cctacatcct tcttcctctt tgattattag    9840
tgatgctaaa atatttagat gtttattcac taatatttgt gaatcatcct ttctctgagc    9900
ctgggccctt ctaagttctt ctcccatata attcattctc tctcatagaa catagaaatg    9960
ggtatcatct tctccacttc acaggtgaag aaacgagact cagagaacta acttgcccac   10020
gattatacat tctgtaaaca atgaagctac cttcataact cattctgaaa ttacatgtac   10080
atgtgtttgc atgtgagtgc ccaatgaaca tggctttgtc aaggatgttt cctcatctag   10140
tcaccgagaa gtgagactca atcgtggcca tggagatgag aacacaatcc accaattaac   10200
```

```
agtctaaatg aataaagcgt aatttgtgtt ggagtttcac actggggcaa cagctttgag  10260
atggagaggc tttggttgct agcagccatt tgggaaagag agaatcatga aaaacagcag  10320
aaggtatgga agatgatgtc tgtgagaagc tagtctatgg gaaaatttgg ggtgtgttga  10380
caaggagtat catcatccaa ttagcaactc ctcatagtac ccaaggttcc cattttccta  10440
ggatctgggg agtgttctga agggcagatc agagagagcc aagcttgaca ggaaacaact  10500
ggagaacata cagattgggt gcagaccctc tttttctctg gcttccttgg tgatgaatgg  10560
gagtgggatg ttgtacataa catttgccaa tttagcatga gctcagcctg tgctcagagg  10620
tgtccttgtt ctgcctgggt ttctatgaaa aggagataat ttaggtaaaa gtgcctggtg  10680
catagtagga actcttaaca tgagacttct tttcctccta ccttcttagt tcattaaaac  10740
acttctgaac cactgctgcg cagcaagcat ggcctaaaaa agaggttaaa atgttcgtaa  10800
ttaattaaac tgaaagacag taaactggga ttagaaatgt acatatgtct atatgtgaaa  10860
aggagctaag aaattgtgag tggcagtagc ctgtaattcc ctagagtgga ggactctgaa  10920
agagggtgat ttatctttga gcatcgctca ggtgcctttt ttatagagtc ctgctgttgc  10980
tatgaaaatc gtgtctgtag aaatgtgtgc aaatctagaa tggattgcca gttgcatgaa  11040
tagggaagtg tggggaaggg gcaggcaggc tgacacctgt cagtctccag cactggtcct  11100
gaagagaaag aattagaatg gagagagtgc tgtgggcagg caccaccata gatagctagt  11160
gtctgaggga ctccaagact ccaatctcca ctctaccact tgggtgacct attatgtctg  11220
ttatcttagt gttttgataa ataatccttt cactgtcagt gttacctggt ttagttgacc  11280
gaatagtcac acgatcacta cagaatatag tttctgtcat aaaatgaaaa aagccaactg  11340
aaatgatcct gtacaccttt gacgatattt tgtgcacagg acttaagtta ttttccaggt  11400
aagaactatg tctccctttc tctgcacttc tcccacagct tcaattgaac agctatgctt  11460
ctacccaccc ccaaaaagga acaaatattt ttatcatctc acaaggaaaa actaaagttg  11520
tactgagtca cggaactgga gatctgctcg gctctctcac tagtgaagtg accagctctt  11580
acatatcagc cttccagact acatatttca aatttgcacc acaaggaata aataaatgac  11640
tgcctatagt gaaccccata agggtggacc attcaaagtt tcttgctgtg agcaacttaa  11700
aaaaagtgat gtgttgaaag gatggagaca tacagaatcc ttgcgggagg ctggagaaca  11760
agatttagac agtgacaggc aaaaagtcct gggcagccag accacagcca agatcaatgt  11820
cacagttgtc ccattcagac actaatgcct ctgccggtgg gcattgaact caatcgtata  11880
aagtgctggt gagcagggca agtgctgtgc tgacctgaca atggggagga cttgagcttg  11940
aggccctgtg gcagggacaa caggcaccaa agccgcctaa gagccaagga tgttggttgt  12000
tgcttggaac tgtgaaaatg taaaggtagc ttacctttcc tgcctactgg tccctcctag  12060
ataacacatc taaggccacc caattcacat ttgaaaagga aaaaggtcag tctctgttta  12120
catcccaagc aactgctgtg aggggatgga actgacttaa tcatacaatt gttttgatat  12180
cacacagaca accacagttt ttagtttgga aaaaatatgt gtgcattgac ctgagctgat  12240
ggcagcttca tctcccggtc tcgctgggct ttgctgaaac cagaccctaa aaagtatact  12300
tatgatatta aacttgtatt ttttagtgtt ggaagaatta tcactttcta aacagagctg  12360
gataattgga aaaggacagg gggaagctcc tgaaaaactg tagttgagtt tatgcttcac  12420
tgctcataag cagagactgg catccgcctc ctaacttatt gccactgaac attttatgtg  12480
aagttctgtt tcagggactc aattaaatct atgtttcacc cagctctctc tatatgataa  12540
```

-continued

```
gtcatggtct accagccttc ttccatggca aaataaaact ccatagtgga ttcaaccatc  12600
attgctactt gaaaatgcct cagagtcatc tttttctatt tctactttta cttaagtttc  12660
ttctttttgg acacattctt aattttttta attaaaactc tatcctttta gggatatatg  12720
tcaacatatc aactgctttg tcatcagaat ttaaaaagct gaagtgagga attgcgtttt  12780
ggaatgaaag ccacgtgagc agtaagggca gccagccaga accttgggga agtgaatgaa  12840
agcagaactg tggtggaaga gtttaaatcc cctttacagt ccgtcatcct cccccatttc  12900
ccagcctcta gggccgactg gaacaaaggt ggtgtcatat tccctgggca cactgcctgc  12960
cactgcactt ttgtttttttc cagttttttt tttttttttt tttctttaga gcagtttttag  13020 gttcacagta aaattgagag gaaggtacag agacttcttt cctatatact cccgtttgga  13080
caaatatatg ataacatgta tcctcctata atattacaca gaatagcttc ttccactgct  13140
cttaaaatcc tctctggtct gcctattcaa ccctctcttc tgacctctga cctccattga  13200
tgttttctgt ctccacagtt ttgccttttt tggaatcatg cagtatggac ccttagattg  13260
gcctttcact tagtcatgag catagtttcc ctgtgtcttt tcatgacttg atagctcatt  13320
tcctgccacc atactttag tgtaagcacc aagttcattc ttcctgcccc caccttgaca  13380
aagcatacat cttagaatca tttccttgcc accaacttcc tgtgtgggtg agagaaaatc  13440
agattacaca ccaaagtcta aacatctgct tctccactgg tttcctggta cccagtgtcc  13500
tcctgggctt cgagatttcc tgtttgaaaa ccaaatgtgt ttgccacctt gtggtctgta  13560
tttttaaatt tgtttttagc cagatattgt taataaattc attgcctagg gccgtaagtg  13620
taagtgtgtg ccatgtattt gtccttgttt aagatttcca ttccgtttaa caatgatggt  13680
taaagttacg aggctattca tattggacat ttgtacatca gaaatacaga actgtctctc  13740
aaaaccctgc atatcagaat agttagcagc agcatgggaa gaagctattt catttccatg  13800
gcagccagga cccagacgcg aaagctttat agattaaaat caatgcctga attgcattca  13860
gaaagcctga attgcctgtc agacttcagg accagcggct caatgtgata aatgaggcaa  13920
gggagtgcgt gccgcattag ccagcacttt ggatcctttt tcaaggcaaa taccaaatgg  13980
gatgaattac tgggaaacag caaatgaatg tcaagaattt gagatgtggg ggttataatt  14040
tactaattac tgggaaaaga tgaacacagt caatgtgtga aagaatgtgg taggggaag  14100 gctagatcag ggagacaaag agagtgagct gcacagaagg ctcctgtttt ctgttttgat  14160
aaaaagagat ggattttaga ggcatagata cctggttgaa ctcccagctt ggtcattacc  14220
agactgtgtc ataaattgta attagcatga aaagagtata tgaacaccaa gcctcatacc  14280
tggcacatag tgggcagtca ataattaaat ctgccttttc ccagatccct ttctattctt  14340
ttcttattta gcactcagtt gtacaatgat tcagtgtgag aatgagccta ccttcctccc  14400
atggcaggtc aatattcaaa gacagtgaag caaagatgca gaattgagaa acttgcagaa  14460
atgctgtcac aaagactggg ttcactataa aactgctaca tattatgacg ttttgatgcc  14520
tgtacagatg tgtcacatgg caaaataatg gaccatggtt ttattctccc gtgctcttgc  14580 ctctctttg tgacactaat gcattctctg agcccagtgg gagctaggca gagtagtctc  14640
aatcacatgc tcccaacagg gctacagctc caagcagcca agacagggac ttcctagggt  14700
ctcctctctg ccaccatgga taggaaggat atcatctgaa gaggaaccac ggagtaattg  14760
agcaagatgt gaaagagcag ccaagagaca cagatgctta tgctggacac ttgccaacca  14820
gttgttgaag gggtcagacc catcatttac tagttcttta agagactgtg taaggaaaat  14880
atacactccc ctccctttct ctagtgccct cgattttttgg ttgtggatat gggtactcag  14940
```

-continued

```
aatgccgacc acactgacca gtcttccttg cagctgtgcc aagtgatgag gttctggaca   15000
atgatatgaa agcataggta gtatgtgcaa ctccttggaa gtgtcattgg aaaggagagt   15060
gcatatgtcc tctgctgtcc ttccttgttg tgttatgcgt ttgtagtggc tgaaactgga   15120
gcagccatct tggacatgga tgtgaacaat gcaacagaag gagacagggt tcctgaggct   15180
gtctggggcc atgccaaccc tagactatct agatttcttt gtgtaataaa ggaaaaaatg   15240
tcagctattc tgaattttat gttactcaaa attacttaat cttaattaac taatagagat   15300
tttaataaat gttctactaa aatgggtccc ttgggcaaat aaatcctgga aatgttgtgt   15360
attacagaca ctttttaaag atttgcagtg caatttagcc cattacaggc tagtatccgt   15420
gggctcttgc aactcagagt ataatccctg gaccagcagc tcaatatcac ccaggagctt   15480
gttagaaatg cagactcagg caacccaaac ctactgggtc agaatctaca tttttaacaa   15540
gatcccaggt tatttgtctg caattcgttt gagaagcaca accatagatt acaatagcat   15600
cctatggtct ttgagtctgg aatagaagta gcagctgcca gtgggtatgt ctggagatcc   15660
tggagcacag gaatttttca cagccataga atggccgtgt gctcttcaag cctgaggttg   15720
ctgctatcaa cccatgaatc ctccaaaaat ttcagctctg agttttgagt cattttcagg   15780
accccatctt ggttgtcatt gactgagcta ggtttgtggc agacatcctc ttcctcttct   15840
gtagggatct cggagtgtcc ccctggtgct gcacattttg tgtcctacaa ctgctttttct  15900 tggcaagtta catctagatc tacgggaaag gtgagaaggg gtcttaggaa acctacctgg   15960
tgggctgcaa aacctctgtc agtcattttt attctcacac aactcacata tgggcacctg   16020
ggctagctaa ccagaacatc agttgaacta ggttattttg tgtgtgaaac agtaaccaat   16080
tagatcattt cttttttgctt tctggtttag ctggtgatag tatgtcaaag gcattacttg   16140
ctagtggtga gaatcttctt ctccggagcc tgacttcctg ggtttggctc caggctcacc   16200
atgcgccagc tgcaagactt cagtcaagcc tcagttcctt catctgtaaa gtggggatta   16260
gggtggtatc tacctcccag gttggttgtg catgaaatat atatgaagga cttagacttc   16320
ttccttgcta ataggaaaca ctatataact acaataaaaa tatatatata tatatataca   16380
cacacacaca agtaataagt tgttaccact atgttataat ttaaggggtc aaaatctaaa   16440
tcatgtgaat aaaaatctaa aaatgaggaa tgaaaagaag tacaggtatg aattggcaaa   16500
gttttcaatc tgtctctccc tttcattaac gcaaagcaga caatttgaac atccactgag   16560
tgccaaagtt tgaggtccat gcagggcact gtggaaatgc agtgatgacc ccagtgctgt   16620
gattcagtgg aggagaaaga gagatgcaca cataccgtat taaaagacaa atgtagaaag   16680
tgctatacaa tattctgtga aagaagcaaa gtacctgcag tataaatgac tctcatttta   16740
caaatcaata ggtggagctt caaagatatt aagaaaatag ctaagctctc agacctgata   16800
aagaaagagg tgggattcaa actcaggtct gcctgatgtc agagtccttg ctttctctgc   16860
cacactagat tgactacaaa acttaacagg cacttcatag agaaggtaac atttcaactt   16920
gacctcgaaa gatgagtaaa aagccaaacc aaaccaaaca acccactgta cttataaaca   16980
agtctgcagt gattctggcc ctccaatcac cagttttcat attctgtcca gcagtcgtgt   17040
ccccatgaaa caggggctta aagctggagg caaggagacc aattaggagg ctgtgtgggg   17100
acaacaatga gggtcaggac taagagagtg acagtggggt cagttaagaa ataaaaaaat   17160
tctgtaaatt actaaacagt ggattttaaa tctgctcata tcacttcctt aattatcact   17220
tgccatgggg gcaaagagac gcatcaacta agcattatcc ataggtctgc ttctgaagct   17280
```

-continued

```
tctaaaattc aaatggatga aattactttc tgtaatcctt gtgatttaac tgcgtgcagc   17340
ctcacagcca gcaagggagg gggcggggag gagtgaggat ggttaaataa aaacagttct   17400
atttctggca tgctttaatg acaaccttgt cttagaaata tttttttttg caatgtcttt   17460
tcagtgtcat tgaaagtgtt tttaatttca aagagaggct gtggcacggg atgttaatca   17520
atgaaattct ggcacgcttt tctatgaaca gggctcgtta tttatattta ccagtgacag   17580
agatgagttc ttcaacccag gcaatattat cattcatgcc tggttaatta aggaagaaat   17640
gccttaggaa actcatcctg atattagagg ggagaaggac ctattttagg tcttgggata   17700
tttcatttcc ccaaagccct ccctgtgagt cacaggacag aaattggagg cagaatagca   17760
tagtcgtcca gactaaaaaa tgttttggct gaaagactgg ataggcattt atgtattcct   17820
tgcttgtagg ttctgagtgc tttctgttat gtatgcaggg atgcaatgcc agctttttgt   17880
tcctctgaat tcctgtcgtt ggacactgcc aggatttagg gtagggtcag ccctgg      17936
```

```
<210> SEQ ID NO 50
<211> LENGTH: 2563
<212> TYPE: DNA
<213> ORGANISM: Homo sapiens

<400> SEQUENCE: 50
ttcagcttta ttttatagta ttgaacattc ttcaaaacag cccatctcca taaagggaaa      60
ctgggaaatg atgatatgag ccgagttctt cccagttttg agaggcaaga caccgtgcaa     120
gtgcatgatg cctggctact ggcacagtga cgtctcgtcg ctaactctcg ataatcccag     180
atcatgatta aaaacagtcc ctcttggctc ccagggaggc tgataacact tgtcaagggt     240
gggtgggctg attcaggggt actacattcg tgttgtcttg tctgtagtcc cactcctaac     300
ctcagaaagt gagtaaatga agaccctata caccagagaa aacctgtcat tcccgcaacc     360
ttccttttgc cctgcaccct ttcccatccc ccaaagtaca cttgacccct ctctaaagtg     420
gctgaattct acagtactct ggggagaaag tcaagttctt agctatgacg ttggtctttt     480
ttcccctttt gttaaaagaa aaaatgatga gaaatgttcc tttcttcacc atctcctctt     540
tctcttcctc aatttcttag gaacgaaatc acccaagata taaataaaat gttctaaata     600
aagctctgcc taactgcagc gtaagacatg tctgtgtacg tttgtgactg tcagcctccg     660
atggaagtca ttttcatgta attaattatt cttgtcgcag ctgaaagaga caggtgcatt     720
attggtgtac tttggcagac ttctgggtga acttaagaag tctgcatttc aaacacacca     780
aacaactgga gtgcagcttt ggcttttgtt ctgatattgt ttcttgactt ggaaccttta     840
tttctcaatt actgcaaact gaaaaaattg gaaggtaatt tactgataac ttagattttt     900
caatcaaaaa ccttaaattg caaaattaca tattttgggc atgtattagg taacaaaagt     960
aacaaagaat ctttgaactg aacttcctgc tctgaggcag aatgaggatg tgattttttt    1020
tctcttaaag gcaattttgt ttctccagca taaagtcggg tctgtaatcc ctggagccac    1080
gcagggttct gctacctgtt tgtcctgatt gttctcattc agtccaggtg atcagccaag    1140
atatgttttg atgaaaatag caattttgct cacccccaac ccacttgctt ttgtgtcccc    1200
cgtcactacc tcaatttggc cgtaattgta ccgctcccat aacaacagcc aaataactgg    1260
atatttgtgg agggcttata acagggttgt ccacaaagcc actggcaacg ccaaacagac    1320
cctgtatatc agcatctcac aagagagaca gctatccggg ggagcaattc ttggcagctc    1380
ccaatcaaac ttgctgctga ttacctctgc gtttccaatc tgaggccagc accccatatt    1440
tctcccacat ttcctccgta cactcagtct caggaccatc attccctcat ggcctgcctg    1500
```

-continued

```
ggacattaaa acaatgcaca cacagaggaa aacacacaac aaaaactctt tctctgcatt      1560
gagagcacca aattgcagca aagatcaggg aaccacgcgg tctcagggct gtgcttcagg      1620
ttgtgtgcta gctatcagca ccaagaatca aaacatcttt atgggtatgg atacagattc      1680 ccttttgct  gagccactgt gtgattttgg ggagcacgtt cgctgatcag ggtatgagag      1740
ctggatggag aggaagtcgc ctgttccggc ctgcacgtca tgtcaagcga agttagatat      1800
ttccctaccg acagctattt tgatctctca gtactaaaga gaaccgctgc aggtaccctg      1860
aagttgaatc ccacattctg tctgagttta ggactaggac tttgcaaatt gacagctcac      1920 atactttttgc tggtgtgcgg ccaacacaga gatgggcttc agtcaaattc agagggaggg      1980
agggagaagg caacaggagc aagggatggt gccccgtctt caaacgcaga ctcacagggt      2040
ttggaggtgg ccgcagtgtc acacctggag ctacagatgt aacagcatca gagggaactg      2100
caagcacaga gcccagtcct cccactgaag accacctctg gtgtctctgt gggccagtgg      2160
ggtacctgac acctggcagc aaggtgggcc ctaaggcctg caggcctcag gttgggtcaa      2220
gaaatgggtg tcaaatgtgt cccttttggat gaaaattaag tttttaacct aaacagggat      2280
aacgatgttt cacatttgta ggaactactg ccgtttccaa gcaattgctt tgtttactta      2340
atgatttgat caactccatg cttttggcta tatgtttgct gtctgagtgc caagtgtgga      2400
cccaggccag cagctttggt gtcctccaga gcttgggtag atttggactc caaggccctc      2460
cccagccatc ctgaatcaga acttgcgttt taataagatg cccggccgtg gcagggatga      2520
atcatttccc tgtaagatgt gctttggaat tttgtttaaa agc                        2563
```

<210> SEQ ID NO 51
<211> LENGTH: 8474
<212> TYPE: DNA
<213> ORGANISM: Homo sapiens

<400> SEQUENCE: 51

```
tttaacgttc aaaaccagtg ccaagctaaa ttagaaacag gagtctacat acctgtaact        60
tacctcatcg gtatataatt tgtaacctga gatcccctca cagagaagta aaaatagcaa       120
ggctctcaag cagacttctg ctctgctgag tgcaagggca gggtgaggga ggcagcactg       180
gggaaagata aaagggccaa ggcagagaat gccaatcatg tggtcttggc aagaacacct       240
tctctcctat accctgtgat ggtatggaga atatagccaa ggaggtgaca tcaggacctt       300
ccaggcagag gagggtgtca ctgaagttct gagcctgcct aatcccaagt taactagtcc       360
aggaaacgcc agtactcagg caggtgcaga acagatgagt ctgttttcaa gttttgtagc       420
tggctcccaa caccctggaa gagatgattt gctgcatagt tgtctcactc tctggataga       480
ggaaagcttt gtccttcctt atcctgctac atggaaaaag tgacaaagta gaaggagag       540 gaagcttatt ttttaattaa tcacatcaaa aaaatgggca tgtctctgca ttctttgtaa       600
tgattatata ttgaaagcta ttaatataac aaatgcaata ctgagaattt ctaaatcaac       660
accatctttg taaaggaaac cttacttgta ttatttcaaa tatgtttttg tgttaatttg       720
taaaactctg ttcatgtaaa tgggtttttgt tcattcgttt tgcaaattca aatattcttc       780
cagttaccat ttgaagagaa ggtatttttg ttctgcctcc tgttcataaa taggttcatc       840
aggtcttatt tattacgaag aatcaagaca gaactgcaag ctcttcactt tcctaaaaga       900
aagcaaccag gaacaacaca acagagtaga aacaaagagg gctatccaaa cctggctttg       960
aatcctggct ttgctctata agaaatgtaa cacctgagag acttaaataa cttttctgag      1020
```

-continued

```
cctcactcaa ttgcctttcc tataaatggg aacagtagtg cctaccatac tgggttattt      1080
taatgatttg gtaaaatggc atatgtcaaa gcccctagaa agaaactgtc caatagaaat      1140
atcacgcaag ccacatatgt cattttctag tagccacatt ttaaaaaggc aaaaagaaac      1200
tgggaaaatt aattataaca acatattttc tttaatccaa tatattcaaa atattatcat      1260
atcaaaaccc aatcagtaag cttatgttaa tgaaatattt tacattcatt tttttttctat      1320 gaagtcttca aaagccagtg tgtatttcac acatttggac actaaatttt cataggaaat      1380
gcttgatcta tatttagatt tcttaagatt ttcagttgaa aaaacagatt cacatacccca      1440 ggttgttcca aaagtactta aagttttcca aaaactgaac caagtatcag tgttttaaat      1500
ttaaaataat caagattaaa caaaatttaa aagtcagttc ctcagccaca ctagccgtgc      1560
atgaatcttg gatgttgttt caaaaggaac catgagccat ttattcttag cctgaaattg      1620
gcaggcttta cattttggag aattttttaat aggactagca gaggaaccaa cattagggat      1680
tattttctca gtgtggggtt agatgtgtaa tgcatatgtt tgccctgagg accccaagcc      1740
acatactgta aaactctgtt aaaatgcctt tctctgctat taacatttttc ctgtgcacat      1800 tgttcattta taatagtccc agccaaaagt ttagaaagct atgttccccc atagaccatt      1860
atttttatgc taattaatta gcaaaaccaa tatctcagct atgagatcca agctctagct      1920
actcagtttg gctgaaatct gttttttctaa ttattgacta ctttctgcta ctttaagtcc      1980
gccacctaag ttcttggaca gagctagctt ctggagcag gggatgtctc caatggcaac      2040
acagttccac actgagtggt ggagtgggag ggagggattg cagctgttgg agtcactgtg      2100
gatttgggag gaagtaagag gaagaaagga ggagatttgt aggacagact taaaaaggaa      2160
aagactaaga cttttgacaa aatttcagtg aggtgcaatt ctctaaagtt gctaatacac      2220
ttcaacactc ttaaagggaa catagtattc atatacaaca aggagaaatg aggactcatc      2280
tggaaaataa ttctgtgtat atattcttgt gttcttaggc tcttgattct ttgattttat      2340
ttctgaattc ctggaactat attttttattt ccaatttgac aggaatttag gcagattgtt      2400
ttctcattat ttcccatatt tacaatttac attgcctgtc tgattgctta catttgggca      2460
tacagatata cagatatgaa tatacacaca tataaataga tacaaataga tataatctct      2520
cactatctga gttttttataa gggtaagagg gaacagagca gctactaata ctctgagcat      2580
aaaccatgcc tcatgggcta tgtgttccat ctattcttaa caaccaaaga agaaagagtg      2640
attatcccta ggtaacagat gagaataatg aagactagag aggttacata tgtgactaag      2700
gtcctagtat tggtagagat aagacttgaa tacagatttg tctagaagaa cactgaggct      2760
ctttctccta aaacatgttt cttggaaaaa gacttgcaca acacgtgttg cctgcagttt      2820
gttcttaaaa ggaaagttct cctttttaatt cctttattatg aacatttatt ttaactccta      2880
agacagtgtg tacaaatgta tcattgtcat aagacatttt tacacctgtc aaatgggaaa      2940
ggtcatttct taagagcagc cagctgtaag tcaggggttt taaaattaaa gaaggaatta      3000
ggcgtgacag gcaataaaga agggggattgt gtgggagaaa caaaacagtt tgaaaaagaa      3060
cagagaccaa agttatggga tatttttttgc taagggcatc aggaatctat cccacccttc      3120
aatatttggt gcctttctag gcacacatta agatcagcga ttccctaagt tcacaatata      3180
gctacagaac taattctcca ataatctgat aatttactct gttataataa taaccacaag      3240
gactaaaagc ttaactcctt attttcctca cttccagttc cttagctttc aatagaacct      3300
tgaatgcttt tgtcaggaaa ataattcaac tggcacccct tgaggaatcg tggaggaaat      3360
tttgccatca tttgcatttt gagtatttcc cgaatttttaa ttatccttga accactatat      3420
```

-continued

```
gatttcacca tcttatatta caggtttagt atgtatacta ttttttatat tgacccctac    3480
ttttactgat atcattttcc ttagcccttt tcatgtttgg atctctacag ttacaccatt    3540
ctagccatag caaatggcac gtggggaata attaaggaac ccagccaaca aacagaactg    3600
aggccccaga caagttgtcc cagcatcccc agccaagatc cagtaattac ggagcagagg    3660
cgagtgacca atttaccatt ccttaattcc cacaaacttg taagtatagt aaaatggttc    3720
ttggcactgg atttggggag atttattata caaaattaga taccaaaacc aaaaattcat    3780
agggtgacta tttacccatg ttttcccaga acagtcccag tatacacctg tcgtcccaac    3840
ataattatga ttagtgctgg tttcattcac ccttaaggca tcccagtttg gatgacagtt    3900
caccttctaa tatgccatgt tctgtactca aattatggtc ttgccaaatg tctagtcttc    3960
tagtatctta aagtttgcat acagagagcc gaatgttgct tgcttctgaa tttggaccac    4020
agttgtgact gagcatacat aaaaattcag aattctttaa gtttgcctga aagaaaatag    4080
atgcttaaaa tatatattta taaaaagatt tctcaaccgg tgacactgaa aagaccacat    4140
accaaaatgt tatttacatt gtggtaccta gtaacagaag aaacaggtgt aaagagaaaa    4200
caaaattttg ttgccatttc aattttcatt gccacacatt attgaaagaa cccaaagcaa    4260
tagtttcaag actatcaggc aaactagtgt tcaaagacga aggaaaatgt tgttcacgtt    4320
tactaaaagc tgttccttct tcaatctata tagcaagcac aattacatgt gttatttaat    4380
tttcatggca ctgtgagata ggtactacta tcaacccatt ttacagatga ggaaatggaa    4440
gcttgcagag ttaagtagtc tgcacaatca atgctgataa atacaagagg caggatttat    4500
acccaggcag tctgattcca gatcctgttc tcttagtctt tagcacttac tctctattca    4560
aatataacat agagaaatta atttgtctgc atcaaatcaa tttgtaagta tcataaatat    4620
aattttgtga agaaatgat  tctgtatttt cttccttctg gtgaatctat ttctcttcta    4680
ttacaatctg atcagtctta caggaaagca aaatcaaata tactgggtac attgtctgca    4740
attttaagat gctaaaccta ccagtattta gcaatattca cttagattat atactaatta    4800
tacctacata ttataggatg tatattattt ataaaagcca ttgttgagtg attagttcta    4860
caagggctgg tccttggctt gatatttgtc aatttttttt tttttccttt tacaacttaa    4920
ctgataggat attctcctca tattgtctat gaaagtgata caaaagttat atttgagtaa    4980
aataacagag atagctcaag aaattgcata gttgaaagat atttgtccat atacaaattg    5040
gttaagtata gcccacctca gtggaaggtg gtatgtctag aattactgga aaaagtgctt    5100
attagtaatt tacaggaaga aaaacagcct tcgtgtctct caaagaaaga gttcatcttc    5160
aaaccaaatc agcactcttc ccaagaaaaa gaacaagtat acatcccttt tcattgctgt    5220
aacatgggac aggactcctt ttggccagaa caaaaaggca gaacacagag gacttgcatt    5280
aggagagata atgtcaggct gtgcagatag tagaagccag acattctgta gagtaacacg    5340
aataacaaca gtgatatcct tctatggcca tgaacaggtg cttgctaggt gttaacgatc    5400
ctttctgtcc ccattttata gattaaaaaa agatatggga aagttaagta aattgcctaa    5460
aatcagagag ccaggatttg gtctagatag tctgtgctca taaccacagc attatgctaa    5520
acaaagaaca gagatttctc taggaaagaa caaagctatt attttacctt atataattct    5580
atttaatcca aattcatggg atgaggcata aagaagatgg aggggagat  tagaaataaa    5640 tatcaggacc ttagagaacc atatctgtaa tgcttctgta gggttacttt tacgtacaca    5700
atattttgtg tgatccatga tatggaccct tctctctctg tgttctgtat ttcagaagat    5760
```

-continued

```
tcagaaagac ctctaagtca taatgattcc aagcttaatt caagccaacc atccagtatg    5820
gtttgctttt aagttcagat gggcaaactg tattaagatg atggggagga gaggagaatt    5880
attttattca ttgtcgtgat agatataatt aagttgtaaa taactcagaa gtaccaaggg    5940
agaactgctg caatcctaaa taatgattaa accaagccta aaagagacca aaaagaatca    6000
ggctttctga acagaacaga aggctacaca gaaactgtct ttaaatgtga gagcaaacat    6060
acataatggt gacattcaac ttcaggatga attccttact ccagattttg taaagcacag    6120
aaacagtgac ttcgtatttt taattttta aagaaaaaaa tacatagccg gagtgatttt    6180
aatgcattct ttctctgaga ctgggacttg attagatggc aattcaaggt cctgcaaatg    6240
ctgatcatga tggaacctaa ctcctctgtt ggcaggcact ctgatggtag gcacttccat    6300
tgctccatgg ccattattac aaccccaaca gtgccaagag cagatgtttt tttctgttgt    6360
tgtcggtggc atggagtcct atatcccata aatgtaaact aggtttaatt tggactttta    6420
gttagaaaag aaaaagttgg ttcttaaggg gaaagatttc taaggacctc ttcaatactg    6480
tatagcaaaa acacagaaca tgccatatga acctcacttg ggaaatttaa ataggagctt    6540
tagaaactaa cgtgatttgg caagaacgta attgaatgtg gttgtgaggt cccactagca    6600
acatatgctt ttactaagct gtactattcc tttcagtctg agctttttaaa atgttacttt    6660 atattttcta tgattatcat tcagaaccaa aaccaaagta gttaactctg aataaaacta    6720
tcctattata aaattagagc tcatcctgag gaagagatgt ttaaatgtga cccctttctc    6780
ttctctccac cccttccaaa tacactcata aaaactaaag ggggaggagg aaaagtctgt    6840
ttatgattat gaattgaact ttgaaccatt cctattgttc ctgccaagga tttttgaatg    6900
ctaatgtaaa aagatatata taaagtaaga tctgctaagg tattttaaga gtctacagta    6960
atgcaccaag ctttttttcct tgcttcattg ttaaagataa tatgcctttc taacaaaaat    7020
gctttcaaga tgtaaccata ttttgaaatg aatatcataa tacatccttt gcaagcctgg    7080
aatttggaaa caaagaactt gctttaatct gtttttcttc ttacctgata agcaggatga    7140
cagtgctgct ggaggaggtt tagacctgtc cccagtctca tttgctttttc ttcctctttc    7200 ttcatcgtgt gggccctgac aacctttctt tctgaagcta cataaattaa acagggctaa    7260
gactatcaat ttttgtacca gctccaaaac aagccaagac aagaaagaat cctccagttg    7320
atcgacagac ttccagtatt tctgctaaac tggtagagcg gtgaatctcc atgctttcct    7380
ctctaatgaa ataacatcag aggttggatc cttggctgtc tttaattttt tcccttttac    7440
gtagctaaaa gatatttcaa atgatgtaga aagacaatat attctcttta ttgttcattc    7500
cttctatttc acaaatgctt ctagtcttgg ggtatcagct cccctgaaag tcagatctaa    7560
gaacctcagc acacaagccc tgaagtggcc tgaagcacag cagtgaacat gcttcaaact    7620
gatgagttga ttttttcctttt atgaggtctg atcaacaaaa taacttgtga tttttcagat    7680
aggtacataa aggatggttt ataataggta atcaaaggaa gtatgattca atttgcaaag    7740
taaatgtcag tagagccatc tgattagaag acaaggcaat aacatgaagg atctactagc    7800
tccagaaaag actcagcaga tagaagggtc ccaatatatt ttagttgaaa ctggatctta    7860
gatctgactt tagattgtgg aatttcacaa aaccactgca ttaccagaca attatgcatg    7920
catattgtct aattggctaa ctccaggaac aaaagatgga caactgttac agttatattc    7980
tgatgaattc aggctaaagt ggcttgaatc aaggaatatg gtgaccctaa aattataatg    8040
aaaaacaaag caaaactata tatcttgttc tttcctctca tatctgtgga cattaaaaaa    8100
aaaagcctca gcttttcact agtctgaatg gtataggttg gagaagattt tagacatttt    8160
```

-continued

```
ggacttaata gacaaaacaa tgcagttaaa tgtattaagc aatttacata aattaccaaa    8220
acattatcaa aactactcta tgaagtaagt gcaaatggta tccccctta tgaatgagaa     8280 cctgaggctt tgaaaagttg agtgaaccaa tcacttacag ctagtaaatg acagaactgt    8340
ctctgaatca aggttatttt tattgtgttt agacacagtg acttggaaag tgtgtttgta    8400
caaatgaaaa agagagaggg agagattgag agactcaccc ttgcccctct ttgctttctt    8460
attaccatct ataa                                                       8474
```

<210> SEQ ID NO 52
<211> LENGTH: 1938
<212> TYPE: DNA
<213> ORGANISM: Homo sapiens

<400> SEQUENCE: 52

```
ggggctggtg accagaggag gcctccaggc agaaaggggg agtgtctgca gaagccagag      60
gggatatcag gacagctggg agcgcctcca ggacaggctc aggcctggcc cctgcaggga     120
cagtgacagg gagtgggtgg ggctgagctg aggaggctca gctaggggga cagtgcagca     180
atgcagcccc tataagaaga cccaaggccc cttcggcggc ctgcacagac cacggcctgg     240
gcagagagtt cctggctctg gggaggcagc ttaagcagcg actgcgggtg cccaagaaca     300
tggagcccag gcccaaagga ccttgtacct tccttgtcca ggaggctgta ccaccactgg     360
cagggtagag aatcaatgcc aaagtgagct cctcttacag gcgcacacca tcccattcaa     420
tcctatattc ttatcccta aggttcccca agcactcact aagtgctggc ccctgtggag       480
cacctgacag agaatcagac tcctaggagc aagaactggg cacatctcgt tcactgctgt      540
gtctctgggg cctagagcag aggctgacac agaggagaaa tatctgttga gtgaagggat      600
gtgaaaagaa atcacaacca cctgagaggc agaaagtatt attcccattt tctggatggg     660
gaaagtgagg ctgagagaag ggaagtgagt aacttacttc cctggaactc aaactagagt      720
ctgggtttgc tccttgcata gcagcggggc agggaaaccc ttcagcactg atttagtggc     780
ttttcctgga aggaagtggc atctgccaat tagctccctg tctttcccgg ctagtcatgg     840
ctgggatgca ctcacagccc agagaggggtt caggttagga gagtaaggct aagttgttct    900
taaaatgact ggtaaagatt cagtcacagt taacatttac cccaagtact gagcgagaca     960
cagtctcagt tgttcaccaa cctcaggagg aaggtggaat tctcctctat ctcacacatg    1020
gacacagatt ctgtcaagtg aagtgatgtt ctcagtcaca caggtggctc ttggacggga    1080
acgaggcctg tggtcagctg gatgtgagga gttggggagg aagccaatga gggaggaagc    1140
tgtgggcaat gtgatgtctg ggtttcacta ggcacaggga ggggctggga cctggcctca    1200
caaccaccac catgaaggga cggctctgaa gtgacagacc agacacctgg gcaggcagag    1260
gcgttttcat ccagcaggac acctgcagac acgtatcaaa acctgccatc actgtcctta    1320
gtctacgact tagggaaaga gtcatgacaa ggaagggaag aggttgaggg ctgcatgctg    1380
gtatccatgg tggccaagaa gcaacatgag tccacagccc tggagctcag ggtcaagtat    1440
gaaacagata agaaaaccta aaacatgggc tttccaagaa acatgtaaca cagcacatgg    1500
ccccgggggg ttcctggcac acctcgtgat tgtcagatga ggagctgagg cctggaaagg    1560
aagagcgaca tgtgaactaa tgatgaaacc aagacgggtc gcgattgcct accacccaga    1620
gccccagccc ttaggcactt gatgactcct tcctcctgaa cagtgatgtg tcagctacaa    1680
caccacagca gttcagatca tgttcaaagg tagagtctgg acggcactgc tcagcactgg    1740
```

-continued

```
agccactacg tggagttccc gagcacctga aacgtggcta gtccaaatga gatgttctgt      1800
aagtataaaa acacaccgga tttgaacatt ttgtatgaaa aaaggtttca agtatctcat      1860
gaatgatttt ttgatactga ttacatgctg aaataacatt ttctacattt ggttaagtaa      1920
aatattttta agttaatg                                                    1938

<210> SEQ ID NO 53
<211> LENGTH: 1638
<212> TYPE: DNA
<213> ORGANISM: Homo sapiens

<400> SEQUENCE: 53
agcccagtca gaagagaatt ctacagtgac atgtttataa ttgtgccctc ctcaagcaga        60
aagcaattta aacacaataa agtattgcat aagaaactgt ggtagacata tagaagcata       120
caatgtcagt gaatcctgaa gatggataca atgtttgatg actgtgttcc aaaatacctt       180
cgagaatcca gacatgtttt ataacttaaa ctgatagata tatattttaa tatatttatg       240
tctataaagc caagaagcta ataatgccat tttctcagtg ttaatattag ctgctttgta       300
aaactaagca aaatattaaa ataatgccat attttggata aacagtagac tgattggaac       360
tggcatcttc aaagccacca aagcattcat tcacagctca aactggagaa tttactccct       420
gttttttttt aatgaaacaa ggtaaatttt gagctgcttt cttaattcca ttttctaagt       480
gattatttta acacaaacta ccctgagtct agctggaaag agaagagcaa agggagagaa       540
agtccactat ggaatggcag ggctccaggt cacctgctct tctggaaagg tccccagaaa       600
ttctggcatt gtgttgactc agattcttta acacttgtat tgtacacatt aaaaaggagg       660
aaacctttaa aacactagta ggaggggtca gttgcttacc cagaattcct tctccaggca       720
ggtatagctg gaggagctgt tagagccatt ctcctgctat ctgtcatttt ctcagatgtg       780
ctatcaacag tgcttgccac taaacctgct gagatagtca ctggcccatg agagacaaag       840
cttgtcactt aaccagagca ctttggttgc aagatgtgac caggtggttc catgaacact       900
taggtcctaa ccccccagatt cagggaaatt tgagcttctt ctgagtgata tagaaatgct       960
aagactgtgg gactttagcc agtgtttctt tctcttggtg gacactggcc aacatccatc      1020
atcgaaagag ccatctctgc cctgagcttg ccaaccacag aaaactctga gaagaatagg      1080
cttctacaat ctcatggcta atctgtgttt tcccagacgg taaaagatct aaacataaac      1140
acaaattcaa aaaagcctaa caaaccaatc atgaagccaa acaaatgcaa acatggatat      1200
agtttcagga tgaatggatg aatcccatgt gctatttggt atgcagggaa tctaagggaa      1260
tgtatttata gtctatttcc tgagagagta atagcaaatg acatccacag gttcttaaat      1320
tgcatcactg tcatcctgga tgtccttatt tcctctactt ctgaatgcca gatttgggac      1380
tttaattatc aaatgggtgt ccctgttcag atgtctatac ataataaagt cagaagggag      1440
tttaatttga gactttgtga aaatttactt aagaagcatt tctatagcta tatagaaggg      1500
attcttctag attatttaca gtatgagttt acttaatctt ttgagagatt tttaagagaa      1560
agtattttta tggtctctta cagtgaagaa actgcccaag tttccagagg atgacagagc      1620
cggatgcaaa cccgggca                                                    1638

<210> SEQ ID NO 54
<211> LENGTH: 9353
<212> TYPE: DNA
<213> ORGANISM: Homo sapiens

<400> SEQUENCE: 54
```

```
aatgtgaaag gccctgagaa accccaaacc acagctttcg atcaaccaca gcatagtggc      60
cctctccagt tctgtcagct cctcgccgac tccagtttgt agaacagtgt ggagaactcc     120
agcatgttaa ttccttatgt ggattgagag cgttttgtgg tcagcacagt ctgaagctgc     180
catgtacttc accaagacag gtgttccggg gtgtcagggg agagaagagc agcgtctgtg     240
aacgagaacc tgggggtcta gagcactcag gtgctctttc taggggtgag tgggcaaaca     300
ccacccacac tgtcatgtaa gtttccacaa tccagttgtc acttccagct gccaatgctg     360
aacttcatgc tcctgtcttc cactttgggc ttggtagaga tagcagcccc tggagcaggc     420
tgtcttggct gaatacatct taccctctcc atcactgcca gtcgcgaatg aaaattatgt     480
gaaatatctc acttgataaa tctctaattt atattgtgta aaaaagacca cagggaccag     540
ataaaacatg ttaggacaca ttgctctgtg gctactagtt agtaacccct gaaaaagcct     600
taggcagggc agggcagcgt agttgtggca catggtttgt gttcccaggg gcaacaagag     660
tattccattt cagtttggag atccttgtca aagccagtac attttgctca attgatcatt     720
atttttcttt ggctgagtta agtagcttcg ctctttctaa aggatcaatt ccttgtctca     780
ggagcatttg aagcttctgg atgaggatta gaatgattga aatctactgt gacctgtgga     840
gtgactaggc aagtctcaga tgcctctaac cctctctgtt tttctctcta cagaaacttg     900
cttcaagaag gagtctctac tttaagtgcc aggctaggag cctctttatt ggaccacatt     960
agttccctac agcccaattt tgaattatta ttttattctt tcttattctt taacactcaa    1020
gaaacataaa gcctgtgatg tagttcatgt tgtgagttaa gggaggtaca agaagtgtgt    1080
ctttcaggtt gagaaacaca tgccaagatg gaaggcagag cataaatgca cgggggagaa    1140
tgtatgtgaa ggataagggt ggggagcagg agtggtgggc agcagtgcag gcctggcact    1200
tgctgaaggg aaagagagtt gggtaggaag aatctagact acagcatagc tccaagatat    1260
gggaagccca agaacagagg agttgccact ggggcctggg ttgtgcccag ggaggggagg    1320
cctcagtgtg aaggctgcag ggagcccaaa ggatccatag ttaaggcttc atcctgctac    1380
tcctaaacac tgcttctact gagggaccaa aaaagcttaa aaaccctcct ctgtggctaa    1440
agtggcctca tggcactgat gtattcaatc aactggaagc agaggtcagc tgggaacttt    1500
ggggattgat ttacttttaa aaaaaaaaaa atcggaagtt gctagcctct tctttctgcc    1560
ttgaatgtct agagctggac ctgtcctcct gtgaccctga agacagtaga tgggttcttg    1620
atgacattct gagaacgtca tctatgccta ttctgggctg cttgttgaat gagaaaaata    1680
aacctctctc tacttcttat gtgagaaaaa caaaccactt tgttgaagcc tctgttagct    1740
gagttatgtt attgcaccca aatgcccaaa tatcagtgaa acttagtggt gtgtcagaca    1800
gcccagatgt tgatgatgtc atctggcttc tgaatacaac tgtgcctgag actaaaccca    1860
agccccggac ttttcagcta ttagagaaag agagttctct ttctgcttaa gcagtttagg    1920
ctggattttc tgtggcctgg atggaaagac ccctgatacc aaaaggttag aagcttttac    1980
agttccttgt ttggaaaccg ggtcctagtg tcccttgcgc aggatgcttt tctgactttt    2040
gtggcctgcc accattcgca gtgggtagtg tgactcagct tcccattccc aaaactccag    2100
agccacattg ctgggtccct tcactctgct ttactctcct cccaagagta gcatgggcca    2160
cgtgaattca tccatgtcct gaactaatct ggttgttcta ccaggttact cttaagttca    2220
tgggccatca cccccttgta cttactgagc tccaggggttt tcatctcttc tgagaatcga    2280
ccgtttagtc caatcttagt acagaccagc attaataggc aattaccaca gggagataat    2340
```

-continued

```
acagagggaa aaatggctaa aaatatacag tgaatcacag aaaattacat ctcttaaaac    2400
ctacagtgta ttcctattgc catagcaacc cttggctagt aaagacagag atgatttatc    2460
acaggctttc cccggagctc ggttctgccg gaagcacctc cagcctgtgg tgagttccag    2520
cgaggagggc aatgcagaca cgggttttct ctcctccatc ccttccagtg gcatttctgc    2580
ggaagaagac ttgagttcct tctataaacc caggtcatct cccggcccct ttctgagatg    2640
aaagtggctg tctctaacct ctgacaacgc ggcgtcctgc cgagccagcg gccttccagg    2700 aggggcagt ggggcgggga catgaggagc tgtaccagac cgtctgaaca aatgaggaga    2760
ggagaggagt tctcctcctt tccttttcct ccctacttct cctctcctct ctaccctgct    2820
acttccttgt gaaatggact ggagaggaag tcatgtcctc acttggaaat gagtctggtc    2880
tttaggaaga ttataagtat gtaaataaac atcttgttat ttcgttggaa ctctaaaatt    2940
cactggcata gatctttctc ataatgtaaa aattagattc ttgatcaagg gatgttaaaa    3000
gtgggtaaaa atttgatgag aaacagtgta tttacacaat ctcaaagtag atcctcataa    3060
aacacctatt gatttcaaag gaaaaataat acagtagaga ggactgataa tccccacctg    3120
aatcaaatga tcaaaaacat cgcaagggac aaatgggaca gattgatagc atatctcctg    3180
atgtgtgtgc taaggacatg atatcacctc tgtggttttc ctgccaaaaa ggtacaaccg    3240
gaatctaatt gtgaggaaac atcagactaa ttcaaaagga gggcagtcga taaataaatg    3300
gcttacattc ttcaaaaatg tcagtgtcat gaaagacaaa gctgaagaac tattctaatt    3360
gaagaaacct aaagtcgtga cattgttaag aggttggtgt tggatcaaaa cattttttc    3420 tctttactta taaagaacat tattagaata actggtgaaa ttttagaaag atgtatagtt    3480
tagataatag tgttgtgtca atattaattt cccgagttag ataatggagt tatgaaagag    3540
aatattcatg ttttttagga aacatacact caagtattta gggataaagg gggatcttat    3600
ctgcacctta ctctcaaatg gttcagaaaa cagacatagg gaaggaaaat cagaagcaga    3660
cagggtaaaa ggacacagga attgtctgta ctcttgtatt tttctgtgaa aagtactttg    3720
tgcttttctg taagtctgaa atggtttcaa aagaaaaagt tcccatctgc agactcaaat    3780
ccttttcagt gaattttctt cccagtcttt cttttccctcc ctctgatggt atgctccgtc    3840
ctcacagctc cctttacaaa gcgaattctg tatgggggag tgtgaggaag gggtgtgtgt    3900
gagtgtgtgt gtgtgtgtga atgtgtgggt gtgtggatgt gagagtgtgt gtgtatgtat    3960
gtgtgtgtgt aaatgtgtga gtgtgtgggg gtgtgtgtgt gaatttgtgt gtatgtgtgc    4020
gtgtgtgtgt gtgtgtgtgt gattgtgtat atgtgtgtgt gaatgagtgt gtgtgtatgt    4080
gcaactactc cgatgtcaca gcaaaccata aagccgggat aaagtcagtt gttacgatgc    4140
cgaataaggc caggaatgaa gtcagaagcc ccttggtggt tcttttcagg tttctgtgga    4200
caggagggcg tggtctcggc gggatgcact cccagctcag agagtgtgag aaaaagaccg    4260
agttcctagt ctgcatgctc gccgctctc actgtctccc cctcccctgc tctctttctc    4320
acacactcct ctctctttcc tcttctgtcc gagagtgcct ttgaatactc tggaaccatt    4380
tctctctggg acagacatct ctccacagca gggttcttcc ctggggccag agagcaaggt    4440
tcagtatgca gagcccgcta actttggtat aatgatagct atgggtttaa tgtatattgt    4500
gttgaggttc attccttcta tacctaattt gttgagtttt catcatgaaa ggatgttgaa    4560
ttttgtcaaa ttgttttcca cacctattga gatgatcaaa tggttttat cttcattctg    4620 ttaatgcgat atatcacatt tattgatttg catatgttga actatcttgc atccaaatcc    4680
cactgatcat ggtgagtgat tcttttaatg tgtggttgaa tttggtttgc tagttgttct    4740
```

```
gttaagggtt tttgcatcta tattcattaa ggatattggc ctgtaatttt cttgttatgt   4800
ccttgtctgg ctttgatatc agggtaatgc tggcctcata aaaagagctt ggaagtctcc   4860
tcttctagtt tttttggaag agtttgtgaa ctgcacctta gatattgaca ctgtcaacaa   4920
ctcttggttg gcctttggtc tttggcgttc tagatttttc tttacttctc ccctcctgat   4980
taagggtcat gtgtctctaa aactccacaa cggacacagt cccttcaggt gctccgcctt   5040
ctcaagctgg ctctccctaa ctggcctaga cagcagcaaa gcccagatat ttccacgtga   5100
ctcatgcaac ccccttgctt ccaatgtttt gcctcctgct ggtgctcaga agctcagagt   5160
ggtattaaag gggcaacagg aaagcagcaa gactgccccc accccacttg ctccatctac   5220
ccactgtagg gaagcaactc cagctcctaa ttatttattt tatgaagtgc tgcccttggt   5280
gttaaaatca cctcagggca cagagcacac aattttaaaa caaaagatac aaggcagagg   5340
cttggcaatg acgggcactt tttaaaaatc agcaataaaa tgccagtttg aggctcaccc   5400
cagggctctg aagattctcc aagagggctc tgtcgatggg aggggcaggg agtgagtttc   5460
ctacagctgt ttgctcacga agctgcctct ctactcactt tccttcacac tctctctgag   5520
tttttatgac tcagcttgag gccagaatca actcatttat tttcttcctg tacctggctc   5580
ttggggctgg tgggggtccg tggtgtctgg caagggcaga gtggcaggcc tgctttaaga   5640
gcctggcgtg ggggccagca tggcagctag tgcgtcactg ctgggccttg ccagtagtta   5700
aaaaccaaat aataatattg ataatcacaa taataataat aatatggtga gagctaatct   5760
tgactgaggc ttctgtgagg tgggtatctt ggctcatcat taagggttct tcagctttta   5820
aagatgtgtt tagaatcaga ggggaaaagt ccaaagcaac catgttattg gatgggaaaa   5880
gaaaagtacc atgttgaagt cattttagct tgaaggaagg tcacagccac tggtaacaga   5940
gatactctca tggcagatag gtttacctaa agcacgagca atgaactaaa gctggaatga   6000
tcccagctat aattcccagc ttcagtgcct gcatgacttt ataaatgaat ttctaattct   6060
cagaactcaa acagtcattg ccaaatattt attgaccatc tctttctgcc aggccctgga   6120
gggatctctc aggagaagaa acattctcta atcaccacag gtttctctcc agagacctca   6180
gcccagcacc tctgcaaggg gagagaggag aggcgtcctt cagctcattt atgcctgtat   6240
tgatcgctgc tgcctcaccc tcgatgtcgg tggttaccat ccagtcctgt tcgatctgat   6300
tcccatgcaa ccatgttctg gaattccctg agcactactc cacctgaaga gcagcccctg   6360
tctctcctgg acagtaatga ggtttccttt gcagtctcac actggcttac tatctcatcc   6420
cgccaagcat ccccctgcta cattcatttc tctctatgcc cgggtttatt cagctgtgtt   6480
ctcctctgct ctgtgggcga caggagactg tcacagccca gttggaattc actttatctt   6540
tccctctgcc ctatacgctg agcaaacatg tgcagttggc atttcagcag tggaaattct   6600
ctgaccccct ttgctgttgc ctaaaacaga aacctcagtg gctttgcagg aaaattccac   6660
agtctcctgc aacctaaatt tagctatttg ttgaatatac atgatatgcc ttgctgttgt   6720
gccctcaaga ggcttatgaa gctgttggtg aaataaaaca gacacatgtg aaacaatttg   6780
aaaacagcaa agcacggtat aatcagtatt atcattaggt gccaaaatgc gtgatactaa   6840
aataccatca actagtcata gagctgacac acactgagta cccaggcaca tctcatttca   6900
acctcatgac aagcccatga ggtgggctta ttgtccccat tttatgcatc aacaaactga   6960
gtcacagaga atttaatagc ctaaggtctc ttggctggta agacaaccca gctctgttca   7020
actccaaagt gtgtgcattc tcattctact ctatgctcaa ccactgccct gcttagctcc   7080
```

-continued

```
ataaaggtgg agtctaggtg ttttgcttgt ggctgtgttc cagagcccag tgctaggaag     7140
catgctgcac ctcttacaga aagatctata ggaaaagcca gaccagctag atcgctttct     7200
cgagtcagat gtgggacaaa tgttgagggg tttggaggat gtccaagttt ggccatccca     7260
gtggtgtagg gtttgcgttt gatcatgaag agtggagaaa gagaaaagga aactaacaca     7320
tacagaaaca cacatacacc gcatgaaaca acacaaaccc cacatacccc aacactgctc     7380 ctcttttttga ggttctaaat ccagttcttc ctggcctctt cctgcccctc acctgccttg     7440
gtgggacctg cctgctttta tgcgcttaag tctgaatcac acctggagag cggggcaggc     7500
ttaatcctat tttttatccc ctgagatggg ttagtccttt gcaggctata tttgttaaaa     7560
tgaattgaaa tcaggagtgt aagacttttt ttttgaattt gtttcttttt cttgtctctt     7620
tttgggaagt agcaatggta gaaaggaaga acagtagaga cactcctcga tagttacaag     7680
gggagatgaa gccttgggtc tgatctgtcc cacattagat tcccatttga aaaaaagaga     7740
aaggaatgaa gctacctccc tcatcaagtt agcctggggg gtctgccgca aagaggattg     7800
aaggggaaat gttcaatttt accgctttgt tctgctgggt tcttctcccc aggacactgt     7860
ttagtgcact gagtgaagta gaaaatgaag agcaggtgag caatcagctg tgaaaagctt     7920
taatgggccc ggcacccctt tgggaatgag gctcggctct tgctagtgct ggggaacaac     7980
atctctttca gttcagtagg ctttgttttt gtaatgggaa tttaactccc tcaggtggtc     8040
ccgggatgga ggaataactg tgctcagcag cagtggcgct gcagcatctt ctaaagggaa     8100
ccaaggccac tgtccccaaa ggggcccctg gctcactggg aggcctttgg aaatctcaga     8160
cttcctgggt gggagaggag gagatcatgt gaccccgtga acagcatgat gctgtgatta     8220
cctggggctt cctagcaagg gcactgggac aggtcctgga ctgagagctg caatggattc     8280
agacccatac attggatccc cttttttatgt ttttgagtag aaaactttat aaattatgtt     8340 tggtttttaga actgtcctct aatgtaactc tgtgcagaga ggtttacgtt atctcacata     8400
atccttacaa ttatacacgg taggtggcat tattcttgcc ttacaaatga gaaattgagg     8460
ttcagagagg ttacataact tctcagggtc acacagtgga gctggattcc aaatgtaagt     8520
tcatttgacc tcgtgttctg cagccaaaag agcccacttc aaaccgaatt tctacttccc     8580
aactaaatgc cactggcatt tttaaaagta cttgagatgc acctagaata gactctgatt     8640
tttagtattc cctttttcagt tgaagaaaca gattcgagaa gataaagggtc acacaggtag     8700 gaaggtagtg gagagccaag actagaaccc agacccatgc gaggaaaaat agggatggaa     8760
agcccagggg aaagctgcaa aaactggtca agctgactgc cccttttatct cttccttcct     8820 caaattcacc tccctacccct cttccacgtc cctctctttc caagcattgg gccagttcca     8880
tttccacgtc ctgagccagc tgtcataatc cctgcaaggt gttagctgat aacagcctgt     8940
ggaaggattg taaatgttag cccagcggag gatatgaaag gctgtagaag tctaaaagca     9000
aatgtgtgct aagacggtga cagagggcct ggccaccagg cagccttgca agatggcatg     9060
caccttggag tattcactca gcgtctggtc tgtccccagc cttgctagtg cagacactat     9120
cttctcttgc ctcaaatttg actggatgca gggatggtga tttgtagtaa taagctcaga     9180
gagaaatgca aacaaaaaaa ccaatttact aaagtataat aagacataaa acagctaagc     9240
tgactttagc ttgaccagat ctttcctctc acaggacaag aagatacctg gggaatcaag     9300
gtctttcagg gctctggaat cagtgcaggt ggagttagat aggaagacca gag           9353
```

<210> SEQ ID NO 55
<211> LENGTH: 8756

<212> TYPE: DNA
<213> ORGANISM: Homo sapiens

<400> SEQUENCE: 55

```
cagctccccc atcactgtcc ttacacgcca aatagctgtt tctccccagc tgaacagagc      60
agtcctttgg tgttcagaag acatctttct ctatcatata ttcagatgcc tatgttggga     120
atgcagccaa agccctgaga gagaacaagg tgctacagag tgcttgatca ctcatcacat     180
tcccgccttg accattggtc cagagccctg aggctaccgg aatgggtgaa tcactttgga     240
atcccagcat aactctgggg caattctaac agagaagcag ctatatatag ggcccaatct     300
tccagttttg tcttttacat aaacattagc ttgtttttcc cccttcttag gaatcagctt     360
ttcctctgat ggaggttgtt tcactctgac cttatcctga gaaaactccc tccttatctg     420
tgggcatgtc ttgactctag cagaagtaga cataagtaga gcgggtttgt tcattgactg     480
tggcctttat aagttgcacc atgatagacg aggctgctat ttctgggtgt ccgcccccat     540
cattaccatg cccgggggctt tacaaaatag ctgggttgaa tcacactgac agaatctttt     600
agtcactttc aattctgcca aggaaatata ggcatgagct ttcagattct aaattaactt     660
tgattcctac cagatcccag tcccttttag gtcacaaagc atctgaaaac tcagttgaac     720
actttcattt aaaaagaaca gataagggat aaataattga agccaataaa ggattaagat     780
ctatgtcaaa taaagatttt atccaaaatg taagaaaaac ggagatccca ataaactatt     840
gagatctgtc caaactttcc aaccctgaat ggaagccaag acagaaatat ccagttaaag     900
gggtcactga aatgtggttg gctctttccc caagagcagc tcatcctggc attagaagct     960
gggctcaagg agccacatgt ggatttgaat ccaaagagcc aaagaagaac atctgatgag    1020
gccacaactg agagaccagg agcaggtgtc aaaagctgaa atatgggagg gatggaggga    1080
aaatattgca atgtatagaa acattaggct cccctaagaa aacaagtgaa attatcacat    1140
atttttatca aatggaaaag aaagtctcca aggcaaagga cagccccaat ttgtgaaggg    1200
tgaagctgga ggacagacac ggccaccaga gagcaggaaa tgcacttgat gccatagaaa    1260
aatctttggg aatcagctgt actggcagcc caggagaact gttgcactca gcagaaacca    1320
agacagcagg gttctctctt aatggctctg ctcttttctg atatggccag cttttccctga    1380 tgtggaagaa atacaagcag gctgtgtcac agacactctg ccttcatggg gctaaggcag    1440
acagagattt gggtgcaagt tttttaacat aaacttcgcc ttgtacaaga tccctcctac    1500
ccatagcatc cttgaatgag gactaccagc cctccagtta aagacttaag gattctagat    1560
tcatccaagt aagacctaag gagaattcac ttgccttaat tttgggcaaa tatggaccat    1620
tcagatataa cacatacaca cacacacaca cacacacaca cacacacaca cacacagaga    1680
ggataaatgt aacactcaga gatagaaaaa ggttgggaga gatgaaataa gagcaaagag    1740
aaacaagaaa tgaaagagag atggataagg tagttaatga aaggaaggac agcactaatt    1800
ttgcagaatt agatctgtaa tgtggaggat aagcctgagg caatctcaga atgcatagca    1860
aaaagacaca gattaaagtg ataaaagaga aagtggaggc cagaaaatga agaaatcatc    1920
atgtgagttg gctgcatact agctctaaat gtttcttcta ctataaaatg gggtgataat    1980
actactctat ggggtgctat aagggttaag aaaataagta attagaaagt gcctagcatt    2040
tagaaagtat caaataaatg gtagttgtta ctactattac tactaatatt attattaaat    2100
aatgagcaca gggtcacaag aaaaaatcaa taccactgac tgtggtcatt ttcctgagac    2160
taagttagtt tgtcagcaag tagattttttt ttaagaacat agctgctata gttccttttt    2220
```

```
tttttaaaga atgtctgctt tttatcttct acataaatta taatttaatg aatacaaaat    2280
gtttaggtaa aacttcctaa aagaattttg catacagttt ctcattgtct tctgagatta    2340
aatgttacaa tggagaaatc agagacaagc ttgaggttct tacatggaat cttttatatgg   2400 aataaaaatt gcagatataa cattgtcttc gaagcttagt aactccatat atctttctgt    2460
cttttttttt cctttctgga ttcagttctc ttaacctgcc ttctatgata tccttcaatg    2520
ctgtcttatg tgtttgttct tttccagcaa cattgctatg cttatgttgc ctttatcttc    2580
catgaccatc attttttcttt ctaacaattt atatacatct ttactcttta atttactcaa   2640
gcctctcctt ctcttgaaat tattgcacta aagtgacttc ttttttctata ttgtagtttt    2700 cagttttttt cctctcactt tttctccttt ggctatctta gaatgagtct ttatctctct    2760
gttttttttt caaaggtgcc atgttctttt taacttctct gcatggctgg ggcaaaggga    2820
tctgagtcct gggtcattct ttctgaatat attcagagat agtctttttt ctaattttca    2880
ttgtttgccc gcagaccacc cacacaggag gtatgtctgg ctcgcagaaa atcctaactc    2940
acaactggag gcccataaat ctggaccatg cctgaaatct ggagggttat gtatcatctc    3000
tcagcattct tttcaaattg attccaaatt caccaatttg gcagatattc tctctagtct    3060
gattggtact tgtagctcta gctatatttc ttcagatgat ttttcttttc tgctttatgt    3120
tccgtggatt attttatagg ttacacactg gagactatag taaacagact ttttaccaga    3180
agtccaatgt agtcttttaa aaataaaaat ctgatgttac cccatcattc tgcttccatc    3240
atctgctttc cacccacatc tccttttctc cttcactctt ctgcctctcc tctgaaagct    3300
gtgccctctc tcctggaagg ctctgccgtt tcttggttct acttgaagct cagtttaagc    3360
atcacttatc gaggatgctt tttctgaaca ctctatatcc tgttcccca cttactatgt      3420 caaatctccc ttcacatctg ttagaaagtc ccataagaac atctcgattt ctctcaatgt    3480
tgtaatcatg tggtttgggc aacaaatact gaattcaaat tttaaattat aatattcaaa    3540
ggaagtttct ctaatctaca ctggacatgt tcgcagcaaa gtacaaatgc attgtgaatt    3600
catttgaagt gttgcatgtt agatattcac actagaacaa gcaaatttaa tgagagtgtt    3660
taataataat gggtgttcca ctgtttcata aagttcacca gggcctaggc tactgcctgg    3720
cacatagaag atgctcaata aatatttgtt aaacaaatga atgattgcta tatccagatt    3780
tatctctcta cctacatagt ccatctacat ccaaataaaa ggtaactagg aggtaggaag    3840
taccattggg gtggaaagag aatagtccct caagataaat cagggtgttg actcaagttg    3900
ttttgtcagc ttgtctcatt ttgttttcct acttcttatt cataggtaac cactttgtaa    3960
acctagatgc aaaatggaaa gcctacagat tccatgctaa cgagctgtgg agacattctc    4020
agcatctctc caggctgtca aagggcttag atcaagcatt cttacacatt gcctaagctc    4080
ttctcagaca tatttgctcc aggctttat caactgccag gaaatgagca gctgtgagtt      4140
ccaaacctaa caggtatgtg gacggtcagc atgtcccatt ctgatcactc aggagagaga    4200
cattgttttg gggtcaactg tgtctgatac cccttccctc ccagtgacca gcagtttgtg    4260
taagcttggg ctcctgctaa actgggggat ttctgccctc agcctgggga cttctgccaa    4320
gcagcacagc ttcccagatg cacttagctc ccagtgcccg tgttttttga aatgtcacgt    4380
ggattccaag ggcagagata gctccggtaa tgtctgtggc tgtttaaaat gtggttcact    4440
gtgatgctga atttgtttta cctttagaaa gctcagaatt taattatgtt ttcttttcag    4500
cccttaatag tattgaaagc caacggtttt aacagctctc aggttgtact gggtcttagt     4560
ttttgcatgt agtgcctttt tccaactaat tacttttttaa atgtagtaag agttcttttt    4620
```

-continued

```
tgctttaatc tgtcttagat tgatattact gtgttgtctt ttaaatttaa ctattatttg   4680
ggtggcttta ggggttttct aatagaatca tgacttttag agctaggaag gctcctgaca   4740
tattttctaa atctcttctt ttagaagtga agcaactgag gtaaatgtgt taagagactg   4800
gctcaggttc tccaactagt ggtgaagttg ggattaggaa aaccaggttc tctggtgctc   4860
atttcaaagg tatttccact atagatgctt atctagatat tttcactgtg cctcagaacc   4920
accaccacct ttaatgaaaa tacatctgcc aacttgtatg gaaaagaaaa agcagtgaat   4980
gataggtaca gtcaatataa tattgttacc acccaagcaa gaaatgccaa tagctactaa   5040
gtgtttctgt gtgttggtac agcaactgcc gaaatgtaga tgccctgttt cttatgatag   5100
ggtcacagga gatatcagaa agtataataa gcatattgat gatattgatt atttagattt   5160
gcagtggata ttgagggagt tgcttggcat ccagacattt tcaaatgaca catgataggt   5220
taaaagtagc agaaaaagcc tcatgttctt tttcaattag taatactgat agagtacaat   5280
taatttagta aggctttata ttttggtta taataataac aacaataata gttttcatgg    5340
catcttatgg tttgcaaagc tctttcatat ttacaatctc atttaattgt cacaatcaat   5400
attttagata agtatctccc ctttcaaaag atgacattga gactctaaat ctcatagctt   5460
atctgggaga aattagattt taatccagct tctttctatt caaaatctca tgatctttcc   5520
atcgtcattt cttcttcaa aattgattca acaagaggaa aattattagc ctaatctatc     5580
acattaatag acaaagcagc aaaaactggg ttttgtggct gtattagaac agtggaaaca   5640
gccttctttg gatgagttcg tcctggttca cattttgcca atgagggaaa cctgttccag   5700
aggtgggaat agctcgaact tcctggaacc tgagtagctc agatatatta gcagaccaca   5760
gcgcttctca gcacaagctt ggtctttta tacatttctg aagactcaga atggatacac    5820
acacacaaac acattataat ctcaatggag aaaccataga agggaaaaaa caggatattg   5880 tagttttaa tagagattag agatactcta taattagaga tgctcatgaa ttcccataga    5940
aaaggaaaag agaagatcac cttctaaaaa tctaagggaa tcaatcccaa acttaagaag   6000
gtaaacagtt gcagatgtca aattgataca taataaacaa ttcctgcgaa cctgagataa   6060
attgccagaa aatcacacaa catcaaacaa tgtattcatt caacaaatgt ttatgaagag   6120
gctactacat gccaaaccat gttctcagca ctggggttag ggccaagaac aaaatagaca   6180
attctttcta agggagggag acaggcaaag cataagtttg tgtcacacct tgaatctcag   6240
tgcttgggaa caacagagcc aagcaatgag catggatact aagacggtcc agccattgag   6300
aaggtcgcat ctgagtcaag gcctgaaggt cagtgaattc accatgtgga tatttgagaa   6360
aaaagtgttc aaaagacaat tggccagtgc aaagctgtca ggggagcctc cctgtggggt   6420
taaagaaaca tcaaggcagg gagagtccag tggcttctgt gtagatgttg ggctggacga   6480
aggaatatca cacacagtct tggagacctt tgtatgatag gaaggatttg ggctttactc   6540
tgagtgagga gtgaaaacag gtattcacaa taggacttgg atgatcattc tagtggctgt   6600
gttgaagcac atctccactg ccaccccccc tcctctccta acctccatca tcacttacct   6660
caattattgt ggataataga ggcttgggcc aaggtcaggg cgtggaggtg ataaaagagg   6720
acaagttctg gatgtatttt gagggaagag gcaacaagat ttcctggggt ggcatgtgag   6780
aagaaaagga gaatgctcag gatataggcc tgaccaactg gacagatatt taataattaa   6840
ataatagaca catgggaact actggaagaa gatgctaaaa gcttatgata tactactaaa   6900
atgaggactt taatggtctt gttcccctca gagcctagaa caatgcctca acaggcactc   6960
```

-continued

```
aataaatact tgttgaataa attcataaat taatagtaat tattaaaatc tcctctctga    7020
gctaagttta agttggcagt tctcaaactc tagcatgcaa tgaaatcacc tcattaaaaa    7080
acagattgcc catccccaga gtttctgatt cggtaggtct gggatgtgac ccaagaattt    7140
gcatttgtaa aatttctggg ccatgcagat gccactgctt cagttaacta gaggccaaaa    7200
tccaaatacc cctatagatt ctgacaacaa acagagacat gagaattgga aaggaagagg    7260
taagacaata tatgcagatg gtctgattct atatgtagaa aaaatatcag acccaaaaaa    7320
tgaggagact acactctatt gagaggcatc aaccttgtta caaccaagaa atcctttgtt    7380
gattttatgg gggttttgga cgccattttt agaaagcaaa tgtctaccaa ataaacagca    7440
tttatttttt aaaaattcaa catatggaaa tcaatagatt atatggttca tttcaaaagc    7500
aagtaacaaa agtaattagg atatctctgg aaaagaagca agtggagaat ggggctagca    7560
gatattaaaa catgttttaa aggttctatc attaaatgtg tcgtattggc atagcaatag    7620
aactgaatag aaactccaga aatcaaccca gtttcataag aaaatttaat gtatgatgaa    7680
acaaatcagt agtgaaaaat gaggatagcc acatcatgca ctaggataaa ttctaattgg    7740
atcagagatt taaacgtgga gagagggagg gaggggaggg gagggcaggg caggggaggg    7800
gaggggagtt ggggaatggg gaaaggtttt accctatgac tcaaaatcca aaagccataa    7860
aaaaagatcg atagatttga ctatacaaaa attaaaggac acaccaaaaa atagtgaaag    7920
gcaaatgaca agctaagaaa catacttgta tcacagacaa cagggcaatc ctaatatata    7980
aagcacttct aaaaagagag actaaaaaga gcaacaacct atagaaatga gcaagagcta    8040
tgtacagact ggcatagaaa aagaaatgca aatagctctt gatcatatga aaagatgctc    8100
aataacttac aataagggaa acacaaatga ataggacact gagatagcat tccaaaagtt    8160
tgacgactga caagattagt gaaaattgct ggtgggatat aaaatgacat aatatctaca    8220
aaagggaatg gccatatcta tcaaaatcat atacctttga cccagctatc ccacttctag    8280
gaatctatcc caaagacata gtggagaaga gacagggcta ctcactgcag tataattttc    8340
tatatccttt tgtccaataa ttgattgaat aaactatgat gcatttacat agttgagacc    8400
taaaaaggga taaatatgta tgtgtgtgtg tgtgtgtgtg cgcgtgtgtg tttcctaaaa    8460
tatacacaca ctttatacat acacttcgtc ttagctattc tacttctaaa tttatcccat    8520
acaaatgatt gaaaataaat taaagtttga ccgcctggat gttttgtcat atggaacaat    8580
tagaaaaaac ttacatgtcc catagcaggg ggttggttaa agtgtttgta gtgaatacaa    8640
aataattgga gagctccttc tccaagaagg cttccctgat gccccacatt tacacagctc    8700
actgtgagtg cctctctatg gcactcatca cctcatgcct tgcttttgaa tgattt        8756
```

<210> SEQ ID NO 56
<211> LENGTH: 4556
<212> TYPE: DNA
<213> ORGANISM: Homo sapiens

<400> SEQUENCE: 56

```
tcagcaaaac ctcctgcccc ctctccagct gcctggtaaa gttaaccttg gccctttgtc      60
ctaagggcta tgtctttatc catctttcta ttatcagagt ctaattcaat cctgacctga     120
gggcagtcac tcaacccacg catgttctgg gctcccatcg aaaagcccca gtttccagca     180
gtcctcagag tacatgtgtg gtgaatccct actatgtggg gatccaggaa caagagccaa     240
ctggccctcc aagactccac ctcagttccg attcctgcca tccgcaaact gccactgaga     300
tggcagctct gggggcagcc ttccccaccc ggcagacaga ggctggcact catctttgct     360
```

```
ctaatgaagc aatgacacag tgatatctgc ctttcctacc tggccaaagc ctccctgggg      420
gcagaaagga ccatcctgct cttgctgtgt cctagggcca cgcttggggg cgcccagagg      480
ccataaagac catgtgcctt agctaagaaa caatttgaca cgtgccaacc cagcctctgg      540
accctgtcag ggcctgctag caagcttcct gagggcaagg ctgtatcttt catatgcctg      600
ttattgccct aacatctggc ctgggcctgc tgcctggagc ataacaggcc tcgtacatat      660
ttgttagatg agtgaaggat gaggtaagtt acaactgctt taagttcact gcctagtaaa      720
tggccttaat ccaaagatcc tttggatctt gagccaaaat tatattgagc caaaatctac      780
ttccctccaa tacagattat gtgtaccatg aaagccccat atgcatgtga agatggacat      840
tatactcttc caaaagcctg gatccaagct gaacatagtt cccgtagcat ttctcatcgc      900
agatgcaaga tccttcaccg tgtggccacc tttatcagga caaatgcttt ttttcaagta      960
catcttgaaa tatggttcgt acctgtgaat ataaccttat ttgccggtct ttgtagaatc     1020
aagtcaagat gaggttataa agtgcaatgg ctgatagctg tgtaagggag agatttggag     1080
atagacacat gggaagaaac ctttgtgaag acagaggtag agactggagt gatgggcctg     1140
aagaatcaca ggattgtcaa accactggaa gctaggagag gcatcgaaca gattctccct     1200
cagagcctct agaaggagcc aaccgctgac accttgattt caggccttca gaactgtaaa     1260
agaatacatt ttaatacatt tctgttgttt ttaagccact cagtttgtgg tactttatga     1320
cagcagtcct agggcactaa tatgttggac caccaccccc cttgatcaat atattattct     1380
ttgcaatcac atggttgcct taaaaaatta aagactacta aattaataaa atgatttatg     1440
gctggacaca agataaacac cccaaaatca aggcattcat ctttaccagt aagctattga     1500
aaccataatt caatatccta ttcacagtag cacccaaagc cgtaacacat agcagtaaac     1560
ctatgtggga tctgataaag aacacttttt aaaggtggag aaaataacaa aatcctgaaa     1620
gggaaggaaa ggtccatcca acgagatatt agaacatatt aactcaagag tataaaacag     1680
aaaaacacca taaacaggca gatgctagtt gacgtctgtt acctcctcca gaagcaagct     1740
cagagtgagg tgagatgtgt tgagaattgg ggcacttagg tgcttacaca gactaaaaat     1800
ccttgttcac catttatcat tagcagcaca gaacgtcatt tctacccaga gagatcctgg     1860
cttaaaaccc catcaaccaa attgcttttg gggtggaaag gaagcccctc caccttattt     1920
tgcaatgata tgaaaagctg ttctcgagga gaaagaaagg gggagaggta ggaaagatag     1980
cagcttgtgc tatctactga tcacgcctgc gtttctttgg ctagttctgc cacttgccgt     2040
tctctgagag gggtttggta attaccagga caacttttct cagtccagtc atttgaattt     2100
ccagaacaaa attaggttgg ggaaaccccc tgaatttgca gactcaatat tctctgtttc     2160
atcagaagtt tgctgagcac ctgtggtgtg ccaagctctg tgccagcccc caaaggttcc     2220
tgagggttcc caatacacag ttatttcaac aggatggatt tgcacgaagc tggtacacag     2280
acctgctgag gaaggggcca gccaagcagt catgtgccac tggatccgct tggttttctc     2340
cacctcatta catgagaatg accagatggt ttataaatac aatcattttt attgagtagg     2400
aagtaattaa aatgtttata cctgaggcca tttttaggaag aacttttttg ccatggtata     2460
gtcacagggg ccagatccca gatgctggtg tggggtgaag cgaggatgag gaccagggag     2520
atgatgccca agtgagagga tattgtgcaa ggagctggca aatgtggctc aatttttacag     2580 agcagtggag ggagctgcat tagggggctgg cctagttcag tggatggtga cctggacaca     2640
cattataatc agctggagag ctttaaaaaa aaaaaagatc tgtgctcaga tcccaggcca     2700
```

```
gcccagttaa atccgaacct tggggagac actcaggcat tcaggtatct gttgttgtgg     2760
atgaatctct acaggtgaca tgtgaaagct ctgagaacag agctccggcc actgcttagt     2820
tatacctgac ctgggcaaat aaaatcacac acacacttac atgcgtatac acatatacaa     2880
gtgtgtaaaa tctggttaat gttctctgtc atttcctttc ctttgactaa agtaattgta     2940
ttgaagatct ctcaggttgc tgagggcatt atacttgtgc cttttttaagg gtttgcctac     3000 agagtgtgga gatgggggagc ccacaaggat ttttctagaa gtttctatcc tcagagattt     3060
gctctaacag agggtggtca gttctgaatt aggcatcctc ttgctcatgc ttctgataca     3120
tttggacttc agagtcctat ccttatgccg ctagtcaccc agtgattccc aaggaagaaa     3180
agcatcataa gatttagaga tggggcttcc ctctctgtga ttaacctagg tccagttcag     3240
aatgaagaaa ctgaaaagag aaaatccaac cctttttcaca tccaacccca ccctgtccct     3300
gggtggccct taccactgga aaagcctgcc caaaaacttt ggtcctaaga aaaaaagaaa     3360
ctggtgcagc tgcttttatg gaaggagcta gaccagagcc aacaagtcag gcctctgtaa     3420
gaatcttcca aggaggtaag gcggggagaa aaaggattcc tcatttacat tgagagtaaa     3480
cttcctgtcc tattaaacaa tgaggcattc aaaatccgcc tgagtaaaag tccctgatg     3540 caatgagagg gtgagcaatt tcatgtcagg ctgttgttat gggatttata catgtcctag     3600
ctagggcttg aggtgaaagt cagagccaaa aacaatagcc ctaaaccccca catgcacaga     3660 aacctcattc cagtggagtt tccttaagag agcacagcag actttcaca aacaaagtga     3720 cttcaaaggt agccttgcat cactgcctcc tcccttccct tcagcccaga cctggcccct     3780
ctgtttcttg gtttaattta tgaggttctc acacacattg caaagcaatt atctgagctg     3840
ctggccaaca ggaaggtaat tgtaactgag tacttccttt gtcaaacgct gacgctggcc     3900
accgcgaggt gataggaggc gtgccggcag ctcagcaccc agtgacagga tacctttctc     3960
ccccacccac acaatgctgt ctgactgaat tctccaggga ggaggaagcc agtgggtgag     4020 gaatgggga attttcttac atcacttgac gtgcttgctt tcactcgcaa aatcctgagt     4080
catgactgaa gctgtattgc ctcaagctcc ggctgaaacc aggggttata ggtttggaaa     4140
cctgattcca cggctgcctc ttgtccaatt cagaggaaat gtgtattatt tcagttgatc     4200
ctcttcaagt tgaagtgcct ttggattgag gggattacgt gagggaagtg gctctgtagt     4260
ggcttagtaa gccaatgcca tgcgagtgaa caatatttga cattcggtga gtttacagaa     4320
agggcagtct ctctgtttgt ttaaaccaga ttaagtgaaa ggaaaagttt ttcttttccca     4380 tcccaagaca aatgtgaaac acatgttttc cctttttgact ttgtaagtac aaggctcaaa     4440
cagttctccc caccccctcg gccatgagtt tttaaggatt gcagaatgtt tcctctcttt     4500
ggtggccaaa gccaatgtga gcctttatat ttccagacag tggagctgat gatgat        4556
```

```
<210> SEQ ID NO 57
<211> LENGTH: 3748
<212> TYPE: DNA
<213> ORGANISM: Homo sapiens

<400> SEQUENCE: 57
gtatgttcaa gggctaaatt gcttagtagt tgtgcagcta caggggagaga ccagttatag       60 ccacaaagtc cttggaggat aaaaaaaatgg tggtggtggc gctgagaatc cttgtgagga      120
gggctaggct ttgttctggg cagtaagaga gcccagggca cagaaaacat gattaaatgt      180
gtgttgaata aatgaatgaa taaacacttc attggaggga aaacaccagt aagacattgg      240
ctgtgtcctc aaggtgctca ttccccgttg gaagacacag gcccattgcg ctaactagaa      300
```

```
cacaagcgag aagacagtaa atggaaatgt tgttgagcct tggtagggct tggcaaggtc     360
tcttatggct ctgctcctgt atgctgtctc tccattctgg aagccctttt tgctgcagtg     420
actggctcca tccacctgcc agacagacgc tttcgttccc tcttgaaaag gcttttgctt     480
gatggaggag gaaaccaggg aggaaaagag acgcatctta ttctcctgag aagagtcatc     540
ctgtttgtct ccattggcgg ctggctttat ttggcttcta tttggatggt gaacccattg     600
ccttgaggtg gggagaggag gagattctgg aaggatttca gtattgaggc gcccctaata     660
cctcccagat gaaaaactag gagtgatcct cccaagtgtg cgtgctgaca tttgctcccc     720
aatgcactaa gcataagctt gttttattgt gtttacaatt ttgtattcag accgtaatat     780
tgcaaacatg aatgtcctag acagtagaga tgtccaggct tttctctaaa gccagagcta     840
atcctgcacc agagatccag tttgatgaac tcttcagtgt tcccaaacct catgtgctta     900
tgagagatca gatatctgtc ttaagcagct ctaccctact gcctacccag gagaggatct     960
tggcatgtgc ctgcctgaga ttgacctcct gccctgtgac cctgagtata gagcagagga    1020
caggcagtgt tgcaaatatg ctcctcacaa atccagatag gagatatgat ttaacactat    1080
cttctccttg aaccacttga taattttttt ttcaatcgca agaaaactta attcctgttc    1140
cactgtctct agctctctga gggataatgc tctgacaatg tagacaagga ccagatgtgc    1200
agtggatggg tcggctgctc caatctggct gtggagacgt gagggaggat tggggagaca    1260
gttgtatgta gtccatagtc aggataaaag gcctttgcga gttcctaagt atggtttctt    1320
gagtctgcgc agaagggcgt atgtgggaaa cataaacaac acaaaataaa acggtttgat    1380
cagaaattat agttattacc aattccacaa atcattctcc tcctttatcc tagactacaa    1440
agaagcatca caaattattg acaaagatat tctggaaggt taactctgga ttaaatcaga    1500
cttctctctc agcagctggt gcctctcatc taagatcaaa aggatcttga accttccaag    1560
tgaactgctg tcaagcaaac agcaggagaa cctctaatat tatttacata gcattttctt    1620
tttccaatta tgtattggtt tcttcttggt acaagtctag cttataaatg tggaaaccaa    1680
gacacagaaa agaaaacaat gttaaagtta ggtagagagt cagtaagaca ttaacccaca    1740
gataaatgtg tctagatatc acctctactt attcaacaat ccttttcagt tgcctaccaa    1800
aaatatgaag tcatttttgc tgagggtgca gtaaagcatg ccaacttcat tttccaacct    1860
ggagtttctt gggcctatag gaaacggatt agagtctttg aggctttggg gaccttgttt    1920
gcaacgttcc tctaaagtag accttataat gaatggaagc aagagaagag tgccagatta    1980
ttaatgctgt caatatcctg tgtctctgag atgttgccct tatgtcaggt accagtgagg    2040
aggaaaaagc agaaatgtga actctcagtc acctactcag gccaaggtct ctgtctagga    2100
actgctatgt gtgagtcaat ttcctgatga cagttttcc ataccatgct gagtggaatg    2160
tcttgtttat cagccctcac acctggtact gtggcatcat gacgattgtc atagtctatg    2220
ggaaggtgac aatactgtgt gactcccagt ttcagactca gtcattaagc agaagaaaga    2280
atgggaaggc acagagatca gagggagaag gacaaagaga tacaaggaga gtgacaggaa    2340
agaagaaaaa atgactgaga aactcctaat gcaaagtggg taatgggttt tgaaaataac    2400
agggtgagcc aaagagaaag ggacaaatga tttagcagag agtggaacat atactggtac    2460
ctccacctac tgtaccccaa gccttgtgtt gaacctggac aaacagtctg gcccttccag    2520
ggactcccag cacaacgaaa ctcaaaggaa agaagagcag gaagttggtg ggtttcaggt    2580
gcttggaaag aagtaggctg acatctgact cacctattca actgcaagca ccaacacaca    2640
```

-continued

```
cagaagcttt cagatgagat catctggtcg tgacttgcaa aagatgattt ggtggcatat      2700
ggggctaggc acttatcaac attttttcttc cagcacagca aaaggtgggt agaattgcag      2760
ctcttttata ataataaata atgttatgga aaggaaaaat gaagtataga gaagggacag      2820
accttaaaaa ggatgctcaa tataagaaaa acaaacacac attgttctcc ttgatccatt      2880
gagaggatat ggtaggacag aaaacacaca gaaagacgta ggcctaagcc tgcttttgcc      2940
acttactgac cttggtatct tacaatggga aaataatacc tactattcag ggttgttgtg      3000
acggctgatg atgagatgtg catttgttag gagatcagta actgtcagcc attattctac      3060
tatctgttag cttcaagcag cagtgtgagg actaacttct ccaggcagct cctccatctc      3120
cccagttatt gttgttttat ggtactttgg aaaggagttt caagttcatt tggttcaagt      3180
cgttcctttt gtggtccaga aaggtgggtg gctgattcga catcaattag tggcaaagct      3240
gggagcagag gatcctaagg ccacaaggga gtgctgagca caagattcag tagaaaacac      3300
atccctcata gcagctctct gggttcaggg ctcctggaag cctttggagg gagacaaatg      3360
tttttcattt aagaaagtga ttatttagtg actcctgcac aacctcttct gcagcccctg      3420
gatctgatta cacagcctgc cccacgaggt gggaggagaa gctggcatgt ggcatgtggt      3480
ttaaacgtag ttgatctttt taaaatccca cattttagcc agtctctcag ctccacatga      3540
tctattctca gaaaatgcta accggccaga aggaaagagc aagagaagaa aaggaaggag      3600
aaagagtaaa agagaaagaa aagagtgaca atgaaaagca agtaagaaaa gtgaagagag      3660
gaaagagaaa gatggaagaa gagcgagctg gagcaaaagg gagagaagta gcgaccctga      3720
aacagtgtga tgagatatgg ccatagta                                        3748
```

<210> SEQ ID NO 58
<211> LENGTH: 5013
<212> TYPE: DNA
<213> ORGANISM: Homo sapiens

<400> SEQUENCE: 58

```
aaatagtgtc ttctggtttt gtctctttgc tgagacagtt gcttgggatg gctttggaaa        60
aacttgttcc tgaggccagg aagggctctg ggaagttttc ctcagctctc gaatacccca       120
cttatgccct caaacaaaaa aatgagttgc ctttaggatg attcatttca attatttctt       180
ctcccttaaa gctgtttggc tctgcagggg tttggggagg caaggaggcc agctataggt       240
gcaaaacagc ttcatcgctg gagggacacc atgcccaagg tgggaatggt aataacgatg       300
aagacccgag aaacatccat tccttggaaa aaccccatgt ggtgatggtc aagtgggcac       360
taccctctag acagtgtcag gaatgagaac ttaagacagc ctaatgaaaa tcagcctaag       420
gatttttgcc agaacaattg agaatgagac tctttagagt cactaaaaca tggataagaa       480
tacttgctgc cttaggtagg tactcaaggt cacagagcta aggtgcagac agcaagcttc       540
aactcaggca gtctgattgt aatgcctatg tgctccctgt gaccttacta agccatttaa       600
tgtcatctcc atgagggagt agagaggagc ctataagcgt taaggtggga gacaaaagga       660
agaagtcaga tgtacatctg gctatggtgg actagaaata gatcaactta cattagggaa       720
cagggtcaag aacctataaa aatttatgtt gttgaaaatg accataaaat tgatttctga       780
atgacagtga aggagctttg tgggcctact acctagtgaa accagtgaaa attatttaaa       840
gcaaacattt acagccttgg gcatataaca aatgaagaaa acctattcat gaaaattcag       900
taagagggta agtggaaatt aaaaaatata ctcctacaac cagtggatta aaaaagaaaa       960
aggaaaatca gaaaatactt caagatgaat gagattaaga caaaacatac taaaacttat      1020
```

-continued

```
gggggcagcta aagcaatgtt cagaggaaaa cttatagttg taaaagagaa aaaaaatctt      1080
aaatctataa cctatcactt taagacacta agaaaaagaa gtacaaacta aacctacaga      1140
aaatagcaga aagataataa taaaaatcac agttgaaatt aataaagtag gaacagaaaa      1200
acaatggaga aaaagtatga tgccaatcta gttgtcttaa aatgtcaatt gacatacttt      1260
tagctaggtt gaccaagaaa acaagaagac tcagtactag aatcagaaat gaaaggatat      1320
caatactcac cttggaaaac aaaaaagatt ataaagaaat atataaatca ttgtatgcca      1380
ataaattaga taacttagat taaatagaga aatttctaga aagactgaaa taactgaaac      1440
ttactcaaga attagtctga ctagacctat aataataaaa aagatcaaat taaaaataat      1500
aaaaactacc acaaagttaa gcccaggtcc aggtggcttt cctactgaat tctactaaac      1560
atttaaagga gaattagtac tatctcttta aaagtttcca aaaagaaatt taagtattta      1620
tttaatgatt ttaaagatca gtattaccct aatatcaaac atacaaagac atcacaacaa      1680
agaaaacaag agatgaatat tcatgaatag gggtgtaaaa ttctcaacta aatactagca      1740
acctgaatct aataacataa aatccaggaa atctaatttt cagtcaaaac aaggctattt      1800
tcaatgcagt tctgcctcca tttctgattc acaaacacac ttcccaggaa agaagcctct      1860
tgtatacatc tcatgctagt gtgcatgcag cttgagaagt cagctgcatg gagaggagct      1920
ggcagaaata aaaatttttc tgaaaaattc agagaaaaca acaactgtaa tgtacatatc      1980
attttgcaca atggcccgaa aattataggg aaagaacata gatgatgtga agaaaaataa      2040
tatgaagaaa attaattttt gttggttttt cagactttct tggaagaaac agtatttctt      2100
tcctcatatc cattcatgtt aagaattcct aggatgtctc aagcacaccc tcaataattt      2160
acaattgtca agccacaatt tgtagacact cacaacttta aattaaaagg aattcctaga      2220
gaaaagttat aataattagt ttgtgttgtt tcagttagga tgtttttgtc cataaataat      2280
agaatatcag atgaacagtg gctgagacaa taaagtcatt tattactcac ctagcaagaa      2340
gcctgcatgt aggcagttcc tgggctgttt catcagctca acaatggcac taaagattta      2400
acatatttct acttatttcg tcatccttaa ctgttggagt tttgcctcat gctcattgcc      2460
ttgttatcat aaaacggaag ctacagccct agacatcaca tctgtgttca aggcaggaag      2520
aaagaagaga taacacaaat aaaactcttca ttcattggta tcttttataa aaaacacaac      2580
aaattttttt ccccaaagac tcttggcaga cttcataacg actagactga actgggtctc      2640
acagccatcc ctaaatatga gtaaagctgg agaaaaacct gattagtaaa agtgaaaggc      2700
tgctaagatt ggcttaaaac aaccatgatc tagtaaagta cttccttgaa caaaatcagg      2760
attctattag ggaggaagtt gagaatggct gttggttggg ctcctcacag gtatccacaa      2820
atgccatgta atgttctttt ccctgagcta ttttcccttc tatccaatcc cattcttaga      2880
gtctcccaag gagttagata ggttctgtgt gtcacagatg taaagttaga ctctagtaag      2940
tgagcggctc agatgctctc caaagctttc taaaatattt ctcagaatga aagtaattct      3000
gtggttaaat tcttttgagg aaatactatc tttaaaacat agagcactta agcactctta      3060
taagacagag gtgtgctaga tgccttagat gtattatcca acttaaaagc ctacatttgt      3120
gaaccctggg agagcgggag ctgggtcttg tttatagcta tagctgtttt ctaccagagt      3180
gcctggcaca tggtaagtaa tcagtacata tttaataaat aaataaatac aacttgaaga      3240
caacaaaaaa tacttttttga tggcaacatg gataatgaaa gtacaagttt cctcctacta      3300
aggtaatcga tgggatagaa ataatcgcat gtctttttct gatgtttact aatcctcact      3360
```

```
taagttcaaa aatacttttc cttggatccc aaatactagt gagagcacag ctggggttct    3420
agacctcact tctgattcta actccttgca ttcaatttac cgtgctacat tacatagagg    3480
ataagcgaag ggggccagtt gtatctggaa ttagaatgag gttcttctca ttctaaagaa    3540
atgtgatatt gtataattac ctaagtcata aatgtgttta tgcgtagcta agtttattac    3600
attagcttca aagcctaagc agctccacac aagacaccag acattcacat tcatagggct    3660
ggagggcata attcaacaca ccttgtctgc caaatctttc ctgtgcttga actagagaca    3720
aaatgaggag ctcctaaata gttgacaatt tctaattcat tctttattt ccagtgcctt     3780 tgtccaaatt gtaatagcat aattctgata aacaagtaca ggtatccttt ccaggtatct    3840
aggtgccaag tgcccatctg cctaatgggc acagggtgga ttgggtagta ttacatgtac    3900
ttttccattc tgcccttgca tgtcctcatt catcctagga tagagtgttc ttctttgcta    3960
cgttatgggg ctacaaaatc caaattgaag ctgagcaaga ggtttaggaa actcaatttg    4020
agaaaagccc tttggtaata ataagtttta attactattt tcaaccttat tttttattta    4080
aggaaacttc ttccatcctc tctcagcccc actacagaaa agacctgtga cccagactgg    4140
ccaatctgtg tactggacca cagtggcttg ttcaaatttt agcgcagaat tagagtcttg    4200
taggattaat atttgaacac aaagagaaaa attctctttc ctttgaggat actttgaagc    4260
tgcagataga tgactcctag taaatatttt gccatttgtt cagatcttat ctgcaaaatg    4320
aggttaacaa acacaagtgg tggtggtgat gacacaagac atttattgag tgttacttat    4380
ataccaataa ctaccctaag tgcattacac atattaactc atttaatctt cacaaactta    4440
taattatgat tactgttata ttattgctat aggcacaatt tgaacccagg cagcctggct    4500
cttgagcctc tgctgcctct aacagtacag gaggaggagg aggacaaaga gaagaacagg    4560
tttccaggat actgtgaagc ccttggatcc agccgtgtct gaacctaggg cacctggatt    4620
cttggttaaa tgacccagta catcacaatt gttatttagc cagtttgagc tgagttccta    4680
ttccttgaaa cttgcctaaa atactctacc accatctctc attctgattg tgccttatca    4740
tactgcttta ccataaaaac attgtagaaa tttggaaaat gcaaaggat accataaatg     4800 aaaagaaatt gcatatgata cagccaactt gagattatta tttttgtttt cttccagtct    4860
gtttttaaat catgtacata tacacctgta aagttgtata tgtttcttgt ctttccttt     4920 tcttttata ttaaataata tgtgttcccc tatattaaat attttgagac cataattaat      4980
ggcaatataa tttgtgtgca cacgtgtgtg tgt                                   5013

<210> SEQ ID NO 59
<211> LENGTH: 1153
<212> TYPE: DNA
<213> ORGANISM: Homo sapiens

<400> SEQUENCE: 59
gggtcttctc accctagaga atctaccatt gctcagctgc agggcgacac ccaacagtac     60
agctgggtaa catagaaaca cacactgact tcatttacac agtccctgcc cagagtcaat     120
agaaaagtcc agtccagatt cgtcctttgc atcataagaa caggagcctg gctggatttg     180
gaccccaatt agtttgctaa tccctggaat aaactaaagg ggccctgag gcaccttcca      240 gcagaccctt tttcttacca ttagtgaaaa aggtctgtgc ggtgggggca gtgtgtctat     300
gacctcagct tgaccacacc tagacagggg ggaaaaggtg gaattagtcc gtctttccta     360
tatcaggccc aagcctgtct agggcaggct tctgttctga gcgtattttc cattcttccc     420
tccacctttc cactcactca acaaataccc tttcccctta aggtgatcaa aataagcttc     480
```

-continued

```
tgttgctggc acccaaacct ccctgactga caattacact ggtagtctca cttgtccagc     540
ccagtggatc ttctgagcat gcattcgggg tcaggggccc ccaaagtgct caggattctg     600
ggtccccatc accatcatcc ctgggatggg tgatgtggtc ccagtccctg accatactca     660
gtttgaccct ggagtctctg agtccccagg tggacccagg caactcacgc ctctccttgg     720
agtaacatgg catcggtgca tcaagcacct taggcgtggg tcaaccaaac agtaaggggt     780
tgcatttgtc agatgtttct ccagaggctt aagcagtgcc cggtagagac ccaagtcaaa     840
tgtgtctctg tgaaagggga ttcactggct catgtaactg aggaagacac aggtgtgact     900
gggagctcct tcacctccca tcccagttca ccacaggtgc acactgctac ccaattcctg     960
ccactagtgg tgggtcctca ttgtcatctg gtcagtggta cctctccagc atcagagcct    1020
gcctcccaga cccattccca gcacccactg tcttcgatct ggataggagc agagcatagg    1080
catgctgatt ccatgattta ttgagggagt gatcttggga gactatgagg gaggcaggca    1140
gaacaaggaa ggg                                                        1153
```

<210> SEQ ID NO 60
<211> LENGTH: 2938
<212> TYPE: DNA
<213> ORGANISM: Homo sapiens

<400> SEQUENCE: 60

```
gcactggttc tcattgctcc atcaaatact aaactctaat tagtgacacc gtctccagcc      60
attctagtgt ctaaaatatc acaagtcaca gtatgaacga tcgaagttga gccccaagtt     120
agcagaggta tttaagttac atagttgatg aaaatgcaaa tggagacata acaagtatga     180
aattcagtca ccaccaagga actagtctgt gaacacttag gattttcacc aagatatatg     240
cattgttaat gctttttcct tctaattaaa aaagaaaatg gataacagat gaggaaaatt     300
tgatgtgatg gtttttagga aatgcacaaa tgactcatgc actcgatttg acaagggtac     360
tggtttctat ataaagaaac aacttaggcc caaaatagaa gttgtgcaca gcagattgta     420
actgatagag gaactgcaca ttccaagtag tgtgaagtgg tcgcaagagc agtggctctc     480
ctgctctggg gctgagaacc cctctccttt gtttagcctg gagaaagccc cagtgaagtg     540
aaagctgtga gcacaaaggg ctgagaggca agcaggacat tgtgttcaga gtcaggattt     600
cccagctgga aaggtcttta cagtgcatca gttaaggtta gatgcagcag cttggaaccg     660
aagtcttaga ggagcactct caggctgcag gctgggtatg cacaatgttg tcagggtcct     720
ggcttcattt tcctgcacca ccttacctgt ggcccccttt ctagtgatgt tatttggggc     780
aagttgctta atctttctga gactcagttt cctcatctga agaagaagag taattgcaat     840
acccatttca caaggataat gagcagatta attaaaataa tacctgtctt tgcaacagtg     900
atacagcaag ccttggctgt ttttatttgt tttgttcagg acttgtacaa tgccaggcat     960
atagttggag ctcaataaat atttgtgaat tagttattat cattattatt gttgccacaa    1020
aggacccaca agcgacatca agagcccact ccatatagca cctaggaaga gcctaattta    1080
acccaacttt atttccaacc agccaagctg gagtgcaatt gtcaaaaggc agctgatgga    1140
cagcccagcc cacgtcggac cggtggagcc caggactccc aaatgctgtg cctccgccag    1200
accagacgct gctaatggct tttgttcgtc tgccaattct actgcccatc ctcctctggg    1260
aagaaagagc agaccggaca gagtccttca gaggccgacg catgccagag gctgggagac    1320
ttggaagggg agtgaggaga cagtcactgg ggaagacagt tctcagggat ccgcaaggc    1380
```

-continued

```
cctggaggtg tttctgtctt tgtaccttgg ttgcctctgc gcaggcagcc ttgcttcata      1440
tcacctgcac ttccttgctt ctagagggat tgtggcaaga aagctcgcag aagtcaaaac      1500
aagcctggtg atatgaaaac catatgaaaa cttggcaggg tcccatttca gactaatggg      1560
cctgccagac atcaccggcc cacagacact ggccctttgt gaggtcgggg actggctccc      1620
tcactcccat tctactaaga cagaattaaa aaggaaacaa gcaaggcagc cagtctcttt      1680
tctctcatcc acgtgcttcc aaggttagaa acagagtaac gtcaggtact ttgagtgatg      1740
aacacaggat gttgttggcc aggcccattc acagtgcttt tcagtcctca cttgatcttc      1800
atggtagacc catttcaaaa atgaggtcgc tgaggtttct ggggctccca aggttccact      1860
aaaaaatgat ggcccagcca gctggggttc agatgcagac ccatctggcc aaaaaccttg      1920
acctttgttg ttacagagct acctcccaga tgaccttttg attatttcag acaaatttac      1980
caacattcaa aattttgctt ttagctttct gtttcctgtt ctagaaagaa atcgagacat      2040
aacatttttt tttcatgacg ttattgaatc tttggacaat actgtaacat gccattgtta      2100
tttatacctg aaattcctgt atttcaaagc ctgttgggtg tggagggaga ctattttcca      2160
gagccatcat tattgcagta ctaaaataag tgctctttta aagcaactta aaaaaatcaa      2220
aaactgagat aagtggctgt gcaagtataa tgacttgttc tttgttccca aagactggaa      2280
aaacaaggtc ggtatgcaaa tacacctgca gattataatc tgtatgtaat ttacaattca      2340
catctcttcg tgacatggct tctgaaaaaa tctgaagata ttttaaagac attttaaaac      2400
ttgataaact tttgtaagtc tggcaagacc caggtgctct gaattcctct cttatggatt      2460
acggggctgg aaattgaacc ctctgctaga agctgcccgg tcacttctgt aaaggccctg      2520
atcattttag aagacacgag gatctgcgcc ctcatgaaga gactcatgaa ggcctctccc      2580
acttagctgc aatgaaggaa aggaagggggg aaggagagtg atcaaaggaa agggagtaaa      2640 acccctaat tgcccatggc aggggtcaat gaatcactcc acgtgcacat ccaacagctg       2700
gtgagaagag ctgaatctgt agggactgat aaggaacaat cttttattta tgttttattt      2760
acagcacatt tttttaatgc aggccagggt ataatattta cttaagaggt aggaactatt      2820
tagatgagaa aactgcttat acttctagca tctgaaccga agtagagagg ttccaaaaat      2880
ccaaaccata tgcatgtact gcttttaaag aatgcactat tttttctcaa ttgccaag       2938
```

<210> SEQ ID NO 61
<211> LENGTH: 2081
<212> TYPE: DNA
<213> ORGANISM: Homo sapiens

<400> SEQUENCE: 61

```
ctcctctaaa acacttatca cttggttctg taatgcttac agtgtgttac agtgaaaaga        60
acatgggctt tggaatcaaa cagcctgtgt gaaagctggc tctgccattc atctgcctga       120
gcttaggtta ggtacttcct ctctctaagt cagagtgcgg ctactgatga ctcccctggt       180
tgttgtaaga attagagaat ggaatgcata tgaaagtacc aaacactgtc agaagcagta       240
agtgctcact aaagattgga tcttctcttc cctagtgaca gtgcgtgact taaagcctgg       300
cccactttat ttattttgtg tatctccaga gcttagcaca agatttggta aatgggcatt       360
atttaaaaac aagaaagtgg ctaagtgctc tatcaagggt gaaagtggaa tttctggtac       420
cttatctgaa gtccccctg ttgcaggttc tcaacatctg ttgtcaatct tcctattagt       480
taattaaact cctccaaaca ccatccttga ctgttgttgc ttctggcttt ttcccaatga       540
gtcaactctt caaggaaatg aaagagcctt tgcacagaaa ggccagaaaa ccctagttgg       600
```

-continued

```
ccagcatcct ttgggtctaa gctatagcag cgcaaattag cccagccatt tatatgcaaa      660
agccttgaag attgtttgaa aattgcctac ctaaggagtg taagttaaaa ttgattcaaa      720
aactgtttgg ttgcatctag gaaagtgaat gccaaattgg tcttttcaaa ttcaaatcta      780
agttaacctt caacttaaaa cctacagcgc ctcttcatta tcacttagat tcaggggcag      840
aatctcttcc ggcctgagtc cctaagtgga ccagcctggc tcccacattg catcttagca      900
cttcagctcc tttgttttac taatttccgt gtgtccagga tctggtgctg cactgttgag      960
ttgtgctgaa tcactgttat ttctgggttt aatttctgca gttaggctca gaaatggggt     1020
aactctgtgt ctcatgggca tggtgaagca ggaggagcac cccttcctca agtgataaat     1080
tgcaatgaag caaccatgtc agaaaaaaat tagggaacca ttgatcctca tacaataata     1140
cacttatgta ttttcattgg aaagagagtt atctgtgctc tgtgaacatt attggctagc     1200
cctggataac caattttatg ttttcacaat aaagttgagc catgttcaga tttttatccc     1260
agggagtttc cctggatatt gacgttgaaa gagcccatgg gggacatttg caattggaac     1320
tatatcccta gatgcctcca caagacacat acaccagagc tgtcaaaagc agagttcttt     1380
ataacctatc acatgatagc tactggcagc ctcgagctaa cccccatct cagttaaacc      1440 ttcctaacag catccttaca gatgaaaaac tgaagttggt gtgacttaag tatctcgcct     1500
taaggcatcc atccattgaa gttgccttct tggtctaaac ttgagcctgc ccagttcaaa     1560
aggctttctt tcagcctaga tctaccacta cggaggtttt tatatataac gtattttaat     1620
tacttgtgtt cttgttatca tagatgtatt ttaagagaat agaacctgct tttctaaagc     1680
tcaagtactt ttttataaca gccacttaat tggacacaat actcagacat gtcagttttt     1740
atatagctaa aaactgaaat aaaactgcac attaaaaatg tattttgcca attttctgca     1800
atgaaggtgt atcatttta aaattagaga aaggaaagca ttgtttcaaa ataactttgg      1860
attcaatcaa tatggtaaca ttatcagtgc attctgggtg ctgggctgat catgcgtgtg     1920
tattaatctg gtttatttta accgcaactc tgaggtagac gcatttgcct gatatttaa      1980 ataggctgtg gctggaaatg ttaagtaaca tgttcaaaca ggcactatgt gctggagccg     2040
ggacttaaac caggccttct ctctaagtgc agcccccttt c                         2081
```

<210> SEQ ID NO 62
<211> LENGTH: 3911
<212> TYPE: DNA
<213> ORGANISM: Homo sapiens

<400> SEQUENCE: 62

```
cataacacag tcttcagccc ctgccccagc acctggcaca gataaggagt gggaatgttt       60
gcagaagaaa caaacttcag ccaattcact ctgagttccc ctggacctgc tcctccgttt      120
gaacccttct tgtccctcaa gtttcctgcc ccttttctca ccagcagtcc caccttccac      180
tgtttttctg gaaggaggtc agacacagga ccatttgaaa ttcttgccag attggattca      240
cctgtagtca aaatcccgag aatgaatgtc aggcttcctg tcccaaacct ccttgggcca      300
gggccctcag gactttccca gggacagagg taggcagaca ggccagagaa gagtcaagca      360
gagaggatgg tgaggaactt agttcagaaa tgatacttaa aggctggcag ttgccaagct      420
ccatccgagg gcatcccaga gaccccaggg cccttcagga agcgccatcc tcatggtatc      480
ccagccagcc tgagtggcag gggtcggggc caggccagcc tgagcccagc acgtgtaatg      540
accatcctga caagcacttc ctcccatgcc agctcacgga gctggcatcc cgggcagctg      600
```

-continued

```
ccaggcacct gctgccggag agaaaagccc catcatccca gcctctgtgg acagacaggc      660
cggctcggat tccagaaagg catgcaaggt cagagtggag cccccttcccc ggatgtgggc     720 tgagcagcca gcacagggag aagaggagcc aagcggccag ggtgcagaag ggtgaggaag      780
atgagaggca agggacaacc tctggtcctc ccccccaggcc ttcacttcca ctaagcatac     840
tcttcatact cattgtcacc ctcttgattg cgggcagccc tgcccagcct tcccagctac      900
cagcccccac caggactctc ttggcacccc agccacccag tgtcctcctc ccttccaggc      960
cagccaccac ctccatgctg ccctcaccac ccactgctgc aaggccccca tcacagagcc     1020
tcaaagccaa tttctctccc agctgaaacc cacccagccc caagcatagc tataaagcca     1080
cacatctgcc ttctgccagc cctacctgcc accctctctc ctgtggacac actgacattt     1140
gaaggatcaa tgaatactga gcagcagggc cagatgagag gctccagaac cagagggtcc     1200
ccttcctcac tcaactccca tcaagtgaga tcagccacat gggaccagct ggggaaaccg     1260
aggcgtctgt ccactctttg tttacaacca gagcatctta tagataaaac cagacaaggt     1320
ccctgtcctc atgtagctca caatcaagtt aggaaaacag gttctaagaa tgaatcccag     1380
gtcccatcca ccagatcctg cctcctacag caggagccta aacaaggcaa gttcctgttg     1440
aggcagcacc cacacgtcgc tggtgatggt gaagacactg gcgtctctgg tactgtgaat     1500
gcagctgttt gaactttccc ttgggcacag agcacaaagg tgccaatttc ttctgttaac     1560
caatcaagaa tttacatgag ggctccctct gtcaactgat gcgcttcctc cagggaccag     1620
ctttgcatac cagagatctc agggagagga ggctttggat ctagtctcaa aacaataaac     1680
caggtggggg accaaggcca ctcattcacc ctacatttac ataactaaga aagctattta     1740
agtggctttc attgaactgt tatttcattt taaactgtct ctgtgacttg tggacacaga     1800
gagtggacgg cacttaaatc ctcctcgttg gtccccagag ccttgaggct tatctggaga     1860
acagacctcc cacagcaccc tatcccagcc tccacacagg ctctgctctg agtgcttttc     1920
ggcagggaaa aggaacacgt ccaggtggaa atcttccaaa tgtgtcttcc ccatcaccct     1980
gtcaccagat tgttctcagc aaaaactttc tcataaattg tctttgcctt tggcttttca     2040
cacacaaagg tcacatagtt gtctgcctct ggtatcacac gtgtagctgc agaagtggtt     2100
tcagaggttc ccacactgga atctccagag gaattttgat caagaaaagg gaaagttcag     2160
caatgctcaa cccgggtttc aagacccgcc acatacagga cccagaccct ccctgccca      2220 agtgaaatca ttaggactca acaggataag ctccacgttt ctgacttgct gcataactcc     2280
aaaacatctc ttgtcactat ttgcaaaacc ctgcaggggc ctcagaaaag aatcaactcc     2340
attattcctg cctctaaaga gttagcaggg cactgggtaa atgcatgaat gaccgaatag     2400
aaagcaaatg aaaataacaa caaccttggg gagttgaggg taaacattag attggaaact     2460
ggaaaatcgt aagttcctag agtttgttgc ttcatcgcgc cgattaaatg gtggactgca     2520
taagctctaa ctggaaagcg ctctgcaaac tgagcacgga tatggctggt tgcaacacat     2580
cacagtctta gaaccacttc caccacctca ggttaacacc ataccccggc tctgtccttc     2640
actgactttc atcagacacc aataatctca caacacgaaa cttgcgtatg tgaagtgggt     2700
tgccatgtaa agtgagtttt ctaccagagg gatcttccat tctgtcttgt tcaatgcttt     2760
taacaaacgc attgaaggct tgtttattca atctgcatct caaagctcgg atgcatagct     2820
aaccatgtca gatggccaaa tcgggatcat caagaatgtg aactccttga agatgggtag     2880
aaactgtaac acgaatccta acagttggca cacataaaac tcacatttgt gctccaaaaa     2940
ttggcctgta agtgcataac gggaaagtga tttgacagca gatcgatcaa aagacctgag     3000
```

```
gcagttagtt ggaccgagtt ccacaggaac aatggtatat agtgtgaaaa gtggagcgtc     3060
cctgagagag cggtcaatcc ctggactcag ttcagcacgt cctgaatgct ttgctgtgaa     3120
gggcctggca cctgagcgtg acatgagatg ccacatgtct ttataagctg catatctcaa     3180
aaggacttca ggtgaaagga ggtgccagcc agttctgtat actgattcca acgtcacacc     3240
aaatctacag aatcaaaacc tcaagaagag ttagagaatc tatttttct ttgagtgaaa      3300 atcaaattct ggtaattttc ttttttaaaa ttataataaa atttaaaatt atataagaat     3360
gttcttattc ttaggtaata taagctgaag tattagaaag gtgaagtgtc atgccttaat     3420
ttactttttt aaaaaaacag caaattgctt ttaataattt ggaaaaaaga gaaagcaaac     3480
gagacaaaat ttggggggag ggaatcattg cactcttcaa cttttctgta ggcttgaaat     3540
ttctcaaaac aaagtttagg ggattaagct gttagctatt ctgatgtgaa aacatgagac     3600
ccactggaca gataacctct gctattccat ccagcctgag tgcctggctg aggctgactg     3660
agttctttgt ggcttacaga gctgaggcca cagtgacccc tagaggtact tggccccttg     3720
accacagtaa gcccatcccc ccactggcat ggggcctgtg tcaatgcatt ggccctaatg     3780
atgctcccgg aaaaaggaac agatccccga tagacaatct ccagaaggat gaccatccca     3840
gatggaggct aggcgcagga gtttcacacc tgatgtgagc ccagcctgac caaatccatc     3900
agaatgaact a                                                          3911
```

```
<210> SEQ ID NO 63
<211> LENGTH: 1009
<212> TYPE: DNA
<213> ORGANISM: Homo sapiens

<400> SEQUENCE: 63
aactgaaaga ttttcaatga atggaaatgg aaatgacact gcaaaatttc taagactagg       60
tcatatatga ttaactgact tctacctggc tttctcgggg tcttttgtcc ttggaaccca      120
gccaccatgt tctgaggaag cccaagccaa acagagtgtc ctggccaaca gacagctaag      180
gcctcaccag agaccaacat caactgatgt tgaatgaccc tcatgtgaat ccagcccctg      240
acattgtggg cccagataag ccatactgct taagccgtct gaatttctga tctgtaaaaa      300
atggttgttt catcccacta agttttggt tttaattttt catgtggtca ggcccaacaa       360
tcttttgtaa tttcttattt cagttgtaaa cagaaattca tcttgtttct acagaggtga      420
taaatgatct atcctatttt ttgtcaactc aattctaact gaagcattct ctggacactc      480
ggaactaaaa attcacgttg gctcagcaaa atgcaaatga agagctctgg tgcaaatgct      540
attatggagt gggtaaattg agaatgtgtg ataatcgaga tcacatgtcc ccattctcac      600
ttccagttgt cagtttatgc tgcctcagca aaacgagttc tggggcaaat gctgtataag      660
caaatgttat aattacccaa agatagctac gatgaaaaat aagaagaagt caagttgaaa      720
acgccagaac gcatgaagaa ctcagaataa gacaagagag atgggtttgg agacaaaact      780
gtcagaatag agatgagtaa aaggatagta ataatcgttc ctgattattg gaaattattg      840
ccgtatttct ccctgtacag aaaattatgc aaagtttttc acctacatac acacatagaa      900
agaaatctct ctactttcgg gcagaaaaaa atttgttgag gcactttggc ctagcatatc      960
actgattaac ataaatgtta catatgtgct tagaaatgtg ttctccaag              1009
```

```
<210> SEQ ID NO 64
<211> LENGTH: 1804
<212> TYPE: DNA
```

278

<213> ORGANISM: Homo sapiens

<400> SEQUENCE: 64

```
tggaagctca caatggcatg gtgtcaaaag gaatgagcct ctaatctgac ctgaaagcat        60
agtgcagacc acagatttct gcctctgaat cggaatattc ctatgtgatc ctggctgaac       120
tgttagacat tctagagctt cggtcctcag cagtcaatag aaaaagaaat ctatcctctt       180
acccttacag tattgttctg aggatcaaat gagctctatt cctcttaccc agatcagtgt       240
tcttattacc acctgatgca tcatattgat ttacctgatt gtttgacttt aaaatgtcag       300
ttccataagt gcgctttgtt ttgctgtaat ctcagtgctt agaacttggc acacacgc        360 cccaaaaaaa aaaagcgag gggaggagac aagaaaaaaa taatcagcag acagtgatag       420
cagagtatgg gacagtgaaa gagatttcag tgggccaacc atacaaaaca aaggacagga       480
gaccccatgt tccctgctgc ccatcctcat ctcctggctt ggatgcatta gagcaaagcc       540
tcagtgtaat catgggcatt tggattgttt actcctcgtt aaccaccctc tttgctcact       600
taattggtcc aaagcctgtg gcatgagtaa ctaactgtgc agcgatttgg cacgtggtca       660
gcagcagtag cagccgtaat gtactgcact catactctgg gtgcagttcc cacacggtaa       720
tggagctcag acaggctgcc gctgcctgca gcacctttga tgtcctggca aacacaccca       780
tgggacttgc tcaaccacag gatcttcact cttggcttct tatgggtgcc caactagttc       840
ccaggtccct gctgtctgag catcttcac aagtgggcag agaaattcac acccctggtt       900
taagggaact aaatccaagt tgcgtgcctg gccacctccc ctcacacctc tcctccttgg       960
attgctctgt tacactcacc tcctgcctgc tttcccgtaa aggtcgtgcc tcaggcctt      1020 tgcactagct cttcccccac atcagtactc ttaataaaga atggttaaag aagatttgga      1080
gcttgactgc aagcgtttgc accctagttc tgactctaga aagtttttaa ctgctttcat      1140
ttttaaagtg gagatacagt ggagtcacac taagaattat tgcattaagc tgtgttattg      1200
catgtaatcc caacaacgtg tgagggctca gtgtttattt tcattatcac tctatgtatt      1260
acctccttgt gaggaagccc accttctggt tgaaaagagt tggggcccca gttctatccc      1320
tgtctatctt ctgctgcccc ttcccaaggc aacccttctt tgggatctag ggcttcttga      1380
aacagtttga aatcactttta gcccattctc cttcattcat tgaagagagg gaaatatact      1440
gcttaaggtc acagtcagtc agaggcagag acaggactag aaccttgggt tgtttctgcc      1500
acagttgggg tccccaggtc tccctgctgc ctcaggagat tgtgctgctg ccagaactcc      1560
cagattctgc tccctccctt ctcccagtct cagggataat cctttaatga attaagtgga      1620
gcaattatgg ggggtgggga ggctttggta ctttgtggta accaactggt atctcattta      1680
ctgtcagttg tgtacttagg gataaaccca cttactttcc tctcccctc aagttagcag      1740 tccctaccag gcaaagggga taaagtgtga acatgaactt tctcttttg cctcctctcc      1800 agag                                                                    1804
```

<210> SEQ ID NO 65
<211> LENGTH: 14186
<212> TYPE: DNA
<213> ORGANISM: Homo sapiens

<400> SEQUENCE: 65

```
ttctctttca agagcttata attttctgta aaaccaaac attatcctttt gggcacgtgt        60 gttttattct ttctcttgat tctgtgttat aaagtttgat taaaaaggaa agatactttt       120
tgtctcccac acaaagaatg ttcataattg taattttttgg gacttgttgc catacccttg       180
```

-continued

```
agcctccctt tgtttaaaga gtatttttaa tctataaaga agtatctgtg tgtgtgtgtg    240
tataaaatca aaacggcata cctttttgag aatatttagt gattcctgaa gactatatta    300
tagttgtata aagaattatt tagcaatcta atgtggtagg tgatctggta ttatctgtct    360
ctttggtcac atgaggataa ggctgcccat ctcggttatc catgtcctgg gccttaggaa    420
gaaggcagcc agaatcttag aatttgaact gagaaaattg aacacaagtt agcagcctaa    480
aatataatga ataaaaattg tatgattttc tcatctttat tttgtgcaga caagaaactg    540
aactttgcaa gtattttctg taaagggtga ataagctatc caaagtgagg attttatgta    600
gaaaacatct ccagctgtgt taaatataaa gctgtcagtt ctttgaatat ctccttgcaa    660
taattaatca tccttctcag ttaacagcac agacagtaca gcacaggtaa gagagtaggc    720
tctgaagcca gtctttgtga ctctgggtac attgctttca tttacaaaaa gaggatgata    780
tagtacctac catagtgttg gggattaaat tagttaatat atataaaaca cttagaacat    840
agatagtaca tgtatttact gtttgttctg tataatacat tttaagtggc tggttttagt    900
taagttctct cagagagttt ggcatttgaa ctggtccttg aaggattttg taaaagtgaa    960
acataaagaa ttaaaaatgg taaaagctat gtgaattaag tagaggaaga tctttgtttc   1020
catttattgc atactagcta tgtgcctgcc tctgagcttt acattatctt attcaatcct   1080
cataataacc ccaagatagg tattttaagt catttaacag atggcaaata gcccacagaaa  1140 agtagccact ttttcaaact cacaaagtca aatgtttggc ctagttctgt cagactgtaa   1200
agcccatgct tttaattggt atctaatact gctttcctat agtagactat cagattatca   1260
ttccgagaga ctctggatgt gtgtttgctg gtcatttcaa aggctgaaga gaaacagaca   1320
tgcctgtcct tgccaaatac attgtttccc tatcattctg tcacttggaa gtacttgttt   1380
ctgacctgga ataatggtat tgtggttatt ggcgtttttg ttacctttct tactagaaat   1440
tatgcagatt ccccaattat atccagatgc acaccttata ttccaaattt tgttgcctgg   1500
gattgactga gtacccttt gagttcctgc atcagagacg tgtttacagt tgtgttccca    1560
gtcttcagca tttatggttt cattttgtca aatttgtttg aagtataaaa acgataatct   1620
taattctgtt actgatcatt ccttatttgt cacatcatct ttttttgaaa cgtttaggga   1680
attaattaat aattttatac tcattctttt tccactcaca tatctcactg gctttgttca   1740
gaattaaata taaacccagt aaaactctct tacaacaata ctcttgtatt cgttctggat   1800
tgtcacatag gagatgtgtt taggtatcta acttggtttc agcattgtac gacagaatct   1860
gtggcaaatg tggcatggca tacattatat atggatattc ataaactgct tttacaaaca   1920
tttccagtta ctgaaccagt agcactgttc cagtcagtat ttttgtctgt acatgtatgc   1980
atgtgtgttt tcccatttt ataaaaatgt gttaaaagta aaatgctaat gctgattata    2040
caaagatagc atttgacaaa attccttcat aactctgaag aaaatattct atgataatgg   2100
gtagagttat ttacaacatt aaacaaaaag tatttgagag caaccgttaa atattatcac   2160
agggtaaatt cagcaactga aatccttttc tcatagtttg tattaggaaa ttaatagtct   2220
ctcagatgta tattggtttt ttcagtagtt attcttgtgt gatatgcatg ctcatgtatg   2280
tatgtatttc ttaaaaatca ctggactttt gtggacttaa ttgttttcat agtttttca    2340 attttacata ttttaaatta aagcaaatct atggaatgca gatttactta tatcacttag   2400 tcttttttcct ttcttttcaga aaagtggtgt ggaaacaaaa tggtttttagt attgccttat  2460 aaacaaattt aagatcatga gtttctttta ttatcctctt tgttcatttc cttgaactac   2520
```

-continued

```
atccctaacc taaatcagct ggagacaggg aagaaagtgt tagattctta ctcagtttag    2580
atcctctgcc aggaaaactt gtaactaaat taacgctttt ttaaataaaa ggagtcattt    2640
ttaacaataa cgtcagggca gcaggcatcc atgaaatgta tggtcactga tcattagatt    2700
ctaatgtgtt tactattttg aaactctagg gagaagaaaa cttatttttg catatgttgg    2760
aaaaatgtat cctcatgggg taatatagat aaatttgtaa tgcgtatttt ctaattagat    2820
tatttaggag aaattaccac tttctcttta attattagca ttaactttat catttttgtt    2880
tcaagatgtc acagctattg ttcagcactg aaattatata aattattagc tgaagtgatg    2940
actggccatt tattctgtta tttctttcag aaagtctgtt gttgtaaaca tccccgactg    3000
gaagctgtaa gacacagcta agctttcagt cagatgtttg ctgctaccgg ctattcacag    3060
acatcctctt gatattctgt cccggagtgg agttgaggag gctataaaat gtgtgggaaa    3120
cctcagaaat ctttagctgc attcttttac tgcttgctcc taataacagg atatgccgtc    3180
tcgagctgac ttagcgtgct gctgctggcc ttagagaatt tagttaaaaa aagtgttatt    3240
cctgtttctg ccctgtcaat gaaattttag tctttataac ctttccaagt aggctggagt    3300
ttaacatccc aacaattcag gagactgatt ttctccattg taaattctgt gggttcttca    3360
tcactaccac ccagcagtat gcaatctaga aatttcagct ttccctatac ttaatgtgtg    3420
tgcaacattt ttctccgtcc tcttgtgata ttacagctcc taatcagaac tctcctctaa    3480
gactgcaaga ctcaagccac taagcctgtt tacatttgct aatgggtatg catgtctttt    3540
tatattaata ttttttcctaa tattttcaga ttgttgcttt gcttccagct gccctgaaag    3600
cagctgtatt gtatctattt tttgtgtttc cccacagatc tgaataatcc agggcttttc    3660
tcacagatga cactcagtgt ggactagtat aattttatag ctttctgagt tttaaaaaat    3720
tgttatttta tttctgttag tctttacatt tctattttat tggcattttt cttttcaata    3780
aagcattgtt ttttaaatca tttatttta ttaaactgct aaacatacta tgttaggttc    3840
catacatgat taaaccaaaa gataaaggtc ttgccaatct aatgtttac atgctttct    3900 ttgattagat tataagcttt ctgaggtcag agacattaaa tcttgataat tctatttttt    3960
ctgttataaa cagcaagtaa gcaccttgat gtatagtact ttagtaatga ttttataaat    4020 gctctttttgt tagagtagta gtttataaga cttatttggg gatgggggtc agttgcttat    4080
tttcaggctg agttattgct gagctcagaa gtcttccctg ccaaggtaga atgtaatgtg    4140
ttctgtggta ataggattat tttgtttgac caggtgacac tgtttatttc ttataaaatt    4200
ttgatatatg ctttaaaatt tagtaagatg gatgcataat ttatgcagtg aaatttgaaa    4260
ggtttttcaa aatgataagc caaacctaag ctaaatgagg gggattcttt ataataaagc    4320
tgttatactc tgcccagcta ggccagttat ccctagatgc tacagattaa tggcaatctg    4380
ttatgtaaca tttgttctat attattctgc cctaatgagg tgaatcaaag acgatgtcag    4440
ttttaattct ggatgcccctt gcttcagtat agttaggtac agccttttg tagttttcag    4500 atggcttctt tatgttttta tattgaagaa ccactaactt cccattggcc tataaggtta    4560
gcaattgatt atttaggctt gaaagttaga tcatcagtat ttgtcaataa gcctgtaata    4620
acttgtttcc ctagcccta acttagtgtt gaagaaaaaa attgtggtat ggacttagaa    4680
agcacagaaa ttacttatta tttaagattt gttctaccaa ttgatattta aagtaaaaca    4740 ttttttagcca ttctgtaaat gacagtattc ctgagtatat ggtttaggga caacttttta    4800
agcaaataac tattacaaaa ttgggtctaa tttatttcat tgtacaaata ttctttagaa    4860
atagtcatat aaatacactt tggacttgtt ctcattgtct ccacacctca gttccttcta    4920
```

-continued

```
catgagtcat gggcttgagg ttacccagaa aggactgtga acctataacc cagcatgcat      4980
gtggtattgc gtcagcatgt tccccttcta ctcttgttac agctttattc attggatcaa      5040
tgtgcattat ttgctgtgtg tgctcagttt ttgtttcttt tttttagttt gaatatctgg      5100
gcttagttac tttttaaaat aaggctgttt cagatagttt gcctagcctg gttaatgtgg      5160
gtggacccat gctacatgtt ttggcattgc ctttttttat ctgtaccata ttacaaactt      5220
cctagtaatt tgacattcac tgctgtcttt gctttagctt tccaacaggt ttggtgaaaa      5280
ttgctgttca atatcagctt gcatcagaat tacggagggc ttattaaaac acagattgct      5340 gggcccaaa aaaagtttct gattcagtag gtctggggtg aacataaga atgtgcttta      5400 gttcccaagt tgatgctgct cctctaggcc caagaatcac agagctcatc ttacattctt      5460
ttgatattat gccaaatcct gaagtttgat tataaaaagg cccagagaat tgaatgtgtt      5520
ttcagagaaa agcagaagaa aaaaatacgg ttgtaatagt agttaaaaca gaaaagcagt      5580
atggttgtag agtggggtgg cggggaggta tatgttaatc ttgagaacaa tgctttttgga      5640 aaacaggagg ttcctgaagt cctgggttac ctgtgaaatg ccaaagattt ttagtttgct      5700
ggcagtgtta tatgtagttt tacttccaaa tttgaagacc tcttctttga tgcaagtgtg      5760
ttggtaggaa ctgataatag ttagtggaga tatttgtggg aatatatttt taatcagaaa      5820
gaatgcaaaa agaggggag acatttcttt gagacacctt aatgacactg ggaacagtag      5880
aaggtggaaa tgtgggaaag atgtgcctga gatgaaatta tctgaatgtt gaggggagg      5940 agagggttga tgcatcatac tggtcatcaa gtaagttctt ataaatgcaa gtttgattgt      6000
tttgaaggga aggatatagg aaggctggat aatcagctac atttagatat ggaacactac      6060
aggatgtcgg catttcaact cacttctgcc ttttccttgg attctacact ttctctcagg      6120
atatctttcc gattgagtct tgcctcattt agaatgctgt gcctgttctt tttttcaaca      6180
gagtcttacg taaagaaccg tacaaactta gtaaagagtt taagtcctgc tttaaaccaa      6240
gtttcagttc atgtaaacat cctacactca gctgtaatac atggattggc tgggaggtgg      6300
atgtttactt cagctgactt ggaatgtcaa ccaattaaca ttgataaaag attttaaatg      6360
ctagttatta ttaatgctgt gttgtaggtg ttcagtaaat agttgccata atgcttaaag      6420
cagacacttg tttttattaa taaagatgat gccaactttt tggtttagaa atgctttgaa      6480
tctttgatat tgttgtaata tagtggcaaa gaattttaat cccagcttct ggcgctatgt      6540
tacttgggga agttattaat ctctctgtgc ctcagttctc agtcgactaa attgaattat      6600
aatagtacct gataggattg ttgagttaat ttgaaacttg ccaaattttt acattatttt      6660
ataatttata gtactttaac atattgcaat gcattacaaa gcatataatg taaaggtagt      6720
tttatgaagt gtcaaattaa gcatatttgg gaattgccca tcaatttgtt tttgaacctc      6780
agtggaattt ctttcatatg ctagatgtga aaaaagcata tgcatgtggt ttaggctaca      6840
aaatagcctg taggttaaat tcctaattct agtgtttaat tctttttctt cttgtttaat      6900
ggccatatgt ttatatcttt atattacata cattcctgat tatgtaataa ggtctttgat      6960
catgtgggct atcagatttg cctcacttta agaagctata catgaaacta tgttgtactt      7020
aagtgaaaat ttgattcttg tttgaatgca gtgaaacatt ctacttacag ttagctgtct      7080 cccacccta caggaaggta catgccttca ttttttacag aatttttttt ctgattaatg      7140
tgtttatcag ttttatgtta tgaaatctgg atatatgtta aaatgtctca gtttttcccct      7200 tgtttaccat attgccatta tagataacat aatgtaaaat tggatgtctt tgataatttt      7260
```

-continued

```
gggatatgtt ctgaaattaa atttgaagat ttggtatctt ataattattt ggtgagcatt   7320
tggcatgaat tatttagctt ctccccttta tgatttattt ctctcatcga tttctatggt   7380
tctaatgtct cctgtagact tcagtaaggg aatctgtaat atataatagt tatcttttag   7440
ttatatttcc actttttttta atgtgttttt tttttagtaa atgtcaaaag tgttactcag   7500
taacatatta tgcaatatta taatcaacta acctcttcat tgataatgac ttcatattga   7560
gaggtttttt aaatctagaa attgtttttaa attccaggtt aaaatgtaaa ggtattttta   7620
ttttttaatt cttctcaaag ctactagtca ttataaaaca acaatttcac atttagaatt   7680
tttatatgta tataaattag attatttttta tattagcctt aactttctttt aattttatga   7740 aaaacaacta gtcccaaggg tatttttact atttaatata cattattcct gtgattcaaa   7800
atcttagcag tagaacctgt tgagctactt aactttttctt gggactatcc aggtgcagtt   7860
ataactggtt tcaaagtttt tccttgcttg tttcaaaatc attccttaaa aaatgttcag   7920
tatttttctt ttgtcaaaaa atatgtgggt tgttctgttt tttaaaatag tttgagaaac   7980
ttcctttgcc acttgtttttc tgtgcaaatt gtaagagctc aaattccctg ggggtaggga   8040 ggactttat aaggtttttt tggttgaagg gtataaaagg cacttaaaag gtatacagtt   8100
acttttattt atcccagtca ttttgacatt atgataagct ttccccactt tataggttat   8160
ctgaaaattt ggtggggggc tttatttata cttaatataa caaaattatt ttcctatgtg   8220
tagtcaatag cacatacaaa aatgtttgta gtcagtagca cagtattcac caaaatactg   8280
agttattttc aagtaaaggt ataagtatga atgagttgtc agtccttctt tttcagataa   8340
ctttctaaat taaacttttt taatgttata agtgaccaga ctatgtcact gatacaatgt   8400
catgattaga tgtgcagaag actttacatg gatgataaat gaaacatata gaaattaata   8460
tcagattaaa ctaaaacatt aagcaaagta tgcttgcata catatatatt taatgatatg   8520
tggagaatct ttgtgcttca tagtcactag acctaaagta gaagcagttg tcaagaatgt   8580
ccaactgcta ttcatctttg tggccaaagt aaatttcaga ttttttttttt gaatggtttt   8640 ctctttatta acccatcatc atgacaagtc tgtcaagtga cacatgtgaa aagcagatgt   8700 cctttttaagg aggcagtgca atgcaggaga aggaacatta ttagagataa aggaaaaaac   8760
cagaattcca ctcaacactt cctcaccaaa tgtgtgtggg gatttctacc aacaaccaag   8820
ttctttactg cagattctcc agtggatacc agccaggtgt cctctaattc agttcaattc   8880
tattatctac tgggagatag tgtcagatcc cgcaagtgga gggctcagtc ctacaagact   8940
acccctactt cagatgtcag tcacaagcag ttagcggttt gtgattctga ccaactggct   9000
agaggtcccc ctcctcaagt gtgattaatt tgctagagca gctcacagaa ttcagggaaa   9060
cactttacat ttacccattt attataaagg atttatgaag gatacacatg aactgccaga   9120
aagacaagga gcataggcaa gatacaaggg tcacggagct tccaggtgca ccaccctctg   9180
ggaatattca tgtgttcagc tgttcgaagc tcattcgaac cctgtccttc tgagtttctg   9240
gaggcttcat tacggcatga ttgattacat cattggtcgc cggtcctgtc gtgtccctgg   9300
aggttggagg gtggactgaa agcttctcat catgctttga tctttccgat gaccgacccc   9360
accctgaagc tatctacggg tccccagcaa cattcatttc gttaacattc ttacaaagag   9420
attccaaggg ctttaggaaa tggagatgaa gagcaaatat atcaatatca caaacatacc   9480
cttgggaatt agacctctga tctaatctag gctccctcac ttgccatttt tgtgaccttg   9540
aacaagttgt tcatcttttc tagttctctg ttaaaaaaat taaataaaa aaagctatca   9600 ggttgttagg aggactagat aagagaacta tgtgaaggac ccgcacagtg ctagcaacaa   9660
```

-continued

```
agttgtttag taagtgctat ttgcttccag tgagctccct cagtgtgtac caccaaatca   9720
catgtatccc agtcaaatct taaagtccac cttgaatctt taaggtgtgt ttttaaaact   9780
gcttttgttt tgatccttgg aagttaaatt ttttacacaa gcattcaact gttagcttca   9840
aactgaacag aaaatatctg tattatttca ttatgtataa aaaatgatta agcctgcctc   9900
aggcagttca gagcaggttc aaggagtaac attagactaa tcagagtgcc taaaaagctt   9960
tatgcggtcc aggttgtaca gggatgttgg aacagtaaat atgaaggttc gagataggta   10020
gaatagagca ggttatatta gagaagtctt tctaaaattg tgttggctag cctgggattt   10080
gaacttatac cgtgtatgta tgtccatgtg taacaggttg catgcaagaa gcagtgttca   10140
taaaaggtgg caaacttgtt ttacttgttc agtcttttca gatcagtact tataaaacat   10200
atttacagta aatatcttat attaaatatt agctaaccct attaaattgt gtgtccttgt   10260
gctgcatcat ttaatgacta agttggcatg tgatttgaga tagctctaag tgctaatgga   10320
tttgaaggag ttaaaggcaa aaccaggaag agaaaactat ttttaggaaa aagcgatcat   10380
acaacaggcc ttaaatagaa gaaatgagat atcttatctt tactatgtaa cctttaattc   10440
cttacacatt ttgacttcat attttttgta tgtaaatgag aatgttatag tcttgtaaat   10500
tccttttcct ctgtgactac attcagttat tttatgtgtg tttgtgcatg tcggtaagca   10560
cagtatttag tagaatgagt tattggttaa accttgtaag ggccacctgt ctcttaaatt   10620
gtaatgagga tttgattaga taatctagat aaatcactaa gcactcagaa aatatcccat   10680
tcaaaactca gttccagtgt caagtctttg atttggaact ccaaggtagt tggtcctctc   10740
tttgtgccat aaatgtgcct gtactcagta gtgctaaatt gctatcaact agtctaaatg   10800
tacactaatt catctgtgtg tccacttccc ttctttcccc tccctgatgg aagatggtct   10860
gggagcaaag gtgacaggta atcttttttt aaacagctaa aggattggat caatttttca   10920
cttccctttt tcacactttt ttccttttac taagaaaaag tgcaaatgga gaaaactgtc   10980
cactaaatat gaattaaagt gctattatca gaaattgtgt aaaagcaaca taatggcact   11040
ataaaaaggt ttatcttaga atcaaaaacc ttgggtttat attatagcct gctactttct   11100
agtcatatga cagtcaagct atattacctc tttggcttac aaaataggtc atctgcttgt   11160
tatgattgat gtgaaatatt catacaaact accactgtgc ctggtaagta gaagacactc   11220
aaatatgtct tggagttaca gttaatgttt aaatttgaga aaaaccaact ttatcacata   11280
gatacagttg tttactgcta gaaattttat ttaaattagt tgatactctt ggttaggtaa   11340
tgaaaaacaa tggtttttatc tccattatgc tgtgataggg aagagtaaca cagttcaaat   11400
ggcatacctg acaattaagc atagttaatc acacaagaaa caagtctcta cttgatacct   11460
ctccatcatt gatactttgt gccatacagt gaaaacagaa ccatctaggt gttcacggat   11520 ttattttttcc ttatgaaagg tagagagaaa attattccca atacaaaatt ggttattagg   11580 tgcctttttaa ttaggcgtaa gggcatatga acattaccta tgagaatttt gtcaaaatta   11640
tttcccagtt actgttttaa aacagcctct cttccccact tctaatttct cctttctatt   11700
ctaccaattt tactccatac ctttttgcta aataaacatt ttcttccaac tctgtttggt   11760
gttttttttt tgatctgctc ttcaaagtat cagctagtga ttaggctata gaactctaag   11820
acagtagctt aaacaagatt tttttttttaa cccctgacac aaagacaaag ctttttcaga   11880
aactcttatg ttttttagctg taagagatca tattgtcact gagcaaagta cttacaattc   11940
gtagtcattt gtcaggaagg gtgaactgac taaataaatt atcctaccac cacaatccca   12000
```

```
taactctaaa cttagatgtc aaacaaatat acacacagct aaccacaaaa aaaaggaaat  12060
cccagctgcc agaagtgaaa aaacagccag aatagtgaac tcagcagctg aaggtacact  12120
gacctaggtg gatgatagtg ttggctgtgg gtctcaccaa tggaccctga gactttaaca  12180
gcaagagata tggcctgact atacagggaa gctggactga caaagccaag accttagaag  12240
gtgcagcctc agaaggagga tgagcaaact tctacaaccc agggaagcta caaagttagt  12300
tattttaatt aatattttca tgtatttcct taaatcactt agcttagaac tatggaaagt  12360
cagaaacagg ccttggtagg taaattgccc aagtcgtggt gaattcttaa agacagcatt  12420
ctataggaaa tattttagtg ctggcagttt agttatttaa tggtggaaac ttgaaatttg  12480
atctttgaaa tataaaggaa taaagagtac attttagaga catcaagctc tacgttgaga  12540
agacattgag agattacatg agtaacaaga aagagaaact ttctgagaat gcacagctct  12600
tttacaaata acaaagcatt tagttttctt taggcttggg gcaagacatt aaatccaccc  12660
ctggtttata aacagatcac accaagttta gtgtccactg atatctggaa gactttaagg  12720
gtattacatt tttgctatta ggatcttgtt gcctctagca acatttggtc ccaggacaag  12780 aaatagggc gggtgaatgg gagagtcatt aagaaagcat gtagaattga agaaacctga  12840
aaataatgga agattctttc agaactcatc ccaaggtctg ggtaaagcct gtaatgtaac  12900
atacataatt ttgtaaacac accacatcag ataactacag atgttttgga cagcagctga  12960
ttgtttaaaa ctcatttcag agtaccaggt attggaggga gggagatggg ggttgaaaca  13020
gtggggtaga attcagtgga ccaggattct ataccttta aggcaattcc tgattatatg  13080
tatttataag aatgtgagcc tcagtcacca cattccttca gggttgggta taaaacgaaa  13140
tacttggaag atataaagat tgtagatgac aggttttatg ttcaagcagc attgacattg  13200
ctactgtaaa agtataatag ggagtttatc aatgctgtaa tatggtttta aaggcttttt  13260
tctaactata gatacttata cattttttct tttggcaatg atttttaggg agaactaaat  13320
cattcttgta gccagacttt gcaaatgaaa gaaaacaagc caagggaacc tcacttagga  13380
tataagacac tcacaagcat gagtgttgca actccagttg tcgtgttttt aataacacat  13440
ttaaaaagta tagacggtga attcccacta agtgtgtatt ctttgctgtt taccagggtc  13500
agcatgagct gcgaatctgc atgcgtgtct gtcccacatt gtggttacct gtttggcagt  13560
tttgcaacat tttaaccccca gatttttatta tttttcaaac tcattctcct cctcctgttg  13620
agactctgtc ctgcggggaa tgaaacaaga ctctgtcact caatctgttg aacatctatt  13680
tgagaattag gttcagattc cctggcttaa gccacttaat tatctagcca ggagttttca  13740
aatattttta tagtggaacc tgctctttaa aaagaaatca ttcaccaaag cccaccatgt  13800
aaagcacatg aacgtgaacc cacctgctaa ctgattccct ggttacccct tttagcacct  13860
gaggcacaca ataagaccac tgagttaacc caccttctgt tatccatctc tggaacagac  13920
tctccaatat agccattgta aaccatcctg tttgtaatcc tgtgccttcg tatatccagt  13980
tcttccattg tgaatgcttc atcatccttg atatttagtt gtccttgata taatctttc  14040 ctagaaatct gccctgatac ccttgtctgt gttccttgc attcattcct ctatctttgc  14100
tacactgtat ttattagtca gactctccca cactaatagt gttctttttg gaacatgtct  14160
tattcgatat tctgcctcca gggcca                                          14186
```

<210> SEQ ID NO 66
<211> LENGTH: 9518
<212> TYPE: DNA
<213> ORGANISM: Homo sapiens -continued

```
<400> SEQUENCE: 66
tcctgtccaa cccagtaaaa ttagaggata ttgtgtatta aatgtacatt ttgcattaat      60
tcttgtaatt aactcatgta aattaattca gtgccaggca tatatgaagc cataattaat     120
gattgtgttg ttttattatt gttaacaagg ttcctattgc attgcattca aatgatgaag     180
caatttccta ggtaggaaca acacttcttg aaacaattaa aatgcagtca cagagtttct     240
ttaaaatggg gtttaaaaat tccatttcta ggcacctaga gaatacttct ttaagagcac     300
aagggatata tataattaca ttatacatat tacttaccaa tacgtaagca ttctaaaata     360
tgtgtagtga tacctatcca tttcaggata gttattacct ctggacaagg aaaataaagg     420
gaagaaagat ggaacttcag ctgtaactat ggatacatga aagtctatta gagtattttt     480
tctgtgctta attttttggt ctataacatt aaagtgttga cattaacttt tacatgcagt     540
tttattactt agtaaaactc aaatatcacc tcccttggaa accttgctgg aatcttctgg     600
aaatctccct ccttgggttc ccacaggtcc tgttcagttc agtacccttt tgtggcccac     660
atctttatga ctcaggtgta aagtgttagg atctcaattg cagtgactgg tgctaggatg     720
gctgttatta tatgcctaaa aaatacttat aagtaatgaa gccaacttac atattctgta     780
attgctgatg aggtgtgctg atggttgctg ataaaaatga ggaaggaata tgaagaaagg     840
tacagtcatg aaacaatacc cctgataaac ccagttgtta aatcctcagg ctgccacaac     900
aaaataccat aggctgggtg gcttatggaa cagtttctca cagttcatga gcctttgagt     960
ccaagattga ggtgtcagct gattcagttc ctggtgggcc cttcctggct tgcagatggc    1020
tgcggtctct ctgtatcttc acatggcaca gagagagctc tggtgtctct tcctcttctt    1080
atgaggactc tgatcccatc atgagggccc tacccatgtt ctaatctaac cctaattacc    1140
acccaaagga cccacctcca aataccatca tattggaggt taagacttca acatatgaat    1200
ttgggggaga catgaacatt cagtctataa catcagtcca aagttaattc tctacctgtg    1260
atcattttat agaatgagca ggcagggttt ctgctctagg ggatgctacc cctggtcaga    1320
gactcgtgtg gatttggcag ggaggaaact gcagaattgt atggcctctt tcatcggcat    1380
gtttctataa tctcttcaca tacctgaatg cctgaagagt aagtgaattt caacactatg    1440
tgctttgtaa ttctcatcag cttgtcattg attgctctcc cgtcaagatg atggagaatt    1500
ttagcttttg caaacaatta tagaatcttc tgatcaattc acagtctttg aatggtctgc    1560
atatccttat gcaaaagtca tttcaatttt taattatttt agaaagtgat ttgatgcatt    1620
cattctttaa ggtaaaataa aacataagca taagcagtta gaattagata aattattgta    1680
aaagtcaatt caataatcaa ttattacaaa tctaaataac tatgcacatg acggttgggt    1740
atgttagcat aaccagataa ttggttattg atagaccgta gggtacataa ttattcatta    1800
cctggatgca atgctgattt ctcgctgtgc tgatgtatgt cattagctac attttaaaga    1860
agaccttatt cacttgctta aggctccata gaaggtagat cttgtttttt atctctaaac    1920
aaaaaagatt tcttttacat tttttatcat gacataaaat tgtgtacttt cctcatttag    1980
aacttcaagc tcctgggttt gtaagaccaa ctgccaagcc tcctaaagaa gtttctggga    2040
gtccctcctg cttattccat ctccataaac ctcaggattc aaactgatga ctcaccatat    2100
taggtttctg gcaatagact gatgtttctc gccattgctc tctagagcac tgtaatttta    2160
gccttaagat atcatgataa tttctcctac ctgcaaattc acactcatta aactgggtga    2220
taattatgca aggactcact aacaaaaggc caggcaacaa ttccataatt aatgtctagg    2280
```

-continued

```
ttcttgtttt tccagtgata gatttttttt tctcttttca gcttaaataa agatgacatt   2340
gtcgtgatca ttgtaaaact agccagtaaa aaatacatta gactacagaa aagaaagtcg   2400
ggttctgttt caggactacc ttgtctgttc tccacaactt tttagtctct gtaggccaat   2460
tgcactagga accactctcc catctactat tattactaca aaacacacag caaactgtgt   2520
gcaagcacat acatgtttat tcacctgatg agcttttact ttaactatat ggctgacata   2580
atttgctgct ccgtagaatt caaaaaaaca gtcacttttt aaaggatgca taggtataat   2640
atgactcagt aaatcacaga agaaatacaa tgaccaatac atatttgaaa cactgttcac   2700
atctaccagt aatcataaaa tataaacaaa agaaagaaat ccaatcaaag ccagagtagg   2760
actccctcta tggagggctg cattttgtgt ttgacattgg aagacgtctg acacgaataa   2820
cttacagaaa gccctgaaga aaacaagaca aatggcaccc agatgaaagg cactgggttg   2880
tcagagcctg ggtgatgagg acaaggatga aggagaacag taaagccacc tttcgcacaa   2940
taaattatga gataaccctg gaacgacagc aaacagctgt cggtttcctc agagctaaca   3000
gcagccacct ctgctgcttt ttccaccacc agctcctttg acaaccagcc taacagaatt   3060
gatgatcaaa gctctccagt gtggcagcaa agcctttgcc gggggaaagg tctttaaatg   3120
ttactggagc gagaagggaa agtgccaggt aggaataacc ttgacagaat aaagtgaaca   3180
acaaagtgct ggaagcaaac tgttaagagg gtgtggatac agctcgtgag gtggcggctt   3240
tgtggaggtt ttcactggtc cccaacaaaa aaggacaatg tagcaagttt cccttatacc   3300
tttcacttaa aagactgtcc tttattccaa gatttcttct ttcacagttt tgatattaaa   3360
tctccttttg tgaaaagacg atagaagatg gtgttcttcc tctctcttat attcatggtg   3420
aaataaaatg ttggcaacaa aagtatatct caataaagct gttattttaa aatatagaaa   3480
aaaatctaca gagaagatta cagatggttt ttagttcttc tttgtatagg catcctaaat   3540
tctctattac catataatgt tatgttatca gagagttata aatatttcaa aataattatt   3600
tacgacatga ggtttagaga gtgctgtaac acagttgcat acaaggtaca gggtggatga   3660
aaagttctgg tgctatttgg atgtaggggg aaaaaaagct tgagttgagt cttgaaggat   3720
acgtaggggg tctccaggtg gatgaggtag aagggcattc tgggagagaa cagtatgttc   3780
agaggctctg atgtaaagta tcctgacctg cttggtaatt gtgttcgtta ggtatgtctg   3840
gattttaaag cctgttggga ggttgcagtg ggggtagagg gaggccagca agataaggct   3900
gggtgagctg gaggactgag gttcttatgg ctgcattcag cagagaccag acattacctt   3960
aagaagcctt caaggagtac attgttaaga gaaacggcat ctgtgggata aaaagaggca   4020
gaaagatcta agcaatgatc tcaggctgga aagaaccaaa cctttggcag agtctaaaac   4080
ccaggcgctg aggatttgcc gtggtccacc ttgcatggtt actgagcacc cagtatttgc   4140
aggcttaaaa taacaagata gagtatcacc actacctcag ttagtctcat tattgaggga   4200
tttcagatac aggagcaact gaaggtagca aagcaaacaa cacaatgtgc taagagagca   4260
gtttcccttt tacaaaatag taatgatgaa ttattttcac caagtaaaat tcaagctttg   4320
aagggctgga gtggacttgg ttaaagacta agtaactgta cctttatttc aattgcatga   4380
actaaaacta caaacaagt gaagacatgc actgagaaag tggagtatac tatgacggta   4440
aatagttttt tagcatttta atgacagaga gagattgtgt gtgtatgaca catcaacaac   4500
aaataaataa aagaactggt gaggatagat gagtcactga gaatgtttaa aactatttgg   4560
ctcccccagg agatgaccag atagtcagtg aatgattcag catgggaaat aaccagtaag   4620
agcaaatgcg aatgctaaag ggatatgaaa atctcagaga tggggaaaac agggtcttca   4680
```

-continued

```
cttgccactg agagttttaa aaagattatc tcaggggata gtaaaaggca gggcttcaac    4740
ctgcttgttc taaaggtagc tcataaggta tagtcgagaa aacaggaaga agcattagtc    4800
actatattta gctattaacc caagattcca gcaatttctg atgcctgcag cattcatctc    4860
tgttctgctc ttataaaacc cttccagagt gacttgggtg agagtattgt cttagtctgt    4920
ttgtgctgct ataacaaaac acctaagaat aattaacaca taatagaatt tttcatagtt    4980
ctggaagctg ggaagtccag gtgagggcct agtctttgct ttcaagatgg accttgactc    5040
ctcatgtggt ggaagggatg gaaggataac aagggaacta gtttcctcca tcccattcat    5100
gaggctttca ctctcatgac ttaattacct cctaaagacc ccacctatga ttaagaccag    5160
gctcatgatt aaatgtcaac ttgtgaattt tagaggatgc atttagacca cagctagtac    5220
ctagagggtc tctatacaca tttttaaatgg catcttacat gttcacccag agacaccata    5280
aagttgctgt cagataagga ttttacaaga agagccagaa atcaagattt ttgtataaaa    5340
ctccagagtt ttaaatgttg gctcaaacta aagaaaattg tgcaggccaa acaaaacata    5400
tctgcaggcc aattttcagc ctcaatctaa gtaagagttg ttgtaagaac aaattaaatg    5460
agtttaaaat aagatcaggc aagtactcac tctgctcgct tcaccacttt ggtgttcata    5520
tgttaactga tttaagtctc agaacttatg agggaggtgt aattactacc ttatgtgata    5580
aagaaagtaa ggaagagaag ttaagaacct tgttctgtca tacagtcaga agaagtgggg    5640
cgggatttga accagaccca ggcaatcgga ttcagatttc acctctctta atcaatgcat    5700
tatgcttgca gtacaagctt ctgatccatg atagacagtc tgtgtaattt cccttccaca    5760
tcccctcagg tgctttgagg caacttcagg gggattttct gatgctaaga aagacagttt    5820
ggtattttaa atacaacaaa agttgtcatt tcaattaggt atctcaaaaa ctactgtgat    5880
gttcagtata atgatggaat ctatatagtc ttgactagga gttggaacag tcacgaggac    5940
gtatatgctc agctcttggt cgccaaagga caaagttgca ctgaagatgg tgaaatgtta    6000
catcttcaga gaagaccacc tctcctcacc tgggctccca agtagtgcag acttggatag    6060
atggatatgg ctggacgaat ggatagatga atgagtgggc ttcccaaagg tatccatcta    6120
tctgcatata ccaggagaca cttttgactc ttccattaca agatgaatta caaaatagag    6180
tgtcaaagtt aaacttatct ggtgtagtta caattgtagt gtttaatcat cttcactaag    6240
cattccctaa aaaagagctt agtgaaggaa ttccatagga ataaatgtcg ctccaatgta    6300
gctccggaca acattgatat tgaggcgatg ggggatgcca tccacccgaa tgtccacaat    6360
agaaaatgat ttaaattttg gtacagccat agaattacta ttagactacc aaaaacattg    6420
tttacaaatt atgtgtaata aatacttatg atccaatatt aaatgagaaa atgatacaag    6480
tttatacagt atatgtaaaa atgtatcatt taagtgattt tttcttaaac aaaaaaagac    6540
atcaggtaag taaatttatt gattacctgc aataaggata caaagtaata gacaaaagaa    6600
aaacaaaacc aagatatttc aaatagttga ggagatgaga agctctcaaa taattagatt    6660
atgaagaaat agatggcaat tgaaacgtga agatatataa cagttgctat aatatccaga    6720
agagagaaat tacctttggc tgtggatcca gggcaggcta ggaggagcat gagctgaacc    6780
agaagttaac tgggatttag gcaggctata gagcattcca ggcaggaatg ggagggatgc    6840
aggttccagg ctgatgcaag tatggaaaca tgcaatatat gtttagtgta atgcaaggga    6900
aaaaacttgg aacctcagtt ggaatcctgg ctccatgatt tctctttaat agggtatggt    6960
aacctctaag gtctcaggat catcagccat atacagggac agtaaggtat ctcataggat    7020
```

-continued

```
tcctgtgtgg attaaacaag attaaattcc tgtggatatc ccttctttct cttcagcttt      7080
ctttgttgtt catttattca ttaccattca tttagcatgt gatgtagcaa gcaatggttg      7140
gctaggcttg tttgctccga tcctgccctg tgccccaccc ttcctgccct gttgggcccc      7200
agagtctgac ccctatggac tgtgtaaggc tctcttgctc tctggcttcc agttgggctt      7260
ggccaggaaa taattgggag gaggaagaag cggggcaact tacccagtca ccgcttgtcc      7320
cctgcgttgc catggctgtg gtgggtagct cctctcccat agcctccgct cttaccatct      7380
ccaaacacag ctctgcactc ttgccccttc agttctaccg gtggggatag ctttccacag      7440
tggtaggccc tgggtgccgc atcatgtgtt ctcttaaccc tgcccacgtt tctgtacctg      7500
gttcctttct caaattccct tcagttaaac tcctttaaga atgccatctc ttgctggtac      7560
cctgatacaa ccataaacaa ggtagacaac atccttgcct tatggggctt atgttctggt      7620
aaacaaccat attaacataa tagctttgga tacagtgaaa aataaagtaa agtagtgaga      7680
caataatggc tgagaggggc tactcgaggg aatgatattt gagctgggac ctaaggaatc      7740
agagggagcc agcaatccaa agatctggga gacttctatt ttaggcagta gaggcatagt      7800
aaaaaaggct aggacaggat gtggtgttgg gagaatgaaa agcagtgggg ctgagaaagg      7860
gtggtgggag ctggtcagag aggcagtggg gactggtcaa ggatggacac agtgagccat      7920
ggagaaggat ttggacttta agagtgtcag gaagtcttcg aagggcttgg gtggggagta      7980
atttgagcca tatttagtag acaaaggatt acacatcagg cagagtggag ggtactgctc      8040
ctgtccaggc cggagttact ggcatgatct agagtgatgg cagtggaagt ggagagatgt      8100
aaatggatga ggtcaacttg cactgtgatt ctgaactata acaatacttc agtctttccc      8160
aaccagtatc ctaggctcct ggaagattgt gaaaactcta tttttttttt ttacatttat      8220
atgttcattt tgattattac atatttaaat ataaccccat ttaattttat ttctaagacc      8280
tccacagtgc caaataattg cctacaataa cagcatttaa catactgtgg tgtttttatt      8340
cagacatact tagaggaaat acaacattca taggtgcata gttcaataaa ttttcacaaa      8400
ctgaacatct ccatagaagc agcacagttt aggaactcaa catcaccaag actccaggaa      8460
ccctctcctg tcctctccaa gtcactactc ccacaccta gtttagttta gctggttgtt      8520
gaaatttatc agtacctgag aagaggggga aatcaggaga aagcagattg ctaaaaatcc      8580
caccctggga tgtggttagt atgggattcc caccaggaac aggcccacaa tttctgttcc      8640
tgcttattgc acctggtaat gaagaactga gcttgcaacc aggttatccc caaagcataa      8700
gcatatcaca gtgatataat tgtttgcctg atccccatca atggacacgg ccctttgcat      8760
aatgtttgtt gatggctgtg actcttctgc atgccttagg tgagtcatga gaggtcaata      8820
aaacagtgat gccttgactt ttggtttgc caggtccaga ccaaaaggtt ttattaatcg      8880
agaagaaaca cagctgaatc agcttctagt cacatgtact tccctattca ttagactgcc      8940
agggttaaaa gggaagcagc caaagtttgt tttgatgtaa ccctttcatt accccatggc      9000
ctcatgcctc ccacttgtcc ccggagcacg tcactggatg cacacatacc cccgcccatc      9060
attccaattc tgctctctgt tatgtgacag tgggtggtat tgggttaatc agaggaatgc      9120
ccgatgtggt ttggtgggca tttgaaagtt aagaagcctg cttctaggtc aattctttag      9180
gctaactagt ggaaagtgac agaaacttga ctgagcaaga aataaacaga aaccccagta      9240
attaattagc tcctacagag atcagaggtc aggcatggtt gtatgatgtc attatgagag      9300
acttctctcc atctcttggt actgcttccc ttggctctgc ctctggtgac aagatggctg      9360
tcagtctcaa gcttgaatct cacctctcag caaccccaat ggagcacata aacttctctt      9420
```

-continued

```
tccaatgtcc tgaaatcagg ctttgtctga ttgaagaggc ctagttctca tgctcatcct    9480
gggagtaaag tcagcaccag ccaaaatgct aggaccaa                             9518

<210> SEQ ID NO 67
<211> LENGTH: 3021
<212> TYPE: DNA
<213> ORGANISM: Homo sapiens

<400> SEQUENCE: 67
cggggtgccg gcctctcccc ggctggaccc aacgctgccc ggggctgctg caagagcggc      60
cccgcccgtc cgccgcccaa cacccgctct tcctccgcac cgaacacttc gggcttgcag     120
gagacaactg tcacgccctc ttcccttttc tctaagacgc tgcacattct tgcccacatc     180
tgctttcttg tgtgcaggcc tcccagggta tgtccgtggg agtgaatcac tggctcatag     240
ggtgtttaaa tgttcacttt tggtgatatt gccaaattga gttccaagtg gtcataccag     300
tttacacacc caccagcact ggatgagtgt tattttccca catgctcacc aacattttgc     360
agggtgacac agcagttgcc tcctgctgac atcccagata tgcaaatgct ggggctagga     420
gcatctgtct cagctggact atcacctcct ccttcaggaa ggccccccag tctaccttag     480
ctgactggca gcttcccata acctcgcgtg ctttcccatc acagcactgg gaacttgagg     540
ggtgactgtc tcacagcgga ctgtgagctc cccaggaaga ggtcaatttg gggccattga     600
acaggctgaa aggaacacaa agttgctaca aatagtactc atctacttga agtaaggagc     660
tttctctaat caaagtacgc ccttgggatg gcagtagcca cctacccacc acacctctgt     720
gtcctcagca tctggataca gcagtagctt ccttttaaac agcacatcgt tgcttttgca     780
tcagccagaa aaaaaaaata cttttttagaa gaaaagtaca ttatcatgag tcatagtatt     840
tgagtacagc tggcctgagg tgaggctgga ggcgccgccc ccggtgactg ggtactcagg     900
gttgggttga gccaggaggg tggtggttgc ctcaggctct gagggatggg cagggagctg     960
ggcggggtcc tgagacattc aacctcagct ggttcctggg ttccgggccc tggagcagtg    1020
agggaagcca gttatatggg aggcaggtga gtcaaaggag ggtcaggctg ggtgccagag    1080
aggagggcca ctgcttctgt gaggggggcct ctggggcctt ccgtccatcc ccagtgggca    1140 tatgggggaca ccaccgaggc ccagagacct cttgcccagt cccccaccct ctgctgagct    1200
ttgcccaggg tgtagccagt tggcctcagg gccaggctgc cagggtcagg tcagctccca    1260
cgcctccacc ctgggcaggg cccaggcctg cattcatggg tgcgagaggc ctgagccctg    1320
gatgggtgtg gttgtgtgtc cttggggctg gtgtttggc gtgagtaata ctgtatagat    1380
gtaagtgtgt gtagtgtttg caatgttgta gtgtgggtgc atgtgtctgt gtgtcctgtt    1440
tgttgagagg attcattgca tgtggttctg ttaggagtga taatggggtg ttttgagaca    1500
tttcctcctt ggtctctttt ttggtgtgtt ggttatgttg gtgtttcggt atgtgcgctc    1560
agtgtgttgg tgtgcatttg gcaggttgtg tctattggtg tgtggctgtt gggtttgttg    1620
tgtcagtcgt acatccacgt tgggctgggt gtgtgcattt gtatattgct ctgtgggtcc    1680
ctgcaggttt gggagtagat gggagcggcc ctttgtccag ccacaggaaa accccacccc    1740
cctcatcggc aggggacttg ggagggggcc agactggtag gctccagcct cccgtccatt    1800
gttctggggc ctctctggaa aacaggatgg gaggtgaaag gtggacacag gcctggaccc    1860
ccacactccc tgaaacaacc aggggcacag cacagaatcc ttaggaggga gggcctgggg    1920
cccattttgt ggatgagaaa actgaggggt ttcattccta ttaaagggag agagcctgaa    1980
```

-continued

```
gccccacacc ctttatgtgc ccacccacag cctcctgccg ggtttggggg atggaaaaat      2040
gacaccccag aaggaaacaa aacggtcttt gtggtttcca tttctgaatg cttaccatgt      2100
gctaagtgca gatcataact ctgggttaag ttcatatttt gtacccattt tgcacaggag      2160
tacactgaac cataaggcaa caatttattc ttcaaaggac actatctaaa cattactgta      2220
tttcaagtag tacgctgtgt gaccttgagc aagttgctta ccttctctgg gcccctagt       2280 tcagctccac agcatgacca aaggagccgt ggttcctgct ctcttagagc ccatagcctg      2340
ggcagggagg aggaggcaag gaatggcaaa tacacaagaa aacaaagatc atttctgatg      2400
gtaaaagaaa gtagcctagg gggatctgag aaggcctctg gggaggcgac atttgacctg      2460
agacttaaga atgaggagct ggcaaagacc tggctgatca gtgttctagg aacaagtaac      2520
agcaagggca agggccctga ggcaggacag agctattaat aggaggcctc tgggctggtg      2580
agagaaaggg aagggggccca gttgggtagt gggcagggga ggagtttgga tcttattctc      2640
cgtgagatgt gctggttctg gggtagtggg ggggcctgtt ctcctgttac aattgggggt      2700
ggggacagcc agagccaaag gtcttccccc acagctccgg cagtcccagc ccagaggcgc      2760
cggcctggcg gctggaagat tgcactgtgg gcacatctgg ggagcagctg ccgagccagg      2820
gccagagtgg gtcacgtggc acgggcagga ccgtcctgga gcctacaagg ccaagactcc      2880
taggaggggc agtggagaac actctggacg agaacacgtc aacgaggagg aactgtgcac      2940
tgtagacgtc caggcaacgg ccccctgcac cccacacagg gacagaatgc cacctcccag      3000
ctttgtgatc tgaaacaagt c                                              3021

<210> SEQ ID NO 68
<211> LENGTH: 2909
<212> TYPE: DNA
<213> ORGANISM: Homo sapiens

<400> SEQUENCE: 68
acctttctgg gccctgtttg ttcctctgga tacaatacag atgtaatcag gcttcctggg        60
ccccatgtct gccctggagg tcagttgcct gcattgtcac atgctaaaat cccctatgat       120
tccaaaggct ttgaataaca gtgttggttt ttactgaaga ttcgggggggg aggttgggtt      180 atatcaccag caaaacatcc ttaaagattt cttgaaaact tccccgcaaa tacccttttt       240
ttttttagtg ttatatagag agagatgagt acttttttgc tctcaaaggg cctctcagct       300 ctattttaa taattgtatg attttataaa tttaattcat agcaatgtct ccttccaaga        360
cactgataat cattataata agcatttatt atactcacag tgcctcttaa atcctcacaa       420
tccagtaaac tataggtact atttcccttt tctctataaa acatttagat ctgtgacttg       480
ctcaagtcaa acagctgcca ggtggcagat ccaacattga gacctagtcc tgcctgactt       540
tggatgctgt gcttttttagc ccctgtgctc actgcaccgc cccgtccctc ctgtcggccc      600
ttacccaaaa gtgtcgtatc tctgggaata ttaacaaagt tagaccattt ttgctctgaa       660 gattttttgcc ctctgctgaa gtacaattgg aatcagtttg aacaaatcat gtttccacca      720
accaacatct atggtgcact tggcactata acaatgctgt tgattcatta tttaaaattt       780
ttaaggttga gataatagaa acccaactta aaaaaaataa ttttgattca gataaacaaa      840
gtctaggtct caacccaatt caaagcctgt agattcagct caaataataa ctcctattcc       900
tcctcttttt tcctggccct gctcttctct tcctgtcttc attctgtatg catcaccaaa       960
agcctcaggt tcacatctcc caactcagca accccaaaga acagagaatg aatgcctctc      1020
tcgatactca tttatctttg attagctctg cccaagtccc atggaccaat cattatggac      1080
```

-continued

```
tgtgattgat agccccatca atgccatatg gggtagggga gaaattaccc aaagaaccca      1140
aaagagaaga ataggaaagt gtgtgggaga agccaaagaa tagatgcaac catctaccac      1200
ctggtctctg ccatcaaatt agttgaggac atggatacat gaaccaaaag ataatgtgaa      1260
gaagcataca cttgcccaat ggttggcacc ctgtaatgag aagccttctg aagatcgccc      1320
ccagaggcct tctagcctgc agttcttgtt tggcttcctt ctcatcccca cgccaccact      1380
caccagtttc ctgtgagcgt ttcttagtgt caaccccagt aatggtggca ggaacaggag      1440
agaggcccag cagacaaaat ggtaaagctg ggagattccc actcgcatgg cagcaaatga      1500
tcttttcatc agagcaagca gagtaaacag gagctggcca tttggtgaaa cacgtagcgt      1560
aagacccaag aaaggaataa gaaagagcca agaggaaagt agagaaaaaa ttaatttgaa      1620
atgaaactag tttttgctgg acatgtagag taatagtaca gcctttcttt aatggaaaaa      1680
ctccattcat tatgcttaga gagtcacttg gcctctcaac atgctttaaa gtcatgggct      1740
taataaagtc cagactcgga gtctcttagt tttctttttta tgtatttcat gtatatttca      1800
tgcctcctgt cagttataat ttttttaaac aaagtttttct taaaagactg cctttagtga      1860
gaactcctag aaggatttat aaaccaccag gtttttctgtt tctgtcctaa aaacactgga      1920
gtaagtggca acaggtcttt ggggagctgc ccatacattc ttcatatcaa cgtggctaga      1980
gtgatctgat ttgagcaaca gaagtcattg aattcttaga agcatcagtg atttttgtgg      2040
aggctctaac ttggtatcaa tcttgacaat tgtgatttag aatgtcacgg tttttatgaa      2100
tttgttgaca taattaaagt atccaagggc taccacatga atccttgttt tcttagggac      2160
tgaaagaaag agtcgtgatt atataagata tattccagtt ctgaaaagga aacgagtcag      2220
taacaatgga aggatttcct tacttttctg ctactgttct ggagagcggc acagtccaga      2280
tttgtttaac caaacctgtt aacttttttca taaatttact ggattgtaaa taggagttaa      2340
tttactccct atccaaatta tatattaaat attttggaat actaaggctc tggctttacc      2400
attgataatt ttgattaaaa aaaaaaagac acaccttgat tttgtttgat gtgctgtgct      2460
tctttgacac tagcagtgga ctatttgctt atcaatggaa ttcaaaagaa aaatgacata      2520 atttttatttt tggggaaact cagtcttatt tcctttcttg tgtgattctc caaggaaaaa      2580
tggagaccag aaatttggtt aaaatataac ttataactgg caacccacaa ctcattattt      2640
tccatacttc aggtatgttt tgttctactc ttaaggggaa aaaaacaacc tatgtaaact      2700
aaaattcagt aacccagaat tcatcaagtt ctctgttatc tagaggcact tagcagaatg      2760
gtttaatacc tggaccctgg ggtcaggctg cctgggttca aattctgtct tgccaggcca      2820
ctgcacttca ctgtgcctca gttgtttcat ttgtaaggtt aggattatag ttgtaacatc      2880
tttatagggt tgttttgaag atgaaagag                                        2909
```

```
<210> SEQ ID NO 69
<211> LENGTH: 4306
<212> TYPE: DNA
<213> ORGANISM: Homo sapiens

<400> SEQUENCE: 69
ggatgggggt catgttgctt cacgcaggcc aggatggccc tgagatgcct ctatgggcac        60
cgcctccact ctccagccag tctgcccgct gcactcctac tccgaggtga ggtcccccag       120
tggcatccct cctgctacac ctgtgactcc tcagtgtcca cgtggccctg aagcctttgc       180
ggaggaaacg tgaattgcat caggaatgaa agaaacgttg tcacccactt cacgaatctc       240
```

-continued

```
ccgagccagc gttggggcca cagggccact gactccagga gaacaagggt ctctgccttg     300 tgtaggggggg tcatgctgtc attccccaac ccgtggggca aatagggact ctcaatgggg    360
agacagcacc ccccttgca aagtggccca ggcctggtga gggccgtggc tgtcccaggt      420
ggacaagtca gggagaaaca cagcactcca ggcacccgag ggtgcttctg gggcctcagg     480
aggagctggg ctgtgggtgg ccgggcccca ggcccatccc gctgagggca gcattccggg     540
taggcccagc aggtgcggcc acagacagct gagcttcccg ggatgcttgt ggcgtgaagt     600
cagctgccca acccggccac tggccgcacc ccggctattt ttggatcctg cagctcagag     660
cctgccttgc tgctcccgcc cctggagctc ctggaagtct ggtcagagtg tggacaatgc     720
ccctcttgtc atacatctgc cccttcccca cagcccccac gggccaccct cctcccccag     780
acacagctgg tcctggctgg gctggggtgg gctgcctggc tggaggaggc tggccttgga     840
ccgggccctg gcatcacggc aaagctggga ctcagggagt cggaggcgag aggctgccag     900
ggttgtcctg ggccgtgtct gtgtcagctc gtgtccctcc aggataagtg gcaaggcaca     960
cctctctctg gcagagaggg ctctggaagg ttttcccagg gtcctcctcc ctcaagtcct    1020
cccatgccct gaggctggtc cctgagggtt ggtcggggac tccagtcctt gctgctcaga    1080
aaagcatgcc cagtgtccct cgccctgccc agtgtacgtc caaggctgct gaaaatggag    1140
aattccttta cttctgcctt cattccttgg acagatatta aaacctggtg tccaggggta    1200
aatcaggtct ggttccaact tcaaacaggc agccctgacc gtgcagcccg accttggact    1260
gggtaccgtg accttggagc aggcagccct gacctggagg catgcagctc ctgcagaacc    1320
agatgtgggt gggggggccc atagtcacct ctttgttggg ctggggaggt gggttcccag    1380
cttcggacca ggtgaatggg ggatgcaagc gtgggtgggg caggtgaagc aggaagggca    1440
gggacaggtc agatgacttt agcatcacgg cggtgggacc cgctgtggtg ttctgagtca    1500
ggaagtttgg ttgcagacaa gggtcaggag agaggtgccg agggcatgaa aggaggtgtg    1560
ggaggttatt agggagacat ttaagtcgat caatcgtgag ccacctgtgc ctggatccta    1620
cctgtcagaa cgcctgagtg gccccacgtt ccagcctaga dacaatgctg aagactctgc    1680
ccgtggagtg gcctgaccct gggcacaagg tgatgggcag agcagccagg gttgcctgtg    1740
cccagcctgt tgtgcagcag tgggggacag agaatgctcg ctgcagggga aacaggcctg    1800
cccccaggct ctgccctggg gcccctgagc ttactctgtc cccaggctct agctcacccg    1860
gctctgcctg tcttggctgt tataacaaaa ccatagacct ggtggtgtag aaacaatgta    1920
tctctctttg gtcgcgaagt ccaagatgaa ggtgctggac tgtgtctggt gagggccgct    1980
ttccatagac agtgcggcct cttttctaag ggcaccagtc ccattcacgg gctccactct    2040
cacaacctaa tcacctccta aaggctcaca atattactgc actgggggac aggtcaacat    2100 gtgcatttttg ggggaacaca catttcgacc atcacacctc cgtaacagcc aaccccgagg    2160
tccagcctag gtggctctgg gagttggtgg ccggaggtcc acagagcagc ttggggctgt    2220
gcccagctgg gccccttcca ggcctccagg tgcggccaca cccatgtttc ggaggctggg     2280
gacacagcgg tggctctcca ctctagcaag cgtgcagcac ccgccagcag gatcctctgg     2340
ctgcagaaat gcgtaagaag aggcgtccgc gggacccagg ccggatgccc gtggagaggg    2400
aggagccaag ggggctccgc agtggaaagc agtgggagcc tcccatgggt tctctgctgg     2460
gctgcatcac cccaaccctc tcaggagggg aagccctgag ccccccttgg ggttgattgt    2520
ggcagatgtc aggggctgtg accaaaagga tgcctgggcc aggtagagaa acctgggaga    2580
tggccccgtc tgaggcacag cgcacggtgt cttcatcctc ctgtgtggac tctctgggtt    2640
```

-continued

```
catggaggag ccctgactta gggctggggt taaatgtgcc ccccaacccc tcccttcacc     2700
cctgacccac cttggccttg gggaggagaa gaaacaccct acaggaagat gaggaaaacc     2760
tgtccccaca ggctgctggc tgataccccc gacttaggac gagcctgggt tggggagccg     2820
tcctgccctt cccggctgtc atggaatgtc aggtttctgg gagcctctgc ttcctgctgc     2880
aggctctgcc tctgagttca ggaaggagac aggcccctg gtcatgctgc caggaccaca      2940
tggctcagct tgctgggccc ggggagggta gaggctggcc atctttgctg tttggtacct     3000
ccttgtcagc ccgtggtggg ggcccagggt atggcgaggg tgggaggctt ctaggtcctg     3060
ggggtcagga tgaagggagc ccggggagca gctcttggcc ctggtgggtc tgggctccaa     3120
gttgtggtca gaggtgacag ggtgtcctcg ggcctgtggt cagtgccgct gggcctcatg     3180
gaggtggcgt cttggatgac aggagagagc tttttagggc tcagattagc ctgtgagacc     3240
aaaaccaggt tcagtttcca aataacactc aagagacctg ggcttagcat tggcccccca     3300
gctttgcagg agaggggtgg gtgcccacgg ggaatcaagg ccctgcgacc caagcccgcc     3360
aggctcagca ctgaggaggg aggcgggccc caagactgtg cagtctcgag gcgtccaagc     3420
cacagggcgg agcggcggga gcgcagccga gagtgcctcc tttatgcttg ggccaggcgg     3480
ggccacgggc ctgcagccat aaagttgggc tgtggatgtg ccccagatcc tgctggtgga     3540
gcccaagacg ccgctgcccc cacactccgg agcttccgcc cggcccagac atccgtgtgc     3600
agtgtgggag ctgaggaggg gcccccccagg atgctgtgtg gggtacacac agcaggaggg     3660
ggcagggcag gacgcagttt cccttcaggt tggggtcctg accaggggac agagccgcac     3720
tgtctcccca ggcctgcttg gggacaaagg ccatggatgg gtcttaggaa gtggcttcag     3780
ggctggactc ctcttttccc gttttcccaa ataaggtgtt cccagttccc tgggagaatg     3840
agtgagggct ggggatggct gactttgtgg tgaaggtgca gagagtagat tggggttctc     3900
tttgatcccc tacaaagaag ggacgcccgt ggtgtgcttg tagtgagatt tggccctccg     3960
ccccaaggca gcagcgcggg agtgcggggc tgggtcctac ccaattaccc accaccaggc     4020
tggcgagccc aggagcctcc agagagcggc gaggtggttc tgtttcgacc gcaggccagc     4080
ttctcctggc tttgctttgg aggcgcccag aggggtggct gaagggggc tggcacagca      4140 ttcttggggt gcctgggggc ttggaggttc tgagcctggg ccgggccgga gactcaagtc     4200
cggctgaggt tatcagcaag gtctctgaaa gctgacagag cagagcaagg atacgcctga     4260
cgctgtgcaa ggtttgcaga gtcgctcagc ctctctgggc ccactt                    4306
```

<210> SEQ ID NO 70
<211> LENGTH: 3237
<212> TYPE: DNA
<213> ORGANISM: Homo sapiens

<400> SEQUENCE: 70

```
gatccaaacc gaggaagtgg gaggccgcgc acagcctgtg gtttgtgcag caccctctgc      60
cctgttctta aagtaagaaa ctgatgtctc taggagccct ggtcaactgg aattggggac     120
ttggggtttg gttgagcctg ctaggccatc tgaacccaca gcaagctgat gatagactgc     180
aggaaaagct ccgtccttca ccagccccat tccatgacgc actcaacgac cctgcctcca     240
aggaacaagc ttgcagatac taatcagggc tgaggccctg ccactcaata attacccact     300
gtctcatcat aatcccggaa ctaagcccct gcccaatcca tctgggaccc ttttccatct     360
attgcacagc tcaagaatac gtgtgtaagc tattacctct ggttgtgcta tctgtccct      420
```

-continued

```
gagtatagat tcatggcagt gaccaattag gttgccgtgt tctttttccc cctttgcttc      480
caattcatcc tgtacttctc agcactggta atgaagcaga ttcatcgggt gcagaaatcc      540
actcacctct aaaagctgtc tcatatgatg cctaatattg taggatactt taaaaagagg      600
caagatcata cctctgtatt ctgaggcttc tttaagccac tctcgacctg ccactgcctt      660
ctgccaggaa caaatcacac atggaggaaa atattcctga ccctaatcca gaaatcaaac      720
agctgagaag tgaagagggc aaatgtgggg ataattgaat cctgcatccc tgaatgagaa      780
cccagtatca tgccaagggt gaaatccaag acacgtatgt ggaaactcag gttctgctgt      840
tggccggcca gtccctcaac ctcttaaaga ttccattttt gccctcgcta aaacagcgtc      900
tgcttcagtt gctctgaaag ttaactgaga cattccatgt aaagcactca actttacaaa      960
tgataaaaaa agttagctac ccctaccatt ttctgaattc ctatagccaa aaccaaaaaa     1020
gttagctctt gatcaaattg tgctgactat tttgtgtgta tacaattcat cttccccaaa     1080
aacatataca ttcctgaagg gtaaaattca catcttgttc ttttgtattt cctacaggtg     1140
accatttata aatgcttact cattcctgta tttgaacata agaacacatc ataaacaatt     1200
ttgaaggtga cagggacaag tagttagtta taattctcaa ataaagaaat tagataagga     1260
tgggtttcgt tacagttagt tgtagaattg cagaaactgc atggggccca ctggtcaaga     1320
aaacctacct gaaacggcag gggctgtttt cagtgtacac tgtcagggca caggcccagc     1380
tcttaattag caggacccca tttcagatct ttgctgatac tgacagggtt ttaattagtt     1440
aaatctacaa gttggctctt gttctctggc agagaggaaa atatgctaac atgttccaaa     1500
acaccccttc caggctttga ggaagtaccc tgaagaagga ccaccctttg gaatttatac     1560
cagcagccct gacagctgtt ttgtatttat ttctacggtt gggccatttc aatttggggc     1620
ttttattcat tatataagca aatatttgtt aaaggatcag gcacggatga ggtatgtttg     1680
tcaggattgt aattaaggtg gtgtgtatac cagggttgca agaggacaga ggggttgggt     1740
cttcaaccca ctgtgtgtta ctttgaaaga ctcacagacc tctctgggcc acatctggcc     1800
cacatgctga tgcatgtaca gtcctcattc ctactgtcct aaaaggtaga gagaaataat     1860
taatttggat aaaacatttt aaggccctaa tacattagct tttggcaaat tatttgcctg     1920
cagtgtatac taacgccctt ttattttttca gattgtcctt ttcaaagtga atgatgttat     1980
caatgagtac tttgctgaag acataattat ttctctgaac agtttcctga tttgccagtt     2040 gttgcccct gaggaaaacc agcctcagaa gtgtggcact cacttctcag ctcccctggg     2100
catcctgcat cccccagcat tacttgtaaa tatttcaaat tcttgccaca cgagaacacg     2160
tagcatattc acacatacag tattgactct cttataggtc aactccttca tttcgtttaa     2220
tagctttcat cttggaaact gtaaaattca tcagttggct cctctcctcc aagtaggatg     2280
tgtctacctt gataaggtgg ggaaactgag gctgtgtagt tacaagtctt tccagggagt     2340
cagcctcttt cttatgagga gttggaatgc ctgaatccca gccaggcccc cacactagag     2400
ttctccatga cctttgcgct ctacatcaaa cacacctgtg gcttctgtaa tgtgaccttc     2460
cccctcctcc tggacctccg actccttaat cctccatcag tttctttcca aatttaagcc     2520
ctccagaact tgctctttct agtgtcctta gtatcatccc tgtatagaac ttggaagctc     2580
cttctccagt ccggcccatg ccctggctct gattcttaga tgtctgtgcc tggaaaaagc     2640
ctatctcctt aagttccata tggccccaaa taagcccatt aatgcctctc cccaggaacg     2700
tatttcctct tccaaacaac agtattttac ttccagcagt ggcgccacac aatttgacac     2760
ttcccctttc tctaattgct tactttgtgt gtctgttttg cctcctgact agactgcaaa     2820
```

-continued

```
tctttgaggg aggaggttcc tggagcagga ggcccccgga gagtccctaa taagtgccaa      2880
atgcaaaaag gttgaagtca ccagttgaga aaatccacat aaaatacact tttggcctgt      2940
ataaaatcag catgatgttt tctcctgaga ggttcacagc atataatttt agttcctatt      3000
ctccccaatg ctcaggttac tccaggaagc aatttggggt gagagaaaag caaggccctg      3060
ctgaattagg gaaaaaatgc tctaaaatat ctccacagga aaacttagtt ccacctgact      3120
gaacattccc aacaggcaag gtggaaatac ctcgttaagg gactgcaaat caagcagtgg      3180
gttcaaatcc aacattagct gcttatggtc tgtgcaccct tgagaaaatc acttaac        3237
```

<210> SEQ ID NO 71
<211> LENGTH: 2130
<212> TYPE: DNA
<213> ORGANISM: Homo sapiens

<400> SEQUENCE: 71

```
cgcaacagca ggtcctctct ctgtgagaca gctatgtcct cctgaagtat agctttgaca        60
gctgatacct ggcatttgca aggtaaagcc agtgttaatt aatgaggcat attttcaact       120
ctctgttaac taaaagtcat catattcaaa aatggtcatg atgactcgcc aggaggagag       180
ccagaaggta agtttgggca ttttctccct tgaccctgct cctctcatga caaacagcct       240
caagtttgag aaagctggtg aaggttggga gaattatcca cttggtatgg atggaattgt       300
ttttctgggc ttagggaatg gtgccttcat tagcaccaca ttcttgtcaa aagagctaac       360
tctctaccat ctatattaat tttgatttta cagagatact cagaaaagat ttctgtaaat       420
agcctaatca taatatcaac aaacatgctt ttaaaaaaaa tcttagaaac aatagtccat       480
tcgcctagta attagttaac acccaagcat gccttcaaag gaaagcatga caaaatgact       540
actttctaga aaacctatca gccttgtaat ttcagttgtt catttgcttt caggttgaaa       600
tatatatatc ttaaatgtca gtgatatctt ccatagatgc ttacccagtt gaccagatat       660
gcagccatga atgtggaatt cactaagctt gaaatcctgt tttcaggcta cacactagat       720
tttctaggtc ttgacactgt ttcctttcat ctcttttaat catgccctaa attcctccag       780
caccatggga ccagccaaaa tacaggtatc tatccaaaaa ttttaacttt gtgcaaaggg       840
ctctggaaat ttaagttaac ccactgcctc cacttttctc tccaacggaa accagaacca       900
aatactaaca ttctctccag aaaaaataag gaaataaatg tgcaggaagc ttaggataat       960
attgtcacat tgagaatctg tcccattcta gtggggtact cagaaaataa acaaatgca       1020 tctcatgaag ggaataaaat ctgaatcaga acagagacat atgatggtgc taaagaccag      1080
agccagcata acccatgctt tacgggatct agcattcaaa tcattttggt tagccctgtg      1140
gactgtgcct cccctccccc aaaattcata tgttgaagcc ctgatcctca atgtggttgt      1200
atttggatgg tttctcttct ggtgaacttc aaacaccttc tccttggccc tttccctaaa      1260
cctttctctg ctggaccacc agagcaagct ttctgagttc atactctatc gcattgcagg      1320
cttctattct gtttacagtg aatgctcctt gcatgtatta aatcattgaa acatctcaac      1380
aaaggccata ttcttatcga tttgttaagg tgagccaaag gaagcctcct tatttacctc      1440
tgtgtttctt cttcacccct ctcccacctt cttctccacc tatcacaacc accaccacga      1500
gccttaaaac gttcaggatt cccaccctgg gcctgacacc acacgcccga caggccttcc      1560
atggctggca ggcaggcccc aaaagagaac gatctccagc tgcatccaat tgcttgcagc      1620
ttccccaaca agctgcattc ttctgccttt tcacatgtaa attcctctta aatgtctgtg      1680
```

-continued

```
cctaaacctc atcgccgctt ggcacctggt gaattccgct ccttcttaga aattcggcat      1740
aagcattgct ccctccaaaa gccttctctg acgcctgtag gcctcaccac attcatatcc      1800
atgttacgga acttagcaca ctgcaacact acccttgaat atctttctcc aaaggggaag      1860
ggctacagtt ctatttatct ttagattccc agtgcctgac acatactagg tttttgaaag      1920
caataaataa atgaagaaca tgaagggcaa acacaagggg acagctgtgg agtgtataat      1980
acccatatta attgggtttt attaactaca gaaatgattc taacttttgt aactccagaa      2040
cctctttagt tatcacattt cttggttata catgtagaca tgcatgtgaa atttttattc      2100
cgtaaaccat acttgattag acaaataatg                                       2130

<210> SEQ ID NO 72
<211> LENGTH: 4564
<212> TYPE: DNA
<213> ORGANISM: Homo sapiens

<400> SEQUENCE: 72
tggaggtcat ccaggcctgt gcctggtagg accccaacat ttaccactgg tctgggcaaa        60
ttgctgcttc ccagaagtgg ctttaccaag acaagacctc acttaggtcc caagtgaggt       120
tagccctctt tttatcatga cccaagccca ggaaggagg acacagggcc tattacatta        180
tgtctggaaa gttggagggt atccagtcgt gttgcataac ctgtgagagg ccacggccac       240
atcccaagaa ggatcccaaa gatgagcttc acccaccaat gctcctgaga tggccaaagg       300
caggctcttt actccagaaa ccagacagga ggcataggga gagagagatt tgagtattaa       360
atcctgggct gagacggtgg gacctagtgc cagctctccc atggagtgac cttaacaccc       420
cgtttcatgc accaagcctc agcttcctca tggacaatgg acttgcaaac cctgtaaagt       480
ttttgttaag ctccagcaag acaggtatga gaagtgtgca gtgggaagac acaatgcgag       540
ctattgttag tgtctgggag gtggcatgag gagtatgcca ggctggcagg aaatgtgggg       600
gacctggcac ctatgattcc agagagtgtg cccaggagct aggtgtctaa ataagcaaat       660
gcaggcctcc ctgatggaca gtcatgcacc ccgaaggtct gagtgggtag ttatgggcac       720
cccaggtttc tggaccagca gcccttggag ctggaagcag aatagagaca gagtctggtc       780
agggttgggg tgggctgttg tgaagctgca ttgtgcattt gctgtgggaa tgctggcagt       840
cacatgcctt ctattgcctg cccggctggg taaaactgag cttctgtgcc tttaaaattg       900
tttgacatct ttgagattgg aaacagagct ccccagtgga aggccagcag tagctatgga       960
atgctattct aatacaaaac ttactctcgg tgtttaaact gataatccca ctggcaggct      1020
ttggagcgaa atcacctatt atggaaaagg ccccgattct ctgggctgat ctttgcccat      1080
gtgggctagt gagaatagag ctgtttccc tctcaggcta agcccatct cccaccctca        1140 gctgacgaga caaccctgag attctagtcc ggatacagga ctgagagctc agggctggcg      1200
gggagtcccc atggtgtttt gctctaagac actcgctagc ccaacccctt aggggtgcct      1260
gggctggcgg acaggtctcc attccaggct gcctccctcc ccagaccata atgtcaggat      1320
gcgggtttcg cagagcctgg gtactgcagt ttagtcagct cccggttcct tcctcccact      1380
gcggggaccc ttgtgaccgc ctggggactc tccagctaat ccctcctggg cggccctccc      1440
atggtcaagt cctctgttcc aacggagctc tggaggcaga gagagcaggg ttaaatcctg      1500
gtctgcaaga ttacttaggg caagttctta ggcctttctg atctttagtt tcttcccctg      1560
tcaaatgggt atagtaatca cacacatttc aggttaagag aatgaaatga gctagactag      1620
aatcaacagc ctagcacggt ggctctcaaa gtgtggtcca ggagtccgca agaccctttc      1680
```

-continued

```
agggtagctt tgaggtcaac actgttttca tgaaaataaa gatgttattt gtctttttaa      1740
atcataaaaa catgttactg aaaaacattt tccaaaatta cattgccttg agtcaaaagg      1800
ttagtgatat catcaaaaag tgaacaacta cttagtaatg taaatgaacg ttgacttgtg      1860
cctaagacag tccttggaac gtagaaaatg ccatatgagt tttgggaacc atttgaaatt      1920
ggcatgaagt ctttattcac ctaaacctct gaaaagcact gctctaggag cagagaaaaa      1980
gggggattgt acacatgact gggaaatgcc tgcaatatgg tcactgcaaa ggctgaatat      2040
taaattgtga ttatataaaa gtataggatc tggaaataaa acctggaagt gaaatattga      2100
ccaaaagaat tctaatgagg gtttctagat ttaaaagcta agcatcaatc taacttagct      2160
gttatttact aataaatccc tactttactc caagaatcta agaggcttag aagctggttt      2220
gtgcacagct gaggccaatc tgagaggcta cgggcctttg ttcttccatc gcctcaaggg      2280
ccagacctgg aaaaagagag agggtttctc cagtgctggc ctgcctcgga actacctggt      2340
gcttaggaac aagagtggtg actgggccca ctctggcacc tgctgagtca tagtctctgt      2400
ggttgaggtg ccagattcat atttttctga aactccttgg gattcatcag caggttacat      2460
tttgccaggg ttaacaccca tttcctcggg tgaggatgtg gttggggagg agggcatggg      2520
tgctcatcac agccctgtac ctgccgtggg aagatgtgat tagggacaac ctcctgtcca      2580
tccaaagctt cattgtcaaa aacacagcag ttctgagtca ttaatgtgac ttaggtcttc      2640
aaagtttcgt aatcattttg ctggcttggc ccgaaagtgg cacatgttcc tctggtgcca      2700
gtgtttgcta gaaagaaagc tgagggcttt tacatttttc acctgccacg cctccagggg      2760
ctgagggttc ccttatatca gaagccagag caatcactga cccagtccta ttatgtccac      2820
tcttggtgat ggcaaaaatt ctgtgaggtt gaagagagag aattgttctc ccaattaaaa      2880
aacagaaccc ctaacaccct aaatgctctg ctctgttcag tagcccaggc tacctttgag      2940
aatctactcc agccacctcc tcctcagtcc taccctccga cccgccctga ggctggagtc      3000
ctgctggcac ttggcattga cacgggcttc tccagggtct gagatcttgg agggaagaac      3060
cgttgcccat agatcaggga gctgagagga caccagcccc ccgtctccct tcctgctttt      3120
ccaaatgcct ctgcaacacc agggtgctgg gcgcatggga ctgagggcct ccctctgggc      3180
cccttctcac cctgggctac ccaagtcttg gaccctgtg gaacatggtc agccttctga      3240
tgagtccaga agcatttctc caacatagtt gtgagcttaa gggaattaaa cttctctttc      3300
taagctgcag atttcctgag gcccaaacag gcaggaggct ctgaatatgg ccgcaagagc      3360
tcaggctgtt actgcccctc ctaggtgcca gccccaggca gggtttttccg cccacccccc      3420 aggtcagcct ggcatagagg gtctgggggc ttctcccctt ggggaaggca gcagaagcaa      3480
ttgtgctctg cttggggtga aggtgttcag ataaaaatgc ctggtggagt atctcggaac      3540
cacagaacta cctgtgaacg ctgtggtgct gtggtctgaa aacagggttt tggagacatc      3600
agtgggaata aatctgtgac tgcatgatac agaacaagct cctcactcag tggtctcaga      3660
atgtcttctt cttcccccag acatgtgcag acttggcctc tcctccccac cagcccctat      3720
gtccctactc gcccaggagc ccccagcaca tcccaggttc tgccatatgc acacactgcc      3780
cccagctcct ctccctgtgt ctgcctgctt aatatctatc ccactagcca ggtctgactg      3840
aggttctccc tatgctcttg atttaaaaaa aaaaaaaaag ctttggaaac aaaaatttca      3900
atccctttgc cactcactag ctgatcttaa catagtggtt gggagatccc cgttctgcta      3960
gctgtgtggc cttgggcaag ttacctacct ctctgtgcct cagccttgct ggctgtgagg      4020
```

-continued

```
attaaataaa ggtgacgtgt ctgtagctaa cttagagatg cgcggctccc ccatcctatc      4080
tggcagcagc ccctcccact acagcatctc ccactgggca gctctgggaa ccgaacatca      4140
tgcattttcc tgatctcctc cctccctgac actcctggct ccggcctcag ggaattgttc      4200
acctccttaa gcaactgcct cttcaaaccc aggccagtgc ggttcctgca gcctggagtg      4260
ccaccccttc tctgctgggg aactcctatt tataggagtc gggcaaatgt cctcctcttg      4320
gaaatccttc ccagcttcag ggctctgccc tttactccca cacccttggg tcaatgtttg      4380
ccctccctgg actgtgacct cctccaggaa ttaggctcgg gccccagagt cctacacaca      4440
gcaggggctg gggctctaag ttaaggtcgt agttgatggg tcagcctgat tgagctgcgt      4500
gtgcagagga tctgaactcc tgcagacacc acttctgcat gagtcttggt ttgccgctct      4560
gcaa                                                                    4564
```

<210> SEQ ID NO 73
<211> LENGTH: 3037
<212> TYPE: DNA
<213> ORGANISM: Homo sapiens

<400> SEQUENCE: 73

```
atcatcaagt ctccacaata ccagttcctt aaaggagaat gttttttgttc caactgaaac        60 caaaatattt tagtgaattt tgtcttcagt attacttcct tcctattcta atactgtggt       120
caaaagtata acttttggca aactctttca tagcggaatc tgcttagttt gcgaatttga       180
agttagctgt tgtctttact ctttatgtag gttggatgtg cctggctagg ttattgctga       240
ggataagaag ctggcactgg aatggtaaag tgccactggc cctttttggg tatgtggtgc       300
ccagacctga gctgctattt agtctgagag gaaggcacaa agagatcagt gatttataga       360
ccctctgtag gaaaagaaaa aaaagcaaaa caaaaaagtc caataaactt aagatacttt       420
tccatcagca gctggttttg ccggaaatat ttcttgtatt gaatccagct ttagaaattc       480
ctcctgtagt ctgaagacct gtcatcaggt caatggatac tatacccttt ctaggtacta       540
gcatctctag ggttggtact ccccaaactg cctttactgg tgcaaggtca ttctgtgggc       600
aggcttaccc aaaggagttc atgaagtaga tagagctcca caggacgcca cggactggga       660
gtatagagtg tcctttcttc acagcttcac tgtctaattg attatttctt tatgtactct       720
ctatttccag tggggtactt gggattcttg ttctttgtga tcccagactt actgactttt       780
ctagatgagc cagattatat tgacatgctg acaaggacag ctcacagaat gatgggtgaa       840
tatatttccc ttcccacaga gtaaattttc tagatttgcc caaatatatt gtaaaaattt       900
gttctttctc tggtaaagat tctaccacag tctcaaacaa tgcatcaaat aaacacatat       960
tagtattgtc tatagcatat ataaagtata aatcttgtga gaaagttatc agagaaatcg      1020
acattttatt tgtctccata gagtctgtgt tttaatgggg gagtcaggga aagtctaaat      1080
gaaggttttt tttcaatgt atatgatcct gttttgaatg ttctactgtt gtggggagta      1140
gaaagtctct accaaacttc acagagatct gcaatacttt tactatttca tatttctagg      1200
gcagcatcta cctcatgtga ttttattcta tttaatataa gtgattttta gaatctatac      1260
caatgcaact tggttacgta gttttttcatg caaataaaaa ataaaacaac aacacacctt      1320
tgatggaagt tctggtattt ggttctgaaa aaatgatctt gtggattcag atccctttga      1380
gtttcatggg ttttttgaaaa gtattactga gacaaggaag ccagaatagt ttgggcatct      1440
gacagcctct gaggtggtga ggacaatgct ttcctatttg cagtttgtga cctctgtacc      1500
acaaatagtg ggcctgtcag cctttcatct gtcagagtgg atggaggaca acgttccagt      1560
```

```
gaccctgcaa ttgtttatcc ccggcccctg cttcctctcc tctctgactg gttaactttc      1620
tcacctgtga cactgaaagc tgggtagtac agggatggag caaggcgtta ttgaattccc      1680
cgccagtcaa agggagatgc aagaaagcct ctgctctatt ttcttttaaa ggagattgaa      1740
gagaacgttt gtgtcatgtg tcatgatgtg aatttggcgt ctaaactgag aagcagagag      1800
ttcattgttc atctttgtgc ttcgggctga caattcttta ggtggttttg ccctttgtct      1860
agaagagtaa tgttacacgt ggagctcaaa ggaattttcc tgcttactat ttaatagtac      1920
aaataataac tttaatgtca tacagaaaag acacttccct ggagtgggag aagagaggat      1980
ggggcagact gagtgtttga atcgctctag atcagagttg cagttttgtg gtttctcctt      2040
tggttcataa gctgtatttg ctacaaaaca ttttagaaat cttagcataa aacatcctct      2100
attgcctcag agtcgtctcg aaataatttc ccttaattag gtctaatgga ctgtctcatg      2160
aatctccatt tggtctgaca gaggtaatta gccatgaaca attgtacttg gccgttttta      2220
attagaccag ttttattttt acagctgcca attgaagaaa cctaaagact ttactgatcg      2280
tatctatttt tttttttta aaacatctat ttaaatattt tatctctgta gcagacaatt      2340
ttgcttatct aattccagat tcctacagct tcttcttcct gattgccacc tccctctcca      2400
tggaagattc tgacacgtct aagccaattt taatagtttc atttgcttgt tgctgattgg      2460
tttaggaatg gaaatgtgac atagttccag ccagtgggat ctgaggagag ctcacctggg      2520
aagctcctga gatggtttct ttgctgataa aaatgagtta caggaaaaat catccagtaa      2580
tgtctgcgtc tgtgacagac catgtgacag acttaaactc agagtaacca gctgggcacc      2640 ccaggggca gagctgaaag aagaaaataa cctggctcat tgataattgt tgagccccgg      2700
tttacccact tgaagctggt ctgcttcttg caatctgaga tacatgttct ttgtggtctg      2760
gccccactaa gtcaggattt tctgttactt ggatctggaa atgaatacca tctggattat      2820
gttccttaga aaggtaacta ctgccactgt atatccttgg actgtattga gctttaccat      2880
ggggtttcca gcctgagagc cagctgtgag ttagcagatt ctgcctcatc ctcttctaaa      2940
tcatttgcct catgttcttt ggagtaaatt cctatctcag gccagtcatc ttctacaggg      3000
attattggtg ttggcatgtg ggggaaacag actctta                              3037
```

```
<210> SEQ ID NO 74
<211> LENGTH: 2495
<212> TYPE: DNA
<213> ORGANISM: Homo sapiens

<400> SEQUENCE: 74
agtgagctag ccagcccagg gataaaagcc atgaattaat gaggcttctg agaatcctca        60
gcaattggac tgaccccctg cctagcttcc cagggtggtt ccaagcaagt gtggcctaag       120
tagctgacag caggaggtgc tgataggagt agtggagttt gccagaagag aagctagaag       180
aaagccttgc taccctaaat agtgacagct ggaaatcacg agggagcatt ctgtttggga       240
gtcatgaccc ttcccgtcac atttctgcat ctggcaggct gttggagaga tctgtgtgac       300
agcctcacct ttcagcacct cagtcacacc agggagacag caggagtgag gaggaaagag       360
agaagagagc ttgcgcctgc ttcctaaact ccttctctct gggtcaggac caggttacag       420
aggtcaccag tcatgtggta acatcctgat gataagctgt gtccatgcat gtgcatatgg       480
gatgctgcca actaatttcc caagagccag gcagataaca taaacgtgtc aaatcagctg       540
gatataaggt gaattggaga atgatgagta ttatgctaac ctggagagct tatactttgc       600
```

-continued

```
ctaaagtatc tcaaagtttc agtaatatgt ggccaaatat aacaatgtag gcaggattta      660
gcttgtgggc caccagctga tttcacagga gaaattgaca attacttcta aattgcaaaa      720
taaactgaac cccaggtctc taggctgtcg aatgggtgaa aagcaaatca ggagaactat      780
tagagtagca atcagagtga aattaacatg aaccacaaga gaaagccagg caggggaaca      840
ggaaaacatc aagcattttg cttaggaatc agatgaccag tgctgttcaa tatgccagtg      900
tttgtatttc tttccttcaa ggctcctgcc cagcagatat gaagacttgc agttcattgt      960
ttaagaacta ctgtatgata acaatatctc ttgtttttaa atttatacat cccttttttt     1020
ttttgtctca ctgtgaaatc ttttcaacat acagagaagt atagatgaga taacgaatac     1080
ttcatcattt ggtcatgttt gcttcagcta tttataaaac tcttcatctt gacataattt     1140
tagattttga aaatcaaata ttaacacctt atgtaaccac agcacaatga tcaaaacgag     1200
gacattaatt tgatacaata ctcttaacta acctgcagac cttactcatg tgtcactaat     1260
tgtccctctt tttttctggg ccaagatcct accttgcacc tgggacagtt cctcaatctt     1320
cttttatttt gtatgacggg atatttttga aaaggactgg cccgtgattt tgtggaatgt     1380
ctctcaattt ggatttgtct agtattttct catgtttaaa ttcaagttat gcatttttag     1440
caataccaca gaagtgattt tgtgcctttt cccatatcag gaagtactca atgtcaacat     1500
gttccattac aaagtgatgt tcacttggat cacttggtta aggtttctcc aatgtaaagt     1560
tactcttttc ctctttgtag ttagtaagta ttaataattt atcattcaga aatacttcga     1620
gaatgcaagt atactgtttt ttattataat tttatgtact aattttaata tccattcttg     1680
cctgcaacaa tctttggtgt ttgccaaaag gtgatttttc tatgccttct ctctgatgta     1740
ttcatttagc cagctatta tttatagctt tatgggctaa tggaatttgc tttataagct     1800
ataacccatt gctatcactg ttttgttatt taaggtgttt cagattgggc caatgtcctg     1860
tgttctttct agatgctcct gtgaacactt cttattcaaa tttttttgtt tcccacggtg     1920
gatgttttta ctgtcctgat gtgggaccta tcaaccctat atatatttcc atccatgact     1980
tcatacattg attacatgtc tatgtatcca taaattacag tagggatttt tgcatatttt     2040
atgactctgg gtaaatgaaa tattataaac acatgtaact agactttcac aaattaatat     2100
cactcaaaag ctcattcatt ttaactgctg tgtcacatac cgttgtagga ttaaacaaat     2160
gtatttattt tttcatcact tgaaacattt tgattgcacc caattttgc ccttatataac     2220 atgttcttgt aagctatctc ctgaactatt atgttacagt ttcattgggt tatatactta     2280
gaagtataat tactaggcct tagtatgtat gtcttcaatt tcattagatc tcgtctccaa     2340
aatggtttta tttgtactcc taccagtgat acgtgaattt ttgtaggagt gaaatggtat     2400
ttgttgtttt tatctgcatt tccttaatta ttggtgaagc tgagcatctt tcatcctttg     2460
tgcatttctc tctgtaagc tgttcataat ctttt                                 2495
```

<210> SEQ ID NO 75
<211> LENGTH: 2248
<212> TYPE: DNA
<213> ORGANISM: Homo sapiens
<400> SEQUENCE: 75

```
gtaaaaattt cagaattgcc ttacaacaat tttcaaataa cacaccctgg ccactccaca       60
caagagtgca aaggacagag cccttaccta gtggctggca tccttgttgc tgattgctaa      120
cctgtatctc ggctccgtct ctgccacagg atccttcata catgtgtatg gacatcacaa      180
agaaatgcct caggggggta cagtgggcgg cccctggtga gggctttggt actacatgct      240
```

-continued

```
gatggttttc tgagttgagg ctgcaggtaa gggatggagc ggatcatggt ctttagagag        300
atgcgaagtg acgacagaga cttcgaaggg agtggataaa taagaaataa tctggaccgg        360
atacgtcaga ggtgggtggg ctctggtggg agctggcaga gagaaatcct atctgttggg        420
acatgtgtgc tcaggactgc aggaagatct ctgaggcagg ggagttcaga ggaagcttcc        480
agagctttct ctgactttca cgtagtcact ccggcttgtt ccatgttttg ttagttttca        540
tttcatgaac attttgtaaa tagtgtaata tggtaaatat tgtgaacata gacataggtc        600
ttaactcctt acccacacgc ctattataat actaaagaaa gcatttctct ggcttattca        660
aggccagcag ttgtgcttgg cataacacac aaaaaatctc attgttgctt ccatgaaaat        720
ggagatttat tagatagagg aatgtgtaaa agtatcagca cttaaatgca tggacagtgt        780
ggtgccattg aagcgattgt gaaacatctg catggaaatt tttggaaaac agacttggct        840
tataaaatcc ttgaattcaa tgtacaaatt cattttctc tagacatatc tagattcccc         900
cagtattcca gaaaaagccc atctcttgaa tgggataaca tatgcaagtg ttttgtaaac        960
ttaaagcact gtaaatagat aaatcattgt tattagtaat aaaattccct aatatcatgc       1020
aataatctaa gtgagaagaa taggggggatg tggatgagaa gcagaggaaa ggaattgcct       1080
ctcgacttgc actttgttgg atgcttgcca ggccggatag gccaccccag agacagaagt       1140
tggcttgtat ttatttgtcc cttaattctg aaaacataaa ccatcacatc aatccatatt       1200
ttctttgtga attttctatt attttaccgt ttttacattc attcattgca caaattcatt       1260
ggggtaaaaa gactttattc cctcttatgg aatttatagc ccaaagatgt aaaaaaaaaa       1320
gtcttatttt taaaaattgg cttatttatt tcttatttac tcactggatt atttttatcc       1380
atctggaatt tattttgttc catcatgtgc caataaccta tgtcaggttt tttaaacact       1440
attttccgaa cacttttgc taactatgga aaaatacaag aacttaagac tatattagat        1500
tttcttgtgt tgagtaattt ctttgggaaa cgagcctgga ctatccaggt ggtgtaatca       1560
caggatactt gaaagggaag agggaggcaa agaggcctca gagacatgcc acgtgggagg       1620
actcagctca gcactctggc tttaaagatg gaggaagaga ctaggagtca agtcacacag       1680
gaggtaaagg cagggacgga ttctctcctg cagcctcgag caacgcagcc ctgccaacgc       1740
ctggatgtta gcctggtgag agccatgccg gatttccagt ctgtaaacca tacggtaata       1800
agcgtgttgt ttttggctag tttgtgtaac ttagtacagc agcaatagga aaccgatatg       1860
taagtgaacg tgcagaggag ctgggttggc gttgagtttg tccactctca ctcccacgtg       1920
ggaaagtact ggttcttccc tgggctggcc tggactgtga gtgaattatc tcctcatatg       1980
ctgtctcctt ccttctaacc ctgagttcag tccaagctca gcagctcaac ccacagccac       2040
acacttacaa acttctcaat ccttctggcc cacttctctg tggttcccaa ttaattttct       2100
gaaaagaaaa aatcagttct aatacgtaga aatgagcatc ccatccaccc tctaagccat       2160
ttaggacatt tagtaaaagt gattcttaca aaatttactc ctaaaattct cgtgtagttc       2220
cagtctcctg cctagcgctt cagtcgat                                          2248
```

<210> SEQ ID NO 76
<211> LENGTH: 3309
<212> TYPE: DNA
<213> ORGANISM: Homo sapiens

<400> SEQUENCE: 76

```
cgcccccggt ccacgctgct gcggggggctg acgtgtctgt ccaccccccgg gaatcccccca        60
```

-continued

```
ccctcttcct cggaccttac acccgccagg ggagtagcgg tggaaggaga gagagagcga      120
ggttgcgggg ggagtacgtg tgagactgaa ttctcccttc ctctccctcc cggctcgtcc      180
ttttagcaag taagctagtt atggacacct tctctgccca tgacacccac tccctaggc       240 tcaggtctag ctagaattta gggggtccta aattcacaca aaatcctttc cactccccat      300
cctggagttg aagattctcc caatgagcct aaccttcagt gtgagggttg gtgtcaccca      360
tgagcccctg ggggccctga gagggctgtt ggggtgacag agttgcagga tgcctgcttg      420
ctggggagga taccccagcc cagaagaggg aagggattaa actcagtccc catcccacct      480
cccagcacac caggcagctg ccagcaactg ctaaaaatac ccagccctgg ccctggccat      540
tctgctcctg gactggaagt tgcccagagt tggggaaatc caggccaatg gtgttgaatg      600
ccagcaggag ccagccactt cgagtcgtca aggtctccct tctctctagc tgtaggctga      660
gccagccacc cagggcacat ccagggcctg gaggttcagg cccccaccca aaaggggcat      720
aaacacaggg tgtggtcaag gcatgaggag tgtcttagct ccctgctcat ctctcagggg      780
tctgagggtt gcaggtcagg ctgtgaggta ttttgtgaca gggacctgct atcagacgat      840
tgtgacaagt gtggtggggg tgggagggca tccatttggg gctcaggtga catcacagat      900
ggatggaccc tggtgggctg tggtaggttg tcatggagac ctgggccagg ctctttggtg      960
ctgcatcagt ttccttggca acgcctaaga aggccttgga ttgaggaggc tggctcggta     1020
agattagggc cctcttgtcc ttgaggtctt caaataggca aaagctgggc tgaggggcct     1080
gcccatggtc ctaggggatc ttggaggcct gagcatcccc tgctggttct ggcttcctga     1140
acgaactcca gtgggaagag gaagttatgg gcagagcctc ccgttagcag gcaagtctaa     1200
agagccacca cacacttccc atgaggaatc ctggctggct gcctgtgccc cctccaaccc     1260
catgactgtg ccactggaaa gagcctcctc tgggtgtctg gcagagggcg ggtggggggt     1320
agctgtggcc cttcccagag ggggccatgc aaagaaggag ggctgggttt cccctctggc     1380
aatctgagct cttgacctca gcagtgtttc ttcattgcca agggaactgc aaccacaaag     1440
ggccactcaa gccccaggca ttccgtggct gctccaacag gccagagaca ctcaccacaa     1500
gctagatatg gccaggggcc ccagggatta acaccaggac acaaccttga gacccactcc     1560
caccacctgg ttctcccagc tctcttggct gcccaggagg aataaacaga ttataagaca     1620
aaacaaacat gaaatgcaga ggcagttggc tcaagtcggg cacacagtaa tatctcacta     1680
agagcacgtt tatcatgatc atccttcgtt ggatggggca ggttaggtga atttgtggtc     1740
cctctcctgt ttctgctcca ctctctccag gatggtggtc tgtccaggag tggggcagag     1800
gtctcagagc atctggggtt ccagaaagtt ccctgggcac tggcccagga tgcacagatg     1860
gtgccctgca ggcagccagg ggccaggcac tgatgagtca agagtgacaa gagaacatca     1920
tgtcagcagt ttggtgtccc tcaccccat ggcctggctg ccaggaaggc cagccaaatg      1980
actcaatcac acctgcctcc cttcatccct caacacagac accatggcca cctcagacag     2040
ggactgtccg gcagaggtac acacgtgggg aggccttcag ctcgggaagg agccctcagc     2100
ttcctcatct gtgcgggata cagtgcctag atcatcagag ctaggcctag acccatttaa     2160
atctcccaag ggcagtccca agtggttgcc atgactatcc ccctcacaga tgaagaagct     2220
ctgggcaata ggggctgatg gcttcacctc tctgatctta ggtagccaga tccagcactc     2280
ctcttggtca ttaggtggcg aggccactcc tcctaagagt gagctgagaa taggagttgg     2340
ggttcaggat gggcttagcc ccttctgtag gcaacggcgc ccctgccac tgaggcttct      2400 ctgcccaatc atatctgggc ctcagtaggg atgagtattg ccatcagaga atgagactaa     2460
```

-continued

```
agcaggaagg atgctccccc tgggaaagtg atcctaacca gctaagccaa agtctgtcca      2520
ggtgaccaaa tgcaatctgg gcatagggcc aaggggaggc agaggcctta gacccgagca      2580
cgtcacttca cagtgctgag cttccctact caacactggg ggtgacacat gcctttggga      2640
gggctgattg agagggtgcc tcaggttccc ttcaacagag aagtctgatg tcactgccct      2700
tatcagggac cagacggcca tcactacagc tggaaaagct ggcatcacac ctactagtgg      2760
gcttataaaa tatataccac tcctgggcca aaaagcgcaa acctggactc actgaggcct      2820
ttagaccaat ttccagttgg caaaggaaca aatcagactg cagaacttga cacattaggg      2880
aaatccagat atgcctgggt attagatggt gttgaggaac tgttcatttt ctgatcagat      2940
aaatattgtg gctatacagg cttatattga cttaggatgc agtacttcaa agtgaagagt      3000
caagtctctg cagcttactt actgatattt atatatgcac acataaatat ggcccaatat      3060
gtcaactgac tctactggtg gtggtgagca tacaggcaca ttcgtacact actctttcca      3120
ttttgatttt attttacgaa aagttgcaag tacaccaccc tttagaggca cttactacca      3180 ccatccccccc ctcaaactcc aaatgactcc accatgaaag acaccaaggc atgctgggaa      3240
ctgaatataa attaacttta ttacaaaaag caaaatgtta gtttctcatt gtgagtgatt      3300
caagaaaac                                                              3309
```

<210> SEQ ID NO 77
<211> LENGTH: 2385
<212> TYPE: DNA
<213> ORGANISM: Homo sapiens

<400> SEQUENCE: 77

```
agaagccttc cctgctccat aagagcagcc tgccgccccg gcgatgcctg tgcctctccc        60
ggcgcgcagc agctggagtg gtttattacg ttgcaggcac caagtccatc ctctcctgta       120
aggacagtgc ttagtctcta acatgggggt cctcttgcct cggagaccag cgtacacaca       180
gcccgttgcc cagggagcgg tccggccaga gtgggccagg gggtgattgt aaatgtggc        240 tgcaacaggc cctaacagga aagctctgtg tcccctactc agcttggctt aacactatgg       300
agaaagttct taattcccta attgcctagt tcttgggaga ggcttggctg tgcagttctc       360
aggtccagat aacacacact ataatcatct gctgagccct gaggaggggc tctgtcctgg       420
ggcagcagtt gcttttggat tggtataaag accatgatat tccttttgcc acggggtgga       480
gcaaaatata gctgggaaat actgttttgc aaagattttc tcagtgatgg gaccttggat       540
cggagacaga aaaatttgtg tccaggtctc acctgagaac tgaaaaacgc gaaatttggg       600
gattctagtc ctgacaattg ttgcaacttg gaggagcttt gagaggccca gcctctcaa       660 agagcacaga caacatctga ggatagcaat gcaataaaag aactactcag ggagcgtaca       720
aggtgctaag tatgtctttc attgtctgaa aattgctgag ggcaacagaa aatgtgtatg       780
tattatcact gttaattaga gtacagcctc acttcttctg ttctctttat ctgcttctct       840
taccttcttt catgagcggg agatgggttc acaattaaag atgttctctt tagaatataa       900
gacttgcaga aaattatttt ttctcctatt tatagaagtt atatttgcat taggagcctg       960
gtaatgtctc ataaatattt cctttttagat aaaatattaa ttaaaggagt ttgttgagtt      1020
atactctgaa atcctaacta aatagcttct aaaacaaata ttttaagcat tttttctcat      1080
gtcaggagaa ttcttcatac gtccataaac agcagatatc tatcagtaag gtattttgca      1140
atatttaaca taatactgta gctgctaccc agtttaaaaa aacaaaacca ggcattgcca      1200
```

-continued

```
acactgccaa atccatgtga gattacctcc tcttccctca agaaccagcc acctgagttt   1260
tttctctttc ccatggcttt taaatgctaa acagacacac acacaaacac acacacacac   1320
ctactatgtt tgagacactt tgataggtgc ttgagagaga ccaaaaggta taatggtggg   1380
ctttgatctc aaatgtctca catctaacag ggaaggtggc atgtctgcgg gggaagtcaa   1440
attaacagca taggttttaa ttcctaggtg ttaattggga gctggtgtgg aattgacagg   1500
aatgctaaca cagctcggag aagaggagct gggactgact tctgacggca aggctacgca   1560
gagtctgaaa ctaaggtttt gatgagaggg agaggactgg aaatcaaggc ttgggcagcc   1620
tcgggagaac aggctcagac aagtcaagtc ccctcacact ggcaggaatt tcagacctgc   1680
tagcagaaca gttttttccaa gatcatattt ctaattgtta tgagatgaac ggtgtcccaa   1740
attcagatgt tgaagccctg attcccagtg cttccggtat cctcataaga agaggaacta   1800
ctttgaggac actaggagaa ggcagctgtc tcccagccga gcagaggcct caggagaaac   1860
caactttgtt gaaccttgat cttggactcc taacttccag ggctgtggga aatcaatttc   1920
tcttgagcaa aagagatcga cgatagagta acatcaaagg ttctgtgaac tgcaggtgaa   1980
cagacgatca tcttcaccta cggggctcat cgccgtttca ttcctgtgct tctcgggagg   2040
aaagttaccc ggagcagcct ggtggaaacc caagcgtcct ggctgcagtc tccaactgga   2100
gtgtgaatgc tttccttctg acggcagaca gctgagaacc tgcagggtta agtgcacagt   2160
ccgggaaggt tctgttccca ggacagcgct atcgagtcca ctgggcgctc cacgcggtct   2220
acctaaaggg aacagcctgc ggcgcggcac tattcaaagg gtggggagat gaaaaatacc   2280
gtgctgctta gcattgatga cgcttgcttc agggaaactg actagaatct atttagtctc   2340
gagcatttct gagaggcaag caggcctcag ggcactgcag aggga            2385
```

```
<210> SEQ ID NO 78
<211> LENGTH: 2732
<212> TYPE: DNA
<213> ORGANISM: Homo sapiens

<400> SEQUENCE: 78
tgcctgcctg gccaactgtg ggggtcacac cccgtgtgtc cctggtctca attgcaaagc     60
gctgtggagg tgaagtggca ctgcccactt ctgaaggtca tccaccaatg ctcctgcctc    120
ctgtagatcc agtgaagttc tgggctggtt ctgagccgag ggtgtcttgg gaggtcaagc    180
ccatcatcca aggagccctg atgggggggt cctcagggcc tagccgaaga gtcagttccg    240
ctccatagca gcctgatggt tcaggtcagt cccaggccca tgagaaaaac tccagttctg    300
caccaaaaca cagtggcctt tggagtccat cagactccaa gcattaggaa gggccaagct    360
cttctcccat tggtagttct cacacacctg tgggtccaga gggggctacc cgccatgatc    420
ctggagctgt ggtctaaggg atctctgtat acctcagctg cggtttggtg tttttttatta   480 gtgaatggct tagctccaac ttctcaaggg aacatgctgt gcccttatct ttgtgtgcct    540
gcatgacagc acacagccag catgcaaacc atgacctcat atgcacttaa cacttgacta    600
tatctctggc gactagactc tctttggaca gggacttctt aattctgtat ttctgaatgg    660
cctagtgctg gctgtgacac agggtagtta tataattgat ggtgttgatt tgaattttga    720
ataaattttc taaatgagtc gacattatga cacaatggat atagatgaga ccattaatgc    780
atttgaaatt tacactagtg gacacatgat ggtagatgct atgatacagg aacccatgca    840
aattccaact ttgagaaact agtaacctat ttcgaaatta tacctttctt catgggcaaa    900
gatgatccaa gcatggagga catgacattt aagccttctt cccagtgtaa gggattggga    960
```

-continued

```
gtgagaaggg atgaattctt cctggggcag gaagggagga tgaaatcagg aaaggcctcc      1020
cagaggagat gtttgaagga tggacaaatc cagatggaca atagagtatt ctaggctgga      1080
gggtattaac caaagcattt ctttgggagg agaacagtct cctctgctct cactgtagct      1140
ggtggcttga ttgctgacca aggtcagggt gacacctttg gccagggcat ttgcttctaa      1200
gtcagccaag ggctctttct gtctgaaaat agctgcctga attcatttcc ccattagtcc      1260
cagaggccaa agataggagc aggctttctc caccagcagg gcagaaactg cagctagaaa      1320
gccggccctg cagcatgagg aaccctggg gagctggcag gagaccttga ggtctgaccg       1380
gctgtgtttg gatggaccct ctctagctct ttcccccatg tgactgaaaa ccttatcata      1440
atgaaagctg taaaaatgcc aaactttaac cttattaaag tcacactgtt ctggtcttgg      1500
caaccataat aggattttac aactcaacct ctactagagt ccttgaacag cccagggtct      1560
gtcagggtcc gtgatgggtg acttatgcct tcagggactg gtgcccaccc acattcccac      1620
cctcccgtgt ccatccacca cccgtgtcac cgtggccttc catatggcct cctgttttgt      1680
tactcataga aatggagaaa tttccactac catggacccc ggaaaaacat atgagcatcc      1740
ctacagcatt accagctgac ggtatttttcc tccggattaa tgaagcacag tggaattta      1800 gcagttctgt aatgattaat atgtcaaatc catattgcag gagagggaaa caggaaagcg      1860
atgtgagaac ctaggagggg ggatagcaaa gccaaagaag gaagggaagg aagagaagaa      1920
caagggaagg tggggagaga ggaacacgcc acagggggtta ggctcgagct aggaaggtgg      1980
gtcaagtcag ttcctgagga gaggtctccg gagcagtgca taaggttcta catgtcggga      2040
ggtcatggac cttaaaggta tggggtttat ccctagaaaa aaaatacaca taaaggggtt      2100
tactaagccc ctaaacctcc atgagaaaac acaaaactgg gttcagctga cggtgtttgg      2160
actgtgtcat ccctgtcagc atcccctctc tgatgccttt cagcaagttt ggaaagatga      2220
caatggcgtc ctctgtcttg ccctgtgaga ccctctcctc aggctgcaga ggatgaggtc      2280
ccttcctcca actctaggca gtccagtgcc acatgaagtg gtgtccatgc tgtgcgtgaa      2340
catgctccgc agtcttgaga cacggctgga caaaggaact ggccaagcca ccaatgggaa      2400
atactttgca atgcaaatga gtcctccaaa gccaagcatt cctctcctgc taattacttt      2460
tacctggttg cattacatat tctgtatagt caggagctgg ctcaatgtta atgtcattgt      2520
ctcctgaaat ccaagagacc tgaatttcct ttctttcttg atctaagcat gtagtcatgg      2580
gccagaatat cacatactat cctctgaaca tatgcttctt taacaggaaa gaaaaaatca      2640
ggttctatat ggccttaaat cgtctgtgat gggaactgta caaaggtcaa caacaaacac      2700
tagtttacat actcagtagg tgaaagagtg ag                                    2732
```

<210> SEQ ID NO 79
<211> LENGTH: 2973
<212> TYPE: DNA
<213> ORGANISM: Homo sapiens

<400> SEQUENCE: 79

```
aatttgaaga cactgagagt gttgcaaaaa aaaaaaaaaa aaacagagag agagggtgtt        60
tcagttgcct gcaccataca tctcgctggt tccgaataat gcaagtctct cttctgttct       120
tgagtttcct gccccttaaa tatcgcttta ccagaaaatg agaaagtctt cacccaaaaa       180
aacagcacag aagtgaagcc aagtgactgt aggtttcata gcctggtcaa cagggaggca       240
gctggcgatc acttcctgcc tcaccctgga ggaaggagct actaaggaaa gggacgtcta       300
```

```
agctgaaaca acttcaggtg gttcctgtcc ctctctagag actaaagtct cactgcatgg    360
aatgcccttg atatccagac tgggaaaatc taagcctgtg gacaggaaga aaagtcattc    420
atttacattc gtttatcact cctactactc atgagagtca agtgagggtg tctctgactg    480
cttcacccct tggttcagcc cagtgaaagc tggtcaactc ttaatgctca gatccgtaat    540
agcacaacca ttttagtatc tttctctgaa gactgcaaca cgctgtcatg atattagtca    600
actgacatta ttatagtgga ggctgctcct tgaaagccct tcactgcctc cctggggtgt    660
gggtggagga tgagataagc agctcacaag tgggacagaa ccctggctct gcggaaagcc    720
cgggcttcct gtgtgagcgc atagacagcc ctgtagtccc tcagccctgc ctgccagaaa    780
cccaagcccg aggatgcccc tccagatgtg tgctggaact gagctttctg aaatccttct    840
cctggggcca gacactcatc aaaggccaac tctatcgcag catttgagtc acctgttatg    900
tttgagatcc gccctgtgtt gggagctgaa acctgttggc tggtcttgct ggggtgaagt    960
ctggaagagg actcctgctg tacttctgag gtccatgctg cagctcacag ccagtgtggt   1020
cagccgaatc agctctgggc ggcttattgt gaacaaagga gctcagttgc tggggttcac   1080
tcctatccca tcagaataca agctgcactg gggctagatg tccacggctg tatcctcagc   1140
acctagaaga gagtctggga ccaagtgtga acatctataa accgttggca ggatatttag   1200
tatagcaata tctttggata aacaaacaaa attatgttgt tggaaaccaa acgacaccac   1260
tgatgaatgt acttaggcta cttaatcaag aaatagtcgc aatgattcta cttctgtctt   1320
cttttttaaa aaaaatttaa ttagttgttt tattttagaa tagcattact gattaccttt   1380
cttccctgga aattaacaca tttcgtagag acttaaggat gcatcaatga aatacttaga   1440
attgaaagag gaaaattact tgatttctca ggatgtgtgt gtctattggt gctctagcac   1500
agttatgcca ctgaaaactg atgcaacttt tgtgaagcaa cagctgtagg cctctgtgta   1560
acacttcctt gtgtagaact taggttttag aaaatatcag aaaagacctc tttataggct   1620
taccacataa gtacattgtt ttcatccccc agtagactgc gattggcttt gactggggag   1680
ttcctcattt gtctccgggg ttggggccca cttctgtttt ttgacactga ccagctatgc   1740
tgtcttcata gaaatcaggc agtgggcagt gacctggttc ttactaactc ttgtgatgcc   1800
tcacgcgatg ttatatctgt caccagcacg ctctcctctc ctgagagagt gttagaaaat   1860
tgcgtggtct gggagtgcag gggttaatga acagttcgga gatgcttcct ctccttgtgg   1920
cccagatgtc ttcgggaatg cttgaatcct ctcccttgc atcgtagggt tacctgtcac   1980
atccctttca cttgcaggga ccatgtctgg acaaattagc caaagactat acctatgttt   2040
gaagcaaaat ttaatattcc tccaaaatta tggctttcca attctccatg gctcctctta   2100
gacaacaaat atttctgagc actgccgtgt tccaggcagc tgctgagatc tggatctgat   2160
gggtaaatac acacagaccc cacctctgct ctttcaaagc acgccttaca ctcaatgaga   2220
acaaagagga atcacagtta ttggcatagc tcattttttt tgtcagatcc agttttgcca   2280
tatgacaggg ccaaatctat aaaacattgg gagctttata ggagataaaa tacctctaaa   2340
gagaattttt atagcccaaa ttcctatcca gagtctccag cccctttggg tagacagccc   2400
cctcaagatt ctcaggagc tcatcacatt ccccattggg cagtgtgact agataagggc    2460
caagggcatg agtcagtgtg ggaagtggcc cagctcagct cagccactgt ggcaggcaag   2520
aaggatgcca cgaacacgcc aatggcctca gggaggtggg tgggtgaagt gtggtggggg   2580
tcatgtttgg ttatgtaaat atgactccag gcagagccag tgctgagttt gatgatggag   2640
gaggattgga ggtaaagcta gagctctcag agccttccct gggatagaga ttcctgctga   2700
```

-continued

```
cactgctggc catgatagtc tgtctgggga gccatctcac cttcagcttg tgcagagaag    2760
ggtggctggg gaggtttgca tagctggtag gtgcattgat gccacttgtt tctccacttg    2820
gcttcagtcc agagccccac tctgggctgg tggctgggta agaccatagg taaacagtag    2880
acttatagta tggtttgggg gctattttgc tatgacacgg gcttaatggc cctggtgtct    2940
tcatgctact ctgtatgctt tgaaacaatg gct                                 2973

<210> SEQ ID NO 80
<211> LENGTH: 2353
<212> TYPE: DNA
<213> ORGANISM: Homo sapiens

<400> SEQUENCE: 80
attgtcttgc aggaggcccg cgccaggctg gtcaccgggg gccctgctta atcgcaaatg      60
gtgcaaccca gttttttgatg ttctaaacta ttaccataca agagaaaaga aatttagaaa     120
caaacagacg gaatacatta gccacatctt ttttcttaga cccttctgat attggttaaa     180
gctgctttgc tctttacttg gaagtagttt tgactacttt taaagtaaca tttgccaaga     240
gaatgcatgc tttgtcatga ttcctcatgt ttggggaatt tgagatttga gttctgggct     300
gagtggatca ggagcagcta ctcagccttt ccagttggag tagaatgggg acaaggaatg     360
accaatgagg tcaaaggaag aactaagcac tgtccccaaa atgcattctg gaaccattgg     420
gctgggtgct ttacttctct ggatctcccc tggggtcccc agagccttac taaagttagg     480
gtttctctgt agagtgttct gaaaagcaga gaaagtcctt gtccaaatgg aatccccagt     540
ggttaagatt gcttagactc atacccatga atcaaggcaa tggatgatgt cttctaggac     600
agatgtcaaa accagctctg aggaaggtgc ggtgtgagca gggagagggt aggctagatg     660
tctcctagca ttttcaatcc tctaaactga ggtcagaaag gaggaaaaca ctgtcttcac     720
tgttcattgc ctgcacggca gcaggagaaa taagggaata acaccaattt gaaaccatgt     780
gtatgcccat cccgtactcc atatctctcc tgcatcccct ttgttcctgg acatttttat     840
aactgtttcc aaccggaaga agtgcatgaa ttgatacttt ggcatcaggc tagatgtgcc     900
actcgggttt cttctctccc cccctcctgc tgtgtgtgtg tgatgtctaa aggcctcccc     960
atctggacac tcacccacgg cattggacat tttccttttca ggtttatccc acgcagtcct    1020
attccaggaa gcctcctctt ccccacttag tgtgtagaca actcactctg ccaacaataa    1080
gtagtatgac aataaactag tttctaacta ctttatgtgg attaactcac tccccatcca    1140
gttctctgaa gaaggtgtta ttgtctctgt ttacgttgag gaaactgagg cacagagtgg    1200
catggcattt ctcttctgcc tctccactct gtgagcgatc tgcgtttagc agcgcctgcc    1260
acaggggtct ggctcttagt gaatgattgc tcctggatct cccaaactct tcatatactt    1320
tcacatcccc aagattcctc ctgccagctc catctgtgaa acttgtgggc cggtatttga    1380
agaatgacta aaggggaag aggttttatg aacttcagac tgtgaactca aggaagagag    1440
tgagtcaggc ctccacattc ctgaaatact ttcaggaggc tcagtgacct cagacaataa    1500
gaacctgagg cagaatgtcc ttgggaggcc ccccaccagg aagaacgtga gggcagatgc    1560
tctgctgtgc tgccttctgt ggttcctgcg cagtgtgtgg gttaggaaac cactagccag    1620
aggcccaggc ctaccgagag cgctgccttg gttttgccag gctgactcct ctccctggaa    1680
tgcttgaccc caaatgcttg tgagcttgtc atcccagact cagctcatgt gtcacctcct    1740
ctgtctgcta caggtagaag aggctttgtg gttgggacac cacagggaat tgcgcttgct    1800
```

-continued

```
tctctcactc ctaaacgccc tagaaaaaca ttgctttcaa catgtgtgcc caatacattc     1860
ttcaacctac tgaggttggc aacagctcca aggttgagga gtgagccctg tgccggagat     1920
gtgggtgctg ccttgcttct gaggtacaga gactttttaac ccaggcgcta ttttcagagc    1980
ggagacatag ctattcaata agtttaaata attacaaatc tttctcccca gcttctatct     2040
ccgtccatct ctttcctcac caagcttaaa cccaggtatg aggtgcaacc atccacaaag     2100
ggaaagacag agcaaacgag aggctgacag gtaaagaatg agtctcaccc aagatgaaaa     2160
tgttagaaaa gctgagggag cacattcagt caagctcctc caagctgcac cactttccaa     2220
cagaaacaag ctaactaggc tgtgggttac tgcaagtgaa ttgtaggctc gtctgcctgt     2280
agtgccatct agtgcctctg gtctaaggaa gttggtgggc ttggccgtgt cgtataacct     2340
cccgtgtcac ttc                                                       2353

<210> SEQ ID NO 81
<211> LENGTH: 2251
<212> TYPE: DNA
<213> ORGANISM: Homo sapiens

<400> SEQUENCE: 81
gacccaaatc agatactcgt gagccaggca gtgacttggg ctcgctttga ttggcacaaa       60
taaacagaaa atgtctataa acttctttag ttggaatcag aagtgggctt tacttggatt      120
actcctcccc agggaggggc atgacaacct atttttaaag gctcaagtgg aaaagtcctt      180
ttgcagctgt gaaaacaccc tcagggtcag cccccccacc tccctgcccc ccctgttaac      240
cgcaatgggg atgtggtctc cttgatacgg agggaggggg ggaggccgtc ccctgggtgc      300
tgggggaggg agttgtggcc ggcatgatcc tattttacac aggaagaaac agacacccag      360
ccaagaccct catttctgca agtcaaattt agatacaaag aggcacctca tggtgacgaa      420
aagcatctaa agagaatttc ccttgttcct gggcgtgagt gtgaaaatgg gttctgctag      480
cttttgtgcc tgtggttatt ttaatgaata gctgtgtaaa cattattctt tttgcaattt      540
tcttcagcaa gttgtgactg caggctccct cttccctgat gcccagaggg agcacagttc      600
gatttaagga ccgggcaaat ggatgtcatc cgtgtactcc acccattcct gccccaaaag      660
gccaactttc cgttgaccat tattttggat ttctgagttt tggcgcttct ctggcaagtc      720
actgtgtatc tctgagcctc aggctcccct ctgtgacagg gagagtgcca ggttgccccc      780
agggcttaaa tgagctactg acacgcagtg ctcacctcag caggagacag gcacagctgc      840
ctgagtgagg ctaaacatga gccccggggc agcgtggcag agagagcacg agacaggacg      900
catacccaaa tcaaggctcc aaagctttgg gtcagggcat cttgccctgg agccagaggt      960
ctggcaaatg tttatcatgg gggtgggggtg tagcatctgc cctgtctctg gtgtaaatat     1020
tcccattgta gcagatgtct gaaagagatg ggaagatgca tttcagcttt tgggaaccca     1080
agtgactcca tgacagcact gaaaaggcat ctgacaccag agctgggccc agggtagagt     1140
ccactaagcc ttcaggaagt caaggacgtg agttttggag tcagatgggt tggtcctaac     1200
ctggctcctc cacctaccat ttgcgtgttt agaccttgtc agctataaaa agaacacatt     1260
gagagaaatg tagagtcatg gattaggtgg aagaaccacc cggtcagaaa cagaacaaag     1320
ccaagcccca ggcgatgacc taagcggata aaacacaagg gagggtgagg gaattggaga     1380
tctgccacgt ttgacagcga agctgggttc cagccaggcc agtccacggg gcgctgcttc     1440
attctgctga ccatccatca ggagctggtg gcaatcacta cccacttcat ccttgggtga     1500
atcacttaaa gcaaaagaaa tacagaaccc cggaatcttc catagtacta tggaccccctt     1560
```

-continued

```
tggctaaagt agcagacaga tacattttag attctactct ctagatcaca agcctcctag    1620
tttcttgttt cgggagccct cgatttcctt gaaggatgct ggcgtttcat aacagtcaga    1680
cttctcgctt tgtgaaatcc cgtcctaatc tccaggtcaa taaagtgact catctttggg    1740
cttaacatcc ttttgtttag ggagaaaata gtttctactg agtgataatc tatttataaa    1800
acgttgcatc tgattagcca ctattttatc ttccaacaat gcttaggctt tcgtgtttta    1860
aggaggaaaa tttagtgggt tttcttggcc aacctcaaag gtgtctgctg ggattggttc    1920
attttccgga atgcctaatg gattgtgaaa catgcccgcc tcccagcaag gtacctcact    1980
tggcctattg tgtacgacaa acatcttctg ccctcatgag ctgggctgct gttgatccct    2040
tccagccgaa agcatgcacc agagaagagc aattagtttg tattcctaca aaaattttca    2100
tggattcaaa ttcttcatag aaagaatgaa ccagagagta aactgaacca cagattaaag    2160
ggctcatgtc aggcaattct ttgaacagtt tttttggttt tgaaccatca ttatttgtaa    2220
tattctctga aaagccagca ataattgtt t                                    2251
```

```
<210> SEQ ID NO 82
<211> LENGTH: 4498
<212> TYPE: DNA
<213> ORGANISM: Homo sapiens

<400> SEQUENCE: 82
ccagggaggg gtgggggatc tggggaaacg gtcttgaaag agctgtattt ccaaaatgtc      60
tagaagttgg tccggtggga cacccaaagc agcagaataa acaactccca ttgaagttac     120
aataataaaa tgtttcatga taagttaaaa tattctttat attattttaa tttcttaaaa     180
ttaagaatta ttaataatca ttaagcttat aataaaaaat taaaaaccag actaggaaat     240
gaaccacatg agggtgtgaa ctggtaaatg ggaaaattag ccccttaagt atctgagaca     300
atagaacaat ttgaaaaaga gtatcaaata gttatggtca aaatacagag ataaaatgat     360
aggacatagg actatgaaaa aagaacaggt aaatttgaaa aagtacagct ataatatgta     420
gaaataaaaa gtttagtcat ttacatataa aaaacctcaa tgattgaagt caaaaatcta     480
ataaaaatag ctcattgaaa aggggaaaga aaagtaatat attattgttt ataaatatag     540
aaatttaaaa taatatatta acaaatagaa ttccagcagc ttacatcatt aatagatcaa     600
aagagaaaaa tggaaagatc atcaccatat atgctgaaaa gccatcagaa tttggcatcg     660 acatatataac aaaccctctg taacatgaaa caaagggtaa agttcagccc ccaaaccagt     720
gttagaaata ctagttctaa atgcaagata tgaatgtcct ccttcacccc tattcttttc     780
tgaacagaac tggccacctt tatgtgttta tgtgtgaaga ctctgttaca acatcccca     840 gttttctagt gtatacatgt gtgtatgttc ttcatgatct taagtgctag atgaggcttc     900
acattccata gtgaaaggtg acttgtgaca aagtctgaac caacttcaca ccacatctca     960
cggttaggag cactggaaat ttttttaaaga ttaaatacac agggacagat ttcctgttca    1020
ccccatctgt ggttattcca gtatatggaa taaaatgcat gacaatggga gagacaggaa    1080
gcctatacta gtcattaagc atctatggag gggaaagggc acttcccttt caatttccca    1140
ctaccctgat ttcaacttca catggaattt cacaagataa tagcaagtta gtttagagga    1200
tgtttcacag aacaggctgc tttgctgaga cctcagaggt gtcagttgaa caagacgaat    1260
gatttgcatt tggctatttc attcctcaag gtcagtgctg gcacgtccct cctctggctt    1320
tagagattat ttactgacaa aaataagtcc agagaagttg tcaatactca aggtcacatt    1380
```

```
gctggttagt gactgaataa tttgtgccat ctgctaggta ttactcttta tacctaccaa      1440
ctcatttaat cctcatatca actcacgtgg taggaatcat tagattttat ttatttatta      1500
ttagtgggaa taggttgtat ggagccaatc tggtccaccg attgacttgt gcacgtcctt      1560
accagtcctg taggacatca aactgcaacc ttggtgtctt gggcaagaag caccaactga      1620
atgatctagc ctaaccagtc atacccaaaa gtaatctgtg tgggagaaga cagctgcttt      1680
taagccaata aaattcaagg caggtaagac gacttagtta tgacactgct gtctccttct      1740
cctggtaaaa atgcttaccc gctgtggctg ctccctcagt gcttctacct ggtgcctgac      1800
ctttcagtct tcctaataaa tctgcctgag cttcggtgcc tcctcaggtg tcacgagggg      1860
agtttgtaga ccctttggga gctgatgtca aatgctcaac aaatgttctg ttaagttagt      1920
gctgcagtag tctggaaagg agaagattaa aggaataaaa tatgcccccca acagttttgg      1980 agaacactag ccagtgggga ctctgctctg tcatctaagg tgaccatatg gttggctgat      2040
aaatgataac aattttctgt aacacgtggg cttttcatct tcccaacagt ctggaggaaa      2100
aatattagat atgatgacag gagcagtttt taccatgtcg ttaagggccc aaatgtagtt      2160
ttagattcca tagacactaa atccagcaat gccacaagaa tgcctgtgca aacaggatct      2220
gtgttgcagt taaaattttt tttttatttc tgatatatac aaagaaaact cacttcatct      2280
agcttaaaca aataaggtta ttttgttagg aggtacaaag tatcagcaga atccaagaga      2340
gcaggtgttg ctgggtctct cagggacctg ccaccaggtt cccacagggc atcggccacc      2400
aaggaagaag ctccctctcc catctttcgc ttcctgcatt tatttgcttt attcttccct      2460
ccatacagcc tgcctttctc tgcctctcct gggcttcaca tgctcagttc cagacctgag      2520
caatgattga cttgctcttg gtccctgtta taaattccaa gggaaaataa tagaactggc      2580
ctggggaggt atgtagggtg gcctagagca tctggcttca gagagggacg taattctggg      2640
tgggagttaa taatctagag gagattgtgg atgatacaga caccaatagc ctctgggacc      2700
tctctgatct atgacagagc gatttctgtc agggcacaat tgctttgcat tacaggctag      2760
gaatctgcaa gtcagtgttt ctgctttttt ggaggtttac ttcatatctt cactgggtac      2820
tattgaagag gtgaacactg ggtataaata ctgttcttat tactgtgtta cgcacgcacc      2880
tgagaagttc taagaggcga ttctatccag gtttaaataa ggagctttgc agaggtagta      2940
tatctcatga tcatatttga gatatctggc agaaaaaatg ggtgtgttct tgactgtccc      3000
tagtccttga gtttggaggc acttctcttc tatccttcca aggctctctg ctattcaccc      3060
atgccctctt gtcaacttta gtgtccacaa gtacctgata gggacctcac cctgcctaaa      3120
gcaggatttt tggatttgcc ttggtttctg cccatgctgt tccccatact tgagattctt      3180
ttaattcctt ccgtgtctct aactcataca tatcatttaa ggtcaagttc tgtacctttt      3240
gtcatggttc actgggcttc cttactttag aactcattca gtagtgattc actgaacagt      3300
tacttataca gcagagtgct ggctggttat gttgttcgct agggctaaac aaaaaaattg      3360
atttcctcac agttatggag gttagaagtc caagatcaaa gtgtcagcag gtttgaattc      3420
ttctgaagcc cctcttgtca ttcctctctg tgcactcgtg tctctttgtg tgaccaattt      3480
tcctcacctc tttaaaggct ctatctccaa ataccatcac attctgaagt aggggggcatc      3540 tggacattaa cttatgaatt ttggagggac acaattcagc cccaacacca gtggagacag      3600
gggtgaagaa gacgtgcatc atcttagagc tcctgtagtt tgacggtgtg gtagggaaca      3660
caggtattaa ctatttacat gactaggcca ttagttacca ctgtgggatg atgcaagaag      3720
tagaatacaa atgctggaaa aggtagtctg gggaagtgag actgaaagtg tgagatctga      3780
```

-continued

```
aagaagattg gatgggagcc agccagctgg aaagagagag agtcaagtat tccagacagg    3840
aagatctgtg aattccatac ccagggaatt gaaagaacca aagtcaaagg gccagattac    3900
acaggacctt atttactgac atcctcattt catgcttacc tcggactgtt gtcaaaaatc    3960
ttttaagggg agtgttggcg tgcacaattt gcttctcctg attcaaggga gaagacttca    4020
actccttttg tattctctct ccacatatgc aacatagggc tggacatata gtaggtgctc    4080
aagaaataaa tgtggatatg agaaatgaga tgaatagaag cactcttggg tgtgtttctc    4140
caggctctga aaggtgagga ctttgatact ataatgccac ctagtgttct tgttattaca    4200
acaacacagg ggagcagggt ggtgctagtc ttcaatccag aaaattggaa atcaatttgt    4260
ttcatcagca taaattgata tgtccgacca cccatccttt atccattcat ccatctgtgt    4320
tgatgccccc tgcatctctt ctatgagctg aacatgtcac gcgcctttct actccttgtg    4380
gttctttgat tgctcagttt tgggtctttt tgtcctccta taagtaaggt ctcagatacc    4440
agtatctaga ttctctgagc tcccattgtg ctttctgtta aaatggcata tactaaat      4498
```

```
<210> SEQ ID NO 83
<211> LENGTH: 1706
<212> TYPE: DNA
<213> ORGANISM: Homo sapiens

<400> SEQUENCE: 83
ggctaattaa ctcttagccg gcgggaccct cctcctccga ggttggccag gagcagcggc      60
atcccaggcg ttcctgtctg atgtcatagg ctgccggcga ttgcggagaa tcgccaccac    120
gcctttatga aggtcccaac tttgccatct gatacccttt actactgaca ggcgctcagc    180
caatcaggag cggcgagcgg ggtctgggga cccggagccg ccgaagccgt ctcgggaacc    240
ggctcttaac tctttgcggc gcagccgccg aggcagcagg gccaggcggg aatctgggaa    300
ggggcgccta aagagcggat gcccgagggc tgcgacgccg cggggcttgc aggtggcgcg    360
gggctgcggc aggggagctc ctcctgggga tggtctccca tattgaagga gagaagatta    420
tccaagggga tagctcattg agaggtcacc tttcaattct gccttccata gctgtggtcc    480
tcagccttca gccacaatgg aagtgattat gtccataggt gtgagttcaa agtacagtgc    540
agagtcacca ccttaaatct tgacccttac acatctcctt tcctaggagc accatgaggt    600
cagctgctgg gtcacagaca ggggtagtgt ggtcagctca cctatgttgt tccaggacct    660
gtggtcctct cttagcaaat cccctcccac caaggtcatt attgtgtgag tggatctcat    720
ggtcttcttg aagagttctt gtctctagta tcacctcttg tccattttct cttttttattc    780 tctcacacat cggagcattt attcatcttt agaaaatgca tttagggatg tgagcaagtc    840
actgtgacct tgaagtctct caactcccag ttactcccag cacccacaag gcccatacaa    900
gtgtgtgtgg gcactatgag gaagatggtt tttacacttt gggctcacat cacgagattc    960
attttaaatt gtgggaagac atgagttgac ccagtaactc ccactgtgtg aacaccactg    1020
tgtctgtgag gaaggcccttt gcaaatcctc aagtctctca gactcgcaga aatgcatttg    1080
gaaatatggc cctcgagagt gggtggcccg tgggaaaggg ctgtgagccg ctgagtctcc    1140
agggcttccg aagttgcttg gcataggcat tgcctaatat ccatgagctt aaatgctact    1200
gggaactcaa tcataatgta tttacattct tataaatcca aattactgct tggaaaccat    1260
ccagcaaatt catttctgag taagacaaat acatgaaaat cttgcattat gtggatatgt    1320
gtccaaaata ttacaataaa tatcagtgaa tttgcattca aatattaggc tattttttccc    1380
```

-continued

```
aaatatggca gtgctgtgat tatgtgataa acatgaaaaa ggcaaaatgc ttgtttacat    1440
tttgtcttca attttctatt agcagggttt aagtgtagtg agtttgtatt ttctcttatt    1500
taactggcca ttattctctc tgaaaatcat attataaata acctacacag cagaaagaat    1560
gcttgatact gttaaattat tcttttttctt tttaattaat accttcaccc ttgtgtcttg    1620
aatagaataa tctaagcaca gacaagatgt gttggatcat agttaaaaca tttaaattta    1680
ttactggaat aaagagccag agtccc                                          1706
```

```
<210> SEQ ID NO 84
<211> LENGTH: 2000
<212> TYPE: DNA
<213> ORGANISM: Homo sapiens

<400> SEQUENCE: 84
```

```
cgtcacgtgg ccgtctagac accctgtcgc tttaaaaaaa aaaaaaagcg attgtgtttc      60
gcaaacaaca gatcgggttt ctaaaagcta tttctccccc cccccccgcc accgccaccc     120
cctcccgggt ctgtagaggg gtaccgatgg aggggagagg tgggggggcag agaagctccc    180 agaatggatt gagccccggc cggagcatgg agaaattgga aaagcaggga gcaccgagcg     240
ggcgagtttg gagctgagcg agcgggagat cctatattgt agtaggatgc caacagtgca     300
gaaccctact ggacggacag aaaaggccac ataagctgca gttgtataac atcataattt      360
tgttgtaaat taaaatatgg cttattgaaa ccttgtgtga acattctaaa gcaacctgtg     420
aagacagcag ctgagaaagc acaggagaga atggagaagg agtgatccca gcactttggg     480
taggcaaggg aagacgaaag agacagaagt gggattgatt ccaggctggg gcgttgccgc     540
ggttaagaac tagggccaac agcaatcccc acgttaggcg agcacttggc agagtttata      600
agattttctg ggcaagtttc cgctctctag ggtcccattc ctctccctaa atgagagtgg     660
tcagaccagg cttcaagcaa cagaaaggat taaataagca gaaagtagag gtcataattc     720
taattcagtt tcttggctaa atggagaatc tgaagaattt tggagatctg agtagtgcta     780
aggctctgta atgagaggcc ggagcacaca cagggcaggt aggtttcatg ggtgtttcaa     840
gagtggagtc tgacgtcacg gtttgtctgg gtggaacatg catgtacttg cagagatatg     900
ttcccgtata gtgtaattgt aggtgtatta attcaggtgt caccccctctc tacacggctt     960 tcctcttcca ttttgctacc ctaggtagaa gtgggtgcgg tgctgagcaa gtagctacaa    1020
tgattggtgc tttatagctc cctggcatcc cctgaatcag ttaacatccc agctttcctg    1080
atagccccac cccatcacat tcttatccct ctcctctcca agaaagaagc cagaagcctg    1140
gcagtagagt cccagcaggc tggtgtgcct agaaaggtag tttctttctt tcccttcaca    1200
ggcacaaagg aggccaacaa acaccagttt cagactattc tgacccttaa gaaaaaagtt    1260
taagagtcca aactatttcg ctttggtgat agtaatcaaa ccctaatcat ggtgccgcca    1320
caagtcacag agaccaaaat agcagagtta tgacaaacaa ggatggaatc agctaaagac    1380
ctggctatta atcaccggcc actctcttga ccggctgctg gaccataaag gaaaaatctg    1440
gagaatgcag taaaatgagg ttcaagccag aagggattat aaacgttaca tagcccagag    1500
agtctccatc ttcagtccat cttatttggt actttttctt tgctttttct attttattga    1560
tttttggcaa tgcatgcaca atggtacaca attcaagaat acaaaagggg aggaagaaaa    1620
agatagcttc ctggctgcca gcacccatgc ctctggcagc caccattaca gccaaagagg    1680
cagaacatga acattaggtc tctgctttgc tctccagtcc cacttgcctg gtcaatatct    1740
caaaggcacc ctagctctta ggtcccagat agccaaacag gcttttcctc cagagctact    1800
```

-continued

```
cctcaccata tcacaaccag aaaccaagga caacctctcc cttacccctt atcctaccac      1860
ccaaagccta tcatctccaa aatgcctctc cacttatctg cttttctcca gtctcaccca      1920
ccacaaccac ccagcatctg tccgggactg gtccacacct tacctctggt cttcctcaga      1980
cccacccagt ccctctcccc                                                  2000

<210> SEQ ID NO 85
<211> LENGTH: 4772
<212> TYPE: DNA
<213> ORGANISM: Homo sapiens

<400> SEQUENCE: 85
cattccttta tgagcctgcc aaatcaaaga agcctttaca actggctgcc taagaatacc        60
agggcacaac aggaaacatg ttgaaatatt attgaaaaca atattggaat taaaattaaa       120
aggtatcctt tgttataatt gggacccata gcattttttc attatgcttg ctgccttacc       180
ggctttatga agtttggaaa actagttact gaattttaat atgtgaaatc cacacctaaa       240
aagagcagac catgacccca tagaagtcta aaaatacccct ctgatgcctt cagaccttga       300
ttctgttata atattcttag gttgccaaat taagaattcc tgctaatgca gaccataatg       360
taaaggaggt tcggtttgtc cacccatgaa ccttatgtaa aacttatcac atttctgctt       420
cctttctgct gaatgagagc atctatttat aggctacata acatgaaaag catgggaggg       480
ttttctttca ggcaataaaa atgtgatcta agtcttccct tgtaatgaaa aacaaacagt       540
ttgacgtgta attctgtaac tgcttaaaag agtcacttat caaaacagat cttttagtct       600
tctaacagag tgtgtaaatt tgggtaatga gttaccaaga cttgaaaggt gtgttgtaac       660
atattcaata aatggttagt gctagtgtga gaggaaggaa gaaagggtca aacttccaga       720
aaacattagg tgggtggcag ggtgactctc ccaggaccct gaattcctga tttcagcagt       780
gggcacatga ttctgactcc acaaatcata atgagctatc tctatgggaa cagtgatcgt       840
acttccttga gttggaagtt gagaagcctg aagctcctgg gctgatcatg catttgcaag       900
attaagtatt tccaatattt attattataa accacatatt atttgttact atcgctgtag       960
tatatgacct ggaacgctag actaaggtat atgcatattt ttaaaaaaca acttactgag      1020
atgtaattct atatcatacg gttaatctac ttaaagtaca cattcaatgg ttgttagtat      1080
atttatagtt gtgcaactat cactacagaa tagtttagaa ctttttatca ccccaaaaaa      1140
tattctatgc ccattagcag tcactcccca ttccaacccc agtccttggc aaccactaat      1200
ttctttgtca ctgtagattt gtctattctg gacatttcat ataaacgaaa tcataatgtg      1260
tttttttttg tggtggtttc tttcacttag cgcaatgcta tcaaggttga tctatgttgg      1320
agaatttcat cctttcttat tgctaagttt attttaatag tgtaacgaat aagataaagt      1380
ggctgtgatg aaggtctgga aagcatctgc ctaaaggcaa atatagtgat tactctttac      1440
atataacctg aaatccagaa caatatagca tctgaggata aaataattta ttgtagggcc      1500
taaggtttgc atcctgatgt atctgaaatg tgttccatat taccttggct ttcaatttct      1560
ctaattttct atttgattag aagttattca ttttgggggc aatgatgaaa ttccaattcg      1620
aactgtctta tatctttaa tcagaatttt cccaaagcac aaaagtgaaa atgtagaagt      1680
tgctgtgttt cattagtttc attcttttga atgttgctac actgaaagcg ctgtgtgaaa      1740
ttattacaag ttttcaaatg gttgtaaaag aagatgcata tatgggggact cactcaaagg      1800 gcattattta aaaaagaaat ttccagccac ccagatctca gggtagctat gtccattcaa      1860
```

-continued

```
ggatagagaa tccaccatct gtatgattat ttttacgtct gaactttttt atacaccaga    1920
gagactcaaa actttcaggg tcatttgctc agcatgtagt ggaatgtcct gcgcaataga    1980
ttccaattaa tatgaccatg ttcaatggcc ctttaccacc aatgatatct aactgctttc    2040
cacttggctt tatatggtac ttctttgtta cagctgcaac caggtctatc gcccctttga    2100
taaaaatttc agttacccca gggagaagct ttcaacttta ttaagtattg aagtctgtac    2160
atttgttctt ctttggaaga gcagatcaaa agcacgcttt ctaagtaagt aatctgataa    2220
attaggatag catttgcaga cttgggcaat atgttttcc gtaattgaaa cctgagaacc    2280
tgtgtcaact gactatacta ttataaactt cttagcattt aacaagagtt tcttttattt    2340
tttgaaagta aatagaattc cttgattcga tttaaccaat tctttagcat gctgtttcct    2400
ttttgttgtg gttaggaaaa cctcaatgta ggtttagaga tagaaaactg acaatcaaga    2460
aaaaaagcaa ttagatgatc aagttgtgca gacaaaagcc cgtgttgtcg tcttatctct    2520
ggcattaatt actgtaaaaa cttgagcaag ccacttaatt tttctcatct ttgaaaaggg    2580
ataattggct aaaattatgtg taagacttct gctgattctg aaattctctg attctaagtc    2640
ttaggcagaa tgaggctaga cacagaatac ccggccattt ttactttggc ctgcttcaat    2700
tccaggtttg gtttggcaat ggaataatat ggtgctattt ggtaggaatg agatatatct    2760
ggatcactta aaactggagt agtaatacct tccaaaggag actagacggt tgtatttctc    2820
ccacagtccc aagctactag aatgttgaaa acgcaccaga tttgaaaatt ggctcttctt    2880
cgcatacatt tacaataaaa atacaaataa attcagattt ctccatagct gatgggacaa    2940
attttgcctt ctgtgttcgt ctgaatctga gggttacctc tgtattttca aagatttaga    3000
ttgcgacctt tgaattccaa ttcgtgggat ttggatgctt aaaaaggaaa ctatataaat    3060
aaattttagg tatgtggttg tgttaaaatc ctcttatttg ttttgaactt agaatggggtt    3120 ttttatcatg catgattttg taacatcatt caatgataaa aatattagtt cactgactta    3180
ctcagatttt ctgaatcttg acccatttcc ttatacaatt gttaatatca ccactaatct    3240
catcagaaaa gaagtgttga aaaactatca agttcatagc agtagattca agatttctaa    3300 aatttttaatt ttctcttgaa agctcacatt ttgatcatag gcaataaata ccatctttgt    3360
ttttcttgaa acgacaggct tactttgtcc attaaaatta aagtctgcaa tctgaaaatt    3420
catcatttgt cagtcttttt tttcaagtaa aaatgatgtt ttatgaaaat gtatgctggt    3480
atgagtttct tttcctagag acaactatca tatttcaaga aatgctatat gcacttccat    3540
tttgtaatac ggtttttattg tgagtgcgtg atggtgaaga atgactaggg ttcaatattg    3600
ttacagtctt gaatttcccc ttcgccagct tcttactgct ccatttccca tgaagttaaa    3660
acaccaaaag taagaaacta ttaacactga ggcccactca ttagcaggga cccgcttctt    3720
aatgactaga ttttcttgtc ttgtgtctcc cattttctaa tattgtcata aaggttgtaa    3780
aaattcaagc caaaacactt tatatggtat ataatttttt aataaagtta aaacataagc    3840
taatattaca ttgataatta caaatatgtc ctttgacagg aatatctgta atccttcacc    3900
atgtgtgatg cacttggtgc ttgaagattc tttaggaact gcatatatgc agatgaaatg    3960
aagttcttta ctattatcct tatcaacata aatttcttga gaatgtaaag attccctgtg    4020
agaacccaag aacataaatg ctaacaattt attcactaaa actgaaacta agatttgaaa    4080
atttaaagaa gataatcttt gagtgctagg aaaagctaat cattttcttt aatcgctctt    4140
aagcttcatt cttcctgaaa atttaaagtc ttcctaatca gcaaatacta caacgtgtaa    4200
aaatcataca ggtgtacagc aaatgtgtct ttaaaatttt atgtcctact gatttgaaaa    4260
```

-continued

```
ttaaatcata ttttaaatgt attaagagaa atcccatata aaagaatgct aggatgaatc    4320
tttcagtgag gaattctatt gttagaaaat tctctctaat tatattttga gtgtctggat    4380
ttgtgtattt catgtatttt aagtcaagat atgttttagt agaagctatt acaaaagcat    4440
ttcttttcat ttacaagtta gaataatacc aagtcattct agtaaagtat cctgaaggaa    4500
aaaaacaact atgagtcatg gctgagtttg ctaccagtaa tagaattaat tttagtatgc    4560
attttccttg acctcacacc aatagagcta tttaacaatc ctgggctgtt ctgttttaca    4620
cagttagact tcatggatcc aaatcctggt tacagggctt gaacaggcaa gccttaaact    4680
ctgtgtgtct acttcctaaa atataaaaga gaataatgtc actacttcat gggataattg    4740
tgaggattaa atgaatacat ttaaagaatt ta                                  4772
```

<210> SEQ ID NO 86
<211> LENGTH: 3625
<212> TYPE: DNA
<213> ORGANISM: Homo sapiens

<400> SEQUENCE: 86

```
ataagctagg attcgctcct gagaacagca catcaggctt gggtgtgtgc gatgccactg      60
gagacgccac aggagaggct gctgggcagc tctgactgtg gccgaccaca tcaaagctct     120
ttgtaaagca ccaccccgtg ttgagtagtc cctccaggtt ctgcaggggc ttgctcaacc     180
cgtgtttatc cagcagagac accattaaca ttcacataca gaaaacaagc tgtgagcgct     240
tctgcattgg ctggggaaat ggccatgtac atttcatcct gacagatatt gtagtaaaga     300
gtgcccccat ctagcagaaa gttggtcgag gcaacacagc atttcctgca tcatcacccc     360
acgtgcaacc ctgtgctcag ccgtggaaca tcaatcataa caagttgctg ttcagatcat     420
ttcctgtggg actaaccatt aaggacacct tttcttcaac aaaaccacat ctgttgcatg     480
attaataacc acagctaaca attatttagt cttattttgt gtcaggcact ggcttaggta     540
ctttataaac gtgccttctt cacagccacg gtatgagatg taggtactgc tagctttccc     600
ttacatgtga gatagcaccc cacattcaca ggccaaatgc cagatggcat ggggtgctag     660
ctctgagaac acccaaacct ggggcctctg gcaccacccc agccaggata tggggctgag     720
aattgaacta gaaagctctt cccagcagca caccaggagt tcgacctgca gggtgtcggc     780
cctgtggagc tgtccgggca cactttgaac cctggttctg ctgttaacta gctgtgtggc     840
cccgctcatt tgttttcact ggtaaatggg agtaaattaa taacccaccc acagaactgt     900
tattagggac agttgaaaaa atgcatctaa agcagaatag acaaaaatgg atgcaatttt     960
tagtgctagg cctttaagaa gtggccctgt cctagaagca cattaatctc gggctgaaaa    1020
tgatatttta actgaaaatt atgtaatctt catgaatttt ttaaaaaaga ctataaagct    1080
cctcacaatg acttttccag cattgtgctt tgtgggattg gggaggaaac ccaactccag    1140
cctcttcgat tttcatgtgg ctttgatgaa cccatgtgct tttgcttggc tttagtgtgt    1200
gctcctgagg gcctgcttag cgccaggtgg cagtgagccc tgggctgaag cagctcacga    1260
caccctcctc ccctgagcag ctgcccagac agctgtccaa gatggcccca cgagactcaa    1320
ctttgccaaa agagcaagtc aggtagctca gcatactcaa taaaacctga ggggctaatc    1380
ccattctaca gcagtttccc tggtgactca cagtcccccg accttgccta tgcaatgagc    1440
acgtaggagc caagcgtagg agctggaaac acttttttcct gcttccatgc aaacccggag    1500
gtggctgcca tcatcgtgtt gtgagcgtat tccccaaaat agtaaccaca ctattctaca    1560
```

-continued

```
atatcccata tggcgtggtg catgcctgct gagacacgtt ttacagcacc tgtcagggag        1620
gggagtgggt gggcaacagt tagaaagcca ggtcagggag agggattcct gagaactgca        1680
gacccatgag gatggagggg aagcagaaac taggtttaac cccaaggtca tcatttgaag        1740
accacagtta atggcagcca aggctcagga atagggaaga tgcagtaatc aagacaggct        1800
ctctggcagc cttgcacctt ggggtatagg tgaggaggct ggcaagggca agggcaggga        1860
cacatttcca ttacagaaac aaaattgctg gttggagctt tcaagggcac cagaacaagg        1920
tgcacaggga cccaggagct gagggtggga cccagtggga gttgcacaca gccctgaagg        1980
atttgtgccc ccaggggctg agatggggac ctcccaggag catcgtctga gccccatttg        2040
tgcagcatgg ggagcaagtg gagccagaga ccagggtgag acagcctcct ccaatgcctc        2100
gaggctggga tgtgcctccc tgcacctgat gccatttggg acagagaaat gagccggctg        2160
ctcggaagac actctgatag tagagtgtct gcagtctgtg ccttaaagag cctggtaaaa        2220
cctaaaggag aggttcaaac tgagcacaga aactggggag cttcatggta aatttgattt        2280
cctatcaaga caagattagt cagaaaataa aatcctgtgg gagttccagg ttcctttggt        2340
ctgttctctg gggaacccca tttatgaacg ggaacttccc aggatgcaat ttgaatcagc        2400
cctggctact gaggtctctg gctcctggga acaaacagct tttgccaaac aagcactgcc        2460
aggaatcgtg agttcataaa tgaatcctta ggagcaccat taattgccca atgagcgatt        2520
tcaggcaaag aggtctctga tgtctcctag atggcaagtg agtgttggaa cttgcccca        2580 agatttggag ctctcgtgca gctagtcaag gggatgatgg tggtgaattt ccagcgacac        2640
tgccaaggag tgtttgcatc cacccctgac tccattgctt ttgttgcaga gctttgttct        2700
ggcctgcaga ggcacagtgg gtcttcttgc ttggggaggg acactgctac tgtcacatga        2760
gaacacgtcc aggccaaata catatgaggt acagccaact gcgtgctgaa aggtaggaga        2820
gcaatgcctt gggtgcagca agacacatca gcccagcgtt tataaatggt tttttggaaa        2880
catttataaa gtcaccacac cctttcatg taaaactgta atttgtgtat tatttaacca        2940
ttatttaaga atgtctgctc atggtgaaat gtttgtcttt ccaatattta attaaatttc        3000
atttcatggt ttaaagattc ctttgctttg acttgtcttt atgcaaaaac gatcagcctc        3060 attttgtgt tctaactgag tggaactatg caaatgtttt gattaaatga taaactattt        3120
tgccagaagc agctatttcc acaggaggct atgctactga attatccaag caaaatggaa        3180
tgatgccagt cgctggcaga tgtagggaaa ctgatagaag cttctaaatg tgtctattat        3240
caagcaatca aaataaattt aaaacaaaaa caaacaaaaa aactcaaaac cttaagataa        3300
agttggtaga catggtcaca cgtagtggtg ggccagtttg cttggtatct tccacctaaa        3360 cttttttggca ctcaatttac acattctgaa actttccaag tttgttcctt ttcatttgga        3420
attcccttcc tatagaaaca gtgttaaagt tggttgtgtc tcaggccagc ccatgagaaa        3480
cttttcaata catagtatat taaaacacgc atctgcaatg aaaagtgtgg aaaacaaaac        3540
gcaacaatat caatcattca aataggaaaa cagtaaaaaa aatttaaaaa attatcttat        3600
ttctgaggtt ggttctgtga aaatc                                              3625
```

<210> SEQ ID NO 87
<211> LENGTH: 2068
<212> TYPE: DNA
<213> ORGANISM: Homo sapiens

<400> SEQUENCE: 87

```
agtggctata ggcacggagg gatcagggag catttcaaat gctgtcacat cagcagcacg          60
```

-continued

```
cttcccacac aaaccccagg ctcctgcaga ctggccaggg caccagatgc taccagttca      120
ctggaaagta cactgacctt ggagtcgggt tggagtctcc cctctgccat tgcccatctt      180
gagacaggta gttaataaat atatagaatt ccagagtcca ccctgtatcc ccagagcagg      240
tgtatgtccc cccggagcag atggaaaccg tttgtatgct gagagagtct gcagatttaa      300
gatgacagtt gctcttagcc tgcacctgag tatattccag ctctgcaatt cggagttggg      360
cattgaaaag ctaggcctgc ccttgctgag gaaggggaaa gccatatcca acattgctgc      420
cactgtatac cgagccctgt gccccagcaa actcttccag tgtacttcct aactcagtgt      480
gacctcaggc aagtcgcttg ccctctctga gcctccatct cctcatttcc acccgttgca      540
attccccaaa ccacactgcc ttccattatt atgaagcttt gttattaaga catgagcgag      600
agagaaacat tcctagttgc tgaggaagac attagtaaaa ataaaccagg aagcagaaaa      660
attcaaaatc cccccacgaa aacctgcacc tgctttgtag ggaaggaatt ggctacagga      720
aaagaagggt gaaaaagcca acaacccact tagcaactac cactaaagat caatactgga      780
ccaaaataga atcccatgta ggaagcgatc ttgcttcaca gccccagaaa gaaaaaaaaa      840
aagttaacat agagaagcca tttaaagcag aaaaaatatt tgtatgtaaa aggaaatatt      900
ttaggtagga gttgaatacc aaatgatttt gggtctctgt ggggagtaat gaggcgcaaa      960
cacacaattc tatatgcatg taatattatc cacgctcgga aagcttttaa atcacagaaa      1020
tgcagttagg gaccattgta caaaataaac atcccacttg gtgtcttgct tgccctaagt      1080
tccttgatct agagcggcac tgccagattt ttacagcccc gtaaattaac gtggtgctga      1140
tttgattgag ctaaattaat aagacttgtg ctttgttgca aaataactat tacagtatgt      1200
tgtggggacg cactgccgat aaggaaattg gtgcctttaa caatcccact gaagtttcat      1260
ggaggatttc aaaaccaatt ttaattaaaa caaaagccaa tgtgtggcaa taatgtgggt      1320
gttaaggaga gaaatgcaa aatgtctttt taaatccatt ttaatatgtc ttaaggactg      1380
gatgatcgat gtggtgagag ccagcggctg acactgagct gggaggctgc ctgtgcgcct      1440
ctctccagtg acaatggcac caggctcacc cggtgggcct ctgcgctggc tctcgatttc      1500
cagacctggg gtcatctccc aggttgaagc tccggggaag gaccccttt ctcagtccag       1560 gggactgtgg cacttcgtcc tccacacagg ctggagcaga ggtagacaga gcctcagcct      1620
ccaggcggct ccagcctcaa agcaggttct ccccagctcc cttaaggcac ctctgggaag      1680
cctggggatg gggattgaat aagaaacatc tggagtgcac tagcaagagg aaggtggtgc      1740
cctgaggcag agcagtgagg atggaaaacc tgcagaccag gcagaggcct agacctgcag      1800
tgaggagggc cccgaggctc gaagctggag ccgctggggg cctggggcca gagaagtccc      1860
cagagccggg gcaggagtgt gagactcact ctaagtctca acctccctca cctcggtttc      1920
ctcagctgta aaatggaaac agtgatagaa tttacatcac atagctgctg tgaggattaa      1980
atgaggttgg tacctgacac acaaatgcct aagatagtta ttgatataaa aagaaccata      2040
atatgacctt cttttttacct gtcatgtt                                       2068
```

<210> SEQ ID NO 88
<211> LENGTH: 1279
<212> TYPE: DNA
<213> ORGANISM: Homo sapiens

<400> SEQUENCE: 88

```
atgcctactg ataaggcccc gtgccactct ctgtatctgg ggctggacct ctctggagcc       60
```

-continued

```
aagagacatt ggtgagctca cggtgctgcc ctggtttgga cagagagaag tgtcagtgct        120
ccacgggagg gctttgccgc tggggtttct cagaggccag cggtttgacc acggcagctt        180
ccaggaactg ggatggcctg tctggggcag gagcagggag aatggagccg acaggcagga        240
gcaactagaa tcccttgaaa gaattcaagt tcctttaatg tagactgttc ctaatacaca        300
acggggtgat cagagccagt gaaacagtaa gcagaggaac tcgaagttcc gcccagtgct        360
gagattctat ggtttgcagg atattacagc tgtaatattt taaatacttt aaaatcatga        420
atacgtatca gttttaattg atccaggcct aatcttagct agaaggaaga aggcccggcc        480
actatctgag ctctgttatt tgacaggctt gcctgtcctc ttggcactgc ttctttcttt        540
cattgtttaa tttattgctg ccacaagatc cttaaagcaa ctcattgagt gtccaggatt        600
aaattagctc ttggatgggt aactatatcg gcctttaggg tgaccaacat cctggtttgc        660
atgggctgag ggatttcttg agtgtggagc ttctaggggt aaaactggga aacctaaata        720
aatcagtcaa cccaaccact tcagcaattg ggcaactggg tttttttccat tcaaatgcct        780 aaaatttttg agactgcacc tctggtgtac ttactaagaa actgttgtgc ctaacgtctc        840
cagatcttgg ttgttgatgc aacaagcaca caacccctgt cacagacatg ccattttaag        900
gccctggtgt tgcatccaag aaccactcag agccttacat aaacatatct tctaatgtcc        960
ccaaagcact ttaatgatga gtgtgcctct tgccagcaag cacattacat gctggctgtg       1020
gagtattctt aggattctca ctgctggctg ccacacgacc ctgcttagtg cttgggagcc       1080
acagctgtgt atctctgaac ccttctttct caaatgctag tgctctgtga cttccagttt       1140
tctggcaaat tcaccgttgc ccggcatgag ccctccaagt gcccttcttg tggttagctc       1200
caaagctgaa tgtctgtgtg caagcccctt aatagaatct agacaagatc aggcctcccc       1260
tctgccaaac ccctttctg                                                    1279
```

```
<210> SEQ ID NO 89
<211> LENGTH: 3490
<212> TYPE: DNA
<213> ORGANISM: Homo sapiens

<400> SEQUENCE: 89
aaggttttac tttatcacat taccaccaaa acatctatca aactatagtt acttagaaat         60
agatatattt taagaaccca cacaacacac ccaaggacat cagaaagagc gttccccata        120
tattatctct gggctatgcc ttcccatgca gcgaaaatgc cactcaaatt aggctgttca        180
gaaaacagaa gtgtaagagt ttaaattccc ttcttctttt acagaccaac tgtaaaacaa        240
acaacctgta gtatcaacaa taaaaaagta attgcttgag cttctcattc tagaaagaca        300
gagaaagagg gaaggaagga aagaaaagga aggaggagg gaagaaggaa ggaaggaagg        360
aaagaaagaa aaaagaaact ctcaatggct ccccactgcc cacagaaaaa ggccacgctc        420
tttggcatag cacatgttcc tccataatct tgagaaccct cattcctaga attgccttct        480
cctttatctg tcctctgacc tcttatccct taggattctg ttcaaatatt atctcttttc        540
taataattta tcatgctgca tatgtgtctc atgatgcatt taatgatttg tttgcctgtc        600
cctgccaata tgttgtgatc ttaacaacca agagcttggt gtttgctaat acctctatct        660
agcattggat attgaaagga cagtttaagc accactttc tgtaaaatgg gaaaaaatac        720
tacccgtcag cattttcatg agattaatat tatacgcaga agggcctagc atactgccta        780
gaatgtgtac ctatccatta gcatcataat accaacaata tttaagtgaa tgcttaaatc        840
ttgctttata aaattatagt cacagttatg caaaatatac ttcattagat ttgggcaaag        900
```

-continued

```
ctggcaaggt aaaaggcagt ttggaggctg agctgcgggt gacttctgga atgctcattg      960
ctgactcact tagccgtcta tggctcagct tccaagactc gccagtgagt attaaacacc     1020
agccagccca caaggtaatc agtccaggag agcagctgat aacattcctg gagttctatc     1080
aaaacactga aggcttacta tgaggcaatg acagtggtgg atacaaaata aatcaggtgt     1140
tttcctggct ctcagctcaa gcttcatgcg ggcagcagag acatatacaa gggacaacaa     1200
gacaagctgg aattggcaga tgttatagta gagatacaag caaatacatt gatggtgcaa     1260
aagagagatg aattttattt gagggaatgg gaagcaggaa cgcaggttta ttctgtaccc     1320
atgctgggcc gggggtagct catttggtct tctaatatgg tgagatagag aatgttagat     1380 gagcaccta aggcccagag aggtgagata acttagctaa atcacactga tagtacactg      1440
gcctttctgg ttttgactgc accagctaat ccccaaggga gctgaaatgg ccacatggaa     1500
gcagagcgcc aagtagggag aattgagtgc cccagataga agggtgtaga caaaaccata     1560
gaaagcaagg gaactgtata tttaaacgtt tcaatacaca tacacattgt gaaatgatca     1620
ccgcaatcaa gctaacatat tcacctcaca tgctttttat ttttattttt tgtggtgaga     1680
acctactctc tcagaatcca gtctttacct atagtcactg tattgtatct tagatctcca     1740
ttacttattc atctgcttag ctgaaacttt gtgccctttg accaacaccc atggcaacca     1800
ccattctact ctgctgattc tacctacaag tgagatcata cggtatttgt ctttgtgtct     1860
ggcctaagtc acctcacata ctgtcctcaa ggcacaccaa tgttattaca atataatgcc     1920
cttctttgac caacttaagg tatttcgtat ctatgatgcc catttcctgc cgacatttgc     1980
cccagtttat ggatcggatc actgagacaa gcacttgttt cagtaacttg tgcaaagtca     2040
tgacacaaga cagagcagac ccttaaacac ctggtgctaa caatctactg tgctctagac     2100
aaagtgaaga agatgtggac cctgagcctc agtttcctca tctgcaagat ggacataata     2160
ccttgtctca aagagatttt gcaacttcac aagaccgcac ggcgggggta tctactgata     2220
gggagataag caaatatttc ctgtaaccct ggaaatgtca ttagggccct tagcaaaaga     2280
gttctaatgt tcagagagac tatctggaag agagaaatct acaactgaaa gagatgggca     2340
ctcaagagga aaccaccacc tttgcacatc tgagccacta acaatgactt gttgctgaat     2400
atgcttctta gctcctacta gtaaagtctt gtcaaacagg aaacaggttt ttaaggcaac     2460
ggggtccctg tgagttcaaa cttctgcttt caaatgttct tacaagatgc acaattggca     2520
ctgacttaca ggaaatattt aattggaatc ggaaggcgct ggctccacgg gcctggtttt     2580
atattgtcta caggcttctg ctgaaatgat tttggtgtgt aagcaccagt ccgtcactta     2640
tttattttgc caggggggag taaaaccaaa acatagccca aggggtttct ggggcacaag     2700
tgcaatctgc acagggttag gaaaagagtg ggggagaaaa catgcaaaaa ttcctcttaa     2760
aaaggaaagg gctgggactt ttatgagctc agtatcagtt gcttgagctg ataagcactg     2820
gtcattaaag gaaggaaaag tcacctttgt gtatataaaa tatacaagat tcgtagtctg     2880
aaaagactga acaggaaagc attgggtaaa tagcggatat cccttaaagt ataatgtgaa     2940
aatcaaataa cttcaagaag gttttaacaa caatatgaca gtctagcgca ccttggtagg     3000
agggtggggt gcggacagaa gaagagcatt tcctggaaat cctataatga tttcattttc     3060
taatccccaa atgaccttgg tccatgggga ggccctccct ccctcacccc aggccttggt     3120
tttttgagtc ttcatctgtg tgtcatcatg gcccttagat taggcctccc agggtagaca     3180
acaatcctcc tgtctctcag agaccactaa ctcttcctta tcccttattt ctacttcctc     3240
```

-continued

```
tcggaacctg cagattccgg tctgataagc atatctgcat tagaagccag atttgcatat      3300
ctcaggactc acccttggaa tattcaacta actggcctgt ccccattcgg tcacaattgt      3360
aggttcctgc aaaatgatgg tttatgacaa gtgttcttcc ctcaggctag gttagaaaag      3420
attttctcca gtagaaaaca gacagaaaaa taccttattt ttgtagaatt tctaccatgc      3480
aggataaact                                                            3490
```

```
<210> SEQ ID NO 90
<211> LENGTH: 674
<212> TYPE: DNA
<213> ORGANISM: Homo sapiens

<400> SEQUENCE: 90
tggacaagag acgcttctgc cttaggtggt gagagaggag cgctggcggg gtggaggagg       60
cctctaatag agagcgggaa gagttatgtt gctttcccag ttagaatcac aggataataa      120
agccagcaga ctccaagccc ttagcacaga gcgtccttaa tgaacagtcc cctcattctg      180
ggggagcaca gccctgagca cagcctcaga cgtcaacatc ccgaaagagt gagagtccca      240
gtgccgtgag tcagtgtctc actgagcttt ccccacatgt tcctccttaa aatgaatcaa      300
gaaaaagaaa gagacaaacc agagaacagc ctgatgtctt tggccagatc tcagcatact      360
ctggacagca aagcaagagg agtctcaggt tcatcgtgga aaacgtgtgg tttctggctt      420
ctggaattta aatgattgtg tatcttcttg tcttatcaat tatccccttt acgtaaaacc      480
atctcagact atgtgactga acgctaaacc atataatctc taattcagta ttcctctttg      540
tagacccaga agaagatacg agacaatgtg gaaatgcaag aacaagaagg attcttaact      600
tttacttgtt tctaaattgt tagttgtatt gaaactagtc agttgaatgt gtcccattca      660
cactcttacc tcac                                                       674
```

```
<210> SEQ ID NO 91
<211> LENGTH: 4676
<212> TYPE: DNA
<213> ORGANISM: Homo sapiens

<400> SEQUENCE: 91
aaaatttatg ttagcatgaa cactgactcc ttggaaatta taccaatgct caacaagcaa       60
atttttagaa agaaaaatag aggaggacaa agaaggaaga aggcaagctg caactataaa      120
tttctaaaga gcagcttgtt aaataaatgg tttctctttg gaaggcagat gtttatcagt      180
aaatgctcct ctgaagtgca gcttgttaat ctgcagggag atgtctgggc acttttgttc      240
caaaggtcgg gatgagataa aggggaaag cttgacagct gctctgggat ctgtattcat      300
gaagcaaccc ggaatcaggt ttatgctcac agctaatcac agactttcct tctaacatac      360
agaatggtgt gcccacattt gtgagtacac aaacgtgcgt gcacgcacgc gcacacacac      420 acacaccta cctgattctg gcatagcaat aaggagatta atattcagaa agagttctgt      480
accagaactt tgtaccagtg tttccaacag tggtgtacag cacactggtt tgaaaccagg      540
cttgaagtct aaaacaagag agctacctac tgtttaaaat cttgggaaag acttttaaag      600
aatgttattc tccatgaggg cggggaattt tactttctta gcattgtatg tcagccctgg      660
cacaggatct agcccaatac atatttgatg aatgaacaga taaatgaatg aatgcacaaa      720
tgccatatta cagcaaatat ttcacctctt ggggatctta gaggaaattt gtccagccag      780
catttcctct ctctaatatc ataccactat ttgagctcat tggaagagaa gcttaaaagg      840
cagacataaa tgtttattcc tctatcgctc agccttgata accaaatacc aatcaactct      900
```

-continued

```
acaaaaaagc acacccatcc ctctggatgg aatgggacat ccatttccct acagaaggca      960
tgttttatcc ctaatgttgg taggaaaatg gttgggtaaa gtcctttccc tctccccatt     1020
ttgggggcag tcatgtcctc attactgttt cctctctctc ccaaatatat ccacaaatgt     1080
ttgctactta tattacaaaa cctttagaaa attctctctt cccaccttcc agagttctca     1140
actttcccgt cttcaacccct aagtaaaatt tcaaaggtgg catccaaagc caaaccgcac    1200
ttttcacttg acaaaaccca ataattactc tttcttaagt cagatgctcc tgctaatctg     1260
atacaaacca tccaaaatta gcgccttcct tccccttcaa tgccaatggt attaaatgac     1320
tcaactctgc ctcacaccag ccccttgtca ggacacactc tcttgttctg tagcatcttt     1380
tccattcacc atgataaacc atcttcttca cttcagcacc cctctctata gcttaaataa     1440
agtcaggctt ggctctttcg acacagggtt atagcagcag cagatgctct gctatctggc     1500
atagttggga aaaatgttgc ttaatctata ttccagttaa aggacagggg tcacatttat      1560
caaacttggg tggtcaacct tcaaatacag tgattcacat ggtaaagtgt acttagtact     1620
gaagtgacac tgaattttga tgagtctttg atgattcaga aggtactgca ggaatattgc     1680
aacacttatg agtcatcatt attatcagcg atcactggat tgtaggtttt gaaaggccgc     1740
tgatggatgg accagatttg cttctgtgca ctgggacaca gcacatcctg aacttgcctg     1800
gaaaatctgg agggcactag ctggcatctt ggcgtctgtt caacaaatat ttaagttcct     1860
actatgtgcc tggcagaatt gctagatttt tggttctgac atatctactg catatgatga     1920
tcttccttga gtgccttagc aaatagaatg ggtaccatgc ctccctgtct cttttaggaa     1980
aaggtttgtt ctatttttcc cagtgttaat tttaacaaat ggagaaattt cacagggtct     2040
ttctcttgat tttatctgat ctgttgggaa tatggagtgt aaagcataac taggtttctg     2100
aattattttc agttgacaat tttctaactg caaaagagaa caaactcatt tctatgccaa     2160
acaggactaa aaaacattca tggatgtgtc cacttccttg taactcacca atttattttg     2220 gttgggggggg gggcggtaag tccactgatt gatatttgat ccctaacttt attcaagaca    2280
agatttaatt tgaaggccca gtggagagaa atggtcctgc agaccaggaa gcagtcctgg     2340
ctctgctggg gaccgctgtc tgtacttcag cattcccaat ggttttaaac tggatgttag     2400
tacttgccca tagcaatggg aaatatctga tggtgactgg aaggctttat atgagccatt     2460
gtctgaaaag agctgcatta atctatcata tcaggtattt ttaattaatg gtatttggca     2520
ctatatacca actcgatttt atatatttta ttgaaaatat gcacaaaata aataaaacaa     2580
tgtcacatga ttaaaggtaa gcattgaaat tctttcagat aacctggagt ttctctttgc     2640
cgagtttctc tctgggtgaa gaaacaagat tgtgagagtt cagagttcct tcctcacctg     2700
ctgcaagttc acactcagca ggtcgccaga ctataataat acttaaaagc aagggatgag     2760
gcaaaaggca tctttgaaaa ttacatttga agaatgcagt gtaaatggaa ttagatattc     2820
cagtctagtc acatcgaatc tttccaaaac tcatcatttc tcccatctct tagcaaatgg     2880
tccagccatc cctcattccc caaactggta tctgggcact gctagcagca aggatgcacc     2940
actcttgccc ctcacctttc tagctgctgt ttaccctaag atgttccttt ccttaaaaac     3000
tgtatttgac atatacaaac attacctaca aaatcaccat accagatttt aggttatcat     3060
tccactttgc ctttattttt tataatatat taagtaaaca tatttaatat gtaaaaaact    3120
gttgcatata gtaaacactt gtaagcctac caggaggaac cagaacagct acttggcatc     3180
tacctatgtg ctcctgtccc ttccacttcc tccttctgtg ggtaattact atgctcaatt     3240
```

-continued

```
ttggtttatc agttaccttc tttttttttta gtatacgtat gcttagacta catattcttt      3300
ggttttgctt gttttttgggc tcaataaaaa tagtacgccc catgtggtct cttcaaactt      3360 gctttttttcc tattttctga gattcattct tattgtgagg tatagctgta gttcactcat      3420
ttccactact gaataaatatc ccgtagaact attttcctgt agacagaatt tcactttttc      3480
cagttattaa cttaaatatg taactatgaa caacatgcaa gagtttgctg gacatactgg      3540
gagttctgca aatgttcaag tctgtaaggg ataattgttt tttagcagtg gtatgttgta      3600
caagtcccta cagatctaac actgtagacc caacctttgc aaatcttatg gatataaaat      3660
ggaatctcac cctgaccaat gctacagaac atctatttat ttaaaaggta gtcttcacta      3720
tttttctatt tttttaaata ggaattctct atatttgtga ttatgaatcc ttcatcagtt      3780
atttgtatta taaatgtctt ctcatgtgga tcactcactt gcttaatata agccttgagt      3840
tttaacagaa ttgacttaac catcttgtcc tttatgatta ctactttatg tctcaagaga      3900 ttcttttcctg ccctaaggct tttttcatcc aaacactgac aatttttgct ttttgtatta      3960
agaaatgagt gactttatgc tgcccacttg tccaactccg cacgggatat cagagcccag      4020
ctgagaacct gctcaatcct ggaaacaata gatgttaaca cccttaacag taactttctc      4080
tcctcatttc ctttttgggg tacgaaaata tgaaattatg ggagacgaaa atgcccagaa      4140
agcatggctg cttgaccaca ctggggcaaa tggcttcagt gtttctgaca agcaagcagt      4200
gagcttttgc caaagagttc tgcagccatt tagtccagcc ttgaaaacga ggtcttccga      4260
agagaacaga gctacacctt ccccgtcaga atccactgtt ataaccactt agattaaaat      4320
gccccatttc tcacagtatc attttgtcac agggtcacac ttctctattc aactcagttt      4380 caggctttttc ttctaagagg aaaaaaagac gactaagtgg cctcctagat tccactgtaa      4440
aaacagaaaa aagcaggttg acttgctttg aaatcaaacg atgtcttcag tctgtcccca      4500
tctcgaggga ccagggaaac cacgaacccct gctcactgct cttcacgcaa ggtcccaaaa      4560
aaagcgcctg ttttccaggc actgcaggcc tgctcctcta caaggtccac taaatagtct      4620
tcgaaaacca gaagcaggta agtgtcagcc agatgcactg ttgttgttat ttttaa         4676
```

```
<210> SEQ ID NO 92
<211> LENGTH: 11241
<212> TYPE: DNA
<213> ORGANISM: Homo sapiens

<400> SEQUENCE: 92
```

```
ttagattgtg accatggaaa tgattgttag aactttaaag gtcatttcct ctttgcagaa       60
agaatggctg ggattagacc tttatgttct cttttttggtg acccagtccc tgagccacat      120
gggatttgga acatttgaag agaatactca atgaacacag aagcagtttc ctaatgctga      180
gaccactgaa gagcattgtg tctcagtgct aagaaaaaaa aattaatcaa agtggacaca      240
gttttctaga tagctatgtg atctttgaca agttacatta tttctctgaa cctattttct      300
catcataaga ctggcaaaat gtctcaagac atcatctgct cactaaagtg tatgcatcct      360
tcttcctggg tacgccactt tcgggaagtg gtatttcctt ccacagttta tccagtcctt      420
tctacaggat gatgcacata gtgacctgac agttcccatc ggtatcccac catatctctt      480
ccttgcaaaa gggcagctac actttctgct gtccaactta ctcaccaata aagactgcca      540
gatgtagaaa aaaagaaccg aggaaaatgg gcagaaaga aacctcttga cgtttgtttg       600
aaattaaccc attgggtgac cacagtaatg aactacttct cccactttca ctggattggc      660
agctttgatc cggaaatccc aggtgcctga gtgaggacag agctatgaaa attcaagcgg      720
```

-continued

```
gatgacattt tccaaggaga gttggattag tgcaggggaa aatgctgcca agctgaaaac    780
cttttagtat ggggaacgag aaactgcata agcaacatca tacctgcaac atgagtttat    840
tcacagtgaa gagctgtgac ctttgtgtga aggaaacttg ggctccgcag ccgacgtttt    900
tctaatgcta atgttcccct tcccagctgc aaaactcatc tgcactcttc tcatgctttt    960
cttctccttc ctgctctggt tattttttccg ggcacacttc ttacactgtc agaacttaat   1020
attattttac aaccctgagc caaaccttgg gagcttgaag aatagctgag aggcagacac   1080
aagcatgaac tgaccccctt tacacacacg tggctcttaa gataggggaa cccaggactc   1140
tgctggtgtt gtgggaaatg gtttgtcctt atctgaactc agtttgtgtt gggggggctt   1200
cttaaattct gaggatgaga aagtgggttc agaaagtttt actgctctag tgtcacagac   1260
ttagcaatga taaagtcagg atttgtatct agatttactt acaccatgat ggcaataatg   1320
gccatttact gagcatcgaa catactctaa ggacttcatg tctatttctc tcattattct   1380
ttgtaattct atcatcatac caattttaag gttaaaaacc ttagtgaggt tttattactt   1440
gttcatgtct actgggatga gactttatga taaagaaaaa gcgcaaagca aatgagagct   1500
aaatgttcct cttgcccatg ccacaggtgt tccaatagca catcttcaat tactagtttg   1560
atcttaagaa tttcataata agaacctaat aattaggatg caattgaggt gcaattctaa   1620
gcactttcag atcatcagca atccttctgc caacaaaga ttgtggtgtg gggctaacga   1680
cactttacag ttatcaaagg atcacaccca agacagacgg atttttctaa ttgtaattgt   1740
ccctcttgtc acacctcact cagcttcaag gagtgaatgc atgaaagctg ctgagaaggt   1800
gaataattat tccaggggac atgtatgcat ttcatacgtt tgagttcagc tcacagagag   1860
tgaatcaccg aatactggac cataggcatt gtgtctatgt ttccaaaaat atcacaatta   1920
tttatggtat attattgttc ccctcttttc tgataagaaa acctttcctc tagtgtattt   1980
ttatcttctc tcaggattgt ccacagaact tggactgcag attcgttagc agggactggg   2040
gctgctttaa gtcacataaa attctgtcaa ttgtctgctc attacgtctt ctataacata   2100
ttgtagtctt ttggtttttca aatatactac catgctattt ttcagcaggc aagcctgggc   2160
agatattttc tccattggtc tacagataat gctattttcc attttctgcc ttggaaaaaa   2220
ccaacatttt tacaaatgtc tattgttttc ccgattcaaa gagctatcag catttatttg   2280
atataacttc caaaagagat catttttagga gtacttacta catatgagaa ttgtcttcac   2340
acaccctgat ttccatgagc atgagaccag agaggtactt ttcccctaca gtggttacag   2400
gaggttgtac catatgaaaa tgttttaaac catctaatgt caacaatttc gtacggttcg   2460
atctaatacc acatgtggaa catagcaagt aaataaatat ttgttgattg gatggtatgc   2520
atttagccaa ctaaaactta aaggaggtga aactatttac ccagcagaga aaatcactct   2580
cttcatatcg gcagcaagtg ggctcttgtc tttgagacaa aaacaaatct ttttgctgct   2640
tcaattcatt cacttgttca ttcattgacc tttcagtaat tatttagcat cttatgtgac   2700
ggcaccatgc cagctgagaa aatgcaagcc cactgtcaaa tgttgcaaac acctagaggt   2760
gccacttcct ggtgataaga ctgaggaggc aggagccagg ccaggaaact cttttaagga   2820
gtttgtattt tatcttgagg gaaatgggga ggcgtaaaag gtattaaaca aggcagtgac   2880
ctattcagct ttatgtatta gtacagatca tctgaaaaat gatttgagga tgttttttcaa   2940 ctaaaaagtg aactaatggg agttttttgct tatggaatca aatttgtagt tttggtatct   3000
ttccatcttt attatattgg tcttttcatt atgtcaatta tatctctaat cattttggag   3060
```

-continued

```
tggctttatg ttcctaagga tggattgtcc tgggtggagg agtgagttca gatcacctat    3120
aattgctgaa aatagaaatt ccctttacca ggacttcagc aatagacaga catgagcaca    3180
ggacctagga agatgtatct tgagttgctt acaatttgca ctgaaaataa aaaaatcttc    3240
ccttccctcc aacaagagcc tgaacaatgc tctagaagag ctattttcca gcacacactc    3300
atgtctcttc tccaacactc aaagatttaa aagagtcgct gaaaagcttt taaactgaaa    3360
gacagaaaat aatactttca ttgcattatt ttaagcattt attttttct tgttgtatca    3420 tttaattttt gtctttgttt tttatgaaat atttacatct gtctcattat aaaagtgaat    3480
taagttagca tatttagtaa atacctacta ggtagacaga ataatgcaga catgttagga    3540
tggcctggag tagagaagtt ggaagggaag tatgtatttt gctgacttga atgagttaca    3600
ataaaatcag tgagtaagca ggaaaacaat tccttcacta agaattggca ggtcaaccat    3660
tacttccaga taagtacaca gtcttgtgaa gatttgttca acaagtaatt actgatcatt    3720
tgccatgtgc aaggtattgt gccatgtgct gggggttag aaaagaatca gaaatgaata    3780
tactcaagga acaatgccat ttctatgaag actataaact gtgaaatgat ctttatcagt    3840
caagaataaa caaaacaaaa cattgactac aatcacatcg ctccagcagc gtcatcattt    3900
caacatctat ttggcttctt tgcttctgta actgtgtggc tacaatttat ggttgtaaat    3960
atggatgaaa aatttaaaat gttccttctg gaaatgtctg gtccaaggac ttaggatcca    4020
acctgagttc tttgcatggg agatttgggg gaatttgcaa tcgtgactca aggaaagggc    4080
tcaatttttt tcctgaaatc aaacttctct tacaagatgc atttgagtac attaaaggta    4140
aatagcacgg aaacatatgg tttgaatttc ccatgaaatg tgaaagtttt gataagcaca    4200
tacttcagaa agataaatttg gcctctgtaa aaccagaaca tttaagaaat ccttctagag    4260
actttgccaa aacccagtgg actgtttttg cctacagctt ccacttcagc cagacccta    4320 gtgacccggc caagtgaaac agagaactca gcatcttctg aggggatgtc tgccaatctc    4380
aaccctggta tatgttcaag ggcttccagc tcatcctgtg agccaagaga acaatttgaa    4440
aacgctggac tcttagcata tctgcttcgg gttactttga gagacagtgt gtgtgagaac    4500
aggatccatg ctggaaacta tttgcaaaag ccccacttcc ttctgccagg ccagcttctc    4560
cgcaacccag acagtccgag aacaaaaaaa caaggactat tgtcaaatta atagcactcc    4620
ctaaaaaagt atggcaggtg gtgagattct tggccattga gttccagcca aaacatttca    4680
catttttttc tcctgaggga ggcactggag cttgctgtga gtcagaagtg gggggctgca    4740
gcagagaggg ccgcttgagc atcttgcctg ttcctgatga gaattagtca attcttggaa    4800
agagggaaga gctcgccttg ctctgctacc cacttccaga ttctctgctc agccttgggt    4860
tggagagtga gtaatctaat gtgattctgt ttattccact caatacatat acattactga    4920 gttttttattc agcatcaggc cttggctctg tctctagctt attttctcac atggctatta    4980
cccacagcaa ctttagaaat aacagcccag tacaaagagc caaacttatc ctttcgggag    5040
acaaagacga tatttaaaga taaccacaaa gtatggagtt agcacagagg acagtggaat    5100
cagaagactt tgaagagatg gattctaagt aggttttgat agaagaatga agttttgaaa    5160
acacagggat gacccttcca ggcaaagaga aacatgtgca aggacatgtt gttttcccga    5220
atgaagctct ctcccatttg taggaaagtg gatgggagga cagcagagga tgccgagaaa    5280
ggctagaaca tctcaagctt gttccactgt tttcagctgt aggtaaatat taaaatatgg    5340
aaaacatctt tctcctagtt caagtacctg gtgtttaacc caatgtacct tcttcatgca    5400
ttgtgtgatg tgctctttc tactgcattc aatcaaagcc atcaagccca attttctata    5460
```

-continued

```
aaatgaaggc ctctgaagaa agggaagaat ggctctgctg ttcgggagca ctcacccagg   5520
aggtacctag gtgcctggga ctgtgcaaac aaacttgaga gtatattatg atgggaatgc   5580
tgaggaatga ggcagattgg ggttgagatt ccaatgggtg agctggaaat tgtctgggaa   5640
ggaatgaaat cctgaactaa gcaaaatttg gtgctgtttg ccctatggca caaggtcaga   5700
aagtgcagga gtcagggaga ctggggtctc gttccagctg aacacaactt gctgtgcaat   5760
catggcagat ggctttccct gaaagtgaaa tggattagac catgaaactc aaagaacatt   5820
tcagctccaa tatactataa tctatccatt gtcagcaaat gctcaacatt aagttaaaat   5880
taaaacaaat tatgttcaaa tgtatacatt cgaaagatca gtgaaaaagg gaatattagt   5940
acaatgtgct agacacatgc tatgttctta ataactgtgt aaaagtttct ttcatcccta   6000
ttttgcatat gagtggatga aggctcagaa aagtttccg aagttctctc aactcccaaa    6060
tgagagaggc agggtttggt agcaagtcag tgtgggtgca aagcccctgc tccttttttt   6120
tgcaccatca tcctgaaaca aagtttatta agcactttga gtggacgagc agagtggtct   6180
gccttccaaa gtcaagagga tgctgttaat ggaacaggga aatgccaagg ctgtttccta   6240
atcttggcat agaagtgtgg catcatacag aggctgctct gcacaaagtc ttgtggagtc   6300
cgccactggg gcaaagttac aggggtaacc aggcaaactg gagcccactc actggaaaca   6360
gcttccccac tccccgcct ctttatccag gtcagtgggg ctagctttgc ttcaacatgg     6420
ccaataaaac ctcaccccag aaaccttccc cagtgtaacc ccaattggag aaaagccatg   6480
tgaattgaag cccagtggcc aattcggatt cagtctgagc aaggtcatga aaacactgca   6540
ttgctggctg gttggttgca ggcctcctgt aaccaaataa tcacaaacct tgtggttaac   6600
acagaaattg atttctcaca aatatgaaaa agttactttc acatgtggaa gctagatgtc   6660
taagatcaag gcatcagcag gttgaggttg ttcgaggcct ctgccctttc tccctctctt   6720
cttctaagga caccaattgc attggactag ggtccatctg tgacttcatt taaccttagt   6780
catctccaag gccttaactc caaatacaca ctggggatga agatgccaac atacacattt   6840
tgagagtgca caggtcagga aagaaggtgt tctagtgaaa ttttcattgc aaatatattc   6900
atggaaaaac atgagggcag ttagcaatgg gatttagaaa cacttagaat agtagttgca   6960
aatagatgac cacattgctc atggagaaag tgattctttt caagtgactc attcaaaatg   7020
gctgctgcat agcacatgat gaaatgctgt gacagatgag gcagaagaat gacctcttta   7080
gcgatggtta cttgaactca ggagaaccag gaacactttg tttggtggtg acttcatctt   7140
gaaatctttg gcctagcagc ctacagatgc tgagtgattg ttaaatggac aagtgtattt   7200
gcaggaaatt caattcctgt tttaaaatta cttattcctc cttccaaagg ttttgtcaat   7260
taatgtgaca cttaaaagcc ctttgatgtc ttagactcag gaagctgagt gtgcaccaga   7320
atgcacaatc ttctccagaa acgctggaaa gcatctttca aagcctctgc ccttaacccc   7380
aaccctgggg atctctttct cttttttgtgt aggtgacgga gctgagggct ttcttgctga   7440
ggtcctcagc gttcttccct catcagtcca atcctgctct gaaggggcca gtgcctctca   7500
aggtgcttcc caacatgaag gacacttgtt atcctgtctc tggcgatcct agctcctgcc   7560
cagtctgctc actggaatga ttcgccaagg accatagata gtcacactgg aggatctttg   7620
aaaacactca tttcaacccc ttcattgata aaataagcaa ataagaccct agaggaaggg   7680
actgttttag gagaatcagc aatttagaac ccaggcttcc tgattaccat ccaatgtctt   7740
ttgaatacgc cacatgtgtt tctctgagtt taatttcaag gcactctgtt aaacctcctt   7800
```

-continued

```
gctaagtgtt ctgatttttt caccacgtgc tcatttataa ttattactcc ctcagcattg      7860
tagtaaactg tatctctgtt ccctgaatgc actgtgcatt ttgcaatgaa cctgttcatc      7920
ttgttctttc aggacttatc attcatactc tcttcttctc aagtgttact attctcttct      7980
cctagggcac aaatcaactc aagcattgaa ttgctttatc attccaggta ctaaaagttt      8040
aatttcagaa gtttcaaggc atgggcattt cccacttctg gcagcatctg ctgcatcgtt      8100
cctttcccat cattctttcc ccccttcatc ctttcccgtc tcaacttaga gccacattca      8160
actaaaaatt ttcaagcaga tgccatgtca gatgcttaat atgtgtgagg tcatttcatt      8220
ctgacaataa ttcagggtaa acattattat ccccactttt caagggagaa aactgaggct      8280
caggagggtg acgaactggg accaggtagt gaagaaatag gtggtccaca tgtgaacaaa      8340
ggttctttcc tgctcactgg gctttaggct acattgttac ttaggtttga tgggagttct      8400
acttgatagt aaaatcaggt gaaattatcg ctgtattcca tttctctggc aatagatgtg      8460
gtgacgtgct gtctgccagc attatgcatc gagttacatc tcttcccggt tcccacatcc      8520
tgtggataac tcaagcgcca gccagccgtt aaaatcattt cttccaaatg agggtggtgg      8580
gacctgacat gtggatgttt cctgcttcca aatccaagaa atgaaggtaa ctgactccaa      8640
gctaaaagag aatcatcctc atctgtggca tcacttagca gtgttctagc tgcggctctg      8700
cagtcagcaa ggataagaaa gctgtggggt cagagctgtg gaaggagggg agcttgaatg      8760
ggaggaggta ggagcaccct gcctggagat gcagcccaga ggataatat gtgaatctca       8820 catgactcag cccctgtgca ggtaataaaa tctcaacgag acatgagctt atttaagaaa      8880
acacgcagga agaattcatc attgatgtgg ctattttggg agatgaaagg gagcgtgaaa      8940
cggaggaaca tgtgaaaagc attcaagctg agtgagtgtg atagaaaact aagatttccc      9000
ttcataattg aacagtaaaa atcaagtgtg tccccatctt tcaagtcttc ggattggaag      9060
agtgaggttt gggtgcagat gttggcagtt ctttactccc tggataaaca gattgtggtt      9120
ttgatttgga agggattgct tttttatttt attgttgcta agagaaacca ggtctcaaat      9180
gcaatctctt gggctgggaa tggagattcc ccacgccccc ttgaacgtgc cagcatccct      9240
gtgaaaagag gcactgctgt tagatgctgc tattacctca tagtgagagc agaaatcctt      9300
tttctatcac ttgcaggaga ctctcagtta aacacgatca gctacgaaga tgacgggaca      9360
caggggagag tcttctgcct ttgatgagat gtgccagatg tggatgttcc cagctactct      9420
attctctccg gggttctcac agcagccttg tttatcttcc agacatccat ccagccttat      9480
atcccaagta ggaaaggggt ctccaacctt gattcctttc attgtttttc ctatctctga      9540
ttctgtgtct tcctacttct gacttctgac atcaattgtt cattcagtcc cacatattta      9600
tgaagtccta ggtctctgtt ctcccgtcta agcccctcc cttcactttt tctgatgctc        9660
agcccatgga aacacttgtt caccatttgg attttcttcc tggttaagcc acccagggca      9720
aacatccctc aaaccctact gccctgtgac tctggcatcc gaaatactct cagggttgcc      9780
agaccccttt agaaaaccta cacattcacc ctgcagtcta ccttacgaat gccacagttg      9840
ctctgatatt gtctctcttg gcctagaaaa catcaatgac tttctactgg tccaaaccaa      9900
tcccaaaagt gtctcctgag gatgaatcag tggagattga ttctaataca agattcaaag      9960
cagtgtcttt ctgctctttg taaatattta ttgaatccct ctctgtgtag gaccttaata     10020
gattctgtgg atacagtgat gacaaattag atgtgtgtgc ctcgtgatag ttaccatttg     10080
tcatggaaga catcaaacaa ctaacactgt gaagatagtt tgaagaaagg caaagggtgt     10140
tatataaatg caaaagggggg aatgggtctg gcaaacatag tctgaaaaat cagagaagat    10200
```

-continued

```
tgagacctag agtgtgagga gggattcatt aggccaggtc cagggacaat agtggcaggt   10260
ggcaggaacc atatatgtca agaccatatt gctggaaaca gcagatgtgt tcaggaccca   10320
gaaggaaggt ggaatggctt gaggacatgt gatgctttca agcaatgatt cttgagggac   10380
tttgtataat catctggaac acacactaaa tatctgattc tcatccccaa ttgttgaata   10440
agagtctctg tggatgaaac tctggtagat aggatacaaa aatggttgtg tttttcactc   10500
tctcctaagc ccatgacatg tgtgatgtaa cttcgcagct cttggaggtg gggtctcttt   10560
ctttgatctg ggctggtggc caacagaata aaaagaagta ttgccaacta tgaccaagac   10620
tcaagaagta gtgtgtgctt ctgaccctct ctcagaacct gcccccctcc ccaaaacaag   10680
agcagactag cctggtgcag aatgagagac cacatggagg accagcctat tatccctctg   10740
agaccatcct agatcagcct atagcaagcc agtccctgac aagcaagtcc acccagatca   10800
gcagagccgc ttaccctagg acatcagtaa atccagagac caatggctta aacaataatc   10860
attgcaacaa taataattaa gtcactgagt ggttatttat tctgttacta gagacaacaa   10920
ttagtgagat aggcagagga ggtcagcttg agtaggactt tgtaggcatg atgtgaattt   10980
ggtgttttgt cccaggagtt atgtgaaatt actgaaatgt tttgagcatg aagtggcaca   11040
attaggtttg tgttatagaa aaatgaactt ggctattctg tggagtataa atggtgggag   11100
cagggattta gaatgaatca taggaatcaa cttggtatag tttagttttc ctttaaatat   11160
ctatattggg ctttagcaat gtatgcgatt acaaggagga aggctcatat cctgtcttta   11220
aatctagtga gaacagaaag a                                             11241
```

<210> SEQ ID NO 93
<211> LENGTH: 1397
<212> TYPE: DNA
<213> ORGANISM: Homo sapiens

<400> SEQUENCE: 93

```
cttagtcgca ggtccccact agtgataaag gaagcgatgc tgctgcataa tagagaattt     60
gtctgacttt gcccagggtt tctggcacag accttatatt gttatccatg agacccttag    120
accacacttg agtttatgaa ctcacgatca gctcctagat agcttcagga tgagagctgc    180
tcaccagaaa gaccagctgc atcattcgag ggctgggact ttgaaccagg ctgacctcca    240
gaagaggctg gagagtgaga ctttatatgt caaatgagaa aattggtatg atttatacaa    300
gcattttgcc cagaagagca tgccatgctg agtaatccca agtgaggaca taataaactt    360
ttggaaagtg ttttaggtcc ttctcttaac ctgcctctgt actttttgag tgaagaggtt    420
actacagatt ccatcacact gttgtcttct gacattttgt tggtttcagt aaggtcagga    480
tatttttcat cctggatttc cttgaaggca gagtccaaga atagggttcg tgttcaggta    540
gttttataag tgataatagg aagcaggagt gtaaatctga gctttctaag aagaaaacag    600
actatgcctc agcattgtcc accagaaggt aaaatggaga agcaattcac tattgtctcc    660
agcccccaag ggctattgat tgcccacatt tatttgttac ttgaatgagt gctgagcaga    720
gtgtggagta taaagagggg aagagcagca gacacgtgag ttgaggcact gccagcctga    780
aacaggccaa aacctacata gaattgttca gtaaggacaa gggtacatga gttggtgtac    840
aacaggttgc atatactgtg tatttattcc cttgagtccc tccttgcaag gccaccgcag    900
gtgatttata tcaccctacc taaggctaca gctcctgttg ggtggcccat gaacctcgga    960
tctgagccaa ccaacttctg gctccgacaa gagacccagg taccaaaatg aaacctggtt   1020
```

-continued

```
ctgaattgga gaatccaatg ctctagggga tagcaatgta aatctgccaa acccaaaagg    1080
ctaagcatca tgagattggg aaactgtaag aaacatctac tcaggtgaat ctaaaaagaa    1140
aaattacaaa gtatgtggtc aaaatattta tcagaaaata ttttgtacaa acaaacagga    1200
gaatttatta ctgaggaact gtaagtttta gaaccatatt ttaaagtaga ctttacacca    1260
tgtggtaaaa tccccaaaga atataagaaa atgtagtatc catgaagaaa gaacaagaaa    1320
ttataaaata aaaacaggtg gatatgagtc aagaacagaa agatttttgg agggagttgt    1380 cttttttaaaa caagctt                                                  1397

<210> SEQ ID NO 94
<211> LENGTH: 5008
<212> TYPE: DNA
<213> ORGANISM: Homo sapiens

<400> SEQUENCE: 94
gtggcagttt tgctaagaag aaaagcaggt gaaagtggga gattccaaaa gagaccagag      60
agaaggcagt gtgtcctgcc caatctgccg ctagggtcag agaccagctc cctagtcaca     120
ctcggccaag gcaggctgcc ggctgactcc aactctaaac aaagccaggc agccgcccag     180
gtgggtgaag gctgcagatt gcgctcaggc gtgacgccgg ggtgcaggtg ggagcgacgc     240
ccgggtgcgt gggtgcagcg ctcgcccgcc cgcggttagg cgcaccgcgg gaaccggtca     300
ggtgcgccgt gtggggcggg gcgggcgccc ccaggctggt gcctggggca gaggattcgc     360
ctgcttgacg cgctgatgcc ttgatttggt ctgacaagtg gaggctgctt tgagaagcgg     420
cctgtatttt tgacattcag gaagctagaa ataaccagct gggctcctgg cgctctggcc     480
gcaaatgtct tgcgctttcc aggcaactgc cagattgaag gggcttttcc ccatgtagac     540
ctgtgctctg tgtgctagga ggccgaggtt ccagtccagg ctcggcttct gactccctac     600
tttaggctct cccacaagcc tcggggggggg taaacaaaag tgagaggtga agctgctgca     660
gcgaagtacc ccttcaaaat cttcagtacc cttcagacag cgctctatca cataaactgt     720
acaactccag tcaaccagca gccgcctggc tggcacagga agagccaatg caattttgca     780
cagtcttgct tgaaggtatt gcctggcaaa tgggcaatgg ggaaccacag ggagggcctc     840
gagctcgctt tggcactctc acgaagtcca ctcttcattt aaaacgttgc tcagccttaa     900
gggggcctga aaaccacagc ccccaaggga gccaggtctg ttcaaggcat tgcttccaag     960
tgagactctt cacaagcctt tttttcttgga gaccaatgga gcagcgttaa tctggcacag    1020
atgagcactc ccataatgct caacatctct ttccaagagt ggagagagat gatgcagaga    1080
tagtcaatca tcccaatata aaaattagtg gacaattggc aaataggaag gaaatattta    1140
ataattgtgt tgttcatgca tctatcccag aaatgaattc aatcaaacac tgcattatga    1200
gcatgaattt gtgttacatg atagactcag ggatggcaac aaaaatattt gagtgctact    1260
ctttgctcga aactctgctt tacttttgct cattcaccat gtctcatgaa ttcccctgtc    1320
ctttgatttc tggttcttta atattctggg attcaatctt tctccccatc cccactgcct    1380
tgattcacaa cctccatcat ctgtcagtag atttattata aagctctctg ttatggacct    1440
cccacacctc agaatgtgac tgtttttggga gacaggggcct ttaaatgggt aactaaggca    1500
aaattaggtc atatggctgg gccctaatct gatgtcctta taagaagaaa gtaggacaca    1560
gatgcacaga gagggaagac catgagacag ggagaaaccg gccatctgca aacctaggaa    1620
ggagtcctat cctacgttga tctcacaagt ccagattcca ggattgtgag acaatccact    1680
gttgttcaag ctccagtctg tggcacttag tcatggcagc cctcttaaaa taacacagcc    1740
```

-continued

```
ttctgcctgg gctctgtgct tgttccccag ttaaattcag aaaagtctaa aaattattgt   1800
tgtttatctg aaattcggtt caactgggtg tcctgttttt tatctggcaa ccctgtacag   1860
gaccctttgt gactgctagt gaacagactg aaccaaaatg aatttgataa gaattgtttc   1920
ccccagttaa cacaatagaa aaagatagtc aagattgatt cttggctttc aatattcttt   1980
caatttacca ccaacccttg ttcacagttt agaattatct gaggagcatt taaaaatatc   2040 catacccat ccctaaccaa ttagaatggg agttactaaa tggggagtta gaaaggcagg   2100
gcagggagag aggccaggca agtgtatggc cactctcagg agccaaccct gcacttgcac   2160
agccctgaga gtgagaacct ccttaaatct tatgccctat acacctgttg tagtcaggcc   2220
ctatttaaag ataaagaaaa agaagggttg tgcagaagag cttccagggg atttctgagc   2280
agtcctgggt cccagctctg tgtttcattg ctttagaagg aacatcgacc tttccgagca   2340
atgaacatca gctccagctc ataggcatga gtcagggcag gcttcaccag gccaggttcc   2400
tgaaatgtaa actcacagca ggctctggtt tcctctagaa gaccactcct aaaaggcttt   2460
aaatgcttag gttccttgtt cttttttcagt tcaggctggt gattgagtag ctttagtcat   2520
tggcatccta aagattctgt ttcacattca agcatggttt taaattacta caagatgtaa   2580
tgaaagtata ggtttcactc ttctctccaa ggtttttaaag actctcaccc ctgttctcct   2640
tcctccctct ctgccttctg cccttttctt gctggtgatt ttctgcccca tcactggcag   2700
cctggtcagg agcacctcat taatccaccc actggtacag tgtgcccaga acagccaagg   2760
ccaaccttgg aaggccaact ctctgaacag tcccttcctt tacctctaag ttccgtgatg   2820
tcatcagcat tctgccctgg ctggcggcca gatccttaac tactgattcc cagatctctc   2880
cacgttttaa aattctagga aaagaaactg tacttttcca gtgctaaaaa aggatgggaa   2940
tggttggtgg aagctcccag cacagctaaa attaacttct ttcttttgtg ataattgaat   3000
gattttcaat gatgttcttc ctataatagg attcaaaaag ttttcctcag gggaaaattt   3060
ggaagagaaa aatacaaggg aaagggttct ctcagtagca atttccttgc aatatgaagc   3120
tcatgaaatt acatgggtgt atctcactta gcttaataga catgtccctg taaatttcat   3180
ataaatggaa tgtttaaaaa attaaatcac tgtaagtgca gctaaataaa ggaagcccgg   3240
ggtgactcac tttataaagt gaattatctt tatgtaatgt acatcatcct cccccacaca   3300
ctgatttata ttataatttt gaatttttca gaggctggat tctcataagg taagggtgcc   3360
tcttacgatg acaactggac tgaggtcaca gctgttctca tactctgaag ctgaactttt   3420
ttaacgttct ctggggagtg tgtagatgcc agggttctgc ggggatttaa gctcttacac   3480
tgacccagac tcctcctggc ctatccctgg agtgatgtgg gaaattgtca atgactggac   3540
agtggaagaa gtcatggtag acaagctgag gctagaagca tgatctgtgg ccagaagact   3600
acggccctgc gtctgtcctc tagctgggga ttctctgagc ctcggtatca ccccagccag   3660
ttgttaggat ttagatatga aaactgtgct gttgaattct taagcaaaaa aatgactaac   3720
tttgaggaag acttcaaaag agaggtgaca tttgaaagtt acaagtatta tcttatttaa   3780
ttccttagta ttggtgagat gtccagctgg ttgcccacct agtatttaaa aggcactttt   3840
taatttacat ggccaggcag tgtggctggc taaaagtctc tattttccag tctccctggc   3900
aggcagctat ggcccataag atggaaacag atcattgggt cagacttaaa agcttcttaa   3960
aaggggtata ggctatttac ttggagtttc taagctcttt cctcttcttc ctggttcttg   4020
cctgaaatga agacaagacg gctaaggctc tagcaccaac ttgtgacctt gagaaaggca   4080
```

```
aggggagtct ggtccctggt gaccgtgact gcttagcaac cttggactgc cgagctccag    4140
acttgcttgt ttaaatgaaa gaaaaataaa ctatcttact taagcctgtg ttatttttgg    4200
caattgttat tagcatctga cccaatccct aactggcata agctcctgag gccattaggc    4260
agaggtgcgt tcccactacc ctacactgtt ggggcaagcc tgtggctcca gggcacccga    4320
agagcctaga gtgtttcctt taaattgcaa ttcctttttt gtcaggccct ggcatcaagc    4380
acacagcctg gtcagtagca ctcaatatat gttgaaagaa tacaatgaat aactgccgct    4440
cgaccatttc ccaaggagct gttttttctga ggggtttttca cttctcggat ttccacagga   4500
cagcatcagt acgaagcttg tgggacatcc aaagtgcttt gagatttaaa aaaaagaata    4560
aatcggaaat gataaacatt taaacaatga agatatacat aaagcctcat ttaagtagta    4620 tgtttttaaaa ggtgaagcaa aattgtgtat tttttgtaga ttttaaaaat ataattaaat   4680
gggatgaaac tgctatccca aatcccttttt aaaaaattat ttttgagtga ttgcaaaata   4740
acaaatataa ctttgtaaaa gaatcgaaat tatttagaaa ggttaaatat tgaaagccct    4800
ttcatagaac agtttggtaa atatcctttt aactcttctg tacataaaaa tcatgcaaat    4860
agatgcgtat aaataagctc atgatgtgta tattattttg caacctttgc tttttttcact   4920 taacatccta tcttgggcat ttccccacgt ctgtgcattt agattaacct ggttctctgt    4980
aaggtaatag agcatccttt atcccaat                                        5008

<210> SEQ ID NO 95
<211> LENGTH: 3639
<212> TYPE: DNA
<213> ORGANISM: Homo sapiens

<400> SEQUENCE: 95
cacagaggaa gattcaacta tcccttcttg aagaagttga gaagaaacaa ctatgttcac      60
cagtctaccc taacacaaaa ctgagatttc actgtttcaa gaaaaaggct gaaatacagg     120
ctagggaaaa aaagctcttt tggttaactt tcagtaaggt agaactttcc aacactagaa     180
cttaggcagc agctgccttt gaggcttctc tgcaaagatg ggttctgaat tcaaaatgat     240
gaacttgaga tcatcggccc ttcatctttg actccaataa caggacagaa ttcacctgag     300
tcaggtgaat aactgcagac tatggacatc ttggtatgga agggcttgaa agggatccac     360
tacaggcaca gaatcacagt cctggaggcc accccatcag acagccctca tcttccactc     420
cgtactctcc tgaggggaca ggactcatcc aggctctcat caagtctgca acttgtgatt     480
tgtctcttcc aagcagagtt tggtggtgag aattctgact gattttgtgt ctattgctac     540
ttcaacagtt attgatcatg gatacattgt ttaaattgtc taaaccttgg attcctcttc     600
tgcaaaatga ggaaatgata acttcagaaa gcagagagcc cctttttggg tgtcttggtc     660
ttggataagc ctttgatgga cttttgggtt atacaaaagt gatgcccagc tcctgttttc     720
aaatagtgag gttgagatga tgagaagata aactgctttg cctgggaaat gcttcctaca     780
tgtgttaaga ggaagcatgg tgttggaagg agggagaaca tacctacctt ataaatgatg     840
agaggcagat gtgggttaaa acataaacca gcctgaagtt gattcctgac tgctacttac     900
cagttgtatg tccttgagca tcttaatatt tctggtacct ggtgtcccca tctgtgaatg     960
gggggaataa caatattaac tttgtttttt atttgactga atctcattgt tgtaagctca    1020 ctgtttatc tttggaggga aaattatcac tagatatcct gaaagtgaat gggagttgtc     1080
agtgggagga gagttggttc tgggcatggg ctacttttca gagatgatat aaatttagag    1140
ggaaaaatgg ggccagtgat ttactctccg gttgagaata taagttgcta atgtagagtg    1200
```

-continued

```
tgtgaccta gctcttctaa actttcagtg tcgttttagc aatcctcggc ctctcctgaa    1260
tgtctggaga cagggcctgt ctctcttgcc cccactccgc ccccccttat gaaatggcag    1320 ccctggtgc agagcctttg ccaatgggag gctgggctca ggttgcccgc ttacttagca     1380
caggacaagg caagaggcca aggcgatttc ctctctttta ctgcatcata aaaaagcatc    1440
tcattcttca gacacctctt agtgctcatg tccaggccat gattagcaga taatctccta    1500
ggtctgtggt ccatgcacgc ctgcatccca gctgccaaga cccacctgag aggaaagaaa    1560
aggtctgtgt tgaagacccc ttcccacggc cttgagggcc cacctccttg aagttgctcc    1620
tttctgtctg gggggtaatc ccagccctct cctccttgct gacttggctc cccggctgct    1680
atataccttc tcaaagagaa ccccgccacc aaccacccag acttcctgag ggtcacacca    1740
caaagagacg gcagaagacg gatggaatcc agatctctat ggtctacact cacctggcca    1800
ttttgggact atttctgggt gtttcctagt aaatgcttgc tgagatgggg cctgagatcc    1860
caggggactg gccctggatc taccctggga aatcatcaga gctgccatgt tgcctgttca    1920
gctcagcagg gacatctagg aggggacagg aagaggtggt cagcatggcc actcctcttc    1980
cagcctggtg agagcatagt agagagagca gcatgggctt gagtctgaga cagacctgag    2040
ttctagtcct ggcatgccac tttctagctg tgggacattt gacaatataa gtcatctctc    2100
tggaccacat tttaaaaata aataaaaatg acaggcatta cactgtaatg gaccaagaga    2160
gattctccat agagtactca ctacattatt attattatca tcacaaaact aggcaaatca    2220
caacctatgt gagtctcaaa tttgtcctct aaaatagtgc ctagtgggtt ctccagttag    2280
cgttagtttt cttcacttca tattgcaagt ccaagaggga gttttggtag cagaaagaaa    2340
tgcaagttaa ccgaaggtta aggctcaagt tctatcactt ccaacatgtg cctaacacat    2400
ctatatctac atcaatatct tgacatatat gttcccagtc attttttttc ctttttttaa    2460
aacaaagact gaccattcta ctatatttga aaaaagtatg ctcatgaaaa ataattaata    2520
gaaaaaagtt gaaacatgaa tgtagtaaaa tcagaaatag ctctccttaa gaataaatac    2580
atcatcctat tgttttttgta ttcatacaca tacgtatcta aaaacacttt aataaaatga    2640
gatcataact gtaaatgcta tcttaaaata tgaagtatta actttaaatt tactggaata    2700
caacagaaaa aaatatacca aagtaaaact atagaaattg ttgaataaat ttttctttac    2760
tgtagcatag tattttttga aaaatcttct caggttaatt aaatgattat ctaaaacatc    2820
aaaaggtggc agtcatcatt tcttctgaaa ctacatggtt caattttagt atcagttgtg    2880
tttgggctgt gaaagataag ggcattagtg ctcagatttc ttccagctcc cttcccaaca    2940
aaacttaagt cttgttagtt accttgttat ttttacactg ttcagatgta tggctctgac    3000
tagaatagtt ttatttatgc attaatccca tcccccgatt aacttctatg gggcagaagc    3060
agatggagca gcttcataga gaggtattgt ttaattcagg aaatagattt gctaccacta    3120
atgatatttc attcctaagt ttatttcttt tctttatttc ttaactggct gaatattatt    3180
gtcacatagt tttgttcaag aagggctcat gggtgctgta ttcctggttt ttcatgtctg    3240
agaaagtatt gctttttat accattcttg tatgccataa tatcctgggt gcactttctt      3300
tcccttagac attgtgaaca ctgtcttttg gcatgaaatg ttgctgtggg agaggctagg    3360
gcaagcctga tttgaacccc tttgatgtgc ttttcctgac tgtatgaatg ttcaaagtgc    3420
cattatttaa ctaacttgta tcttgaactg tctgcatttt cctggaacat ggtatgtctt    3480
tcaacttgca tattcaattt ttttatttag atgattgtaa aatttttactt ttggatttgc   3540
```

-continued

```
atacttcttt attaggtgtt ttaaaatcta ttatctttgt actttctcta atgtttttgt      3600
tttaatctac ctttacttta tctcagactc tcatccatg                             3639

<210> SEQ ID NO 96
<211> LENGTH: 1146
<212> TYPE: DNA
<213> ORGANISM: Homo sapiens

<400> SEQUENCE: 96
acttctactg agctgggttg aattttctta gccaacattc tgctctaatt gactagtgag        60
agagaaatga gcatgcaaat aaagccttca tagaaacagc tacacagctc caggctcctt       120
ctcctttttg aataactaag attgtttctg gcattgggga cagctcctcc aggcatttca       180
aaaccattag gcacagagga gggagagatt aatgtcaaca ggaggtacta ggaaggcctc       240
ctgcaggatc ctgcaggaaa acacactcct ctgctaaaac catggctcca aagtgcaagt       300
cttccaaagg cagaaatccc tcttcccttt agcacccaca tctgagtcac cagcaagtcc       360
tataagttat aactacaaat tttattccaa tatatacatt tttctgccta tttctactac       420 taccaccct atccaaggta catcatccag tgctggtttt tcctactaat gctccttgga       480
cctcttcttg ccaacccaaa ccattcccta cacagcagca tgagtaagct taaaatgcaa       540
accagaccat ggcactctct tacttttttaa ataattatca attttgttta aaattaaatt       600
taaactcctt accatgggtc tctaaatatg catgatttgg tccctgctta tcttttcaac       660
ttcatcccat cgatttcttc ttcattattc tgcattcata aagacctcct ttattttgtc       720
caacacaaca cattttttccc agctcatggc tttgtacttg ctgttttctc tgccaaggat       780
gcctgatatg aaagaagaaa aaaagaaaga ggaaggaaa gaaagaaaag aaaggagaag       840
agggaaagcc tgagctaagg cacaaaggcc agaagtagaa ttagaaaaag ataagcactt       900
tggtggtgct taagtataaa cacaatgatg ataaaaggat gaagaaacaa cagaggctaa       960
gaccagatta agtaaatatg tattagctgt tattgctgca cccagaattt agcagtttaa      1020
aacaacagtt aatctcacac tttcaatgtc agcaacttgg gagtaacttc tggttcagaa      1080
ctttttatga ggtttcaatt aagacacagc ctggacttta gcatttaaag tcttgaatgg      1140
gactag                                                                 1146

<210> SEQ ID NO 97
<211> LENGTH: 1820
<212> TYPE: DNA
<213> ORGANISM: Homo sapiens

<400> SEQUENCE: 97
atggatagtt accagtctgg tatgtattct cactttttctt cacaactcag tgaaggtact        60
gttattctta ttcccatttt acagatcggg aaattgatgt ataaggacaa caagctccag       120
gagggcaaga ccagcatctc tttcactcac ccctgtgcct ggaacatagt aggctcataa       180 ataacctatga aatgaaattc agtatgactc ttagattgga ttctagtttc aagacaactc       240
cccaaacact tcaccacaga agagaacatt agaattatga gactggagtc aagaagatca       300
gacaggaggt tgttgtaatt caagcaagag atatgaattt cagctaaggc aacattatga       360
aaggatctgg taacttttac ttattattaa agctctattt aatccgcttg ctataaccta       420
gttaataaac ttggcagcat tagtgcactt ctcagatcat catctgagtg cctgcctcac       480
actgtgcaaa gagctttaca catatgctaa ttccttactgc agcactggaa ggtagatatc       540
attatctcca ttttacagat agaaacacca aatcaaagct cagggaaatt aagcagattt       600
```

-continued

```
gccaaggtca cacagataga aagcaggtaa gtgcatagcc agtctattta gccctagcta      660
gttcctatta atagtctatt gaatgaatct acaacaatat ctgttgatga ttatttaatg      720
gaatttctgg atcctaaggt agagttatgt tataggtatg tgttttatca tattacagaa      780
gtatccatca attcatttta ctgattgttc ttgacaccaa tgtcctttga tgttgccttt      840
tctgcatctg tggaaataat caaaattttg tagtgttgct ttattaacag gatgaactct      900
tgatgttttt tctaatatga aacccacttg ttcatacttc tttatgtacc aatggagtct      960
gttcattagt atttagtttt atttaagact attatccaaa attcatatga ctagtctgtt     1020
gtttcttttc tggtatagca tggtcagctt tggagatcaa tgtaatacct acttcataaa     1080
aataaattct ctttcatgat ttgaaataat ttaagtagca ttataattat gttattatta     1140
aagacttggt tcaatctggt tctctttatg ggggtgtatt cagttacttt ctctatttaa     1200
gatcatttgt ctctggggtc aattttagtc acctgcattt ttttctaaaa actcatctac     1260
attttcaaag ttatttccat agagctattg taagtagtct ttaagttatt ttaatttttt     1320
ctgtgtccat gattatttct cttttgtcct aattgtgtat atttaccatt tctccctcat     1380
tttttaaaat taggttggtt agtagcttat atataataca gtgttggatg ttgttttgtt     1440
taccaatcaa aaaaattaat agataataat cccattttat tttttttaaat gattgtttgc     1500 cttcaacact tatatattaa tttcttatat tttgtaacag atatagcact ttcccctttt     1560
ttggttattt tttatttggt tcttactatg agccatatta agaggtaata ccctcttttg     1620
ttcttttccc tgcatcactc tcaaataata cagtaagctt ttcctacttt tcgtgttttc     1680
cctactttcc cctaatattt tgatgtacta tccattacat attaatataa ttaccatcta     1740
gttgaaattc tacatgtaaa tattcagtac ttaccatgta aattttttctt cattctttat     1800 tgttgaagaa ttagcctgaa                                                 1820
```

<210> SEQ ID NO 98
<211> LENGTH: 5410
<212> TYPE: DNA
<213> ORGANISM: Homo sapiens

<400> SEQUENCE: 98

```
gtagagaaag gacaagaaga gacaggaaaa gaactagatg catagcaaat cttcagggtg       60
agttgtcttg tgcactttt gtttcaggta cttgatacac acatcaagt atcttgggga      120 atccaattga ttgtataaat tacatagttt tgtgagaagt tgagcccctg gatggagcta      180
ggagagggga tcggagaaca gccttggttt aatctttcat gtaacttgtg tgcatggcaa      240
gtctttttcc gtctcagtcc tcatgttttc ttcctatgat aggagaatat ttgaataaat      300
taggagccct tgtattggtt tccatcactt gtgtgttcat gaactcagca gttgtaatta      360
ctttcataag ataattgctt aaactcaagt atttctaact tgcagtttct cacaattgca      420
tctaacctgt aaattactat atattttaag ctgaaatatt ttaaagtgaa ttgcaggccc      480
ccctaaatat ttccaaatgt atctctaaaa accatttttct taaacagtcc taacctctat      540
tttgtgttca gtttctcctg acatccccac cggaacccaa tctgtgatcg tgcgttgcac      600
ctggcctgga ttttttctggt cacttccctg acagtgtctc ctggcttgcc gctgtgtccc      660
ctgtttcttc cagtgcagtg tatgggtctt tggggtgcac tgaggtgatg gacgcttagt      720
ccagtctggg gccagaattt ccaggagatg ctccctgaga ttgtcttgag gggcagatga      780
gactcatgca gccatagagg gagggaaggg cattccaggc aggggaaca cccaggcagg      840
```

-continued

```
cattggggca gggagcaaca tgggtctcag ctctacaagc agctatgggt tcccctggag      900
tgtgactcgg catgaggctg gccatggagg agcagaatgt tccaccgagg aactgggact      960
ttacgttgtg agtgatgggg gctcactgag aggtgtcaag aaggggcagg caagtcaggt     1020
ctgtatgtca ggagctcagg tgagtggagt gcccgaggga ggtggggtga agggaggtgg     1080
gcacccaggt gagagctagt gcagggctgg ggaggccaag gcctgggcag tgggagagga     1140
ggggcagaga tggacagggt agaactgagg gcacctgcga ttggtagggg tgatgaggga     1200
gggagaaaag gccattgcca ggtttctggc ctggttgcca ctgcccatta acacagggag     1260
gtgaaactgc ctaaggaaga accctggagg atcaggattg gttctggaaa gtgttggagt     1320
taaggtgcct ggagtgcctg gatcgtgttc cacttattag gggtgggccg acccaggcgg     1380
cgatgctaag caggtgctct ggcgtgcttg tctaagctct gaggagaggt ggtgggtatg     1440
gtgttgtcag cagatgcaca gcagctggca tggtgagaat ggatgatacc accaggtcat     1500
agacagaaaa ttgcagtggg ccgaggtggc cgaatggtcg gagaaggggg aggagaaacg     1560
aggagcatgt ggatgatgcc aaggagggtt cgaagaacag cagagaaatg tatagcgttc     1620
cacaccccag gtccagagag acaaatggaa aaagtgccgt gcgctgggaa acagggcgga     1680
cacggtgtcc cttgccagtg cagtttggag taggaggagg agaggaacaa tacagtggct     1740
taaccttcca gtacaggcat ttggccccag gaggaaagag gagggaggat gagataaaaa     1800
tgacagtcga agtactggag tcaaacaggt gccgcatcac ctctgttaac ccagccacat     1860
gttcatcctg gaacccaagt tcctcatcca ggcctcggtg gtcccaggaa ctggccaagc     1920
ctgcattctt tctcccataa gcctccacag attagagcat ggccactccc ctgccttgca     1980
cttctgctat tcctcatcct ggcccccttc ccagacttct ttgtcccgcc aagtcccgtc     2040
ctttcaaact gagcgtttgg gaggtcttct ctgtctacca gcagaaacca tctcacctca     2100
gtaatggtga gcccagccca ctttttttctc ccacacaatt gagatgtctc cgaccagcct     2160
cttcagtgct ggatacttct tgcattctat gaatttagga tctctacgtg tttctcaaca     2220
cacatgcata cacaaggaca cacgcagaca cacacattag cacacagaca tacacacaca     2280
gtgacacatg catacaggga cacacacatg gacacatgca catatgtgca catacactga     2340
catgctctga cacacacttg acacacacgt gtgcccacac gcgcgcacac acacacgcac     2400
aaacacacac acacaggtaa cattgacagc tgtggctgta gaagtgcttc caagggcctt     2460 tctttttttgt ccttgtctgg agtttacagc acttggaaaa tgtcaggcgt gggaggcctt     2520
ttggtcttgg gttagggtaa actccctcca catatttgga gagcctccag gccctgcaaa     2580
ccgctcacga agcagataac agtgaccttg ctgtgaggga ggacggcccg ccgaggccag     2640
ggagctgtgc tggcagctga ggttacctct cctccccgct gcacctgggt cggctctgat     2700
gtcaagacct cccccgctcc atccccggtt gggctcccgg ccctctttgt gccggaaaca     2760
aggcccagct gggaggaggg gagggcagag cactgctctg tagttccagg tggagaacag     2820
cccagctctc ccctaggggc tgcaggctga gtgtccgact ccaaccccct tgcctttttg     2880
caggcccaaa gcggcttctc caggatggcg acagattttc caagactcat cccaggctgg     2940
aggggcccca gctgcaactt cactggtgtg tgtatgtgtg ggtgagctga ccctgagagt     3000
ctggtgctag agggctggag gtcatgtcat cacagaaccc tctctgctgg cccccttcaag    3060 catcctgttc agggagctca ctgctaccag gggctggagc ctctccaggt ttctgtctct     3120
gtcacttcct taactcttga gctactcaga ttaggactag cccttcttcc acatatgtga     3180
aaacagctgc attcatacat tcagctacat atagctttga atgcaaggcc tggctgggag     3240
```

```
ctggggatag acacatggtt tgctacatag ttggtggcct agtggaggag gcagacggca      3300
ggccctggtc agcgtgctga gtctggggga ggagcaagcc tgcaggagga agttactctg      3360
ctggggagcg gggccttaag gtgctccaga cagaggggac aggatgcgca aagctgtgtg      3420
ggtctttgcc ttaggcaggg gtgggagtca gcatttagtt ggagaagggg ttcaggggcg      3480
tccagtggtg tgggcagagc acagggggct gcagtggctc tggcgagagg tggtggtacc      3540
taaagttgtg gcagtggcca cggggctggg agctgtaggt ggagttgggc agaccaagct      3600
ctcctctgca tggagctcca gagtccacac agatgtctac ggatagctcg aagccctccc      3660
tgatcagcca gctccctctc tttggccccc atttgcaagg aaagttcaaa tgcggtgctc      3720
aggatggaag cagacttcta atgtgactta ccgtagttcc atctgcttat aaaaacataa      3780
gtcatgccct ttttcacgcc gaaaagtgtg aaaaaagaat tttatatttg caaaagtttt      3840
ccctagaagt tgctgcctgg gctccagtgt tccatggtca ggtcctctgg agccgctgcc      3900
gcccgggcct gagggcccag gcctgtgact tcctcctcct gtctgtctgc ccgggagccg      3960
gcaccggcac ccaaagccga agccgcctcc ctcttatcct ctgcgagatc agcccagcca      4020
ggaaggggcc ccagccgtct ggctgtctga gccgggaccg gttggcgggt gctctggcct      4080
tcctcattag cggggtctcc actgcccttc ctctcgcagg ctaggctgtg gctcctatta      4140
tagctactgg agggtttttt agtcaaagag caccatgcat catttattat tttaccattc      4200
actcagacgt tccctgagca cttcctatgc tgctgctgga cccagggatc agccaactag      4260
ccccaaacgg cagatcctct gtggagagtg aggaggttgc tgggctgaat caaagtgctc      4320
tcacgcacgg tggaagttgc tacgtgcaaa gagatgcggg caaccaagtg ctctgaggtg      4380
cagaggaggc agaggccatg ccaaggagag cttacggctc tcagcccttc tccgtgccag      4440
gcgctgggct gagcacttca catgctaatc ctggaggtaa tccatggggt aggtacgatg      4500
actatttcca gatgaagaga ctgaagctta gagttaagtg atcccagtga gtacaatgcc      4560
tggattcata gccagaggct gtgctttgaa gccccagttc agttgccctc ctaccatctc      4620
tacccactcc cccagcccct tggggctgca gagcgacagc aagctacttc gtcatattgc      4680
atctcagttt tcctgtctcc taagcttgtt gtgggtttta aaggaacaaa gcctctagtg      4740
tgctcagcag tgactggcac agaatacatg ctccataaac gttagccatg tttatttttg      4800
taattgtcac tactaggtgc tttgtaggag gccctctcg  ggctggtgca tcctctgcca      4860
tttctgtctc agggtcagcc cgtctcccca gtgctcacaa tctgttcatt aagatcatct      4920
ggagtctgag tcccttctta ttaaaattgt aaaaatatac agaaccacaa gttaccattg      4980
taactatttt taaggattca gttgagtggc attaagaata actgttatgc aaccatcacc      5040
accaagaatt ttttgctatc ctcgactaaa actctatcca taaaacacgg agtcccattt      5100
ctcctccccc cagcccctgg caacctctac ttcgcatctc tatgtatttg actcctctgg      5160 gtgcccata  taaacgaatc atacaatgtt tgtctctctg tgactggctt atttcactta      5220
gcatgatgtc ctcaaggttc acccatgtgt cagaatttcc ttgttttttga ggctgaataa      5280 taatccattt gatggtttta tttatccata tggccacctg ggttgcttac acattttggc      5340
tattgagaat aatgctatat atatatacat acccaaatgt acccaatata tacttcaacg      5400
tccacaacta                                                             5410
```

<210> SEQ ID NO 99
<211> LENGTH: 2690
<212> TYPE: DNA

<213> ORGANISM: Homo sapiens

<400> SEQUENCE: 99

```
cagtgtgtag aagactggag tgggagttga ggtggtatct gattacatct tgatatccac      60
actaatgagc atacatcact ttgtaacaaa cgggctgttt ctgagccaag accatgagct     120
gatagtgtgg atggtggctg ggacaggga gagagcccat cctgagggac ggtcaaatcg     180
taataaagta gcaacaaata gctaaagctg gagtgtaaca gacaggtaga actgattgag     240
gttcaaatga agacagagga gaaggaacta aagatgattt gggggttctc tgcttgatgg     300
aagtggggta gaggtgtcat gacttgcagg acacagaagg gttgaggatt agatagcagt     360
aaatacatgc atgagggagg aagggcatgg tttgggacat gttgagatcc tatgttgaag     420
atcaccatcc agtggggaca caggcaattt cagtgcagtg tgattagtga ctggatgagg     480
aagcttagag aaggttccaa aatggaggac acacagaatt tggttctaga ctacaggttc     540
ttaatcattt tttttccagt aaatggcagt gtggtttaaa aaatcagatt caagtttgac     600
aacttgttca aatgaagctg tattggttct aaatagaatt tatatgaaag cacaataaca     660
tattaccttg ctgaagtaca cacacacaca cacacacaca cacacacaca cacacacact     720
actctcacct ctaaatttct ttctcccgcc agatggcact atgcttcaat atttaaagct     780
acagatatgg tgaactcagt tgtctttatt cttctcgcta tgtggacctt aataaatggg     840
cttaatgaca tatgctgaac taacatccta actgctactc ctgtaaaata aaaagcagcc     900
gagctatatt atgctttatg aaatatttat aactgccaaa cacaaaggca gtaagaacat     960
tggtttatac agcaaaagcc gaaactctat ttaagtgaag attaatgtgg aaatgttatc    1020
acattctcac actgcaaaac taaattgata tagaggtgat aaatgtggat agacgtggaa    1080
tatacatata ggcacacatt atacatttta cctgataaaa tataccagct gaatttgcct    1140
aaggaagctg ctaaagtcag atttgatgac gatttgtgga agttaccttg tggggcagcc    1200
caactgctag aacatttcag gaagttctat attgatggaa gagaaatttt aattatttct    1260
cctaaataag gagagagcca ttaggtgtgg gattttgtgt tctctttcaa atttgaatag    1320
acagaaggta tgtagaaatc aacatgatct tttcctttat tcacatataa ttgtaaataa    1380
catgggtaat acaatttcca aatctatta ctatgttgtt aaagtagttg gaatggttcc    1440
tagatttata acatattcca caggcagcaa tttgaaaatc tttgagaagt ttaaaaaata    1500
tctggcttac aatcatctca ttaaggtata aaatcagggc ttatatttta tctgattgtt    1560
attctcagat ctacagtttt ttaaaagaca agtcttggtt ccttatagat ctatcagctt    1620
ccctccatgc acatttggct catgaatgta tgaaatactt tggacgtatt tctattaaat    1680
tgctttcctg gggaaataca ttatagttct cttttattta gattaatgag tttttaggtta   1740 atctgtcgtg aatcctctgt aaatcagatt cttgatagtt aatatttcat ctttgtatat    1800
ttaaaatcag ttcacatgtt aagttaaaga tgaaaaagag aactaaatca gcaatattgt    1860
tatgtgcata aattaatgtg catgtatgtc tgctttaagt ttagtttata gaagttttaa    1920
aaaatgaaaa ttggcatttt tctacaaaga atgatgcctt ttgtcttcct acctgcctaa    1980
tttcccaaga agagatctag atgtcagaac atgctgattg actatatttt ctaagaaaaa    2040
ttttagaatt attaatatat ctatactaac taaacacatc cacttacctg tttttctggt    2100
actcttggat atagtctttt ataggatttg agctgtgaat agacaaagaa gatcatttgt    2160
ccagctttgg ttttagtttt tctaggactg cattgcacaa gccttttccc agggtgcatc    2220
ctagcagctt agtcttcaaa tctcagcatt ggtatgtggg gctgcgttca gcaaataata    2280
```

-continued

```
aaaatttagt tgttttgtca tctggacctg cattatgttt gtgcatgcac ccatatatat    2340
atatatttat taaatataca tatatattat atacacatta tatccattta tataaatata    2400
cagatgttta tatacaaaga aaagttcaaa acattgatca ttgtaatcta tggtaataac    2460
attatagata tcttggtata ctgttttatg tttcctaaat ttcaatgata tattttattt    2520
tgaatcagaa aaaagttaaa attatagaaa tttaaataat acataattta aaattctgaa    2580
tactataggg aaagagtaaa cttaacattt ttctaggtag ttatctaatt tctcagaatt    2640
atttttgaaa aaagccatca tttctctata taaaatttat tatagactaa                2690
```

```
<210> SEQ ID NO 100
<211> LENGTH: 579
<212> TYPE: DNA
<213> ORGANISM: Homo sapiens

<400> SEQUENCE: 100
gtgtgtttct cggcgcgcaa agctataaat aatggcacag atcattaaac cccgagagca      60
ggcccagccg ccccgcaaac aagatgaagt acaaaccacc acgtgaggag gagagaggga     120
ggtacaaggc agagccccag acccagcctg tacctctcag ctgggtccca gtgaacttgg     180
gcctccaagg caccaccagc aggacctggt gtgactgcac atgatcagca gacccttcgt     240
tttgggccca gttgtcaggt agcaacccct gaaaaaatca tacagcagct gaagtgaaat     300
acaacaatgt cttcagagca cttttaccca cttccttcta aaaagatctg agatggccta     360
ccgtataaga cacacccatg aaagaacaag aacagataaa gaagtggatt ttaaaatgtc     420
ctgggaaaag aaacccaaga atggacagtt actgcagagg aacccaaaac ttagccctca     480
gcttcctaga tgaaaccagg tagtagctta aaagcctctt cgcctacacc agaaataaac     540
tgagcaccta ctattagtca tgcatcaaag acatgatca                            579
```

```
<210> SEQ ID NO 101
<211> LENGTH: 3793
<212> TYPE: DNA
<213> ORGANISM: Homo sapiens

<400> SEQUENCE: 101
agcaatgaaa aggggacgga gtgctgtggg gttcagccag tgaaatgtga agaaactcca      60
ggtcctagaa tgtggaatcc aggagagcca caggcttgca gtcacgaggg ccaggccgac     120
taagaactgg agaggctggg attcaccggg aggcatggga tggaaggggt tgtcaccaca     180
caggagccag gaacccagag acaggcagct gcaatgcaga aagaggaaaa gacatctttt     240
gaggaatgtt cgcagcgtga agcatttggc gtgatcttca ggacccgggg ctcagcctgg     300
gtggtgctga aagtgacccg gggctcagcg ttgttgcctt tgcttcttta actcctgagc     360
tgcctctgtg gtccccttgg gctcccagag ctgctttgcc tggagggtca gagagaagaa     420
gcgccttgga ctcacttgtg tgtcaaaaag gagtgtttgc aggccctagc agttttttat     480
gattggccat atggctctat taagttcaga atcaaagata tattttttga cttatccata     540
agaagcataa gagaaattta aataatctta ggtgtttttc tgtccatttt gcataaaatc     600
acctgagtgt tttatcaaaa tgaagatgag gaaacggcct gcatttctag gggtttattt     660
gctttttttt taaatcattg ctggttctag ttggaattgc cctttgggac tctcaggtct     720
ggatagttct ctgaggctga tgagcgtggc agcgtgcccc tggtgcaggc agccaaagaa     780
ctggaatctg actcagggc agagaaatgg gttaggggtg aacccaacat ctctgctcac     840
```

-continued

```
ttggtccttg aagcttttct tggcaaggat ggtggtgggg gacctgagtg ccatcgtgtt      900
caaacaccca cagtggtgac atcatctctg catctgtaca gtgcacaggg tgtggttaga      960
gcaggagttg gaaggagaac agtcatagct tccagtccca tctgcttctt gtctctatgc     1020
ccagaacctg accctggaac aggactggtg cacagaagac cttgtgtgag tcctttggta     1080
ccacgtttgc tgcacgaatg tctgagacac ctcacagtcg cttgttcagc ctctccctcc     1140
tctctccgct ggggaacatc atccctcatc actggaagaa attacaagga ttgtgtaaac     1200
aattacaagt attctacaaa cagtgagcat gctggtttgg cccatctatt tgtaagaaaa     1260
aacatggggt tttatggcaa tgagttacag ctctaactcc tggcacaatc acaaatatca     1320
gcacaaaaca ccaagttatg tctcccttct gtcctaaaag ggtaactact tcattcctaa     1380
tattactgca caccaagtct ctcaatccgt taccaatttt atccttgact cctgatgaaa     1440
cacaaatctc tttgatcagg ttatcacatg gcataggatg gtggttgctt cagggaaata     1500
atttaaagta ctttgcagtt tgctaggtgc cctggggcat agtattcttt gggcctccta     1560
aggttctgat ggtgatactg atttaacgta tagaatagtt tttaaatgtg aagtgctaca     1620
gggaccacta tgcagggagc tgaagggcta ttgagctgga cacttgagca ttggctgcat     1680
tgaatgataa atattgttct cttcctcaaa atagaaaatg acaatggaaa acttttaata     1740
atgtcaacat tggtgactag aaaacatatg tgcctcctta tgaaagcagg ggtggtgact     1800
gaatagaatt gttttgtttt tagagaacga ttttcttttt gttttttctt cttttatagt     1860
attttactta aaaatccaag taatagtatt ctactgtatt gcgaaaagtc agaacactta     1920
tgtattttta tttaaaaacg aacgttttag tcagcaccca atgcaacaaa agcaaactag     1980
aaattgctca gcaataaaac aggttgattc tcacctttgc tgatttagcc gcatggaacc     2040
taattaatgg gtagattata catttgctca acaagtatta atgggttcta ctcccgcgag     2100
accctcatga agtcctgagg ttgcctctcg ttcacaggga gctccatgag gctggaggac     2160
ttcatcagtc ccaagaaaca cgtgggcctc tcagtaggat gctgcagggc agagacctgg     2220
ttctgtagct gactccacct ggctaaggag cctctgggct gtggatacac cacctacagc     2280
tgctcatcag gtgcagggca ccagattccc aaattctgct gaggttttta ctctggtctg     2340
tcactgactg gtcctgaaca aagtcactgt tttactttgt caaggatatt ttcatgcgaa     2400
atgagctcag gtgcacttca aatcttctcc cacagccact gtccccagga cacggggctg     2460
gatacccagg ttgagagagg ctccagcacg cccacaccac ggacccaaag ccatcctact     2520
tcaactacaa tactcattgg aggagatctt tcagatctga cacagccact aggtcaggct     2580
ttttgaaaaa ctgaactggg gaacacactg gattggaacc cagcactgta tgactagaaa     2640
ctatagcatg ttttccttgt gagcataaat tctaggatta caggcacaat tttaaaagac     2700
atctatcaat attggactgg catgatcctc catgtttcag tttactccat atcctgttat     2760
tagtaatggt atatatcaaa attacagtgg cctcataggt atccagccat tttcagaagt     2820
ctttggaaat tcttggatga tttctaagat ttaatttatt tttaaatgct ttttccttct     2880
atgcatataa atatatataa atatttacat atacatgcgt gtatatatgt gtgcatattt     2940
gtttttatgt acaaacttat agacacacac atatacctta acttgagaga atggagattt     3000
cagcagagaa aattgtagag acatggccat gagacgtgtt tatttgtaat tgatcccttc     3060
aaatgtagag aaacaaggac atttgatggc catagacttg gaaagatttt ttttaaatac     3120
aatcatcttg ctatattttg aaagtcaatt ttagcacaat ggagaaacat atttggaaga     3180
catttaggtg tgaaagctga gttttgttga tatttatggg cagagaaaac ttcctttttg     3240
```

-continued

```
actattctgc agggccagag acagattgat cagttctagt gtttttgaag aaaaattact    3300
ctctgtggct gacgagcttc tgggaggcag gaattgtccc agtcaccagc acccaaagga    3360
atgcccaccg tttaataaac atcccatatc ttgaatgaat aaaaaaatgt taccgatata    3420
tggtactatc agtttctagg catggttcat gccccaatta aatcagtttc aggaagtagc    3480
cttttttgaa acacacaaaa tcttgaaaaa tgctggtgaa aacataaaaa ttatctggga    3540
aagtcagaga aatggctcag agtccgtgat tttatggaga gcataggcta ccaggagatg    3600
acagtgctct tcatgtaatg agtgtggctc tgccatatga gccaggctct gtgactggac    3660
caaccagtga aattataagg attataattt agatataaac agaccctgat atttattttc    3720
caacattaga acaggctatc acgtgagata ggaaacatta cggaagcatt ctaagaaagt    3780
tagataaaaa ttt                                                       3793
```

<210> SEQ ID NO 102
<211> LENGTH: 4515
<212> TYPE: DNA
<213> ORGANISM: Homo sapiens

<400> SEQUENCE: 102

```
cactagaagt ttagaaattt gaaagagaga atctattttt ggataggctt tacccaccaa      60
atgatatcag gtttcctgaa gatttttaaa ttactgaaga aacaagttac taccagtaaa     120
gggtttagat actcacagga atcccatttg gtaagcttgc tgcaagccca ctatgtgaga     180
ggtgctagtg ctagaagtag ctcaagggtc taaaactctc cacactaatg gattgagctc     240
ccagtgtatt gctacattat tttatttttg gtccagatat atctgcccta attgtagcta     300
caaatacctt tttacgtaca ggctttttca ttatctctct catttctact tctgagtctg     360
ccctgaggta ctgttctttc accatcgcat ctttcctctg atggacactt attatgccac     420
cttgtgggaa cctagaactt attctcccag atgctgtgag tgctgctggc agacagccct     480
tagatcttag ctccattcag aaatccttag ctgaagaaag aaaaaatcca cactcaataa     540
tggaagtgaa gacataaggg tctggccttg ggcccagttg gaacatctgt aaaggcctgc     600
tccatttgca gtgcatctca tagatttaca gtgagactgt cttacctctc agcttggctt     660
cgcctcctac ccacttttgt ttccttttct tctttcttcc agtattgatt ccaaaaacat     720
atcatagtaa acttcctgta tctccttctc agttctacat cctaggaaat ccaactcaca     780
gcctttctct tttctgctcc tctaaaaaac tgccacttat gcctgttctc tgagaaactc     840
ctatcaagac tgggtgaaac accatttctc acacaaagcc ctctctgcta cttcaggtga     900
caccccaaac tgagttttag tgtctttttc ctatgatgat aatagggaaa agaggaggta     960
attacaatta ttagtattat ataacttagt ggctatttga tccattgata ttaacattta    1020
aggttttatc tttcaaaata catgtagatg gttaacacat atttctgtga agccacagaa    1080
aagcacggaa tattactttt ttcaaagtaa aaaatacagt gctatctaca ttgtaggaaa    1140
ggcacttgct gtttaatagg gaactaaaaa accactggct attgagtttc aaatctgaaa    1200
catccttcag gcttctccgc atgtgaaact agatcaagaa gagaaagtct ttgctcttgg    1260
tgaactctga atcccattgc ttcttctttg tccttaatct ctcccttcct gaactttgtt    1320
cctccagcct tgctctaatt ctctattcta aatccctcat aattggcatt tctaaagtgc    1380
ttctgagttt gttttttactg aatcctaact aataaccagt gtacactaca ctcaccatga    1440
tcatctttac cacacagaaa gtttgtaatc ccatttgttt ccttttaaat ctgctactat    1500
```

-continued

```
ttcaacattg gcaaacattt cttatcaact ataaaaaaaa aaatggcact ccacagttca    1560
acacatatga aatagaattt gaaaaaatgc attaatggct acaaagcaaa aaattaaagg    1620
caatggtttt aaatgttgag atctacttca tgtagataca gaacaaagaa taacctacat    1680
tataactgct cataaaaaat gccgtgcagc aacatgggtt tccaacacat ttgataacct    1740
gtttctgtct cccccttcct ccattaaatt gaactctctg aattattcat gaaggctatt    1800
ttaatgggat aatttttct ggcgaacgct gacactgata ccaaagaata tctctaggta    1860
ttcatcttgg ataaataagg ctcctggtaa ctagtttct tgatgcttca ccttattcaa    1920
atgaacatat atggaagtaa ctaatgtaaa ccatttttta acccttaatg ttttcaatat    1980
gtttctctcc atgtatgtat agtcaaacat atgtttacac aggaattagc cagggtgttg    2040
aattaaatga aagtaaagca gaaagttaag caattctcag gtgaacttgg gcaggacatt    2100
aagaagaaat ttaaagtcca cagtttccag ctgtgatgac agttcggcat tgctgtggga    2160
atagcccatc tctccacagt actttggcca tagtcagaac caatcattca cttgaatgtg    2220
tacattaagg gttcttagcc caggatagta ggattttagg gagttgatga atcctttgaa    2280
atggaatatc aaattttctg tgtattattt ttcttctgaa aataaagttt atgacattca    2340
tcagcttctc agaggtgttc ttgactacca ccatacttct aaatggcaag aattcttatt    2400
tcacacagaa aagaccttcg gcagccagga ttctctggat ttccctgttc atgtgtgtgt    2460
cagaggtatt tgtccctcat taaatttagt attataaaaa ttcacatgca aacctttcaa    2520
cttggaaaaa attgtacttt gggttaatta tatatcaact tttacagttt aattttaca    2580 aatatctttg agttttttcct aggtatctac aagtctgctc atattttta aatattaccg    2640 caataatttt tgattttat actaatgcac aataagaact taagttagat actggaattt    2700
attttagtca caatgtaaaa taaggattta tattaccttt aaagaagcaa aattctcaga    2760
aatacagctt tccaacattt ctaatcattc tgtaataaat cttttaagac actgaggtga    2820
ctgtcactgc tggatgtgtc ctgggggctt ttctgtcaga ggagatagtg actcttccca    2880
tgcagattaa gctggtgttt acagatttgc cctgggtgtg cattttttatc ccgctgtgat    2940 caagtaacac cacctgacga gtgccagaca gatctctgga taagaaagtt cactatgccc    3000
tcactttgca caagatgcag ccctaatctg gagaagagtc tgtttcttgt tcttttctca    3060
gtgatactgt tatgtacact ttacctttag gtgaagcatt aggaatgaat ctgtctgtgc    3120
tgaaacttag atcatgaatt gaaatcaatg tacaaaccaa cattagggtt tctggagaca    3180
tgagaggagg cctgtgtgac aagtggaaaa catctaaaaa tatttgagtc cttagtaatt    3240
tcaaatttgt gtggagagtt ttcacagaca aaactagtga cataagaaat cttattcgca    3300
aaagctaatc aggctccaga tgctgtgagt gcaaaccact cagccccagg tccttttacc    3360
ttttcaccat ttggtcttaa agcattttta atatccatga aacaaaactg gctgtttttct    3420 tcagatactg aaactcagct ctccatattt cgatttctta cttcattagc caagttatga    3480
ggtaaatgat tagctaacta gagtttgtca caattaggaa gtgagaatga aattcaattt    3540
gtgtttagaa gtttattttg cattaagctc ttctatctag ggtttttaaac cacacagaaa    3600 aagcttacac ttgttaggtg gtagagttat tttttagttg catacattga tataagtaat    3660
tcatctttga ataagctcaa aacttgggtt cacatttttcc ttccttatat ctcttatttg    3720
agacttacct aatgaggaac ctgacatttta gagggtatta attcaccaaa agccactttc    3780
atgcactgtt ttgatcagta atggaaaagt cacactccat ctatttggat agtgtttttgg    3840 agtatacaga tcaatatgat tcaaaaagta atgtataact aacaacaaaa tatcagtgaa    3900
```

-continued

```
tgcactaaat atttgacatg agaattcaaa tccaatctca caggtgtttt ttaagccttg    3960
gcttgagtca ggtctgctaa tatcccattg gtcaaagcaa gaatgagcca agccaagaat    4020
caaaagaagg gagaagtgag ggtgatgact atattgaaca aaatcccaca caggaaatgc    4080
agaagaaata tgtaactgtt ttcttgtttc cttttaaaat aaattttgtc tattaaggga    4140
atatatatga attgtcatta attttatta taattaacta attattaatt taaatccttt    4200
tccactgcaa ggtctactat aaaaagaaat tcagagagac ctgggattct agtatgtatt    4260
tgttatcctt gttctccaaa aggttaaagg ggggtggtag tgtataatca taactaataa    4320
taattagaac ataagaatct gaaaatcaat attgaggggg atctaattat gcccatggca    4380
tttattttct tagtttgaga atggtgtgac aggtacggat gaatccaaac attccataag    4440
ctcctcaaca tttcagcttc cctgcagtta agctatgact tactctagcc aatgaaatga    4500
ctgtagaagt ggtat                                                     4515

<210> SEQ ID NO 103
<211> LENGTH: 470
<212> TYPE: DNA
<213> ORGANISM: Homo sapiens

<400> SEQUENCE: 103
tgagtcacaa gaggctgaaa gtgacctctg ggtgtctata attaggccct gcctgacgtc      60
agggcaacgg attttctggc ttggccaagt tcaccgtgcc aggcactgag ttaagtccat     120
tatgcattcc ctgacacttg cagcaacccc actaggcccc cattctccaa ggagaaaact     180
gaggcccagg agggtcatgc cctgctgagg ttactcagat caaggaggtt tcaactgagc     240
cagcaggaca gaggtgtgct gaggcttggg gccattcttc tgaccacttc tgctcctttt     300
tccctttctc taattttttc cccacatggc cctttgcctg aaatgccctt catatctatc     360
aggtttctgt gtaattgtca cctcctccag gaagtcttcc ctgacctttt cttctttgaa     420
ctgatctctg aaatgatctc tacctgttta ttgcttgttg atgtgaactc                470

<210> SEQ ID NO 104
<211> LENGTH: 1086
<212> TYPE: DNA
<213> ORGANISM: Homo sapiens

<400> SEQUENCE: 104
gaatcatctc agactgatga gactcttttc acatcagaat ataaaccagc caaggtactc      60
tatttgaaaa tgcagagcct gggtcttgta atgaagtgcc tgggtaaaaa gagtctaaat     120
gtcattgact ttgagttctg gagactggaa gttcaagatg tcagcatagt tggtttctgg     180
tgagggctct ctccttgggt tgcagatgac tgccttctgc tgtgccctca caggacagag     240
agagatagca aactctgttg tttcttctta taagggcact aattccatca taaggccacc     300
taacctcatc taacaaattg cctaccaaag cccatcctca aataccatca aattagagtt     360
atgtaattat aaaattctgt gctcaataat aagaaaaaca attaaaaaaa tcaaaagaat     420
caaacaaaca tgggtgacaa ataagcaaag aagaagatgc tcagcatcat tagtcattag     480
gaaaatgcaa attaaaacca taactactga atggctaaaa ttaaaaagac tgaccatacc     540
aggtgttggt gaggaggtag aggaacttga actcttatac cttgctgggg aaagtataaa     600
acagtacaac cactctggaa aacagtttgt cagtttctta gaaagttaaa cataaaccta     660
ccattttatc cagccattca ctcttaggta taagagaaaa aacatgcatc tatatagaat     720
```

-continued

```
tatgcataaa tgttcataga atcttcattg gtaatagccc caaactgaaa caacccaaat        780
gtccatgtac aggtgaacaa accggtatat cagaaaaaga gtatgcagta tgagttcatt        840
tatataacat gctaggaaac gcaaactaac gtatagtgtt agtggtttct ggtggatgag        900
gagatgtgaa agaacaggaa gaaagtgtta caaaagcaaa gaaacttttt gaggtatttt        960
cactatatta attgtggtta tggtttcata gttgcatatt tatgtcaaaa cctatcgagt       1020
tgtacatttc aactatatgt tatttattgt aagtcagtta taccccaata aagctgtaaa       1080
tattag                                                                   1086
```

```
<210> SEQ ID NO 105
<211> LENGTH: 15
<212> TYPE: DNA
<213> ORGANISM: Homo sapiens

<400> SEQUENCE: 105
tacaacctgc ttact                                                          15

<210> SEQ ID NO 106
<211> LENGTH: 16
<212> TYPE: DNA
<213> ORGANISM: Homo sapiens

<400> SEQUENCE: 106
tcatactata tgacag                                                         16

<210> SEQ ID NO 107
<211> LENGTH: 20
<212> TYPE: DNA
<213> ORGANISM: Homo sapiens

<400> SEQUENCE: 107
gtggggaggt cagctacaaa                                                     20

<210> SEQ ID NO 108
<211> LENGTH: 20
<212> TYPE: DNA
<213> ORGANISM: Homo sapiens

<400> SEQUENCE: 108
cggaaatggt ttgaaatgct                                                     20

<210> SEQ ID NO 109
<211> LENGTH: 20
<212> TYPE: DNA
<213> ORGANISM: Homo sapiens

<400> SEQUENCE: 109
acagacctgc agcagtgaga                                                     20

<210> SEQ ID NO 110
<211> LENGTH: 20
<212> TYPE: DNA
<213> ORGANISM: Homo sapiens

<400> SEQUENCE: 110
gctagggaac gcagaacaag                                                     20

<210> SEQ ID NO 111
<211> LENGTH: 20
<212> TYPE: DNA
<213> ORGANISM: Homo sapiens
```

-continued

```
<400> SEQUENCE: 111
aaggcttccc agagaaggag                                                    20

<210> SEQ ID NO 112
<211> LENGTH: 20
<212> TYPE: DNA
<213> ORGANISM: Homo sapiens

<400> SEQUENCE: 112
actgggtgag tctcgctgtt                                                    20

<210> SEQ ID NO 113
<211> LENGTH: 20
<212> TYPE: DNA
<213> ORGANISM: Homo sapiens

<400> SEQUENCE: 113
tgggacagca gagctaaggt                                                    20

<210> SEQ ID NO 114
<211> LENGTH: 20
<212> TYPE: DNA
<213> ORGANISM: Homo sapiens

<400> SEQUENCE: 114
agattccagc acgcacttct                                                    20

<210> SEQ ID NO 115
<211> LENGTH: 20
<212> TYPE: DNA
<213> ORGANISM: Homo sapiens

<400> SEQUENCE: 115
aaagggaaga gggaaaacga                                                    20

<210> SEQ ID NO 116
<211> LENGTH: 20
<212> TYPE: DNA
<213> ORGANISM: Homo sapiens

<400> SEQUENCE: 116
cgtctagaac cagcccagag                                                    20

<210> SEQ ID NO 117
<211> LENGTH: 20
<212> TYPE: DNA
<213> ORGANISM: Homo sapiens

<400> SEQUENCE: 117
cagccctgct ttagttcctg                                                    20

<210> SEQ ID NO 118
<211> LENGTH: 20
<212> TYPE: DNA
<213> ORGANISM: Homo sapiens

<400> SEQUENCE: 118
ttcgttgggg attttactgc                                                    20

<210> SEQ ID NO 119
<211> LENGTH: 20
<212> TYPE: DNA
```

<213> ORGANISM: Homo sapiens

<400> SEQUENCE: 119
tttggagatg gaacctggag 20

<210> SEQ ID NO 120
<211> LENGTH: 20
<212> TYPE: DNA
<213> ORGANISM: Homo sapiens

<400> SEQUENCE: 120
tctggtatgg gggagacttg 20

<210> SEQ ID NO 121
<211> LENGTH: 20
<212> TYPE: DNA
<213> ORGANISM: Homo sapiens

<400> SEQUENCE: 121
agctctgggt tggactgaga 20

<210> SEQ ID NO 122
<211> LENGTH: 20
<212> TYPE: DNA
<213> ORGANISM: Homo sapiens

<400> SEQUENCE: 122
tgcatacatt ctggcagagc 20

<210> SEQ ID NO 123
<211> LENGTH: 20
<212> TYPE: DNA
<213> ORGANISM: Homo sapiens

<400> SEQUENCE: 123
ggttgggtgc ctattaaacg 20

<210> SEQ ID NO 124
<211> LENGTH: 20
<212> TYPE: DNA
<213> ORGANISM: Homo sapiens

<400> SEQUENCE: 124
ggttcatgag cctttggaag 20

<210> SEQ ID NO 125
<211> LENGTH: 20
<212> TYPE: DNA
<213> ORGANISM: Homo sapiens

<400> SEQUENCE: 125
tgttaattca ggggcacaca 20

<210> SEQ ID NO 126
<211> LENGTH: 20
<212> TYPE: DNA
<213> ORGANISM: Homo sapiens

<400> SEQUENCE: 126
ggtggagagc cactgaagag 20

<210> SEQ ID NO 127
<211> LENGTH: 20

-continued

<212> TYPE: DNA
<213> ORGANISM: Homo sapiens

<400> SEQUENCE: 127
tctctgtccc ttgtgtgtgc                                                                20

<210> SEQ ID NO 128
<211> LENGTH: 20
<212> TYPE: DNA
<213> ORGANISM: Homo sapiens

<400> SEQUENCE: 128
cttggaggtg tgggcatagt                                                                20

<210> SEQ ID NO 129
<211> LENGTH: 20
<212> TYPE: DNA
<213> ORGANISM: Homo sapiens

<400> SEQUENCE: 129
gagccaagtg cacacagaaa                                                                20

<210> SEQ ID NO 130
<211> LENGTH: 20
<212> TYPE: DNA
<213> ORGANISM: Homo sapiens

<400> SEQUENCE: 130
tggtctgttc ctggccttag                                                                20

<210> SEQ ID NO 131
<211> LENGTH: 20
<212> TYPE: DNA
<213> ORGANISM: Homo sapiens

<400> SEQUENCE: 131
gtggacgaca agggaggtta                                                                20

<210> SEQ ID NO 132
<211> LENGTH: 20
<212> TYPE: DNA
<213> ORGANISM: Homo sapiens

<400> SEQUENCE: 132
cggaatggct cctacaacat                                                                20

<210> SEQ ID NO 133
<211> LENGTH: 20
<212> TYPE: DNA
<213> ORGANISM: Homo sapiens

<400> SEQUENCE: 133
gaggctcctg gatctctgtg                                                                20

<210> SEQ ID NO 134
<211> LENGTH: 20
<212> TYPE: DNA
<213> ORGANISM: Homo sapiens

<400> SEQUENCE: 134
ttgggaggca aaggtagatg                                                                20

<210> SEQ ID NO 135

-continued

```
<211> LENGTH: 20
<212> TYPE: DNA
<213> ORGANISM: Homo sapiens

<400> SEQUENCE: 135
gaaatgagtg gtggcagtga                                              20

<210> SEQ ID NO 136
<211> LENGTH: 20
<212> TYPE: DNA
<213> ORGANISM: Homo sapiens

<400> SEQUENCE: 136
cttaggtctg cgcctaatgg                                              20

<210> SEQ ID NO 137
<211> LENGTH: 20
<212> TYPE: DNA
<213> ORGANISM: Homo sapiens

<400> SEQUENCE: 137
gcacagatgc atagcctcaa                                              20

<210> SEQ ID NO 138
<211> LENGTH: 20
<212> TYPE: DNA
<213> ORGANISM: Homo sapiens

<400> SEQUENCE: 138
gcagcctgga cttttctcac                                              20

<210> SEQ ID NO 139
<211> LENGTH: 20
<212> TYPE: DNA
<213> ORGANISM: Homo sapiens

<400> SEQUENCE: 139
tcacctccaa gtgggtcttc                                              20

<210> SEQ ID NO 140
<211> LENGTH: 20
<212> TYPE: DNA
<213> ORGANISM: Homo sapiens

<400> SEQUENCE: 140
agctcggtct gtcgtgagtt                                              20

<210> SEQ ID NO 141
<211> LENGTH: 21
<212> TYPE: DNA
<213> ORGANISM: Homo sapiens

<400> SEQUENCE: 141
caaggcttaa taccgccact g                                            21

<210> SEQ ID NO 142
<211> LENGTH: 22
<212> TYPE: DNA
<213> ORGANISM: Homo sapiens

<400> SEQUENCE: 142
aatgtgcata gtaaccaggc tg                                           22
```

```
<210> SEQ ID NO 143
<211> LENGTH: 19
<212> TYPE: DNA
<213> ORGANISM: Homo sapiens

<400> SEQUENCE: 143
atggggtctc tggttctgc                                                          19

<210> SEQ ID NO 144
<211> LENGTH: 22
<212> TYPE: DNA
<213> ORGANISM: Homo sapiens

<400> SEQUENCE: 144
caataccatc ttgctccgtg aa                                                      22

<210> SEQ ID NO 145
<211> LENGTH: 22
<212> TYPE: DNA
<213> ORGANISM: Homo sapiens

<400> SEQUENCE: 145
aagagatacc gctatgccta cc                                                      22

<210> SEQ ID NO 146
<211> LENGTH: 19
<212> TYPE: DNA
<213> ORGANISM: Homo sapiens

<400> SEQUENCE: 146
gctgctcgcc agtaaaggg                                                          19

<210> SEQ ID NO 147
<211> LENGTH: 16
<212> TYPE: DNA
<213> ORGANISM: Homo sapiens

<400> SEQUENCE: 147
tgcttgctag tgtggt                                                             16

<210> SEQ ID NO 148
<211> LENGTH: 15
<212> TYPE: DNA
<213> ORGANISM: Homo sapiens

<400> SEQUENCE: 148
aggtgtgcga tagag                                                              15
```